US008951735B2

(12) United States Patent
Stacey et al.

(10) Patent No.: US 8,951,735 B2
(45) Date of Patent: Feb. 10, 2015

(54) GENETIC VARIANTS FOR BREAST CANCER RISK ASSESSMENT

(75) Inventors: Simon Stacey, Kopavogur (IS); Patrick Sulem, Reykjavik (IS)

(73) Assignee: deCODE Genetics ehf., Reykjavík (IS)

( * ) Notice: Subject to any disclaimer, the term of this patent is extended or adjusted under 35 U.S.C. 154(b) by 643 days.

(21) Appl. No.: 13/002,619

(22) PCT Filed: Jul. 3, 2009

(86) PCT No.: PCT/IS2009/000008

§ 371 (c)(1),
(2), (4) Date: Jan. 4, 2011

(87) PCT Pub. No.: WO2010/004591

PCT Pub. Date: Jan. 14, 2010

(65) Prior Publication Data

US 2011/0294673 A1 Dec. 1, 2011

(30) Foreign Application Priority Data

Jul. 7, 2008 (IS) .............................................. 8746

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/136* (2013.01); *C12Q 2600/172* (2013.01)
USPC ............. 435/6.14; 378/37; 600/410; 708/424

(58) Field of Classification Search
None
See application file for complete search history.

(56) References Cited

U.S. PATENT DOCUMENTS

| | | | |
|---|---|---|---|
| 4,376,110 | A | 3/1983 | David et al. |
| 5,223,409 | A | 6/1993 | Ladner et al. |
| 5,288,644 | A | 2/1994 | Beavis et al. |
| 5,445,934 | A | 8/1995 | Fodor et al. |
| 5,700,637 | A | 12/1997 | Southern |
| 5,744,305 | A | 4/1998 | Fodor et al. |
| 5,945,334 | A | 8/1999 | Besemer et al. |
| 6,054,270 | A | 4/2000 | Southern |
| 6,300,063 | B1 | 10/2001 | Lipshutz et al. |
| 6,429,027 | B1 | 8/2002 | Chee et al. |
| 6,733,977 | B2 | 5/2004 | Besemer et al. |
| 6,858,394 | B1 | 2/2005 | Chee et al. |
| 7,364,858 | B2 | 4/2008 | Barany et al. |
| 2011/0015081 | A1 | 1/2011 | Stacey et al. |
| 2011/0117545 | A1 | 5/2011 | Stacey et al. |

FOREIGN PATENT DOCUMENTS

| | | | |
|---|---|---|---|
| EP | 373 203 A1 | 6/1990 | |
| EP | 619 321 A1 | 10/1994 | |
| WO | WO-90/02809 A1 | 3/1990 | |
| WO | WO-91/17271 A1 | 11/1991 | |
| WO | WO-92/01047 A1 | 1/1992 | |
| WO | WO-92/09690 A2 | 6/1992 | |
| WO | WO-92/15679 A1 | 9/1992 | |
| WO | WO-92/18619 A1 | 10/1992 | |
| WO | WO-92/20791 A1 | 11/1992 | |
| WO | WO-93/01288 A1 | 1/1993 | |
| WO | WO-2006/063285 A2 | 6/2006 | |

OTHER PUBLICATIONS

Agami et al., RNAi and related mechanisms and their potential use for therapy, Curr. Opin. Chem. Biol., 6:829-34 (2002).
Altschul et al., Gapped BLAST and PSI-BLAST: a new generation of protein database search programs, Nucleic Acids Res., 25:3389-402 (1997).
Amarzguioui et al., Approaches for chemically synthesized siRNA and vector-mediated RNAi, FEBS Lett., 579:5974-81 (2005).
American Society of Clinical Oncology policy statement update: genetic testing for cancer susceptibility, J. Clin. Oncol., 21:2397-406 (2003).
Amundadottir et al., A common variant associated with prostate cancer in European and African populations, Nat. Genet., 38:652-8 (2006).
Amundadottir et al., Cancer as a complex phenotype: pattern of cancer distribution within and beyond the nuclear family, PLoS Med., 1:e65 (2004).
Antoniou et al., A comprehensive model for familial breast cancer incorporating BRCA1, BRCA2 and other genes, Br. J. Cancer, 86:76-83 (2002).
Arason et al., A population study of mutations and LOH at breast cancer gene loci in tumours from sister pairs: two recurrent mutations seem to account for all BRCA1/BRCA2 linked breast cancer in Iceland, J. Med. Genet., 35:446-9(1998).
Bennett, Efficiency of antisense oligonucleotide drug discovery, Antisense Nucleic Acid Drug Dev., 12:215-24 (2002).
Bergthorsson et al., Identification of a novel splice-site mutation of the BRCA1 gene in two breast cancer families: screening reveals low frequency in Icelandic breast cancer patients, Hum. Mutat., Suppl 1:S195-7 (1998).
Bernstein et al., Study design: evaluating gene-environment interactions in the etiology of breast cancer—the WECARE study, Breast Cancer Res., 6:R199-214 (2004).
Bier et al., DNA microarrays, Adv. Biochem. Eng, Biotechnol., 109:433-53 (2008).
Bosher et al., RNA interference: genetic wand and genetic watchdog, Nat. Cell Biol., 2:E31-6 (2000).
Breast Cancer Association, Commonly Studied Single-Nucleotide Polymorphisms and Breast Cancer: Results From the Breast Cancer Association Consortium , J. Natl Cancer Institute, 98:1382-96 (2006).
Broeks et al., Excess risk for contralateral breast cancer in CHEK2* 1100delC germline mutation carriers, Breast Cancer Res. Treat., 83:91-3 (2004).

(Continued)

*Primary Examiner* — Jim Ketter

(74) *Attorney, Agent, or Firm* — Marshall, Gerstein & Borun LLP

(57) ABSTRACT

The invention pertains to certain genetic variants that have been determined to be susceptibility variants of breast cancer. Methods of disease management, including diagnosing increased susceptibility to breast cancer, methods of predicting response to therapy and methods of predicting prognosis using such variants are described. The invention further relates to kits useful in the methods of the invention.

53 Claims, 1 Drawing Sheet

(56) References Cited

OTHER PUBLICATIONS

Brummelkamp et al., A system for stable expression of short interfering RNAs in mammalian cells, Science, 296:550-3(2002).
Burnet et al., Normal tissue radiosensitivity—how important is it?, Clin. Oncol. (R. Coll. Radiol.), 8:25-34(1996).
Carter et al., Methods and strategies for analyzing copy number variation using DNA microarrays, Nat. Genet., 39:S16-21 (2007).
Cass et al., Improved survival in women with BRCA-associated ovarian carcinoma, Cancer, 97:2187-95 (2003).
Chappuis et al., A significant response to neoadjuvant chemotherapy in BRCA1/2 related breast cancer, J. Med. Genet., 39:608-10 (2002).
CHEK2 Breast Cancer Case-Control Consortium, CHEK2*1100deIC and susceptibility to breast cancer: a collaborative analysis involving 10,860 breast cancer cases and 9,065 controls from 10 studies, Am. J. Hum. Genet., 74:1175-82 (2004).
Chen et al., Clinical development of antisense oligonucleotides as anti-cancer therapeutics, Methods Mol. Med., 75:621-36 (2003).
Chen et al., Fluorescence polarization in homogeneous nucleic acid analysis, Genome Res. 9:492-8 (1999).
Chen et al., The evolution of gene regulation by transcription factors and micro RNAs, Nat. Rev. Genet., 8:93-103 (2007).
Chi et al., Genomewide view of gene silencing by small interfering RNAs, Proc. Natl. Acad. Sci. USA, 100:6343-6 (2003).
Church et al., Genomic sequencing, Proc. Natl. Acad. Sci. USA, 81:1991-5 (1984).
Collaborative Group on Hormonal Factors in Breast Cancer, Familial breast cancer: collaborative reanalysis of individual data from 52 epidemiological studies including 58,209 women with breast cancer and 101,986 women without the disease, Lancet, 358:1389-99 (2001).
Cotton et al., Reactivity of cytosine and thymine in single-base-pair mismatches with hydroxylamine and osmium tetroxide and its application to the study of mutations, Proc. Natl. Acad. Sci. USA, 85:4397-401 (1988).
Cuzick et al., Overview of the main outcomes in breast-cancer prevention trials, Lancet, 361:296-300 (2003).
Daly et al., High-resolution haplotype structure in the human genome, Nat. Genet., 29:229-32 (2001).
Dawson et al., A first-generation linkage disequilibrium map of human chromosome 22, Nature, 418:544-8 (2002).
De Bock et al., Tumour characteristics and prognosis of breast cancer patients carrying the germline CHEK2* 1100deIC variant, J. Med. Genet., 41:731-5 (2004).
Dempster et al., Manual likelihood from incomplete data via the EM algorithm, J. Royal Stat. Soc. B, 39:1-38 (1977).
Devlin et al., A comparison of linkage disequilibrium measures for fine-scale mapping, Genomics, 29:311-22 (1995).
Devlin et al., Genomic control for association studies, Biometrics, 55:997-1004 (1999).
Devlin et al., Genomic control to the extreme, Nat. Genet., 36:1129-30 (2004).
Dias et al., Antisense oligonucleotides: basic concepts and mechanisms, Mol. Cancer Ther., 1:347-55 (2002).
Dumitrescu et al., Understanding breast cancer risk—where do we stand in 2005?, J. Cell. Mol. Med., 9:208-21 (2005).
Easton et al,, Genome-wide association study identifies novel breast cancer susceptibility loci, Nature, 447:1087-93 (2007).
Easton, How many more breast cancer predisposition genes are there?, Breast Cancer Res., 1:14-7 (1999).
Eerola et al., Survival of breast cancer patients in BRCA1, BRCA2, and non-BRCA1/2 breast cancer families: a relative survival analysis from Finland, Int. J. Cancer, 93:368-72 (2001).
Eifel et al., National Institutes of Health Consensus Development Conference Statement: adjuvant therapy for breast cancer, Nov. 1-3, 2000, J. Natl. Cancer Inst., 93:979-89 (2001).
Estivill et al., Copy number variants and common disorders: filling the gaps and exploring complexity in,genome-wide association studies, PLoS Genet., 3:1787-99 (2007).
Falk et al., Haplotype relative risks: an easy reliable way to construct a proper control sample for risk calculations, Ann. Hum. Genet., 51:227-33(1987).
Fan et al., Illumina universal bead arrays, Methods Enzymol., 410:57-73 (2006).
Farmer et al., Targeting the DNA repair defect in BRCA mutant cells as a therapeutic strategy, Nature, 434:917-21 (2005).
Fire et al., Potent and specific genetic interference by double-stranded RNA in *Caenorhabditis elegans*, Nature, 391:806-11 (1998).
Flavell et al., Analysis of the beta-delta-globin gene loci in normal and Hb Lepore DNA: direct determination of gene linkage and intergene distance, Cell, 15:25-41 (1978).
Frayling et al., Genome-wide association studies provide new insights into type 2 diabetes aetiology, Nat. Rev. Genet., 8:657-62 (2007).
Fuchs et al., Targeting recombinant antibodies to the surface of *Escherichia coli*: fusion to a peptidoglycan associated lipoprotein, Bio/Technology, 9:1369-72 (1991).
Gabriel et al., The structure of haplotype blocks in the human genome, Science, 296:2225-9 (2002).
Galfre et al., Antibodies to major histocompatibility antigens produced by hybrid cell lines, Nature, 266:550-2 (1977).
Geever et al., Direct identification of sickle cell anemia by blot hybridization, Proc. Natl. Acad. Sci. USA, 78:5081-5 (1981).
Goffin et al., Impact of germline BRCA1 mutations and overexpression of p53 on prognosis and response to treatment following breast carcinoma: 10-year follow up data, Cancer, 97:527-36 (2003).
Gold et al., Genome-wide association study provides evidence for a breast cancer risk locus at 6q22.33, Proc. Natl. Acad. Sci. USA, 105:4340-5 (2008).
Goldhirsch et al., Meeting highlights: International Consensus Panel on the Treatment of Primary Breast Cancer, J. Natl. Cancer Inst., 90:1601-8 (1998).
Gorski et al., Breast cancer predisposing alleles in Poland, Breast Cancer Res. Treat., 92:19-24 (2005).
Grant et al., Variant of transcription factor 7-like 2 (TCF7L2) gene confers risk of type 2 diabetes, Nat. Genet., 38:320-3 (2006).
Gretarsdottir et al., Risk variants for atrial fibrillation on chromosome 4q25 associate with ischemic stroke, Ann. Neurol., 64:402-9 (2008).
Gretarsdottir et al., The gene encoding phosphodiesterase 4D confers risk of ischemic stroke, Nat. Genet., 35:131-8 (2003).
Griffiths et al., Human anti-self antibodies with high specificity from phage display libraries, EMBO J., 12:725-34 (1993).
Gudbjartsson et al., ASIP and TYR pigmentation variants associate with cutaneous melanoma and basal cell carcinoma, Nat. Genet 40:886-91 2008.
Gudmundsson et al., Common sequence variants on 2p15 and Xp11. 22 confer susceptibility to prostate cancer, Nat. Genet., 40:281-3 (2008).
Gudmundsson et al., Frequent occurrence of BRCA2 linkage in Icelandic breast cancer families and segregation of a common BRCA2 haplotype, Am. J. Hum. Genet., 58:749-56 1996.
Gudmundsson et al., Genome-wide association study identifies a second prostate cancer susceptibility variant at 8q24, Nat. Genet., 39:631-7 2007.
Hay et al., Bacteriophage cloning and *Escherichia coli* expression of a human IgM Fab, Hum. Antibodies Hybridomas, 3:81-5 (1992).
Helgadottir et al., A common variant on chromosome 9p21 affects the risk of myocardial infarction, Science, 316:1491-3 2007.
Hill et al., Linkage disequilibrium in finite populations, Theor. Appl. Genet. 22:226-31 (1968).
Hoeller et al., Increasing the rate of late toxicity by changing the score? A comparison of RTOG/EORTC and LENT/SOMA scores, Int. J. Radiat. Oncol. Biol. Phys., 55:1013-8 2003.
Hoheisel, Microarray technology: beyond transcript profiling and genotype analysis, Nat. Rev. Genet., 7:200-10 2006.
Hoyal et al., Genetic polymorphisms in DPF3 associated with risk of breast cancer and lymph node metastases, J. Carcinog., 4:13 (2005).
Hunter et al., A genome-wide association study identifies alleles in FGFR2 associated with risk of sporadic postmenopausal breast cancer, Nat. Genet., 39:870-4 (2007).

(56) References Cited

OTHER PUBLICATIONS

Hunter, Genetics: a touch of elegance with RNAi, Curr. Biol., 9:R440-2 (1999).
Huse et al., Generation of a large combinatorial library of the immunoglobulin repertoire in phage lambda, Science, 246:1275-81 1989.
International Preliminary Report on Patentability for corresponding International Application No. PCT/IS2009/000008, dated Jan. 11, 2011.
Interntional Search Report and Written Opinion for corresponding International Application No. PCT/IS2009/000008 dated Jan. 28, 2010.
Jeffreys et al., Intensely punctate meiotic recombination in the class II region of the major histocompatibility complex, Nat. Genet., 29:217-22 (2001).
Jemal et al., Cancer statistics, 2008, CA Cancer J. Clin., 58:71-96 (2008).
Karlin et al., Applications and statistics for multiple high-scoring segments in molecular sequences, Proc. Natl. Acad. Sci. USA, 90:5873-7 (1993).
Kent, BLAT—the BLAST-like alignment tool, Genome Res., 12:656-64 (2002).
Kim et al., Strategies for silencing human disease using RNA interference, Nat. Rev. Genet., 8:173-84 (2007).
Kim et al., Synthetic dsRNA Dicer substrates enhance RNAi potency and efficacy, Nat. Biotechnol., 23:222-6 (2005).
Kohler et al., Continuous cultures of fused cells secreting antibody of predefined specificity, Nature, 256:495-7 (1975).
Kozbor et al., The production of monoclonal antibodies from human lymphocytes, Immunol. Today, 4:72-9 (1983).
Kraus et al., Detection and isolation of novel protein-tyrosine kinase genes employing reduced stringency hybridization, Methods Enzymol., 200:546-56 (1991).
Kurreck, Antisense technologies. Improvement through novel chemical modifications, Eur. J. Biochem., 270:1628-44 (2003).
Kutyavin et al., novel endonuclease IV post-PCR genotyping system, Nucleic Acids Res., 34:e128 (2006).
Lavery et al., Antisense and RNAi: powerful tools in drug target discovery and validation, Curr. Opin. Drug Discov. Devel , 6:561-9 (2003).
Leach et al., Screening with magnetic resonance imaging and mammography of a UK population at high familial risk of breast cancer: a prospective multicentre cohort study (MARIBS), Lancet, 365:1769-78 (2005).
Lerner, How to make a hybridoma, Yale J Biol. Med., 54:385-402 (1981).
Lewontin et al., The Interaction of Selection and Linkage. I. General Considerations; Heterotic Models, Genetics, 49:49-67 (1964).
Lichtenstein et al., Environmental and heritable factors in the causation of cancer—analyses of cohorts of twins from Sweden, Denmark, and Finland, N. Engl. J. Med., 343:78-85 (2000).
Maniatis et al., The first linkage disequilibrium (LD) maps: delineation of hot and cold blocks by diplotype analysis, Proc. Natl. Acad. Sci USA, 99:2228-33 (2002).
Mantel et al., Statistical aspects of the analysis of data from retrospective studies of disease, J. Natl. Cancer Inst., 22:719-48 (1959).
Marques et al., A structural basis for discriminating between self and nonself double-stranded RNAs in mammalian cells, Nat. Biotechnol., 24:559-65 (2006).
Martino et al., The role of selective estrogen receptor modulators in the prevention of breast cancer: comparison of the clinical trials, Oncologist, 9:116-25(2004).
Mathieu et al., The poor responsiveness of infiltrating lobular breast carcinomas to neoadjuvant chemotherapy can be explained by their biological profile, Eur. J. Cancer, 40:342-51 (2004).
May et al., Crossover clustering and rapid decay of linkage disequilibrium in the Xp/Yp pseudoautosomal gene ShOX, Nat. Genet., 31:272-5 (2002).
McManus et al., Gene silencing in mammals by small interfering RNAs, Nat. Rev. Genet., 3:737-47 (2002).
Metcalfe et al., Contralateral breast cancer in BRCA1 and BRCA2 mutation carriers, J. Clin. Oncol., 22:2328-35 (2004).
Mockler et al., Applications of DNA tiling arrays for whole-genome analysis, Genomics, 85:1-15 (2005).
Moller et al., Survival in prospectively ascertained familial breast cancer: analysis of a series stratified by tumour characteristics, BRCA mutations and oophorectomy, Int. J. Cancer, 101:555-9 (2002).
Myers et al., A fine-scale map of recombination rates and hotspots across the human genome, Science, 310:321-4 (2005).
Myers et al., Detection of single base substitutions by ribonuclease cleavage at mismatches in RNA:DNA duplexes, Science, 230:1242-6(1985).
Myers et al., Optimal alignments in linear space, Cabios, 4:11-7 (1988).
Myers et al., The distribution and causes of meiotic recombination in the human genome, Biochem. Soc. Trans., 34:526-30(2006).
Narod et al., BRCA1 and BRCA2: 1994 and beyond, Nat. Rev. Cancer, 4:665-76 (2004).
NCBI Database Accession No. Pr005049093, sequence-specific oligonucleotide (SSO) probe for *Homo sapiens* variation rs999737 (Mar. 1, 2006).
NCBI Database Accession No. Pr007592512, bead microelement (Bead) probe for *Homo sapiens* variation rs999737 (Jan. 11, 2007).
Nicolae et al., Measuring the relative information in allele-sharing linkage studies, Biometrics, 60:368-75 (2004).
Nielsen et al., Peptide nucleic acid (PNA). A DNA mimic with a peptide backbone, Bioconjug. Chem., 5:3-7 (1994).
Nyren et al., Solid phase DNA minisequencing by an enzymatic luminometric inorganic pyrophosphate detection assay, Anal. Biochem., 208:171-5 (1993).
Orita et al., Detection of polymorphisms of human DNA by gel electrophoresis as single-strand conformation polymorphisms, Proc. Natl. Acad. Sci. USA, 86:2766-70 (1989).
Parkin et al., Global cancer statistics, 2002, CA Cancer J. Clin., 55:74-108 (2005).
Patil et al., Blocks of limited haplotype diversity revealed by high-resolution scanning of human chromosome 21, Science, 294:1719-23 (2001).
Pearson et al., Improved tools for biological sequence comparison, Proc. Natl. Acad. Sci. USA, 85:2444-8 (1988).
Peto et al., High constant incidence in twins and other relatives of women with breast cancer, Nat. Genet., 26:411-4 (2000).
Pharoah et al., Polygenic susceptibility to breast cancer and implications for prevention, Nat. Genet., 31:33-6 (2002).
Pharoah, Genetic susceptibility, predicting risk and preventing cancer, Recent Results Cancer Res., 163:7-18, 264-6 (2003).
Phillips et al., Chromosome-wide distribution of haplotype blocks and the role of recombination hot spots, Nat. Genet., 33:382-7 (2003).
Plasterk et al., The silence of the genes, Curr. Opin. Genet. Dev., 10:562-7 (2000).
Prevalence and penetrance of BRCA1 and BRCA2 mutations in a population-based series of breast cancer cases. Anglian Breast Cancer Study Group, Br. J. Cancer, 83:1301-8 (2000).
Rafnar et al., Sequence variants at the TERT-CLPTM1L locus associate with many cancer types, Nat. Genet., 41:221-7 (2009).
Ragoussis et al., Affymetrix GeneChip system: moving from research to the clinic, Expert Rev. Mol. Diagn., 6:145-52 (2006).
Redon et al., Global variation in copy number in the human genome, Nature, 444:444-54 (2006).
Reich et al. Linkage disequilibrium in the human genome, Nature, 411:199-204 (2001).
Renwick et al., ATM mutations that cause ataxia-telangiectasia are breast cancer susceptibility alleles, Nat. Genet., 38:873-5 (2006).
Reynolds et al., Rational siRNA design for RNA interference, Nat. Biotechnol., 22:326-30 (2004).
Risch et al., The future of genetic studies of complex human diseases, Science, 273:1516-7 (1996).
Risch et al., The relative power of family-based and case-control designs for linkage disequilibrium studies of complex human diseases I. DNA pooling, Genome Res., 8:1273-88 (1998).

(56) References Cited

OTHER PUBLICATIONS

Ronaghi et al., Analyses of secondary structures in DNA by pyrosequencing, Anal. Biochem., 267:65-71 (1999).
Ronaghi et al., PCR-introduced loop structure as primer in DNA sequencing, Biotechniques, 25:876-8, 880-2, 884 (1998).
Sanger et al., DNA sequencing with chain-terminating inhibitors, Proc. Natl. Acad. Sci. USA, 74:5463-7 (1977).
Sheffield et al., Attachment of a 40-base-pair G + C-rich sequence (GC-clamp) to genomic DNA fragments by the polymerase chain reaction results in improved detection of single-base changes, Proc. Natl. Acad. Sci. USA, 86:232-6 (1989).
Shi, Mammalian RNAi for the masses, Trends Genet., 19:9-12 (2003).
Siolas et al., Synthetic shRNAs as potent RNAi triggers, Nat. Biotechnol 23:227-31 (2005).
Smith et al., A genome wide linkage search for breast cancer susceptibility genes, Genes Chromosomes Cancer, 45:646-55 (2006).
Smith et al., A high-density admixture map for disease gene discovery in african americans, Am. J. Hum. Genet., 74:1001-13 (2004).
Stacey et al., Common variants on 1p36 and 1q42 are associated with cutaneous basal cell carcinoma but not with melanoma or pigmentation traits, Nat. Genet., 40:1313-8 (2008).
Stacey et al., Common variants on chromosome 5p12 confer susceptibility to estrogen receptor-positive breast cancer, Nat. Genet., 40:703-6 (2008).
Stacey et al., Common variants on chromosomes 2q35 and 16q12 confer susceptibility to estrogen receptor-positive breast cancer, Nat. Genet., 39:865-9(2007).
Stacey et al., The BARD1 Cys557Ser variant and breast cancer risk in Iceland, PLos Med., 3:e217 (2006).
Steemers et al., Whole genome genotyping technologies on the BeadArray platform, Biotechnol. J., 2:41-9 (2007).
Steinthorsdottir et al., A variant in CDKAL1 influences insulin response and risk of type 2 diabetes, Nat. Genet., 39:770-5 (2007).
Stephens et al., Antisense oligonucleotide therapy in cancer, Curr. Opin. Mol. Ther., 5:118-22 (2003).
Strausberg et al., Emerging DNA sequencing technologies for human genomic medicine, Drug Discov. Today, 13:569-77 (2008).
Stumpf et al., Demography, recombination hotspot intensity, and the block structure of linkage disequilibrium, Curr. Biol., 13:1-8(2003).
Styrkarsdottir et al., Multiple genetic loci for bone mineral density and fractures, N. Engl. J. Med., 358:2355-65 (2008).
Sulem et al., Genome-wide association study identifies sequence variants on 6q21 associated with age at menarche, Nat. Genet., 41:734-8 (2009).
Terwilliger et al., A haplotype-based 'haplotype relative risk' approach to detecting allelic associations, Hum. Hered., 42:337-46 (1992).
Thomas et al., A multistage genome-wide association study in breast cancer identifies two new risk alleles at 1p11.2 and 14q24.1 (RAD51L1), Nat. Genet., 41:579-84 (2009).
Thompson, Applications of antisense and siRNAs during preclinical drug development, Drug Discov. Today, 7:912-7 (2002).
Thorgeirsson et al., A variant associated with nicotine dependence, lung cancer and peripheral arterial disease, Nature, 452:638-42 (2008).
Thorlacius et al., Study of a single BRCA2 mutation with high carrier frequency in a small population, Am. J. Hum. Genet., 60:1079-84 (1997).
Torelli et al., Advance and Adam: two algorithms for the analysis of global similarity between homologus informational sequnces. CABIOS, 10:3-5(1984).
Tulinius et al., The effect of a single BRCA2 mutation on cancer in Iceland, J. Med. Genet., 39:457-62 (2002).
Vickers et al., Efficient reduction of target RNAs by small interfering RNA and RNase H-dependent antisense agents. A comparative analysis, J. Biol. Chem., 278:7108-18 (2003).
Wall et al., Haplotype blocks and linkage disequilibrium in the human genome, Nat. Rev. Genet., 4:487-97 (2003).
Wang et al., Antisense anticancer oligonucleotide therapeutics, Curr. Cancer Drug Targets, 1:177-96 (2001).
Wang et al., Distribution of recombination crossovers and the origin of haplotype blocks: the interplay of population history, recombination, and mutation, Am. J. Hum. Genet., 71:1227-34 (2002).
Warner et al., Surveillance of BRCA1 and BRCA2 mutation carriers with magnetic resonance imaging, ultrasound, mammography, and clinical breast examination, JAMA, 292:1317-25 (2004).
Xia et al., siRNA-mediated gene silencing in vitro and in vivo, Nat. Biotechnol., 20:1006-10 (2002).
Zhang et al., A dynamic programming algorithm for haplotype block partitioning, Proc. Natl. Acad. Sci. USA, 99:7335-9 (2002).

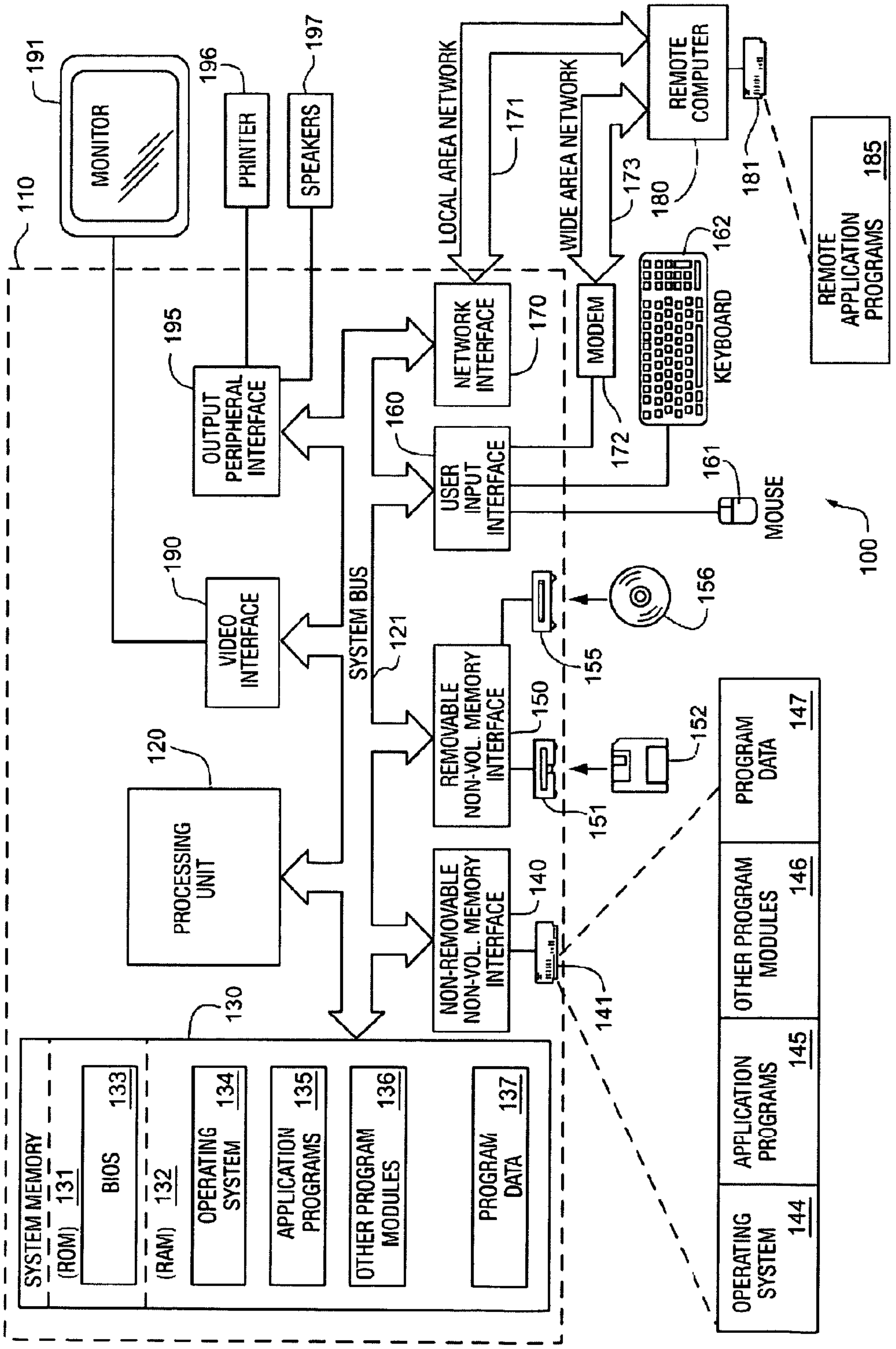

MONITOR
191
PRINTER
196
SPEAKERS
197
REMOTE COMPUTER
180
181
REMOTE APPLICATION PROGRAMS 185
LOCAL AREA NETWORK
171
WIDE AREA NETWORK
173
110
OUTPUT PERIPHERAL INTERFACE
195
NETWORK INTERFACE
170
MODEM
172
KEYBOARD
162
USER INPUT INTERFACE
160
MOUSE
161
100
VIDEO INTERFACE
190
SYSTEM BUS
121
156
155
REMOVABLE NON-VOL. MEMORY INTERFACE
150
151
152
PROCESSING UNIT
120
NON-REMOVABLE NON-VOL. MEMORY INTERFACE
140
141
SYSTEM MEMORY
130
(ROM) 131
BIOS 133
(RAM) 132
OPERATING SYSTEM 134
APPLICATION PROGRAMS 135
OTHER PROGRAM MODULES 136
PROGRAM DATA 137
OPERATING SYSTEM 144
APPLICATION PROGRAMS 145
OTHER PROGRAM MODULES 146
PROGRAM DATA 147

SEQUENCE LISTING

<160> NUMBER OF SEQ ID NOS: 562

<210> SEQ ID NO 1
<211> LENGTH: 599
<212> TYPE: DNA
<213> ORGANISM: Homo sapiens

<400> SEQUENCE: 1
tttctttttt cctctttttt tttttaggcg gagtctcgcc ctgtcgccca ggctggagtg 60
cagtggtgca atctcggctc actgcaagct ctgcctccca ggttcacgcc attctcctgc 120
ctcagcctcc tcagcagctg ggactacggg ttcacgcctc cacacctggc taattttttg 180
tatttttagc agagatgggg tttcaccatg ttagccagga tggtcttgat ctcctgacct 240
tgaaaataca caaattttct aaagggagaa gcaaaaaaag agcagtacca gactgaagcy 300
ggattacaaa gataggaagg ctctaggttt tgtccttagc accttttctc tgcatccatt 360
tggccactgg cagatgcttg gcctggaaac ccgaagagtc tctttgaacg tctagaatgt 420
tgccagaagc ccccatccca gggcctaacc cacttggccc caggttctgc agagttgagt 480
aggaataaca ttgaactaca ttcccaggaa aatccaactc atgtattcat gataagtgtc 540
aaataaactc actaggttct cgtgtgtcta gcctcaactg ggtttgttca ggcagtcat 599

<210> SEQ ID NO 2
<211> LENGTH: 599
<212> TYPE: DNA
<213> ORGANISM: Homo sapiens

<400> SEQUENCE: 2
aagagacttt ctgagcattc tatattccca ttaaattctg attttaaaaa ggaccctaag 60
cagttccttc tttagcctta tttctgtctt acaatacctt atattcagct aaaagaagac 120
aaatgacact tttaccatcc ttcttggaat ccttttatcc aaatgtacag attttaggat 180
acctttcctg tctaagttaa tgtgggcagc agtttcacta atttttctgc cactacataa 240
cacgggttgt tgtttttcca gcctccaaag caattttctc actacctttc caggctctak 300
gaaacagtcc gttgctgctt tctggtgtct ctgctcccca ctcctaaagc caagggcaca 360
tattctagat tttgttatga cagcacatca cctctttgca tcgacttctg catccattgt 420
ttattgctgt gtacaaaaca tcccaaaatt actggcttaa aacaacaatt ttgttgttgt 480
tgttgctatt ttataagtga agcatttgaa aggggcttag caggaatggc ttagctctgc 540
cctacagtgt ccaaagtgcc aggtaggatg gctgagacag ctaggcccct ctcctccat 599

<210> SEQ ID NO 3
<211> LENGTH: 599

<212> TYPE: DNA
<213> ORGANISM: Homo sapiens

<400> SEQUENCE: 3
gatagtacaa ttaaaaaatt caatttaaaa tggcttgtta gagagataga tgccagatat 60
tacttgacaa gccagaaact agagacacta agataaaaac aaaataaaac aagaaattaa 120
gattgatgga taaaaataat ctctcaaaga tttatttgga tttaatctaa atttaaggtg 180
ccatatatct ttactcgtga aagaaaattg aatttttgag gacactaagt agtttgagaa 240 ataccttct ttaaaatctt cttctttacc taaatgaaca ctagtgtcct ggttttctty 300
ctatccacct actaattctt agtctccttc tttcagcact taaatattct tgtaccatag 360
gtgctattcc tggacatctc tctttgtact cagcacagca tcttcctact tcaactctta 420
tcttttggtt ctgacttcca attcttatca ctaattcatt gctgttcaga cccagtttat 480
ataaattcac ttctgtgtct accagttcct caaaacggaa accatcattc ctgaatcatc 540
ttttcatttc tccctttca tgtattttgc atctcaatgt gaggcatcac gtagttaaa 599

<210> SEQ ID NO 4
<211> LENGTH: 599
<212> TYPE: DNA
<213> ORGANISM: Homo sapiens

<400> SEQUENCE: 4
tttcaggggc agcgtagact tctcctcctt catcccttct tcttctctcc ttggcccagg 60
catctccagc agcatgagct ttgacgagga tgaggaggat gaggaggaga atagctccag 120
ctcctcccag ctaaatagta acacccgccc cagctctgct actagcagga agtccgtcag 180
ggtgagtgag tgagtctgca tccacagcag tttttggagg actgctcatc cgttagaggt 240
ggactgcatg tgaagagatg gactcgtatg cctttaggag cttctctgct ggcctcttay 300
gtccctctac cttgcctcct aacctcttca gctaggccag cagggtgatg tatgggggga 360
gatgcagttg gacaggatga cctctgagga cctcccgtat ctcccatctc cacctctagg 420
aactgttgag ggcagggctg ggaagatagc ttctgacccc aggcccaggc tggccaggcc 480
ccaatcccag gatccttccc tctctcccac cgccacgtta ggaggcagat ttggatccca 540
gaccaccaat ttgggctgct tagggtcctt ggggctcagg cacctattct gcatcccca 599

<210> SEQ ID NO 5
<211> LENGTH: 599
<212> TYPE: DNA
<213> ORGANISM: Homo sapiens

<400> SEQUENCE: 5
atcactgggg cctgaggcga tcaggctgat ctgctagcgc tactcatccc tgccttcatc 60
taggaaccgg gcaggcatgg tggagcccca acacactgca gcatgaggcc actgcactca 120
gaaaggcttg tgtcacatcc tagctcttct acccttcacc catgtgacct tggcccggtg 180
atttcacctt ttgagactta gtcttctcat ctataaaatg gggataataa tacctgcctc 240
acaaggctat agcaaggatt aatgagatca tacaccgtga agtttggctc tggacctggr 300
atacagttaa cacttgataa agattgtcat tgttgtcact gtatcaccac tcctctgtgc 360
caggcagctc tcatgctgga taccagggac cctgcgatac accagagcca ttcaggaact 420
ccttaaggaa ctcagaatct gatgaggaga tgtgccacaa agacaattta aacaaataat 480
agatgatggc tcacacctgt aatcccagca ctttgggagg ccgaggtcgg aagctctcct 540
gaggccaggg ggttcaagac cagactggtc aaggtagcaa gaccccatct ctataaaaa 599

<210> SEQ ID NO 6
<211> LENGTH: 599
<212> TYPE: DNA
<213> ORGANISM: Homo sapiens

<400> SEQUENCE: 6
tttctacccc agtcatcacg gacaatgcaa gttctacctt cctcacgaag tctttcccag 60
tgactgtaat ctgcatagat ctccctcttc ccaggatcct tgctgtaccc acaagaagaa 120 caccccttggc tgtgccatta ttgtctcctc ctttcatatt agccccatct ctgtaagtag 180
attttaagct cctggtactt ggattctacc atagtgcctg gcctgtggca ggagttccat 240
atgcagggct gacatattgc atagttccag gggtcccgtt cacatgatat gaatggggcy 300
cctggagtta cacaagttat agccctgtcc ataagtcctt ggtgattgaa taaaactcat 360
tccaggacct gaaaaagaaa caattattgt gatcatggtt cagttcaaat cttcaggtga 420
ttattgaaca gctactatgt actaaccacc aatgatacaa aaaatgaata aaatggctgt 480
tcctaccctc tgagaaacta tagtcttgcg acacagaaag gtaagcaaac agatcaccat 540
aatacaatgt gaaaagtgct aagatagaaa catgggtaaa ggagatggca cttgatgtg 599

<210> SEQ ID NO 7
<211> LENGTH: 599
<212> TYPE: DNA
<213> ORGANISM: Homo sapiens

<400> SEQUENCE: 7
cagcgtgcat cctctcattg gattagcctt gagtgtactg tgttcattcc tttctcacta 60
cccttgtctt tgtggttgcc tcgctgcctc agctatccca tctgtaaaca gctgattgca 120
gtgaggatag aatctagcta ctccaagtgt gagctgtgta tcacctgggc tgtattagaa 180
atgcacactc aggtgctgcc accgcccctc ccccccgacc tgctgaatca gaacacatgc 240
ttcaccaaga tggcctggtg atttttgtgc acactgcagt ctgaacagca tggattacar 300
gtgatttagg tcaggctctc agtacatggg ggttctcact gtctcccctg ttctcagata 360
acttccctga gggagaagac ctggctgttc agttctctgg tgtttccctc gaagctaagt 420
agtgctaaga tagaatgtgc actaagttga ttgattggtg ttagttttag aacacaaatc 480
cactggtatt attgcactaa tgaatttcca ccttaatcct cttaagggac acatctgttt 540
gctacattac attaagattt ttaaaagatg agatcattag taaacttggc aagtgtgtt 599

<210> SEQ ID NO 8
<211> LENGTH: 599
<212> TYPE: DNA
<213> ORGANISM: Homo sapiens

<400> SEQUENCE: 8
tgcacggtga ccctgagcac ctcctgtgtg tcaggccctg tcccagagga agggcagagc 60
tcagccagct ggggcaggca ccaggcaaga ttttatctag gcttgatcac atttcttttc 120
atcttcatag aaccatgaag tagcctcatt ttacaggtgg aattcagagg gcttaagtaa 180
cttgcacaag gcctcacagc ctgcgtggaa tctgtggcac tttccccact gcagtacact 240
tccgtactgt tggatcgatg tgaatctaga gaccagggat ggaggaagtt aaaggggtgy 300
tctgtggggg tcttgcagca ggagcccctc ctgcgggcag ctgtgcagcc tcctctcctc 360
tcctcccctc ccctcctcct ctcctcctcc tttcctcctc ctctcttcct cctttcctcc 420
tctcctcctc ctcttgtcct ctcctctcct cccctgtcct ctccttctct cttcttcctt 480
tcctcctcct ctcctctcct cttcctctcc tcctcctctc ctcttcctct cctcctcctc 540
ttcctcctgt cctcctcctc tcctctcctc ctctcctctc ctcctcctct cctctcctc 599

<210> SEQ ID NO 9
<211> LENGTH: 599
<212> TYPE: DNA
<213> ORGANISM: Homo sapiens

<400> SEQUENCE: 9
tgaactcctg ggttagacag gaagctgtcg gggaggtttg cttgagcccg ggagacagag 60
gttacagtga gccgagatcc caccactgca ctccagcagg gggcgacaga gcaagaccct 120
gtctcacaaa aaaattataa aaatataaaa aaccaaaact acaatgtaca cttatgaaag 180
aacaacagta agaaagggaa attacatttt agtataaata cataaaattt tgattcatac 240
ccactgaaaa tgtttcaagg acacctaggg gtcctcagac cacactttga aaacaatgck 300
ctatactgta gtgcctcttc agttagggca cgctatacaa atatttacaa ggcatggtct 360
caggaacata cttaacctaa aaaatatcct aatgattttg ctaaatcacc cattcaacaa 420
ttattaagtg cttacaatac acgaagtatt cttatacaca aggcagagaa tcaaagagga 480
aaaaaaaaat cctccttgtg gcacttacat tctacgaaga gacagccaca accaataaac 540
aaatgaacta tctattctgc aaataagtgg tatgaaggaa aataaaagca aggttttac 599

<210> SEQ ID NO 10
<211> LENGTH: 599
<212> TYPE: DNA
<213> ORGANISM: Homo sapiens

<400> SEQUENCE: 10
gccctgggtc tatcactgcc catgtcccag ggcacacaga ttcagggctg tctgtgaccc 60
tgtcttgttt cccctgctgt tgggtctggc ttctcctcaa tggcaggaac caaggctgac 120
catctgtgac tgacaggtcc ctgcagcccc acccccagca cagggcttgc ccacaatacc 180
aatgcagact gagtgagcac taagtgtgcc cagcagatgt tccttgagcc agcccctttc 240
agagtcagaa cagaaaaggt cgtgaaatcc atgctggaaa gaattagtga aacaccagty 300
ccgatctttg ctagaaacat ggagacagca aggcagagaa agggaataaa acacacaaag 360
agaagtgggc tgtgtttact gcagaaacca ccgtgcaggt cccatgagtg aaaagggaca 420
ctggtgctct cctgagcggc ttagctccca cctgcaggcc tcagtaggcc tcccctgcca 480
cataatgaca gcactcagtt cggctcactt caaaagagtg caaaagtaca agctaaaata 540
aagagacaca aattttcgtc tttctttttt cctctttttt tttttaggcg gagtctcgc 599

<210> SEQ ID NO 11
<211> LENGTH: 599
<212> TYPE: DNA
<213> ORGANISM: Homo sapiens

<400> SEQUENCE: 11
agctggtctg tagtggagct tgcagaggcc cccatcacga tctgctggga agaccaagca 60
aggagagcaa cgtcaacttt taaaaattat cttcaaattg tgtgtaatgc acgtgcactg 120
aagaaaaatc aggacatgta gataaataaa tcactaagat cacctggggt gctaaaggcc 180
tcagtggtct aaaatcatag cagctgtgtc tcctgcagag cgtgcttcct agtgatggcc 240

-continued

```
tcctcctgtg gggctttgca ggccatgcgt ccctcccaga gacagctatt gaggcagtgk    300

gctgaggagg ccacagcagt gctcagtcgg ccagaagggt cccccttcccc acatcaccac    360

acagctggcc aagaggctcc acagctattg gatctgcggg gctggaaatc catctgctcc    420

cacccccatc tgaaacacgc tccccttcgc tgcctcctaa ggaagatgtc agcctctgct    480

tgcatttgcc acctcctctc ctccttgagg aaccccatct gctaggaaat gacatgagcc    540

taggctagcc ctcaccttga tccagaaccc aagctacccc ttacctttga cctggtggc     599
```

<210> SEQ ID NO 12
<211> LENGTH: 599
<212> TYPE: DNA
<213> ORGANISM: Homo sapiens

<400> SEQUENCE: 12

```
aggcaagatc tcaaaggctg aaaaggagcc tgaattctgt gcctctgaag ggagtcaggg     60

gagaagcttt gccccttgga aggtcaccca ggtgtggtgt ggaggagaac cgtaagcccg    120

aaggaggtga gagatgtctg cgctggggag ttgatagggg atagacaggt gggaaggctg    180

aaaggtgggc tgtgccccct ttggtgacac attaggtaca ggatatgctc aagttggagg    240

gtggggctgc aagtgctgct ggctgggatg gggagcccag ggaggctctg ggaaggagck    300

atgttcactt gggcacctgg ggacatggga tgtgcaggga gccttctggt ggtttcaggt    360

agtagaggtg ggaggttcag accaaccttc cagattcatg ccagggccaa cacaggcctc    420

agcaatgtct taccggccct gggcctctga aagaaagagt ttaccccact ctagtcggtg    480

ccaccatttc tgagcaggca tcctgtttaa aacaggaatt tcatgagcat tttgggaggc    540

tgaggcaggc gggtcgcttg agcccaagag tttgaagacc agcctgggca acatggtga     599
```

<210> SEQ ID NO 13
<211> LENGTH: 599
<212> TYPE: DNA
<213> ORGANISM: Homo sapiens

<400> SEQUENCE: 13

```
cggataattt atccccactc cctccttgcc tcaccccagt tctgacagtg gctgccttca     60

ggagttacat cctcttgcag cccctcttcc acggctcccg gtcttcctcc gggttctggc    120

aacaacattc catccccttg tccttcaggc ctcagggtgg tcgcagctcc ccgctggggc    180

tgcaccctcc cacggtggct tcctgggccc tgccagtttg caccacggta cgctgtctca    240

tcgttaaact ctcctccctt aaactctttg agtgggccga ccatttctc ccgagaggcm    300

ctgactcaga ggagcctgat cctcccaggg ctgtgtgcct gtcagggatg gaaacaggag    360

ctggggagtc gtgcaaatgc tccgggagaa atgtcgatgc acggctgccc ccgtggccga    420

ggcttctgca gcatgacgtg gcacgcgctt cctctattcc tttaacaagc cttggctggg    480

aggcttccag gggtccgttt ccatgctagg caggcgctgt cctcatggag tttacagtca    540

ggggttaggt gctactgtgg gaggcacagg gctttgagca gcagaggagg agaggagct     599
```

<210> SEQ ID NO 14
<211> LENGTH: 599
<212> TYPE: DNA
<213> ORGANISM: Homo sapiens

<400> SEQUENCE: 14

```
cagggatgga aacaggagct ggggagtcgt gcaaatgctc cgggagaaat gtcgatgcac     60

ggctgccccc gtggccgagg cttctgcagc atgacgtggc acgcgcttcc tctattcctt    120
```

taacaagcct tggctgggag gcttccaggg gtccgtttcc atgctaggca ggcgctgtcc 180
tcatggagtt tacagtcagg ggttaggtgc tactgtggga ggcacagggc tttgagcagc 240
agaggaggag aggagctggg tggaggggcc aagaggaagg aacaaccaaa ctgagaatcy 300
ggaggacggg aaagagatgt ctgagaaaag gagctggggg agcgacgcag ggacagtggt 360
gtttctggca gaggaaacag caggtacaaa cccctagagg agagccagat caggagtagg 420
gggcgggggc atttgacagc tgtcccccct gcccggggac cagggagctg aagtgcattc 480
acagaggaga ggtcggggag agaaagctgt gaagggggca ctggaggact gcagccctcc 540
ctgccccacc ccaagcccca ctaaggggtt ctgtctttac cttcagggcc agagggcct 599

<210> SEQ ID NO 15
<211> LENGTH: 599
<212> TYPE: DNA
<213> ORGANISM: Homo sapiens

<400> SEQUENCE: 15
cccactaagg ggttctgtct ttaccttcag ggccagaggg cctttggaca cagccagatt 60
tacatttgta aaagagccct tggtccacag cgtgggaaat agaaatccgg caggaggcag 120
gtgactcctt cagaggaact aaggtatggt gagctcgcca gccgaatggg ggaagtgaac 180
ccacacgagt gaatctgaac ccccattttc cggacgcgga cacaaggccc agaaagggcc 240
agatcttgct caggtcacac agagaggcag catactggga tcagggagag gagaaaggar 300
ataaccaagg gctggagcca cctcgtcctg gaaggaagac cccttcagaa gggattcccg 360
gggcaggccc tggccacccc cgtgtttcct tgcagggctg ggggggacct ttggatccac 420
tagaccccac cctggcagga cctgaaccct cacctggacg caccccaggc acctccaccg 480
gcataggtga caggagcttc ccactgaaat catgcgaata ttaagctaat caaagccttg 540
cttgggaagg gatgggactg ggaaggcggc cctaacgagc tgctgcgtgt cactccctc 599

<210> SEQ ID NO 16
<211> LENGTH: 599
<212> TYPE: DNA
<213> ORGANISM: Homo sapiens

<400> SEQUENCE: 16
caagagagaa gtggtttcca tactgtgtgt ctgtcctagc caccaaatca ggtttgggaa 60
ggggtcaagg ctgagattac atggcctttt tcacagacct atggtttggc aacttgagtt 120
tgaagacacc aggttatggc ttttctgatg aagcctgttt ctcagtccca aaataattaa 180
ggatccaagg aattaaaagg ttcttcctta aggaggcctt gttaagctgg gcagataaac 240
ctgggtggtc tcagagggcc cttccatgtc tgacctttta ctgctcgaag tagaaaattm 300
ttagctgact gctgggggag ggctccatgt tgctatctgc aggctgattg gctggctcca 360
cctcccagat ggtgagtgac atctttgagc ccatgcctct acttcatgtc ccagaacctt 420
tagctccaac tggcactcac tagctggttt catgtaaggt cagtccaaca aaacagaggg 480
ctccccttgg ccttttgaaa gctgagttag acttgcatgg tctttgcggt ggcccaaatc 540
ttgatgatgt tcacagatca gactgccacc agtcacggac aatctgccaa tccaaggct 599

<210> SEQ ID NO 17
<211> LENGTH: 599
<212> TYPE: DNA
<213> ORGANISM: Homo sapiens -continued

<400> SEQUENCE: 17
tatagacttg ggcagtgcag ggaccatttc tcatgtttgt ttctggccaa tatcgtttgt 60
gctcttcctg tgtttgtaga gattctgcag taggaggcct gcttctttga gccagaagtc 120
agaactcatc cttccagctt cccttgctgc tagggcacag gtgtgtttca tgggctctgc 180
caattagact ttcttgtata tgaccttgat tgagaaggta gccccttgaa gcagtgggct 240
gggggactcc atctgttggg agtgggtggc aaaggcatcc agctttggct gggggcaggm 300
cagagcttct ggtgcccagt tccaagcacc ccgggaaaag ttacagtgga gtggagctgc 360
aggctgggtg ctggctggca gcagggctgt tgatgctagt gcaactctag ttgtgtggtg 420
ggtgttgtcc tggctgtgtc ccatgcctac ctctttttgt cctcctggag attctaggag 480
tcccaaatat cccttaataa attcattttc tgcttaagcc agtcagagtg gattctgttg 540
tttgaaactg aaagtctgac agatacagat agtaacctgc tttcaaagct ggaccagag 599

<210> SEQ ID NO 18
<211> LENGTH: 599
<212> TYPE: DNA
<213> ORGANISM: Homo sapiens

<400> SEQUENCE: 18
agatctgggt cctctgttat ctccacacaa gtccctcctt ctgccatctc cctttaattc 60
aacaaatatt tattcgataa caattggttg aataaatgaa gaaatgtgtc tctactctga 120
ccaactgggc aatggagata gaacagaaac tgctactcac aatccaatat ccagtctctc 180
cttttcccgg aataacagaa tttgtagctg gacaaacagg gccgctcaga gtagagatcc 240
ccttccccag ccttccttgc tgacagatgt ggccttagta tgtgcttctg gtccatgacm 300
tacatgcaga agtgccaggt gccagcctcc tggaacctta ctcagagaca gcaggttctc 360
tttcctttgt ctcctctgtc ttgctgtctg gaattctgat gctgccatct tgggccttgg 420
ggctgaggga cacagcctca ggagggccac agatgactga gtctggtccg tgtgggcctc 480
ctcggccaag ttgctgtatc agccatggat cgctggcctc cagactctga atgtgagaga 540
agacaatctg tcctgtttta gccactgctg ttctggattt ttcagtcgtt catagctga 599

<210> SEQ ID NO 19
<211> LENGTH: 599
<212> TYPE: DNA
<213> ORGANISM: Homo sapiens

<400> SEQUENCE: 19
ttgtggcctt gggcaagcga ttgaaccttc caggcagagc ctcctcatct tgaatatggg 60
caaaataaaa gcacctacat cataggattg gcaagaagta agtgaaagaa tgttactgga 120
agaacaaaac taccttttcc ccaggccaag gggactgggg atgttgggtg gagatggaag 180
aagaaagagc ctcctctgaa aactaactga ggccctaaac gtaatttgat agctttcggt 240
ggggctgggg gtagaagaac attgaagaag tggggtgccc aagttcccat tttcagttgy 300
ctgttgggtg tttaatctac ctctgccatt tctgctcact cacactcaaa tgccttggat 360
ggccgggttg gtgttttctc cccacatgga aatcagagga aggagccagc gggattgaga 420
tgaaagaaag tggctgaaga atgtcccgag aagcctgagc ctgaggtgag catgggaaag 480
tgagcctcca cctggaaatg gggcagaaat cttaaggaga acataggatt ttcccactag 540
gtggcaaatg agggtttgaa tcaattttac cttgatttca aagtgccagg tgatgctgg 599

-continued

<210> SEQ ID NO 20
<211> LENGTH: 599
<212> TYPE: DNA
<213> ORGANISM: Homo sapiens

<400> SEQUENCE: 20
atgatatata gtgttgtgct ttatagggaa tccttatagc taaagtctag aagtctgctc 60
agggaaaaag ctaacaatca gtcaagcaat ggtaattgag ttcctaccaa gacctatcac 120
tgggcacaaa ctgaaggcca ggcctcaact agatgggggt catggcatag gactatgaaa 180
aagcacaaag taacatataa ttaaaaatga acttgcatgg taaagtctga tgatgcggta 240
gtcaagggac tagagagtgc acaggtggag ggaatgaagg tgacatgcta aaggaccccr 300
ggtaagagag aacacagtga gattcaggag ggagcaaagc tcagtgattg ctctatgctt 360
agtgtgggga aacactgagt gccttaaagt cagaaaacct ggaaatgagc accaggcttt 420
tttctttagc atttgtataa ctttgggcag acctcttcat caagcctgtt tcatcactgg 480
taaaatgaga ataaaagttg gccatccttc aaatacggtg atcaaattgg ataaatgtac 540
tccaaaaact gtagtttgag ttagcagagt tagcttaggg agtggaagga gctaggcat 599

<210> SEQ ID NO 21
<211> LENGTH: 599
<212> TYPE: DNA
<213> ORGANISM: Homo sapiens

<400> SEQUENCE: 21
tagtttgatt tcacagaggc aatttgtaac aggacaatta aacaatgaca tctgtgccct 60
aaaagtcaaa gcattgttta gtagtgaaag cagtttgaca caggtacata cacaatatgc 120
tgtataactg aaggcacgtc ttaattcctt tctgcattaa tttatttttt tgttttgagc 180
acttaaccca gcagcacagt ctggtggacg cgctaggagg gtcttctctt attgggaaag 240
aagcttgcat tcctaccatg gggactctg tcaaaggcga agaactctat ctgatgaatr 300
tatttacaga attatcacta cacagacata taaagagtaa tgtatataat cgcttcaaaa 360
taagttctta ctagaatcca attaaactaa ccttgctggt acctcttctc ccaccttgct 420
ttcaactttc cttgcccttc tattcccatc tcaatttaga aagaaaaaaa aaacacaata 480
aaggaagaat aaataagaaa ataatctttg gcctgtgggg atattttatc catctcttct 540
aagggatgga cttttatgca gagagagaat ctttggcagt tgcttataga atatgcatg 599

<210> SEQ ID NO 22
<211> LENGTH: 599
<212> TYPE: DNA
<213> ORGANISM: Homo sapiens

<400> SEQUENCE: 22
caattctcgt gcctcagcct cccaagtagc tgggattaca ggcacctgcc accacgcctg 60
gctaattttt tttttttgt ctttttagta gagatggggt ttcaccatgt tggccaggct 120
ggtcttgaac tcgtgacccc aggtgatctg cctgcctcgg cttcccaaag tgctgagatt 180
acaggagtga gccaccatgg ctggcagtga ttcatgaaat ctaacagagc agaagaggta 240
gaatatttgg aaataaaggg aaatatgaaa gaggaaggga gagtacattg tctttcttay 300
ttactgagag tatatcatgc acctaaccct ggagatggtg tttagggatc aagagtaact 360
gagataagtt ggtgaaagga atggtcctgt catgaaggag gtttcaagtt tacagggtgc 420
ttaggcaagt tgaactcaat tataagagtg ggagaatgtt catttgggca attgtagggc 480
actaaccagt tgattattgg atgtgacttt atagaaaaat cttctaggag acattggcaa 540
ctaagttaag gcttaaagga aggggagaga tgacctgggt acgggagact ctggctgtc 599

<210> SEQ ID NO 23
<211> LENGTH: 599
<212> TYPE: DNA
<213> ORGANISM: Homo sapiens

<400> SEQUENCE: 23
tttttcccat aagaaaaaca accagaaact gataatcccc aaacctataa catgctaata 60
atttttgata taaatagctt taaaattgat cactgccgta agtaatatac taaatgtaat 120
tcaaaagttt ttagtgacgt tggcgtcatg gtagtgcaca ggcacattat tctgtggtaa 180
caattgttta gtctgtcttt ccctaatgcc agacaatttg caatcactct ggctcccaag 240
gcgtttttct ttcagcattc tttctccttc ctaatttggg catctgattt gctgtcgtcy 300
gagaaattga ataaatgcag ttgttagaat tgcatgtaaa ataggaatca atgaagcctg 360
cacaaccagc agtgtggtga tgagggctct gtggctgcag agattttgga agattgggta 420
gctacattcc atatgatagg gttttcctta agactgatcg aaagaattca tgaggtcact 480
tggtccgacc ctcttatgca gtatatgagg aaactatgac tcagctaata acaatgagcc 540
aatatgtatt gagtatttat gatggtccaa gcaatactgt acacgcatga tctcattcg 599

<210> SEQ ID NO 24
<211> LENGTH: 599
<212> TYPE: DNA
<213> ORGANISM: Homo sapiens

<400> SEQUENCE: 24
acccctctat ttagtcactt agtcaacatt tattgaggac ctaggagctg ggaaaacaat 60
gatcagataa acaatgaatt aataagtctc ttgcgaaact aatagttaag tgtgcgagac 120
atacaaatta aagagatgac tatgatacag tgttgaaagg actgtaatgg ggtgagtaag 180
atggaacacc tagaacaggt atttacccca atcttgagta catcagggaa ggcttcctag 240
aggaggtgat gtctaaactg agttttcatg gctaagtgca agttagcaga agccagatay 300
ggaaagtgat ggagacagag cgcaggacag aaagtaaggc atttcaagca gagagaacag 360
catcaacaaa ggtatagcta tgagagtgac atgggttagg ggacagcatg gcagttcagc 420
aggactagag ggagacttct tatgtcagac acggggtagg caggcctgta atagagctgg 480
agaatatggc agcggctgct catgaagatc ttcaatgcca acaaaataag cttgggcttc 540
gtcttgaatg cattggaggt atgtattcaa acctcattca gtgaattttt tgtttagta 599

<210> SEQ ID NO 25
<211> LENGTH: 599
<212> TYPE: DNA
<213> ORGANISM: Homo sapiens

<400> SEQUENCE: 25
cctagtcact attaatgtct gacaaattat atagccagta gacaactttg agttatcttc 60
tggcgatatc aatgatgtta caacactggc gatggcttag cctgaacagt gacaagaggc 120
taagagcttc tgtactgatg tctgattatg taatattcga ggtgtgccaa aaacttctaa 180
tcaggataaa tgagttctgg ggggtgaaaa gaaaaatgca ttacctatgt tagcatagat 240
tctgagacgc tcatcaggaa acacatttca tggtctcaaa agagctctgt ggttcttctk 300
tgaaaggcga gtactttcca actcgacaaa ggtttcacta ttacttggtg aaactgagtc 360

```
aggcactgtt ttgcaagtaa actgagtaaa agaaacattc atttatacaa attgcaaatc    420

cttctgattc cacagaagag ctaatttcca cattcagaac acgtgaactc ttcggcagga    480

tcgacttcat tctacttcag catgaagtta aattaaatcc tccagagaaa ccaatttggg    540

gaactgtctt tttaaaacac tattttttct tcttcttctt ctaacagatc tgggtccta     599


<210> SEQ ID NO 26
<211> LENGTH: 599
<212> TYPE: DNA
<213> ORGANISM: Homo sapiens

<400> SEQUENCE: 26

gtttgagctg ctggcacctg tgcagtagcc acagagccag gtttggagca caggtgtgca     60

tggagccagg gtctgaagtg caggtacaca cgaaagagcc acagttctga agtcagggac    120

atgtgtgggg ttgggggggg tgacatccct catcccaggg cagtgtaaca gtagctcatt    180

ctgggggagc aaggagtagc attatctcct tctccttgga gtctgtggta gcaatggctg    240

ctgtttaccc agtagtgaaa ggcgccaggg ccccctgcgg agtaagctgc tggtgtttgy    300

tacccaaatt ctgcatttta cttacatttg atgataccta ctaacttttg ctaatatttt    360

aatcgcacac tttctacttt gttttgatag cacactgtta atgcaaagtg gtaatcatcc    420

ctaataaggg gccactgctg gaaaatgcag aacaaggcag aggaggccct agcatggatc    480

caacctatgg agaactgtca gaacatttgt gctcagcttc cttggtatat tggctagcag    540

tgtttgacat gaggcattta gtgtgggagc cggccaaaga catatttagt gagaaatac     599


<210> SEQ ID NO 27
<211> LENGTH: 599
<212> TYPE: DNA
<213> ORGANISM: Homo sapiens

<400> SEQUENCE: 27

tgattttgtt tcccccaaag attaagcaag gcaaagactt ccattcttaa cattttgatt     60

caacatcgta atggaggttc tagtcaatgc aataggcaag aaaagggaaa ggcattactt    120

tggtagagag agaaacagag aggactccgg tgactggtct tataagggca ctacttttat    180

tggatcagga tgccacctgt atgacctcat ttaaccttaa ttacctgcaa atatagtcac    240

atttggagtt agagtttcag cacataaatt tggtggggtt tggggagaga cacaattcar    300

tccatagcac ctagggttag acaaaatgta ttagctacaa tgccaacagc atgatatatt    360

aaaaaaaaaa taaaccataa actatcaagg atctagaatc agaaatgcca tttgacccag    420

cagttccatt actggttata tacccaaagg attataaatc attctactat aaagacacat    480

gcacacttat gtttattgag gcactgttca caatagcaaa gacttggaac caacccagat    540

acctatcaat gatagactgg ataaagaaaa tgtggcacat atacaccagg gaatactat     599


<210> SEQ ID NO 28
<211> LENGTH: 599
<212> TYPE: DNA
<213> ORGANISM: Homo sapiens

<400> SEQUENCE: 28

aatttggaag tgtttgaatt gcttaaaacg tgagacttta caaatggttc tgctatatat     60

atatatcttt attcagattt ctcttttgca tacctgccta ataattgaat gaatggatct    120

aggtctagaa gagtgtctag ctccttttac atcattgcag gtttgtgtct agcaaaatta    180
```

aaccaattta taaatgtata aattccacca atggcagtca tatatgaatg tatgtcccct 240
ggatcctcgc cttcagtgat ttttttaaa aaattgtcta ttgttttgct agcttaattr 300
gcatacaaag atacctaaaa tttgaataac tttcatttat tttactatta atgagtgtgt 360
atattgtgtt tgccatggtc ccttactact tcatttctat gatggaaatc tacagaccac 420
aaccgtgagt gaagtgctgt gtcaagatca taaagatgac cagggcatca ctggtaccct 480
caaagggcac atagtataaa tgaaggatac aaacgtaaaa ggaaaaccac aacaaaaaat 540
aagttacacc aaaaaaatta aatactatat agcaataaaa aggaatgagc tgctgacac 599

<210> SEQ ID NO 29
<211> LENGTH: 599
<212> TYPE: DNA
<213> ORGANISM: Homo sapiens

<400> SEQUENCE: 29
tgagaagacg tgttctgtct catgctgttg tcaggtatgt ttcatattta ggcataaaca 60
gtgagagaaa ttaaaatttc acaacagttg agtcatttct gccactatga acacttgtag 120
tttatttgta gtttctcatg atttttatta atagcaaagc tgttgtatgg tttgggatca 180
tttttgcact taaatgatta cactctcacc atgttgccca tgcttatttc agtcagtact 240
aagcaataat tcaattgctt ttcccagaga gcaactcaaa gctcacatac tgattgaatr 300
accgttctgc aaaaagcgag gagttacatg gggaaaatac catagtataa gacatgatca 360
caaagttact gatatcttac gcatctcaca tctaaaatga aagtttccct attttaatta 420
atacctacga ggtgtaagag tttgataccc taaatgctcc caaccgagac atccttctca 480
aaactctgtg cagaggtgtc taaaaaccta tcagaaagcc aaatgtttct ctttccttta 540
caatgacttt gaggagatga tgtcttaaga tgaatttagg atgatatcta gctaagtgg 599

<210> SEQ ID NO 30
<211> LENGTH: 599
<212> TYPE: DNA
<213> ORGANISM: Homo sapiens

<400> SEQUENCE: 30
gtttaaaaaa agaaagctat gaaccacaaa cactgttatt aaaattggaa ccaggaaaca 60
tgacccatta aactgtcaat taaataaatt atcaaatcaa ataacaagat ctttgtctgc 120
agatgatggt agggaaaagg ctgaaaggaa aactggcaaa tacatgttct tcttaaggca 180
attgagagct aggccctgaa attatgagaa tttgcaaaaa ctgtctaaga gaaataggat 240
gctcgtatat atacccttct ttagattcat aataatctaa cgacttatga agaattactr 300
tatcaccagt taaacatcaa atgtatttcc ttaaaatgaa tgtgttatta attgtattta 360
attttccagg aagaatgcag aatattatta ttaaacatct tatgcatttc atatatttcc 420
tgtttataaa ttactttccc aaattatgta tcatgtttcc cttattgttc tcaaaattca 480
gcattactat ctcacttttt tctcattttc agagattaaa gttaagaaaa attaataatc 540
tgtgacagaa gttctgcaat ttatagcaac tcacacaaga gcctgctgaa atacattat 599

<210> SEQ ID NO 31
<211> LENGTH: 599
<212> TYPE: DNA
<213> ORGANISM: Homo sapiens

<400> SEQUENCE: 31
tgcactcaat attgggctag gatccatgtg gatgcggtct gacagaggat gtcgacttgt 60
ctacaaactg caggcataaa ttccaaattg acagaggaag cagagaagct tcaagaatga 120
atattaggtt ggtgtaattg cagttttcac caaattaata gcaaaaacag caattacttt 180
tgcaccaaca gtataattaa gttgaattag aaatcagagt agcagttcaa tcagagaaag 240
aggtgccacc taacaaattc ttggggcacg ttatgtagcg gataaaaaca aacaaacaar 300
caattcaaga cccatgaggg aatttatgat agaaactgga agtttctcag ccagtatcaa 360
tgcattgata ttagagatgc aaaaaagaga tgaataagga agtatcttct tcttaaaata 420
atatgcaaca ttgttttact agtcaacaaa ctttcatgtc cataccctaa aaatataccc 480
atcaaaatag atattaccag acagacaatg actaactata gttacagaat tggaaaccta 540
ttacaaaaat cttaaatgta tatgcatcat ttgtattttg agaatagagg gctgtattt 599

<210> SEQ ID NO 32
<211> LENGTH: 599
<212> TYPE: DNA
<213> ORGANISM: Homo sapiens

<400> SEQUENCE: 32
aaaaaaaaag aaaaaagctt gtacatcagg ctaatatgtc tgaactcttt ttgcaatcac 60
aaacctttag agctcgtaag aagaggctta acacaattgt ttgactttag aaagcacctt 120
cagcaggtag gaacatctca ttttcctcct ttggacattt aacagatgga attagatatt 180
tttaaaagaa gcttaaaaat gaatagtggg ggttatctac caagctcagt acactaagaa 240
ggtggttaca aatgcagcaa gaggcacagt gatttaaaac acctcctcgg gaactcacam 300
atatttgttg aatccactgt tttcaaagaa aggcaattcc attattgcca aaacccatgt 360
ttgttgtttg gtttggatga ttttctagca aagacttgct tcccctactt tgatctgttt 420
ttctcccctt cttggctgtt ctgtcccact tttcgagcct agtttcacct ctggtatttc 480
tcagtcatat ttctttattc tcgataggtt aatcagctaa cacctctgcc gtgtggtatc 540
ccaaaacagc aacccagtta agctgagcct ttccccttta ctttccaatc tttgaatca 599

<210> SEQ ID NO 33
<211> LENGTH: 599
<212> TYPE: DNA
<213> ORGANISM: Homo sapiens

<400> SEQUENCE: 33
ccttgacttt gttatgtcct ttgctttcaa tctctttctg atccttggga atttgactac 60
agccttaata ataaacagaa cagatttttt taaaaaaaga ttcatttcta caaccctgcc 120
ccttcccttt ttatttttcc acttagattt agtaggtaaa agatatatgg gggaaagatg 180
ggtgggtctt tggaaatata aaagatgaaa gtaaaattcc ttttatttca atgtcatcaa 240
accagctgtt ttgacagtgg ggatgagata gagctctgcc atgggaacct gggagctgtr 300
atggagtgaa ccagagagaa atatctcacc aattaggagt attaaagaaa agataagagt 360
gtagaggagg tgaagagccc tccagaaacc attctgggct atcactaggg tgaagaataa 420
gataagggtg agacctacca aataataaag gagcttttag tggtggggag gaaggagaat 480
gaacaagaga gatgaatcct attctatagc aatggggaaa taaagggtgt tcctatgggg 540
aactacttac cttttttttt tttcttgaga tgaagtctcg ctctgttgcc caggctgga 599

<210> SEQ ID NO 34
<211> LENGTH: 599
<212> TYPE: DNA

<213> ORGANISM: Homo sapiens

<400> SEQUENCE: 34
acttatctct cctgtattga acttcctcag gattttatgc cttatagcta agaaatattt 60
aaaaattgtc atcatagcta ctaaacattt tgggctacag tgtaagctat agaaacatta 120
atgtctgaca ccatttgcac ttaattaggg aatccttggt agttgtttat tggaaggatg 180
gaccctacta atagaaattt ggggcaaagg gaagaagata ttctaaagag caataaaact 240
ttcaacctaa ggactttgta gaaatgctat tctgctcact catgggcata atgaccacay 300
gttacagagg cagttgaggg ccagcctcag gttccagcct ggattttgaa tctcagctcc 360
tagttaaaaa ctgggtggcc ttgaaaaagt tatttaacct ctttgtgcct acattttctc 420
atatgtaaag gaagaaggaa aaagaaagag tacctacatc agagggctgt tgtaagaatt 480
aaagctaata taatgcaaag cacctagaat aatagtaaat gccagatgca tgtgcttatg 540
taactgtttg ccattatcat ttctagggca atcccaattt catctctgtt ttcactaat 599

<210> SEQ ID NO 35
<211> LENGTH: 599
<212> TYPE: DNA
<213> ORGANISM: Homo sapiens

<400> SEQUENCE: 35
acaagttcct gggtcaccta tccctttgcc ccctttgctc actgcctgcc cttgtgcata 60
gactgtcata gggatggata aacacagtca tgtgcacact cttgcttatg ctttccttgt 120
agcctggaat gcctacccct tacttctcat aaaagaccag cagttcttta cttatttcag 180
ggtccagctc atccatggac tcttctcaat ccgagaagca gggtgcatca taatagtgct 240
ttgacccact gatttccttg gctcaggttc aggagctggt gcttgacaac cttctctggy 300
ctttgttgct tctaatctat tcactcagaa gatgtaacac caatgtagaa cctaaaatat 360
attaacctcc ctgaaggcag ggataacaat gataaagtca gttatgtatt atgaatcaac 420
aaactctgtg gaagatgtta cagaaatgac atgcgtattt cacatcaggg tgctattatt 480
acacgtttaa taaaatgaag gaattaaagc tcagataact tgaatggttt ggctggaggc 540
atttgttaga agccaaactg ggactcagat tcaggtctgt aaaacttgac actgtcatt 599

<210> SEQ ID NO 36
<211> LENGTH: 599
<212> TYPE: DNA
<213> ORGANISM: Homo sapiens

<400> SEQUENCE: 36
aaacccttgc ccattcagtg acatcagaaa gcctctttct gtgtccattt ggttttccca 60
ttggctgaag gcaaatgccc taacatgaga gaccttttgc aaactgacct gtgtctctca 120
atcctttccc actttcccca gccaaactgg ctgactcact ctctcaatgc tcttcataga 180
cattcccatg gtatgccctc ttcctcccag ggcctgcagg attctccatc cttttatacc 240
cacgtataac caattcaaaa tctccaaagc catcaagatt cttgggcctc tccagtctgy 300
ggaatcgtac ccacctttga atttttattg actctgctct attcaactgg cagtggctta 360
atggcagccc ttatattttc tcatatcaca attcagtgtt ttatgcatgt atagttttct 420
ctttgcaatt ggaattttct tttcttgagg tcagcatata tatttcattt attttcgtat 480
tcactgtggc agcacaaaag ggtaagtga accgaacatg gagtccgtga atcagaggct 540
ctaccacatc ggaattatgt ggtcatgaac aagtcatatc gtttctttac attgtagtt 599

<210> SEQ ID NO 37
<211> LENGTH: 599
<212> TYPE: DNA
<213> ORGANISM: Homo sapiens

<400> SEQUENCE: 37
ctcagacttg cctcaagtct gtctagttct gtttctacaa ctttggaaag aagttcagga 60
acatatgtat tactcaagag aagtgtatga tgaaaagctt actgcagtta aatagcttat 120
gacttcatga acatttaagt gcatttacca caaacggata atgttattta tgttttggaa 180
taaatagagc tgaaataaat atgattacta cctgcaagta ttaacattaa gaggtatgta 240
aattccttgt attgaaaagt atatatatct gaactttttg cttgccacaa gtcttgaatr 300
acaagtaaca aacatctatt tagaactcac tgggatcaag gtcctatgaa taagaaaatg 360
ccatatacaa agagaaactg gactcctatc tttcaccata tataaaaatt aactcaagat 420
ggattaaaga cttaaatata aggcctggaa ctacaaaaac actagaagaa aacccaggaa 480
aaacgcttct agacattggc ctaggcaaat aattcatgaa taagacctca aaagtagatt 540
caacagaaac aaaaatagac gattaggact taattaaact aaaaagcttc tgcacagta 599

<210> SEQ ID NO 38
<211> LENGTH: 599
<212> TYPE: DNA
<213> ORGANISM: Homo sapiens

<400> SEQUENCE: 38
caaagattac ttacagataa ggaagagaaa agccagagaa aaaggccagt gatgtatgaa 60
ggaaatctat gttttttgc aaagcatcag caataaaagg tataacctaa aaatagtttc 120
tgcttctgtg ttcagtcctt gaagctattg ccaccaccag ccacttgttg attcattagt 180
tgtcattgtt tcttcatctc tgcccaaact ctgatcattc ttccctcatc tgctctcatc 240
tgcacacgca tgcatacaca cacgtgcaca cacacacaca tggcccttac tttggtaacr 300
taagtcccag tgttgagttt aagaagtcca ctctctagct ggtgaataaa ttggtgtctt 360
gttctgatat tatatgaaag acggtgagtt gagtcttctt atgggcaggg atgatgcctt 420
gcttatcctt caccctcaaa gttggtgtcc actaaatact gaggaagaaa agatccctcc 480
taaaaatgcc cttctctgag aactattatt ttcaactaac agaggttgag tacctggaga 540
tcagggtctc actggacagt gatgtttatt agtctttgat gcaattaagc aagtggttt 599

<210> SEQ ID NO 39
<211> LENGTH: 599
<212> TYPE: DNA
<213> ORGANISM: Homo sapiens

<400> SEQUENCE: 39
aaactctttt tctcttttg aacataaaaa aaaaatcccc aattacttca ctgcttgtgt 60
caggcttgat tcttaaaggt ttgaaatgtt tttcagatgg aagagactgt ggcagccaaa 120
catgtatcgt ctttcaagtt atgtcagttc catgattttt aacaaagaaa agtcatctgg 180
tggatgacaa tgcttgacaa aaatcaaagt aatgcttacc atgtagatca atttattcaa 240
cttactggaa aattgtatag aggaagagaa aaatctctaa tattacaaac ttcagcaccy 300
ctaaagggaa gtgccagaaa gttcattgat aagtcctggt ttatggtgtt tcttcttttc 360
cagtgctcag gccactctta aacatttggc ataaagtagt gcattaaacc tctaattccc 420
ctagggtact aaatgatacc tccctatttt gaatatctga tggtgggttg gctttaagaa 480
atctaccaga cctgcttctc ctcccatgat agtttatcaa ttccattatc attcaactaa 540
gtagagtggc ctagaattgc ctgagcttcc tgaggaatta aagataatca tcatcaata 599

<210> SEQ ID NO 40
<211> LENGTH: 599
<212> TYPE: DNA
<213> ORGANISM: Homo sapiens

<400> SEQUENCE: 40
caactggttt ctctgtgctt tcatgttctg gtctgtaaaa tgggtaatta tggctagcac 60
cctcctcact gaactgtgat gaaggcgaaa cgagcccacg tgagccacgt tctcagaact 120
gcatttggta tgtggtaagc aacatgttag gtaggttatt tttactttaa ttcaccgttc 180
cttccaagct actggaatgt ccctcttcca aatgtaaatg tgaacaagga aaaacacgtt 240
ctttaataca tgcgttgttg cattttgaat gttcagttgc cattgagaac atatccctty 300
gttatgaaag gaagtactaa agaaaaagag cctgtggtcc taaagggccc ctcaatctca 360
gacacagctg ataagctgga ttatctcatc aaggttgtga gaggaatgga aacaacagga 420
gtgtccaggg ccatttcatt gctcttgtta aatacgatga aaattgacca agtagtagcc 480
catggcaata ggttagtcaa actaagactt gactaagagg ctgatcataa taatgtaatg 540
agaaaaatga gcaagacatt tgaatggcaa ggttgtgtgg gtggcaggct tgtcgttga 599

<210> SEQ ID NO 41
<211> LENGTH: 599
<212> TYPE: DNA
<213> ORGANISM: Homo sapiens

<400> SEQUENCE: 41
gatttagggt cccaggaatt cctatttcta gaaggaatgt gctttagact tggagcatcc 60
tcagagagct ctataagact cacgggatta ctgaagcaat tcagagctct aacatctctg 120
catctcaaat ttcttttcaa ggataattca agtagggaag cccttctgga aatacaggac 180
ttgaaagcaa ataaaggcat tctattaaga attaactaaa attaatacaa gaatatattc 240
cattaatttc aatttaaatt aatagggggca tattataaga cattggtatt actaggatgy 300
tcaacacgaa tagttttaaa atgaatgtaa aagcttccct ctcttaatgt tttatataat 360
gcaattaaaa aaggaattca tttagctata atgtgcacat atatattttt aatataatta 420
tgtgtgtatg ccacagctat ccatttacag atttaactat gtataatttt aaaaatttaa 480
gcacatacaa atataacatt tataaggact tatttatttt agatacatac atctatgtat 540
atcattcata taaaaatggc tgtggaggaa aacattgagt atatcgtttt cagtttatg 599

<210> SEQ ID NO 42
<211> LENGTH: 599
<212> TYPE: DNA
<213> ORGANISM: Homo sapiens

<400> SEQUENCE: 42
gagttacaga tacaaacgta aagaaaacag cctctgttct aaaaaaatat gtatgttctt 60
gtgaagtaga ttggtggcaa aagagtgatc tatctatcta tttatctata tatatatata 120
tatattactc ctagcataat acacgcaaac acacacatac acacacatat atgtttagta 180
caaatatata tatgactcta ggtcatatat atactctagg agtataaaga agagacactt 240
aatctagcca cgttaatgga cagctgggag tggatggtgt gtttgagatg agtaagagay 300
acattaatta gttaaggctt tctggatgaa gtgaaaaact taagcaaaga aacagtcaca 360
taagtaggaa aatgagatgg tagaaagaga tggaacatga tgtcagagag aaaatggtgg 420
tatcatgaag acatttgtga aatgtattta tagataaaag catgaattga atacctatag 480
gatgccattt gaattgaata cttataggat gccatttgaa aatttaagat gggaataccc 540
tgaccagatt tatattttct gcatgtaatg taactctggt atatagttgt gatatgctt 599

<210> SEQ ID NO 43
<211> LENGTH: 599
<212> TYPE: DNA
<213> ORGANISM: Homo sapiens

<400> SEQUENCE: 43
aactcaaact taccaagttt gtttgatata ttataattta ctcatagtcc aaattgaggc 60
tatttgcatt ctgggtgtct ttttctgttt tgcctccctt tgatgatttt aggaacttta 120
cggtgaattc atctcagaaa tactgcttca cgatatccag ctataaatct gaaagacaga 180
atctgagaaa caggccaagt ctagaaagag gaagacatac ttagggaaat gaacacaaac 240
actactgtac caaatagaaa atacgcaagt gcagatgaga cacactgcct ttatcttcay 300
gttattccac atagtaaaat gaattccagg tggtttatga gagttgcata aaaaagttac 360
accacaggaa tcatggaaaa attttaagta aagtctgtat ttatacgtag ggatatgtat 420
aattatataa agcaaataaa agtcctctga attagatctt acttgtttaa tgtatgagga 480
aaataataca gtgttatttc ctaaagtagt tgcattgtct gatgcttgag gaagcaatga 540
gagatgaaaa atgggaaatt ttacatgtaa tcactgcaac aactatgagt acaactgag 599

<210> SEQ ID NO 44
<211> LENGTH: 599
<212> TYPE: DNA
<213> ORGANISM: Homo sapiens

<400> SEQUENCE: 44
tttggccatc cttccgtcta ccagttaaac atttgctttt cctcatcaat agaaatgatc 60
agattctaag caaatacatg caactgaaac aaacatgtgg gttgttttgc acatccagaa 120
ataatatcgt atactcatta aaacaatcag gttttttggg gggaatttta atttcatcat 180
catagttata tcctctgtaa aacagatcca gaagtttaga aacacacctt gatttatatg 240
tgtttgatat ttgaccaatc agcagaaact caaagaattt acaggctgaa aagacaccam 300
attttcccgt tgtacttcat agataaggaa cccagggcac tgcagtgttt gttttcccaa 360
aatagcagaa ttagttaatg gcagagctgt taccagaaaa gagttccgat tggatcctgt 420
gtgttcggat gcttatttat ttaccatgtt tgtgaataaa ccatgcaaac cgtggcagaa 480
gtgaggatgt tagcatttat aaatctacaa gaagagtatc cacttagaag aaatagctag 540
gagaaggtcc ctacaggggg agcttgcttg acatgatcaa gaaagtcttc atagttgga 599

<210> SEQ ID NO 45
<211> LENGTH: 599
<212> TYPE: DNA
<213> ORGANISM: Homo sapiens

<400> SEQUENCE: 45
agaatagtac aatttaaatt aatatgacta actacaggtc aacctaataa tccataagag 60
aactttctgt actacgtttt tcaactttgc cataaatata ccataattaa aaatttaaaa 120
acattaaaaa tatacaggtt taagggactc gattttattc tcagatttct caaagacaca 180
cactagcaat ttagatatac ttcttatttt cattgtttgc tacattgtag gaaaataaaa 240
acccataaag aactacacaa catttacttc ataaagcttt tgtttaaaac ttgttcctay 300
ctcaataaaa tgattataat tgttgtcttt actcactact tatctttagt ataaatcccc 360
tgaaactatt ttactggatt aaaatctgta ctgttgtgat aaatctagat gaaataattt 420
tattggaaat atattaatgt aatgaattaa tgattaaaat aaacataata ttttaataga 480
atggtatttt tcagtgaaca aattatttgt gttccaaata taaacaccca tagtggatct 540
agattttcat cattcattat ctatgaatgg agaattttct gtttaaattt ggtaaccta 599

<210> SEQ ID NO 46
<211> LENGTH: 599
<212> TYPE: DNA
<213> ORGANISM: Homo sapiens

<400> SEQUENCE: 46
ttaacccagc actacatccg acagctgtaa gggctttcag ccataataaa tctctgcctg 60
acttcccaaa gcaaacagtg ttgaggagag tgatccctcc aataacattt tgtcagctca 120
aatcaccacc ataacataag tgattcagac agtctgaact gactccaggc tttccaacct 180
ccggtcttta tttcctattt tcttttactt atgaactgtt cttaatattc tgaagactct 240
gaaaatgttg tgttcattcc ttgagattgg cggaatgccc atttaacaag tggtttttty 300
tccccctctc tctttgagaa gattctgcct cgtgacctga ttagattagt gcatttggaa 360
acaaagctta ttcaggtctg gtaatttaga aaaaaaaaat aatagaatag ctaaactcta 420
atagtataaa attaaaacat tattagtaaa tatttttgga aattaaggga aacaatgtga 480
ttttccttga tatgtttaat tccagaaagc ctgatgttca cacagcatgt aactatctac 540
tgtgtatgta catcagtgct gccctaaact ttttggcatc agagacctgt ttcatggaa 599

<210> SEQ ID NO 47
<211> LENGTH: 599
<212> TYPE: DNA
<213> ORGANISM: Homo sapiens

<400> SEQUENCE: 47
acaaggaagg tattatcttt atattgctaa atcacatatg cattttacaa aatgattcac 60
aaatgcatca ccagcaggtg cacacttcaa agcaaaacat ttctgtgaat ccctggcaaa 120
aataagggtg tagcctaggt tttgtaagac agcagtggca gggaagagga tgagtgatac 180
agggaaaacc agccagaagt aaagtactta cagaagatct tatcttccca gatgaaatta 240
tccaggcttt gggtgcacag aatatacaat gcagaggtga acagagaaat caaggattgr 300
gcaagacaag acaaaacaaa tgaaacacca caaacaatac aaattaatca aaagatgaga 360
cctgctgcaa tgcttcagga tcagcaatag ccaatagtct tttctagaaa atcctgaacc 420
cgaaagtggt tccctttttaa gttttgcaaa ctctgggagg cgatgacagc ctcctgcaga 480
ttggcctttg gctgatcaga tttcagcagc tcattcacct ccaaggccag gttctcatct 540
tatacatcag tggagctttc gcttaggtga gggcccatat ggtaagtttt actgtgcaa 599

<210> SEQ ID NO 48
<211> LENGTH: 599
<212> TYPE: DNA
<213> ORGANISM: Homo sapiens

<400> SEQUENCE: 48

```
ttacagacct tccaatgaac agttaagctt tgtagtgtgc ctcctcgaga aacagctgtt     60
tgtctaacct ttgaactgac cgatacatta atctgaagca taatttagtt ctgtctgagc    120
tcttgggtac agcatgaata gctggcttgc tcatattata ccagtctcca aaataatact    180
ttatgtgctt gtttaaaaat agtcattttc ccttcccaat ttaattatgt atgattattc    240
gataagggga tgccagagct ggtgtatagt tcctacactc ccattctgat aactctactk    300
ctatctagcc ttgatcctgc tgttatttcc tgatattcat cagaatccgt aaagcagcta    360
ctctctggag cctcttttca caccaaagag aaagttgcac ccagggcttc gctcaggtga    420
ggagagatta agagagtgat gcacaggcac aagcgcccac attgtgatgt gctgcggttg    480
tcgagtaaca ttgtagcatt caacaaaata gccttattct gagggagcct cctgtggagt    540
ctctttttgc aagctggaga aggttcgtag cacacaaaag tccgattttg taattcctt     599
```

```
<210> SEQ ID NO 49
<211> LENGTH: 599
<212> TYPE: DNA
<213> ORGANISM: Homo sapiens

<400> SEQUENCE: 49

cgatgtatat atgttacaat ggttcatata tatgacacga tatatgtgat atatgatatg     60
atatatatgc tataataata cgtaggattc aaagacgatt cttcatggga gtccacccca    120
tgtgtatttc agtatagtag tttttttaa atttgtctca ttcgtggcac taggaaatgt     180
atcagtctct cactagttct tacattaatt gatcaatccg agatgtactc acatatgatt    240
tgaatttaga tcccatatct cctgtaggag cagcttggat ttcccacttt tcaagagttr    300
ctccttttcc acccagggct gcaagtagat caccagtttc tttgcagttc cctcagatga    360
aaatagttat ttagttcctg ttgtagagac agatcaatat tttgtgcctc tgctttatgc    420
atatatctca gttgtaggtg cccacattct taggacctga aatcctgact accatttttg    480
agggttgtag aatttcatgc tccatacaat acaaggagtt agacttggaa agtaaatgca    540
caggaaatga ccacacagga agtggaaaga atgaggtcta tagaaatagt tagaggtga     599
```

```
<210> SEQ ID NO 50
<211> LENGTH: 599
<212> TYPE: DNA
<213> ORGANISM: Homo sapiens

<400> SEQUENCE: 50

gagtgggctg ggcatggtag ctcacacctg taatcccagc actttgggag gccaaggcag     60
gctgatcact tgaggttagg agtttgagat cagcctggcc aacatggtgc aaccccatct    120
ctactaaaaa tacaaaaaaa aaaattagct ggacaaggtg gcacatgcct gtaatcccag    180
ctactcagga ggctgagtca ggagaatctc ttgaacccgg gaagcggagg ttgcagtgaa    240
ccgagatagt gccattgcac tccagcctgg gtgacagagc gagactctat caaaaaaaam    300
aaatcatgaa tgagggacat ttttcacttg agagatgtct tctattttgt agtaaaaaca    360
cactttttag tatttacctt tgggtcttat atctcctcat cagcctctgt ggccttgtgg    420
ataaaactat ttaccatcct ccagcattct tcgtgaatct ctccagattt atttctggtc    480
cattgccctc aagggagaac cacgttctcc cttcactcat cagcctctgt tgatcagacc    540
tcctgggagc accaccctgc ttctctggca gtgcacctgc tctttgtaaa actagcata     599
```

```
<210> SEQ ID NO 51
```

-continued

<211> LENGTH: 599
<212> TYPE: DNA
<213> ORGANISM: Homo sapiens

<400> SEQUENCE: 51
ctcgggaggc tgaggcacaa aaatcacttg aacctggaaa gcaaaggttg cagtgagctg 60
agatcacacc actgcattcc agcctgggaa atagatagag actctattgc aacaacaaca 120
acaaaaaatt caaccctcct ttcaatcaaa acccgtaaca atattctaag ccagagttgt 180
gtaaactact ggaatgtatc tctttccttt caaggagaaa aagataacat ccttgctact 240
gctcagctat caagtgaagg caaaagcagg tcaagatgaa tttaaacaaa ttattcaaar 300
ttcaatatga aataggttgg agactccatt atggttggca acaagtcatt aacaggtagg 360
atgcaaatag agaagtttag aaaattgaaa agctgtgagg acgttgcctt gtggtatatc 420
ctaaacaaca gcattgggag tgttttcaga gttcttatgt gaccaccgaa gtcctgccct 480
aaccaacact aatgctgctg cctccagagt agcaataatg ggtgtgatgt ctttgactgc 540
acattttttg ttgtgatcca ttcaaatttc tactctcccc atatgacttt gtaatccat 599

<210> SEQ ID NO 52
<211> LENGTH: 599
<212> TYPE: DNA
<213> ORGANISM: Homo sapiens

<400> SEQUENCE: 52
acaaagaagt aaaatttatg tgtaggtgaa actgataact tcacagaata agctctgtga 60
gatttttccc tagagatgtt tcacactttg tagcaagagt gagtcattgt ttggaagaga 120
gaacctcaaa ggcactggtc tccctgctaa tgttcttgca ttcttacagt tttttaccct 180
cagagcagca aaggaacacc tttaaaccta aaacatcaga tccctgccct gcttaaagcc 240
ttctaatagc ttatctatac actgataatc aaacaagtaa aactagtgca tgttttacam 300
agtcctatga agggcaacat gaactagtac ctgcctatct ctccagcatc acttcctgcc 360
actgactcca tgctttggct cacaggggaa taagccaagc tcatggcctc agggtctttg 420
cacttgctct ttccaccttg aatgctctcc ctctgtattt ccccatggct ttctctctca 480
cagcatttaa gtctctgcta aattgccttt gctttgagaa actttctctg cacactctat 540
ctgaataact ctcttcctaa gccccaacca cctcattctt ctctctagca ctacctgat 599

<210> SEQ ID NO 53
<211> LENGTH: 599
<212> TYPE: DNA
<213> ORGANISM: Homo sapiens

<400> SEQUENCE: 53
attgttcaat taaatgattc catacattta cttctcataa aggtatacat tgggaagtaa 60
ttcacaatgt attctcctat aaacaccaat taatggtaac tattatattt gattcactcc 120
atgtgatatc gtctccaaat tttgaggaat atgatttgat ttctaattat tcagacattc 180
taaaatttcc aacttgaact agtacccccct tccaacgatc cttacttaat aaatattttt 240
gtcttccaaa ttattaacat ttccctttct aagggctcct tttctccatc ttgctattar 300
caattctttc caaaaacaag aattccaaaa gcaagaattt ccaaaaataa gacagaataa 360
aacaaaacct tcctccatcc tttttacact actaaaaatt ttattcaaag aattgaccac 420
tctttctggc caggtgcagt ggctcacgcc tgtaatccca gcactttttg aggctgaggt 480
ggatcacttg aggtcataaa ttcaagacca gcctggccaa cataatgaaa cctcatctct 540
actaaaaata caaaaattag ccgagtgtgg tgccatgtgc ctgtaatccc agatactag 599

<210> SEQ ID NO 54
<211> LENGTH: 599
<212> TYPE: DNA
<213> ORGANISM: Homo sapiens

<400> SEQUENCE: 54
taaaaaccca ggctttggag tcagaaccac tttaggttga agttccagct ccatttctca 60
tttccaagtt gctttggatc agcttcttac ccatccttaa gtctgtttcc atttctgtaa 120
agcaaccacc ataacgtgtc ttttgctgtt tgttgtaaga attaaatgag gcaatgaatg 180
taaagtgctt ataataaata gtagctggtt aatgaggaat tactactatg atttggtttt 240
aaaaagtaaa attggtggca gaatttggag ggcatatgat gagttcagag tgatacatay 300
ccagtaagta tttagaaatg tacgaccaag gagagcaaaa gtcccaaatg ggaactgcta 360
agtctagaga tggtagttga atccagaaac acggatgata gagccttcca agggggcata 420
tatagagatg acagctgggg acagatcctt gagaaatacc tgaatttaag cagtaagaag 480
aaaagccaga aaaagcacac aggaactttt aaacataaga gacacatctt ttaaattttc 540
ttatttaatt aaattagtat catttgctct atttatgaaa aaaatacaaa tttgaattt 599

<210> SEQ ID NO 55
<211> LENGTH: 599
<212> TYPE: DNA
<213> ORGANISM: Homo sapiens

<400> SEQUENCE: 55
tatatttttc taaagtaaag tcttcaagaa gttttaacat tttattaatt gaattaccag 60
caagatgaaa gcataggaac cttcctttca tctgatattc taggaatctt tgaaatgttt 120
gtatttttgc tcagtttaat attgtttgaa taaatctatg aatattttta ttaaaataaa 180
gattagctct gcagaacaaa ttcagtgcaa agtacttcaa aacttaaaag ataatagggt 240
aatttttatt tacaagtagc atggtatatt gtgggaaggc ggatatggca agcccacacm 300
gttataattc caagtatgcc attaaaatag ccacaggaga ggtaggatca acatgttctg 360
aattgtcaaa tgaatgagaa atcctgagcc ataagtgaag ttttctcatt aggttatagt 420
atgtttatag atttcaagac tgtgatttta tagtagctat gaaaatattt tcagataaat 480
gaaatatatt aaaataagct taaactcaaa taactgaatt atgaattatt atggaaggta 540
tctagagcat tctttttgt tgattttctt tattttattt tattttttga gacagcttt 599

<210> SEQ ID NO 56
<211> LENGTH: 599
<212> TYPE: DNA
<213> ORGANISM: Homo sapiens

<400> SEQUENCE: 56
aatcttttag gcctttagct aaccactttt ttttgtctgt ttgatgagtc atatgagtct 60
atgaaatagt tatttaaaat atttaaactc tgaggcactt tttaaacaaa ggtttgacat 120
aggcatgatt tttaactgag aaaaatatct agccaagtgt gatataaaag ttaaaaccac 180
acctcaagaa taggcatttc attttttttt tttaccctga gcaaaatata atgatctatt 240
ttcaaataat gtgtatgtgt gtgtggacac ggatggggag ggattgggtt ttatacgcay 300
attttaaagg ctcaaagggc ttatacacat caaatggttc ttcaaaaaca acaacgtggt 360

```
gattgaagtg taaatgaatc atgaaatata tggattaaat atgcctggat ttattacaca    420

taattaaaaa tttaagactt gctttgggca aaatatgact gaggttttct attgaacccc    480

aaacactcag aaacattgaa acattgtaat accaaatctt tccaagtttg taaggcctaa    540

aatttctatt gatcctatta tatattttcc cttagaaaca tatcaatgct tattttaag     599
```

<210> SEQ ID NO 57
<211> LENGTH: 599
<212> TYPE: DNA
<213> ORGANISM: Homo sapiens

<400> SEQUENCE: 57

```
tattcctttg attgagctgt taagtggcag ctcaactacc ccggagttta ttattccttt     60

gtgtctgaaa tgtgcaggaa ttttctgcta cctgagatac acttacagat gaacatagac    120

atggtaaaaa aaaaaaaaaa aaaaaaaaaa aagtactcaa tgcattctct gctatatagg    180

aggacccttg aaaggtctgt tgagtgaata gtaaatgttg ctgcatttct tttactttta    240

caggtttcct ttggggagtc tagaatttga taaacaatcc gacccattgt gttgattgtk    300

tacctaatat gatcaaaact cttttcgaga caagccagat tgagattcca acaggtttgg    360

tctattaagg acaaatgatt ggataaacag gtttctctct ctctctctct ccctctttct    420

ctctctctca tacacacaca cacacacaca cacacacaca cacacattta tttatttaaa    480

atttatttat aatgctaaga ataaagtgat aaatgctcag gagatgtcac agtgcattat    540

ttacattaat tccttccttg ctggatgaac cagcaattcc catgaaagag ctgaaccta     599
```

<210> SEQ ID NO 58
<211> LENGTH: 599
<212> TYPE: DNA
<213> ORGANISM: Homo sapiens

<400> SEQUENCE: 58

```
tacacacaga cacacagaca cacagagtgg aatattattc aaccttacaa aaggagatct     60

tgccatttgt gacaacatgg atgacctgaa catgttatgc tcagtaaaat aagccagaaa    120

caaaaagaaa aatgctacat gatctctctt atatgtggaa tcttaaaagt tgactatgtg    180

gaaacagaaa gtagaatagt ggttaccatg gatggggagg tggggaaaag gggagctgtt    240

ggtcaaaggg tacaaagttg tagttatgta ggaggcataa tgtacagcat gagggactay    300

agttaagaat actgtattat atactgaaaa tttgctgaga gagtagattt caggtgctat    360

caccacacac acacacacac acacacacac acacacacac acaaaggtaa ctatgtgaga    420

gatatggtaa cttgattggc taaagtataa taatttcaca catgcaaatc aaaatatatt    480

ttgatataca ttagtaaata atgtatatca atttataaat gtattataaa acttaaatat    540

gtacaataaa attaataaaa atgaatttaa aaaatagttc tgcatttcaa aagatccca     599
```

<210> SEQ ID NO 59
<211> LENGTH: 599
<212> TYPE: DNA
<213> ORGANISM: Homo sapiens

<400> SEQUENCE: 59

```
gttggaagtt tttttgtgta tttttccaga gactttttat gccatatatt tatatttaat     60

acatattata catattcttt tgttctctga tatttatgct tatcagtgtc ttagaatatg    120

tcccatacca gaatctggtt tgctaattct ttttttctag ctttagatat aagtatatca    180

taatttattc aactaatacc ctacagatgg acatgaattt tgttgcaaaa tttttgtgat    240
```

```
tttaaaggtg aaacagtttg ccttgtaata aatcaagtta tccagtacat gtttcaaaay    300
agacattaga gaaatccctg gaagtagaag agctgggtta aaaggttagc aacatctgta    360
attttgacat atataatatt ttagcagtgg gtatttattt ctagataaat taaaataata    420
ataatgatac agcgcaaaac gataaaagct gaaaggaaaa tatggtgagg tataaatgta    480
gaaaggacag agatttctcc tccaaatact gtttctcttg gcccataatt taatcattaa    540
aatatcaaag ataaaattgt agggcaaata aaatatccca cttggacaaa aatcagtag     599
```

<210> SEQ ID NO 60
<211> LENGTH: 599
<212> TYPE: DNA
<213> ORGANISM: Homo sapiens

<400> SEQUENCE: 60

```
ggctttgtaa aatacatcta ataatgaaca ctatacctga tgatttcaca catttcttat     60
ccattttaag aaaattctgc aactatctta atgtttataa atttatttcc aattgtgttt    120
gttaatcaga gaagatttta agcaattata gctaattata aatcacattt taccagagtt    180
atctaatatt gcagcttggt cattctgtgt cacagtaaga tatgtattaa ttatttcatt    240
cctctctcat catgacacag tacagtctga gacctggctt cagtcaccac tttctcacar    300
tagaatttca gagtagctgg agttaattaa tttagatttg actgcagctt gagatcatcc    360
tttctaagcc accccttac ctagtctcgg cagaccagta ttacctcatt tactgtaacg    420
gcatcctgga tatagagcgc tgggtattgt ttcacctgtt aaccctctcc tctcagatct    480
gcttgaaaac aatctcccaa catgcatgta actagttaga ttttctcccc tacaagttct    540
ttctcatgga aatcctttcc gagaaaataa gcctgtatgc acagacagac acacagaca     599
```

<210> SEQ ID NO 61
<211> LENGTH: 599
<212> TYPE: DNA
<213> ORGANISM: Homo sapiens

<400> SEQUENCE: 61

```
ttgtggaggt aaaaaaaatg atatttttcc agatattatt gagaagtcta ttatataaat     60
accttaagac ttgacaatgg gggtgagaag caattatctg tgtaataata atgctgataa    120
tgtagagaat tacttcaaat tgccattact ttgtaaagac gagcacaaag gtttattgct    180
ttccctctga aaagggattt ctacaaagta gacaaaataa aatttcagtt aatgtctggc    240
ttcactccac tccccagact ggaaccttgc tttggtgtta agttaggaaa ctgactgcar    300
tgtttgaaaa tgtaagtaaa ttcatcagtt tcagaatcat ttttggcttt ccattgttat    360
agaagccaga agttagtgag aaataatctc ccgtttcctg ggaaatttca tcaatgtatc    420
tatataacag aaatgactac atgttcttca actctttaag tgcatatttt ccaaaactcc    480
agttagtatc tttatgaata tttaggaaag actgaggctg tatcgagaaa ttttctgtaa    540
tagacaagct atgaaattgc tctctccttt ctcaccttca aatttagagt gtggcccat     599
```

<210> SEQ ID NO 62
<211> LENGTH: 599
<212> TYPE: DNA
<213> ORGANISM: Homo sapiens

<400> SEQUENCE: 62

```
gattttcttc cgattacaaa aatgatatat gctcactgtt aaaaaaaact gtgaaaataa     60
```

-continued

```
atataagcat aaaaggaaat acattcccct gagtctgtat catgggatgt taatcaattt    120

taacattggc cacttttatg catattatgt gtacacatag atttacagtc ttacgttgaa    180

ttatatcaca aataggatgt ttatatgtgt tttcttctca ctgttacatt tttgcaatca    240

tttttcttat atttcaatat tgtatctcat cccaatgaat tgtatttggc aatgatgttm    300

aagtccaaat ttagcacata aaaaacaact cacaagttgc attactgtgt tttctcacaa    360

ttaaaaaaag gaatgaggcc tggcgcggtg gctcatgcct gtaatcccag cactttgggt    420

gtccgaggcg ggcggatcac ctgagctcag gagtttgaga ccacctgggc aacatggtga    480

aaccccatct ctactaaaat acaaaatatt agcctggcat ggtggtgcat atttgtaatc    540

tcagctacgt gggaggctga ggcacgagaa ttgcttgagc cctggaggca gaggttgca     599
```

<210> SEQ ID NO 63
<211> LENGTH: 599
<212> TYPE: DNA
<213> ORGANISM: Homo sapiens

<400> SEQUENCE: 63

```
tgttaactga aaagcctact aaatgatcca aagtttattt taccttaaaa aatatctttt     60

tctgtaatac ttagtttcac atcataaata atcttatctt aggtcatatc gtatatttca    120

atttatgcct aagagaaaga accaagctaa attaaaacag ctggagattc cattaatcta    180

acatatatct taataatttc agattcaagc tgctaattct gccattagag ttaaaatttc    240

aaaaaaaaga taaatccatc agagacaatt aattaaaatg gagcagatac agggttaacr    300

aaactctata aatcaaatgg cctcttactt tcccttagaa acaaataaat tactttttca    360

gagtacaacc cctacttttt taagtagtgt caaatgtaat tttttttgg agatctcatt    420

aagcacttta ggagaaattc ctggtgatat tgttgaccaa acaaagccag actttactgt    480

ccttttatga gctttgccat tggtcaactg tatatgcaag atcactcttc ttgatattta    540

tcaggtaaca ataggtaata cactttctga cataaaataa gaaaatcacc tttggtttc     599
```

<210> SEQ ID NO 64
<211> LENGTH: 599
<212> TYPE: DNA
<213> ORGANISM: Homo sapiens

<400> SEQUENCE: 64

```
actctagatt ctcggccact ggagtctgaa gatactctct ttgagaatgc atattatttt     60

gctcacagct aaaacattta agtatcatag ctgatcagtg gagtgagatt aaaaggtttc    120

ttttttgaat catcagctag agatgtacaa gggagacagc atgcagggtg tgttcagaag    180

agcttgctga ggtgctcggc tcttagcatt aaaaatgtga tgttggtata tcatcctgat    240

agaaaacact gctttccaaa tcctagtcac tggatgggag gaaagtaaga acagattctk    300

ccaaccacta ctgatttgtt ataattctcc ccattgaaat tgggacaaaa tttgtaacat    360

gctactctga aattgatcac attctcaatt ctgtcaatag cagagaattt agcctcaaca    420

ccaccaattc aaaatagttt aggtcttgcc cctgcctgat tatgtaacag aaaagcataa    480

agtttgcagg gtggagcggg aggatttttc taggaaactt ccttctcttc cattaacgtg    540

tgaatgagta aggacagtta atctccgctt ctgatataaa tattaggggt agaggctga     599
```

<210> SEQ ID NO 65
<211> LENGTH: 599
<212> TYPE: DNA
<213> ORGANISM: Homo sapiens

<400> SEQUENCE: 65
agaaaaataa atacagaaaa tatgctacat atacacaatg gaacatcgtt cagccttaaa 60
acacaaggaa atcctcaatg ccatctgaga caacatggat gaacctggag gacattatgc 120
taaggggaaa taagctagac atagaaagaa aaatacttca taacatcact tatatgtaga 180
ctttaaagta gtcaaattca tagaaataga gagtagaatg gtctttccag gggccaggga 240
acagggaaaa tggggagatg gtcaagcaat acatagtttc agttatgcaa gatgaaaatk 300
ccctataaac ccactgcaca gcaatgtgaa tattgttaac aaaactgaaa tgtgtgtttg 360
aattttacta agaaggtaga tcttaattga tttcaccaca gaaaaaaata aaataaaatg 420
gtaactatat gaggtgatga atacattaaa ttatcttgat tgctatcatt atttcacaat 480
gtatatgtat atcaaaacat taagtcatat atacgtatta ttatatataa attatatata 540
tatatataat ttttgtcaat tatacttcaa catagatgaa aacaaatatg acaagcctt 599

<210> SEQ ID NO 66
<211> LENGTH: 599
<212> TYPE: DNA
<213> ORGANISM: Homo sapiens

<400> SEQUENCE: 66
ggcaactttt aaaatagttt ccaatgatcc cctgactcct gacatttata cttatgtgta 60
atttccttct ctcgagtatc gtctggattt attggcttgc ttccaacaaa tagagtacag 120
caaagtgttg ggatgtcact tctgagatta agctataaag cccaactttc atcttgcttg 180
tcctttcttg ttgtctggtg tacttctctt attagctatc ccatggaggg aatcacatca 240
cacagaactg gagggaggcc tccagtcacc aacctgtgaa tatctaattt ctcaaccatk 300
aagataatct tggaagatga ttctgtccct gttgaacttt cagatgagac ttcagtccca 360
actgacagag gttcccactg agctccacct ggatttccaa ctcagagaga ctgtggtgta 420
acaaatgttt gctgctttat gcttctgttt caggacaact tgagcagaaa tacatagtgt 480
gcagaaatag atcactaaat cacctgagga actcaagtat ttagaaaagg aaaatatgat 540
ggagactgag aagaactggt catattggta actgggaagt caggagaagg tgtaatatg 599

<210> SEQ ID NO 67
<211> LENGTH: 599
<212> TYPE: DNA
<213> ORGANISM: Homo sapiens

<400> SEQUENCE: 67
atctgatatt ctaggaatct ttgaaatgtt tgtatttttg ctcagtttaa tattgtttga 60
ataaatctat gaatattttt attaaaataa agattagctc tgcagaacaa attcagtgca 120
aagtacttca aaacttaaaa gataataggg taatttttat ttacaagtag catggtatat 180
tgtgggaagg cggatatggc aagcccacac cgttataatt ccaagtatgc cattaaaata 240
gccacaggag aggtaggatc aacatgttct gaattgtcaa atgaatgaga aatcctgagy 300
cataagtgaa gttttctcat taggttatag tatgtttata gatttcaaga ctgtgatttt 360
atagtagcta tgaaaatatt ttcagataaa tgaaatatat taaaataagc ttaaactcaa 420
ataactgaat tatgaattat tatggaaggt atctagagca ttcttttttg ttgattttct 480
ttattttatt ttattttttg agacagcttt ctattctgtc acccaggctg gagtgcagtg 540
gcacaatctc agctcactgc agcctccacc tgttgggcta aatccatctt cccacttca 599

<210> SEQ ID NO 68
<211> LENGTH: 599
<212> TYPE: DNA
<213> ORGANISM: Homo sapiens

<400> SEQUENCE: 68
agtaggaaaa gagacaataa acaagataat gataaatact aaggagaaaa aataagacag 60
ggagaagggg taggaccgtg ttggaagtta agattttagc tggaatggcc agagaaggca 120
tcaggaaatg cagtttgaga gaaaacatga agacgaaggg aaaggcacat ggatatccaa 180
aagaagagca tttcaaacaa gggaaacagc aaatgcaaag gcactgaagt gggaacatgc 240
ttggcatatt caaggaacag tgaggaggaa gccagtgtgg ccacaacaaa gtgagacagr 300
tagaaaagta gaagcaaatg gggaagagaa ttacataggg ccttttgggt catgtataga 360
ctatcttttc atctaagcca ggaagccact gtagagtttt gaggaggggga gagatgtgag 420 ttgacttaag cttcaacata atactatctg gcagctatat tgagaataga ctgaagtggg 480
gaaggaggaa ggaggcaaac cagggtgaca gagtaagatg gaatagagca accaaataac 540
caactggttg aatgacccta aacaaaacgt ttccatgaat acagtggtgg gactctaaa 599

<210> SEQ ID NO 69
<211> LENGTH: 599
<212> TYPE: DNA
<213> ORGANISM: Homo sapiens

<400> SEQUENCE: 69
aaagcctcaa gccaagaacc agagagatgg attgcaaatg ccaagaccaa aggggaagaa 60
ggagctttgt gaagggtgtg cgtgtgtgtg tgtgtgtgtg gtgtgtgtgt ttgtgtgtgt 120
gtgtgtgtgt gtgtgttcct tttgttcatt ctcacagctg caagatacat ctgcttaggc 180
cagcttttga aatctcagtc tggccagaac tccaggccct cccaccctac ttaagtcagt 240
ctataaatgc aaactgcaac tatctgccag gcccctccta ggcctgctgc atttattccy 300
gacttgcttc ttctcaagtg ccgtgcccca ttaggttacc aattcttggc tccatctctt 360
cttcacaaat ctgtttcttc tcctttggtc ttggtgtttg caatctgtct ctctgttttt 420
tggcttgagg ctttcctata gactatctta gatactgctt actcccttca gatggtttca 480
ggcagctggt tccccaaccc agccctactt gccagctcag gaaggggctg cgaggaaaat 540
gccatccttg ggtttccctg cagagctcca ccctctctca ttcctcctct gtctcacgc 599

<210> SEQ ID NO 70
<211> LENGTH: 599
<212> TYPE: DNA
<213> ORGANISM: Homo sapiens

<400> SEQUENCE: 70
ctcccatttt cctgagacaa agaccgcact gagagcaaag cagggcaggg gataccagcg 60
gcccacccaa acgcccaagt ctttgagggc tcaggttccc actttaggag gacaacaaaa 120
cttacgccaa accgaagcgg gccttgttcc tgcatgttgg gcctctggcc tggcccagaa 180
gactgggcca tcaagagtgt taaccgctgc cattggctgg tccttcactg acagcagaaa 240
cttggccaat ggcaatcaat cagggggccc gcgctgcctt aaataccagc agagcaaacr 300
gcctcagaca aagctgcgcc gtgtatcaat taccgagagg ctgcgtgctc ctctgggcgg 360
agggagccgg agcgagcggc cagggctgct gccccagctg ataagggccc gcattgttcg 420
gggacagctg gcagcccgat aagggcctgc tcgcccgaga taatggcagt gggcaggcgc 480
ctcgcggcag tttagaattt cttgggtctc caagaaaggt tctattaagc ccactgaccc 540
caattgaata ttaattagct aattaacgga tttattgttc cacgccattt ctggagagg 599

<210> SEQ ID NO 71
<211> LENGTH: 599
<212> TYPE: DNA
<213> ORGANISM: Homo sapiens

<400> SEQUENCE: 71
tgctccctcc agctccctac tgggatctca ccagccccag ccttttcctt ccttcccacc 60
attctagagg aggctgcgtc ctctggggca gaccctttcc ccatccgttg aaagcaaact 120
cctagctttc caggtgggca gagtagagtc ctgactttgt ctactcccct tccccactta 180
aagagggcag agggtcctcc ttctcatttg agagaatgaa gctaagagac caaccagtcc 240
ctcagcctac agggtttggg ccacacagag gtgtctgcag ggtggacaca acacatcaay 300
gtacagccca gcaaccagct accaggtcct tcccgggctg cagacatggc acaggcagcc 360
ctggggacat caaattcttg agccccacca gtcttgggac agggagcctc atctcacccg 420
cactggccat gcctctgagg aaggcagggc acaagtaggg aactggtaac tcaaatcact 480
tagctttttg ctagccagag acacatgcat gagacctagg cccaaatgct ataaaggcca 540
aggtgtggac agctgcatga ggtgaggttg gagcctgagg atctgagctc tggggaagc 599

<210> SEQ ID NO 72
<211> LENGTH: 599
<212> TYPE: DNA
<213> ORGANISM: Homo sapiens

<400> SEQUENCE: 72
tggttggttg atagcagtgg tggatttttt tgaaatggct agtttctgtt tggtagttag 60
agaagaaagg ctaatcgtgg tttgcgaggg aaggggtata atgaggtggg tttgaacccc 120
ccatcccgtc atagccaaga atttagtttt caaggttact ttggggtccc gttggccaag 180
agatgaccca tcagtcagtt ggtgggctta gaattttatt tttagtttat agacctatcc 240
tttccttttt atagctctag ccaccacctc agtgatttgc atctcagtgc taagttactr 300
taatagcctt tttgacgttt tcccagaccc tagtttctgt ctatattaga gcctatattc 360
tgctgctgga ttaatcccca tcaagtaccc ttctcatcaa ggtccactgt atcaaattta 420
tatatcacac aagttagcat tttaactcct ccccatcttt acttcttatc tcttcttact 480
tccctaaatg gagccaaact aatttggtag taagtcctac ttaatggttt ctttgttctc 540
aatctcatat acacagtctt ctttcctcct ggtgtgcttt tgcttctctc ctattcttt 599

<210> SEQ ID NO 73
<211> LENGTH: 599
<212> TYPE: DNA
<213> ORGANISM: Homo sapiens

<400> SEQUENCE: 73
aagaatgtga gctatacagc taaggttaga tgtatggaac tttctaaccc taatgactgg 60
gaggtcctgg aagaaccttc tttgcagccc tggtcctaga ttctgtgtat tcaacggagt 120
ctcaggcacg ggaacaccct ttaaaaggac ttttcctctt ttctgtcccc tggtgttcac 180
atgcatctta ctttgtcctt tgccatctgc cacctctttc ctgccacttc tcccaattgg 240
cctttgtttt acttcccttt gtgattcccc tggcatctct gcttctcact tgttcttccy 300
tcatgtggtt tgggtgtctg tctatccttc cctggctcta ccattcctgt cctgtccttt 360
tctctgtctg tgcctgtgct tggccccagc ggactacatc gtgatgcagt ttggccgggt 420
agcagaggat gtgttcacca tggattacaa ctacccgctg tgtgcactgc aggcctttgc 480
cattgccctg tccagcttcg acagcaagct ggcgtgcgag tagaggcctc ttcgtgccct 540
ttggggttgc ccagcctgga gcggagcttg cctgcctgcc tgtggagaca gccctgcct 599

<210> SEQ ID NO 74
<211> LENGTH: 599
<212> TYPE: DNA
<213> ORGANISM: Homo sapiens

<400> SEQUENCE: 74
atttattcta tagggctgtt ttcccttcta aaattatatt aaatttaggg taagtcccat 60
gacttttctg accattttca ggtaaccaga ggttgtcttg tcagtaatta atgcatcctg 120
tctgctgtaa taaaaaaaaa aatcttgaaa cgtcagagtt acaccatctc tttcccagca 180
cggtctgctg taggccagct gcctgtgggg accttgcaca tgacagtcct gaccctttcc 240
agggtccaag gtggaggggc aggtaggtag gagaggagat ggttgggaaa ggtcttcaay 300
gactgtactc tgatgagttg ctgtcccgtt gttctctggg ccctttctct cactgggctg 360
tttttgtggg ttggtggaga ccaccccatc gctggagtct caccctgcac ctcccttgat 420
gagggtgata ctttctcccc gtagccgatc ctatggtttc tttctcaggc tctgggaaac 480
ctggtctccc tcagtgtcac ctcctccctt ggaggagccc tcttgtcctg gatctaagac 540
agtcacatct ggctctcttg ctgggtgcta cctctgtcca caagagacac tcatgtgtg 599

<210> SEQ ID NO 75
<211> LENGTH: 599
<212> TYPE: DNA
<213> ORGANISM: Homo sapiens

<400> SEQUENCE: 75
tgctttccat gaaaacattc ctttctcctc ctctgcctcc acctccattt cctgatgggg 60
gagaatgata aagagccaca ggcttcggtg accctgatta ctaggtaaga taacagggag 120
aaaggactta accactggcc ttcagagaaa tatggatgaa cacaagggct aggctactga 180
agaggctcca gaaacctcag acatccccaa agtacctaga gagccaccta ccacctcacc 240
caccagcggg catgtgcaag cacacagaag gaaaggagca tgcacagctg gggggcggcy 300
accggggaga agccacctgt gcctggctga gcaagaccca gctaggaggg tctacactaa 360
atctactaaa atggggaggc tctgagagtg ggcacgattc ctggtaaagc agtgttctag 420
aagagctgca aggggacgag atgggaccac gattacctag cagtgacaag cttgtaccag 480
gtgggtgttc ctagctaacg acaagtgcgc aacaactctc cctggtgaat aacaaagaat 540
ccccagccaa cagcagctgt tgtggagacc aagggcaact gcgatggctg tctccagga 599

<210> SEQ ID NO 76
<211> LENGTH: 599
<212> TYPE: DNA
<213> ORGANISM: Homo sapiens

<400> SEQUENCE: 76
tgaaggacag aggcctctgg ggcaatgctt tgctgctctg ctgcggtctc cagggtaggg 60
accaatctct gctgcccttc ctggaaggcc agcagagtcc aggccaagca tcccagcagg 120
caacaaaaca gccctgcttt ctgccttctg caccccactc ccaggtgttt tattttgtct 180

-continued gctctctgtc cccagtgaca gtgacagctc ttggaggttg ataaataatc agaggtcata 240
gtgttcagag agcatcaatg ttgtgcccga cagagatgga tctgacctgt cctgagctcy 300
agaagcctgg agagagaggc catgtgtgtg tgcatgcatg tgtgtaggtg tgtgtaggtg 360
tgcgtgtgtg tgtgcatgtg tgtaggggtg tgtgtgtgtg cactacatga actgtgattg 420
gccaaaagga ggctgagggt aagtgctgta gacccagacc ttttgtgtgt gaatgctagc 480
ttcatcattg accagctgtg tgactttggg caagatcctt gccttctctg tgactcagtt 540
cctctgctgt gaaatgggta tgctaatggt gcctaccttc tagggtggct atgaggatt 599

<210> SEQ ID NO 77
<211> LENGTH: 599
<212> TYPE: DNA
<213> ORGANISM: Homo sapiens

<400> SEQUENCE: 77
aggcacccat aaaatccata caggaagttg gaaagaccag ggcgtgagtt tatacagcca 60
aagtttcctc gtaccgcaac aaggcataca caactttacc tttagagtcc tttgtagggt 120
gtattaataa agaagctctg agctgcaagt aacagaaacc ccagattcaa ggggacttaa 180
acaatgcagt catctggagg tagggtgggc cccaagtgta taccaccagc agtttaatga 240
agccattgag gacatagatt tttccattcc tccattccgc cttccttggt gccatcttcr 300
tcttaagact ggtctccttt atggtcatga tggctagcag tgacaaaaag aaccacctct 360
ttccttattc acatatagaa agataggaaa cctctcatcc tgtcatggga tattagtcct 420
tagtctgata agaacaattt ggatacctac acaccctaga ccattaatag ggtccaggta 480
cacttctttg ttttggacta atcatctgtg gactggagct tcaaagtccc ctaaatgtcc 540
actacagagg gtgtctcagg tagatgctgt cttgttcctg tgagtgagga aggcgctca 599

<210> SEQ ID NO 78
<211> LENGTH: 599
<212> TYPE: DNA
<213> ORGANISM: Homo sapiens

<400> SEQUENCE: 78
actagcaccc aggcctgtca tggtctgttg tggggggctg gtggaggggg ggctgactcc 60
cagaggcctg agtggggagg ccagatcatg ggtaacatct cttgtgatgt cacaggggac 120
aggagagagt taagggtgga tcccatgagg gctaacccag gctgacatca ccagtgaaag 180
tgagagtcac atagtcagag tcttaggatt tagtcagtac agccaggaag ggcaacctgt 240
ttatttgttc ctggaatgtg ttgaccaacg caagttcccc caagtgatcc ctgagcacck 300
tctatggaaa cacagagtgg gtgggctagg aagaaaagcc aaattcaact caggtgggga 360
tgggccacag tggctttgat gtcctctatg ggcatttggt gcctccatgg ccttgaacta 420
acctctgccc ttaagccttg tcccacctcc tactcgtcac tgatgccctc cgggctgggt 480
gggtgggctg ggagggagaa ctacagcagg ttaccagggc ctctagggct gggagggacc 540
tggactggtt ggagagattg cccaaagcca agtcatctgg gagaacaatg ggggcggga 599

<210> SEQ ID NO 79
<211> LENGTH: 599
<212> TYPE: DNA
<213> ORGANISM: Homo sapiens

<400> SEQUENCE: 79
ccttgcccat cacatccttc ttggcagtat catccacccc acggtttcaa ccacccatct 60
ctggctggac caagttcaag actcaagtat cctgcaaccc tctggtcatc tgcacctgga 120
catcccacag gaagctcata cccacagtgg ccaaatggga actcctcttc ctttccacgc 180
atttcaagac acctccattc cctccaacct ccaggcctgg aagatgagaa tcaccctccc 240
catctccctt ttcttcaaac ccgccagtgc catctgacgc caagcccagc tctgttctcy 300
atctccttcc tctcatcccc caaacagctc tgtagtcacc actcaaactc ctcctgtagg 360
aagccctccc tgactctcca gcaggcctgg gcatgccttc acctgttttc ttgtgccctg 420
tacagccatc cattcagcag ccacgctagt gtccaactgc atagctgact gcctgggctg 480
gctctggaag gtaggggcag ggtctgatct gaccctgggt ccccaacacc gaggccaagt 540
gcagcatgag ggtcccaaa gaggtttctc aaatctggga acttgtattt ctgctgagt 599

<210> SEQ ID NO 80
<211> LENGTH: 599
<212> TYPE: DNA
<213> ORGANISM: Homo sapiens

<400> SEQUENCE: 80
aaacaggaca gacaagttgg gtgtgggggg tgttcttgac atgtgctccc agccttcctc 60
agaggccgag acccctgggt tgcagccagg gaaggggcgg tatctggtcc ctgggcccag 120
cagataggaa ggacagcacc atctttcttt ctgttcaaac acagacaggg ctgcagacac 180
acagttctgg cctgtgtgtg cgacttgtac ataattcaga ggctcctatt gctctggcct 240
ggataaaatg taccagcagg ggcagcttgc acagagaaca gtgagctgat gccagggagy 300
acttcctgaa aagaggtgag tggcccagag gcttggggga ttaatataaa ttggacaaat 360
gaatattgtt aatgccaaga actgtttact tgtttgtgga gtaagtcagt ttataatcca 420
tgttcaaact ttatctcgtt gaaccttcat aaaagtccag tgtggaagtt actattaaca 480
gacaagaagg cggaggctca gaggctgagt cacttgccca ttttcttttt ctttttttgag 540 atggagtctt gctctgttgc ccaggctgga gtgcagtggc acgatctcag ctcactgca 599

<210> SEQ ID NO 81
<211> LENGTH: 599
<212> TYPE: DNA
<213> ORGANISM: Homo sapiens

<400> SEQUENCE: 81
acctcacatc ctccatgggg agttagacca tcttgcagca caagcagagg gtgccctccc 60
aggcctgccc caccaagccc acccaacacc cacccatgtt aaagcctttt tttggagaaa 120
attgttattt tgctctgagc ttccctccct tctttaaacc aagtgcggag ggcttcaaga 180
cgttggggga catgggaacc tgaattgtcc tcacatatca cagagtctaa aggcagtgtg 240
tggtggtgga atggggagag ccagggccac cctgggaatg gctcatgctg ccaggctagr 300
caaaggatat ctgatttttc cagtggaccg gatgagggcc tgtggaggga gctggaggcg 360
ggtggggtga ggacctccca acagagggta ctgctggaac tgatgtctga ggggagaggt 420
tgcaaaccag agggggcatt gttcctttgg gtgggggtgg caggggtggg ggggatctag 480
atgagaggtc cccaggggag gaggttcact gaaaaacctc ctggagaatc ctgtgagtta 540
gagtagaatt tggacatcta ccatgtctca gagggtcccc aggccaggtt acaactgta 599

<210> SEQ ID NO 82
<211> LENGTH: 599

<212> TYPE: DNA
<213> ORGANISM: Homo sapiens

<400> SEQUENCE: 82
cccagggttg cagcgcagta tctctgagcc ccaggctcag caccaccact tccccagcca 60
ccctcggaca agccccccttc aggctggagc ttgataccct tctgggtgtt tcttttctat 120
tcacttggtt gatttttttt ttttttggc tgactataaa agtaatatat gctattgaaa 180
acaattcaga aaagcagaga aaagaaaata aagatatata tattctatct ccaaagataa 240
acactattaa acgatgtaag agtatttctt tctagccttt ctctatgaat attttatatr 300
cctatgtatt ttgtattaat acatatacta tacattcatt caataaaaaa cccatgctgg 360
gcgcagtggc tcacacctgt catcccagca gtttgggagg ccaaggcggg aggatcgctt 420
gagcctttgg agtccaagac cagcctgggc aacatgggga gaccctgtct ctacaaaatt 480
aaaacattag ccacggttgg tggcgtacac ctgtggtccc agctacttgg gaggatggct 540
tgagcccatg acatctaggc tgcagtgagc catgtttgca ccactgcact ccagcctgg 599

<210> SEQ ID NO 83
<211> LENGTH: 599
<212> TYPE: DNA
<213> ORGANISM: Homo sapiens

<400> SEQUENCE: 83
gaaatcctgt ttctgctaaa aatacaaaaa ttagctaggc gtggtggtgt gcgcctgtag 60
tcccagctac tcgggaggct gagacaggag aatcacttga acctgggaag cggaggttgc 120
agtgagcgga gatttcacta ccacactcca gcctggccga cagagtgaga ctccatctca 180
aaataaataa ataatagtac ccatcacaaa acttcaatat gtaacgacat tttgcccatt 240
ttgttcaaca gattctaaat ccatattgca gggaagccgt tatggtctct aaccctgttr 300
actcttcatc cttgatgtct tccccaaggt gacattcctt tctagttttc ttctgactcc 360
tctgctgctt tagggcagcc tccacttggg ggctccttct tttgcctgtc ccctgaatgt 420
gggtgtttcc cagcgctctg acctgacccc atccgtctct cgctttccac actcctgctg 480
ggtaaactca ccctctctca tagccttttt accttctgtg ggttggcgag gctcacattt 540
caatgaggtc tgcatctccg ccttcagctc agacccttttt cccagtctca gaccaccat 599

<210> SEQ ID NO 84
<211> LENGTH: 599
<212> TYPE: DNA
<213> ORGANISM: Homo sapiens

<400> SEQUENCE: 84
acttagtgtt cacaaagtcc tctgctattc attattttat ctgtgtgtct catcatcctg 60
cagactatca gtcctatttt acagaggggt aatttaaatc atgggtacat agccaagaag 120
tggcagacct ggggcaggat cccaggtctc ctaaccccca agtgagggca tttcacactc 180
catagcacag cagggctgaa ctgggctgaa gcagattaga ggtggtttgg cagggtgtag 240
ggggtggtca gagctcagga gtccctttc tgagtgtcag ggatgctaag acaagggagr 300
acagccctgt agcccacctg ggcatcactg ttattacagg ctcagcagca cctaagggag 360
aggagaacaa gacgggaagg gaaaggcagg gctgtagtta acacacatcc tccatcccac 420
cagcccttca ggcctggtct tgcaggcact ggagctggtt ccatgggttg ccagaggaag 480
cctgagagag ggaggctggg agagggggcg gggaacctga tcctgtgtat atgtcaatac 540
ccaacaaaaa cttgtgtagg ggggtggggt gcatttgggt tactggagtt acacagaca 599

<210> SEQ ID NO 85
<211> LENGTH: 599
<212> TYPE: DNA
<213> ORGANISM: Homo sapiens

<400> SEQUENCE: 85
gtgccttggg ttcaggctgg gctgaagtgt caggggagac tcctggaaga aggggctgga 60
gctggacgac aagaaggaaa gaagcattcc agatgtgaag aacagctgga acagaggtgc 120
agcagttgcg atgggcaggg tgatcgtgga acacagggag gggggtggtg aggagggctg 180
aagtgggaga tggaggattg aactgctaca tgatgggaac cccctggata aggcactcag 240
agggtcagtg agcattatta gaggcaggac agatggccct cgccactcaa tccctctgar 300
tttcccaatc ctctgtcccg ccactcccgc taactctaca gcccctctca gttctcacca 360
tctccccttc ccatttgccc atgctgtctc ctctgcctgg tcccaggccc ctcccatctc 420
tgcctgttga gccccctcat ccttagaggc ctatttcaaa ggatactata acccccaggg 480
aaccttccag gcccctagac agaagcatga cagcatgcac agcagcatcc cttcaggtgc 540
cctggagaca caccatcctt catgcatctt gctgccgtct tccgttttct caagtgtga 599

<210> SEQ ID NO 86
<211> LENGTH: 599
<212> TYPE: DNA
<213> ORGANISM: Homo sapiens

<400> SEQUENCE: 86
gtggggtagg gaccatgtga aagccgctaa ctggcctggg gagctaaggg atgttggtgg 60
cacagtacag tctctttgta aacctcacac caaccttatg ttgtgatagg taccccattt 120
cacagatgag gactcagcac agagaggcta agtgacgttc ccgagaccac acagctggca 180
cagagttcta tccacccatc attatcaaat tctagggtaa agctgtgtgg ctttaacagg 240
ttactctccc tctctgagcc tctgtttcct catctataaa agaagaataa aggtgctacy 300
tggcagggaa ccaggtgagg gactgggcag gcagcaggct tcagagggtg aagcatgggc 360
attccctgca aaagaaatgg catcagacta tggctgagag actggttgga agaacaaaga 420
agagggtgag ctggaggctg aagttcaggc tgcggacttg agggtgccct gtcttcttca 480
ggcccagggg ttgggagtag gcaagttggg cccaggaagt tgggactggt ctctggagcc 540
tgagggctgg gagaaggcag ttttgccttt acttgttgaa cttgacgcta agaaacctt 599

<210> SEQ ID NO 87
<211> LENGTH: 599
<212> TYPE: DNA
<213> ORGANISM: Homo sapiens

<400> SEQUENCE: 87
gcagggccca ggaatcagag agagagagca gggcccagga atcagagaga gcagggccca 60
ggaatcagag agagcagggc ccaggaatca gagagagcag ggcccaggaa tcagagagag 120
cagggcccag gaatcagaga gagcagggcc caggaatcag agagagcagg gcccaggaat 180
cagagcaacc agggcttcag cccacttcgg catcatactg gctgggtggc cttggaccac 240
ttgcttaaaa tcactgaggc ttcagcagaa tacagactaa agaaagtcaa tttttatttm 300
aaatagaaaa taaaatcatt gagcctcctt ttctctctct aaaaatgagg taacatccac 360
ttggcaggac tgttgtgagg atgaaaatga cataactcat gaaaagtgac gtgtcaccct 420
aggattagga gcagctgtga ataacataac cctacaataa cagtgccttg aacaagaggg 480
tttgtttctc actcaggtaa ggatctggga ataggtgatc caggagtggt gtggggaccc 540
tgctttgcta aatcctctgg cattttaggc tcctgccaac tcatgactcc tctatgcca 599

<210> SEQ ID NO 88
<211> LENGTH: 599
<212> TYPE: DNA
<213> ORGANISM: Homo sapiens

<400> SEQUENCE: 88
tttaatgata gctattggat ggacgcagta tggagaggaa gggacagggt agggactctt 60
cattcattca gtcatgaatg aatgcattga gtatcttctt tcttctaggt gcttgcctgg 120
atcctgggga gcaaaaaaat cccagtaccc agcaaatgag tcaatcacct gggtccctgc 180
cctctgttag tggttgtggg gaagcctggt ggtggtgaca aacctctctg tctgggtagg 240
cttctgcagc tcagagtctt ttgagtacaa ggactgtggg aaatctcaga tcccaaaagy 300
ttcagactct gtgattcagg gtcaaggaat cagagattac ttccactcaa agcccccaag 360
gagtctttga atccagctaa ggaatcttaa catgttaaaa tctcagagtc gaaggattct 420
ggaataaatg tattaaagac tctgagctgc aaggcatctc agaggtcagg ggttcctgtc 480
tgcagcccca ggcagaagcc ctcttctcag tatcccaaaa aggcaagcac cgaggcacct 540
ctaagaagag agagcttacc tccttcagag gcagccccgc attctttttt aggacaggt 599

<210> SEQ ID NO 89
<211> LENGTH: 599
<212> TYPE: DNA
<213> ORGANISM: Homo sapiens

<400> SEQUENCE: 89
tgccggccgg tggagatagt tcagcctcct gcctgccacg tcaccaccag gagcaggcgc 60
taagctgctg cgggcctagc gggctgcctg aggaatccca aaccagttat ttggagcttg 120
cttgagaagc ccctcccagt cctttgaggt tctggctggt gggggtgggg gctgtcaaga 180
tggtacctgc cacgtggcat ggctgggagt gggctcttca gctgcctcct cagggaagga 240
aggctgttgg cctctgctgt ggtctgagct ccagcatcac tggtctggat cagaggtggm 300
ttttgagtag ggtggccata tgcctattgt cctggcataa taattagtag tgcccatttt 360
actcttataa gtgtccttgt ttgtgcaata aattatatgg ttgctctgcc tttgaggctc 420
cagttctggc agggaaggag ccagagctgg gagggaggtg tcttggggtt tattctaggc 480
cccaagatat ccccttcatt ttagggtgag actcagatct ccccgctcct tccagacatt 540
tttagatctc tgggccttcc ctcctctccc cacctccctc cccttggacc ctttgctta 599

<210> SEQ ID NO 90
<211> LENGTH: 599
<212> TYPE: DNA
<213> ORGANISM: Homo sapiens

<400> SEQUENCE: 90
ccagctactc ggaaggctga gaattgcttg aatctgggag gcagaggttg cagtgagccg 60
agatcatgcc actgcactcc agcctgggcg acagagcgag actctatctc aaaaaaaaac 120
tttgttgcat gaaaggaaga atgaagaagt aaaggacttc ctctgactct ctcttatgtg 180
cactgagggc agggaagggg ggtgccttgg ctggtggagg gaggcctcag aaccatgaga 240

-continued atggagtgag gcctggaggg ctgcagagat ctgtgggaac tgcagaattt gggcacatgy 300
tgtccagttt acaggccact tccaacccag ggtctttttg ttgttgttgt tcctcggaac 360
tacctggaag aggaagacag gcttgaaagg aaccatggct ctcactttgc aggtgggcat 420
ctaggttctg gatggtggtt tgagggttag ggagacactg cctctccagc aagggtcagt 480
gggacctgag aggggcctga aggccctgcc tgctccccag agccttcccg gcacctcatg 540
tgccagttct ccttggcact tgggctgcca gcctttgccc ctgctcttcc ccctgccag 599

<210> SEQ ID NO 91
<211> LENGTH: 599
<212> TYPE: DNA
<213> ORGANISM: Homo sapiens

<400> SEQUENCE: 91
aatcacttgt aaagccagag ttttatacct agctaaacta gctttcaaga gccgatttaa 60
aagaaagaca gttttaggat ttttttaaaa tgaagtttat atcagtcttg agtcttcact 120
gaaagaacca ttaaaatatg tattatatca agaaaaactc agtttcaagg caggacatag 180
aaatcaagaa actatagtgg acacagaaat aaataagtta aaatagactt acttcaactg 240
actataaaat aactaaatct agagtttaaa ataaaagtta aataaaaaag taatatgttr 300
agataatatg ttagtagaaa gagtatttac tgggtaaagt gtgctaagag tcttgccttg 360
ttcagggagg aggataagat attgaaaatt tcagactttg aaacatatat aattaaatgt 420
gtatggtaaa actttaaggt aattatgaat agaaaagaac atcaatctat aggttctaaa 480
ccaacaaagg agaaagcaga atatagaaaa tctcaccaac ctaagagaag acaggaaaga 540
caaaaaaaaa atgaaagaag acaggaaaga agaaaaaaac ctaagagaag ataagaaag 599

<210> SEQ ID NO 92
<211> LENGTH: 599
<212> TYPE: DNA
<213> ORGANISM: Homo sapiens

<400> SEQUENCE: 92
agggtcagag gtcaccccaa acctccagct gccaaccaac tttgcctgtg ccaaaagaac 60
attattttgc attgaaaatc aaggctcctc tccctgactc aggaacaatt tgcaggaaca 120
acctctgcat cagctgtgaa gagggctccc tgattaaata aggcctggaa tgcatttgat 180
gttgaacaaa acagttctct gacagctttt cttacttgcc attagaatgc ttccccttca 240
gctgaaactt ggtaagataa agtgaatccc cggggaccct tttgttttgg tgtacatatY 300
tgaggaattt ttgtggcctg tgttccattt ggagttaagg ttcttggtcc ctgaagttct 360
tccaggcttg gtggtagaag ctggcaattc agaggcaggc tgtgatgaga gtagaaagcg 420
gataccaggc atgagggcag aggagagcaa gtggccctgc cctgggatgg gaagcctgag 480
ggctttttta cagtccccaa ggagagttcc ctgacattca acactgccac aaggcgcaga 540
gtggaaagtg gagttggggc atggtggggt tgaagctgga ttagaatgga cttggccaa 599

<210> SEQ ID NO 93
<211> LENGTH: 599
<212> TYPE: DNA
<213> ORGANISM: Homo sapiens

<400> SEQUENCE: 93
ctttgtttgg tgttggtgtg ttctgtcatt acagtcccct actgctttcc caagctaatg 60
taatggaaca cagggatgga caagccacga gggtctgcag ggacctcaat gtctccataa 120
atgctgggct gattttgcaa agctgctttc ccaacggggc ttggctaaag ctgcttttca 180
aattagtttt gtagaggaaa ggagggcagg tcagctccca ggtaccagtt gggtgacctg 240
gggcgagtcc cttaacctct ctaagcctca gtttcctcct aggatgataa tgctaatacr 300
agaatctcct tgaagacagc catgcatgtc tccacccatt ctggggataa cagaattact 360
ggcggattaa gtaacgtgat acttacaagg aacatggtac agagagtgga atatggtcaa 420
taaatggtag ctgccatttt tgtagtcatt agaagaggcg agccttgaac gactagcctc 480
tgttgaaaat tacaaacaag agagtggcct acatttgcaa acagtgagca tagccaccca 540
ttcctgttag ggtcagcaac tgaccctccc ttcccccgcc ttcacttttt tttctttag 599

<210> SEQ ID NO 94
<211> LENGTH: 599
<212> TYPE: DNA
<213> ORGANISM: Homo sapiens

<400> SEQUENCE: 94
atcattcttt ggccgctgtc agctggctca atgggactta attattggga taatgagaac 60
tgattttcat tgttttaatt ttggggaagg ggtgagaaag gagggacttt tcttcctcat 120
ctgggtgaaa ggatgctaaa ctgtggcctc taacggtccc gtatcctcca ggctgctgtt 180
ggctcctgtg tttgctgttc tttatcagtg ctgtaagaga gtgttaggat ggtcatctgt 240
gtcagtgtct cctttagggc ctataaacct ggcaggatgt gtcctcagaa gagcatttcy 300
gtgctggcat ccacggtgag cagctgtacc aaagcaatag agggacagag agaagccact 360
ggacagagct gcccatgctc agccccttcc aaatgcctcc aggacatgag ggaatcctac 420
cctgctcctt tttttttttt tttttttttt tttaaataca ggatctagag aattcaaatg 480
atctgctcga ggcaaacata ggatcgtctg agttccttgc accctgttca aggttcaaga 540
gcctaggact ctactgcaga ccacaccaca acactgttgg atcatcagac ctcttctag 599

<210> SEQ ID NO 95
<211> LENGTH: 599
<212> TYPE: DNA
<213> ORGANISM: Homo sapiens

<400> SEQUENCE: 95
ttctgttaac gagaggccac tgaagctggg cgatgcctcc cagcagggga cgggcttgtg 60
agaaggagct gcttgttgtt gcccttcccc agagaggaag ccgagtgcag gcctgagcgg 120
gcagctgggg ttggagaagc ttcacgatcc cttacttatg gccacagagt tcatcagctt 180
cccacgacca gcacccatag ccttaacccc ggggtgggtg gaaactctgc tatctcctca 240
cagggctccc caccaccaca agggcacctt cccaagagcc caggagaggg ctggctttcr 300
ggcctggtgt ggtgttgata atcaggtcgg gttgagctga aatggaaaac cttgagagtg 360
aggtggatgg tgggctccag gctggcatct cccactgaaa gagccgggtc gcagagacac 420
actcaacaag tgccagtggc ctggctggct gaggggacct cagagcacca gtgtttggga 480
ccggggctgg gaaggccctg ccatccaccc tagtgacatc cgtcatgtgg ccaccaggtt 540
cccactgggt gaacacagcc tctcccctca ctgagccaga ttccagcctc cggccatag 599

<210> SEQ ID NO 96
<211> LENGTH: 599
<212> TYPE: DNA
<213> ORGANISM: Homo sapiens

<400> SEQUENCE: 96
agcttactag gaaagaacgt tgaaaaacag ctgctgatga tatatctgag actatttctt 60
ataggaaact gtaggtctat ggaggcagga gaaataatca cagcccagca accagaagct 120
aggatgcttt cactactaag ggagagatca ctaacaccat agctgggaaa gatcttaaat 180
catcacttga ttctgaacca gagacctcta caaaatctct aggatagaag aaaatgagga 240
gaaagaagaa agaagacctt actctctaaa ttagtatcca agcaaaaata ttcaacactr 300
agaaaaccag tcaacaaaat caacatttgt tatctaatct tgtccaaaag aaattaaaat 360
aatggaacaa tctgactaaa actttaaact aaatttgcct aaatactcaa agagaaataa 420
catctacttt aaaaaggata ttgtgaaata aagcaggcag aaataagaat tggcaaatat 480
gaaaaagaat gaattaaaaa gataaaatac acagatagga taaattctag acatgaaata 540
gatgaagata aaattagtga ataggaagat agtatttaag aagccaccaa aacgtagtg 599

<210> SEQ ID NO 97
<211> LENGTH: 599
<212> TYPE: DNA
<213> ORGANISM: Homo sapiens

<400> SEQUENCE: 97
ccaagaccta gctctctgga aatatcaagg gttcaggggg ctgggtcata ggcttgcttt 60
ccttctagct cactgtgtgg acctggataa gttgcttggc cttacccatc caccccttagt 120 agcctcttct ctggcccctt ccatggttct gtgcagagta aagaggtagg acacacagta 180
gggcccagaa gggtctcctg gcagtcactg atgccagatt cagctctctt gactctccat 240
gttggtgacg acaccaccaa ttttcctttg cacacatggc ctcaccttga aaattcaagr 300
gtctacagtc aagtcacttc tgcttctagg ggcctcccag aagcacctag tattctgttt 360
caagtccttt gtccagctgc tttcaaatca ccaaactcct ctctccctcc cctccattac 420
tacccatgga gatccagagg agggacttct taacttctca gacagtgaat tgagggagct 480
cagagatttc ttttattcct ggagcacaga atgtaacgta ggtgcaccag atcaaaggca 540
tagcagcagc ctgagcttct ctttgaccaa gtcctgggag gcaggctggg tgtttgtgt 599

<210> SEQ ID NO 98
<211> LENGTH: 599
<212> TYPE: DNA
<213> ORGANISM: Homo sapiens

<400> SEQUENCE: 98
gtaagcaatg ttcaatccag aaagaacatt tcaagcagaa ggaatagcaa gtgcaaaggc 60
ctggaatagg aacaagtgtg atgtgtttgg ggaacagtaa ggaagccaga gactggagta 120
gagtgaaaaa aggggacaac tgtgatacat taggtcagag cagtgggcag gggccagcca 180
tggaagtggt gactttgggt tttgttctga gcttcacagg atgtccttgg aggttttgga 240
ggagagtgat gcagcaaaga tgaacattca gaggctatag agaggctcat ggaacaacar 300
tgggccagct tgggttaaac actggcattc agacacatgg caatggtagc tgcacctcat 360
gggtggtgct tccagtggga actgttgaga gctacatgtt tcgacagggt gaggctgggc 420
ctgggagctc actacctcta ccaattagtg ttaagcccag aaaaaggaaa tgctgcagtt 480
taaattgtag ggttggaacc tgtgagtcat ataagcccca gccaaatggg ccatggtggg 540
ctctgggaag ttactggtgc agggtctgaa gcccccagct gggctgtttg gccacccat 599

<210> SEQ ID NO 99
<211> LENGTH: 599
<212> TYPE: DNA
<213> ORGANISM: Homo sapiens

<400> SEQUENCE: 99
agaactggct ctaacaggct aatagcctac ctggcccctt tccagcagga gaaatgccat 60
agtccttccc agaagcacat cttatatgca cagtcctcac agagtgtgtc tgtgcatcag 120
aatcaattaa tcatgcctgt caggaggggg aatggcccct ctggctgaaa cagtggaagg 180
agccctcgtg attgaagacc actttgcctt ggaaactcat gcaggtcaga ggggaaagtt 240
gagtctagat ggcatgcggt attccttggg tatgttttct catccctgaa atttgcccay 300
gtcacccaac taactgcttg tagcaaagct gtattgtcag tgcaatcctt tggggccttg 360
tttgggcctg aagaagccat tcatttctta aagaagaaaa agctggcaaa gtggaatttg 420
tagtaacagc tgttagtatt taaaactttt gtttcaagat cttcaggcac ttaaaaatga 480
ctttaaatgg ccactctgca agagtctatc ttttacaagg cagcctgtga gatctttctc 540
aaaacaagcc tcatctcatc tcctctttta ttgagatccc cattggtcct ctattttgt 599

<210> SEQ ID NO 100
<211> LENGTH: 599
<212> TYPE: DNA
<213> ORGANISM: Homo sapiens

<400> SEQUENCE: 100
gcaggccctc gagctaaatg gcatcattct gagacgggag ctccttcagc tttgtcctca 60
aaggcactgc agcttggtga atgaacatac cggctttaga gtcacactgg tggcccgact 120
tgtctggtct ctgtagtttc ctctgctgga aaaggaggac aacagtcttc catgcagagg 180
gcgagtggga ggatgaaatg aggtcatgtg tgcaaagttc tcagcatggt ccttgtggca 240
gcaatgtaca cgagctattg tctttgtcct cagagctgct cctgtctgcc tcacagcacr 300
tctctgaagc tgtctttgca gaattagacc acatgaataa tttggagagt ccataactgt 360
cctagaaagc ttttggtttg tcctttttct ccctgtgaaa gccctcgtca ccctggaaat 420
gccagttctg aagaggcaac gcttacaacg catcaaattt tctctccaag tgaccctgcc 480
tcaccagaca tttgcagccc ttccagtgat actgaaagaa ccactcaaca ggtgggggcc 540
agatctttgc aacggaaaat gccacttttg aacgccaaac ctctgcctga cgaaggctg 599

<210> SEQ ID NO 101
<211> LENGTH: 599
<212> TYPE: DNA
<213> ORGANISM: Homo sapiens

<400> SEQUENCE: 101
ttaaggagtt ccagggatgg gatgtgggag cagcaaagga gttaggtttc acttaaggtc 60
cttgggaata aataaatatt ctgtcactag gatgaatggg gttggttctt cacagatcat 120
gtaaagggac aggcttagcc ctagaaccaa ctcatgatct agatgagttt ctgttcagat 180
ggataagggc atatctttga gcaccaggtt ccatgggcac atatctggtt cattattctt 240
tgctttgctt gtgcaaaatt attttcaaag gcaaagacac ggggacaaag ttgggctcty 300
tgaggctgtt ccttgagcaa agaggtgtat gcctctggct gcccacttgg cagtggatat 360
cttcatgctt cttttttcca cccaaatatt atggccactg gagtatttgt aggaaacagt 420
ctaaaaaaag acaacactca cttccccttg cttcaggctc ttcacagtca actccactgg 480
catgtttcag gcacctgctg tgtgccaggc attttttttc agaatggaac aatattgccc 540
ttgtctttaa tgccttaact gtctagcagg aaagacatta ttatgagtac ctggggcag 599

<210> SEQ ID NO 102
<211> LENGTH: 599
<212> TYPE: DNA
<213> ORGANISM: Homo sapiens

<400> SEQUENCE: 102
tgacacaatt cagtccacca tgggagacac atgctttttg tccatggcct tatagggaat 60
ccttgggtga ctccgtatct gtgtgtaagt atatgcctgt gatttgtatt catatagtgt 120
catatacaca caaataccta tatatttaca tgtatatata tataaatatg tatatgacat 180
ttactaatac atatctctaa taggtatttg taatatatat aaaaatacct gtgatttgta 240
ttgatatagt gttatatata tgtgtgcata tatatatata cacacaaaaa aacctgtccr 300
tatatatgtg tctatagaga caaataccta taaaatagta ggtaattacc tatctatact 360
tataatagat atttttaata aatatacaaa tatctgtaca aacacctgta atttgtactc 420
atgtagtgtc atacatgtaa tataaataca tctaaatata atctgtcata catatgacac 480
gatatgaatt tgtaagtcat taacctgtga ttaatacaca tcccaggggc attttttttt 540
tttttgagat ggagtcttgc tctgtcacct aggctggagt gcagtggcgt gatcttggc 599

<210> SEQ ID NO 103
<211> LENGTH: 599
<212> TYPE: DNA
<213> ORGANISM: Homo sapiens

<400> SEQUENCE: 103
gtcaggcagg gaggagacaa gaatcaaggc tgagtgtgca ccatggaaga agactgagct 60
ggggagttgc tacaggtcca tcgggttact tgaggctcat cactgcccag ctttgaatag 120
tcctcagggc gaatctactg tcctcggaac aggactatcg cagctctgcc tctccgtgcc 180
agcctcggag agttctgatt gcagtttttc acccgccttt aatgatcttc tcttccatag 240
gctaggaggt gatgggggta agggagggct gcaggaagac tgattgcagc cgattcactr 300
tgaaacgcaa agcgtaacgt gccgtggatg ctttgcaggg ccttgatgag atctgcagca 360
gatgagccgt tgccttggcg acgctaatga aaagcaggct ttagagaggt ccaagaaccc 420
ccgtgggctg agttgtctcc cccctctgca gctctccttg cctccccacc aacagcctca 480
gatcaaactc cccgaatatt tataaaatct ctaccagaaa cagagaaagt cagccgccca 540
gccaggcgtc tgcccacgtc tttccggagc tgctggagtg acactctcca acgtggctc 599

<210> SEQ ID NO 104
<211> LENGTH: 599
<212> TYPE: DNA
<213> ORGANISM: Homo sapiens

<400> SEQUENCE: 104
ccaacagggg cattccgttt gtggtttgct gagattccct ggaaagcaag cttgggaggc 60
cagggtctgt cagaacacaa gaccaatgtc ttctccaaaa cttggatgaa cagaaggtgc 120
ttacaagctg acagggagtt atggggaagg aagcagaatt tccagtttgg ttccaagtct 180
tttctggtct tgacctttag cctaaaaaca gagggcccag ttgttctcca ttattactgt 240
aactcaaaag gagacacatg ggtccgggag agagttggga ggcaatacta ggtttgcacr 300
ttctgagttc atggacaccc aaggaactgc ccctccctag gataactaga gccaagccac 360

```
tggacccttc tcatcctgtg gccttgtcta caattttaat cattttgaag atgaaggttt    420

tgaagatgaa ggcccagcct caaaaaggaa taaccaagaa caaccctctc tccctccttt    480

agtttagatg cttccacagt caaatgtaaa attattcatg tgcttttact cattattcat    540

ctgattttat gtaaaaaaaa aaaaaatgga atcctaggct ggtcactgca tggtgttct     599


<210> SEQ ID NO 105
<211> LENGTH: 599
<212> TYPE: DNA
<213> ORGANISM: Homo sapiens

<400> SEQUENCE: 105

agggcagagg aaggcaagtt ccccgtgtgg cttctcaggg accagcagcg tgagggttcc     60

acgtggcaac gctgctggag agatgtttac atctgggcac tggcagagcc ttctggacag    120

gccatcaagc cagagggagc aggccctcga gctaaatggc atcattctga gacgggagct    180

ccttcagctt tgtcctcaaa ggcactgcag cttggtgaat gaacataccg gctttagagt    240

cacactggtg gcccgacttg tctggtctct gtagtttcct ctgctggaaa aggaggacar    300

cagtcttcca tgcagagggc gagtgggagg atgaaatgag gtcatgtgtg caaagttctc    360

agcatggtcc ttgtggcagc aatgtacacg agctattgtc tttgtcctca gagctgctcc    420

tgtctgcctc acagcacgtc tctgaagctg tctttgcaga attagaccac atgaataatt    480

tggagagtcc ataactgtcc tagaaagctt ttggtttgtc ctttttctcc ctgtgaaagc    540

cctcgtcacc ctggaaatgc cagttctgaa gaggcaacgc ttacaacgca tcaaattttt     599


<210> SEQ ID NO 106
<211> LENGTH: 599
<212> TYPE: DNA
<213> ORGANISM: Homo sapiens

<400> SEQUENCE: 106

cagccgtgtg gggagagcac gcctgaggcc tgggactggg tagtgagtgc tgaggaggtg     60

ctttgccagg cctccggaag aatggaattt gggagtgctg gggtaagcag ttaaaactga    120

ctgcctgggg gatcatggga attttatata gggaagataa tttgaaactt ttgtaccccc    180

tccacactat tctggcttgc tctctccacc ctctgctagg atgttcattc actggcatgt    240

ttgttttctc tgttgactac tcttcatggt tataaatgcc tctctttaac tattttttam    300

atttttggaa gcaactcctt ctctggaaaa tttgctatta tttcccaatg tctttagaaa    360

acctggactc atcccccacc cctgcctttc tagaacacag atcactgcta gggttattga    420

tggactgggt acagcagaac ttccagagtt ttcgcccatc taggctggct gatagggaat    480

tccatattgc atatgaagga aggatgtgct tagcaaatac catgaaacaa catttgcagg    540

ggaaattgct aatccactaa aagaacaaac tgtctccaag cactccaaca acattcatt     599


<210> SEQ ID NO 107
<211> LENGTH: 599
<212> TYPE: DNA
<213> ORGANISM: Homo sapiens

<400> SEQUENCE: 107

gcaagtatgc gtaggcggcc ttcagagtca aacaaaacag tgaggtcttc aacactgggg     60

ttcatgaaac agtttacaag agtagtgggg atgcaggctt ggtgtaaatc tctttattcc    120

tgccaagttc tagtctaaat ttttgtgttt ccaagataaa tgaaagttag ttaaattgat    180
```

tttgagattt atgtatctta tgcaaagttg gcagggtgtc cacacttcca ttaggccaac 240
tctgccaaat accattgaaa ttctgataca catttgtctg aaggtctcct tggactttcm 300
aatggggtta atttattctt tgacttaatt ttgcaatatg tcattttttt gttctaattt 360
cctgagaggc tgtctggtgt aacaaaaaga gtcctagatt aggaatcaga agtcccagtt 420
atatcattca tagggcaagt catttaatat gcctcaattg ccttatctac caaataggaa 480
ttgtgctact tgctttgaaa accatacagc attatacaaa cgtagggagt ggttggcccc 540
agcggtggct gtatggttga aaaggaagtg attctctagg tctcatcgaa gctgtgggc 599

<210> SEQ ID NO 108
<211> LENGTH: 599
<212> TYPE: DNA
<213> ORGANISM: Homo sapiens

<400> SEQUENCE: 108
tcttccattc tttagctgtg agaccgtggg caagttaatg aacctctctg ggtttcagta 60
gcctcgtcta gaaaacagga atcataactg cccacctcat ggaattgttc taaggactaa 120
atgagttaat atgtgagagg ctcttggaac agggccaggc ccatgatggg ctctctggtg 180
ggctctcaag ctctcgccag ccgatgatca ttgggccctt tgatgctgag tgggcagaag 240
ctgcaggtag gggacaagtt gtcccagtgg caaacagaag aaaattgtag taggaactgr 300
ttagggcctg tctctgtagg tggtttgatg gggagggaga gatgaaatcc aatgggacaa 360
gagggaattc acatcattag tataaaaggt tggcaaatgg gcatgggacc cttccttctt 420
agtctccaga ggccaagatg caggtgcctg gcacctgggc tggctgaaag tggggaatgt 480
atcagggctg gcatttatag tgatgccact attgtctaat tatgggcaca aagagaggct 540
cccactgtct gtgcagcccc tcaaatcacc cagggaagaa atattggtct attcccagc 599

<210> SEQ ID NO 109
<211> LENGTH: 599
<212> TYPE: DNA
<213> ORGANISM: Homo sapiens

<400> SEQUENCE: 109
atcaactgtt tactaaacac tctatgctat ttaaagggac aaaggcatgg ccaggtccta 60
tcatcaggga gtctaaatct ggggtctgca gctgagccag gaggggggtc cagtgccctt 120
ggcagcctgc tgtaaccttc tgaccctctg tgtccagccc ccatccccat ttttacctcc 180
agccaagctt ccccctatgg gggttaacag ggtaaatact gtccaggccc ttccctcaaa 240
gaagctgcaa atctagtaag agaataatat gtgcgtatat gaaactataa tttaagacay 300
tgtgatcaat aacctaaagg gaaaggctct gaggacatcc aggggtcttg ggctcaaagg 360
ctggagcgcc acacacacac acacacacac acatgcacac acacacacat gcacacacac 420
acacatcaaa tcacatatta gctcgtgtct tcatgagctt tccagtttgc aaaccgctca 480
cacatacagc atttccttta aacttcacat cagccagtga aggggctttg taagcctgac 540
atgtaagatc taacaaccct cccagaatga tagaattggc agaggggga ggcagagac 599

<210> SEQ ID NO 110
<211> LENGTH: 599
<212> TYPE: DNA
<213> ORGANISM: Homo sapiens

<400> SEQUENCE: 110
tgggaaataa aaagatctgg gaactgacag tagaaggtgc cttgatcaca atcacaatag 60
gagatgaaca agagtatagg acattagagg cagcaaatgc cctaggctag cttttagact 120
aacttttgaa atcagtgttc atatttattg tttaactttt aacctcagtc tccactagag 180
gtctagcctc cttggtcttt taccattacc tgggcttcta ctttgagatt gttctgtaca 240
tccaccaacc atgaaaaggt gaggtaattt ggaatttaag aatacagagg ctccagaacy 300
aaaccagagc tagagtgtgt ttgaactttg gctctacaac ttgctagtcc catgaactta 360
ggcaagctac ttaacctttc tgtgcctcaa tgttctcatc tataaaatgg ggagagtaat 420
aataataata ataacaataa taatatatat aaagcactta ctagtaccct tggcacatta 480
gtgctcaata aatattagct actattaatc aatcaatcaa caaatatgta ttgagcatcc 540
acaatgttcc aggcactgtt ttagttcttg ggacagatca atgaacaaaa taggcaaag 599

<210> SEQ ID NO 111
<211> LENGTH: 599
<212> TYPE: DNA
<213> ORGANISM: Homo sapiens

<400> SEQUENCE: 111
aggtcatttg gcaaatgctg gtggagccag accttggccc caggtttgcc tgtgcttaag 60
ccacagtatt acagaaggct caagacccac agagatggtc gggccagcag cccgtagcac 120
ccagctgtca gatgagaaag gatttattta ttgatgtatg tattttacta gcagcactgg 180
cattagagtt tctttgtcag tgagggttgg agtgatgggt tgattgaaat gaaggttgct 240
gagatgacct ggtgggtcct gctaacagca gatggatgtc aaaacatttg cattcagggr 300
gagataaagt caaaactggg acaaatcaac tttctctcag ctccagggct ctaaggtcct 360
ttcttcgctc tcagccttgt tgggaaaaga gaagaacccc ctgccacatg gtctctctgg 420
tgtgagaagc tgacagtcca ctgctgagct ttccctgctt tgccacaaat agaggcacct 480
ccccacacaa ctccctctcc tgctggaatg ggaagagagg acactggctg ttaagaagag 540
ctctggggat ctcctgtcct ggggcaaact cagtttctgg agtcccctct tatagggct 599

<210> SEQ ID NO 112
<211> LENGTH: 599
<212> TYPE: DNA
<213> ORGANISM: Homo sapiens

<400> SEQUENCE: 112
cgcgtgcatg tgtgcgtgca cgccggtgca cacgtgggaa tataaacatc cttggctccc 60
cagctcctgt gtgctggatc gtgctgagtg ggcgcaaagt tctgcatgtg tccgaggcag 120
ggaggggcag caccagcaca cctaggcgct ctcatttata cattgaaagg cgggtggggg 180
ggacaaagga gaaggtttgg gaatggctgg ctgtgtgccc gtgtatgtat gggcacatct 240
cattgttgat atgtcttggg ggaaattgag ggaaattttg tgcttgggta tgtgtgcacr 300
catggtaggc gcccacactc aagtgtgcag agggggaagc tgaaagaaag tttcgagatt 360
ctgtgaacat tctcagttag aaaaaaatct ggcaactccc cataccacag gtgggtacac 420
attcaatgct tgtgaagttc atttcctgta ctagttacca gcccttgttt atacaggaca 480
caagatgtgc ttggtagcaa aagctctagg tctccggggt gagttgaggg agagtgtgta 540
tgtggagggg gtggggaggg agtgtgggca tcaccgcaca ggtgctcttg aagtacaca 599

<210> SEQ ID NO 113
<211> LENGTH: 599
<212> TYPE: DNA

<213> ORGANISM: Homo sapiens

<400> SEQUENCE: 113
tctgattcca gtaagccacc ccaataactc ctgcggtgcc cccacggctc acctgccaaa 60
gccactccca cctgatccca gactatccac tcatccctgg cctgtgactt gtcccgacct 120
cccagtgggt cctggcttct atcactgacc ttctaggtgg tgacttcaat cttgatatgc 180
tcttcccctg ctgaccttga cttcccatct ccaaattgcc agtgtcatat caatagcatc 240
acagcataat ggctaatgct tctgagctct tactacacct caggtactgt acatgttttm 300
gctcatttaa tcctcatcac aaccctagac agaaccctat gaagaatggg tagtagccca 360
tcttacgcgt gaggagacaa aagcacagag agatgaaaca gcctaccaag ggtgccacag 420
gtcatatgtg atggagtcgg ggaatcaaac ccaggccagg gagtgtcatc atccctcaca 480
tctggatttc tgctacagtc acctcatact actctatctt atttccagtc aactcccagc 540
agccagggtg aactgtatgt acaatggatc atgtcctcca ctgctcagag ccttccagc 599

<210> SEQ ID NO 114
<211> LENGTH: 599
<212> TYPE: DNA
<213> ORGANISM: Homo sapiens

<400> SEQUENCE: 114
agaggagctt tctcttggcc ctggcataag tgcccggctt tccatctgcc tatcatttac 60
cccctcaaca gtgggctttg atgtctaccc tccactacaa gaaaaagcat ttgtaggaat 120
gcctcttggt gtatgtgggg gactgcccct tagtataggg aaagttgtcc tccatacaca 180
aaggttttgt atcctgcaag tgctgtattt tctatctgtg tttggttgaa aaaacaaaaa 240
cctacatata agtagaccca ggcagttcaa gtccatgttg ttcaagggtc aaatgtatty 300
ctataaagca aaacaaagaa gcatattgct taggaatgtg tctgtcgtgc tcaaaatgga 360
gtgaatatca atggtctggt ggcatcaaaa tggccagttc tgtgacagta aaagaggttt 420
gtgtcttatt taatcttttg ataataataa cagctatggt gtatcacagc tttaccaagt 480
accagacact gttctaaggg ctttgcatgg ttcactcact ccttacgtca tccctcggtg 540
gcaggtgctg taattatcct tatattgcag acaaggacat tgagacagag gtcaagcca 599

<210> SEQ ID NO 115
<211> LENGTH: 599
<212> TYPE: DNA
<213> ORGANISM: Homo sapiens

<400> SEQUENCE: 115
cagtgtgtca cagccagatg agtgattgtt agggaagaca aagcctgtgt ttagagttat 60
gcaagtatag tggggagagg gcatcttatt gctgactcac gcccactggc aacccagcct 120
gattcatcta gactgctgca gaccactctg catggaagac ctctgctcag aggatctcag 180
cccactgcat ggcccaccaa gagcctctga cattcaggcc gcttggttct tctggattca 240
gttcttaggt ccccgaaagt ggtaaaggag agaggagaaa actagttcat tttcagccar 300
gagtggcccc tggcacacgg gacactgctt gctttggaca gaggccactc acaacaggct 360
tccccttctg ggtgtggtgg ccagcctgcc ctgacaacag tgcggcctga atctgtgact 420
cttagcggct gcttgggact gctgcaagac tctttggtct gtgacttgcc caagagagaa 480
gtttctgggc agaacgggga gctcaggaaa gaagaaagtt acatccgcac aaagtttcaa 540
ttataaagcc caataataac gatgaccaaa acaaaacaaa aaacgaaaca aaatgaaaa 599

<210> SEQ ID NO 116
<211> LENGTH: 599
<212> TYPE: DNA
<213> ORGANISM: Homo sapiens

<400> SEQUENCE: 116
cttacctttc atttcagagt tcctaggaca gggtctgtta catagtaagc cccaacaaat 60
atttttttga atatttgcaa gaatgttaaa tggaaaaagt gcaacatatg ttaatataca 120
tgatgattgc agcaatagga aagtgtctgt agggtggagc cttagccttc agatccctaa 180
actgtcgcca tgatttgtgg atgttataac tcctccccca cactgtaggt gagtgtggta 240
gaaccaactc ttcaatgtat caaaaacttg tttctggcct ccctactgag tccctgctak 300
atcctccagc aggaaagtac agcttgcaag gaagccccat gttggcaaga gaaggcatgc 360
tgtcctggat ggtgtgggca tgcctggggg ctctcgtggg tggggtgggt attggggtct 420
tctcttatgg agggagacca ggccagactt aaggcctgca gttcacgatg ggaagtacc 480 agcttgtgag ccaggtgctc tcacttgtac tgttcctaag ccttgttttc cgttcctgcc 540
catgctgagc cgaggggaag agcgttgtga gcttgtgtga gggggagggt ccctgaggc 599

<210> SEQ ID NO 117
<211> LENGTH: 599
<212> TYPE: DNA
<213> ORGANISM: Homo sapiens

<400> SEQUENCE: 117
aaaagaaaaa gaaaccctgc aaaacaaaaa acaaaccaaa acccaataaa aacccaaccc 60
caaacagaaa caaacaaaga atataaaacc atgaattaaa aattagatac aaaaagattg 120
acttgcatga gaagagaagg ggctttggaa gaagtctgca cagtaacagc cctgagctga 180
aaccttgtta cctttgtaat aaatctgcct ctgcctgatt tctcactgcc tccttttctt 240
gtccatctaa gtgccgccca acctctccag ggttactttt acagtgcttt ttgcagtttr 300
cagagtgaag cactttttgt taacttccta aacggtccca tgaagacctg tcctggtctt 360
tcctcttcaa cttatgggtg gaaacaaatt gttttgacat cactcggaga cactacttgc 420
tgcagtcagg acagagtcct ccattcattg tgacctgggg atttcctttc cacctgggtg 480
ctgaagctct ctgttgcagg aagcatgtct ggttatcaaa aattattatc ctcggtcggg 540
cacagtggct tacacctgta atcccagcac tttgggaggc caaggcgggt ggttcacct 599

<210> SEQ ID NO 118
<211> LENGTH: 599
<212> TYPE: DNA
<213> ORGANISM: Homo sapiens

<400> SEQUENCE: 118
cacagtggct gcagcagctc tgattaatgg gaaattccaa gaggaaggta gacctgggga 60
gaaaggagtg gtggctgcag agtccaactg cccttcttgc caaacacgga gattctgcct 120
tttgccaacc gtggaggctc tgcgtaggag attttatttc aggtgatggt gctcaccttg 180
gagggatctg ttactcattc ccatatcaga tcatagcttc aggctgcagg aggactcagg 240
caggctcctg accgcagctt ctgtgaatca ccagacaccg gcagtccggg agcggctagy 300
gtctgagctg ccagtgcccg gaagtgagag aggttatcca gtcttcctgc tgctcctcca 360
tccaacctca gcagcaccat gtgcctggga gcagggaaag gagagctgtt gggcagtcct 420
gtccagaaca atagtcaagg atacgagtgg ttttttgttc ccagaactga gtgcattttt 480
gtggacagtg attcattaca gaatacgcca gtactagaac cacagcatgt ctgtgcagtt 540
tactaggcac tgggacatag gttagcctgg ctgatcctct catgaccctg aaagagggc 599

<210> SEQ ID NO 119
<211> LENGTH: 599
<212> TYPE: DNA
<213> ORGANISM: Homo sapiens

<400> SEQUENCE: 119
attgaggcaa acattaactt gaggaaaaac aaaaagttgt acaagaaagg gcatgtaatc 60
ctgtacacaa cttggcacag acaggaacaa tattaacatc ataaatttta aaatcactgc 120
ataagaattt gactaacatt gtgacagaac aatattggaa aaggaaatgg actataaaga 180
agctaaaacc ctccgcatga cagaaggtca gtgtattatc taaaattgat agctcaaagt 240
acagcagtgt actcacacta tttagaaacg agtggctctg gaaagtgtgt atgttaagar 300
ggggtgttgt aaactagggt cagatgtctg tttctgatat cttgttataa ctttttatta 360
ctcttggcct tttaaattaa gataaatcat tacattacta aaaagaaata atttaaaaat 420
taggctgaga aaaaaattgg ctgttagagg aaaaaaatatt agtaattagt aaatttttgc 480
caaggcaaaa atccttaaaa gaattaagga tagcctatat aattaaaaag tctgaaggtt 540
tcattttagg tgccagtcac tgaagttttc agattaaaat ttaataaggc aaattccaa 599

<210> SEQ ID NO 120
<211> LENGTH: 599
<212> TYPE: DNA
<213> ORGANISM: Homo sapiens

<400> SEQUENCE: 120
tacatgtatg tatcccattg tctctaccca ttttgaagaa caaaactcat tctaggcttt 60
cctggccatc cctcagacac acccgggctg tgcactgagc accttcggac ccaggacact 120
gtgggtctca cttcatcctg tggctgcgtc cctccaccag atgtaaagcc ccagtagcag 180
gaagcacatt aacttacctt tcatttcaga gttcctagga cagggtctgt tacatagtaa 240
gccccaacaa atattttttt gaatatttgc aagaatgtta aatggaaaaa gtgcaacatr 300
tgttaatata catgatgatt gcagcaatag gaaagtgtct gtagggtgga gccttagcct 360
tcagatccct aaactgtcgc catgatttgt ggatgttata actcctcccc cacactgtag 420
gtgagtgtgg tagaaccaac tcttcaatgt atcaaaaact tgtttctggc ctccctactg 480
agtccctgct agatcctcca gcaggaaagt acagcttgca aggaagcccc atgttggcaa 540
gagaaggcat gctgtcctgg atggtgtggg catgcctggg ggctctcgtg ggtggggtg 599

<210> SEQ ID NO 121
<211> LENGTH: 599
<212> TYPE: DNA
<213> ORGANISM: Homo sapiens

<400> SEQUENCE: 121
tcttcaccag ctttggttaa tgaaacttga tggatcatag tgccgagcac tgtgcttcgt 60
gctgggggca caaagatgca ttttacatag tccctgctct taaggagctg agtgaggatc 120
tagtgggtgg aaccaatgta taagcagaaa ccattaaaat aatctagtca ctaatttcaa 180
cagttcccat gagggaagca tttaaaaatg atttcacacg cagagtttgg tccccaattt 240
tagaaaaaac ttataaatcc tgttaaaaca tggcttcagc taagaagtcc caatgaatty 300

-continued

```
taaatgttta tttaacattt aaagcagcag atttacgaga aatctattca aaatgttgaa    360

tttatagtag ttgtaccctt tccacatgtt ttgcttatag ctcaaattag ccttttttaaa   420

aaacacagtt gcttaatgat gctgaattaa tcattcactc agcaataatt aattcttacc    480

agtggaagca cgatgacttt tctcataaaa catggagaaa aacaactcat ttagtgactt    540

agtgacaaag tagtatgttg gaattttgat tgcagtaact gaagatgagt agggttatt     599
```

<210> SEQ ID NO 122
<211> LENGTH: 599
<212> TYPE: DNA
<213> ORGANISM: Homo sapiens

<400> SEQUENCE: 122

```
cttccttccc aaagattgat gccagtctat tccaacccag atcgttgcaa gaggccatga     60

cagcacctgc tggatgtctg gctaggttac cgatatggtc tgtggccatg catgaaacaa    120

agccaactga cccatgaagg gttcaatccc atgatcctga tctcaatagc aaggctccaa    180

ccaactgagc taattacagt ggagtcagat ttgattctgc ttacatggag acactcttag    240

ctgttcatac aacattctta aaacagtgtt gtcctaagat actatgacac aacacacttk    300

ccaagtttac taatgatctc atcttttaaa aatcttaatg taatgtagca aacagatgtg    360

tcccttaaga ggattaaggt ggaaattcat tagtgcaata ataccagtgg atttgtgttc    420

taaaactaac accaatcaat caacttagtg cacattctat cttagcacta cttagcttcg    480

agggaaacac cagagaactg aacagccagg tcttctccct cagggaagtt atctgagaac    540

aggggagaca gtgagaaccc ccatgtactg agagcctgac ctaaatcacc tgtaatcca     599
```

<210> SEQ ID NO 123
<211> LENGTH: 599
<212> TYPE: DNA
<213> ORGANISM: Homo sapiens

<400> SEQUENCE: 123

```
tttggagact acagaaaagc actttgaaga aatacaaatc acttttctca tcacccaaag     60

ggaaccactc ttaacacttt tgtgtcttgc cagaatttta acatctattc ataataatat    120

ctgaatactt tcccaagtca ttaaatattc ttggagcaca tcatctttaa tgacagttag    180

gtaatccagt ctatgtatgt accatgatcc atgtaaccat tgttcccagg ttccatgagg    240

gaaagtgctc tttcttcttg aatgttaaat ttgtccatgc ttggtactta atacatatty    300

gtaaaatgaa tgcatgaatg attgaactat tggaggttta ggtagttgcc aataaggaaa    360

atacagatag tgctataata catacctgca gaaaaataaa tattttttct catatttgat    420

tacttcctta agacgaattc tcaatgttta gttgctgagt tgaaggataa agatttcatc    480

ttggatagga gcagttaccc tcattttaag cattggaggt agctggaaag atggtctcta    540

aatccatctg ggcaggtgaa agagccaggc caagttatga agcccagctc caacctgac     599
```

<210> SEQ ID NO 124
<211> LENGTH: 599
<212> TYPE: DNA
<213> ORGANISM: Homo sapiens

<400> SEQUENCE: 124

```
gacactgtgg gtctcacttc atcctgtggc tgcgtccctc caccagatgt aaagccccag     60

tagcaggaag cacattaact tacctttcat ttcagagttc ctaggacagg gtctgttaca    120
```

```
tagtaagccc caacaaatat ttttttgaat atttgcaaga atgttaaatg gaaaaagtgc    180

aacatatgtt aatatacatg atgattgcag caataggaaa gtgtctgtag ggtggagcct    240

tagccttcag atccctaaac tgtcgccatg atttgtggat gttataactc ctcccccacr    300

ctgtaggtga gtgtggtaga accaactctt caatgtatca aaaacttgtt tctggcctcc    360

ctactgagtc cctgctagat cctccagcag gaaagtacag cttgcaagga agccccatgt    420

tggcaagaga aggcatgctg tcctggatgg tgtgggcatg cctgggggct ctcgtgggtg    480

gggtgggtat tggggtcttc tcttatggag ggagaccagg ccagacttaa ggcctgcagt    540

tcacgatggg gaagtaccag cttgtgagcc aggtgctctc acttgtactg ttcctaagc     599
```

```
<210> SEQ ID NO 125
<211> LENGTH: 599
<212> TYPE: DNA
<213> ORGANISM: Homo sapiens

<400> SEQUENCE: 125

ataagtgata acaatatata aaggcactca gtttcctaag gctgttgatg cccatgacat     60

gcctgcatag ccacactggg gtgttgtcca gttcccagtg agccagctct gcgtccgcct    120

tcagtatgcc tcagaagagg ttctcagttt acagtgaatg gcagtgatgc tttaatgtac    180

atgaaaatgt aagttgtata ccttggcacc cttataatta cagtcaacat tgattttcta    240

tgggcagata aacttattta tgaattaact gttaaagagg gaggaagatc aattattttty    300

tgaaaaaaaa ttatcaccaa tctgcaaaat atatacccag aagtttctct gtttttagag    360

acacatagta acaaatggaa tctacattgt atctatttac aaactggaaa catccaactc    420

ctcttcacca gttagttttg taatctagat gttaaaatgt tagactccaa ggaaaaatgt    480

ttagagttta atgttagaaa agaaaatctt aaaatttttg atcaacttga aaaaagggaa    540

aatgttaaac aacttgcagt tcaatataga aaggtattcc tagacttggc aaaaatgaa     599
```

```
<210> SEQ ID NO 126
<211> LENGTH: 599
<212> TYPE: DNA
<213> ORGANISM: Homo sapiens

<400> SEQUENCE: 126

cttacagctc cagacatcac atgcagacgt gacaatgtct aatggagaag gggcacattc     60

tctcccaatt ctactcaatg agaaaccctt tccttcctgg aggtccttca gcggccattc    120

acacagatcc cactggcaag actggatccc atgctgttct tacaccagcc atttccaaga    180

gaatgaggcc accataactg gcttaggcca attggtagga cccttcagga ggcagaacct    240

gggaacctag gcagggctct gccccacagga agaagcaggt gagcgtgtgg gggtggcggr    300

tggttgtcaa aacccaatat acagggaaca ttacaggaag agtcacttac tttacaatca    360

tgtcatttca taaacatttc ttgacataat tagggaacaa gaggcagcat gaaggagcac    420

agcttccctg ccattccccc cgccacagtg agacgcctgc aaggacacag acacagcctt    480

tccatcagcc ttcctctgtg gatcccccat ccacactgag ccagcaggtc aatggggaca    540

ggttccatgc tgttcagaga aaccagcact gtacacagtg gggccctgca tccactgca     599
```

```
<210> SEQ ID NO 127
<211> LENGTH: 599
<212> TYPE: DNA
<213> ORGANISM: Homo sapiens

<400> SEQUENCE: 127
```

```
gttttaagtc cctccaccta taatgtcttc attccctctc tccaccttga attcttctcc     60

tccttttagg ctccacttga aatcccttct tgctggacaa agcccttctt acccagttcc    120

cactgggcag attgctcctt ccttcatatt cccataagct ccctccacat acctttctct    180

tggctcaaat tctttaagaa atgtacactg ggtgcaaact gtgtaccagg cacatggtag    240

gcattgagta aatgtttgtt gagcccattt gctcccaaag catttctgac tgtgtttatk    300

aaaacactat tgggccatgc ctgtaatccc agcactttgg gaggccaagg tgagtggatc    360

acaaggtcaa gagttcaaga ccagcctggc caaatggtga aaccctaact ctactaaaaa    420

tacaaaaatt agccgggcac ggtggcaggt gcctgtaacc ccagctactc ggaggctgag    480

gcaggagaat cgcttgaacc cagggggcag aggttgcagt gagccaagat tgcaccacgg    540

cactgtaacc tggtcgacag agtgagactc cgtctcaaac aaaacaaagt aaaacaaaa     599


<210> SEQ ID NO 128
<211> LENGTH: 599
<212> TYPE: DNA
<213> ORGANISM: Homo sapiens

<400> SEQUENCE: 128

atgcctttgg gtgggagtcc tgggcagctt ccagatcaaa tgtaggatgc cccactacat     60

ttgaactttc aataaacaac acataacttt ttagtatcag cttatcccaa acatgacatg    120

agacgtactg atactgaaaa attcttcgtt gtgtatctga aattcaaatt gaatgggaac    180

gttttgtact tttatttgct aactctggct gccctacact gagatttgtt aagaaacagc    240

agcagctttt ggtgcccaat tcagaataat acaacaggag tggcttgggt tcaccactcr    300

aattccactc agtgagtgag gttggagtcc tggttcccct cgaggctgaa gaggcctgag    360

gagggaaaat agagctagaa agaccagtgc tcaggctcat cttcctggaa ggggtgattt    420

aggtagttgg ggtgatctag atagttggct acattggcta ccagaaggaa gggttaactt    480

tccactgcgc acatttctac cctccctctc tataattcct ccctgtctga ctgagttttc    540

tttgtatatt gtgttctgca gaagaaaaag gcaagattgg acacagaaga gggaaaaag     599


<210> SEQ ID NO 129
<211> LENGTH: 599
<212> TYPE: DNA
<213> ORGANISM: Homo sapiens

<400> SEQUENCE: 129

ctacttaaat tagaggcaga aagggcatct ttagggaccc aaaaatgatc tcctgaccta     60

tgctacgcta acaaagaaga ccaggggaag ttgctgatgc atgggctgct caggtcatcg    120

taactgcccc ggagtggact tacagcaaga ccatgtgtag actgggaaac tcttggttct    180

tatttgcaaa gccagagtaa ggggaccaat ctggataggc tggcaacttg gaaggattgt    240

gcatccgttt gaccactgga caaatattta gaggtttact gcatgtgcta agcatactty    300

agtggaaagc agatacctaa aacacacctc tgctcttaaa tagcctaatc ttctgctgat    360

ccatcatcta atacagtctg aggagtgctg gacagagggc gtggcgggag gggcactagc    420

ccagccccta aaccgggtta gggaaggccc tttgatgccg aggacctgtc tacaggcatg    480

tcggaacaca gcaggaagct gagatggcac gaagctgtcc acccatcttg cgcccaggct    540

cccttgtgac cagcggcatc caattttgag gctgctgggc ggatttagag aacgttgcc     599


<210> SEQ ID NO 130
```

<211> LENGTH: 599
<212> TYPE: DNA
<213> ORGANISM: Homo sapiens

<400> SEQUENCE: 130
gcagcactct cggggctggg gtctggcttc actgcacccc cctcccaccc cacaccacca 60
ccaagctgct gtctttctga gtcagcttct gtagggtaag tgttcacagc tggtgcagct 120
ctttgggaaa cctaacctcc cagtgagctg agcccctggt gcggccgcca cgcttgcttc 180
tgccccacaa gggcagtaag cacaggactt ctggatggat ctgggagcct gccccttggg 240
atttggcaaa acttcccatc tccttagcta cctgtcctta atcttatccc tgacccctcr 300
agggctttca agatagcctc tgttaacatc actaccctct gcctgtgtag aactttatag 360
aaaggctagg caaaaaatga gacccagaga tatggaagaa actggccaaa gaggggaaag 420
tgggctattt cttttttttt tttcttttt ttttctgaga cagagtctca ccctgttgcc 480
caggctggag tgcagtgaca gcgatcttgg ctcactgcaa gctccgcctc ccgggttcac 540
gccattcttc tgcctcagcc tcctgagcag ctatgactac aggtgcccac caccatgcc 599

<210> SEQ ID NO 131
<211> LENGTH: 599
<212> TYPE: DNA
<213> ORGANISM: Homo sapiens

<400> SEQUENCE: 131
aagatcacac cattgcactc cagcctgggc gacaagcatg aaactctgtc tcaaaaaaaa 60
aaagaaaaga aaaagaaaca gggtttcgcc gtgttgccca ggctggtctc aaactcctaa 120
actcaaatga tctgcctgca ttggcctccc aaagtgctgg gattacaggc atgagccacc 180
gtgcccgggc aatatctact ttgcaaatga aagctttcat taaaggaaga tctctccctc 240
atcctggaag ctctaagatg cttctggtgg gcgagtgggt gttacagagc tctccaggtr 300
gccttgataa gcagcaaggt atggggacca tttttataga ccggtgcttc tggtcttttc 360
cagcagggtg aatgtaatga cctgaatgtt ggtaagcaag cccacattag tctgccacca 420
gaataaaatt tcctggaagt ctccagtttt aactgagaaa ttcctataaa atttatattc 480
tactccatga aatattattt tgttttaaaa ataattattt tattatttat atttaatccc 540
aaatctaagt atatatatat attttttatg atatgaagaa gcaggtctaa ctttatttt 599

<210> SEQ ID NO 132
<211> LENGTH: 599
<212> TYPE: DNA
<213> ORGANISM: Homo sapiens

<400> SEQUENCE: 132
aacctgggag gcagagcttg tggtgagctg agatcgcgtg caccactgca ctctagcctg 60
ggcgatagtg tgagactctg tctcgaaaaa aaaaaaaagg aaaaaaaaac atacagtaag 120
gaatatatag cttcctgttc tggattccca cagtgactag ccagttatta aaaaatcatt 180
tgctgaaata attcatcttt tctccactga tttgaagcac tcttttaatc ataattttcc 240
acattgtggt atgtgtcttt tttccttgac tacctagagc ctcaacaaga ttagtacagy 300
ggtcctccat attcatgggt tctacatcca tgactccaat caatcatgga tcagaaatat 360
tcaggaaaaa aattgcgtct ctgttgaaca catatagact attttccttg acattattcc 420
ctaaataata cagtacaaca gctgcttaca tagcatttgc attgtattag atatcataaa 480
taacctagag attacattta aagaatacag gaagatgtgt acctaaggag ggggcattag 540
gttatttgca caagttatac acaaatactt ctccatttta ttttatttat ttattttttt 599

<210> SEQ ID NO 133
<211> LENGTH: 599
<212> TYPE: DNA
<213> ORGANISM: Homo sapiens

<400> SEQUENCE: 133
aacagatact actattttat ctgtcacatg tggctttgac tggttaaatg taatgctcat 60
ttttcttagt gtctggtttc gctgtcacat agtggaactg tacattactg ggaggtttca 120
gctctattgt ggatttactg acacatgctg aactaagctg tttatttgta tcatctcttc 180
tttttattga gatattatca aaaatgacat acttttatag tcattcagtt tttttaatgc 240
aacaaacatt tattgggcac ctactagttg ctgatgtcgt aggtacaggc atgcaaagtk 300
atttatgtaa gacatggtct ctgcatttcg ggcactttta acctagttga gggaggtaac 360
cataccatac aggctatgat accgatatta aatatgtgcc tagggcaaag caatgaattc 420
tttctggaag gaagtccaca atggagaggg aacacttgaa ctgggcattg tagaaagacg 480
ggtttcatgg tttttattgg tttgttgttg aatgggtgag ggggagaagg ctattatatg 540
cagagggaac tgtgtatagc atataagggg taatgtgccg ggcacggtgg ctcatgcct 599

<210> SEQ ID NO 134
<211> LENGTH: 599
<212> TYPE: DNA
<213> ORGANISM: Homo sapiens

<400> SEQUENCE: 134
acactgaacc agtgaaagag aggaaatcag aaaagaggac tacccagaag ggcctctggt 60
atatgttctg ggaaagacag ttcctacagc ttgaaggtct ttacatatct ccaagtctcc 120
aagtggttca ctgagctaac attaatctaa tttaattctc aaccagattt gaaaaaggga 180
gattaattgg ataaaaatgt agcccatttt ccttcattta ctcctatttg ttttcaatgt 240
ctctttcctt ttctgtctcc tcctatccat ttttctctcc ctgttactct taagtagtgy 300
ctcctttccc catccacccc atctctagcc atcttccatt ctatttccgc taagttgctt 360
tcagttgcag gatgtccata ccttgttggc taaactaatg tttctcagct ttgcatattc 420
agagcttgat atttttcaaa tgggaagaag tgattatgct ctggtagtgc tgattacact 480
cacaagatgt taattgactt acggtaatgc cgatttctgc aagttctgtg tatgtatttg 540
atctacataa caaagggcta aggagctaag tgatgatagg gagaatggta gtaatgaat 599

<210> SEQ ID NO 135
<211> LENGTH: 599
<212> TYPE: DNA
<213> ORGANISM: Homo sapiens

<400> SEQUENCE: 135
tggtctcaaa ctcctgacct caggtgatcc acctgccttg gcctcccaaa gtgctgggat 60
tacaggcatg agctaccgca cccagcctaa agatgtaatt atttttaagt tattcatctc 120
agtatatgaa tgaaattatt ttaagttatt catctcagta acgtttaggt gaatgctgat 180
aataactcag taacttttaa gtgaatgctg ataatcctag catctcccta aattgttcaa 240
tttacaccat aaatttactt ttcccacctt ttaaagggat aatgcaaggg attctaaaty 300
gtggcataag tctggaattc cttagattac ccctttagga agcgaaatta tgtttccaag 360

-continued

```
ttcagactct ggcttaaact tcaaattgtc ccaaaaatgg actagggaaa atacaaaaac    420

tttctacacc aacagatatc tatcttcaat atgtgaagtg tatctttaaa aatacaaaac    480

agctagtagg aaaaacctcc aatataatgt atacctaaag tagtttgttt tctgtcatca    540

ttaagatcat aatgaggccg ggcatggtgg ctcacacctg taatcccaac actttgaaa     599
```

<210> SEQ ID NO 136
<211> LENGTH: 599
<212> TYPE: DNA
<213> ORGANISM: Homo sapiens

<400> SEQUENCE: 136

```
tggggagtta ctgtttaagg ggtacagagt ttcagatgga aaagatggaa gaattgtgga     60

gatggatggt tgatggttcc acagtatctc agtttgttta tgctgctata acaaaatacc    120

acagactagg tactttataa agaacagaaa tttattttct gatagttcta gaggccgcga    180

ataacaagat caaggcacca gtagatctgt tgtcagggga ggccccaatc cctgcttcta    240

agagggagga atactgcgtc cccacgtggc aaaaggtgga agggcaaaaa gcgacagtgy    300

gtccctgaca agccctttta taacagcgtg aatttatgca ggcagaactc ttatgaccta    360

aacaccttcc agaaggcccc acctcccaac actattgcac tggggattag gttttcaaca    420

caaattttgg gggacacatt cagaccatag caaagacaga cacaaaacac cacatattat    480

gtcactccaa ttatatatga gaagtcaaaa gaggcaaatc tgtagagata gaaggtagat    540

tcgtggttgt ctgggcctca gaaggaggat gaaagggagg caaaatggag agtgactgc     599
```

<210> SEQ ID NO 137
<211> LENGTH: 599
<212> TYPE: DNA
<213> ORGANISM: Homo sapiens

<400> SEQUENCE: 137

```
ccaaactgta tcagccagtt atcagttatt gggtggtttt ttttgttgtt gttttgtttt     60

gttttgtttt tgggcagaaa atgcctttct agccaagtct gaacctttc ttctaaggac    120

ctccctaaga tgctattagc ctgtctatgc atattttcaa aagaacttct gctcctgcca    180

ggggctctcc tgaaggtctt ccatgcaagt ctggtttcct tctcccttac atctctgggc    240

aggcaaagaa atctttcttt ctgactagct gcaaatccgg cttttgtggg aatactctty    300

aagaaaaagc aaactaattt caaagacaaa actaggttca aaagtgaata tttatttaca    360

aagaggagat aaatcacaaa aatggcaact taaaaaaatt aacaaatacc acaaaattca    420

gaaaaacaat gtaatatttg tattaattgg ttgcctaaca catggctgtg aaatgttttc    480

ccctacattt tttggccatg ctatactctt tttttttttt ttcgtgctat actctttgat    540

catccctccc tattctgtga tattttctaa aataggtaaa taattcagtg cttcctata     599
```

<210> SEQ ID NO 138
<211> LENGTH: 599
<212> TYPE: DNA
<213> ORGANISM: Homo sapiens

<400> SEQUENCE: 138

```
acaaaaaaag ctagggctct gtttacatag ttttattggg tcatccctgg gattgcaaac     60

acctagtata tcacttgatc acaaaactga gctagttttt attcagcacc tactgtgtac    120

atcatcatct cattgaattc ttccatgaac acttcataga aggtaccagc cttatgtcca    180

tttcacagat gatgaaaact gagggtcaag caggtagagg gaccaacagt ccagtttgca    240
```

ggaactgaag ggtcaagatg caggactttt actgaccagg ggaaactagg aagcttggtm 300
tccctaccca gcgaccttga tttgcatcac acatgccaaa gtttaaacac aagtttgatt 360
aactcaaacc cccgtgggat tttattctgg ctttctgatc attgcagcca atataaatgt 420
cttctttggg tactttcagg atacaatcca aacataacct cgaatctagc tcatgtagtc 480
ggggcctact tgagactgaa gtacttgaca ggcagagaac tcaaaatgga tgggttttct 540
tcagcaagaa aaggaatcca ggctggggaa tattcctgga ggacgtcctt aggaacggt 599

<210> SEQ ID NO 139
<211> LENGTH: 599
<212> TYPE: DNA
<213> ORGANISM: Homo sapiens

<400> SEQUENCE: 139
atgattcgcc tgccttggcc tcccaaagtg ctgggagcac ttagcttatc ttaatgatac 60
tgcaaactca ataaatccaa agcagaattt gacctgtctg catgccccac ccccaaccct 120
gtagtaactg acatcatcat ccacccaaca ataaaaccta aaaacctagg aggattcttg 180
gactctgctg cttcctttcc ttccttaact aattcttcac caagctgggt tgattgtacc 240
tcttcatctc ttttcctcct ttctttggcc acttcctttg tccacgctag atcacctacr 300
ccattaggtc ttaaccagtt cactgcatta gcctggctgg tttctcactt gatattcagt 360
acccccatct ccaatacatt ctgtatgtaa ttgcagggat gatacatttc aaagcataaa 420
cctgatgaag cctggtgcag tggctcacac ctaaaatcct agcacttcaa gaggctgagg 480
caggaggatt gcttgaaccc aggagttcaa gaccagtctg gcaacatggt gagaccctct 540
ttacaaaatt aaaaaagtag ccaggtgtag tggtgtgcac ctgtaggccc agctactcg 599

<210> SEQ ID NO 140
<211> LENGTH: 599
<212> TYPE: DNA
<213> ORGANISM: Homo sapiens

<400> SEQUENCE: 140
agtaaagatg tagaaaaatt acacaagaat attttcagta gaattgagct ctgtaacagt 60
actgggaaac attcattttt aagatgctgg attccacaaa ttcactgtaa tagaattagc 120
ttgtcattta acacaggaat gtaggaaaca caccaggaag ttctacaggc ggatccttta 180
actcttattt agagtctgat ggtgtgctgg gatccattgc gaggtgggct ggtcagctac 240
aggaccttcc ttccagggat gattgtgttt ttgtgaaccc ccatggccgt aatccagtay 300
gattaccagc cacaaatcat cagacttctt ctttgctata tgaatatttt tattacaaaa 360
gtcagataac caagtaaaaa tgctttaaaa gattaacagt tgggaaaatg ggtcagaatc 420
acccacaatc tcaaaaattt agtgtaacca ctattggaac aatggcttag ttccttttgg 480
atgttttgct tgtgcatcac ctttgtggtt ttattgttat aaattagatg ccctccttta 540
ttttcccctc ttaaaaatat cagaagcagt tttctgtaag gctcctaatc atcatttcc 599

<210> SEQ ID NO 141
<211> LENGTH: 599
<212> TYPE: DNA
<213> ORGANISM: Homo sapiens

<400> SEQUENCE: 141
tctttttgaa aagaaatcag aagatcagca attcaaagtc tacactcctt catgccaaca 60
atatactaga actaacaagt ggatacctta gagcatgtac tcttcaattt gccacagttc 120
ctaccactct ttattaaaac ccatgatata cccaatacca ttcatttaag gcacctgctt 180
ggagcctaca gagagcaaaa ggcttgaggg aagaggaaag agcatggtat gattagatat 240
gcattttaaa actctggctt cagtgtggag aattgactga agggagttag agagaatgay 300
ggacggaaga aaaccaatta agcatttatt taattggttt aactggaaat agggtggctt 360
agactagcta gagtagtttt agtggcagag ataagaaggt gacaaatgag gtaatattta 420
tggagtgatt atcaacagaa atggataatg gaatggacgt gaggaggaaa agggagatgc 480
caaagattcc ccttcaggtt tctgacttat gttaacaagg tagacacaag tgccatttac 540
agaaatgggg aacgttggag ccagagcaac tttagcagta ggaaatgagg attaagagt 599

<210> SEQ ID NO 142
<211> LENGTH: 599
<212> TYPE: DNA
<213> ORGANISM: Homo sapiens

<400> SEQUENCE: 142
gtagagccag gattccgatc tatgcagtat gactctagta tttatgttaa ctacttatgc 60
tgtgtaactg ctcatctatc actaagttac tgttttcatc aatataaaaa aaaatgactc 120
caccttcacc atacacatag atttcaaata tttttcctta tgtcaacact ggcctaaatt 180
acttaaaaca tttcatgtga acctaattta gtgtctacct ccacatatta gcctccatgt 240
gaaaggtaca tagtaaacac acaataaata tttataaata tctgataaag gaattaaaty 300
tttcccattc cttcattcct ccaaaggtaa tctttcctac tctgagtcct cccctctccc 360
ctacttcaga acttcagtac cttcttttca acattttcta ctttacccac tgtcgtggcc 420
agcctccaag atggccccca atgaccctca cctcctgcca tttacattct tgtgtagtcc 480
cttcccacaa tgtgtggcca acagaatact ggaaaaatga tggtatgtga cttctgaagc 540
taggtcataa aagtcaatgc agcagcttgg tcttttgtat tacatgctct gaggcaagc 599

<210> SEQ ID NO 143
<211> LENGTH: 599
<212> TYPE: DNA
<213> ORGANISM: Homo sapiens

<400> SEQUENCE: 143
gcagtggccc aatctcagct cacttcaatc tctgcctcct ggattcaggc gattctcctg 60
cttcagctgc ttaagtagct ggaattacag gcagctgcca acatgtccgg ctaatttttg 120
tatttttgta gagacggggt ttcaccatgt tgtccaggct ggtcttgaac tcctgagctc 180
aagcaatcca cccaccttgg cttcgcaaag tgctgggatc acaggcatga gccactgcac 240
ctggcccaac cctgttcttc agaatcaccc tgcacacttc ctgccgcacg gcctttgcay 300
tggcgatttc cacagccagg aatgctggtc ctccagaata tttctaagca tggttcctca 360
cttccttcag gacttttctg gaagcgcttc tcagtgaggt cttcctcgat gatcaatcct 420
atataaaata gcaacctcca cctctgctgg tattcagggg ccagctcacc ctgctttaag 480
tttttcatag taattgccaa taccatgaat tgtcttttga ggggttttct gtctccccgc 540
aacttgaatg caatcttcat gaggacaggg actttatccc ccaccccacc cccactttt 599

<210> SEQ ID NO 144
<211> LENGTH: 599
<212> TYPE: DNA
<213> ORGANISM: Homo sapiens

<400> SEQUENCE: 144
aagcagcagc ccctgtaagc acacgagaca atcccaagtg tcagtgggaa ggagatccct 60
ttcctgatgg ggctgcctgt gtccagtccc tcccagcttc cccagggccc tggggctctg 120
caggcattca gaagtggaag ccagccacag cctgggactg aagaggttaa tgtgcatctg 180
cctccgaatg ttaatgtgtc taggtgatgt cagtgggagc catgaagaag ggagtgggga 240
gggcagttgg gcttggaggc ggcagcggct gccaggctac ggaggaagac cccccttcccr 300 actgcggggc ttgcgctccg ggacaaggtg gcaggcgctg gaggctgccg cagcctgcgt 360
gggtggaggg gagctcagct cggttgtggg agcaggcgac cggcactggc tggatggacc 420
tggaagcctc gctgctgccc actggtccca acgccagcaa cacctctgat ggccccgata 480
acctcacttc ggcaggtgag ttgactggga gccctccctc ctctgggctg tgggtggaaa 540
atgggaaggt ttcacccctg agccaaactg cttgggaaac tttatcacag ttcttgggg 599

<210> SEQ ID NO 145
<211> LENGTH: 599
<212> TYPE: DNA
<213> ORGANISM: Homo sapiens

<400> SEQUENCE: 145
aacagaagct gagcaagaga acatgttggt ttggataacc ggttgcacta tatctgtgag 60
ctctcaaatg tcttcttccc aaggcaagag gtggaagggt actgactggg tttgtttaaa 120
gtcaggcagg gctggagtga gcagccaggg ccatgttgca caaggcctga gagacgggaa 180
agggcccgat cgctctttcc cgcctctcac tggtgcgatg gaaggtggcc tttctcccaa 240
gctggtggat aatgaaaaat aaagcatccc atctctcggc gttccagcat cctgtcaaty 300 tccctttgc tctagaggat gcatgtttat ttgaggggat gtggcactga gcccacagga 360
gtaaaagccc agtttgctag gaggtctgct tactgaaaac aaggagacct ggggtgggtg 420
tggttggggg tcttaaaact aataaaagct ggggtcgggg ggcttttgca gctctggtga 480
cattctctcc acggggcaca tttgctcagt cactaatcca gcttgagtgt ccgtgtgttc 540
tgcatgtgca ggggtcattc tagtgcccgg tgtgttggca tcatcttttt gctctagcc 599

<210> SEQ ID NO 146
<211> LENGTH: 599
<212> TYPE: DNA
<213> ORGANISM: Homo sapiens

<400> SEQUENCE: 146
acgaggggaa ctttcttttc ctcttcctta agcctgggga tgtggccaga accttgggga 60
gctgtggagg ccactgtgag ctgcagacag agtccaagaa gcgggtgaag accctgcggt 120
ccatctcttt gctcctttcc ctcttcccac atttaacaat tagtttctcc catgggggcc 180
ccatcaagtc atctcctcaa acctggccag tgcttcatcc actgctgcct tatcttctcc 240
ccagaaaata cttcttcccc aactgtgagg attatgctcc gaaactaccc cccagcaccy 300
ggtagacttt cacagctgag agacattgac ctcaaagttt aggttgcaag tgagtccaca 360
gaaccacttc cgcacattgc tgttcacaag agaagcaaga agagcaccaa acacggcaac 420
tggcattggg tttgtgtttg cttgttcctt tctgaatcat cagttttcat ttaattaatt 480
aacttatttt tatttatcta tttattttga gacaagatct ggctctgttg cccaggctgg 540
agtacagcgg tgtgatctca gctcactgca gcctcgacct cctggactca agcaatcct 599

<210> SEQ ID NO 147
<211> LENGTH: 599
<212> TYPE: DNA
<213> ORGANISM: Homo sapiens

<400> SEQUENCE: 147
tttttagaaa gtctctcttg ctgtgcattt aactacttca gtaaaaatac tgacaaggag 60
ccaaaccagg agaaaaaatc tacttattaa actggaaata atgtatgtta ggttgctgcc 120
ttctctagta ttcatcggga aagataatat tgaaaacgta catactcagt tgaaacctaa 180
ttctcatagt ggtttctgta ttaccacccc tccttaaaag acaaacatga attatcctac 240
ttcgtttcct tgagttgcca tcagtcccaa attggaggtt ttgataccac gaacccacar 300
cgcacaggta tttgccctcc taaaacttcc tatattccag tacagcccct tctgtctgac 360
caatgcagct gtacctttgt cttcctttcc tctaagtcat ctgctctggc taggtgtacc 420
gtatatcctt ccaggagccc atttccatac tctgaaaatt cctcctaacc ttggaagcat 480
ttccctcatt gttccttgtc ttcattactg catcattagc atcaaccttt tttgtagtga 540
ataaaaaagt agagactact tcttaacaca tgtcctacgt agcagttccc aaattattg 599

<210> SEQ ID NO 148
<211> LENGTH: 599
<212> TYPE: DNA
<213> ORGANISM: Homo sapiens

<400> SEQUENCE: 148
tttatttctt tcctagtatt gattactact ggaatcctca tattcatcag tctgctggtt 60
taatgcctgt tccctttact ggaatgtaag catgattttg gtctttttct cctctgtcct 120
gagtacccag aacaaagcgt ggcctatgga ggacactaaa tgaacgcatg ggggaaaaac 180
gggttttatt gcagagggag accctttgtt tcatacagat cgtttgtaaa cttagatatt 240
ttattagcaa caaattatga tagagcttac aaactccttg agaatcgctg cggtagtagr 300
tgggggtgga gcttctctag gcagcatttc agtgtgtcct agcttggatg ctgtggcttc 360
ccgagctctg aatctatact gcttactctg ggcttatgga gtgtgtagca gggaatcctt 420
gttgaaggat ccccaaaccc ttgatagcca tggacagccc acagtggtca tggagccgga 480
gccagaatgt aattcccagt gtgaccagga gctagagttt aagtcaaggc agcaggtata 540
ctcaggtgca ttttccattc cctttgaggg aggggtggag gtttgagccc cctccacat 599

<210> SEQ ID NO 149
<211> LENGTH: 599
<212> TYPE: DNA
<213> ORGANISM: Homo sapiens

<400> SEQUENCE: 149
catccattat ttctaatcaa cacagcctct cttcaagata agtagtatat agctcccatt 60
ttacagatga caaacttaga tgccagataa tttgcccaag ctcctaccat tgtagtgtcc 120
aagatacata aaatttgatt ttaaagtgtc agactccaaa ggctgtgctt tttctcttgg 180
cctggctgca gtgtagcagg ggagcacctt ggaagaggca tgtgcttatt gcagttgacc 240
atgcttgagt acaggatttt gagagatgga ggcaaaagaa ctttgaagaa ggtgttggar 300
gggtccggag acacaaagaa atacaaaaat actgtatgca ctcactaata cagtccctag 360
atcaatgatg tgtagaaagc ataatgctca actgaaagga gaaaaaaatc cttctcatag 420
cttaagagaa cctgaagtgt cctctcagaa aaacatattt gaggccgggt gcagtggctc 480
acgccagtaa tcccagcact tcgggaggct gaggtgggca gaccacttga ggtcaggagt 540
tcacgaccag gctagccaac atggtgaaaa cccatctctg ctaaaaaaat ttttaaaat 599

<210> SEQ ID NO 150
<211> LENGTH: 599
<212> TYPE: DNA
<213> ORGANISM: Homo sapiens

<400> SEQUENCE: 150
ggaggacagt acatcctatg tgtgttcgcc aaaaatggga aaggtgggta tttaggcaaa 60
acaaaataaa aacctttgga accctttaag aagttacata ccttttaaag gtagtatagt 120
ttctcaccaa gtgatgcatt ttagcatgac acttcttgcc agaaattttg ggataagttg 180
gaataaatgt gtttaaaaca tcatccaccg ccctttttaa attttgtcta aggaattact 240
taagtatagt atttctgaat gtgcctttgt gagtacagag accgtccgtt ctaggaagar 300
gctatccgtt ggatacaaac aaacagacgg tcagctttag tcattaggga agtcaaagtt 360
cctcctggaa gtcccaggag cagctgttga gatttcatta gcatcaatat tgcacagtgt 420
agagttgagt ggaagagatt ctgggacttg ggagaggaga caggggaagg tacccaggcg 480
acgcagaccc acgttagtcc aagagcgcag gtttacacat ctgcattccc tagttttctc 540
cgtctgtatg tttgtgctca tgtggctttg gctgttttgt tttttgtttt tctgtaagc 599

<210> SEQ ID NO 151
<211> LENGTH: 599
<212> TYPE: DNA
<213> ORGANISM: Homo sapiens

<400> SEQUENCE: 151
tggggatttt ttggaattgt ggtttttaag cagtccacct caacagatat tgttacatat 60
ctcctcaaac tgaacaccta tgaaaaaaat cttaatctct ctctgcctga ttcctctgtt 120
tgctctttct tctgcaccca aagagaagat taaataaact aggccccctg aaacaagtaa 180
gggaggcaga aatgcgaatc catgcaaagt gctggtaatg actaaagcga tccaagagtc 240
ttaaaggagt caagagaaac cactgtgctc ctaggcatat ccataacctc ctacaagaak 300
caatacactc tgctgccttt catatccacc acaaatcttt cctttccgat tatcggtgtg 360
atgtgcatag agattttaaa gaacagttaa ggcagggcat gctggcccac acttgtaatc 420
tcagcacttt gagaggctga gattatattt gattaaggtg acaagaggaa aatggaagca 480
atacctgtat atattaaaaa gggagagaga aaataaagaa ggcctatgta gcctgctggt 540
caacccagat gcagaattca accgaacatg ctcatgtgct cattaaggta ccataacat 599

<210> SEQ ID NO 152
<211> LENGTH: 599
<212> TYPE: DNA
<213> ORGANISM: Homo sapiens

<400> SEQUENCE: 152
cagtcagtga ggtgctgttc tgacgtgcca gcccacaggg cccaggggcg cccgagctgg 60
agctgctatt ggtagtggag aggctgcgta ctgggggggt cccgctgctt cccagggcct 120
cgcctgctga cctgggaaga aaaggcagaa attagcccca tccagcttcg cccgtggcct 180
ctgcaggtgg cagcccaagc ctgggcagca ggattgggta cagatgggca tggggcaagg 240
gcccagcaaa ggctagggtg gccctgcctg cagaccactc tgtagcatcc agaccagcgr 300

-continued gtccttaaag atgtgaggtt cacccccacc agacctggca cctgcctggc tcagggtggc 360
tcggggaggg caggggcagg cagtgaggag cgggtgccta ctttggcggg gcaggcagga 420
tggcctggta gttgtggtgc tgctgctgct gctggttgag gatctgcagc tggaggaaga 480
gctgctgctg ctgcaggatc ttggcgtagg atgagtccat ggggggtgcc cccctgtcct 540
gcttctggtc cggggggatg tactggtggt acttgagctt cttcaccttt ggcttcagc 599

<210> SEQ ID NO 153
<211> LENGTH: 599
<212> TYPE: DNA
<213> ORGANISM: Homo sapiens

<400> SEQUENCE: 153
aaagtgatca aataattcct ccataccaca tacctcaatt ttctagcata attctgagtg 60
atgcagagtg ccacacctat cagcagaatg cttattttaa aaatgtccct gatactacca 120
tgtacttttc ctcctcctga ttttcaaatc atcccagtat taacatccat ccctaaggaa 180
tctcactagt agtttcagaa aaatgaattt gatttgtttt acacactgtg ggacagacaa 240
caaacaagac cccttttcct ctgcctcttc gatgcttctc ctgggcatga aaacagcctr 300
aactgtggca acagctgggg atcattaaac tgacagaaat agcttaggag actccaatgg 360
tgtgtgaagg cgggaggaga gcctgagtat cagattaaaa aaaatcaaaa gggcaaaagg 420 aaagggggc agggcaggga agcctaagga gtgtatcaca cctaaatttc ctttaccaca 480
gccaagaaga tgcagtgaag caaatgacag gatacatgaa tgcggcctaa attgcttagc 540
ctcctaccta ttcctagatg gaaggtttag tcaaacctaa aaatgtgggt ctcaatgaa 599

<210> SEQ ID NO 154
<211> LENGTH: 599
<212> TYPE: DNA
<213> ORGANISM: Homo sapiens

<400> SEQUENCE: 154
ctggggcaga gggccaactg caaggtttgg ggaaagcctt ttctgggctc ctattggaaa 60
ggggcactgg gtggatcata gccaaacttc tttgacacac aggggcagca gttgagagat 120
gatcacacag agctttcagt aactcccaaa tggactagag cgtatgagag atgataaagg 180
cccagagaga gaggatttgc ccttgcctta gtccccaccc aaactcactc actgatgaag 240
tatccactga gacttaatgt ctttgatagt gtaacactcc acttaaaagc aaacaagtgm 300
tattttcttg aaacctacaa ttttagttaa aaaaaaaaat tgttaaaaaa aataggagtg 360
gggatggagg acagatcact ctcaaaccag accctcatct gccctggaat cactactgca 420
ttcccactgg taaacatttc tgtctcttgg taagttgccc agaaatttaa aaacatttct 480
aacacagcca cttgtttgtt tgctttcaag agaaagaggt taaaaagaaa catctactcc 540
caggaagagg gcaagctcat aaaatgatag tcctgctaat atatgaccaa aaggagaat 599

<210> SEQ ID NO 155
<211> LENGTH: 599
<212> TYPE: DNA
<213> ORGANISM: Homo sapiens

<400> SEQUENCE: 155
tgggcaacag agcaagactt cgactcaaaa acataaaata aacaaaagac acacacacac 60
acaaaaaccc tgtcttaaat agctgccatc tcttccagca atctagtgcc agggtaagaa 120
gtgtctgaat ttctctcttc cagcagatcc atcccctgca gggactccag aatgttctcc 180
acacaatacc tggagctctc aacctttctt ggttcagaca cacacataca caccccttga 240
gtaactcagt atcattttgt agttcacaga aggatgtagt ccctggcatt ttggtttgcr 300
ctgtagaatc catagccttg tcactttgtt atgctctgga aatgtactga tttcttactt 360
gggaggaaac ttgtgtaagg agatgtgcaa accaccctga aagccatgtg catcctcacc 420
tcttccatta ccccctccat gagctcgaag cgacattaag tagagggaaa tgcttttaac 480
aaatgctgct catgtggatc tgtcagctat tgcttgccta gatttgggca cccatgaagc 540
agggttggaa tggatcattt tgaattgctt ctttgcagac accccttcg cccccatct 599

<210> SEQ ID NO 156
<211> LENGTH: 599
<212> TYPE: DNA
<213> ORGANISM: Homo sapiens

<400> SEQUENCE: 156
tacaaaaaac tacctgggca tggtggtggg tacctgtagt cccagctact cgggaggctg 60
aagcaggaga atggtattaa cccaggaggc ggagcttgca gtgagcaggg attgcgccac 120
tgcactccag cctgggcgac agagtgagat tccatctcaa aaaaaaaaaa aagaaaagaa 180
aagaagaaaa aaaatattct ctctgcaaac tgggcactga taatcactcc atctcgtctt 240
cgatgtgtcc attcattgct gactccacag gctcaaatca tcctgttaaa attattaaam 300
tcccaaagaa atctggaaaa ctcaaaagaa atgtctaagt gtttagaaaa gtagcattta 360
cataattatt atacattgta tataaattct gatagtagat aattagggtt tccaagatag 420
gagaagaaaa tattgacaat tctcttttat tcatatttga caggatttgg ataaagctcc 480
tattgtcgtt tttttcataa cctagaactc ttctaaaaga attttcctca aatttaaaag 540
tgaacttttc taaataactc aaatgtgtcc attctactcc caaaggattt tcttttcct 599

<210> SEQ ID NO 157
<211> LENGTH: 599
<212> TYPE: DNA
<213> ORGANISM: Homo sapiens

<400> SEQUENCE: 157
ctttgggaag ccaagcgggg aggatccctt gagcccagga gttcaagacc aatctggtca 60
acaaatattg actacccact acatgccagg tgctgtctgg gtattgagga ttacagtaaa 120
taaaacaaag ttcttgccct caggaagctg gagacataac ttaaatgaac aaagtcatag 180
atgtgagaaa atgtgaacta tgttctaaaa gggcaataca gtttagccaa tcacatggtt 240
caagtacaag caaattaata tggcagtgga gttagactgg attggaaaaa agaaatatgm 300
ggttgtgggg ggaggttaca aagctacttc attaggcaaa gtataatgtg ttgatatcct 360
gaattggggt agttaaatgc aaagaaggga acgaccatac aatgtacctg gcacagaaca 420
ggaactcaaa tctttgtcgc gttaataatg aatgaagaca ggatttatat aagatagaat 480
gtgtttctgt ttgattgttg gggatggagg agagacagat gtcaaaaatt actaaaggtt 540
ttaagccagg gcagtcatta caacagtatt ctgctaatag aaatagggaa aagaggagg 599

<210> SEQ ID NO 158
<211> LENGTH: 599
<212> TYPE: DNA
<213> ORGANISM: Homo sapiens

<400> SEQUENCE: 158

-continued

```
aggaggagct aggaaagaga gaaggcaatg aaaaggtcac agaactgaat atactcaaga     60

aaaacaggct gctccaaata aatgaataca gactgggcca gtgacgtttg caatcccact    120

gcaaggcagc catggccagc gtcgtcctcc acctgacctc tggctgctgg agaggggcca    180

ctgcccacat ctcccaccac cggggagctc aagcagccag cacctaagca actagggtag    240

catccccctg gcttccctgt gccagagcag gaggcatccc gtggcccagg agagagaccy    300

tactctgcgc agccctagca ccttggagct ggggaagcat ctggaagcac acactcacct    360

gggtggggga tgcagaggtg gcactgagca gtggttcgct gactcgggcc tccaggggtg    420

acggcacaga accctgggac tcatggctgg caggctgctc gggggataag gcatcgctgc    480

tgtcctcatc gaaggaagag ctgtctgcta ctttgggata gttcacctgg cccactgaaa    540

cccaaagctg gtgtgagatt ccacttccag cccagggaac agatgagcag ggacaggcc     599
```

<210> SEQ ID NO 159
<211> LENGTH: 599
<212> TYPE: DNA
<213> ORGANISM: Homo sapiens

<400> SEQUENCE: 159

```
gcatcactgc actccagcct gggcaacaga gtgagactct gttgcaaaaa aaaaaaaaaa     60

aaaaattaaa tttaaagatg agattgatag atatctgtgt tataaagcaa gttttataaa    120

atgttacagg tagaatctaa gagatgggca cgcaggtatt cactgtaaag ttcttcctac    180

ttcttttttt ttttctttct actttacgtt taaatttttt cataataaaa tgttggaggt    240

aaaaatccca aagggttttt ttgttggcag aacttggtaa ggcaattcta aaatcatggm    300

aaattaaaag ggtaatagcc aagacaactt tgaaaaagaa aaaggtaagg agatacgtgt    360

cctaacagac agaaagacta attattaggc aataactaaa ataaggtagt actgacacag    420

agatggacag agagaccagt caaagaaaag agagcctaaa aactaactca tgcacagaca    480

gaatacagca ggcattaaag atcagtagga aaaagtagaa ctattcacta agtggggatt    540

aacagcttga attagaagaa aatacagaat atctttaact tacaaggaaa atgaatact     599
```

<210> SEQ ID NO 160
<211> LENGTH: 599
<212> TYPE: DNA
<213> ORGANISM: Homo sapiens

<400> SEQUENCE: 160

```
atgaccagtc cataaattac ttggcctttg ctcacttcac ctcctcttga tggttctaca     60

gggaatcagt catccaaata tttcctcttc ccccaacaaa aaggataaca gtaacaatat    120

aacactgcct cttcaattac aacagtaccg gccccttcac tactggcttc atttctcacc    180

attcccettt attcacactc taatcactgg taccagttat gcggctcttt actgtgactg    240

cctagaattg cctcttcttc cccatcctac ttccttctct ttattatcca tccccttcgr    300

atgggctagg cttccacaac atcccaagat tgcttttatc actgcttact tttactatta    360

tcatggattg atctcccagt agatggtaaa ttcactgaaa ggaactccat tctactggtt    420

tttttgtctc aagtacccag atacaatact tgaaatttaa aaagaactta ataaatattt    480

gttaatttac tacgtatatt aaccttacag caaacacatc atatatacaa agtcagcaca    540

gatacagaaa aaaaaaaaaa aaaaggaaag agggttctgt cccaggtata aatacacag     599
```

<210> SEQ ID NO 161
<211> LENGTH: 599

<212> TYPE: DNA
<213> ORGANISM: Homo sapiens

<400> SEQUENCE: 161
ttggctcgtt cattcattta ttgaactaat atgtataggt gatacttaca ggtgataaaa 60
caacatgaac agataaggtc aatatttata ggcaataaaa caacaacatg gacagatgag 120
gtccctgccc tcatagaaca tatgctctag cagggaaaac ataataaata aggtgtacgt 180
attataattt cagggagtac attatgtgaa gaaaaatata gtggaacaag agaacagaga 240
gtgacagggg tggtgataat tttagatagg gtacacagag aaggcccttt tgaagagacm 300
gatgactctt ggacagaaac ctaaataata tgacaaacca taaaaatgat ctggagagta 360
ttccagacat aagaaattgc aagtgcaaag gcactgagaa aaggcttgcc ttgaaaagaa 420
aactaaaata gaagaaatga ggactctgac caggcgcggt ggctcacgcc tgtaatccca 480
gcactttggg aggccaagac aggcagatca caaggtcagg agatcgagac catcctggct 540
aacacggtga aaccccgtct ctactaaaaa tacaaaaagt tggctgggcg tggtggtgg 599

<210> SEQ ID NO 162
<211> LENGTH: 599
<212> TYPE: DNA
<213> ORGANISM: Homo sapiens

<400> SEQUENCE: 162
gctgcatctg caaggaatta ttattctgat gattgtttta tatagctgtt gcaaagagtt 60
aattcattct ttccttaaag attccaaatc tatgcaagac ggctgggggg agagtgacgg 120
gccagtcaca ggagctcgcc atcccagctg ggaagaggag gaggatggag gagtctggaa 180
caccactggc tctcagggca gtgcttcctc ccacaactca gcaagctggg gacaaggagg 240
aaagaaacaa atgaaggtag cctgcttaga aatgttcgca cttgctcatt cgctctgagr 300
aggcagaact gaggttttgt tttgtttgtt tttgttttga gacaagttct ccctctgtca 360
cccagactgg agtgcagtgg gacagtcacg actcgctgag caacctcctg ggctcaagca 420
gtcctcccac ctcagccttc ttagtagccg gaactatcac catgcctggc taaattttgt 480
attttttaat agagacaggg tttcgccctg ttgccaggat ggtctcaaac tcctgggctc 540
aatcctcctg ccttgtcctt ccaaagtgct gggattacag gtgggagcta ccatgccta 599

<210> SEQ ID NO 163
<211> LENGTH: 599
<212> TYPE: DNA
<213> ORGANISM: Homo sapiens

<400> SEQUENCE: 163
ggcattctga gaagcaggtt cacttgcctc ttgagttttc aggctgagct aggcagatga 60
catcatacac acaagcacaa aagtattaag ttgctgtcaa aggctgttac ctaatgaaaa 120
gtcaaatgga ctttgttaca gtcacccatt gtataggatt tgtttaccta ccagttcctc 180
tccctgggag accgggctga gccccttgaa gacaggctat gtctggttca cctctgtatc 240
tatacccagg accaatagca cttagtacat gggcagtaaa tacttgcttt aaagaacgak 300
taagtgctcc atgctttcag gactacactg tggaaaagga gagcttggag taggaaggta 360
tatgaaggag caagaaagtc atttatggag gtgggaatga cctaagcaaa ggtctaggct 420
tgggaatgaa gacaggaggc cagcaggagg gtggacagga ggccagcagg agggtggaag 480
ttctttgatt gcagcccaag gaaaggatga gttctggaaa ggatagcagg ggccctccct 540

-continued cccggtctgt atggttcagg cattcaccgt gcccctcacg ccacatctgt tccatcttc 599

<210> SEQ ID NO 164
<211> LENGTH: 599
<212> TYPE: DNA
<213> ORGANISM: Homo sapiens

<400> SEQUENCE: 164
tcctgacctc aggtgatcca cccacctcag cctcccaaaa tgctgggatt acaggtgtga 60
gccaccgcgc ccatcctgaa ttaatcttgt gattttcttt ccatgatgcc ttaagcagtg 120
tttcacaaaa gcgttttcat gctccttgaa tttgtcatcc cagtccttcg ggaacagaga 180
ggagtcggag taagatactc tgcaggagct ctttgggagg atgcgctggt cttcagctca 240
gccacagcac acctaagagc tcatctcctt catcagccta gtcacagctc ccagactctm 300
ctgcacactg acagtgtggg gtgatgctta ttcccctacc tcccccagat ttgcaccgac 360
atacgcctcc tggcaaacct caaggagatg gaggaaccct ttgaaaaaca gcagattggt 420
gagtgctgtg tagagacctg tgagcacaca ttgctgctgg aaggctgtgg atgggggctg 480
agagctcatt cagcatgctt gcctactcac tatcctctga agtctctctg cctttgcatc 540
ttgtcctttt tttacatggg caggctcaag tgcgatgcca tataagcgga atcccatgc 599

<210> SEQ ID NO 165
<211> LENGTH: 599
<212> TYPE: DNA
<213> ORGANISM: Homo sapiens

<400> SEQUENCE: 165
gcgccatcaa cgactctact cagccatgct cacgcccagg ccagccttag agtatctcag 60
gatctcactc tacataaaac tgtggttgat tcaaaatacc agaaaagagg tttctcttcc 120
taagaaccag aacatgaagg caaagcatat gggagaagtg gttcttcctc acaatacacc 180
aggctcaaga tctgcccctc ctataaaggg aagtataaca gagtgaaaac tcttttaaag 240
gtgcaattcc aaagtaaagg aaaattcagt ggcacccttt acacctaatt taaaccaggy 300
ttgacccttt aaacacagtt tgtttcactg aacttgatca attagttatc ttaactattt 360
agtgattgag ctctaaactt ggaaagtcat gagaaagaag agagtggaaa ataaaacgca 420
tcatccttgt tttatgttag atgcttccca tggcatactc ggtgaacaca gccatgtcct 480
aaaagcaatc taccaaatgc tgagagagag aggcacttac gcggcatgat cccttggctc 540
accagttctt cccgggtccg gcgctgctgg agtttcaact gtagcactgc agggcagca 599

<210> SEQ ID NO 166
<211> LENGTH: 599
<212> TYPE: DNA
<213> ORGANISM: Homo sapiens

<400> SEQUENCE: 166
atgacccact ttgctctttc catcatttca tgtcctgcca tttgcccttc cgtaacaaaa 60
gtcaccttca tgagagtact ccttgcgtct gctttaatct cttccaggta tgtcataaaa 120
atgcaaaaat gtacaaattt tgtacatttg ggtgctattt gggtggggag atggagagaa 180
ggaaaactga agaaggtaaa atagaattgg gaaaacagcc taaaaaactc tttgattact 240
ttgatagata ccacttatgg taattcttta gttataataa gctctgtatt taaaatgaar 300
ttttgagacc aagtgttttc tttccttata cagcctgagg ttcagtcatc agaacagaat 360
cgtgtggtga ggccttctgc ttctgccaat tttgttttgt tttgttttca tttcctgcca 420
catggcaggt gctgctgaga agtaccttca ggaaccactg aatattctag ccccatcttt 480
ctaagggttc ggtgatgtag aatgctaaaa gggttcgggc tgttagtcag agagggagga 540
gggtgtccag catcggcgtg ggcctctagt tgttctttta ttgcccttta tgatgtgtc 599

<210> SEQ ID NO 167
<211> LENGTH: 599
<212> TYPE: DNA
<213> ORGANISM: Homo sapiens

<400> SEQUENCE: 167
atatgactcc taatgggaac tgtcactgcc taagcttggg ctatataaag tgcacccatg 60
gaatgtaact ttaacaaaca ccctggccca tgactggacc gtcagccgca aatcccccctt 120 cagctaggac tccaagaacg cctgctaggc ctcacattat tctcaggaca cctgcacaca 180
ggaaggggca cagatgcatg ccaaattaac cttacttcct caacctcacg aggaatcata 240
aagtggccaa actgtttcaa tgggacagtt aaaaccaaaa agatatatgt ccactcggcr 300
ctatttcctt cttcactgca cctgttattt atagtgctgc taaaattaac ttgaatttca 360
tctctaagga ctaaaagaac cccatggcaa ttgtatgtga aggaacacac acaaccgaca 420
gctgagacga agggctcagc tctattctgg ggataccaca caaagaccac aagtctcgac 480
ttctgcaaac aacactcagg tggcaagacc aaaccaagag cctccagaaa ggctgcacca 540
tgaatggaag gtctgactcc ttttgtcaaa aacttggctg taaggacaaa tagcaactt 599

<210> SEQ ID NO 168
<211> LENGTH: 599
<212> TYPE: DNA
<213> ORGANISM: Homo sapiens

<400> SEQUENCE: 168
agcctcccaa aagtgctgag attacaggtg tgaggcacta tgcctggcca agataggtat 60
tattaatcct attttaccga gaagcaaagt gaggcccagc aggtttaagt aatacaccta 120
aggctatccc actaataaga ggtagaacag gatttggaga caagcattct gattccaaaa 180
cctgggctcc ttactttgcc tctctaggat cttctgaaag cctgctctac tgtgataaca 240
ggagtggagt gtgatcacct gggtttattc tctggtgaga cagacaaagg ggctaaaacr 300
gatggttcga ccagagtgaa aggaattcag gtgatcaact tcagtaaaac aaatttactc 360
taggaagttg atttcagaaa aaaattataa ccatagatca gcaacaataa ttgcattaat 420
aaaacacaaa taataaatga gtgtgctact atgtgtcaga ccctgtgtta agtgactgtc 480
atgcttttaa cttatttaat cctttaaaaa agccctgtga ggatgctaca gttattatct 540
ccattttaca gatgaggaaa ctaagaatca gacctttaaa agtttgcctt ctgtcacac 599

<210> SEQ ID NO 169
<211> LENGTH: 599
<212> TYPE: DNA
<213> ORGANISM: Homo sapiens

<400> SEQUENCE: 169
gcttggttat ttgcagattt ttctagtagg ttgtctttgt ctcattgatt catcaccgtt 60
cttttatatt ctagatgcta atcctttgtc agagttatgt gttttgccga tcaacatgtt 120 tcctttttc tgcagatcta atcactcaag gagaagtttg aaaaccattg gcccaggctt 180
ctgttctgtg caccacagtg aaacggccct gtggttctgc acagggcagg tgtgggttct 240

```
tggagtgagt cgcattgtag ttactgactg ctgctgacct gtggtgcttg cctttgcagr    300

tggaacagga ggattttgta atggaagggc atggcaagac tccacctcct ggtgaagaaa    360

gcaaacagtg agtcacagtt tatttaaaaa gagtcctatt acagatcctc ggaaacactt    420

tggttcaaca tgctgataag cgtgtttgtc agagatgtat acgttggaga cattggggaa    480

ctcaccagtt gctttggtgg ctgttaatgc attgcttcta tttatagacc aactaactag    540

aaggacaaga aagttagcgt tacagttttt cacactcgcc taatcaaaat ttatgttat     599
```

<210> SEQ ID NO 170
<211> LENGTH: 599
<212> TYPE: DNA
<213> ORGANISM: Homo sapiens

<400> SEQUENCE: 170

```
tgttctttta atgccaagaa gttcccattt ataaactgaa gttagttaga taattaggta     60

gcttagaaca gtggctttta aactttttga ttggctctac tataaaaaat tcaatttgta    120

ttgaaaccca tagacatgtg aatgtttatg ctgaaacaga agtatttact ttctgataat    180

aagtgtatgt agtcagatac agtcttttaa gtccactttg tatggtacag aacaaatccc    240

taacaagcta attccaaccc actaaattga tttaatgatc actgagggtt gtcttaccay    300

ggtttcaaaa catttagaag gcactactca tgagttgccc catttcagca tatgatcccc    360

acttttgctg gtctaagaat catttatcag tcccactcag ttatcatatc aaccagattt    420

gttagtgact ttaaaaaaac gttaatttgt tacttcagca agtagaagat ggatattttt    480

gatgcccaga gtgttgtctt ccccgtccag ggtatctcat tctgatcaaa ccgaattggc    540

catccatact gagaagtggc tattgatata tttatattga gaaatgaata tgtgtttat     599
```

<210> SEQ ID NO 171
<211> LENGTH: 599
<212> TYPE: DNA
<213> ORGANISM: Homo sapiens

<400> SEQUENCE: 171

```
ttgtgtagag gactgaagtg agatttttct gtatttcaga gtagtagtgt attcattata     60

tattcttcct gtattctcca ccattaaaaa aaactgtgag aattctgtga ggaatagggt    120

agagatttca agtggaggtt atgtgaagac ataggctaga gctggcttgc taccaggtat    180

caaataatag aaagcactta aggtagaagc taatatcctc cttcgttgga ttttagagta    240

gaactaaaag agtttgatgg attgatgtaa tcgttcagat ttaacaggga tgaagtttar    300

gattaagttt aggattaaaa agcccaattg cgtagactat gtaatggagg aagttggaca    360

tagatattga gccttgttaa aaagatgtta ggggccaggc accgtggcac aggcgtgtaa    420

tcccagctac ttgggaggct gagacaggag ggttgcttga gcccaggagt tcaaggctgc    480

agtgagccat aattatgcca ctgtactcca gcctgggcaa tggagcaaga ccttgtctca    540

aaaacaaaac aaaaaaagat gttagagtga tggctggctt taatgagagt ttatcagca     599
```

<210> SEQ ID NO 172
<211> LENGTH: 599
<212> TYPE: DNA
<213> ORGANISM: Homo sapiens

<400> SEQUENCE: 172

```
ctatgttgtc atggctagag atagagattt gtaatttata tgacagtaat agctaaatcc     60

ccattcagaa tagggatgga ctccccattt ggaatccatt aggaatggac taaaagaaag    120
```

aagactgatg tggggaatgt ctttttttggg ggtctggaga aagaagaggc agtaaagaag 180
cagttaaata gagaagaaaa aacaatatgg tctgtgccct cagagtcatt gaacagttca 240
agaaaccaaa gtaagtcagc agagtctgat gcttcaggga gtttcaggaa atgaagccay 300
aggaactgga ttccaaataa tgactaggaa atcactggag accttagaaa ccagtttagg 360
tggtgacaga agctagggtg aaaagcttaa ggagtgagtt gattgatgaa gcatgggcgc 420
ttttaaaaag tatggcagtg aggcagaggg ataagagcta gaaaggtaac agcttgagtg 480
ggtacaggga tagttgcttt gttttgtttt gtttaattca gggttcagga gatctaagta 540
tttgcagtgg acacgaagcc attggagaag aaaagactga agatgcacaa aggaaaaga 599

<210> SEQ ID NO 173
<211> LENGTH: 599
<212> TYPE: DNA
<213> ORGANISM: Homo sapiens

<400> SEQUENCE: 173
ttagctgggt gtggtggcgg gcacctgtag tcccggcttc tcaggaagct gaggaaggag 60
aatggcgtga acccaggatg cgtaggttgc agtgagccaa gatcatgcca ctgcactcca 120
gcctgggcga cagagtgaga ctctgtctcc aaaaaaaaaa aaaaaaaaaa aaaaaaccag 180
tgtctgtctt tcctcttcat gcactgtaaa ctctaagtgt tagctattat cattttaaat 240
atatttattt ttgctggaat tcttacaaaa tccacttaga attcgatatt ctagacatay 300
gtctctttta tgttttcgtg atttttgttt tggaggcttt tggtggtggt ggtggtggtt 360
ttgtttttgg ggtttttttt ttttgaagca gggtctcact ctgttgccca agccagagtg 420
tagtggcagg atcttggctc accgcaacct ctgcctcccg gtctcaaggg atgctcctgc 480
atgatctctt ttaataaagt tagtctaatc tgtgcttaag ggaaacaata aaaaagatgt 540
gtccacctgt gaggcagaat tttaaatgga aaactacccc tgagtttagg cttggtggg 599

<210> SEQ ID NO 174
<211> LENGTH: 599
<212> TYPE: DNA
<213> ORGANISM: Homo sapiens

<400> SEQUENCE: 174
aggggaggga agaggagggg aggaaagata tcttgggagg ccaaggaaag ataagtgaag 60
aaaccaccta agagggcaaa tgcagggctc agtgggaggg gcccagagat gtcctgagga 120
gccctggtgg catctgcctt gacaccaggt ccactgcaga cagtcgcaat ttcatccatc 180
cattcatcta tcagatattg agtgagggcc tactaggtac caggcccact gcagacagtc 240
gcaatttcat ccatccattc atctatcaga tactgattga gggcctacta ggtaccaggy 300
cctgaggata tagccctgaa caaagcagat aacagtccct gccctcatgg agcttatatt 360
ccagtggtac aaacaaaaca gtaaaccaga caagtaaaaa caaagcgtcc ggcatgctag 420
ataatgatgg gtgctaaaga gaaaacatga agcaggagac agaataagaa atattgggag 480
gaggtggaat tttagatgga gtgaccgggg atgactccac tgaaaaggtg acttttgaag 540
aaagaatgaa ggtagcaaga gtttgccata tgaatatctg tgggaagggc cctctaagc 599

<210> SEQ ID NO 175
<211> LENGTH: 599
<212> TYPE: DNA
<213> ORGANISM: Homo sapiens

<400> SEQUENCE: 175
ggtagctgct tcacactgct gtcacagatc aggagaaaaa cgtaaggata agtccaatgg 60
atcttcaaag acagacccgc ctgggttctt tttttcaatc tgtatttatt ttattctttt 120
attttttaga aacagggtct cactctgtcg cccaggctgg agtgcagtgg caccagcata 180
gctcactgca gcctcaaact cctggtctca cacgagcctc ccgcctcggc ctccccgagt 240
gctgggatta caggtgtgag ccactgtgcc tggcctcaac ttacatttat ttagtgtcar 300
tgatgtgccg ggtactatga ggggcacaaa tcatctgtca ggtgatgtca tcatgccttt 360
caccaatgca gaagccgagg cccagcacag ttcaggaaca tgctctaggg cacattgcca 420
ggcagaggca ggctccagct ctcaggcccc tgtgttttct cttgttaaaa gggctctaga 480
accagtgagc ctactaggct ctatcttggt actatcactt gggcaagtta ctctgtgcaa 540
gccgatgcct ccacttccta ctctgtgaaa tgggataaca tcaacagcag cctaatggg 599

<210> SEQ ID NO 176
<211> LENGTH: 599
<212> TYPE: DNA
<213> ORGANISM: Homo sapiens

<400> SEQUENCE: 176
aatcaattgc acaggttgga gagagaatct ttatgcacaa agatgcaact gcagaaaaga 60
gggcaaacat aagtaggtta gactagaata attataccg tgagcttcag agcaaatggc 120
agcttatgga acactttcac atgcaatagc tcatataact ctttaagcaa ccctgtgaaa 180
caggcagggc agttgttatt gcacaattta cagatgtgca aactgtggtt ctgcagagct 240
gctacaaaca ctagagttgg atctcaaaca cacgtgcttg accttttttt gctttctggy 300
ttactgcaat gggcaagtca tagggtgagg agtgctatgg taagattagg ttaaatggga 360
agagagagtc agcagagttt ctgactatgc ccaaatttgt acaaaaataa gaagaaatgg 420
tgtttttttt tttgaaaaaa agaaaaagtc tgaataataa aatgatccat gaatttatgg 480
tgaggactag taaaaaagta aacttcattt aacaattata tttaagctaa gctaggatga 540
agatgcacaa gaaatattta aaaaagtaag acaaacatgg caaaaacaaa atcaacaaa 599

<210> SEQ ID NO 177
<211> LENGTH: 599
<212> TYPE: DNA
<213> ORGANISM: Homo sapiens

<400> SEQUENCE: 177
aggaacatat gtattactca agagaagtgt atgatgaaaa gcttactgca gttaaatagc 60
ttatgacttc atgaacattt aagtgcattt accacaaacg gataatgtta tttatgtttt 120
ggaataaata gagctgaaat aaatatgatt actacctgca agtattaaca ttaagaggta 180
tgtaaattcc ttgtattgaa aagtatatat atctgaactt tttgcttgcc acaagtcttg 240
aatgacaagt aacaaacatc tatttagaac tcactgggat caaggtccta tgaataagam 300
aatgccatat acaaagagaa actggactcc tatctttcac catatataaa aattaactca 360
agatggatta aagacttaaa tataaggcct ggaactacaa aaacactaga agaaaaccca 420
ggaaaaacgc ttctagacat tggcctaggc aaataattca tgaataagac ctcaaaagta 480
gattcaacag aaacaaaaat agacgattag gacttaatta aactaaaaag cttctgcaca 540
gtaaaagaaa taatcagcag agtgaacaaa gaacctgcag aatgggagaa aatatttgc 599

-continued

<210> SEQ ID NO 178
<211> LENGTH: 599
<212> TYPE: DNA
<213> ORGANISM: Homo sapiens

<400> SEQUENCE: 178

```
ttctgaactc ctgctcctca ttcttgagaa atgtaaatgt tttgtaaaat agttttagat     60
tgtgtcatgg ttgtcaatgg ctcataaaat tcatccagga tggctatttt ataacattct    120
ccgcttcacc tgtttctgac taaaatggtt tgggatggtg tcactgagaa acctgatatc    180
ccttaaagct gggaaaacaa tacattctcc tagactggag tgtgtgagta aatgagatga    240
actttaaatt tcttctggaa cctaaagctg tatctagaat tatgctgttg cagatacaar    300
actgtttatg tcctgaaaga aattatgatt gtgtcatggt actaaagaag ctggtgtgaa    360
agataccagc cagtggcctg tttgggtatt ttatttattt agtatcaagt gcctaaatat    420
tgcaaaatat ccttatctgc ttctgcatct atatctgtat ctgttgccaa cctaaaatgt    480
cttacagaga aagcatcgtc tgagtggctt gggttgcagt ttgaaagaca attagcagtt    540
tctttggagc caagaagatt tcaaagaaaa taatggctcc taatactcac atgtggtct     599
```

<210> SEQ ID NO 179
<211> LENGTH: 599
<212> TYPE: DNA
<213> ORGANISM: Homo sapiens

<400> SEQUENCE: 179

```
caacctaaaa tgtcttacag agaaagcatc gtctgagtgg cttgggttgc agtttgaaag     60
acaattagca gtttctttgg agccaagaag atttcaaaga aaataatggc tcctaatact    120
cacatgtggt ctcccacaca tattttttcc tttatcagct aagtacacga tcactgccag    180
tgaaaatgct ctttgctgcc aaggtaagtt caacgaatgt cgctactctg ctcattcttt    240
cctttgagat tgtaaccgtg gtgaaatata taaagacaac atctattaat cctccagcak    300
taaaattagt caattaccta ctttcaagat taataggttt cctttttca acggggaaga    360
acttggattt tgtgactgtg tggctgacat ggcagctcaa taagttggca acaaaaatac    420
tcgccttatg aacaagatat gtctgtcttt attagtatta actagaatgg tagccttgac    480
aatacctaaa acctggacta atgtctagac atcgctctca tgaccaggca tagcatgcaa    540
atttctcgcc attaaaatta tttacatgaa tttaaaaaga tctctaagct tctctctaa     599
```

<210> SEQ ID NO 180
<211> LENGTH: 599
<212> TYPE: DNA
<213> ORGANISM: Homo sapiens

<400> SEQUENCE: 180

```
agttgcagag ataacaccaa cccatcctgt gaatcatatc tactcagatc tgattctttt     60
tttaacttgc atgaaaattc cttgaacctg tataattgtt ttttaatcta aaaatagacc    120
atatatgtag gtatttttca cagttagata agggaactat acataaactc cttttggtta    180
gctcagcctg ggaaaagttt tttttttttt ttaatggtga aaaactttga gattgaaaat    240
atttgattca taggctactt taaatacccc gtatcaaaat atttcaggat tacttgtagy    300
gcattttagg aataaaaata atactacaaa tatgaccact tctactcttt ccacaagttc    360
tcttaacact gctaatcttc ctgtaatttc tgcactaggg aaatacaaat aaatccacag    420
tgaatttcct ctggggtttc tgtctctctt cacttccccc atgcaaggtc aagagactaa    480
```

ttctgaatct cgctccttta tctgacccca gtggtaaagt aaacagtgga aaaagttttt 540
aaatatatga aatcctgttc ctataataga gggcgtcttt aagaaaaaaa gcagattct 599

<210> SEQ ID NO 181
<211> LENGTH: 599
<212> TYPE: DNA
<213> ORGANISM: Homo sapiens

<400> SEQUENCE: 181
aatgacatgc gtatttcaca tcagggtgct attattacac gtttaataaa atgaaggaat 60
taaagctcag ataacttgaa tggtttggct ggaggcattt gttagaagcc aaactgggac 120
tcagattcag gtctgtaaaa cttgacactg tcatttatat gctgcatttc cctttgagaa 180
atgcactatg agaaggaaga agaggcttgt cggttgccag ggcatgttag gtagaattag 240
attatttgcc cttgtattta gtccagtggg ataatgaaga gacaacaaaa cagttctgtm 300
ttctacaatt agacactagg gggaaaagga ttttatttat tgtacacgtg tgaggaggtg 360
tatgaagggt ggaaggaggt gggcactggg aggatgagat gtcatttagt ctgtgagtga 420
ctgtcatctg caggggcctg tgttcagggt ctggacataa gatgaaggac gcagttcctt 480
gtcttcatca tccaagagct acttaataga ccagtgagaa agagaaaatg taggaacaaa 540
gccaaatgga ataaagagtg ctttttaggg aagctcaccg agatcttggc gaacacaga 599

<210> SEQ ID NO 182
<211> LENGTH: 599
<212> TYPE: DNA
<213> ORGANISM: Homo sapiens

<400> SEQUENCE: 182
gacttcatga tccacccacc ttggcctccg aaagtgctgg gattacaatt tcacttcttg 60
atacatgccc cttctagcaa cacaacacac tgatcttgtg ctctcatcga gtctctctga 120
attcctacac actgtgggtc atggggcaac acaaatgttt gacatgaata aggtgacaag 180
gaacagagga agcatatgtt gtgtgtattt ttgctgctca tgcctattcc ccattgtctt 240
actggatgtg acttataaaa cattagaaaa agataaaatt attaagagtt tcaagacagy 300
gagagcagag cactaaatca agtgcaagat cctctgagcc tgggggtctg ctggttctgc 360
acaggttgca agctcacaca tccagccttg ctgtcaacac aattccatcc ctgacaacaa 420
agcaaggtca aaagatcaaa cacgagttct ctgctctgtg atgcttgggc tgagagatcg 480
cctatccttc atcctgctgg aaatccaaac caggaatata aaactgatat tcatcaggaa 540
ggatacatct acgctcacat acgccagcag gaacttgagc agggacccag ctgatttga 599

<210> SEQ ID NO 183
<211> LENGTH: 599
<212> TYPE: DNA
<213> ORGANISM: Homo sapiens

<400> SEQUENCE: 183
ctgatcttgt gctctcatcg agtctctctg aattcctaca cactgtgggt catggggcaa 60
cacaaatgtt tgacatgaat aaggtgacaa ggaacagagg aagcatatgt tgtgtgtatt 120
tttgctgctc atgcctattc cccattgtct tactggatgt gacttataaa acattagaaa 180
aagataaaat tattaagagt ttcaagacag tgagagcaga gcactaaatc aagtgcaaga 240
tcctctgagc ctgggggtct gctggttctg cacaggttgc aagctcacac atccagcctw 300
gctgtcaaca caattccatc cctgacaaca aagcaaggtc aaaagatcaa acacgagttc 360

```
tctgctctgt gatgcttggg ctgagagatc gcctatcctt catcctgctg gaaatccaaa    420

ccaggaatat aaaactgata ttcatcagga aggatacatc tacgctcaca tacgccagca    480

ggaacttgag cagggaccca gctgatttga ctttcctgct catcctgtag gttttctgca    540

ctggatggct tgatttttcc tctttgttaa taatagggtc aaggccggtc aggcactgt     599
```

<210> SEQ ID NO 184
<211> LENGTH: 599
<212> TYPE: DNA
<213> ORGANISM: Homo sapiens

<400> SEQUENCE: 184

```
aaggctgaaa aacatcttcc aagttatgca gtgagtgggt ggcagagatt aaattaaact     60

aagatttatt taaacgcaaa gcccattggt ttttaagaag ccacagttgg cttctatgtt    120

tagaggcagc tgaacacata caaattggtt atgataaaac agtgtgatta ttcagagaac    180

tggtcttaat tttgtaaata gaatctaatt gattaaatga attaacaatg gttatgtttc    240

aagttgacta acaaaagatt gttaagctta gattgaatct gactgtgaca tgctacaaay    300

gaaattatag aatgtcagtg aagagtctct ataggaaaag gtttagcatt catcttgtga    360

taatagagca tttctactca aaagaaggct tattcctacc tctaacttgc tattctctat    420

tgagcaatga gttggatggc ttcaaattct tccaacttgc aaactgaagc ttggagttgg    480

gtgatggtgt gacggattga gcaggaattg agggctggga ctctgaagcg agaaattgag    540

ggtcggatgt ggaggtgagg gacctcttac caacagaagt cctgaatggc tattcttgg     599
```

<210> SEQ ID NO 185
<211> LENGTH: 599
<212> TYPE: DNA
<213> ORGANISM: Homo sapiens

<400> SEQUENCE: 185

```
ggcaagagga tgattttgta tttttcattt gctagttctc ttcccttgtt aaggcagaca     60

aaactcatgt aagatttttt tttcatatgc agaacataaa tgctgtgtga tgcacctaga    120

gggttatttg gatgccttct gaccttttga tgagtgaatt gagtgaaatg gtgtatgtga    180

aaactctttg atacatatat agttctaaat aaatgtataa cattgctgcc tattgtaggc    240

tttccattcg aggatacagt gtgttctcag tgccacactc ctgtgctgat cttttcaggr    300

taaaactatc cagaaaagct ccttccttcc accttgtctt tagtactaca ctgagtagat    360

tgtctttgta gcagatttaa tgtactcatt agtccaagtc cagacaagga aagttactca    420

tgtgaaacta aagaggtaat tactgtgggt agcttgttat taaattaata ttgaaataac    480

atataccttt ttagatggcc taatttgaag agaattcacc tgccttgtct ctatgaatga    540

gaaatgactt agttgagatc tattcctggc aatcaggtaa cactatctcc aaatgtaag     599
```

<210> SEQ ID NO 186
<211> LENGTH: 599
<212> TYPE: DNA
<213> ORGANISM: Homo sapiens

<400> SEQUENCE: 186

```
tgtcatccac cctcctccta ctctctcacc cagctgatag tttcataata acaaaagata     60

ggctaactca ggtgcagaca taaatataca tatatatata tagatagata gatagataga    120

tagatacatg cagatgtgta cacacagcta ttaaatatgc atagaatttt catatttaat    180
```

ttaataaatg tttaaataat tatttatgag ggacagaaga tatttcttag aaacttcaaa 240
acagggaaaa gtatatttgt aatatgtctc cacatttgat tatgtgactt tatctgctay 300
gttagtttag taaattaaaa tgtttacaca taaatatttt aatgccctta tattcatctt 360
tcatggaacc ttcttgttgt ttcttagttt atccactaaa aatctccttt aaaatgttgt 420
ggacttccta tatatcaaat tatgatcaga tatgttagat tatttgtcac aaacataatt 480
ataagtgtca caattatggt cataaacctc ttctagacag gcacttcctt acattggctg 540
tgagctggga tgacatgcga taatgccctt aagattctta gaagcctttt gtccagaca 599

<210> SEQ ID NO 187
<211> LENGTH: 599
<212> TYPE: DNA
<213> ORGANISM: Homo sapiens

<400> SEQUENCE: 187
tcttttgggg gagagctgct ctagatgatc aaaaggcaag cattttatgg aagggagtgg 60
tagaatattt caattcagtg gtgagagtac aattggaagg cagagctgct gtttaagaag 120
aataatgtat tggaaatgtt aacgatactg catggatgaa acaaaagatc gcgtttagaa 180
gcagatttgt aggagatgac acttattttg ggaactgttc tgatgaaagg aagtatcttg 240
aaatctacag aaaaaaagct tgaccgtgag tatcaaattt gtacgcgttg cttttctgty 300
ttactggatg ttacagaaaa tgtttgtatt tagaagacat ttcttcagtt aattatttta 360
tatccttgag agaacagtag ctagtgtatg ttgataggat ttcctaatat tttggggtct 420
ccaaaaactt cagagtatac cccaaaaata aaatattaaa agaaagcatt tgctgtaaaa 480
ccagaccctg ccattaaaaa aaccttagca tcttatttgg gtggtatttc taagtgattt 540
tggctttaac attgatcaaa ttttctttgt ttttggccta tatattattt tataaaata 599

<210> SEQ ID NO 188
<211> LENGTH: 599
<212> TYPE: DNA
<213> ORGANISM: Homo sapiens

<400> SEQUENCE: 188
gaccataaag acatttttag gatactatgt atgacaaatg aaatgctcct ggcatattga 60
gatcattgtc attttaatca atcaagcagg aaatatctaa agcttcaact tatgctaagc 120
tgctacaaaa ctccttggcc ttcctgcatg aaaatttatc agactcgtac aatcccaacc 180
aaatctatca gaacccatat tacaactcat tctgagacct attgatgtcc tcttcaccat 240
gaatcacctt cagtcaagga ccaaagtaca gagtggactc ctggatccat cctatctctr 300
ggccctaaga ctttttctga aagctgaggt atcaaaaagt gctaatgtgt tatggcgaag 360
tgaagtaaaa attttgtaca ggtcttgact gaaagtttct cctttttctc cttaccaata 420
tttttccaat ggtgaatcag aaactctagg ctcaatgctc tccaaaatat attaggaaga 480
ccacggtatg gcatattgaa agaatgcttc cttggggatc aagaaacagg ccatagttat 540
aaattttatt attatggcac aacttttaca tgttttatgt atctgtttta tgtttctgc 599

<210> SEQ ID NO 189
<211> LENGTH: 599
<212> TYPE: DNA
<213> ORGANISM: Homo sapiens

<400> SEQUENCE: 189
tcgtacaatc ccaaccaaat ctatcagaac ccatattaca actcattctg agacctattg 60
atgtcctctt caccatgaat caccttcagt caaggaccaa agtacagagt ggactcctgg 120
atccatccta tctctgggcc ctaagacttt ttctgaaagc tgaggtatca aaaagtgcta 180
atgtgttatg gcgaagtgaa gtaaaaattt tgtacaggtc ttgactgaaa gtttctcctt 240
tttctcctta ccaatatttt tccaatggtg aatcagaaac tctaggctca atgctctccr 300
aaatatatta ggaagaccac ggtatggcat attgaaagaa tgcttccttg ggatcaaga 360 aacaggccat agttataaat tttattatta tggcacaact tttacatgtt ttatgtatct 420
gttttatgtt tctgctgttt tcttctatgc cctgtttact atagaaaagt ttgctacaca 480
gaaaaacagc agatataaaa atatcaaatg actacatttt gagtttcaaa atatagatcc 540
agccataaga tgaaaagaat tgaaaaagtg gtctttattt tttctgactg attaaaggc 599

<210> SEQ ID NO 190
<211> LENGTH: 599
<212> TYPE: DNA
<213> ORGANISM: Homo sapiens

<400> SEQUENCE: 190
aagagaggaa ctaccaaatg cttataaaac tatcagatct catgagaact catttactgt 60
cagaacagca tgtgggaaac cacccccatg atctaacttc cacctgatcc ctcccttgat 120
acatgcagat tatggagatt acaattagag atgagatttg ggtggggaca cagagccaaa 180
ccatatcacc cagtttttgt gcccgttctt ctgggcttgg ccaaattcac gatgggcgga 240
gtagtagata acagaatccc atgacagatt tgaagatctg agaacagaaa caatctttgy 300
accctttttg aatagagacc aggctatcca aaagaaccta gagagagaca gaaatgtgtt 360
cagtatgtat taggtagagg ggtctgaaat aatctcctgg agtttccatg agcctctaga 420
attgggtcag agaagagtaa aattggcacc gtcatccatg agaatagcaa aaggtaggaa 480
aagattttag atattccaaa aatgcatttc ccacaggcac taagtggcat ggaatttaac 540
taagcagtct agggcctcag caaacgtcag agaatgagga tgaaggagtt ctctgctcc 599

<210> SEQ ID NO 191
<211> LENGTH: 599
<212> TYPE: DNA
<213> ORGANISM: Homo sapiens

<400> SEQUENCE: 191
ccaaatgctt ataaaactat cagatctcat gagaactcat ttactgtcag aacagcatgt 60
gggaaaccac ccccatgatc taacttccac ctgatccctc ccttgataca tgcagattat 120
ggagattaca attagagatg agatttgggt ggggacacag agccaaacca tatcacccag 180
tttttgtgcc cgttcttctg ggcttggcca aattcacgat gggcggagta gtagataaca 240
gaatcccatg acagatttga agatctgaga acagaaacaa tctttgcacc ctttttgaay 300
agagaccagg ctatccaaaa gaacctagag agagacagaa atgtgttcag tatgtattag 360
gtagaggggt ctgaaataat ctcctggagt ttccatgagc ctctagaatt gggtcagaga 420
agagtaaaat tggcaccgtc atccatgaga atagcaaaag gtaggaaaag attttagata 480
ttccaaaaat gcatttccca caggcactaa gtggcatgga atttaactaa gcagtctagg 540
gcctcagcaa acgtcagaga atgaggatga aggagttctc tgctccaagg aaattggag 599

<210> SEQ ID NO 192
<211> LENGTH: 599
<212> TYPE: DNA

<213> ORGANISM: Homo sapiens

<400> SEQUENCE: 192
gatgaaggag ttctctgctc caaggaaatt ggagacctta gtgaatgcct gcattattgt 60
atcaatattc catgaattct tgttaaagct ttgactgtat gtgatttttt ggactccagt 120
ctgatatttt tctctcatgg taagttgcct cttttaatca atatctcctg ggaacattta 180
cccaaatacc cgaaagctac ttccctcttc ttccttgcta aaggaagcct gattctgctc 240
aggcctcagg tgaccacata tttcagggaa agtgggaatc ttaccagctc cagcaggtty 300
gtatcaacag gtctaatata gtggttctca aactgtggtt ccttaaattt gcattatcaa 360
catctcatga tgtaaaccta tgaacatcat tgcagatcta ctgaattggt aacccaaggg 420
gtagggacca caacctgtgt tttagtaaac cctccaggct actgtgatgc attctccagg 480
tttgagaacc actggtcaag gataatcatg gcaactccat tctcctagta gatggttggt 540
ttaagatggg tcaatggtat aattccagcc aataaaatcc aaagcgaata tgggagggc 599

<210> SEQ ID NO 193
<211> LENGTH: 599
<212> TYPE: DNA
<213> ORGANISM: Homo sapiens

<400> SEQUENCE: 193
atgcaaagtg acgagaggca gaaatctcga aggctgtctt agaattcggt tttccacacc 60
ttcccaggtc tcatccttgc tggtggcatt ttaacctcat actttgtcct catctcaaca 120
ttcaccccac ccatggctca gcagaagcct ctgcttgagg acattcttcc tttgaagaca 180
caaacatgag ctgattctat tcttggtctt gagttttctt tatttttgag aattgttata 240
aaaacagagt ttcactacgt ttggggactc ctgtttttta gaacaaagaa gagattataw 300
ttagctaaat gcctaacctg gacttcaaaa gggaagaggg gaccatatat tatttgagtt 360
tatgcacacc aaaggctaaa gcaattttgc acatgatctt gtcttacttc gcatgttggg 420
ctagttgtca ttacttttta cctttatttg tttattttcc attgcacaat gactcagcaa 480
gtgagaatac tgtcagaatg tcagcctgtg ccacatttgg aggtcagact cttgacatta 540
tggaaagttc atgaccgctt ctcagcaaat ttcccagaag aaaccttctg aactcctgc 599

<210> SEQ ID NO 194
<211> LENGTH: 599
<212> TYPE: DNA
<213> ORGANISM: Homo sapiens

<400> SEQUENCE: 194
gcttgtgtga acatgtcgct tttataaccc cctccccccct ccacgaacac gagactaggc 60
ttgccagcat tgtgtttgag catggtcaca tttaaaatga agagccttgc aggggttttt 120
gaaggtgagt gggtgggggg gatgtcaatc tgtcagagat gtcaccttaa gtggatctat 180
ctgcctatat gttaccactt gctaattatg gatttgggtg ataattgtca taagctttgc 240
cacaaaatgt gcaataaaat gcattttctg ggggcagagg gtgatgtgag gagcgggccr 300
aagctaggct ctaagggctg gtaatctaca gattgaaagc ctgtaggatt gtgctgtagg 360
attgtctcac tgtttaatgt tcaaatgaat acacatattg ttgtgtgtgt cgggttgctt 420
taggcaacat tgctggcatt ccatttcagg aactatgtgt gtacgcagaa ctgagtctgt 480
agagaagttt ctcttcacat ggccataagc ggccttcagg agtactgtct ccttatgagt 540
gctgtcctgg agagggctaa gaaacaagat caaataaatg gcagataaaa taaggagct 599

<210> SEQ ID NO 195
<211> LENGTH: 599
<212> TYPE: DNA
<213> ORGANISM: Homo sapiens

<400> SEQUENCE: 195
aatctgaatt gcaggcagtc gtcaccacca tagacttagc aaggaaccag acccacagtg 60
ccttaacccc aggtgtgttt atagcaacat caatggtcat gagctgtttc tcagatgtta 120
aattctgaca ttattcagaa ttggatgagt agaatgccaa taacataatt tacaatgcat 180
tacacaatgt acacactgcc tcaggaagac aaagctcact tgaagagtat cccctaggtc 240
gtggccttgc tcctgctctg gggggaaaaga atccaggccc ctccacgcga gtgtgggcas 300
gggggaactg aagtgcttgt ggttctgtac tagatctctg tgggggcagg aacaggagcc 360
acgggtggga ccttgagcac tcatcgggtc accttcgagg tggacaagaa tgagaacatc 420
acccatcact gtggtgaagg gcattgagct ttcagaaaat gtgattgatt gaatgaagga 480
atcctctcca tctggttcaa agtctcagtg gtattctggt gcttatgatg ccttggtttc 540
tgatgaagaa ttgaaaagaa gagtagctga ggagctaaca ttggaacaag ccaagaaac 599

<210> SEQ ID NO 196
<211> LENGTH: 599
<212> TYPE: DNA
<213> ORGANISM: Homo sapiens

<400> SEQUENCE: 196
ttacacaatg tacacactgc ctcaggaaga caaagctcac ttgaagagta tcccctaggt 60
cgtggccttg ctcctgctct gggggaaaag aatccaggcc cctccacgcg agtgtgggca 120
cgggggaact gaagtgcttg tggttctgta ctagatctct gtgggggcag gaacaggagc 180
cacgggtggg accttgagca ctcatcgggt caccttcgag gtggacaaga atgagaacat 240
cacccatcac tgtggtgaag ggcattgagc tttcagaaaa tgtgattgat tgaatgaags 300
aatcctctcc atctggttca aagtctcagt ggtattctgg tgcttatgat gccttggttt 360
ctgatgaaga attgaaaaga agagtagctg aggagctaac attggaacaa gccaagaaac 420
aaactgaaga tcagaaacga ctaaagcaag ccacagagct ggagagagag agggctgctg 480
ccaatgggca gttaaccaga gccatccctc gagagagggt atcaagccaa gaggaaggca 540
ctaaggcaat gcaccttgct aggcggctgg aagagaaagg ccgagtgcta aagaagcag 599

<210> SEQ ID NO 197
<211> LENGTH: 599
<212> TYPE: DNA
<213> ORGANISM: Homo sapiens

<400> SEQUENCE: 197
attgtctagg ccgtggcatg ttggttttct tgctttttct ttttaccttt gattacataa 60
gagtgatttc attttaactt ttggtgatca tgcaagcaag gaaacaaaaa ggagagatga 120
tgtacctctt ttacaggact aatatgtatg attagaagtg aaataaggta tttttatcaa 180
tataaaggca accttggctt atataacgtc tatcgtgaat actgacatct ttacttcact 240
cactaccaat aataaatata ttttctgaca aaaaaaattt taaaaaagta acccctaaas 300
agaacaattg tgttatccca atcaacagga ggcaaatgat ttaataaaca gtgccagctg 360
tcccccattg gaacccacta agtgccagat accgcctctg acagctcatc ttcacttttg 420
ttagagtgat cttcctaagc agagaatctg agggtgatca ttttcctgcc tgatgccatt 480
ctttgggaca tgagtctagc ccatcctgcc catgtctttg ggacatgagt ctagcagtct 540
agcccatcct ggcacaggaa atgctcttct ggatctgatg gcttcctacc tgtccactg 599

<210> SEQ ID NO 198
<211> LENGTH: 599
<212> TYPE: DNA
<213> ORGANISM: Homo sapiens

<400> SEQUENCE: 198
cctaagcaga gaatctgagg gtgatcattt tcctgcctga tgccattctt tgggacatga 60
gtctagccca tcctgcccat gtctttggga catgagtcta gcagtctagc ccatcctggc 120
acaggaaatg ctcttctgga tctgatggct tcctacctgt ccactgtctg gagtcgaact 180
cttcctccct gctcctcaca ctctcactgc gcctctcttc cctggtcaga ctgcctgctt 240
gcaaatcttt ggcatatggt gtctggcttg cctctcggac ttgctcttga tgtcctctcy 300
gtgttgacaa gccaccctcc caccacaccc ccagtcccat ccctctttcc aaataccagc 360
ttcttcttta gatgtcatca cctccacaac acctgccctg aacatttctt ctccccaaga 420
acaattcagg ttttgttcta agatgtttct gctctttagt caccaccacc tccaccatct 480
ccagggcact taccacaggg taatagaatt gactgctttc ctgtgagtct tcccagacag 540
acttcatgtt acttaagggc atggtctatg tgtcattagt gcttgacata tagaaaaat 599

<210> SEQ ID NO 199
<211> LENGTH: 599
<212> TYPE: DNA
<213> ORGANISM: Homo sapiens

<400> SEQUENCE: 199
tcatctgcaa gaaacaatga attatgtctt ctccaaacaa tgtattgaac agacaagctc 60
acgttgggca atctcactgc tttcttcttg aactcctagt tctctgtctc tgtctctcac 120
ccttttacct cttacacaat gtatttcttt aaccccatat tcgcattgaa gagtagggta 180
aaggctcaca aaatctgttg ctttccagag ttcttgccaa tggagtatct ggaagacagc 240
caaatattct cactggctgg gctagcaatc aagagtgtat gccttgatgc agttattaty 300
ttacctgggt gtacctttta agtgcagcct tcttttgcac ctaagtatgc ctagaaaaaa 360
gaagtcttcc aggtttttct gtatcctgaa atttcttgtc tcacttcccc cagtaagtaa 420
catagcacct gctcatttac tggttgtacg tgtgttttta attagacaca tgtcttttgg 480
aggcatttca ggagccgtta aactcttttt ctctttttga acataaaaaa aaaatcccca 540
attacttcac tgcttgtgtc aggcttgatt cttaaaggtt tgaaatgttt ttcagatgg 599

<210> SEQ ID NO 200
<211> LENGTH: 599
<212> TYPE: DNA
<213> ORGANISM: Homo sapiens

<400> SEQUENCE: 200
agccagtaat atagacagaa acccaaagct acttactgtg aaagaaacac aaaatctctt 60
atcaaatatc tttacttctc cacacctgtg ttgttgtgtt ttaaaacttt aatgactcaa 120
agttttctaa ataaatacat gcttagtttt tttttaaatt taactaattc aaaattattc 180
tgtgagttac tagaactgtt caaacactgc ttcttgaaag aaaatcttta ttgttttctt 240
ctggtaagta tacatttact ttaaaacaag attctatagc aaattaagaa agggaatagr 300
ggcttttatc catttctttg gaaatggcca tagagacaat gaaataaaac aaataaggcc 360
aagacaacag tattgtttta ttatttctga gagtgagcgt cagatcttag ggctgaaggc 420
tggcagggct gtgttatttt aggcttggtt acaaatctgg gtaatttaag aagacagttt 480
gtttctagct ttcctgggct ctacagcccc tgtgcttttc cttccctgta ccaattcaga 540
ggccaactcc aggtcaaatt tggaggacaa atgctggtaa tataaatata tgttgctgg 599

<210> SEQ ID NO 201
<211> LENGTH: 599
<212> TYPE: DNA
<213> ORGANISM: Homo sapiens

<400> SEQUENCE: 201
aataactcaa caacagcaat aaaacaaata accccattaa aaagtgggca aagaacatga 60
acagactttt tcaaaagaag acatacaaat gaccaacaaa catatgaaaa aatgctcaac 120
atcactgaca tcacagaaat gcaaattaag accacaatga ggcaccatct tacaccagtc 180
agagtggcta ttattaaaaa gccaaaaaca acagatattg gtgaggttgt ggagaaaagg 240
aaaggcttat acattgttgg agggaatgta aacagttcag cctctatgga aaacataacr 300
gacatttctc aaagaactaa aaatagaact accattaaat ctggcaatcc cactcctggg 360
catacaccga aaggaaaaca aatcattata tcaaaaagat acctgctctt gtatgtttac 420
tgcagcagta tttacaacag caaagatatg gaatcaacct accagtccat caatggatga 480
ttggataaag aaaatgtgat acacacacac acacacacac acacacacac aaacacacac 540
acacacacca tggaatacta ctcatccata aaaataaatg aaatcctgtc tcttgcatc 599

<210> SEQ ID NO 202
<211> LENGTH: 599
<212> TYPE: DNA
<213> ORGANISM: Homo sapiens

<400> SEQUENCE: 202
gagaagcaac ttagattatt actcaaataa gttctccttc aagctttctg cttacaaaaa 60
aaaagctatc aagttatccc aattataacc caatgataca catactcatt ttatgtagag 120
tccagaaatg ttttgaagct ggagttgaag acagttcagt tcaaggcctt acttttacgg 180
acaatgaacc tgaattccag aagtaggaag cttttatgac agaggaggct ggcggaagaa 240
tcagtgcctg aatcagggtc tgctgttgct ggtgcctcgc cacatatcca agtttttaty 300
tttttattct ttatgcatgg tcaaatgtgg ccaaacctaa tgtcttctct ggtttctggc 360
aagaaagcac tatgaactat caccagtttt agcaacgggg accttttgtt ctgtagtaat 420
atacataaaa aattaagatt gagcaagcag ataaaccttt tgtgtgcata attaataact 480
cacacttgaa tttctgtatc tcattagagg tagttgtctc acctttaact agagaagaca 540
agctttattt ttgtagcgct ttgccctatt atgttcaaca ataataattc acggtgaca 599

<210> SEQ ID NO 203
<211> LENGTH: 599
<212> TYPE: DNA
<213> ORGANISM: Homo sapiens

<400> SEQUENCE: 203
agaggatcat cagtcatggt gtccagggag aagctagcag tggtgagagg aagagctaag 60
cgaaatgaac atacagtgtg tttctgcccc tcacacagac atgtgcaaga gacctggggg 120
atgtgcattt gagatgcaag gagcaatggg acacgaagtc taacacatgg aacccactgt 180
cttgttggca gggatgataa atgccaatgg gtaacaatat tctatgattc aagacctaat 240
gaagaatttg aaagtgataa atacagttag taaattactc tagtttagag ttggaaggty 300
agagaagatt tcttttagaa ggtcgaattt gagttggtct ttaaagatga atcaattgca 360
caggttggag agagaatctt tatgcacaaa gatgcaactg cagaaaagag ggcaaacata 420
agtaggttag actagaataa ttatacccgt gagcttcaga gcaaatggca gcttatggaa 480
cactttcaca tgcaatagct catataactc tttaagcaac cctgtgaaac aggcagggca 540
gttgttattg cacaatttac agatgtgcaa actgtggttc tgcagagctg ctacaaaca 599

<210> SEQ ID NO 204
<211> LENGTH: 599
<212> TYPE: DNA
<213> ORGANISM: Homo sapiens

<400> SEQUENCE: 204
agtgataaat acagttagta aattactcta gtttagagtt ggaaggtcag agaagatttc 60
ttttagaagg tcgaatttga gttggtcttt aaagatgaat caattgcaca ggttggagag 120
agaatcttta tgcacaaaga tgcaactgca gaaaagaggg caaacataag taggttagac 180
tagaataatt atacccgtga gcttcagagc aaatggcagc ttatggaaca ctttcacatg 240
caatagctca tataactctt taagcaaccc tgtgaaacag gcagggcagt tgttattgcr 300
caatttacag atgtgcaaac tgtggttctg cagagctgct acaaacacta gagttggatc 360
tcaaacacac gtgcttgacc tttttttgct ttctggttta ctgcaatggg caagtcatag 420
ggtgaggagt gctatggtaa gattaggtta aatgggaaga gagagtcagc agagtttctg 480
actatgccca aatttgtaca aaaataagaa gaaatggtgt tttttttttt gaaaaaaaga 540
aaaagtctga ataataaaat gatccatgaa tttatggtga ggactagtaa aaaagtaaa 599

<210> SEQ ID NO 205
<211> LENGTH: 599
<212> TYPE: DNA
<213> ORGANISM: Homo sapiens

<400> SEQUENCE: 205
aataaaatcc aaagcgaata tgggagggct ttcctgaaag tttcttcacc cttaaaaggg 60
gaaccatgga aggaatgagc cctgctatcc ctttctgaaa tttgaaattg ttgtttgacc 120
atgtgagttt ctgcagcagt ttgtctgaca atgaggaggc aagcctgcgg gtgaagatga 180
gcacactgag gatgaaagag cagggggaca gaaagaactt tgttcttgtt tgacattgct 240
cagctcccaa cctaaccaat ttctggaacc tccctatctc tggatgtctt gttgtatgas 300
atgaaacatt ttccctattt ccttgtttga tctggctgag tcaggttttc tgttaactgc 360
agtccaaagc atgataactg ttacacgtgg gcagagagaa gacctattat tatcattcag 420
tcttcagtgt gattttagga ttttaggcca attattatct cttccaaggg cgtttgtatt 480
ttaggtcctc tattagtgaa tgaaataaat tatctgttct actacaggaa atagaagcat 540
cagactggaa ataggggaat tccatggcag tgattacacg tgcacgtgtg cacgtgtgt 599

<210> SEQ ID NO 206
<211> LENGTH: 599
<212> TYPE: DNA
<213> ORGANISM: Homo sapiens

<400> SEQUENCE: 206
gaatatggga gggctttcct gaaagtttct tcacccttaa aaggggaacc atggaaggaa 60
tgagccctgc tatccctttc tgaaatttga aattgttgtt tgaccatgtg agtttctgca 120
gcagtttgtc tgacaatgag gaggcaagcc tgcgggtgaa gatgagcaca ctgaggatga 180
aagagcaggg ggacagaaag aactttgttc ttgtttgaca ttgctcagct cccaacctaa 240
ccaatttctg gaacctccct atctctggat gtcttgttgt atgagatgaa acattttccy 300
tatttccttg tttgatctgg ctgagtcagg ttttctgtta actgcagtcc aaagcatgat 360
aactgttaca cgtgggcaga gagaagacct attattatca ttcagtcttc agtgtgattt 420
taggatttta ggccaattat tatctcttcc aagggcgttt gtattttagg tcctctatta 480
gtgaatgaaa taaattatct gttctactac aggaaataga agcatcagac tggaaatagg 540
ggaattccat ggcagtgatt acacgtgcac gtgtgcacgt gtgtttgtgt gagtgtgag 599

<210> SEQ ID NO 207
<211> LENGTH: 599
<212> TYPE: DNA
<213> ORGANISM: Homo sapiens

<400> SEQUENCE: 207
ccctttctga aatttgaaat tgttgtttga ccatgtgagt ttctgcagca gtttgtctga 60
caatgaggag gcaagcctgc gggtgaagat gagcacactg aggatgaaag agcaggggga 120
cagaaagaac tttgttcttg tttgacattg ctcagctccc aacctaacca atttctggaa 180
cctccctatc tctggatgtc ttgttgtatg agatgaaaca ttttccctat ttccttgttt 240
gatctggctg agtcaggttt tctgttaact gcagtccaaa gcatgataac tgttacacgy 300
gggcagagag aagacctatt attatcattc agtcttcagt gtgattttag gattttaggc 360
caattattat ctcttccaag ggcgtttgta ttttaggtcc tctattagtg aatgaaataa 420
attatctgtt ctactacagg aaatagaagc atcagactgg aaatagggga attccatggc 480
agtgattaca cgtgcacgtg tgcacgtgtg tttgtgtgag tgtgaggaag ggtgattcg 540 tagatggtca ttaaggcagg tctagtagta ctctctagtg ctaagcattt tcaaggatg 599

<210> SEQ ID NO 208
<211> LENGTH: 599
<212> TYPE: DNA
<213> ORGANISM: Homo sapiens

<400> SEQUENCE: 208
ccttttaact tggctttgga ctggcccaga tttggggttg agggacaaaa agccataaat 60
ggactttgta taatgggaaa gaacatctgt agtagaaata aatgtcctaa atctaaatag 120
ggttattttc aagtaaaatg gtttcataaa ttgcatactt tagtgaagat cagaatgttt 180
gcttgactga tcctatcaaa ctatattaag aacatagagg aagtttccaa cattttatag 240
gaaaaaagaa ataagcatta ctccaaaatt aaaataattt agatgcatgt aggaaagcar 300
acaatgatct cttttagaga agagtgtttt ggttttcaca ggtctgtaaa aacagacttg 360
acaaatgtat aacttttgat tcacttagga tatgtgaagt tattttagca ttgtgcataa 420
taaaagtttt agttgtatca aactgaatat agtaaaatgc caagatattt caccaggatt 480
aagctaatcc ttctctaaca acagaaaaaa atagttgcca ataaactcta tttttaacag 540
ccacttgaga gagacaagat gagacttatg aaaatccctt tcaagaagtt ttccagtac 599

<210> SEQ ID NO 209

<211> LENGTH: 599
<212> TYPE: DNA
<213> ORGANISM: Homo sapiens

<400> SEQUENCE: 209
acatttattc ttcctcttgc atctcctttt cagcatctat ctttcacttc ttaatttcaa 60
tatcaaatgt caatcttaga ttataaagtc tataatgtat gtatatatat acatgtttca 120
tgatctcaaa acctccttat actggtagat atttcttgat ggccaacttc tttactagta 180
agctgattag gcaaatgaga tgattagaac tccctgcatt ctggtttatc ctcgcaagat 240
atttgtaaga gatgtggcct aagactcttt cataatgcct aaattagcca tagtagttay 300
cacccaaagt ttgtagttac tgggttttta aaacaaatca gtctgaaatt acaaaatgat 360
tgtcttattt ttgaagatct ttgaactttc tatagaaact ctgtggtgga agaatgtatt 420
tccttgacag taaaaaaaat taaaaaaata tggagagagt ctttactttg atagtcttta 480
aatgatacta atagtgcaat tttcacttta ttactgtcaa gctgggagtt cctcttttgt 540
ttatagctga gtgagctcca attggattaa ccctctcaca gataatcata tattctgga 599

<210> SEQ ID NO 210
<211> LENGTH: 599
<212> TYPE: DNA
<213> ORGANISM: Homo sapiens

<400> SEQUENCE: 210
tgcaggcata tgaagttcca ggcagaagac ccagataagc caagccgtca ttctaaccca 60
caggaactca gagttttatt tataaaaatt gttttacgct gcttagtttg tgggaatttg 120
ttacatagca gcagacaact aataagatgg ccccacgttt cctgctctgt ggggaaagct 180
ggttggcagg gttagacaca ggttgacatg cagacagaac caaatcaacg tgactacagg 240
tgaccttttg agtttttagt tctagttact catgaatctt agctgcatct ttgctctcty 300
tgtagtttaa ctttccaaac cttccatgca ttctatgata aaccagtccc ctttttcccc 360
gaagtcaatt ttttttcaga tctcttaccc aaatgaagcc taatgtactc tgttcactga 420
actacaaaga atagtcacaa ataattaaat cccatgaaac ttttccttca tttccaggtg 480
aaggctgaac ctatgagata taaaaatagc cagattaaat gagagtggtt agatagtctt 540
tgggatgttt ggagtctgaa tttgttaacc tcctctgtgt tttggaaaag cctaaccat 599

<210> SEQ ID NO 211
<211> LENGTH: 599
<212> TYPE: DNA
<213> ORGANISM: Homo sapiens

<400> SEQUENCE: 211
gttcaaggcc agcctggaca agatggtgaa accccgtcgc tactaaaaat acaaaaatta 60
gcagggcgtg gtggcaggta cctgtaatcc cagttactcg ggaggctgag gcaggagaat 120
ggcttgaacc tgggaggcgg aggttgcagt gagccaagat agcccactgc actccagcct 180
gggtgacaga gcaagacccc atctcaaaaa taaataaata ataataataa taataacggc 240
agccataaaa aagaatgaga tcatgtcttt tgtaggaaca tgaatggagc tataggctay 300
gtatccttag aaaactaaca caggaacaga aaatcaaata tcacacattc tcacttgtga 360
atgggagcta aatcatgaaa actcatgaac acaaagaaag aaatgacaga catggggtct 420
gcttgagggt ggagagtggg aggagggaga ggagcagaaa agataacgaa tgggtactag 480
gcttaatacc tggctgatga aataatctgt acaacaaacc cccatgacat gaatttacct 540
atgtaacaaa ccttcacatg taccccctgaa cctaaaatca aagttaaaaa aattacatt 599

<210> SEQ ID NO 212
<211> LENGTH: 599
<212> TYPE: DNA
<213> ORGANISM: Homo sapiens

<400> SEQUENCE: 212
gctgttcttt tgttaaattt attcctaagt attttattat ttttgatgct cttataaatt 60
gaattgtttc cttaattcca tttgcagatt gttcattgcc agtttataga aacgtattag 120
atgtttgtat gttgattttg tattctatga ccttgctgca ctcgtttttt cattctaata 180
gtttttggtg gattccttag aattttccat atacacaatt atgtcatatg caaatagaga 240
tagttttact tcttccattc caacctactt gcctttcatt tctttttctt gcctcattgy 300
tagagataat tttgaaaagt agattgaatg ttgaaaagta tgcttacttt gttctctgga 360
aaaattgtaa aacttgttta tcattttttt ttgaaaagta agacatgcta tcttagttta 420
aacatcttcc agtcctgaag aggatttttt ttcatgtgtt tattggacat ttgtaccttt 480
ttaataaatt tctttttata ttacatatct atatgtatta tttcagtttc ttgtattaat 540
ttgttagacc tctttatata ttaagaataa taaccctttg gctgtgaaat aaattacaa 599

<210> SEQ ID NO 213
<211> LENGTH: 599
<212> TYPE: DNA
<213> ORGANISM: Homo sapiens

<400> SEQUENCE: 213
tgtctccctt ctggtagcct tgcattgata tttgcatatt tgattgagtg cacctttcca 60
agtgttatga actggctttg ttggagaaag tccacctgag ggtgggtgca agggcactag 120
cagagtgagg tgtggcagtt ctaggtctgg gaagggcctg tggcaaactc cctgtgcatc 180
tttgtcagct gagatcagaa ttggtgaaga ttgcaagggt tttcaacaaa caaggctgtg 240
ggcatccaca gcagcagtaa gggatcttca aagacaaagg ctgctaggga ctccctaatr 300
tctttttctt ccacagggga tgtcatgtct gaaggaatct ttcttgatat ccggtctagc 360
ttgtaggttt ccttattgca agggtggcac tgtttgactg tttgagctgc tggcacctgt 420
gcagtagcca cagagccagg tttggagcac aggtgtgcat ggagccaggg tctgaagtgc 480
aggtacacac gaaagagcca cagttctgaa gtcagggaca tgtgtggggt tgggggggt 540 gacatccctc atcccagggc agtgtaacag tagctcattc tgggggagca aggagtagc 599

<210> SEQ ID NO 214
<211> LENGTH: 599
<212> TYPE: DNA
<213> ORGANISM: Homo sapiens

<400> SEQUENCE: 214
atgcatgctc caaggatgtt ctcaagagaa tacacaaagg taaagaggga ctccaggcat 60
acatactttt ttccttttat ccccactgca ttgcccaaac ctgagaaaac acctttctaa 120
agcctctgtc ttgttaaaac ctagcctctt gagtgtggtc taaaacagtg gaatatttca 180
ttctgtactt gcaaagaaaa atgtaaccag gaaatatgta actctgcaca ttttaatatt 240
tacttactgt agtatatagt taatatttat tattcataat atcagtgtac attgtgtaar 300
ctttattcta gggtgtaggt gactactatg tacccgtggt gatagtttct tagcagagcg 360

```
ctgtggtact agcacactgg gctggttact gatagatctt gggacactgt tcctgtttca    420

gaaccacatg caaagcctgc tttgtaaagt cctaaaataa tgtgagctag gtgaaagtac    480

agctgccttt gactctgcta atcacataat aacaggacat agtcagtttt aagggtagaa    540

tgtcatactt gtgaattgct tcacaaaagg ccaattgtct cttttgggat ttgggccac     599


<210> SEQ ID NO 215
<211> LENGTH: 599
<212> TYPE: DNA
<213> ORGANISM: Homo sapiens

<400> SEQUENCE: 215

tgctaatcac ataataacag gacatagtca gttttaaggg tagaatgtca tacttgtgaa     60

ttgcttcaca aaaggccaat tgtctctttt gggatttggg ccactgtttt aagaagtttg    120

cctcgatgtg cattctaact gcccagccac agactgctaa tcccactcca ccactgaaag    180

aagacccagt ttaataattt gtatcaaaat gggaaaggat cacaggcctg taggttttta    240

tgtggctcac ctcctgccaa agggatggga atttatggat ttcctgaaag aagctgggcr    300

tggaaagaaa gaagagaagg ccccaaactg ccaactaaga agtgtcgcaa tatatttgat    360

gacagtgcag aggaaaataa aacacaaggc acgtggagaa ggaaacctaa acagtccaaa    420

atttccactg agtgttcagg gcaaggagca aacagctaag agccataata gggtgataca    480

taccatatga ttgaagagga tgagctactc tttgccccag tcacctaact ttggcttcac    540

tcctagaact tgcttagggt atctcttaca gagtagctgt actctatcga gtatctatt     599


<210> SEQ ID NO 216
<211> LENGTH: 599
<212> TYPE: DNA
<213> ORGANISM: Homo sapiens

<400> SEQUENCE: 216

tttgcaagcg gatccaaagt attaatagtt accacttttg tacatgtcca agaaaacgtg     60

gaattcaaaa tgagcacaat taatttggaa aaagttatct gatctaaatg aaaagtcatg    120

cttctcagag gggtataaag gcttacttcc tgaaagagca catatgaagc ctctgtctta    180

aacacagtct ttcccaccta acttccaaca gttgaaatac ctgttggtgc ttcttcagag    240

tggtgtcttc tgtgtttccc ataaccattt tatagtgata ttactgtggc gataagaagm    300

tggtaggtac tttgaatcat tttgtgccaa ttacacatgt atcatcaact tcttttgata    360

gatagaaatt cagtcattca tttttcatga aatatgctct ttcatatttt gaacccatta    420

ctgcccaaag ggtttattgc aaaatataca agtatagtca aacaataaag cgaatcaata    480

ataatagatc tacacatggt attatctgag atgatggcag aagttggaag tataaagtag    540

agatctagct aatctaccct gactaattgt atttccacta atattacaaa tacattgga     599


<210> SEQ ID NO 217
<211> LENGTH: 599
<212> TYPE: DNA
<213> ORGANISM: Homo sapiens

<400> SEQUENCE: 217

agaagctgag agatgtagga ctaaaaggaa taaaataaaa tccccgaatc caagaattgc     60

tgaaaacaat gtttcttttg attctcctag ttacaggaga caataaattt tactactacc    120

catttcaaag ctagtttaaa ttgtattttc accacttaaa accaaaccaa cagaagccag    180

tctgatataa agctaagagt ggctatactg atgtcatcca cacaacaata accaggtaat    240
```

ttagtttgta tttatggaaa aactacccgg ttctcatagg caggaagagt tgggaggggr 300
agactctgtg tgtctgggga ggagtaaatg ggagagatgt taaatttgat tatgggatag 360
caccttgagt cagaggatgg gtaggcaata aaacttattt ttttcattat ggtgatttgt 420
atcctaaaag aatggcttaa taatagagta ccaattgttt aaactgagaa tgggttattt 480
ttgaaacata aattaaagac aaataaacag ctaaaagata tccatccccc cccccccac 540 caaaggaaaa aacaatgtac tcaataacaa tgaaaaaaaa tggaggaggt attagaggt 599

<210> SEQ ID NO 218
<211> LENGTH: 599
<212> TYPE: DNA
<213> ORGANISM: Homo sapiens

<400> SEQUENCE: 218
ccaacaagaa aggggtacct cagaaacaca ttgctcatag gcacatagaa tgtgccaacc 60
agggatggcc acatgatctg cagacccaga gcaaaacaaa aatgcaaagc ctcttgttca 120
aaaaagcagg agaaaagttc tgtgaaaggc attataagac aaagcttttt cttttcctcc 180
aggaactcac cctctctcga gagtcatggt gtttcctatt tgctgtttaa taccattctt 240
ggtaaagaaa atttaaaatt gtcaattatt agtatggatt tcaccactca ttttaatatw 300
gtatgatgct agttttgcat gaaattataa gagcatttaa ctagtatgca aaatgactga 360
aattacacaa tgcatgtttt gtagctcatg tatgcatatg cggttgttac cagaacagag 420
gaagcactgc acagaactaa ctcatatata tatatatata tatatttttt ttttttttga 480
gacggagtct cactctgtca cccaggctgg agtgcagtgg cgcgatctcg gctcactgca 540
acctccccct cccgggttca agtgattctc ctgcctcagc ctcccgagaa gctgggatt 599

<210> SEQ ID NO 219
<211> LENGTH: 599
<212> TYPE: DNA
<213> ORGANISM: Homo sapiens

<400> SEQUENCE: 219
taaacattct ttttttatct gacccagctt tcagcttcat ctacttagtt atatcattgg 60
ttgggtaaca ggaattgcca ggatgtcacc cagtgggaaa atcaattcat gaaagaaggc 120
ctggtgctgt gtgtttgact atagagcatc tcttttcttt ctccaagcat atctgtctca 180
gcgcacctgg gtattcctcc cgagggctaa gaagaagttt gaattgccct gctgttaatt 240
aacaacatcc ctttctcctt atattacagg tgaacttgat tcattctctt gtatatatty 300
ctaagagaga gactcactgt gaaaggacac atcactataa aataaagaga aggccaatgg 360
tgaagtgttt gaaagataat tcattgttct agttggttat taaaataaat gtgtctcatg 420
atagaatcca gcatccaagt aggagctaag gatgttcttg ttccatgaat ttagatgttt 480
caaagataca tgcccccgcc ccactcctga catttaatat ctcttagcct ttggattgaa 540
ctcaattgtt cttaatctgg gccttttaca gagggtgcag cagatagagg cttcattgg 599

<210> SEQ ID NO 220
<211> LENGTH: 599
<212> TYPE: DNA
<213> ORGANISM: Homo sapiens

<400> SEQUENCE: 220
ccccatattc accctggatt tatcttctgg tgtatgcaac aaatcactac gttagcagat 60
tatatgatat agtttggatc tgtgtcccca cccaaatctc atgtcgaatt gtaatcccca 120
atgttggagg ggtgcctggt gagagatgat tggatcttgg gggtggattt ctcatgaatg 180
gcctaacatc atccccttgg tgctgttctc atgatagtga gtgagttatc ctgagatctg 240
gttgtttgaa agtgtgtagc acctgcactc tctctctcta ttattcctgc catgtaagay 300
gaatctactc cccctttggcc ttctcccatg gttgtaagtt tcttgaagct tccccagaaa 360
ctaagcagat gctggcacca tgcttcctgt atagcttgtg gaattgtgag ccagttaaac 420
ctcttttctt tataaattat cctatctcag gtgtttcttt atagcaatgc aaaaatggac 480
taatacatta tataataaaa aatgtattat ctcacagttt tcactggtca agagtctggg 540
tacagcttag ctcggtcccc tccccagggt cctacaagtg tgaaagcaga atgtcagcc 599

<210> SEQ ID NO 221
<211> LENGTH: 599
<212> TYPE: DNA
<213> ORGANISM: Homo sapiens

<400> SEQUENCE: 221
tgagtcacat gaagagacag tttttctggg gatctcttcc atttcagcat tggagtaata 60
ttcacgccta atcttttcac atttcttctg ttgtaatagg aaagtttctc ttgttaaaaa 120
aataaataaa taaaactaaa tgttaatgat gtaaatgcaa tttattttat tttagccaat 180
acattgttgt tgttgtttta tccacatgta ttaccatggt acaaccacaa gatatgatga 240
gatcattggc ccagcagcaa gtcttcagtt aggtacacct gtccatgtga tgaattagaw 300
catgcttttc cacctataaa ctacaactta atttgcataa cttaatataa gtagtattaa 360
tgtaagtgtt atacatattt caggttataa ttttgattac aatttgaaga cataaataca 420
attggtttag ttataaaatt acactactta cttgctactt tataactgct cactacctcc 480
ttagtggaac ccagattttc tctatgattt gagaaaaatt actccacatg ttacctagtt 540
atcaaactat attgggaagc agaaaaagct atgaaaggct tcaaagcttc tgagaacct 599

<210> SEQ ID NO 222
<211> LENGTH: 599
<212> TYPE: DNA
<213> ORGANISM: Homo sapiens

<400> SEQUENCE: 222
ttattaatag caaagctgtt gtatggtttg ggatcatttt tgcacttaaa tgattacact 60
ctcaccatgt tgcccatgct tatttcagtc agtactaagc aataattcaa ttgcttttcc 120
cagagagcaa ctcaaagctc acatactgat tgaataaccg ttctgcaaaa agcgaggagt 180
tacatgggga aaataccata gtataagaca tgatcacaaa gttactgata tcttacgcat 240
ctcacatcta aaatgaaagt ttccctattt taattaatac ctacgaggtg taagagtttr 300
ataccctaaa tgctcccaac cgagacatcc ttctcaaaac tctgtgcaga ggtgtctaaa 360
aacctatcag aaagccaaat gtttctcttt cctttacaat gactttgagg agatgatgtc 420
ttaagatgaa tttaggatga tatctagcta agtggaagga gttcctaaca gtccagcaga 480
attttccaag tttctacatt caagtacttg aacatattgg agagaaatct ctaccacatg 540
ataaaaacaa catggagaaa atgttttaag gttatggtca acttagccat acctatttt 599

<210> SEQ ID NO 223
<211> LENGTH: 599
<212> TYPE: DNA
<213> ORGANISM: Homo sapiens

<400> SEQUENCE: 223
tcatttgtat tttttcctct tcactctatt atattaaaaa ttactttta aaagttgttt 60 tttatcctgt cttttttgaa aaaaagaaag ttaatttttt ctcatttttt aaaatttccc 120
tttctcaaca ctatccccat attttcctag tccaatcaat taaaaaaata aaaagacaat 180
gctaataata tttttcaaat aaacctattt catttattta aaattctagt ttataatttt 240
atgctcacag acgtaatttc agtcaccgtt tattgaatat ttgctatcaa ccaatcatcr 300
tgctaaatag tatgcataaa gtaactcatt tcattcttcc aatgacctat ctgggaaatt 360
gctgtatttg ttttagtgat aaaactgaga cttaaacatc ttaatcacct gatcagagtt 420
actcaagtaa agtagaattc aacccaaaat ttggcagact ccaaagcctt caaggtaatc 480
attctgtatg cctccctgcc tcgcaaacat tctccccagc gcaagctaga tcttttcaaa 540
gcctaaaacg gatcatatca ccctgctaat tcaagacttg taaagcccat catggaaat 599

<210> SEQ ID NO 224
<211> LENGTH: 599
<212> TYPE: DNA
<213> ORGANISM: Homo sapiens

<400> SEQUENCE: 224
tttcagggaa agtgggaatc ttaccagctc cagcaggttt gtatcaacag gtctaatata 60
gtggttctca aactgtggtt ccttaaattt gcattatcaa catctcatga tgtaaaccta 120
tgaacatcat tgcagatcta ctgaattggt aacccaaggg gtagggacca caacctgtgt 180
tttagtaaac cctccaggct actgtgatgc attctccagg tttgagaacc actggtcaag 240
gataatcatg gcaactccat tctcctagta gatggttggt ttaagatggg tcaatggtay 300
aattccagcc aataaaatcc aaagcgaata tgggagggct ttcctgaaag tttcttcacc 360
cttaaaaggg gaaccatgga aggaatgagc cctgctatcc ctttctgaaa tttgaaattg 420
ttgtttgacc atgtgagttt ctgcagcagt ttgtctgaca atgaggaggc aagcctgcgg 480
gtgaagatga gcacactgag gatgaaagag caggggggaca gaaagaactt tgttcttgtt 540
tgacattgct cagctcccaa cctaaccaat ttctggaacc tccctatctc tggatgtct 599

<210> SEQ ID NO 225
<211> LENGTH: 599
<212> TYPE: DNA
<213> ORGANISM: Homo sapiens

<400> SEQUENCE: 225
gttttccgga taagcactat aagaactcaa cggaaaagag cagttttttc aatgacaatg 60
catgacagaa gccaaaaggt tttaaagcaa acatacaaat gcgtcatcta atagtccatc 120
aaccagccct tgtcacacag ataaaccttt tatctcactt tcccagattt taatcagcag 180
actggtttgc atgtttcttg tgtcactgtg gcaaccaacc taatggggat tctttatgcc 240
ctgagaaatc aactcatttg ggcctaaatg aaacatttcg ctgtcttgtt ttatctcccr 300
ctctattcac attaacataa tagcttttaa ttggattgta tttgtgattg gagtcagcaa 360
aggtggtgtt ctctcagagg aaattgactg caaggcaagc tgctgagcct ccatctggga 420 gaatttttttg agctattggc cacggggcaa gatggcgtca ggaagtgtca cctcaagagg 480
caacagataa ctcattttc ctacttaatg gaagtccaac aaatttatca taaaggctta 540
cagactcaag tatctgaact agtgtattgg tattcaaatg tatgttctca aaaatagag 599

<210> SEQ ID NO 226
<211> LENGTH: 599
<212> TYPE: DNA
<213> ORGANISM: Homo sapiens

<400> SEQUENCE: 226
gagcacttta gcccaggaat ttgagagctg cctggacaac atggtgaaac cctgtctcta 60
caaaaaatac aaaaattagc tgggcttgat ggtgcacgtc tgtggcccag ctactcagga 120
ggctgaggtg ggaggatcac ttgagtctgg aaagtcgagg atgcagtgag ccatgatggt 180
gccactgcac tccagcctgg acagcagagt gagaactcga aaaaaaaaaa tgatggaata 240
ctatgcagcc atgaaaaaga ataagctgat atcctttggt agaacatgca tggagctcgs 300
tatggtttgg ctatgtccac acccaaaatc tcatcttgac ttgtaatccc catatgtcaa 360
gggtgtgacc aggtggaggt aactggatca tgggagcagt ttcccccatg ctgttctcat 420
gataatgagt gattctcatg agatatggtg gttttataag catctggcat ttcccctgct 480
tgcactcact ccgtccttct gccctatgaa gaaggtgcct gcttcttctt tgccttctgc 540
catgattgta aatttcctga ggcctctcca ttcatatgga actttaagtc agttaaacc 599

<210> SEQ ID NO 227
<211> LENGTH: 599
<212> TYPE: DNA
<213> ORGANISM: Homo sapiens

<400> SEQUENCE: 227
ttctcctgcc tcagcctccc gagaagctgg gattacaggc aaacaccaca acacctggct 60
aatttttgta tttttagtag agacggggtt tcactatgtt ggccaggcta gtatcgaact 120
cctcacctcg tgatccaccc acctcggcct cccaaagtgc tgggattaca ggcatgagtc 180
accgcactcg gcctgaccat ccagctttta tggctccacg tccatcatgt ctgggcagtt 240
ccagcttgag acaaacagcc cttcagtgaa tttacaaggt agattgcaag agccttgcar 300
agttcagaaa accacaagtc acataaaaaa taggtctgag aaagtagtct aggctttcaa 360
aaccctctcc ttaaaaacaa agtgactaat acctaagata tttctgtaaa cacactcaac 420
acatagtagg catttaatac acattagttt ccattccttt cttatttatt taaatcctat 480
ctgaaaacaa catgtattca taaactttta tagctgagtc aaactgtcac aaaaatggaa 540
ggaatgtttg cattaccatc gtgataatgt tgttggggaa agtttgtttc atgaaaggt 599

<210> SEQ ID NO 228
<211> LENGTH: 599
<212> TYPE: DNA
<213> ORGANISM: Homo sapiens

<400> SEQUENCE: 228
gctagtatcg aactcctcac ctcgtgatcc acccacctcg gcctcccaaa gtgctgggat 60
tacaggcatg agtcaccgca ctcggcctga ccatccagct tttatggctc cacgtccatc 120
atgtctgggc agttccagct tgagacaaac agcccttcag tgaatttaca aggtagattg 180
caagagcctt gcagagttca gaaaaccaca agtcacataa aaaataggtc tgagaaagta 240
gtctaggctt tcaaaaccct ctccttaaaa acaaagtgac taatacctaa gatatttctr 300
taaacacact caacacatag taggcattta atacacatta gtttccattc ctttcttatt 360
tatttaaatc ctatctgaaa acaacatgta ttcataaact tttatagctg agtcaaactg 420
tcacaaaaat ggaaggaatg tttgcattac catcgtgata atgttgttgg ggaaagtttg 480
tttcatgaaa ggttgggggt ttgttttctt ctgatgacct aatagtcaac acagtagaag 540
tgtattacat gaaactagac tagaaatata ttacatgaga cttggaaaag ataactcat 599

<210> SEQ ID NO 229
<211> LENGTH: 599
<212> TYPE: DNA
<213> ORGANISM: Homo sapiens

<400> SEQUENCE: 229
ctaggttcaa gtgatcttcc tgcctcagcc tcccaaagtg ctgggattcc agtcatgagc 60
cagtggtgcc tggctcaaat aacttttgat gaaactgaaa acaattcttg tgtcctcaaa 120
atcccgtaag ttggaagtat gaggaaaaag ctgatcagcc ttcagagagg gcatgttctt 180
cagtgctcac ttcgtatatg gccaagttga aatggacgag aagggagctc ccatacagtg 240
gagcctggga aacagcaagg aacataattg aggcactttt tgaaccctca gagcaggagr 300
ccttacaatg ttcttccagc agtatctcag aattgccatg agctgtgact gtggaccgca 360
gctgccttct atcttctgct tttccccttt ctaaatggga gtgtccattg tggttttcct 420
ggcatcattt cttcatgggc tttcaagtgt gagagtttgg ggaaagcatg tttgttttag 480
ttcatacatt tccagctcaa gaagagtcat gtctaggttt gatgaagaca ccattgagca 540
atgtctagat tttgagctgg gtgctgtgaa tggtcaggat ttggggttat ctctttcag 599

<210> SEQ ID NO 230
<211> LENGTH: 599
<212> TYPE: DNA
<213> ORGANISM: Homo sapiens

<400> SEQUENCE: 230
aggcaagttt tagaatgctg taattctgtt tagtaccata actactaaga caaagctaaa 60
ttgagactgg ttgaagtgtt ccaaagttag caacaacaac aaaacaatag cttgacaaca 120
ttttacattt attcttcctc ttgcatctcc ttttcagcat ctatctttca cttcttaatt 180
tcaatatcaa atgtcaatct tagattataa agtctataat gtatgtatat atatacatgt 240
ttcatgatct caaaacctcc ttatactggt agatatttct tgatggccaa cttctttack 300
agtaagctga ttaggcaaat gagatgatta gaactccctg cattctggtt tatcctcgca 360
agatatttgt aagagatgtg gcctaagact ctttcataat gcctaaatta gccatagtag 420
ttatcaccca aagtttgtag ttactgggtt tttaaaacaa atcagtctga aattacaaaa 480
tgattgtctt atttttgaag atctttgaac tttctataga aactctgtgg tggaagaatg 540
tatttccttg acagtaaaaa aaattaaaaa aatatggaga gagtctttac tttgatagt 599

<210> SEQ ID NO 231
<211> LENGTH: 599
<212> TYPE: DNA
<213> ORGANISM: Homo sapiens

<400> SEQUENCE: 231
gaaaacctaa gacttaaaga atgattttaa ctctaaatca ctggggttcc catccagact 60
tctatagtga attccaaagt ttgtttccat ctccttctct atgctgctgc tttagaaggt 120
ggtcagggga gagaagcacc taccaacatc accgtcatca tcattatatt gtttaagtat 180
cttatttatg aaattgtaga ccaccattta tttttatttt aaaaggtgac tataataact 240
tcataggact aacagttggg agatggttaa agttgccatt aatcaaaagt tagtgaagay 300
ttctgtgtta ctatatctcc ttcatgaagt ccacaaaact aaattttcac atcacacaaa 360
ttagaggatt gtttggcttt tcctccagag aactgtttaa accattcact aactctatat 420
gaatttatgt ctccatgtgt tgtccatgcc caaaagaata taaatcattc tattataaag 480
acacatgcat gcatatgttt attgcagcac tattcacaat agcaaagaca tggaatcaac 540
ccaatgccca tcaatgagag accggataaa gaaagtatat gtggtacata tacaccatg 599

<210> SEQ ID NO 232
<211> LENGTH: 599
<212> TYPE: DNA
<213> ORGANISM: Homo sapiens

<400> SEQUENCE: 232
aaaatcccat cttctgccac catttttcta gatttgaact taatgaattt gctcagagag 60
gagcttaggt tacagtttgt tggtggctca tcatggatga tgagatagga acgggtggat 120
attgtatgat aacatcataa tgactgctat agctattgag cctgcctgca caatacttat 180
caaaaagact tgcgtaaatt cagcatgtat gatcagagga cctgggcatc acaaaacgta 240
ctcattgggg agcatgtcaa tttgcaagga atatttagaa agacttaact atgctaaaaw 300
taaactttaa atgatgttat aatggtgcaa tgaacattca tgtacatgtg tctttatggt 360
agaatgattt atattcctct gggcatatac tcagtaatgg gattgctggg tcaaatggta 420
gttctgcttt cagctctttg aggaattgcc acactgcttt ccacaatgat tgaaataatt 480
tacactccca ccaacagtgt tcccttttct ctgcaacctt gccagcatgt tattttttga 540
ctttctaata atggcagcaa gctgggcatg atggctcaca cctataatcc cagcacttt 599

<210> SEQ ID NO 233
<211> LENGTH: 599
<212> TYPE: DNA
<213> ORGANISM: Homo sapiens

<400> SEQUENCE: 233
gaaaaaatct ttctaatagc tgctattatt ttttacaggg tagaataatg tcacttgcac 60
ttgtagtgac atccattcaa tggtatttat tttctctgag accatagatc agatcaaagg 120
gaaattgtct tttctaggtg tgagacctac cattgcccat gggattaggt tcaaactcca 180
taaaactgac caaatcctgc aaagctgttt atattccatc tatacaattt tattatactt 240
atttacacaa atctagatat accttcatct ttctcttcct tccttccttt ttttcccaty 300
tgttcatcca cttttataga gaactgtgca ttccttaaag gaagggactg tgtcctatgt 360
gatttcatac ctgaagaaac aagcaccatg tcttgttctt gatagagaca gaaatcagga 420
cgttcttcat gaattctcag atcctgacta ccgtgagcct actgggggtg gggagtaaat 480
aatgttcctt tttacattcc tagtgtctag tatagcatct gacacatatg agatccgtaa 540
attacaactg agttaaatac aaaagcaaat acgttcagta tatgtagaaa taaagcatt 599

<210> SEQ ID NO 234
<211> LENGTH: 599
<212> TYPE: DNA
<213> ORGANISM: Homo sapiens

<400> SEQUENCE: 234
aatagagtgg gagataaaac aagacagcga aatgtttcat ttaggcccaa atgagttgat 60
ttctcagggc ataaagaatc cccattaggt tggttgccac agtgacacaa gaaacatgca 120
aaccagtctg ctgattaaaa tctgggaaag tgagataaaa ggtttatctg tgtgacaagg 180
gctggttgat ggactattag atgacgcatt tgtatgtttg ctttaaaacc ttttggcttc 240
tgtcatgcat tgtcattgaa aaaactgctc ttttccgttg agttcttata gtgcttatcy 300
ggaaaacaga attgatgtac attcttagga aagtggcagc atgatttctc tgagcacgta 360
acattttgtg tatttgatga aagtggcctg aatttggaag ttatagcaat caaagaagtt 420
taatcctttc ttaggatcat taaatttagt gagctggtat gatttgtgga gggtaaagtc 480
tgcattgaag aatgaaagaa gtagagttta gaaggtcaca tttttctct ctaaattgta 540 catcattgtt attggtttgg aagaaacatt ggagtttttc ataactgagg tctaatgaa 599

<210> SEQ ID NO 235
<211> LENGTH: 599
<212> TYPE: DNA
<213> ORGANISM: Homo sapiens

<400> SEQUENCE: 235
tccagcatcc aagtaggagc taaggatgtt cttgttccat gaatttagat gtttcaaaga 60
tacatgcccc cgccccactc ctgacattta atatctctta gcctttggat tgaactcaat 120
tgttcttaat ctgggccttt tacagagggt gcagcagata gaggcttcat tgggtttatg 180
gaatttgtgt atgtgtctac gtgctttttt tggaggagat ctttctcagc ttgtatgaat 240
ttctccatgg agtgaatgat accaaaaaga ttaagaacca ctgaagtaaa ggtccagcay 300
gttggaatat aaaaaattaa tcctgctttg cagtagtagt atttttccag gggactcaga 360
gttaatttcc acaggaagct aaacttaaaa ggggaggtta ttccttttca ggagaagtta 420
tttagaagga actacaagat gaccctctgt ccttcgagcc taggggacca tctatctgtg 480
agctgccttc tgtgatcatc tacatgaacc agttgcagga tattgagttg gagctaactc 540
tcacactcaa ttttaaagta caaactttta actgcattgt gactattgat cactgttta 599

<210> SEQ ID NO 236
<211> LENGTH: 599
<212> TYPE: DNA
<213> ORGANISM: Homo sapiens

<400> SEQUENCE: 236
ttaagattga gcaagcagat aaaccttttg tgtgcataat taataactca cacttgaatt 60
tctgtatctc attagaggta gttgtctcac ctttaactag agaagacaag ctttattttt 120
gtagcgcttt gccctattat gttcaacaat aataattcac ggtgacagat gtaatccacc 180
aaactcatta ttttcaaccc cgatccattt attttgcatt accaatacag tgttgatgcc 240
tatcattccc tgaactggag tgcctgctga aatgttttat tgcgatatgt cagagtttam 300
ataatagcag gaatgaggct gaagccttcc aaagttgctg tgtgtattat aaaaacgtat 360
gtaatgcacc ctgtactcac aagaacaggt cttaggaggt gtggttttga ttagccaatt 420
acatttggga gaagaatgga ctctatctct tagagagggc cacatctctt catatatgta 480
tatatgtgtg tgtatatgtg tatatatgtg tgtatgtcta tgtatatgcg tgtatatgta 540
tatatacaca tatgtattcg ggtttttaat atatatgtgt ctgtgtactt atgtgtata 599

<210> SEQ ID NO 237
<211> LENGTH: 599
<212> TYPE: DNA
<213> ORGANISM: Homo sapiens

<400> SEQUENCE: 237

```
taactgcagt ccaaagcatg ataactgtta cacgtgggca gagagaagac ctattattat     60
cattcagtct tcagtgtgat tttaggattt taggccaatt attatctctt ccaagggcgt    120
ttgtatttta ggtcctctat tagtgaatga aataaattat ctgttctact acaggaaata    180
gaagcatcag actggaaata ggggaattcc atggcagtga ttacacgtgc acgtgtgcac    240
gtgtgtttgt gtgagtgtga ggaaggggtg attcgtagat ggtcattaag gcaggtctar    300
tagtactctc tagtgctaag cattttcaag gatgaattct atatccaggg ctcaagaaga    360
agtttatatt cttaacacac aaaaattgct tataatatgt catttagaaa ataaaaaata    420
attctagctg ttaaaaaatg attttccctt ttgttttggc aggaagaata caggcaaaat    480
gcatgttgga gattcacacc ctcaccttcc tggaagatag cattttaaga aatatcttca    540
tatatcatgg gaattaaact gggtgtccta ttatattaat ccaaggcaga ctgagaggg     599
```

<210> SEQ ID NO 238
<211> LENGTH: 599
<212> TYPE: DNA
<213> ORGANISM: Homo sapiens

<400> SEQUENCE: 238

```
caccatatgt tctcactcat aagtgggagt tgaacaatga gaacacatgg acacagggaa     60
gggaatatca cacaccaggg catgtcagga ggtgaggggc tgggggagag atagcattag    120
gataaatacc taatgtaaat gatgagttga tgggtgcagg aaaccaccat ggcacgtgta    180
tatgtatgta acaaacctgc acgttgtgca catgtacccc agtacttaaa ggaaaacaag    240
caaacaaaca aaacccaaaa aactcgctga aagcaagtag agctttcatg tagggaacty    300
agagatgtaa ctgtatcctc caaatagcat tggcaggaca ggatttaaat cagtgtttct    360
aaggtgtctt gaatgcaatg catttctaaa acaaaattat actccaagga aaggtggcac    420
atgtgccctg tagaatcaga cataactaaa agccttggcg atgcttttcg actgtgacct    480
ggaaacgtca gtcccacagc ataagctctg tacaactctt gatgaggaat cagaacaagt    540
agatgttacc tacattcaac tgtgcctgta cagattaggc cacagagaca accaagaat     599
```

<210> SEQ ID NO 239
<211> LENGTH: 599
<212> TYPE: DNA
<213> ORGANISM: Homo sapiens

<400> SEQUENCE: 239

```
acttatttac acaaatctag atataccttc atctttctct tccttccttc cttttttttcc     60
catctgttca tccactttta tagagaactg tgcattcctt aaaggaaggg actgtgtcct    120
atgtgatttc atacctgaag aaacaagcac catgtcttgt tcttgataga gacagaaatc    180
aggacgttct tcatgaattc tcagatcctg actaccgtga gcctactggg ggtggggagt    240
aaataatgtt cctttttaca ttcctagtgt ctagtatagc atctgacaca tatgagatcy    300
gtaaattaca actgagttaa atacaaaagc aaatacgttc agtatatgta gaaataaagc    360
attgaattta agtgtcataa ttacttttga taactatttc acttctaagt tttgctacac    420
tgttggcttt tcatctttgt ttgtttgttt gagacagggt accgttcttt cacttaagct    480
ggagtccagt ggtgtgatca cagcttactg cagcctcaac ctactgggct caggtgatcc    540
tcctgcctca gcctccctag tagctgggct gcaggtgcac agcaccaggc ctgactaat     599
```

<210> SEQ ID NO 240
<211> LENGTH: 599

<212> TYPE: DNA
<213> ORGANISM: Homo sapiens

<400> SEQUENCE: 240
accttcatct ttctcttcct tccttccttt ttttcccatc tgttcatcca cttttataga 60
gaactgtgca ttccttaaag gaagggactg tgtcctatgt gatttcatac ctgaagaaac 120
aagcaccatg tcttgttctt gatagagaca gaaatcagga cgttcttcat gaattctcag 180
atcctgacta ccgtgagcct actgggggtg gggagtaaat aatgttcctt tttacattcc 240
tagtgtctag tatagcatct gacacatatg agatccgtaa attacaactg agttaaatay 300
aaaagcaaat acgttcagta tatgtagaaa taaagcattg aatttaagtg tcataattac 360
ttttgataac tatttcactt ctaagttttg ctacactgtt ggcttttcat ctttgtttgt 420
ttgtttgaga cagggtaccg ttctttcact taagctggag tccagtggtg tgatcacagc 480
ttactgcagc ctcaacctac tgggctcagg tgatcctcct gcctcagcct ccctagtagc 540
tgggctgcag gtgcacagca ccaggcctga ctaatttttt catttattgt agagacagg 599

<210> SEQ ID NO 241
<211> LENGTH: 599
<212> TYPE: DNA
<213> ORGANISM: Homo sapiens

<400> SEQUENCE: 241
aggaaaaaat attttgaaat aaaataagaa taagaattaa ggcaacctcc tccacatatt 60
ttactgtcct tctttcaaat agtatcagga aaaaaaaata attgtgatat ttccttacac 120
tggagagctc tcccaagagg atccatattt ttagttcctg tttgtggaag taaagcccgt 180
actatgaaaa ataaggcaga atccttttaa atgacaagat tcagttaatt ccatgtcttg 240
ttcagttggt cttatatccg ggaactggaa gcacaggttt tgtctctaag ataacctgcr 300
atgaatcaga ccattcagtt tttttctttc tttttgagac agagtctcac tttgtcgccc 360
aggctggagt gcagtggtgc gatctcagct cactgcaacc tccgcctccc gggttcaagt 420
gattctcctg cctcagcctc ccgagaagct gggattacag gcaaacacca caacacctgg 480
ctaatttttg tatttttagt agagacgggg tttcactatg ttggccaggc tagtatcgaa 540
ctcctcacct cgtgatccac ccacctcggc ctcccaaagt gctgggatta caggcatga 599

<210> SEQ ID NO 242
<211> LENGTH: 599
<212> TYPE: DNA
<213> ORGANISM: Homo sapiens

<400> SEQUENCE: 242
aacattttca gtgattctta agaaagcagg cttcaatccc ccaacccctc ccaagtctta 60
atttgttatt ataagctaag cactttacct ccaaaaggaa gaatacaatt gtgccattta 120
tcatatatca gaattacaca ggacatcatg ttaatgatca tttattccta gctacttgaa 180
gaataatacc cagtaattat agcaaatgta agtcaaatag taatagcata ctttaaatag 240
tatagtaatt ataagttatg tccatgcatc cgggacaagg gtcttttatg cttggtattr 300
aatctgttct gcaatttatt cttaatatca tcgctggggt tgaagaaagg aagcttgcct 360
gtagaaagga aacttgttgt cctttcacat ttccaataag tcatttgaag aaaacggttc 420
tttgcatgcc ttgctaaacc caattaccac caagacatca taaacaaata ttcattgcat 480
ttacagctgc ttctttattg cacaatgcaa aatgtattgt taaatttaaa ccatttaaaa 540
ggagtaagcg ctcagatttc tgcattcatt ttaaacttaa ttgaaaaaaa atcaagcat 599

<210> SEQ ID NO 243
<211> LENGTH: 599
<212> TYPE: DNA
<213> ORGANISM: Homo sapiens

<400> SEQUENCE: 243
gcagaaagat cacacacaag gctgtcactt cacacttgga gagttgcaca gccactactt 60
tcaatggcaa aaactgcaat tacttttgca ccaacctaat acaagaagca tgacgccagc 120
atctgattgg cttttgggag ggcctcagac tgcttctgct cagggcagaa agtagaagag 180
gagtgggcat gtacagagat gacatctcaa gagagagaaa ctgaggaagc cagactcttt 240
aacaacgtgc tctcaaaaac taatccattc tcagggaagg gagaactcac cccaaaggas 300
agcactaatt tattcacgag gatcctgtcc ccatgacctc cctctaggcc acacctccca 360
acactgccac attgggaaac aaatttcaac atcagttttg gcagagacac cacatccaag 420
ccatagtgca cagtgaaata aagcagtatt cggctgttag atgatactgt tattatcact 480
actgtacaga gatgacttcc ctttaggggt cataaaaggc ctcagagaag ctgtactgct 540
gcgattttat gattttgtgt aactcgtgga ctaaagataa agcaagggct gctctgccc 599

<210> SEQ ID NO 244
<211> LENGTH: 599
<212> TYPE: DNA
<213> ORGANISM: Homo sapiens

<400> SEQUENCE: 244
ctgtcacttc acacttggag agttgcacag ccactacttt caatggcaaa aactgcaatt 60
acttttgcac caacctaata caagaagcat gacgccagca tctgattggc ttttgggagg 120
gcctcagact gcttctgctc agggcagaaa gtagaagagg agtgggcatg tacagagatg 180
acatctcaag agagagaaac tgaggaagcc agactcttta acaacgtgct ctcaaaaact 240
aatccattct cagggaaggg agaactcacc ccaaaggaga gcactaattt attcacgagr 300
atcctgtccc catgacctcc ctctaggcca cacctcccaa cactgccaca ttgggaaaca 360
aatttcaaca tcagttttgg cagagacacc acatccaagc catagtgcac agtgaaataa 420
agcagtattc ggctgttaga tgatactgtt attatcacta ctgtacagag atgacttccc 480
tttaggggtc ataaaaggcc tcagagaagc tgtactgctg cgattttatg attttgtgta 540
actcgtggac taaagataaa gcaagggctg ctctgccctc tggggaaaga atcttaact 599

<210> SEQ ID NO 245
<211> LENGTH: 599
<212> TYPE: DNA
<213> ORGANISM: Homo sapiens

<400> SEQUENCE: 245
atgtaaattc cttgtattga aaagtatata tatctgaact ttttgcttgc cacaagtctt 60
gaatgacaag taacaaacat ctatttagaa ctcactggga tcaaggtcct atgaataaga 120
aaatgccata tacaaagaga aactggactc ctatctttca ccatatataa aaattaactc 180
aagatggatt aaagacttaa atataaggcc tggaactaca aaaacactag aagaaaaccc 240
aggaaaaacg cttctagaca ttggcctagg caaataattc atgaataaga cctcaaaagy 300
agattcaaca gaaacaaaaa tagacgatta ggacttaatt aaactaaaaa gcttctgcac 360
agtaaaagaa ataatcagca gagtgaacaa agaacctgca gaatgggaga aaatatttgc 420
aaactattcc tctgatgagg gcctaatatt cagaatctac aatgaactcc tcaataactc 480
aacaacagca ataaaacaaa taaccccatt aaaaagtggg caaagaacat gaacagactt 540
tttcaaaaga agacatacaa atgaccaaca aacatatgaa aaaatgctca acatcactg 599

<210> SEQ ID NO 246
<211> LENGTH: 599
<212> TYPE: DNA
<213> ORGANISM: Homo sapiens

<400> SEQUENCE: 246
gttgccttga cagtagcaag ctcttgatga agtgtcagca tttaaggaaa tgcacaaacc 60
tttgtacttg taatactttg ctcaagtctg gatttgccca ttgtgcaaaa cagttctcta 120
aactatctga aaaaaaaatt cctttaaaga attatagatg atagtcatta ttaaagttca 180
agtctatgtg acttttaaaa ataaaaatat ataatttccc ctctgtttac ttggttttga 240
agcattagta gcatttgtat atgtaaaaga gtatttatct atgttaatca aaaatatgtm 300
tgaaggtgaa attgaatgac aaagtgaaat gaagtattac atagtattca cgaatatgcg 360
tatcttataa agcgatctgc tttaagaaat tgtataagaa aatatcacta tatttatata 420
agggttatga aataatttta aagctgtatg tttcatagta tatgagttgt tttaaataat 480
aataatccaa aatagagcac aaggcaatat tactaacttg aattttcatt tgaaccccaa 540
tgcttcaatt attgaattaa tcagagaaat aaaaactgat tttatagcta taatgatgt 599

<210> SEQ ID NO 247
<211> LENGTH: 599
<212> TYPE: DNA
<213> ORGANISM: Homo sapiens

<400> SEQUENCE: 247
agaagaagca ggcaccttct tcatagggca gaaggacgga gtgagtgcaa gcaggggaaa 60
tgccagatgc ttataaaacc accatatctc atgagaatca ctcattatca tgagaacagc 120
atgggggaaa ctgctcccat gatccagtta cctccacctg gtcacaccct tgacatatgg 180
ggattacaag tcaagatgag attttgggtg tggacatagc caaaccatac cgagctccat 240
gcatgttcta ccaaaggata tcagcttatt ctttttcatg gctgcatagt attccatcak 300 ttttttttt cgagttctca ctctgctgtc caggctggag tgcagtggca ccatcatggc 360
tcactgcatc ctcgactttc cagactcaag tgatcctccc acctcagcct cctgagtagc 420
tgggccacag acgtgcacca tcaagcccag ctaattttg tattttttgt agagacaggg 480
tttcaccatg ttgtccaggc agctctcaaa ttcctgggct aaagtgctcc tcctgcttca 540
gcctcccaaa gtgctgggat tccaggtgtg agcccctgtc cccagctccc atgcttgtt 599

<210> SEQ ID NO 248
<211> LENGTH: 599
<212> TYPE: DNA
<213> ORGANISM: Homo sapiens

<400> SEQUENCE: 248
ctttgtactt gtaatacttt gctcaagtct ggatttgccc attgtgcaaa acagttctct 60
aaactatctg aaaaaaaaat tcctttaaag aattatagat gatagtcatt attaaagttc 120
aagtctatgt gacttttaaa aataaaaata tataatttcc cctctgttta cttggttttg 180
aagcattagt agcatttgta tatgtaaaag agtatttatc tatgttaatc aaaaatatgt 240

-continued

```
atgaaggtga aattgaatga caaagtgaaa tgaagtatta catagtattc acgaatatgs    300

gtatcttata aagcgatctg ctttaagaaa ttgtataaga aaatatcact atatttatat    360

aagggttatg aaataatttt aaagctgtat gtttcatagt atatgagttg ttttaaataa    420

taataatcca aaatagagca caaggcaata ttactaactt gaattttcat ttgaacccca    480

atgcttcaat tattgaatta atcagagaaa taaaaactga ttttatagct ataatgatgt    540

taattgttta tactggaata gtcatatggc attttagtat atgtgatctc gtttaatat     599
```

<210> SEQ ID NO 249
<211> LENGTH: 599
<212> TYPE: DNA
<213> ORGANISM: Homo sapiens

<400> SEQUENCE: 249

```
atggaatata aacagctttg caggatttgg tcagttttat ggagtttgaa cctaatccca     60

tgggcaatgg taggtctcac acctagaaaa gacaatttcc ctttgatctg atctatggtc    120

tcagagaaaa taaataccat tgaatggatg tcactacaag tgcaagtgac attattctac    180

cctgtaaaaa ataatagcag ctattagaaa gatttttttcc ccaagcttta tttgcagtta    240

taaactaaac agatacttgt aaaaaatggc cacttaaaat gttaatttca tgaatgtttk    300

caataatcaa agctaaaagg attaatgagt ctaagagaaa gatgatacgg aaagaatggc    360

aaactaattc aatgttttta aaaggatgaa aaaatcgtct ctttttacaa aataaaaaata    420

ataacgaagt ccatgaattt aaaaaacatg tgtttattat gtttcacaaa agaaatacaa    480

atttagagtg aagggtggga ggaaagtgag ggtggaaaaa ttacctgatg gatacgaagt    540

tcaatgtttg ggtgatgggt acaggagaag ctcaatcctc accatcacgc atgtaatac     599
```

<210> SEQ ID NO 250
<211> LENGTH: 599
<212> TYPE: DNA
<213> ORGANISM: Homo sapiens

<400> SEQUENCE: 250

```
ttggtcagtt ttatggagtt tgaacctaat cccatgggca atggtaggtc tcacacctag     60

aaaagacaat ttccctttga tctgatctat ggtctcagag aaaataaata ccattgaatg    120

gatgtcacta caagtgcaag tgacattatt ctaccctgta aaaaataata gcagctatta    180

gaaagatttt ttccccaagc tttatttgca gttataaact aaacagatac ttgtaaaaaa    240

tggccactta aaatgttaat ttcatgaatg ttttcaataa tcaaagctaa aaggattaay    300

gagtctaaga gaaagatgat acggaaagaa tggcaaacta attcaatgtt tttaaaagga    360

tgaaaaaatc gtctcttttt acaaaataaa aataataacg aagtccatga atttaaaaaa    420

catgtgttta ttatgtttca caaaagaaat acaaatttag agtgaagggt gggaggaaag    480

tgagggtgga aaaattacct gatggatacg aagttcaatg tttgggtgat gggtacagga    540

gaagctcaat cctcaccatc acgcatgtaa tactcctgta acaaacaagc acacgtacc     599
```

<210> SEQ ID NO 251
<211> LENGTH: 599
<212> TYPE: DNA
<213> ORGANISM: Homo sapiens

<400> SEQUENCE: 251

```
ttgtattgaa aagtatatat atctgaactt tttgcttgcc acaagtcttg aatgacaagt     60

aacaaacatc tatttagaac tcactgggat caaggtccta tgaataagaa aatgccatat    120
```

acaaagagaa actggactcc tatctttcac catatataaa aattaactca agatggatta 180
aagacttaaa tataaggcct ggaactacaa aaacactaga agaaaaccca ggaaaaacgc 240
ttctagacat tggcctaggc aaataattca tgaataagac ctcaaaagta gattcaacar 300
aaacaaaaat agacgattag gacttaatta aactaaaaag cttctgcaca gtaaaagaaa 360
taatcagcag agtgaacaaa gaacctgcag aatgggagaa aatatttgca aactattcct 420
ctgatgaggg cctaatattc agaatctaca atgaactcct caataactca acaacagcaa 480
taaaacaaat aaccccatta aaaagtgggc aaagaacatg aacagacttt ttcaaaagaa 540
gacatacaaa tgaccaacaa acatatgaaa aaatgctcaa catcactgac atcacagaa 599

<210> SEQ ID NO 252
<211> LENGTH: 599
<212> TYPE: DNA
<213> ORGANISM: Homo sapiens

<400> SEQUENCE: 252
tgcaataatg gggtcaaaga tttctataat gacagtctac tttcctctgg gcacaacttg 60
tctgacgacg agaaaaacta aaaagaatga aataaaaagc aaagaagttt cagattcact 120
aataatagtg ttggcttttg agtgaaaatt agctctggaa agaaagtgca acataaagca 180
agacaagcca gggcagaatt ttgcacattc cagtgaaagt tttcaggcaa ttctatccat 240
ggatataccc ttaaaggatg tgacccaggt gagacttacc tgctgaaggc aactaatccw 300
caatgagcaa attatcctgc cctggagggt aagctacaat atcggtccca tgcttcagga 360
agagaaaatc atgtgttcct agaagagaag gaaaccaggg gctagcagag gcttgcctag 420
aaatggaatt gaaatataaa ctgagaagtt tcagttgatt tagaataaca gggtgttcca 480
attagcttac aaaatgtttc tgacaggcaa tagaatcgaa taagggaaca gcagtggcat 540
cacacaaaaa ggaatttaac aaatgctggc actttcatat cccctaggga gatgaatga 599

<210> SEQ ID NO 253
<211> LENGTH: 599
<212> TYPE: DNA
<213> ORGANISM: Homo sapiens

<400> SEQUENCE: 253
gaaaaactaa aaagaatgaa ataaaaagca aagaagtttc agattcacta ataatagtgt 60
tggcttttga gtgaaaatta gctctggaaa gaaagtgcaa cataaagcaa gacaagccag 120
ggcagaattt tgcacattcc agtgaaagtt ttcaggcaat tctatccatg gatataccct 180
taaaggatgt gacccaggtg agacttacct gctgaaggca actaatccac aatgagcaaa 240
ttatcctgcc ctggagggta agctacaata tcggtcccat gcttcaggaa gagaaaatcr 300
tgtgttccta gaagagaagg aaaccagggg ctagcagagg cttgcctaga aatggaattg 360
aaatataaac tgagaagttt cagttgattt agaataacag ggtgttccaa ttagcttaca 420
aaatgtttct gacaggcaat agaatcgaat aagggaacag cagtggcatc acacaaaaag 480
gaatttaaca aatgctggca ctttcatatc ccctagggag atgaatgatg atgaacttca 540
aaagttggaa ctgatttgag tccaatatgg ctggaatagc ttaaaaagta aagtataac 599

<210> SEQ ID NO 254
<211> LENGTH: 599
<212> TYPE: DNA
<213> ORGANISM: Homo sapiens

<400> SEQUENCE: 254
cacaaaaatt agccaggctt ggtggcgggc acctgtaatc ccagctactt gggaggctga 60
ggcaggagaa tctcttgaac ctgggaagtg aaggttgcag agagctgaga tcatgccact 120
gcattccagc ctggacaaca gagcgagact ccatttcaga aaacaaacaa acaaaaacct 180
tgaattttag tcttgcagtt tgcatgtgac atggcaaatg tgagaaacta agcagtattt 240
tgtaattcta gttttctaaa ttctacagca tgagtttatt gtagcatggc tatatctaas 300
ttgttattaa gaagaaagtg ggtagataga tacttttctg tttcaaatga tggcaaacag 360
gaataaatac actcggaggt ttaccttttt ggcattttat tttatttcgc tatagaaaaa 420
ttatttcaga ctttatttgt tggatttaaa atgtttacct tggctagaca cagtagctca 480
cagctgtcat cccaatactt tgggaggctg aggtgggagg attgtttgag ctcaggagtt 540
caagaccata gctagacatc atctctatga attaaaaaaa aaaaaaatag cctggtgtg 599

<210> SEQ ID NO 255
<211> LENGTH: 599
<212> TYPE: DNA
<213> ORGANISM: Homo sapiens

<400> SEQUENCE: 255
tctattttat agaaactgaa gtgtcgcgag agtaagtcat ttgcctgagg tcacacctag 60
agtatgggat tgggtctatg ccttttggc tctgaaaccc ttgcccattc agtgacatca 120
gaaagcctct ttctgtgtcc atttggtttt cccattggct gaaggcaaat gccctaacat 180
gagagacctt ttgcaaactg acctgtgtct ctcaatcctt tcccactttc cccagccaaa 240
ctggctgact cactctctca atgctcttca tagacattcc catggtatgc cctcttccty 300
ccagggcctg caggattctc catcctttta tacccacgta taaccaattc aaaatctcca 360
aagccatcaa gattcttggg cctctccagt ctgtggaatc gtacccacct ttgaattttt 420
attgactctg ctctattcaa ctggcagtgg cttaatggca gcccttatat tttctcatat 480
cacaattcag tgttttatgc atgtatagtt ttctctttgc aattggaatt ttcttttctt 540
gaggtcagca tatatatttc atttattttc gtattcactg tggcagcaca aaaggggta 599

<210> SEQ ID NO 256
<211> LENGTH: 599
<212> TYPE: DNA
<213> ORGANISM: Homo sapiens

<400> SEQUENCE: 256
cttcccattt cagatgaagc acaagtaaga actgtgtttc tctctttatt tttaagaaaa 60
atagcaagag agggtcttgc tatgttgccc aggctcaaac ttgggattca agcaatcctc 120
ttgcctcatc ctcccaaagt gccaggatta cagacgagaa ccaccacatg agcctggcca 180
aatgagaact ttctgaaaaa gatattgcca tctagaaaac ttcttcccct aaagtcttag 240
aatttgatac tcaaatggtt tcctatttga aaaaatttat gattagatgt tttggtaagr 300
caaagagatt tattctgaga atcatggcag ccaccttttg atgggtataa atggtctctg 360
tgaagtgcta tctctactac ataaacacga ctcaataaag atttctttca gcaaatgtta 420
aacccattga tggaactgag tcaaagaaga atggttcttt atattcccta attcaaatac 480
cttgtagtca agatagtagt aatgcattta tttgtcaata ctttatttct ttatcccaag 540
gaaataattg ggttgaattg cccatttgtg gtattttgta agataactga aggaaatgg 599

<210> SEQ ID NO 257
<211> LENGTH: 599
<212> TYPE: DNA
<213> ORGANISM: Homo sapiens

<400> SEQUENCE: 257
cttctactgt tgagtatgat gttctcatac acaaccttta ttatatacaa catttattct 60
catatacaac ctttattata ttgaggtact ttctttctat acaaaattta ctgagaattt 120
ttatcatgaa acaaggtcaa cttctgtcaa atgcttcatc tgcatttatt gagatgatta 180
tatgattttt atccttcatt ctgttaatgt gccatatcac atttattaat ttacttatgt 240
tgaaccatcc ttttatccta aggataaatg ctacttgatc atgttgtata atccttttay 300
gtactgttga attcagtttg cttatgtttt gttgagattt ttttgcatct atgttcatca 360
aggatattgg tcagtagttt tcttttcttg tagtgtcttt gtctgcttcg gtatcagggt 420
aatgctggcc ttgtaaaatg agtttggaag tgttctctaa cttttcggaa gagtttgaaa 480
aggattggtg ttagttcttt ttttaaatgc ttggtcatct ggttctgggc tttttgttgt 540
tgtttttgga agatttttaa tgactgtttc aatcttcttc ctagttatag gtctattca 599

<210> SEQ ID NO 258
<211> LENGTH: 599
<212> TYPE: DNA
<213> ORGANISM: Homo sapiens

<400> SEQUENCE: 258
agagcaacta tgaatcactg acttaggtca ctctgaggtc tttataagag aacttccagc 60
ttcatctttg atttaatatt gaccccaagg ccaagtttta ttggcaggct tctatttgtt 120
tctttccttg aaggtctttt gctaactgaa gagactttct gagcattcta tattcccatt 180
aaattctgat tttaaaaagg accctaagca gttccttctt tagccttatt tctgtcttac 240
aataccttat attcagctaa aagaagacaa atgacacttt taccatcctt cttggaatcy 300
ttttatccaa atgtacagat tttaggatac ctttcctgtc taagttaatg tgggcagcag 360
tttcactaat ttttctgcca ctacataaca cgggttgttg tttttccagc ctccaaagca 420 atttctcac tacctttcca ggctctagga aacagtccgt tgctgctttc tggtgtctct 480
gctccccact cctaaagcca agggcacata ttctagattt tgttatgaca gcacatcacc 540
tctttgcatc gacttctgca tccattgttt attgctgtgt acaaaacatc ccaaaatta 599

<210> SEQ ID NO 259
<211> LENGTH: 599
<212> TYPE: DNA
<213> ORGANISM: Homo sapiens

<400> SEQUENCE: 259
gatagagaca gaaatcagga cgttcttcat gaattctcag atcctgacta ccgtgagcct 60
actgggggtg gggagtaaat aatgttcctt tttacattcc tagtgtctag tatagcatct 120
gacacatatg agatccgtaa attacaactg agttaaatac aaaagcaaat acgttcagta 180
tatgtagaaa taaagcattg aatttaagtg tcataattac ttttgataac tatttcactt 240
ctaagttttg ctacactgtt ggcttttcat ctttgtttgt ttgtttgaga cagggtaccr 300
ttctttcact taagctggag tccagtggtg tgatcacagc ttactgcagc ctcaacctac 360
tgggctcagg tgatcctcct gcctcagcct ccctagtagc tgggctgcag gtgcacagca 420
ccaggcctga ctaatttttt catttattgt agagacaggg tctcaccatg ttgcccaggc 480
tggtctggaa ttcctgggct caagtcatcc tcctgtgttg gcctcccaaa gcactgggat 540
tataggcatg agccaccact tccagctggc ttttcatctc ttggtgggac aggaattaa 599

<210> SEQ ID NO 260
<211> LENGTH: 599
<212> TYPE: DNA
<213> ORGANISM: Homo sapiens

<400> SEQUENCE: 260
taaacttaaa aaagaaatgt cttccttgaa ggaacttgca gaagacctca aatagagact 60
tatttcttta tgaacgcttt tattaggtcg atgcaaaagt tattgcggtt ttggtcatta 120
cttttaatgg caaaaactgc aatttctttt gtggcaacct aatattatct gcaatactgg 180
gggtctctct ttgccccttg gactggtgca attgaatccc atcctgaagt agagagcagc 240
atgacaaggg atttgcaaaa ctaggggact gactttctgg agttcctgga gcttttaacr 300
tgccccaagt tttgtttaaa aaaactttaa gattaacaca gatatattat agaatagcat 360
ataaaatatg cctgaatttt gaaaataaaa tatgatactt caaagatgta tcttggtctc 420
agaaggctgg agtgctttta tatccggaaa taagagctca ttcttctctt ccatcaggag 480
caggaaacat tgaaactgtt gctttggata atgcaatcca ttaactcagt actgccactg 540
tgggcctgga tggattatct ctatgaggca gttatgcacc caggactcac ttctaactt 599

<210> SEQ ID NO 261
<211> LENGTH: 599
<212> TYPE: DNA
<213> ORGANISM: Homo sapiens

<400> SEQUENCE: 261
agcttgtcat acatcagact tcagtgaatc ttgaaggatt gtccttttct taagaaactc 60
aatgggctgc attcccttcg agttttttag agaatcattt cagtatcaca gttccacaca 120
tggaatgaaa agcaacaatg tgtgctgcat tttttagaat atattgtttt tactcattcc 180
aatgtcctgt gcaattgaac tcccttcccc cagcctttat aatattggaa tcggtatgca 240
gaaatacaaa ccactataga gaaaacactt tatgaatgta aacgcttcaa tatggactty 300
ctgcattata gtatcaaggc taggtcacga accagcatgg ccacagtaac agaattcaaa 360
cctggcttcc aagatttgtc tacggaaaag aagatttaaa tcaatggtat gggtagagga 420
ccagagatta gacaaccctg aaagagctgg cccaatagct agatttattt tgaaaaccaa 480
gagacctatc tagaagcaga ttaaagttac aatctatgca tatttgcttt gctaacactt 540
gtgtaattta caaatatggg ctccggatcc agaatgctcg ggatcaaatc ccacccccac 599

<210> SEQ ID NO 262
<211> LENGTH: 599
<212> TYPE: DNA
<213> ORGANISM: Homo sapiens

<400> SEQUENCE: 262
agttttttag agaatcattt cagtatcaca gttccacaca tggaatgaaa agcaacaatg 60
tgtgctgcat tttttagaat atattgtttt tactcattcc aatgtcctgt gcaattgaac 120
tcccttcccc cagcctttat aatattggaa tcggtatgca gaaatacaaa ccactataga 180
gaaaacactt tatgaatgta aacgcttcaa tatggacttc ctgcattata gtatcaaggc 240
taggtcacga accagcatgg ccacagtaac agaattcaaa cctggcttcc aagatttgty 300
tacggaaaag aagatttaaa tcaatggtat gggtagagga ccagagatta gacaaccctg 360
aaagagctgg cccaatagct agatttattt tgaaaaccaa gagacctatc tagaagcaga 420
ttaaagttac aatctatgca tatttgcttt gctaacactt gtgtaattta caaatatggg 480
ctccggatcc agaatgctcg ggatcaaatc ccacccccacc aatctacaat agtgtgatct 540
tggggtatgt ttccaaccca ccataagcct atttcttgaa atttttgtaa tctcctcaa 599

<210> SEQ ID NO 263
<211> LENGTH: 599
<212> TYPE: DNA
<213> ORGANISM: Homo sapiens

<400> SEQUENCE: 263
tccccagacc tctactcccg tctaacgtat atttcttgtg tctacttgct ttttctttcc 60
agattttttt tttgctaaga atgtgggatg gtggcacata atagctgtga ttgtgtttgt 120
gtgtgtggag gggtgtgggg tgatgaggtg agtatattga aaaaaatata taggatttat 180
tgtggacaag gagtattatt ctggcttcag aggttatctg tgaattcata gcaatgatac 240
ggttttgagg gtttcttttt cttttagaga gaggaggagg aagagtgttt aatttttttw 300
aaaaactgaa tgaagtcgag gttagtcaag agtcctatcc tttgactttc ttccacctag 360
aaccttattt ttctttgatc tatgagactg aaaataataa gtccctgtaa acttagctct 420
aaacaagaaa cttgtagcca tatcattgag tcacatgaag agacagtttt tctggggatc 480
tcttccattt cagcattgga gtaatattca cgcctaatct tttcacattt cttctgttgt 540
aataggaaag tttctcttgt taaaaaaata aataaataaa actaaatgtt aatgatgta 599

<210> SEQ ID NO 264
<211> LENGTH: 599
<212> TYPE: DNA
<213> ORGANISM: Homo sapiens

<400> SEQUENCE: 264
atagcaaata ttcaataaac ggtgactgaa attacgtctg tgagcataaa attataaact 60
agaattttaa ataaatgaaa taggtttatt tgaaaaatat tattagcatt gtctttttat 120
ttttttaatt gattggacta ggaaaatatg gggatagtgt tgagaaaggg aaattttaaa 180
aaatgagaaa aaattaactt tcttttttttc aaaaaagaca ggataaaaaa caactttttaa 240 aaagtaattt ttaatataat agagtgaaga ggaaaaaata caaatgagaa aggctactar 300
ctatgctgaa ataatcaagt gactattgag tgtttactgt gataccagcc atgataccag 360
ccataaagca tttagatgct aaatgcttca tctacattat ttcattgaat acttacaacc 420
atactgtgaa ataagtctca ttatgttgat tatgttcata ttacaaatga gaaaatagaa 480
gagcatttag tgacttgtcc taaagttaat aagtggctgg gattggattc aaactcagat 540
acctggtttc acatcattct acttcttctt tctaatttga atgtctgtta tttttcttt 599

<210> SEQ ID NO 265
<211> LENGTH: 599
<212> TYPE: DNA
<213> ORGANISM: Homo sapiens

<400> SEQUENCE: 265
ataataataa agcaaatgac ttataaggca aagaaaagta gacaaccatc agactttttg 60
gcagcaaaaa tttataccaa aaaaagatga agaatatact taagaacaca agagaagaaa 120
atgtgaacca aggattttat atcctaagaa aactttacac tcctggataa agggcacaaa 180
cataatttta tcaatccaca agaactcaga ggatactgga gacaaatttc agacagtcaa 240
aataattgaa gagctataga tgtaagggca ggtgtattta tcacaacttg ctgctacaaw 300
tcacaaaaag agagacacac agatattgca tgtctccaca tgaaagaaag aaaaatagaa 360
aacacctata gtctttgtaa aagacagaat ttgaatatgg tcaagcctta ggaggcagtc 420
acctatttgg aggagataca cagggcaaat ggacatagta aactgtaccc atagtgtttg 480
ctacaatacg ggtcattctc attgcaatcc atactaccaa acattttgca gattaaatgg 540
cctacagcta gtgaatttat gaggaagagg aagggatgga ggagaaacct gaagattaa 599

<210> SEQ ID NO 266
<211> LENGTH: 599
<212> TYPE: DNA
<213> ORGANISM: Homo sapiens

<400> SEQUENCE: 266
atgattttcc atgctttata tttaaataaa acagtagtta ctaaagctta cctctaaaga 60
taatttaaat agaaactgct tattttgaaa attgtcttat ttatagtttt gctttgttcc 120
ttaaataaca agattttatt cctcctccca ctttcccaat ttgtgtactg aaaatcacaa 180
ggaaagaatt ttgcaaagca caaaatttat ttcatgcttt aaggtttaga ctttgtttaa 240
aaaatctaaa aaatttattt attttctgag actttaatct ttttgataag taaagttcay 300
ggaaaaccat gtaattggta tagaactttt cacttgaatt gaatcacata atccttctgt 360
agtagaatac ttttgcatct tgcctggagt aaattagttt ctttaggtta aaaaaaatcc 420
tggaattata tttttcaatt tgaaattcac ttaatatcaa agtgactata attaattctt 480
ttactgatga tctgaaaaac ggtaataaga aattacaaat aacatatcaa agaaatttca 540
taaagtatac ctgataaaaa catttcaagt gtgaggtgct ttatttttcc acactaaat 599

<210> SEQ ID NO 267
<211> LENGTH: 599
<212> TYPE: DNA
<213> ORGANISM: Homo sapiens

<400> SEQUENCE: 267
tttagtgata tttggaatca tacggatttt gattcacatt tcaaacctgt cccttcctca 60
tagccatttg gcccttgtct tctagattga tctataggga attgtgagga ttaaatgatg 120
tctgtggcat ccaacacagt gtgtacattt aagagcactc tcttgatttc ataatctctt 180
tcttccttta tttaggattt tgctttgtgg agtaatggtc aaggacaact ttacttggtt 240
ttatgtctac aaaacagtca tgtgtgaagt aaagagtatg ttattgactc aagagtcats 300
ataattgaac cacgaagtag attttctatg gttaaaaaca ctggttttaa aaatatggaa 360
agtcataaat gagtcatggc aatcttgtga caaaagcaca gattatacag aaatgtatga 420
ttcatctgtg ttttccttaa acttttacct ggtgagagag aaggtttatt gatttgcaca 480
tctccttcta ggattattag agcatatact tgaacggtga aatttacatt caaaatagag 540
aagaataact gccacaaaat ccttcatttt aaattgaggg gcaaaatcta ttacagatt 599

<210> SEQ ID NO 268
<211> LENGTH: 599
<212> TYPE: DNA
<213> ORGANISM: Homo sapiens

<400> SEQUENCE: 268
tgccctcatt ggtaagtata tcctgagcca gacaaaatta ttcctcctaa ttcattttgg 60
ttttgatttc tagtattaat tcaaattatc ctgccaacta acctgtagtg aaattattca 120
accgatagcc tgttagcctt agcgcaaacc cgaatttatt catctgttga gtaagtattt 180
atgttatatg atgggaactc catcaaccct tgggatatag ggaacaacaa agagtaaaat 240
gtccccattc ttatgaagct tataagaaac aaataatact gataataata ataaacaagy 300
ggacaattta tgatagtgtc aagtactatg aagaaaaatg taacacagtg attggaatga 360
gaaaattctc gaagggcatg atatgcttaa gagtattctt aatgggcagg agaatattga 420
aaggcattta gatgtggaag tataagagtc cacagaagtt cagatgatgt gtagccttct 480
agacaatgca gaaaactttt ccataattct acaagcaatg caatagcatt ggagggtttt 540
aaataataaa attacaagtt ctaattaatt tttgcaatct atccatatga caaagggct 599

<210> SEQ ID NO 269
<211> LENGTH: 599
<212> TYPE: DNA
<213> ORGANISM: Homo sapiens

<400> SEQUENCE: 269
tagatgttgt tgttacaagg taaatcttct caacttcact aaagattaat aaagtgtaat 60
ctttctgtag aaacttttct caacactcta aaaaaaaagg ctaactagaa ggaacagaag 120
aacaacatac acatgtaaaa accatattga gggaccaaat taaagataat tatgattgga 180
gttgatgaat ttaaaagtac cagagaaaat tgtatcagga tttttgaata tcctctttga 240
atgataattc tactcgttgc caaagttatt gacagagtat tttgtgttgg gcatggtgcy 300
agctaggcat taggaagtgg agaacaaaat agatttagtt cttatcacct ggagtttaca 360
aattataact actaggaaga aaaaaaggct gagtactcag aaaatgtgta agattgagtg 420
gtcctggaag acacccctga aggttgacca ggaactaagt caagcaaaga gctgtgggaa 480
aactcttctg agcagagaga attccaggaa ctaaagaaag tccaggtgtg gttgaagata 540
gactcagaaa taaagaaagc tgcttgagat cagattagtg aaggagggag ctaccagat 599

<210> SEQ ID NO 270
<211> LENGTH: 599
<212> TYPE: DNA
<213> ORGANISM: Homo sapiens

<400> SEQUENCE: 270
acacaggtgg ccttggctcc acataacctc tctatcacat ctagctctgt ctgccatatt 60
tgctaaccac cagtatttgt attgtatcac ttctgtaaat ctagttcaag ttccttcatc 120
tctcaatgtg tgaaggtccc taggtcccta acaaatgcta tcctaatccc tacctaataa 180
ttctatattg ttacttgtag tagaacctca ctcctgccaa acgtggtact tttctgtttc 240
tagttcagtt caatggagtt tccctttaaa tagggtaatt ctatttgatc tccaacccck 300
agattatttt ttcttaagtt cattcatttt tccatttttc cccctctttg aatattactt 360
cctttatcca tgcatctctt ctaccattcg tctttttctt cactctttct tctcatcttt 420
gatgtttcct tctacttctt tgtctcttta accccaaggt gagaaaaaca ccttttttcag 480 agccctactc agagcaccat gcaatttcat tttctcaagt gctacaaggc aaagattttc 540
tcccctactt gaattaattt attgtatatg taatcgcttc ctcccaaaga gttttgatc 599

<210> SEQ ID NO 271
<211> LENGTH: 599
<212> TYPE: DNA

<213> ORGANISM: Homo sapiens

<400> SEQUENCE: 271
ccactgaaca cagctcactt aatctaggaa agcaccaaaa tggcgccccg cattctcaag 60
aagaaaagaa aacgagattt ggtgaccaac tttgttgtct gccacagact gatttagggt 120
aattacttcc ctcacttatt ttttgctgta atttcatgat ctaactctct attccacaca 180
atatctctgg caatgaactt tattaccact atggcttatc ctggtgtcct aacactcatt 240
caggttacaa ggagaacagg gaataaagag gaccattcag gatgatgtgg gaccacctcr 300
aagcatcagt gtgctctgag ggtcttcagg aaaatacctt tctcgcttca catctctctc 360
ctgctgctca ctcacatgac tactggaagc acattcccca ccaccacaca agcccacata 420
cccgcacaca accctcaccc aatgctggag agaaagcact ccaggaggag aattctgtca 480
tactccttca caccatttca ctcttgaaac tcttcccacc gatatctttc actccggcta 540
ctaatttttc tctttacatt ttgtttttaa cttttaagtt caggtgtgca agagcaggt 599

<210> SEQ ID NO 272
<211> LENGTH: 599
<212> TYPE: DNA
<213> ORGANISM: Homo sapiens

<400> SEQUENCE: 272
atctgttgag taagtattta tgttatatga tgggaactcc atcaaccctt gggatatagg 60
gaacaacaaa gagtaaaatg tccccattct tatgaagctt ataagaaaca aataatactg 120
ataataataa taaacaagtg gacaatttat gatagtgtca agtactatga agaaaaatgt 180
aacacagtga ttggaatgag aaaattctcg aagggcatga tatgcttaag agtattctta 240
atgggcagga gaatattgaa aggcatttag atgtggaagt ataagagtcc acagaagtty 300
agatgatgtg tagccttcta gacaatgcag aaaacttttc cataattcta caagcaatgc 360
aatagcattg gagggtttta aataataaaa ttacaagttc taattaattt ttgcaatcta 420
tccatatgac aaagggctaa taaccataat ctacaaggaa cttaaacaaa tttacaagaa 480
aaaaacaatc ccatcaaaaa gtgggcagag gatatgaaca gacacttctc aaaagaagac 540
atttagatgg ccaacaaaca tatgaaaaaa ttctcatcat cactggtcat tagagaagt 599

<210> SEQ ID NO 273
<211> LENGTH: 599
<212> TYPE: DNA
<213> ORGANISM: Homo sapiens

<400> SEQUENCE: 273
atagacactt agcaaatctg caaggaagaa taaagacaaa gttgtaaaaa caatattttt 60
ttaaaagctt attgtatgca taatttataa ttcatgggac ttagtctttg ggagagaata 120
cacacgcaga tttatgtagc tacagattga atgtaaattc aatacccagt cccttaagga 180
gctgagattg tttgtctcct aaccacagaa gttttgtatt ctagttattt tccagcacta 240
actaaatacg cgaacttgga aaagtcacac tgaatatctg ggacggaatt tcctgatctk 300
aatagtcaga aatataccta aactattcct agggtccctt ccagtttaat ggtggatatt 360
aattatttga aaacatttta gagaacctta actgaagaaa gaactaaggg catcttctga 420
ttggtagact ctcctgttac aagagatgtt caatgtattt tggaagacaa gaaagtttac 480
cattttgttt ccaagacaaa actgtgtgct ttgcactatg ctgagcacgt tgtcaatatt 540
taccaaattt aaatgaatga aaaaaatcta tattataact gacatgagga atcttcaca 599

<210> SEQ ID NO 274
<211> LENGTH: 599
<212> TYPE: DNA
<213> ORGANISM: Homo sapiens

<400> SEQUENCE: 274
ctactctggg gtatagatca tgcttctaag ctcctcctgg ggtcctgctg aggctcaatg 60
ccagctgaaa ccataccctt gctcacatac tttcccttct ctttccttct tcccttgctt 120
ccttagagat tcctcctgca atggcttcct caaaaaagca ttttcataag caacctcatg 180
tcagcctctg cttccacaga agccaatctg agttaagcag ctgtttaact tagcatgtcc 240
aacataaaat tcttgttttc ttctcatccc ctgcccctga acgttctcct ttgcctgtcy 300
ttcttatctc attgaaagta acaacacaag tatcaagtga aaataaaaga atcttctctg 360
atttctttct ttctaatgta ttattaaatt ctactgatat taccaatatc tattcaaata 420
ccaacctagt ctaagatact atcatctgtc ttctagactt caactgggtt cctaacactg 480
atggtattac acaatttttg caatgaagtc ttacccacct ataatccatt ttccataaag 540
cagcattatc attttctaag tcacacactg tagttttaat acaatcccaa actaacaag 599

<210> SEQ ID NO 275
<211> LENGTH: 599
<212> TYPE: DNA
<213> ORGANISM: Homo sapiens

<400> SEQUENCE: 275
aagataatat taacaaaatg aagagacaag ccatagacta ggagaatata ttgcaaagta 60
tatatctgat aaacaactta tattcataat atgtaaatca tataacaaat gtcaaaattt 120
aataataaat tattaagtag taagaagaaa tttgttgtat aataataaga aattaaatag 180
taagaagaca atcaattcaa ataaatgagc taaagatttc aacagatact tggccaaaga 240
aaatacagga gtttctgtaa ataagtacag ggattctgag tatcatttgt catgagggar 300
gcaaaaatta aagcaatgag atttagctac atagctagaa tggctaacat ttaaaaatat 360
caaccatacc aaatattggc aacaataagg aaaaacagga aatttgtgca ctgtgactat 420
agtgaaaatg ctacaaacac tttttaaatc agtttgacca ttaacatata cttacctatg 480
gtctagccat ttcactccta ggcatttacc ttagagaata tatccatgaa aattctttta 540
atgaatttat ggatgatagc caaaaagtag aaacaatcca atgtccacca acaggtgaa 599

<210> SEQ ID NO 276
<211> LENGTH: 599
<212> TYPE: DNA
<213> ORGANISM: Homo sapiens

<400> SEQUENCE: 276
agagtaattt cctcaacttg atagagaaca tctacaagaa acctgcatct agcagcatac 60
ttcaatagtg agaaattcaa agatttcccg tgagaccaag aacaaggcaa ggatggctcc 120
ctgtgaccat agcttttcaa catcatcctg gatgtcctag aattctttca aggttctact 180
cacaactgga tttctccata atcttacatc tcctcatgca caaacttatc acatagcaca 240
cagactggtc ttacataata ttttctttct cttagctcat taagcacttt gtacatctcr 300
tggccctttt cattttataa tgtgtatgaa ttttacctta cagggtgtct cctgtgacat 360
aagcctttgg agagacacaa taatcatgtc atcttctgct ctgtcattca cacaatgtat 420

```
agaacaatga tttgaccaag taagtgctcg gatttgttga tttttaataa gatactatca    480

agtgcttata ccagtgctgg agatcagaga cgacatttat gcaaaatact ttaaacagga    540

gagaggttgc atgagcacaa gaaaagcctt gtctcaaaag aatgctccct cattgcagc     599


<210> SEQ ID NO 277
<211> LENGTH: 599
<212> TYPE: DNA
<213> ORGANISM: Homo sapiens

<400> SEQUENCE: 277

tgagcacaag aaaagccttg tctcaaaaga atgctccctc attgcagccc atttagcttg     60

agtgatgatt ttgatgacct ttctaaatta acacaaaagc tgacaataaa aataagtttg    120

agtacattaa taacgggaaa caggattttt cttacatttc tatttaaagt aatctgaaac    180

aataagaaat atatatgatt tatcctgtct cttggatcta gctgtggaat gattgtatta    240

atcacactgg gtaaagcaac actaaatgaa tgtctccttg gagattttac tgcataatty    300

gcaaaagtaa gcaataatct attatcccct cgagatgact gtcaaggaac ccagaggaat    360

tcatttactt catctctatt caatacatgt ggtaattata gcagttttta ttactaaatg    420

taatattttc attaaatcct ttgccacaat gatattttaa agtgattttt tttggatttt    480

tagctgatga aatatggtcc catttatcat cagttctaac ttcgtgttac tactgttgtt    540

cttaaggtcc ttaaagtaaa ttttaagact caatctaagt gtgtcagtgt tgattacca     599


<210> SEQ ID NO 278
<211> LENGTH: 599
<212> TYPE: DNA
<213> ORGANISM: Homo sapiens

<400> SEQUENCE: 278

cttcatactc caatttataa attataattt acaagcaaat attgttgtca ttatcttaaa     60

aataagaata gccactcttt tgacaagtac acttaagcac ctgcaaatct gtttattaat    120

tagaccatag aatctgtgtt tcattggtgg tcagctggcc aatctgatgg tcttgtcata    180

cacaggtaag aagagacaaa gagccaagag tttgtttgga ggccggagtg agcttgacag    240

aactagatga aattggccac tgggcactgg gacccagaaa ggcctcattg ccacagagty    300

gcaacagagt gtggggtccc attatcagaa tcctttctat ggtgcatcca attggctatg    360

actctcctaa gaacagcgct gcaggaaaat gcaagttcac aggataatga atgcactgtt    420

gcttctctgc tgctgacttt tcccacgaat aaaacttgta tttatttgta ctgctggttc    480

gggctgccat aaaaagcacc acagacgata tggcttacac cacagaaact catgttctcc    540

caatcctgga agctgaaagt ccaagatcaa agtgttgtct gggttggttt cttccaaga     599


<210> SEQ ID NO 279
<211> LENGTH: 599
<212> TYPE: DNA
<213> ORGANISM: Homo sapiens

<400> SEQUENCE: 279

acatgtacat ttgaggagtg gaacacaatt caacccatac cgtgtaccat ggtagtccca     60

atgtccccat tttccaacag caaagtgttt atggaatatc atgttctacc tgtgaccttt    120

ctattctctc ttatacaata ttatgtcact ttcatatcat agttaatttt acatgtattt    180

gttcctcatc tccaaaacgg gtctgcaaac tcctggagag aaaaatctgc atttgaaact    240

agcaggtgca cagcaactat taactaatat aaaatgacat ctgaaagaaa caaagcccam    300
```

aattttttc ccatgcctgt caatagagac ttcagaaaca tatagttatt ttgaagaaaa 360
taactttata ttctttaaaa actagatagt aatttgaaat catactttca atgctacaac 420
agacatttaa atagaggaaa tatccacctc ccattctcca atcaccacct ccctcatttc 480
ccagcatgtt tagagttcta gccttcacca aagactggta tacaagaaag caaattgaaa 540
atccatcatt ttctggtacg gtaaggctca tttattcatt caataaggat ttattgctt 599

<210> SEQ ID NO 280
<211> LENGTH: 599
<212> TYPE: DNA
<213> ORGANISM: Homo sapiens

<400> SEQUENCE: 280
tatttgaaac tctaagcagc atatacattt cccagtctcc tccacatttc ccttttggta 60
gcattctgtt catttttagt tttatatgta ttttagaatt gtttttccct atttctgtaa 120
ggaatgccgt tgggattttg atagacattg cattaaatat gtagatcagt gggggcagta 180
tgaacatttt aacaatatta attcttccca tctatgagaa agggatgtcc ttccatttat 240
ctgtatcttc tttaattttc ttcataattt ttttcatatt gtacaagtca tttacctctm 300
tttttatgga ctggaataag tttcatttta aaaattcaat acataaaggc ctacctacaa 360
atatgtttta tataaactac tccaattatt tattttcacc aacctattga tttctctacc 420
aatgttgaac ctaaatcttc actgttttag ttttaattta ccacatttag tctctcagaa 480
ttcaacaaac cattagttat tttgcctctt actagtgtaa gagattgata tgcttgcaaa 540
taccttgtct caaccttcat ttattattac aaatattcca catttttccc cgtatcatc 599

<210> SEQ ID NO 281
<211> LENGTH: 599
<212> TYPE: DNA
<213> ORGANISM: Homo sapiens

<400> SEQUENCE: 281
atggtataca gtatttacat gcatttaaat tcactataaa tatttacaga acttcaagat 60
gaatgccagt aatataagca aaatatgtct gaccacagtt acttttcatg agtaaatggg 120
ttctgccaaa tggctttttc cctaaaaact aagtttttttg aattttgttc agataatagc 180
aataaagaga caatcactct ctacaacagt tcctaggaag ttgaagaaaa ctgcagattt 240
taagggagat tcactgttag gtgtgttggc ttcatgcctc ttgatggcat tctttagtgk 300
gtatgaattt tgtttaatgg ggagagaaat tgaccatagg aactaatacg agggtgccaa 360
cagagttaca aaatggaaga ttctataagt agaattggga ggctggtgat tcaaatgaca 420
tctttagcaa aaatccctgg gaaataaacc attttcaata gtttgctaga aattattttg 480
attgtaatac gtttctagca gtgacacagc aaatttttag agcttgcaat gtgatatgaa 540
cagcaataaa tcaccaatac atggccgatg gcctcttcta ggcagatccg tctacaact 599

<210> SEQ ID NO 282
<211> LENGTH: 599
<212> TYPE: DNA
<213> ORGANISM: Homo sapiens

<400> SEQUENCE: 282
ggcttcatgc ctcttgatgg cattctttag tgtgtatgaa ttttgtttaa tggggagaga 60
aattgaccat aggaactaat acgagggtgc caacagagtt acaaaatgga agattctata 120
agtagaattg ggaggctggt gattcaaatg acatctttag caaaaatccc tgggaaataa 180
accattttca atagtttgct agaaattatt ttgattgtaa tacgtttcta gcagtgacac 240
agcaaatttt tagagcttgc aatgtgatat gaacagcaat aaatcaccaa tacatggccr 300
atggcctctt ctaggcagat ccgtctacaa ctggtaacag caaccatatc gagtttctct 360
ttatcacaat accacgaggc ttatcatcat tgccatgcct ttagtaacat cactttttta 420
aatgggcatt ttcacaatgt aatctgcaac ctacatataa catgcactct ttattgaagg 480
ccgtacttac agtttgactt tgagtcagct cagcattcta aatcaaacgc aaacagcaga 540
atcatatggc atagacactt agcaaatctg caaggaagaa taaagacaaa gttgtaaaa 599

<210> SEQ ID NO 283
<211> LENGTH: 599
<212> TYPE: DNA
<213> ORGANISM: Homo sapiens

<400> SEQUENCE: 283
atagaaatat ttgaagaaat atgtatttgg ccatccttcc gtctaccagt taaacatttg 60
cttttcctca tcaatagaaa tgatcagatt ctaagcaaat acatgcaact gaaacaaaca 120
tgtgggttgt tttgcacatc cagaaataat atcgtatact cattaaaaca atcaggtttt 180
ttggggggaa ttttaatttc atcatcatag ttatatcctc tgtaaaacag atccagaagt 240
ttagaaacac accttgattt atatgtgttt gatatttgac caatcagcag aaactcaaar 300
aatttacagg ctgaaaagac accaaatttt cccgttgtac ttcatagata aggaacccag 360
ggcactgcag tgtttgtttt cccaaaatag cagaattagt taatggcaga gctgttacca 420
gaaaagagtt ccgattggat cctgtgtgtt cggatgctta tttatttacc atgtttgtga 480
ataaaccatg caaaccgtgg cagaagtgag gatgttagca tttataaatc tacaagaaga 540
gtatccactt agaagaaata gctaggagaa ggtccctaca gggggagctt gcttgacat 599

<210> SEQ ID NO 284
<211> LENGTH: 599
<212> TYPE: DNA
<213> ORGANISM: Homo sapiens

<400> SEQUENCE: 284
taaaagagtg aattttgtag agaacatttt caggggacat tgaaatgttt gcacagaccc 60
ttcagtagca aaatataaac taggaaaaca aaaataagta ctttaaagac tgaacattga 120
gcaattccag agagagagag cgagaaagca agtgagaaag agacaaagga gtgatctagt 180
ctttgcatta aacttattta tttatttact ttaaatcatt catctaatat aaataagtgt 240
ggattcattt agaagcaaca ctgaccagag aaagagtagc ctatcagggg agatctctgw 300
tccagaaaga caaggtcaaa tattcctgtg gatatggctc cctgttttac tcctcctcct 360
gtttgccttc actcctcctc ttctataacc actatcacag tatctgctct tcctttccac 420
taccatcatc accccacctg gaagtacaat tttttttttc atggaggagt tttgtagaga 480
aaaaaatttt aaacttttct atgaacctat gggttttacc tcactcttta taagaaagaa 540
cactggtggt taaaccccat gcaatgttac ccgtgtgtgt gtgtgtgtgt gtgtgtgtg 599

<210> SEQ ID NO 285
<211> LENGTH: 599
<212> TYPE: DNA
<213> ORGANISM: Homo sapiens

<400> SEQUENCE: 285
agatagatgc cagatattac ttgacaagcc agaaactaga gacactaaga taaaaacaaa 60
ataaaacaag aaattaagat tgatggataa aaataatctc tcaaagattt atttggattt 120
aatctaaatt taaggtgcca tatatcttta ctcgtgaaag aaaattgaat ttttgaggac 180
actaagtagt ttgagaaata cccttcttta aaatcttctt ctttacctaa atgaacacta 240
gtgtcctggt tttcttccta tccacctact aattcttagt ctccttcttt cagcacttar 300
atattcttgt accataggtg ctattcctgg acatctctct ttgtactcag cacagcatct 360
tcctacttca actcttatct tttggttctg acttccaatt cttatcacta attcattgct 420
gttcagaccc agtttatata aattcacttc tgtgtctacc agttcctcaa aacggaaacc 480
atcattcctg aatcatcttt tcatttctcc cttttcatgt attttgcatc tcaatgtgag 540
gcatcacgta gttaaacaaa tacaaaatat gggctatatc cagcacacgt accccacat 599

<210> SEQ ID NO 286
<211> LENGTH: 599
<212> TYPE: DNA
<213> ORGANISM: Homo sapiens

<400> SEQUENCE: 286
tatgagttac tcatttgttt aagcattgta gagaggaaaa ctcctgagca taaagtcatt 60
caatttttgg tttgttctag ctcttctcct aactacctgt atgatcttca gtagatcttg 120
ttcccacttt tggctcaaat tttcttattc tttaaaatgg acataataat aatttcatca 180
agttcttata agataaaatg agatgtcatc catatagtca cctataagta acaaaataac 240
tcataaatta ctttctttag tcacttgaat gattacatta accagattaa atatcacaty 300
gaaaacagac aaaacaaata tcatactact ctttatattc aaagatcaat ttgatttttg 360
agtaattttc caccatttca aagatgcatt caaaacatgt atacatctgc agtcatccaa 420
tttcatttac cattatatct taagtgtttt ttcatatctg tgcaccatat tcactgtact 480
caaatattgc atatttatcc actgataagc ttggccacat gtttattttt tctattatga 540
ctatcaatta tatctattta tctaatattc taaatatctt gtattgaata catttatgt 599

<210> SEQ ID NO 287
<211> LENGTH: 599
<212> TYPE: DNA
<213> ORGANISM: Homo sapiens

<400> SEQUENCE: 287
ctgccttgtt tcctttctct ttttcttatc cttctggtat tctcgtgaca catgtgttat 60
acctttttca gtagccccac gattcttgaa tattctattc tgactcatta catctttttt 120
ctcttaattt tttaatttta gaagtttcta ttgtcatatg ctcaagctca gatattcttt 180
ctgcagccat atctagtcga ctaatgagcc catcaaaggc attttttaat ttgtgttaca 240
gcagttttga tctccagtct tttaaaattt cttctcataa tttccatctc cttattctty 300
tattctattt ccatctcctt attcttccat tcttgtacat tgttgctttt tccattaata 360
acctcagcat actaatcata gtttgttttt taattcctag tctgataatt tcaacatttc 420
tgccataatt gactttagtt ctggtgcttg tttgatctct ctctatttta ttttatttta 480
ttttatttta ttttactttt tgccttttag tttaccttga ctttttgttg ttgttgttgt 540
tgttgttgtt gttgaaagtt gggcatgatg tactgggtaa aaggaacttc tacaaatag 599

<210> SEQ ID NO 288

<211> LENGTH: 599
<212> TYPE: DNA
<213> ORGANISM: Homo sapiens

<400> SEQUENCE: 288
ccaattgtta tgtccacgag tacccaatgt ttagctccta cttatgagta agaatatgtg 60
gtatttggtt ttctgttcct gtatcaattc acttaggata atggcttaca gctgcatgca 120
tgttgctgca aagaacatta tttcattctt ttgatggctg catagtattc catgttgtat 180
atatgccaca ttttgtttat ccaatccacc gttgataggc acctacattg attccatgtc 240
tttgccattt tggatagcac tgtgatgaac ataaaagtgt atgtgtcttt ttggtagack 300
aatttgtttt cttttggtta tatacccagt aatgggactg ctgggttgaa tggtagctct 360
gttttaagtt ctttgagaaa tctcctaact tctttccaca gtagctgaac taatttacat 420
tcccaccaac agtatgtaag cattcctttt tttcccttca gccttgccag catctgttat 480
ttttctgact ttttaataat agctattgtg actgccagga gatggtatct cactgtggtt 540
ttgatttgca tttctctgat gattagtgaa tgtggcacat tttttcatat gtttgttgg 599

<210> SEQ ID NO 289
<211> LENGTH: 599
<212> TYPE: DNA
<213> ORGANISM: Homo sapiens

<400> SEQUENCE: 289
agtttgggtg catatgccta aggattttag acaaatatat tacgtaacat taagatgata 60
ctcatctgat ttctagttag taatgggaag ggagcaggat gcttatgttg cataagcagc 120
taaatgtcta ggtagggtta attaaaaaga gacaatgttt actcaatcag ttgtcactca 180
tttcaaatat gtcttacaaa aatagaaata caccttaaaa gttttataat tttcaaaaga 240
aattggccaa tacaaaaact tctgttacaa cgatgaatta cattgattga ttttttaacs 300
ttgtattcat gagataagca ccccttttca cggtgtttta tcctctttat atattgctga 360
attcaaatcg ctgatattct attaaatatc tttgcatcta tgttcacgag tgatactggt 420
ctgtgattat tttcctttaa tgatgttgtc aggtttgaaa taagagttat tctgtcctca 480
ggaaatgagt tgaggagtca ttctttcttc tctattgttg ttcatttgtt taagctgtta 540
aaatcattga cattaaggtc ttcacagtgt ctatataatt tgtaatgatg tcccctcta 599

<210> SEQ ID NO 290
<211> LENGTH: 599
<212> TYPE: DNA
<213> ORGANISM: Homo sapiens

<400> SEQUENCE: 290
tttgtctatt tctgttttac tcttatttct acagtgaatc ccttcatcct gggacataga 60
ttttatccca aatgtgtttc ccttctggga ttctaatgaa aggtcacagg gccaagctct 120
tttatcctgg gcaggattta aattataacc tttgtctctt tactcagtgg tgagcagcag 180
ttgaaatctc tacctaactc ctcggtattc cgactgttat tcttcccatt tccaggtgct 240
ctgggtgtcc taagttccat tttctgaatc caaaagccaa aaggatgaca gttttgtgty 300
tgatttttaa tggggaaaag ttattaaaag tttatctaaa aatttactta ttttggatta 360
tatacaccca gaaagctttt caaaaaaatc taattaaagc atatgggctg tacccatttt 420
atttgtctct ctggtaaaag tgtattttaa ccatgaccta aaggcaatca tttaattcat 480
gttcatagaa ggaatatttt aagaacgtat agggaagacg tgctctatga gaagcgagac 540
aatttcaaag tttttcaaat tcctaagcta ttctattaaa acaaagctct aattttagt 599

<210> SEQ ID NO 291
<211> LENGTH: 599
<212> TYPE: DNA
<213> ORGANISM: Homo sapiens

<400> SEQUENCE: 291
caacttccca taacatactc agctccttga tctcaatctt tcacagaagt ccctagaacc 60
accaatcaac attatcagaa ctgcagctta gatgggattc ctggagctaa ttgttgtcag 120
ggaatgtgaa atcagctaag agccaaaaag tcatcattag atttggtaac cagtaggtaa 180
tgagtgatat ttgcaagtga atttttaaat aactagttta atgggaattc agattatagt 240
gtgctgaaac aattctcaaa ggagaggttg ggaattagag ttagaaagag tggccaattm 300
tttgtgggtt ttgttgttgc tgtttgtttg tttgtttgtt ttgagatgga gtcttgctct 360
gtcgcccagg ctggagtgca gtggcaccat cttggctcac tgcaacctcc gcctcctagg 420
ttcaaatgat tctcctgcct cagcctccct agtatctggg attacaggca catggcacca 480
cactcggcta atttttgtat ttttagtaga gatgaggttt cattatgttg gccaggctgg 540
tcttgaattt atgacctcaa gtgatccacc tcagcctcaa aaagtgctgg gattacagg 599

<210> SEQ ID NO 292
<211> LENGTH: 599
<212> TYPE: DNA
<213> ORGANISM: Homo sapiens

<400> SEQUENCE: 292
gtgtttcctg taaaagttga gaaataatca gaaggaggcg tggtgataag gatggggtca 60
tcagtgggta tctggggtgg ctggcaaagg tctcttttcc gacctggctt atggttacaa 120
gggtattcgc cgtaccatta tacaataaac gatatagacg ctttgggaag ttttctgtct 180
ctgtgttgta taataaaaat acaaaaacaa attttatttg atttttattt ttcagaacat 240
acatgtagag ttaaaaatat tgaaaaatat tatccaagca ttagtcataa ttattatcam 300
catcatttaa gacaaacaat taaggacagt gatactgtca gaaggaattc agaaatcata 360
tcagtagcat aaacagctgc acaaaattgt caaagaatgc tgggtgatag gtgtcatttc 420
tgtctaaatc caaacataca aaagaactgc taacataata acatatgtac taacatagta 480
tctcacttca tttcaggagt tctcctgtct gttagtctaa accaaattca gttaactaaa 540
ttcagtcaga caatacacat tctcactgtt taccttaagt ttcctaataa tttaactag 599

<210> SEQ ID NO 293
<211> LENGTH: 599
<212> TYPE: DNA
<213> ORGANISM: Homo sapiens

<400> SEQUENCE: 293
ctccaaatcc ccatgacgca acagtgtatg agtgtcccat tgctgccata ataagtgatc 60
atgtactcag caacttacaa caacacaaga ccattatctc atagtcttct gcaaggagtc 120
cagcacaggt ctcaccacac taacactgag gagctggcag tactagattc ctgtgtggag 180
gctctagggg agaattcttg ctttgctttt tctagttttt agaggctgcc tccagtccct 240
ggctcctggc tcctttcccc tatctgcaaa gccagcaaca ctgcatctct ctaacactcy 300
gacctcacat ctttctctaa ctacagactg aaaagtttct ccactttcaa aaaatcatgg 360
gattagttag ggccaatttg aataatccac aataatctcc caccacaagg tcattaactt 420
aattaaattt acaaagtccc tttgccatgt aacatattta cagggtctgg ggattaggac 480
atggacatct ttggtgggag gacattatcc tgtctacctt ggacaattac tttgtgtttg 540
tttcttttta acaaaacaaa tacacaagaa tggggacatc tggtaaagga attttgaaa 599

<210> SEQ ID NO 294
<211> LENGTH: 599
<212> TYPE: DNA
<213> ORGANISM: Homo sapiens

<400> SEQUENCE: 294
tctcttctcc ttcttcctga ccttcttcca cttcctccaa tgcagcataa cctagcatgc 60
tcgggccttc atgcctgcta ctgcgtattg caggaaaatt caacaagcag ttgctttcag 120
cacttgtcat gtaacaaagt ctctattggt tttacttata tttgcagttt acaatgaatc 180
ttataagttt actagccaag tggaatatct ttttctttgt ttttgcagat ttttttttcc 240
ttgtggtctt tgtgattctt tttcttttta aatgacttca acttttattt tatatacagr 300
aggtttgtta cttaggaata ttgcatgatg ctgaggtttg gagtatggat cctgtcagca 360
gagagtgaac atggtaccca ataggtaatc tttcagccct atcttcctcc ttccttcccc 420
tttcacgtag tccccagtgt ctattgttcc aattgttatg tccacgagta cccaatgttt 480
agctcctact tatgagtaag aatatgtggt atttggtttt ctgttcctgt atcaattcac 540
ttaggataat ggcttacagc tgcatgcatg ttgctgcaaa gaacattatt tcattcttt 599

<210> SEQ ID NO 295
<211> LENGTH: 599
<212> TYPE: DNA
<213> ORGANISM: Homo sapiens

<400> SEQUENCE: 295
caggaaaatt caacaagcag ttgctttcag cacttgtcat gtaacaaagt ctctattggt 60
tttacttata tttgcagttt acaatgaatc ttataagttt actagccaag tggaatatct 120
ttttctttgt ttttgcagat ttttttttcc ttgtggtctt tgtgattctt tttcttttta 180
aatgacttca acttttattt tatatacaga aggtttgtta cttaggaata ttgcatgatg 240
ctgaggtttg gagtatggat cctgtcagca gagagtgaac atggtaccca ataggtaaty 300
tttcagccct atcttcctcc ttccttcccc tttcacgtag tccccagtgt ctattgttcc 360
aattgttatg tccacgagta cccaatgttt agctcctact tatgagtaag aatatgtggt 420
atttggtttt ctgttcctgt atcaattcac ttaggataat ggcttacagc tgcatgcatg 480
ttgctgcaaa gaacattatt tcattctttt gatggctgca tagtattcca tgttgtatat 540
atgccacatt ttgtttatcc aatccaccgt tgataggcac ctacattgat tccatgtct 599

<210> SEQ ID NO 296
<211> LENGTH: 599
<212> TYPE: DNA
<213> ORGANISM: Homo sapiens

<400> SEQUENCE: 296
gctctgactt acattcttca tttgtaaagt ttgtctgatc tttacatagt tcataagctt 60
gttttgagga tgaaatgagt taatttttat aaaatactta ggatgggatt tgaaacataa 120
taaattatca atagattata agctctgtta ttttaagaaa atagtgctcc tcagacctta 180
ctttagacaa ctctcctcta gagtataaaa tagtctatag agagataaac taggaattct 240
attaattatt tttaattggt tattttaata cataataaag caatgttatg tatagattcy 300
atagcttcta ggtcagtttt tactataaga acactaaaat tagagctttg ttttaataga 360
atagcttagg aatttgaaaa actttgaaat tgtctcgctt ctcatagagc acgtcttccc 420
tatacgttct taaaatattc cttctatgaa catgaattaa atgattgcct ttaggtcatg 480
gttaaaatac acttttacca gagagacaaa taaaatgggt acagcccata tgctttaatt 540
agattttttt gaaaagcttt ctgggtgtat ataatccaaa ataagtaaat ttttagata 599

<210> SEQ ID NO 297
<211> LENGTH: 599
<212> TYPE: DNA
<213> ORGANISM: Homo sapiens

<400> SEQUENCE: 297
cctggaggtg aagcatcttc caaatgacag cctgcagtca atgactgatg aatatgactt 60
cattgcctca tgacaggacc tactctgggg tatagatcat gcttctaagc tcctcctggg 120
gtcctgctga ggctcaatgc cagctgaaac catacccttg ctcacatact ttcccttctc 180
tttccttctt cccttgcttc cttagagatt cctcctgcaa tggcttcctc aaaaaagcat 240
tttcataagc aacctcatgt cagcctctgc ttccacagaa gccaatctga gttaagcags 300
tgtttaactt agcatgtcca acataaaatt cttgttttct tctcatcccc tgcccctgaa 360
cgttctcctt tgcctgtctt tcttatctca ttgaaagtaa caacacaagt atcaagtgaa 420
aataaaagaa tcttctctga tttctttctt tctaatgtat tattaaattc tactgatatt 480
accaatatct attcaaatac caacctagtc taagatacta tcatctgtct tctagacttc 540
aactgggttc ctaacactga tggtattaca caatttttgc aatgaagtct tacccacct 599

<210> SEQ ID NO 298
<211> LENGTH: 599
<212> TYPE: DNA
<213> ORGANISM: Homo sapiens

<400> SEQUENCE: 298
ttccagcact aactaaatac gcgaacttgg aaaagtcaca ctgaatatct gggacggaat 60
ttcctgatct taatagtcag aaatatacct aaactattcc tagggtccct tccagtttaa 120
tggtggatat taattatttg aaaacatttt agagaacctt aactgaagaa agaactaagg 180
gcatcttctg attggtagac tctcctgtta caagagatgt tcaatgtatt ttggaagaca 240
agaaagttta ccattttgtt tccaagacaa aactgtgtgc tttgcactat gctgagcacr 300
ttgtcaatat ttaccaaatt taaatgaatg aaaaaaatct atattataac tgacatgagg 360
aatcttcaca taatacttct tgctaatttg aaaaatgaga cattggttta gaaaaaatca 420
aagagcttat atataaatta aaattctaaa atcaccttgt ggttttaata tattatctat 480
aaatgtataa ctttgtacag aaaaaaagtg ttttccgaag aatttttaaa acttaattta 540
aaaaaatgat gatcaaccta ccaaacacaa actaagagta aatgaaacaa gtggcaagt 599

<210> SEQ ID NO 299
<211> LENGTH: 599
<212> TYPE: DNA
<213> ORGANISM: Homo sapiens

<400> SEQUENCE: 299
cacgaattcc ggacacagca tcacacttcc tgatttcaaa atctattaca cagctacagt 60
aatcaaatca gtatggatct ggcataatga cagacctgta aacatataga ccaatggaac 120
caaatagccc agaaataaat acacacatct atggtcaact gatttttcgg caagaatgcc 180
acgaatacac aatggggaaa gaatagtctc ttcaataaat aaaagtgaga atctgtaact 240
gctgatggag aatgcttgtc tcatctccag cctgtgatgt agtgtaagga tgagggcccy 300
gtgacctggg aagcttggga ttctgtggat gactgaagaa gtttttcacg agaggcattg 360
aaaaatccat taattctttt tttttttttt tttttttgag acagagtctt gctttgtcac 420
cccaggtaga gtgcagaggt gtgatctcag ctcactgcaa cctctgcctc ctgggttcaa 480
acaattatcc ctgcctcagc ctcctgagta gctgggatta caggcacgcg ccaccatgcc 540
aggctaattt ttgtttttgt tttttttgt agagatgggg tttcaccatt tggccaggc 599

<210> SEQ ID NO 300
<211> LENGTH: 599
<212> TYPE: DNA
<213> ORGANISM: Homo sapiens

<400> SEQUENCE: 300
catttgacag tcaattagaa atcacgaatg gatcatgata ttatgttaaa cccatccatg 60
gcccatttat gaccatagtt atttcataac atcttttcct aagtgattga aaagacacat 120
atgtttagtc tattaagaga gacagcaggc acactctggg aataggagag agtttcagtt 180
acaccaattt aggagataac tctcaccccg gtcaccacct cgtcttttct gttaagctgg 240
cttcagactc cagtatctaa tggcagcacg actcctcaga gagcttcaga agcaagtggk 300
agctcagcta ctgaccagcc ctggatgtct gtgacacagt atcatgtttc aggacaacga 360
cacaaatgct agtctcattt gatgacacaa ctgcctattt tgtttatgtg ttatttcatt 420
ttctttttaa aaatggcgca atctattttt ctaacatctg ggcatacatt ttaaattata 480
ataaacaata taaaatcttc ccattctaat gagcatgcaa atcaagctct aaaacatgaa 540
gagaaggttc tttggacatt tagtgttgag tacacattta agtcaaccaa tatttactg 599

<210> SEQ ID NO 301
<211> LENGTH: 599
<212> TYPE: DNA
<213> ORGANISM: Homo sapiens

<400> SEQUENCE: 301
gggcaaaaat ggaaaatgca cagatttaaa atcaggatta gtagctacat tgctatttgc 60
taggtgtgta atcctcaaaa ttaatttaat ctatttaggt ctcattttct catccataaa 120
ctgggtataa tgatactaat atattttcct gtgagaactt ggcaatatat tacatataaa 180
gctgttaaaa catttttatt tatcatgttg ctatatgagg taactcattc aattttgctt 240
gttttagtca ttatacactt ttccaattac ttaattgatc acttctttcc tgaaatacar 300
taaacatcat atactgagaa aactgggact gcaaagtgcc tattaaaatg tcatatgtta 360
accaaatgtt gtcatatgag acaaaatttt gccatgttgc ccaggctggt ctcaaactcc 420
tgagctcaag tgatccaccc acctcagcct ctaaaaatgc tgggtttaca ggcatgaccc 480
accatgcccg gcctcaacta attttctaac taaaatattt ctcaaattac taatcaaagg 540
acttaatcac aatttgttca agaatgaata tacatgtttt atacatgtgt gttggtgtg 599

<210> SEQ ID NO 302
<211> LENGTH: 599
<212> TYPE: DNA
<213> ORGANISM: Homo sapiens

<400> SEQUENCE: 302
ccttgccttt tgtagacatg agggatccag ataccttaat gtgaagattt tcaactgagt 60
tccaggttat aacccataaa acatgaattc tctctaccat aaaaatgaaa gtaatttatt 120
tgctgatgca gaatggtagg tattggaact aaattcagat tagattagaa agaacttcta 180
tagttctttt cattgcattt acacagatac acacacagac acacacatat aagagcatgt 240
gcacacacat accagtcttg caaggaacag aacttttgaa tattaaaaac aacattagar 300
gttatgtatg aggtaattta aattcagttc aatagggaaa tattttgact tcagctaaaa 360
aagaatgtga taaaggatct cgatgcctga tattgaaatt cagtgtctac accttatgaa 420
gtaactggtt ggctctttaa aaatattttg tttgaataga tcaacttaat aatcattctt 480
aatgtaaaat tttatgcatt gtctagaaaa tttcagcacc tcaacatccc aacttaatct 540
tctttcacca aattattatc tacttgcttt gtatatatat actttattta ttacattac 599

<210> SEQ ID NO 303
<211> LENGTH: 599
<212> TYPE: DNA
<213> ORGANISM: Homo sapiens

<400> SEQUENCE: 303
atgtcatttt aaaaacaatt catatgtgca agttacaaag aagtaaaatt tatgtgtagg 60
tgaaactgat aacttcacag aataagctct gtgagatttt ttcctagaga tgtttcacac 120
tttgtagcaa gagtgagtca ttgtttggaa gagagaacct caaaggcact ggtctccctg 180
ctaatgttct tgcattctta cagtttttta ccctcagagc agcaaaggaa cacctttaaa 240
cctaaaacat cagatccctg ccctgcttaa agccttctaa tagcttatct atacactgak 300
aatcaaacaa gtaaaactag tgcatgtttt acaaagtcct atgaagggca acatgaacta 360
gtacctgcct atctctccag catcacttcc tgccactgac tccatgcttt ggctcacagg 420
ggaataagcc aagctcatgg cctcagggtc tttgcacttg ctctttccac cttgaatgct 480
ctccctctgt atttccccat ggctttctct ctcacagcat ttaagtctct gctaaattgc 540
ctttgctttg agaaactttc tctgcacact ctatctgaat aactctcttc ctaagcccc 599

<210> SEQ ID NO 304
<211> LENGTH: 599
<212> TYPE: DNA
<213> ORGANISM: Homo sapiens

<400> SEQUENCE: 304
gtactggtat aaaaacagat atataaaaca atggaacagc atagacagcc cagtaataaa 60
tctacacatc tatgaccaac agttcttcaa caagggtgcc aagaatacac aatgaagaaa 120
ggatttaaaa aaaaaaaacg gttttgggaa aactgtatct ccaactgcag ccacatgcag 180
aagaatgaaa ttggaccctt attttacacc aagcacaaaa atcaactcaa aatagtttaa 240
agacttaaac atacaatatg aaactgaaaa ctattagaat aaaacatagg ggaaaatcty 300
gacattggtt ttggagatga ttttttagtt atgacatcaa aagaacagag caaacttgga 360
caagtgtaat tgcatgaaac tacaaagcct ctgcatagtg aaggaaacaa ttaacagagt 420
aaaaaggcaa cctacaaatt gggagaaaat acttgccaat cttttatgcg ataagaagtt 480
aacatataaa atatgtaaag aacttatata acggaatagc aaaaaaccct caaataactc 540
aatcataaat ggacaaaagg cctaaataga cctttatcaa aggaagacaa acaaatggc 599

<210> SEQ ID NO 305
<211> LENGTH: 599
<212> TYPE: DNA
<213> ORGANISM: Homo sapiens

<400> SEQUENCE: 305
cttcaacata gatgaaaaca aatatgacaa gccttgaaaa tgaataacat aaattaaaag 60
agaatcagaa ttagaagtgg aaagaaatatg tggggaggaa attttaagac tagcaatgga 120
attttctttt ttaataaata tttattttct attacataca gcatttttag aaagtgctat 180
agaaaggtta aatgaagcat atgcattgta aaaatgtcat tttaaaaaca attcatatgt 240
gcaagttaca aagaagtaaa atttatgtgt aggtgaaact gataacttca cagaataagy 300
tctgtgagat tttttcctag agatgtttca cactttgtag caagagtgag tcattgtttg 360
gaagagagaa cctcaaaggc actggtctcc ctgctaatgt tcttgcattc ttacagtttt 420
ttaccctcag agcagcaaag gaacaccttt aaacctaaaa catcagatcc ctgccctgct 480
taaagccttc taatagctta tctatacact gataatcaaa caagtaaaac tagtgcatgt 540
tttacaaagt cctatgaagg gcaacatgaa ctagtacctg cctatctctc cagcatcac 599

<210> SEQ ID NO 306
<211> LENGTH: 599
<212> TYPE: DNA
<213> ORGANISM: Homo sapiens

<400> SEQUENCE: 306
aaaggttata atttaaatcc tgcccaggat aaaagagctt ggccctgtga cctttcatta 60
gaatcccaga agggaaacac atttgggata aaatctatgt cccaggatga agggattcac 120
tgtagaaata agagtaaaac agaaatagac aaaagcttaa aaccacaacg ttacaaggtc 180
aacgtgatct actagtaatt acagtgcctg ctggggcaaa actcagcact tgccagaaga 240
caaaaaacag agtctgagga atatttactg cattcagtca caaagtccag catgcaaccr 300
agaattacta gacacgagga aaaacagaaa cattgacaaa tggtccagag aagaattagt 360
taatcgagtg acccacaaag aactcagatg taggaggtag tgaagaactt ttaaatacct 420
gtgaggaatg tgttaacaaa ttaaaagtaa aatataatgg gtgatatgat ggagaatttc 480
agaagagatt tggaaactgt aacatacaaa taaaatggaa atctttgaat tataaaaata 540
atatataaaa ttaaaaattc atttgatggg attaacagca gattaaacat aacagaaga 599

<210> SEQ ID NO 307
<211> LENGTH: 599
<212> TYPE: DNA
<213> ORGANISM: Homo sapiens

<400> SEQUENCE: 307
tagttgattc atttaaactg caatatagca tcacattgta tgaccatatt ataatttatt 60 taccccttttt tctgctgata aacatttaga ttattttcaa tttttctcta ttacaaatgt 120
tctagttcac agttacatta caaataagat ttgtgttttt ttaagtttgc tttattaaaa 180
acagctaaag agatcagaat aaagatatca gaacataaaa ctgtaggttt tctaatctag 240
aaaacaaaac agctatgtga ctatctctat aggtacttaa gtattctgta aaagggaacr 300
tgactaaatc ctaattgttt attgaaagct ttgcccatat tcaggtttcc ttaattatta 360
aaatttaatc ccagcattta gcaaggctga ggtgggaaaa ctgcttgagc ccaggagttc 420
aagaccagtc tgggcaagat ggcaagacct cctctctacg aaaaactttt ataaatcagc 480
cgggtgtggt ggcatgcacc tgtagtccca gctactcagg aggctgaggc aaaaggactg 540
ctcaagccca ggagtttgag gctgtggtga gctatgatca caccaccgcg tgatcagcc 599

<210> SEQ ID NO 308
<211> LENGTH: 599
<212> TYPE: DNA
<213> ORGANISM: Homo sapiens

<400> SEQUENCE: 308
gtaggatttg ggtgaatga aaattattcc ttgctttcat cactaccttt atagctctca 60
tcactacctt tatagctcat cactgtgcct ttttttcttt cctaagaaag acatcacatc 120
cctctcctct cctcctctgt gctcctgtcc ctccctcccc ctagcaaggt ccaggcaaag 180
ctggagatga ggctgagatc cagagtttcc tagaacgcaa cttaggatgg ctaggaaagg 240
gaagcctgac tgctcggtca ggagggtgca gtatctcttg ctgggaacac agccagttty 300
cacaatgcct agactgtgta tgtctatttg cacaagattg tcttttccta ttttggagtg 360
gtcagacatt ttatttttgt tcaagattat ctggcgtttt agacaaattt gcaaaactgt 420
gcttttattg actttttgaa taaactttgg tattctggag caaatgtatt tatttattgg 480
tatgtgcaat gacaaacttg gtattttccc atgttgacat tatgtatgtt gtagaattta 540
gtgtttgtct aagtacacac atatatcaac aaattaaact tgaatcgttt caacacttc 599

<210> SEQ ID NO 309
<211> LENGTH: 599
<212> TYPE: DNA
<213> ORGANISM: Homo sapiens

<400> SEQUENCE: 309
agggttaaaa ggacctgaat agacatttct ccaaaacaag atatacaaat agacaaagag 60
tgaataaaca cacaaaaaat gctcaatgtc attagtcatc agggaaatgc aaataaaatc 120
acaatgagat accatttcat tcctactagg atggctatca tcaagaagac agataacaaa 180
caagtattga caagaaacca gaagccctct tacactgctg gtggtcatgt aaaatggtac 240
agctgctttg gaaaatggtc tggcagttcc tcaaaaggtt aaacatgtaa taaccatacr 300
acctagaaat tccacgctta gttccagcca cactggaatg ctcacatttt ccaaatgtat 360
acactcaaga gaaatgaaaa cattaagtct acacaaaaat ttgtacacag atatcagtag 420
caacattatt cataatagct aaaaggcaaa aattcaatgt ccatcaattg attaatgaat 480
aaatgaaatg tggtatatcc acacaatgaa atattattca gccataaaaa aagtactgct 540
acatgctaca acatggatga accttgaaaa cattatgcta gttaaaagac gtcagtcac 599

<210> SEQ ID NO 310
<211> LENGTH: 599
<212> TYPE: DNA
<213> ORGANISM: Homo sapiens

<400> SEQUENCE: 310
tttcaaagac agaagaggga tttggagagc aatggaacat atagactaga tagcaaaaaa 60
tatgttttat atcctagaag aaatctgagt actttacatg cggtattatt gttcacatat 120
ttactgctga gcacttaaca atgtgacaga cactatgtca ggctctgaga ttagaatgac 180
aaatagaaca gaatctctgt ctttaaaaag agtttacaga cagggagcat agttacaatg 240
acatggtaac tctaccttaa ccgtcaaatc caatggcttt ttgtcagttc tcactcttar 300
ttttctgcaa tacaaaaaag taattatcac atagtggtca ttcaataaat attggattaa 360
tctgaataaa tccttgtcaa attttcctgc cttaatctct atggcacatt actcttctct 420
ttttccactg gtccttcaac ctattccttc tcaatctctt tcactggttc ttctttaatc 480
cccttcccca atactttgtc tcagcctgtt ctttctttat actttccttc agcaaactca 540
tttattcaag gaatacactg taatttccaa aatgtgtact tctagttctg acttttccc 599

<210> SEQ ID NO 311
<211> LENGTH: 599
<212> TYPE: DNA
<213> ORGANISM: Homo sapiens

<400> SEQUENCE: 311
aaatctattt ttttcctcct gattttaaga gaaattaaaa catgttagtg ctcactgtgc 60
ctgatggtta aataggccct acctcgctaa gttcacaaac tgctgcttgg ttagcaactt 120
acaccccagg aacctgggtg tgcggtaaac aagtaatgtg gctcctggtt tatatttttc 180
ataacacata atagttttaa actgtatcaa gtatcatagg agcaaaatgt tgacatgttt 240
agaaaagctg ctgggagatg tttctacttt ctagggcctg tggaagactt catcttggcr 300
gagggaaaag gcttccaaga atcttccagt tatgcaaagg caaggcccag cggtacatct 360
ggacagagta gggattgaga caaggatgaa ggggcttttc cgaataaagt tgtgttttcc 420
tttgatgaaa agttgttgtg tggtaaaatt tgggacttcc tctggtggcc cagagatggg 480
aatttgacag cctggggact gaagaagaga ggacagggtt taaagaccta ggatttttgg 540
aggagctggg cctaatggag agtcagccat gaaagaactc cctagggtgg gagatggca 599

<210> SEQ ID NO 312
<211> LENGTH: 599
<212> TYPE: DNA
<213> ORGANISM: Homo sapiens

<400> SEQUENCE: 312
cactgtgcct gatggttaaa taggccctac ctcgctaagt tcacaaactg ctgcttggtt 60
agcaacttac accccaggaa cctgggtgtg cggtaaacaa gtaatgtggc tcctggttta 120
tatttttcat aacacataat agttttaaac tgtatcaagt atcataggag caaaatgttg 180
acatgtttag aaaagctgct gggagatgtt tctactttct agggcctgtg gaagacttca 240
tcttggcaga gggaaaaggc ttccaagaat cttccagtta tgcaaaggca aggcccagcr 300
gtacatctgg acagagtagg gattgagaca aggatgaagg ggcttttccg aataaagttg 360
tgttttcctt tgatgaaaag ttgttgtgtg gtaaaatttg ggacttcctc tggtggccca 420
gagatgggaa tttgacagcc tggggactga agaagagagg acagggttta aagacctagg 480
atttttggag gagctgggcc taatggagag tcagccatga aagaactccc tagggtggga 540
gatggcaggt gggccatggt ttcagtaaga tgctattcag gttttcctcc tgcactgta 599

<210> SEQ ID NO 313
<211> LENGTH: 599
<212> TYPE: DNA
<213> ORGANISM: Homo sapiens

<400> SEQUENCE: 313
gtgtgcggta aacaagtaat gtggctcctg gtttatattt ttcataacac ataatagttt 60
taaactgtat caagtatcat aggagcaaaa tgttgacatg tttagaaaag ctgctgggag 120
atgtttctac tttctagggc ctgtggaaga cttcatcttg gcagagggaa aaggcttcca 180

-continued agaatcttcc agttatgcaa aggcaaggcc cagcggtaca tctggacaga gtagggattg 240
agacaaggat gaaggggctt ttccgaataa agttgtgttt tcctttgatg aaaagttgty 300
gtgtggtaaa atttgggact tcctctggtg gcccagagat gggaatttga cagcctgggg 360
actgaagaag agaggacagg gtttaaagac ctaggatttt tggaggagct gggcctaatg 420
gagagtcagc catgaaagaa ctccctaggg tgggagatgg caggtgggcc atggtttcag 480
taagatgcta ttcaggtttt cctcctgcac tgtaatcctc ttatggtttc ctcaagcctt 540
tagaaaagtc tgggacacac catgggctgt gtcagtggtc ctagggttta aggaagggc 599

<210> SEQ ID NO 314
<211> LENGTH: 599
<212> TYPE: DNA
<213> ORGANISM: Homo sapiens

<400> SEQUENCE: 314
aggtgggcag atcacctgag gtcaggagtt cgagtcaagc ctggccaaca tggtgaaacc 60
ttgtctctac taaaaataca aaaattagcc aggcgtggtg gcacatgcct gtagtcccag 120
ctactcagga ggctgaggca ggagaatcac ttgaacctgg gaggtggagg ttgcagtgac 180
ctgagattgc accacagcac tgcagcctgg gtgacagaga gagactccat ctcaaaaaaa 240
aaaaaaaaaa aaaaaaaaaa gaataggtat tctaattcaa taagtatttc cttagtacck 300
actatacaaa cacagtgaac aaaataggct aagtctagcc tcaaagagtt tacattccag 360
gaattcatgg caaaaatctg tagtcccaca tacatagttg acatgcctgc cagggccctt 420
tgctgccaga ggttgcaccc tccctgcttt tctcatggac tgcttgacca taccatgctt 480
ctagcaggta aattgttaca acttggcatg ctattccaga aaggaataca gcctgtgatt 540
tttttcttcc attaggtccc cttaatttat ccccactttt ccactctcac tggcctatt 599

<210> SEQ ID NO 315
<211> LENGTH: 599
<212> TYPE: DNA
<213> ORGANISM: Homo sapiens

<400> SEQUENCE: 315
caggtgagtg taaagatatt ttttcagaca taactgtcta taatagcctg ggtagttctc 60
cacccagact gtaggtggca gctacagggt tagggcagaa aaggccagaa aagtataatt 120
gcacaaattg gtttagtcac actcatacaa atagtcatat gttagataat gtatataaag 180
catttagttc agagtgtggt ccttagtaat tgttcaataa atatcaatta ttattgtaca 240
ctcacacaga tatattaatg tatctataca actttgggga acattccaga tagtaactcy 300
gctttccagg caaaaagaag gtcaaggctc ctgggcccac acaggcaagg ttcatcctca 360
caaatgtcat ttcaacagca ctgcagacgt tgcagggaaa tgccaggtca ggaggctgca 420
atctgaggat acccactctc tcatatccag ccaaagacag gcaaggccga agccagtgaa 480
caaagggcac agcgtactag tactataaag gatggcaaat agaggctaag gtagagcaac 540
gatttcctgg ggcaaaaact acagtgtgct cacaaagatg caggagggac atttcaaca 599

<210> SEQ ID NO 316
<211> LENGTH: 599
<212> TYPE: DNA
<213> ORGANISM: Homo sapiens

<400> SEQUENCE: 316

-continued

```
atattatatg atttcattta taccaaatgt ccagaacagg caaatctata gagacataaa     60

gtagatgagt ggttgcctag ggctggaggt gggctggggg atttgtggag taatagctaa    120

aaagtacagg gtttctttgg gggctgaaga aatattctaa aattggttgt agtgatggtt    180

gtacaactct gaatatgctg aaacccaata aattgtacac tttaagtggg tgaattgtat    240

gatatataaa ttagatctca agaaagctgt tatcaaaaaa aaaaaagact tccctcctcy    300

atgttctatg aaacctgttt tttggggttt ttttttgtt ttgttttgtt ttttttttg      360

gcagagtctc actgtgttgc ccaggctgca gtgcagttac acaatcacac ctcactgtag    420

ccttgacctc caaacttcaa acgatcctcc cacctcagcc tacagagtag ctggggctac    480

aggtgcacac caccatgccc agctaattga aaaaaaacaa acttattttg tagagatggg    540

ggtcttgtta tgtggcccaa gctggtctcg aactcccagg ctcaagcaat ccttccacc      599
```

<210> SEQ ID NO 317
<211> LENGTH: 599
<212> TYPE: DNA
<213> ORGANISM: Homo sapiens

<400> SEQUENCE: 317

```
gttcgccctg gcaagaagca attctgtagc caaccgaact ttggatttga actgcagcat     60

ctgtccttcc ggggtctcca gcctgttggc ccaccttgca gagtctggat ttgccacctt    120

ctaaaatcac atgagccaac tgcctaaagt aaatctctct ctctctccct ctctccactg    180

tggagtcccc attgtggaga gtcatacacc ttaccacagg caggaaatca aggtggttag    240

caggaaaatg agacccaggt gcccaaaaca ctgagcagaa gggagcaagg cctgtaacts    300

caaagtttag aatgaagagg ttagagaagg aaagcaggag atgggacaga atgcacagaa    360

cagcatatgg gacctggact ttgaacgatg ggtagaattt tgatcagggt taagggaaat    420

atgatgaaca cctgccaata gtagacatcc acaatctttg aataccettt cttcatttga    480

cattatccac attgagagtc tcaggttctc aatgtagaat ccaacaaact acatttcctg    540

gcctctcttg ctactaggca aatagttaac tgtttccccg atcagacata cccgtgtcc      599
```

<210> SEQ ID NO 318
<211> LENGTH: 599
<212> TYPE: DNA
<213> ORGANISM: Homo sapiens

<400> SEQUENCE: 318

```
attaatttgc taatatatta aaaagtgaac tggtggtttt gtactttttg tagtacatca     60

atataaaaac ttttgagaat tcccagaact aaggcaaaaa tggcatcaga ttaatttgga    120

gcaacttttg agaaatgctt ttaagacata cccacagact gtccctgtgg ctataaaact    180

gtttgactca ataatacctg tgaatatact gagaaggggc acttactaat tttcctgtgg    240

gtgtttccag gcatggcagt atagcatttc ccatcctctg cagttgtttt cccctttgak    300

agctgagaat tgaaggaggt atagcacatc aacagcagct cagaacctca gtcacggaac    360

ccctcatatc aaacaaaaaa aaaaggttgg gaaacaaaaa tgaaggtcag aaattaaatc    420

aaatagcaac actagagaaa tagctcaaaa aaaaaaacgc caaaagatga ggtttccaag    480

taaaaaatta tcaaagcaca agtgtaaaaa gtaaagtaga gattcctctt caaagagact    540

ttactcccca tataattagg aatagtaact tctcttagaa gcaaaattta ttcaagaac      599
```

<210> SEQ ID NO 319
<211> LENGTH: 599

<212> TYPE: DNA
<213> ORGANISM: Homo sapiens

<400> SEQUENCE: 319
cccatgggga cccagtgata cccccaaaac tcagtcccag gttctcagat gcacctttct 60
ctgggagcat ggccttcctg tgtccaaacc cctccctggc aatggtgggt gagggtgggg 120
cacacttcgg agacaaatga gaaactctta ggcagggccc ctgctaaggc cccagggagg 180
ccctgatttg ggggcagatt tccttttcct tttgctcctt agaaaaagct ccttttgcaa 240
gaagtttccc atatgtttgc tgagctactg ggagcagggc caggatacca agagacgggk 300
tagatcctcc gtggaaacct gctgttcagt tttcccacca caagccctgc cctagggagc 360
ccctggtgca gggtggcaga gggaagaagc ctggcagtgc cacacattgt gaggaatcta 420
atcaaggatg gcttcctgta caaaggactt tgagacaact tgaggatggg gatggcattc 480
ccagggaatg gcaggcggga ggacagctga gatagaagct cagggcaaag atgaggagtc 540
agtgggtccc ctccacattg ggctgaggaa ggagctgagg cctgtgccct ggcagattc 599

<210> SEQ ID NO 320
<211> LENGTH: 599
<212> TYPE: DNA
<213> ORGANISM: Homo sapiens

<400> SEQUENCE: 320
ataattttca ttcaccccaa atcctacggc aagctttgac aatgtaacat ctttatcttg 60
tggttaggaa aatggaccta gagagattat gtggtttgct caaaatcaca tagctactaa 120
gtgcagtagt gctttctata agaccaactt gcctttccac ttggttggaa aatttaaaaa 180
ccaaacctgt cgtaatctat ctgttctgcc cctcccgcct gtatcatgag atgactgaaa 240
attccaggtg gccataaact caaacaagag cctagccctt ggcttattac cggtggctay 300
tacaaaccta cagaccagag cccagggtag tatagagtcc caactctggg ccctgactgc 360
aggtcattca ggtcccagtc acagtgaaag cagactcatt cagctatctg gagaagtgta 420
atctgagggc cacttggcat cctgagttaa cacagggatg ccgcagctgg ggtaaggaat 480
tagagaaggg aaggccagtg ttactgcagt aagagaaaac caggaagtcc atctaggaga 540
tgaaatttgt gcttgcataa cagagccatg gaaatggcta tcccagcatc tcccctcac 599

<210> SEQ ID NO 321
<211> LENGTH: 599
<212> TYPE: DNA
<213> ORGANISM: Homo sapiens

<400> SEQUENCE: 321
tgaccctcat ttaagcccct tctccataac catttcccct ccaggtcaga gtccggataa 60
tagtaataat ggtggtgctg ctgcttctcc atcccctgcc cccacaaaaa agactagttg 120
atgagtcagc accatttatt gaacaaccag gctttcaaat gttgattcaa aatgctaccc 180
ttatagtaaa ttcacatcta tgttttgatt tctctctgga ctctccattc tgtgccaatt 240
atcagtctac catgtcagta gtgtactgtt ttatttacta tagcttaata atatgtttck 300
ttatcaggtg gagctaactc attatcattc ctcttatcta gaattttact gcctatacgt 360
acaaatatct tttccagatt aacattataa tcactttcta agccattggt aggattggta 420
tcacaattaa tgtatacatc tatttattga taattaccat ctttataaaa ttaagtttat 480
tttgtttata gccaaacatt agttgtatct tcatttattt tagtcttttc actcctcagt 540
agaggtttat aggttctaaa cactttttct caaatgcatt tctgggcatt tctgcttttt 599

<210> SEQ ID NO 322
<211> LENGTH: 599
<212> TYPE: DNA
<213> ORGANISM: Homo sapiens

<400> SEQUENCE: 322 gggggaaag gaaaggttag tgactggatt taaggcttga ctgagctcag actccttatt 60
ctagagcagg tctcaggcca gctgaggcca aatctctggg actacagctg aggaaaaaga 120
acgctttcca cctgcactgc caagatggga aacagaaggc tgatcgtggt gggtgtccca 180
tattgataat tttctggggg cctctggggt cactggtatc ctgtggtatc tgggtttggg 240
ctctgtcatt ggctctgagc tgagctctgg gctccaggct ctgggcttgg gttgggttgr 300
tccaaagaga atgttgaaga ttatattatt taagggaatc acagtgagtt cagcttgtta 360
agtacagggt ttggcacacg atcactgatc aaaacagaat gaatgaatgc acactatttt 420
tcactgaccg cagttttcct aatagaccct ctctgctggc tggggccctt ttcaaatagg 480
aaggagacag gaattaaggg ttccaattct tacactttct gctttctgct ttggtcagcc 540
tctgtgactt tgggtcctca tttacaaatg agacagggta atctctatag ggtcttcca 599

<210> SEQ ID NO 323
<211> LENGTH: 599
<212> TYPE: DNA
<213> ORGANISM: Homo sapiens

<400> SEQUENCE: 323
ctttgaacct ttttcttcat ttttaaaatc aggggtgggt atctcatcaa cctgggcatg 60
ggcacttctt ggaggccatc agtaagtaat ccacagctac tttgtatgat cctgtggtgc 120
cacctgctga ccagttttgg ggaggcagcc tgagtcttca agttcttact gagctccaac 180
taagcatatt gtttgaggca ctaaggatat agtaatgaac agacataaat gtataccttt 240
atgggactta aagccctagc agggcagaca agctatgaaa cagatctatc agtgaagtam 300
gtatgttctt tataaacact aagaagaaaa agtaggggag gggagataag aaatgtcaag 360
gtatgtgtga gaatttcaga atggcaggga gggcgtcact gaggtagctc ttgagtaaag 420
accagaagga agtgaaaaac agcagtgtac gtgtctaggg gacacagtga ggacaaaagt 480
cctgaatgcc tggcatgaag aaggaatgga gtggatacca ggcagtaaat ggtgaggaga 540
ggaaggtcat ggggccacgt gcaggtgaag tcacatctcc agctttaact tggagtgag 599

<210> SEQ ID NO 324
<211> LENGTH: 599
<212> TYPE: DNA
<213> ORGANISM: Homo sapiens

<400> SEQUENCE: 324
gttgcagtga gtcgagatta tgccactgca ctccagcctt gatgacagag cgagagtctg 60
cttcaaaaaa aaaaaaaaaa aagtaacgat agggaattca gataaaaaat caaaagtcta 120
atggctatag gctgaagaag gagcaaatga caaggaagta gagatggcaa gtacagccca 180
ctgtatatgg agctggcatg aaaagaaggg ataaaagtta cagtgataac ttgagggtga 240
cttttctaag ggaagagaaa agcatgttta catatttaga ggaaaaatgt cagaaaagaw 300
gtgatggaaa atagcagagc aagggagacc aatgtaggag caaagcccag attgtggagc 360
agacatggga gccagacatt gagtcccctg gcagtaggga tcagctcaga gaaaagaaga 420
tggagtgggt tcaggtgcat atattaataa aaggagtggt gcagggacag aaagtcaagg 480
gggttcattt ctcattgcct tcgttttctt ggtaaaggat atgtttgggc cattatctga 540
gaaaggactc agggtgcagt gggaggaatt tttgagtgta gtgaaggttt ggaaatggg 599

<210> SEQ ID NO 325
<211> LENGTH: 599
<212> TYPE: DNA
<213> ORGANISM: Homo sapiens

<400> SEQUENCE: 325
tccatctggg atgctcttac accaagtatg tacatggctc aatctctcac ttccttcaag 60
tctttgctca aatatcgcct ttctcaatga ggctttccat gaccaatgta tttaaaatac 120
aacactcctg atcttcctgc cctgctttat attcttcctt gcacttacca ccttctaaag 180
cttatcccct tccttgcttg cctgtccctc ccctctggag tagaggctgc attagggcag 240
gcagttttgt ctacttgccc acttctgcat ctgcagtgcc cagagcagag cctattatay 300
ggtagacttc agcaaatatt tattgggtgc atgaatgaag ataacagcat ctgggttata 360
caaagtgctt tgaataacct ctctaactga atgtaagctt atagatatgt tatatagcaa 420
ctgaaaagcg taattgggta aataaggtgg ggacaggttt gcattgagtg actgatcatt 480
cacagtctcg tttggcttag atggtgttta tcaagcagta ggtggctggt tttaaaatgg 540
tgttttgtag aaacctaggt gctgtagggt gtctttcaat gtttgttctt aattttgtt 599

<210> SEQ ID NO 326
<211> LENGTH: 599
<212> TYPE: DNA
<213> ORGANISM: Homo sapiens

<400> SEQUENCE: 326
cctgtgactg atccacagca ggcatgtgat ctaagcctga tagatcaggt ccctcgctgg 60
gcttgctgca gctggagaag aagcagctcc atgctgcttt ggggggggca tggtgctgga 120
aggagttgta gtggatggta taggtgctcc actcatatcc cattggttca cccttgaggt 180
catcttcaga cagtccctgc acacaaactg agctcctatg tctctctgca taaagctgct 240
tctctggcct ggggagcaag ctagggagag ttaccactcc cagagcaact cttaaacaay 300
gaaggagagg agctggcaga taaacacctc agcttccttg ttcttcaggg gctcaattct 360
gagtggtgct ccacacattc tttttgaggc atcccagtag gattgagatc tacttgctcc 420
agctgtaacc cactcaccga gacacccgtt tggggtttcc gccccttctt tgtctcactt 480
acctgctctc tcattttgct tctggtgtca tcttccaaat aaagtggtac acccaaactt 540
ttgccttgga gtttgctttg aggggagccc aaactaagat agaggaaaag ttggggttc 599

<210> SEQ ID NO 327
<211> LENGTH: 599
<212> TYPE: DNA
<213> ORGANISM: Homo sapiens

<400> SEQUENCE: 327
gccatttcaa ttgtttggat aaatagaaag cttcatggtg tatttttcaa agagcttagc 60
attcctttcc tctccccact ccaccaagga agatttggaa attgttccaa atagaaatta 120
taaacattag cctggagctg tgctgtctct gtctggtttt gatgcttttt ttgttttaac 180
taaaggctca tgttgtttgt ttaatcttca tcagtactgc aaaaacacat ggtataagac 240

```
ttaactctgc cccaagcacc ctacacataa gaagggattt tcatctgaat tagtttgtaw    300

ttcaaagagc actgggatag ccagattgct aagaatttgc tcaagtaaaa ctttagaact    360

attggaatct tagagatgtc ttgaatggat ttgttaggat aggatggctg ctgcctgaga    420

atcctctttg aacctgacac tatttttttt ttttttgagg agacattctt tgtaatactt    480

tgtgctactt ttctctctag gttaccctga agagacttac ccaatttatg acctttcaga    540

ctgtatcaag cgtaggcaag aaacaatctt ggtggattac cctgacccaa aagaacttt     599


<210> SEQ ID NO 328
<211> LENGTH: 599
<212> TYPE: DNA
<213> ORGANISM: Homo sapiens

<400> SEQUENCE: 328

ataccatatg ctctcactta cagctgggaa ttaaacaacg agaacacatg agcgcaaaga     60

ggaaaacaac agacattgag gcctacttgt gggtgaaggg tgggaggagg gagaggatca    120

gaaaagaaac ctatcgggca ctatgcttat tacctggggc acaaaataat ctgtacacta    180

aacccctgtg acacacagtt tgcctatata acaaacctgc acacataccc ctgaatctaa    240

aataagataa aaaacaataa taaaataaaa agaaaatcca gacactcaga gaaacatagm    300

gaaaacaaca atgtattttc agttcacctt gcaccctcaa gatgatcttc aattaactcg    360

tttcagaagc ttgaaagaga acagtagaaa atcattattt tttccaacaa aaaatcacaa    420

aattaactgc ttacatccat tgtgagaaat aaagtgtcac gagtgaaact taaaataaca    480

ttttatggac acacttagaa gaaatccaaa tacattcata gaaatggcag aatgatcttt    540

attcccaagc tgtatttttt ttaaagtgag ttaacctgac agtaatgtgc ctcaggaat     599


<210> SEQ ID NO 329
<211> LENGTH: 599
<212> TYPE: DNA
<213> ORGANISM: Homo sapiens

<400> SEQUENCE: 329

tggagcaagg gacttccccc ttataaggct agggcagagg cagcagcagt gaatgaatga     60

taatgctgat tccgactccc agtaactaga aacagcgtga atggggggcg ctgtggtgcc    120

accaggtgca agcagaggag caggctgcag tgtgtccagg tcaaaaaatgc gcttgagaca   180

aaggctgttt ctccctagta cactggaaga cattgatcct tgaatggaag gaggcaggga    240

gaggaattag atcctgtttt tacatggtta atggtcccca agaagctgaa gtttataatw    300

tcctcacctc tctgagccca tctcttatta tagtctcttt gctcccagct ccagccacat    360

tgggctcccc attctcactc aaacatgcct gggaagcacc caccctgagc ctttgcactt    420

gtgccctcca tctgggatgc tcttacacca agtatgtaca tggctcaatc tctcacttcc    480

ttcaagtctt tgctcaaata tcgcctttct caatgaggct ttccatgacc aatgtattta    540

aaatacaaca ctcctgatct tcctgccctg ctttatattc ttccttgcac ttaccacct     599


<210> SEQ ID NO 330
<211> LENGTH: 599
<212> TYPE: DNA
<213> ORGANISM: Homo sapiens

<400> SEQUENCE: 330

tatttccctt cgttcactgt gaggggttga ttcatgagga gagccctggg ttcctggctc     60

aggtttactt ttggccttag gataggattc ccttattaga gataaatact gctgttctct    120
```

tctagctcat tcattcattt agcagtcaat tgctcagtgc caggtgctag gaacagaggc 180
tcaatctcta ccctcagaaa actcagtgtg acgagagaga gcctgacaga taaaatgaac 240
tatgaccctg taagagggct caggatcgtg aatcctgcag gcagagaaac atgagccatr 300
atctgtccct gcattttcta gctgtggaat cttgggtcag ctccttaact ggtctgagct 360
ttggcttcag ggtagtaaag ggaggggtat taaaggtcct ggttaaatga aatcatcagt 420
gtgtgtaaaa cagcattggt tctagctcat acatgataac cactcattaa gtggtaatta 480
tgtttttatt ataagggcta tgctgtaatt cagacatggg cccaaaacta caggaaagat 540
aaattgtttt tgctaaagta ttgccaagaa acttcacagt ttcttgggag gtgggcctt 599

<210> SEQ ID NO 331
<211> LENGTH: 599
<212> TYPE: DNA
<213> ORGANISM: Homo sapiens

<400> SEQUENCE: 331
gccctggcag attccgtggt ctatgccagc caaggcctct aataggcctg aggtcagaaa 60
tggagattcc cagttcaagg tgagctcagt gcaggccttg atacacaaga gacagtggta 120
gggtggctgc taggtagtgg ggtaatgtag ggactgagct gaaactgggt ggtggggata 180
tatcctgagg attgtggcca gccccggctc atgtgtgtac ctgagagaat atccttttat 240
atctggacat gtgtgggaat atatgtgtga atgggagtct atatgtgtag atatggctar 300
gagtgtgtgc ataagtttgt gggggtacag gtgagtcagt gtctgaacat gagtatgtga 360
ccatgtgtat ttcaggggca gcgtagactt ctcctccttc atcccttctt cttctctcct 420
tggcccaggc atctccagca gcatgagctt tgacgaggat gaggaggatg aggaggagaa 480
tagctccagc tcctcccagc taaatagtaa cacccgcccc agctctgcta ctagcaggaa 540
gtccgtcagg gtgagtgagt gagtctgcat ccacagcagt ttttggagga ctgctcatc 599

<210> SEQ ID NO 332
<211> LENGTH: 599
<212> TYPE: DNA
<213> ORGANISM: Homo sapiens

<400> SEQUENCE: 332
tggagcggag cttgcctgcc tgcctgtgga gacagccctg cctatcctct gtatataggc 60
cttccgccag atgaagcttt ggccctcagt gggctccctg gcccagccag ccaggaactg 120
gctcctttgc ctctgctact gaggcagggg agtagtggag agcgggtggg tgggtgtgaa 180
gggatgagaa taattctttc catgccacga gatcaacaca cactcccacc cttggggtag 240
tagtgtgttg tagtcgtact taccaagctg agcaacctct tcagctggga aggccgcaar 300
aggcatagag ggagaggaag cacactgcag ggctgctgtg gcccagtcgt ccgctcagcc 360
aaggagtcag atggcaatgg gtactccagc aggtaggggc acagtgaatg tgtgtatgta 420
tgaaggccac atcaacttta tgtagcaaag ggcttggtgg ccaagcctgg cccttaaaca 480
actgcagaaa gcccttcaac ttcagaaggc ctcactcaag cctgagagaa gttgggaggg 540
tggtggggac aggtaagtgg caggaccctg tcaggattgc aggtgcctgg cttgctgtg 599

<210> SEQ ID NO 333
<211> LENGTH: 599
<212> TYPE: DNA
<213> ORGANISM: Homo sapiens

<400> SEQUENCE: 333
atgctaagtt tatttaagag gtaaatgtcc tgctattttc agaatggaga aaaaaaaaaa 60
aaaacaacct tctgcttcta gaattttgtg ccctacttgt cactgaagga ggcaggctcc 120
gaaagttctc ttatagcttc tgattatcac agtcctggct tccaacacct gtgttcgcca 180
tagatctgga cattatgtgc ttcctctgaa ctagtgtctt gatttttaag gcacattcac 240
tagagtatgt tcaatttcaa ccaaaagcat acgtgcaaca taccagtttt ttcaggcaay 300
gcagagcggg aactgaaaag ctaacaacat tcttggatgg tgtcctctga ctcagaaccc 360
tgagagaaaa agctggtatc ttcccaggta taccttctgt tcagagagca tgagatgaat 420
ggacaaaatc cacaggcgat cataacaaca tccttattcc tttcctactc attcattctc 480
aggaatataa tcacaattaa gaaacctcag ttgattgctg attgcccttt tccccaaata 540
aacacacaga cgcacagaca cacacataca cagacggaca cagagcacct tggagccag 599

<210> SEQ ID NO 334
<211> LENGTH: 599
<212> TYPE: DNA
<213> ORGANISM: Homo sapiens

<400> SEQUENCE: 334
gtgtgtatgt tgtgtctgtt tgtggaagaa aacaccagca ttgatggctt gtagctggtc 60
gtgtccatga atgattgctg gccttgccta tggtctggat cagtccttgt tctccatctt 120
gtttttccac tgtgcagttg gttttgtaga tggctgccgt ctgctttaag gacgtgaggt 180
gttgtaaacc aaccctcggc aattaatttg ggggaagagc agaagaaatg aagcccacat 240
cccttactag cttaccagtt gttaacaggc tggtgcaatc attagtttta taaaaatcas 300
ttttgcaaat aaagttttgc agagggtttc cccactcttc cctcatcccc ttcatggacg 360
tctgagaatc caggccctcc tctcctcctc ctggatgtaa ctcaggcgtg tccgtggcct 420
gcaggcacca gcgggccagc agcactggca gaagacaagt ctgaggccca aggcccagtg 480
cagattctga ctgtgggcca gtcagaccac gcccaggacg caggggagac ggcagctggt 540
gggggcgaac ggcccagcgg gcaggatctc cgtgccacga tgcagaggaa gggtgagcc 599

<210> SEQ ID NO 335
<211> LENGTH: 599
<212> TYPE: DNA
<213> ORGANISM: Homo sapiens

<400> SEQUENCE: 335
agactgtgaa tgatcagtca ctcaatgcaa acctgtcccc accttattta cccaattacg 60
cttttcagtt gctatataac atatctataa gcttacattc agttagagag gttattcaaa 120
gcactttgta taacccagat gctgttatct tcattcatgc acccaataaa tatttgctga 180
agtctaccat ataataggct ctgctctggg cactgcagat gcagaagtgg gcaagtagac 240
aaaactgcct gccctaatgc agcctctact ccagagggga gggacaggca agcaaggaar 300
gggataagct ttagaaggtg gtaagtgcaa ggaagaatat aaagcagggc aggaagatca 360
ggagtgttgt attttaaata cattggtcat ggaaagcctc attgagaaag gcgatatttg 420
agcaaagact tgaaggaagt gagagattga gccatgtaca tacttggtgt aagagcatcc 480
cagatggagg gcacaagtgc aaaggctcag ggtgggtgct tcccaggcat gtttgagtga 540
gaatggggag cccaatgtgg ctggagctgg gagcaaagag actataataa gagatgggc 599

<210> SEQ ID NO 336
<211> LENGTH: 599
<212> TYPE: DNA
<213> ORGANISM: Homo sapiens

<400> SEQUENCE: 336
gttgagaaac tgggaagtcc aggttttggg tgggccagag atatccccat agatctctca 60
gctccccttg cctataggca caaagttgac cttgttctta cccaaactgc tttgcctgtg 120
aagccttctt ctctagtatt tcttatgacc aaagtctcct atttttgaga tactcacact 180
tccttatccc tgcttctact gttcttgtcc ttattgtggc agctcctcaa gtcttccttt 240
ttctagaact ccttcagact tctcctggct ttagttcctc tctatccttc cactgatccw 300
ttacatctac ctctgtcttg tcaacacact cagttccatt gacctctgtt ttcctcactg 360
ccattgtcag tgatttccta atctggcatc aatccaagta ccatctttcc tgtccctgca 420
cacagggagc tgagttgtcc tgggccaatt acccaaacac aagaaagaga atcctacaaa 480
ttatggtctc ctttcttcca ggtcctccat agttcccacc catctctctg tcagtaccca 540
gcatatctgt ctcctgcttt ccacagaagc tatttcagaa tttatttcct ctcctctaa 599

<210> SEQ ID NO 337
<211> LENGTH: 599
<212> TYPE: DNA
<213> ORGANISM: Homo sapiens

<400> SEQUENCE: 337
taactgactg agggggaaag taggagctgt atcctatctg caccacgtgg caagtcatgc 60
atctttatgt ggggctgcat caacccagaa gaaaggagaa aggggtgcct ttgtcagaag 120
agaagtggcc ctgtgatgtg tcagatacta tgattagcat ataatctttt tgttacatag 180
gacaatgcat ttcttatctc ttctccattt caccctgtgt ctggtagctt ttgctgcata 240
acaaaccaac cctcccttaa attagtggct taaagtaata accatctatt attgcttatr 300
agtccagggg ctggctgggt ggttctgcta atttgagtct ggtttcgttg ctccaggcta 360
agcttcttta cgtgtgtgcc ttcagctgga ggctcagcta ggggctggat gatctagggt 420
ggcatcgctc acacagctga cagctctgct tctggaagtt gactggacgt cacttggggg 480
tacaggggta acagggctac atgtctgtca tcaattagca agctagcctg gacttggtca 540
caggacagct caaggttcaa ggaaagcaaa tggaagcagg taaagcctct tttggtgta 599

<210> SEQ ID NO 338
<211> LENGTH: 599
<212> TYPE: DNA
<213> ORGANISM: Homo sapiens

<400> SEQUENCE: 338
catcgctcac acagctgaca gctctgcttc tggaagttga ctggacgtca cttgggggta 60
caggggtaac agggctacat gtctgtcatc aattagcaag ctagcctgga cttggtcaca 120
ggacagctca aggttcaagg aaagcaaatg gaagcaggta aagcctcttt tggtgtaggt 180
ttagaatttg aagtgtctct tctgccatat tctttcagcc attcacaaaa accaccccag 240
attcaaggga taggaaaaaa gactcttgat gggatatgtt tcaagtcaca ttacagaacr 300
gaaagtagaa gaataactta cagccatttt tgcagtctat cacacaccac caactctgcc 360
atgatgctcc atctgccggg gaagaggtga ccagagagtg gacctaagca tagcccaagg 420
gagctcatga gaacagaagt tcatgggggt actcctaagc cttgtataca tatctaatag 480

```
tcttagatgt ggattcaact aggtgtgggt tgggagaaag aaaacatgga gcttcttttt    540

cactaagagc ccctatcttt gctcttacaa tttatataac ttgaaattat catagttgc     599


<210> SEQ ID NO 339
<211> LENGTH: 599
<212> TYPE: DNA
<213> ORGANISM: Homo sapiens

<400> SEQUENCE: 339

cattcattgt ttcctaggag cctcaggtgg gtaagtaggt gataatagca aagagatcat     60

aacctcacca atgacatgtg ggtcaacact gtccttcctc tggcctgtgc ctttcaagtt    120

taaggttcat cagaaccaca cccagaggct ggaaaaatgg tgaagtcaga aggtacttaa    180

gttagagcag ttctcttcag ggtctgctgt gccgcctgaa ggggctggtg gttcctcagt    240

atcccctgtg ggcctggcct taggaagaga acagggctgt agagatgaaa aaggtataam    300

agacccaacc acttgatgtc tcagggcttg cttggaccct aacccattta aacaggacct    360

cgagatgctt aggaatcttt ttttgttgcc gggcagctgt ggcagatttg aaggcaaaag    420

gaagggaggc tacagttgta gctagaagca gacatgaaag ctaatggtct gacccagaca    480

agaggttata actaaaggca cccggagact gcagaagggc cctgggccac tcctggcaat    540

cagggtagcc ttagagggtg tcaggtgtga catctcagca acactggact tgacagagt     599


<210> SEQ ID NO 340
<211> LENGTH: 599
<212> TYPE: DNA
<213> ORGANISM: Homo sapiens

<400> SEQUENCE: 340

ctctttgaaa tacaaactaa ttcagatgaa aatcccttct tatgtgtagg gtgcttgggg     60

cagagttaag tcttatacca tgtgtttttg cagtactgat gaagattaaa caaacaacat    120

gagcctttag ttaaaacaaa aaaagcatca aaaccagaca gagacagcac agctccaggc    180

taatgtttat aatttctatt tggaacaatt tccaaatctt ccttggtgga gtggggagag    240

gaaaggaatg ctaagctctt tgaaaaatac accatgaagc tttctattta tccaaacaay    300

tgaaatggct tgcaagtgtc aaaaatagag agcactttag caaggcatgc ccaagatccc    360

gaaaggacaa gcactgcatt ttcggaagac agaattcctg ttgttggctt cttcatcttc    420

acaaaatgga acaaaagaaa acaacaaact ggcaaacaaa atgagtaaca ctggtactga    480

atcccagcta ggataatgag aaaagagaaa ctgttgccaa attaccaaac taaatgaaat    540

aaatctgtgt ccgccaagca agcctgagca gcagatgggc cgtgctggag ctcacacac     599


<210> SEQ ID NO 341
<211> LENGTH: 599
<212> TYPE: DNA
<213> ORGANISM: Homo sapiens

<400> SEQUENCE: 341

aggacaaagt gaagccactt tcacctcctc ctgatggcta gccctttcta gctggaacaa     60

tcattgacca cctacatgag ccttcaacta cttgcacctc caagggagcc agtcagaggg    120

tagaaggaag cccccataac acagactgcc caccaccttg gccacgatct atgaggacta    180

tgcatgtttt ttaactagca ggtgtcctgc ctacttgaca tctgggaagg tctttccttg    240

tacccacgag ctgctctgca tgtcagagga gccccagctg tgatctgggg ctgtgtgcas    300

aacagcctca ttcaccaaac cctcagctgc cagagcacag gagaaaacac cgctcaagag    360
```

ccatacttct aggccttggt cttcttgaaa cagcccatct gcctaagagg gcacagctgc 420
atttggggct ccctgagggc attgccagga ccacaggatg caaccaggtc cctaaatatt 480
ccagctggct gagaggctgg gcatcccatt gtggaaggca cacacccagg ctggaggact 540
gcagtgaaga cttctgaaga aagggttcag gaccagagcg caaaatgcct gagggccct 599

<210> SEQ ID NO 342
<211> LENGTH: 599
<212> TYPE: DNA
<213> ORGANISM: Homo sapiens

<400> SEQUENCE: 342
ggcccctgtg caacctccac aagacagtgc tggcttccct ttgtgccagc aggaggggcc 60
attccacagt tttctaggtt gtcgcaagcc actcacactt tcagagggca gggactgggc 120
agtcacctgg gccatcccca gccctgggct tggctgagca agacaaagaa gatgacttcc 180
atggtgctga cgctcacatc tagagtcatt tagaaaaggg gacatccagc tgagaggtaa 240
gactcacatc agcaatgcca cctccggaaa tgctgggtca cagcagctgc tcaactgacw 300
aaaggtattt ccagccatag tggcctcact gcccagtgcc ttttaatgct ctcatccatg 360
cagggggcac atttccctac cagaggccac catcccactt gccatggact atgcacagtt 420
atgccagagg caggaggctg ctttccatga aaacattcct ttctcctcct ctgcctccac 480
ctccatttcc tgatggggga gaatgataaa gagccacagg cttcggtgac cctgattact 540
aggtaagata acagggagaa aggacttaac cactggcctt cagagaaata tggatgaac 599

<210> SEQ ID NO 343
<211> LENGTH: 599
<212> TYPE: DNA
<213> ORGANISM: Homo sapiens

<400> SEQUENCE: 343
caccaatgtc atatggttta acttgccaaa gtacttagta ctgtggttgg tatagaacaa 60
actgctcagt cagtggtacc tttgctttgt tttatttaga tgctacaagc ctaacagttc 120
tttcaactca actgtttgtg taatgctaac atttagatag gaagctcttt ctagcaccac 180
caggaacatt ttgactccag attaacatac tcagtggata ggttttactc aagactaccc 240
atggggacaa tcatgttaga gcaggcagtg attgacaaca gttaaacacg agccaaggar 300
ctacctaatt gtgtttagga gttggcattt ctttagctct tatgcaaagc aatgttatcc 360
acattattta aatataaagc taactattaa tgctaactca tgttttctcc attttttttt 420
tttttttttt tttctgagac ggagtctcgc tctgtcgccc aggctggagt gcagtggcgc 480
gatctcggct cactgcaagc tccgcctccc gggttcacgc cattctcctg cctcagcctc 540
ccgagtagct gggactacag gcgcctgcca ccacgcccgg ctaatttttt gtattttta 599

<210> SEQ ID NO 344
<211> LENGTH: 599
<212> TYPE: DNA
<213> ORGANISM: Homo sapiens

<400> SEQUENCE: 344
aatggctata gacaggggtg accctacgtc caggacagtc ttagtttatg cctatcacct 60
tggcataatt atattaaagc tcccttttttc caaagtgttt gaatttggac cttaagttat 120
ttgatcaccc aagccatata aggtgcattg tatggttctc aaaggccgtt gattctacag 180
gccaaataca cctccactcc tcatcacgac tccctgggcc cagcttctgg agctagtcat 240
ggagataatg gtttctttgt gctcctgttg tgaccaggaa aggggatctc ctggctgcam 300
cacccacctg atttaccaag agtgatccca gattatgcag ttgttttgtg agctaactgt 360
ccataaaggt atgacttgtg tactctgcca cagtgccaaa aggccagggg actgatcaag 420
ttcccagcac cctcgtgaga aatgaagacc gcaagaaaag agacagcagc cctggcaaca 480
aaaaccggac ccatgatttt gtcatcctgg gttgtatata cacatataac tgtcatcccc 540
gaaggataaa ataattctgg aaaatccaaa aagaattttc taaatcctaa ataactgaa 599

<210> SEQ ID NO 345
<211> LENGTH: 599
<212> TYPE: DNA
<213> ORGANISM: Homo sapiens

<400> SEQUENCE: 345
ctccatatag gtggctaagt cccaaaatgc taaccttctt ccctgggtga actgattctg 60
cttgggagag ggggtggccc tggggtcctc aagctcaggt ggcagatgtg agggtctctg 120
ttgggctgct tcactcccca tgcattcctt cactccccct cacaaacatt tcatcaccac 180
gtttgaaaat gcctaaaatg caaacaggat gatttaaatt catagcaaat atcttaccct 240
tgcaggattt gggcaggtgg tgagggaggc atgttgggat tgctgtgtgg tggtgtttcm 300
gtccagataa ccttgttcct ggggctaaat ttgaaaagct tatgcccttc ttcgagggtc 360
atggttatag tgcagttgta aaaatataac ttttgatcat ggcctagtat aatatacatc 420
atatgacttt ctggagtagc tttttgatgg aagccaagga cgtaaactta aaatgtcaac 480
cacggaagtc atttgagtgg aaaaagccat catgcattct gagtagaatg ttaacactca 540
tgcactccat agaactcgaa gaagcacaca cgtcattctc ctgcacgcgt accatccaa 599

<210> SEQ ID NO 346
<211> LENGTH: 599
<212> TYPE: DNA
<213> ORGANISM: Homo sapiens

<400> SEQUENCE: 346
cattataatc actttctaag ccattggtag gattggtatc acaattaatg tatacatcta 60
tttattgata attaccatct ttataaaatt aagtttattt tgtttatagc caaacattag 120
ttgtatcttc atttatttta gtcttttcac tcctcagtag aggtttatag gttctaaaca 180
ctttttctca aatgcatttc tgggcatttc tgcttttacc actactgtaa atgtgaactt 240
ttttcctata ctatatttaa cccatttttt atataagaaa aatctgtttt tatatttcar 300
ttttctaatt gtcatttacc atgtgttgtt tccgttaaat tgtttggatt ttttcatatc 360
aattacaaat aattgtaatt ttacctcctc ttcccaattt cacgtcttgt atttatttct 420
tctggctgtt tatattggtc aataactgcg caacagtgtt aaataatact ggtgttacag 480
tataccctga ttttattcct gatgttgata gaaatgattc tgaagtttta acattaagca 540
taatgctgac ttttagtctg aggacatcta agtgtattaa catggtaatt agattaaca 599

<210> SEQ ID NO 347
<211> LENGTH: 599
<212> TYPE: DNA
<213> ORGANISM: Homo sapiens

<400> SEQUENCE: 347
tgctactacg ttctacttgc taatatttta tttaagattc ttgctttcct attcaaaagt 60
gaaattagac cggtgcggtt gttcatgcct ataatcccag cactttggga ggccaaggtg 120
gtggatcgct caaggccagg tgttcaagac cagcctgggc aacatggtga aaccccatct 180
ttaccaaaaa tacaaaaatt agccagtctc ctaacccggt ctcaaaagaa ataaataaat 240
aaatatataa aaaatttatt taaaaaaatg aaattaatct gtagtagttt tcatgtcttr 300
tcaagtttta cgatcaatgt tcatgtatct gcatgtatat atttactata tatacatata 360
taaatgtatc cattaaaatt tatatgatat acatcttgat tttttcatgt aacatgtttt 420
aaagatattc ttatgacagc atatgttttt aagcatggat agatcatact ttttatttac 480
gtattttttt cttcaacttt tattttacgt tccagggtac ttgtacagga tgtgcaggtt 540
tgttacacag gtaaatatgt gccatggtgg tttgctgcac agatcaaccc atcacctag 599

<210> SEQ ID NO 348
<211> LENGTH: 599
<212> TYPE: DNA
<213> ORGANISM: Homo sapiens

<400> SEQUENCE: 348
tcacccccaa gactcctttt gttccctctc attctttgat tctcgaagct gccctgaact 60
cttcccagcc atgtgaacca atacattcct ccctgtatgt gttaagcttg cttgaattgg 120
atttctgtct cttgcaactg aaagtattaa tgactcttac aaagaataag tgagttcgca 180
tgcaaagcat tttgaataga gcctgtcaca gattaaatac tattactggt gcatattatt 240
attatttaat gtctgactcg cttccagtgg agaccatgga tcaagaagct agagcctagr 300
aaagaatcac aaaaaagtca gtttaattct acctaattcc tctcttttgt gtttttcata 360
acttgattat gttgatggct accttctttg ccactgggag atactttata caataattat 420
agctttaata tcttcttact catcattaac aatgggcaat taagtattat tctgttgtgc 480
ttaaaagtca tgttggtttg gccacaactt tgttaccaag atctgagaga caaaccaccc 540
agcatgaatg acccagtcag gttcaagaca tggcaggctc tgcctggctt cagggactc 599

<210> SEQ ID NO 349
<211> LENGTH: 599
<212> TYPE: DNA
<213> ORGANISM: Homo sapiens

<400> SEQUENCE: 349
ctgcgaggaa aatgccatcc ttgggtttcc ctgcagagct ccaccctctc tcattcctcc 60
tctgtctcac gcttcctctg ccgaaggtca gatgcacatg ctgcactgag tgggtgccct 120
gcggcctagg tggcctcagc tttcagcttg gcatatggga attttggagc ttgttgggag 180
gccccaggga ggatggagac atagtgctgc caccactgcc gttttcagag cctcagaaca 240
atctgtatcc ttgggccttt tccataagag ggagtgtggg aatacatatg atttataatr 300
taaacaatat ataccgacag gatgtgaatg aataaaagat gagtaaataa aagcacaaga 360
ataaataagc atcctgcctt ggccttgctc tgcgcagcaa gggatatggt ggaagcatca 420
tggcaggaca gggcagctag tggctgctgc ctcagccttc ctcctcactg gaagcagcca 480
ctctgcccac cctctgtacc ctaaccttga agccctcctg acttcagcag attctacatt 540
aggagctgac ctcttcacac tggggcagtt tggtgcacag aaaaagcaca gaacagata 599

<210> SEQ ID NO 350
<211> LENGTH: 599
<212> TYPE: DNA

<213> ORGANISM: Homo sapiens

<400> SEQUENCE: 350
tctgccgaag gtcagatgca catgctgcac tgagtgggtg ccctgcggcc taggtggcct 60
cagctttcag cttggcatat gggaattttg gagcttgttg ggaggcccca gggaggatgg 120
agacatagtg ctgccaccac tgccgttttc agagcctcag aacaatctgt atccttgggc 180
cttttccata agagggagtg tgggaataca tatgatttat aatgtaaaca atatataccg 240
acaggatgtg aatgaataaa agatgagtaa ataaaagcac aagaataaat aagcatcctr 300
ccttggcctt gctctgcgca gcaagggata tggtggaagc atcatggcag gacagggcag 360
ctagtggctg ctgcctcagc cttcctcctc actggaagca gccactctgc ccaccctctg 420
taccctaacc ttgaagccct cctgacttca gcagattcta cattaggagc tgacctcttc 480
acactggggc agtttggtgc acagaaaaag cacagaacag atactaacta gcattttaac 540
ttcacacaga tcagtatccc tccctcctgc tatcctccag gccctggttt cccaatctg 599

<210> SEQ ID NO 351
<211> LENGTH: 599
<212> TYPE: DNA
<213> ORGANISM: Homo sapiens

<400> SEQUENCE: 351
cctttgcact tgtgccctcc atctgggatg ctcttacacc aagtatgtac atggctcaat 60
ctctcacttc cttcaagtct ttgctcaaat atcgcctttc tcaatgaggc tttccatgac 120
caatgtattt aaaatacaac actcctgatc ttcctgccct gctttatatt cttccttgca 180
cttaccacct tctaaagctt atccccttcc ttgcttgcct gtccctcccc tctggagtag 240
aggctgcatt agggcaggca gttttgtcta cttgcccact tctgcatctg cagtgcccas 300
agcagagcct attatatggt agacttcagc aaatatttat tgggtgcatg aatgaagata 360
acagcatctg ggttatacaa agtgctttga ataacctctc taactgaatg taagcttata 420
gatatgttat atagcaactg aaaagcgtaa ttgggtaaat aaggtgggga caggtttgca 480
ttgagtgact gatcattcac agtctcgttt ggcttagatg gtgtttatca agcagtaggt 540
ggctggtttt aaaatggtgt tttgtagaaa cctaggtgct gtagggtgtc tttcaatgt 599

<210> SEQ ID NO 352
<211> LENGTH: 599
<212> TYPE: DNA
<213> ORGANISM: Homo sapiens

<400> SEQUENCE: 352
caccttctaa aatcacatga gccaactgcc taaagtaaat ctctctctct ctccctctct 60
ccactgtgga gtccccattg tggagagtca tacaccttac cacaggcagg aaatcaaggt 120
ggttagcagg aaaatgagac ccaggtgccc aaaacactga gcagaaggga gcaaggcctg 180
taactccaaa gtttagaatg aagaggttag agaaggaaag caggagatgg gacagaatgc 240
acagaacagc atatgggacc tggactttga acgatgggta gaattttgat cagggttaas 300
ggaaatatga tgaacacctg ccaatagtag acatccacaa tctttgaata ccctttcttc 360
atttgacatt atccacattg agagtctcag gttctcaatg tagaatccaa caaactacat 420
ttcctggcct ctcttgctac taggcaaata gttaactgtt tccccgatca gacatacccg 480
tgtccaactt tggtttgaaa gttatctgtg agaggaaaca gcagtgcttg cttggcctac 540
ctcttttggt gggtgaggcg gcagcagagg tgggacgttc ctgtggctgg tagcggcca 599

<210> SEQ ID NO 353
<211> LENGTH: 599
<212> TYPE: DNA
<213> ORGANISM: Homo sapiens

<400> SEQUENCE: 353
gcagttaggc caaaaaaagt aaaaataaaa ataaaaggca ttcagattaa aaaaaaaagt 60
aaaactatct ctatatgcag acaagttcag cgaggtgaca agatacagta tcaatataca 120
aaaactaatt gtctatacac taaggaacaa tctgaaaaca aaatttataa caacatcaaa 180
aagaataaaa tacttatgaa tatatttaac aaaataagac tttcacacta aaaactacaa 240
tctcctttaa aataaattaa agacctagat aaataaaaaa gaaatcctct gttcatagay 300
tgaaagattt aatattggta agatggcagt actctccaaa ttgcttcagt tcactctatc 360
aaaatcccaa ctggcatttt tttttttttt tttggcagaa accaaagtga tgatccaaaa 420
ttcctatgga aatgctaggt cacaggaccc aaaatagcaa aacaatcttg aaaaagaaga 480
acaaagtttg aggacacatt tcacgatttc ataacttaga aaactacaat aattaagaca 540
gcatggtact ggctaaggat aagtatacag attaatgtaa tataattgag agtccagaa 599

<210> SEQ ID NO 354
<211> LENGTH: 599
<212> TYPE: DNA
<213> ORGANISM: Homo sapiens

<400> SEQUENCE: 354
ttggtttggc cacaactttg ttaccaagat ctgagagaca aaccacccag catgaatgac 60
ccagtcaggt tcaagacatg gcaggctctg cctggcttca gggactcact aagactgcca 120
tggtccttag gcatttttat cttcatggac tcccattaat ggggattaat gtttatatta 180
tatgaccaca ttggcataaa gataaatatg ttagtattat atattaagac atgttctttg 240
acctaaaaat ctattttttt cctcctgatt ttaagagaaa ttaaaacatg ttagtgctcw 300
ctgtgcctga tggttaaata ggccctacct cgctaagttc acaaactgct gcttggttag 360
caacttacac cccaggaacc tgggtgtgcg gtaaacaagt aatgtggctc ctggtttata 420
tttttcataa cacataatag ttttaaactg tatcaagtat cataggagca aaatgttgac 480
atgtttagaa aagctgctgg gagatgtttc tactttctag ggcctgtgga agacttcatc 540
ttggcagagg gaaaaggctt ccaagaatct tccagttatg caaaggcaag gcccagcgg 599

<210> SEQ ID NO 355
<211> LENGTH: 599
<212> TYPE: DNA
<213> ORGANISM: Homo sapiens

<400> SEQUENCE: 355
tcttcttact catcattaac aatgggcaat taagtattat tctgttgtgc ttaaaagtca 60
tgttggtttg gccacaactt tgttaccaag atctgagaga caaaccaccc agcatgaatg 120
acccagtcag gttcaagaca tggcaggctc tgcctggctt cagggactca ctaagactgc 180
catggtcctt aggcattttt atcttcatgg actcccatta atggggatta atgtttatat 240
tatatgacca cattggcata aagataaata tgttagtatt atatattaag acatgttcty 300
tgacctaaaa atctattttt ttcctcctga ttttaagaga aattaaaaca tgttagtgct 360
cactgtgcct gatggttaaa taggccctac ctcgctaagt tcacaaactg ctgcttggtt 420
agcaacttac accccaggaa cctgggtgtg cggtaaacaa gtaatgtggc tcctggttta 480
tatttttcat aacacataat agttttaaac tgtatcaagt atcataggag caaaatgttg 540
acatgtttag aaaagctgct gggagatgtt tctactttct agggcctgtg gaagacttc 599

<210> SEQ ID NO 356
<211> LENGTH: 599
<212> TYPE: DNA
<213> ORGANISM: Homo sapiens

<400> SEQUENCE: 356
cctcagggag ccccaaatgc agctgtgccc tcttaggcag atgggctgtt tcaagaagac 60
caaggcctag aagtatggct cttgagcggt gttttctcct gtgctctggc agctgagggt 120
ttggtgaatg aggctgttgt gcacacagcc ccagatcaca gctggggctc ctctgacatg 180
cagagcagct cgtgggtaca aggaaagacc ttcccagatg tcaagtaggc aggacacctg 240
ctagttaaaa aacatgcata gtcctcatag atcgtggcca aggtggtggg cagtctgtgw 300
tatgggggct tccttctacc ctctgactgg ctcccttgga ggtgcaagta gttgaaggct 360
catgtaggtg gtcaatgatt gttccagcta gaaagggcta gccatcagga ggaggtgaaa 420
gtggcttcac tttgtcctca gggtgatgtg acctcctgtt tcccctttgc acgcacactg 480
cgctcacctt cacacgagca cacccacttc ttcacaggtg tctgcatgca catgtgcaca 540
cacatgagat attcacacac ttccttatgg cctcacacaa acctaatgca ctcgggcac 599

<210> SEQ ID NO 357
<211> LENGTH: 599
<212> TYPE: DNA
<213> ORGANISM: Homo sapiens

<400> SEQUENCE: 357
gcctgtcaca gattaaatac tattactggt gcatattatt attatttaat gtctgactcg 60
cttccagtgg agaccatgga tcaagaagct agagcctaga aaagaatcac aaaaaagtca 120
gtttaattct acctaattcc tctcttttgt gtttttcata acttgattat gttgatggct 180
accttctttg ccactgggag atactttata caataattat agctttaata tcttcttact 240
catcattaac aatgggcaat taagtattat tctgttgtgc ttaaaagtca tgttggttts 300
gccacaactt tgttaccaag atctgagaga caaaccaccc agcatgaatg acccagtcag 360
gttcaagaca tggcaggctc tgcctggctt cagggactca ctaagactgc catggtcctt 420
aggcattttt atcttcatgg actcccatta atggggatta atgtttatat tatatgacca 480
cattggcata aagataaata tgttagtatt atatattaag acatgttctt tgacctaaaa 540
atctattttt ttcctcctga ttttaagaga aattaaaaca tgttagtgct cactgtgcc 599

<210> SEQ ID NO 358
<211> LENGTH: 599
<212> TYPE: DNA
<213> ORGANISM: Homo sapiens

<400> SEQUENCE: 358
ttccagtgga gaccatggat caagaagcta gagcctagaa aagaatcaca aaaaagtcag 60
tttaattcta cctaattcct ctcttttgtg tttttcataa cttgattatg ttgatggcta 120
ccttctttgc cactgggaga tactttatac aataattata gctttaatat cttcttactc 180
atcattaaca atgggcaatt aagtattatt ctgttgtgct taaaagtcat gttggtttgg 240
ccacaacttt gttaccaaga tctgagagac aaaccaccca gcatgaatga cccagtcagk 300

```
ttcaagacat ggcaggctct gcctggcttc agggactcac taagactgcc atggtcctta    360

ggcattttta tcttcatgga ctcccattaa tggggattaa tgtttatatt atatgaccac    420

attggcataa agataaatat gttagtatta tatattaaga catgttcttt gacctaaaaa    480

tctatttttt tcctcctgat tttaagagaa attaaaacat gttagtgctc actgtgcctg    540

atggttaaat aggccctacc tcgctaagtt cacaaactgc tgcttggtta gcaacttac     599
```

<210> SEQ ID NO 359
<211> LENGTH: 599
<212> TYPE: DNA
<213> ORGANISM: Homo sapiens

<400> SEQUENCE: 359

```
ctttgtgtga ggcttctggg gcagactaga agagcttacc tgcttatcac aaactcttgt     60

ctcttcaggc ggcacatgtt acttttccag actgtacgca gggcattctg atcttcaatg    120

aatgaaacag tcttaattct gtttcctaag tcatgggaaa tcagaagccc ttatcctaaa    180

agaggatggg tagactacag gaagcaggaa cagacaagag ctttcccaga gaactccaaa    240

ccaaagcatc ctcatttcac tcttaacaag tatactttta ttgtccatat catgcattay    300

gcattaatca tggtctacct tatgacatct tctgaattta ttgcaatgaa tattttcatg    360

gattccttat catctcaact tggtttgata ctcctagagg gcagtaataa ttaagttgac    420

aacagtatag acacaatgcc atgatcactg ttaagagctc aataattacg tgttagtttg    480

attgatcccc atttcctcac catccattat tttcttccac ctccctgaat tctggattcc    540

gttctatcat tttatgaaaa gttgcaaaaa cttttttttt tttttttttt tttttgaga     599
```

<210> SEQ ID NO 360
<211> LENGTH: 599
<212> TYPE: DNA
<213> ORGANISM: Homo sapiens

<400> SEQUENCE: 360

```
gagatggcaa gtacagccca ctgtatatgg agctggcatg aaaagaaggg ataaaagtta     60

cagtgataac ttgagggtga cttttctaag ggaagagaaa agcatgttta catatttaga    120

ggaaaaatgt cagaaaagaa gtgatggaaa atagcagagc aagggagacc aatgtaggag    180

caaagcccag attgtggagc agacatggga gccagacatt gagtcccctg gcagtaggga    240

tcagctcaga gaaaagaaga tggagtgggt tcaggtgcat atattaataa aaggagtggk    300

gcagggacag aaagtcaagg gggttcattt ctcattgcct tcgttttctt ggtaaaggat    360

atgtttgggc cattatctga gaaaggactc agggtgcagt gggaggaatt tttgagtgta    420

gtgaaggttt ggaaatgggc aaagaggtat tcaggaatca ctccagcttt gcacaggggc    480

tccctttgga gtttaaatgc aaccaaggat tttctgctgt aaatgcaacc aaggattttc    540

tgctctgtcc ctgggaactt aaaagtattt tctaaccagt acattctggg ctgaacttg     599
```

<210> SEQ ID NO 361
<211> LENGTH: 599
<212> TYPE: DNA
<213> ORGANISM: Homo sapiens

<400> SEQUENCE: 361

```
tgctgtaaat gcaaccaagg attttctgct ctgtccctgg gaacttaaaa gtattttcta     60

accagtacat tctgggctga acttggcatc cccaaagcat cctttgagac tggtagcctc    120
```

caaggggccc attctagaag actgaaggtg gtcaggggac gggagaccga gaggccctta 180
gggattagtt gtcagttgtc tcaattctct ttttattaga ttaaagggaa aactggggtc 240
tacaaagggg taaagatttg ctatggatca ccctgatcat tcatgtctgc actgggattk 300
aaacccagtt ctcccaactc ccagagcagg attctctaca ctacttctgc tgtgtctgcc 360
agttcttttg gacagcaaag aggaaatagt cttcaaaaac aatagctaaa cccttcattt 420
gctgaacttt agaaatctgt ttattccttg ggtctttttc ctatctgaca gcctgtggga 480
aagtgcccca gaatgtttaa cattatgagt tggaaggctt cgttcatgaa atcactccta 540
aagtcaaaat ttctttaaca tcagggcact tgttgaattc taacatgggg gaatggaaa 599

<210> SEQ ID NO 362
<211> LENGTH: 599
<212> TYPE: DNA
<213> ORGANISM: Homo sapiens

<400> SEQUENCE: 362
tgctctgtgc cttcacgccc tctgctcctt ttctctgtct ggcttgaggt ttcccaacct 60
tgttctctca ataagtcctt tccttccact ttgctgcagg tgtcttctcc tccaggaagg 120
cttctagctc acccctcctc ctataactga caatgttaag gatccgggct ctgagctcct 180
aagcaacctg tgtttgccct gctcaccaca ccaattccca ggagtggagc tatttgctgc 240
cagtcttggc tcagggtggc ctgatttatc tctgagtgtc taagggctca acacgtgtay 300
gtagatgact ggaagagaag ggtggtgagg atgtagagga gagacacaga tttagtttgg 360
tacggggtgt gaggcagggg tctaattaca gttgttacca aatatccaga tgtcccaaca 420
ccataagttg aattccccat catttttcca ctaatatgct aatgtcctaa tctcttgccc 480
acatttccag gccattctcc ttctttagat cgaagtatca ccacttctta gttggatctt 540
taggagatga ggcgagataa tctctggcat cttagttaac tctgaaatcc cagggtccc 599

<210> SEQ ID NO 363
<211> LENGTH: 599
<212> TYPE: DNA
<213> ORGANISM: Homo sapiens

<400> SEQUENCE: 363
gactggtcaa ggtagcaaga ccccatctct ataaaaaaat aaaataataa taataattgt 60
tttaatgggg gagtgaacaa ggtagggtgg gaacaccggg aggaggggat tgccacagag 120
cagtcaggga ggttgtcctg gaggaggcag agcttgcgtg ggggctcaca gaggatcacc 180
ttttgccagg tgaagctggg ggctagtgga atgaagcatg ttgcaactcc ctaagtctag 240
gattctctag ttgtgcactt gaggtgaaga tgaggctctt cctgttggct ggagtctcar 300
cagaggctct agaagctgag gggcccaagc acctcacatc ctccatgggg agttagacca 360
tcttgcagca caagcagagg gtgccctccc aggcctgccc caccaagccc acccaacacc 420
cacccatgtt aaagcctttt tttggagaaa attgttattt tgctctgagc ttccctccct 480
tctttaaacc aagtgcggag ggcttcaaga cgttggggga catgggaacc tgaattgtcc 540
tcacatatca cagagtctaa aggcagtgtg tggtggtgga atggggagag ccagggcca 599

<210> SEQ ID NO 364
<211> LENGTH: 599
<212> TYPE: DNA
<213> ORGANISM: Homo sapiens

<400> SEQUENCE: 364
aacagaaatg acggagggag aagtgggttg cacaacagag cagttagagc acagactctg 60
gagccacatg gcctaggttc gaatcctgac actaccaagt gctagctctg ttgttactca 120
gtgcctcagt ttccttatct gtagagtggg gataatccca gtacttactt tgtaggatat 180
ttataaggat taagtgagtt aatttttgta aggcacctag ggtagtgttg atgacacacg 240
taagttccta gtgagtgtta ggtaaatgag ggggagccgg agaggccatg ataggtgggk 300
ttcatgtttg gaatttatct ggaggacatt ggagcattag caaggaggga gtgtgaaggg 360
gagtgggaag cttggcttgg acccagcctg ctctgcccac tcacgcacat ccagagggca 420
tccctgggac ccccacctgc ctgcccctcc tgctctctgg tcttccactg ccctcagtgg 480
ccctgtggcc tcaactaacc tcagctgatg tataacaggg ctgtaggagc tggggccaca 540
cctaccccag tacacctggg ggaaacttta tgttccagtt tattgccaaa ggaggtcaa 599

<210> SEQ ID NO 365
<211> LENGTH: 599
<212> TYPE: DNA
<213> ORGANISM: Homo sapiens

<400> SEQUENCE: 365
aagccttgaa cttggatgac actgtcaagg aaacggtgct tgagggagaa gaaagaggac 60
caaggactga gctctggagc tcccatatca gggcaggagg atcctctagg gaggtgggag 120
gaagagcaca gttgtgtggt attctggaag gcaggtgacg aaagtgaaac caaggagggg 180
ccgttggcag gttccctgct gctgctactg gtaagggaga gcaggattga ggactggcta 240
ctggatttag caatgtggag gtcttggtga ccttgaagag tttcagtgga gtgataaacr 300
tgggatgctg gttcaagtga gcttgagaga gaacaggagg aaggaactgg agacaaagat 360
aaggaccact cttttttttt tttgagacag ggtcttgctg tcccccagat tggagtgcag 420
cagcgcaatc gcaatcatgg ctcactgcag cctcaatctc ctaggctcag gtgattttcc 480
cacctcaggc ccccaggtag ttgggatcac aggcacatgc caccacgccc agctaatttt 540
ttaaaaatta tttttagaga tgggggtctc accatgttgc ccaggctggt ctcgaactc 599

<210> SEQ ID NO 366
<211> LENGTH: 599
<212> TYPE: DNA
<213> ORGANISM: Homo sapiens

<400> SEQUENCE: 366
taggcagctt gtgttaacca gctcaattag accctctacc ttgttgcgag gacagaggac 60
tttctgtatc ccgggttctt gccttggtgt tctgaagaat cggatcacac ctgagctcag 120
agaatgagtg caaggtttta tggagtggag gtagctctca gcagatgggg gagccagaag 180
ggacggagtg ggaaggtttt cccctggagt tgaccgctca gtggcctggg ctcttttccg 240
actgccccag ccaaactcca ccaggttccc ccggttgatg gcctgccggc ctgctggcty 300
tgtgggtgtg ctccttctgc cggcatgctc caacgtcctc ttgacaccca gctgctcgtg 360
tcttcttctg ctgatgtgtt ctcctcaaca tccagccact tgtgtctctg cctgctaggg 420
tttcggggtt tttataggca cagtatgggg ggcgtagcag gccagggtgg tcttgggaaa 480
tgcaacattt gggtgtgaag tcaggagtgc ctatcctcac ctaggtctat aggcacaggc 540
cctggggtgg agccctagcc aggggccact cccacctcta cccagcactt ccccgccca 599

<210> SEQ ID NO 367

<211> LENGTH: 599
<212> TYPE: DNA
<213> ORGANISM: Homo sapiens

<400> SEQUENCE: 367

```
caggtgacct cgcctgacca caaatgtgag gaacccgagg cctacagagg aagagtccag    60
ccagtccaca aacacccact gggcaccagc caggtgctgg ggacactggg atgaatgtga   120
ccagctctga gaggctcct catcaggtaa gcacccactt ggctggagct cagaccctca    180
aaatctgccc cagaaacttc tccagccccg tctgacctcc ttttcctccc tctgctccca   240
catccacagg ctccttacag ggtcctcatg acacagtgtc atgtgctgcc tcctttcacm   300
tctgctccag ctgttggaag aatgcccttc ccagccacct ggagcccatc cacccccact   360
cccccatctc ttcttcgcag agcctcactt aagtgccccc caaccccaag ctgagactga   420
tggaccccag gaggaagctc gctcccttct cccctcccc cctcctcctc ctccgggcct    480
ccccatgctc ttgacctccc ttgcaacatc tgtgcactct gcccagggta atgggtcctg   540
gaattgcctc actctctgcc cctcaggacc tgggactaag aaggtacagc tccgctgaa    599
```

<210> SEQ ID NO 368
<211> LENGTH: 599
<212> TYPE: DNA
<213> ORGANISM: Homo sapiens

<400> SEQUENCE: 368

```
atccctgagc accgtctatg gaaacacaga gtgggtgggc taggaagaaa agccaaattc    60
aactcaggtg gggatgggcc acagtggctt tgatgtcctc tatgggcatt tggtgcctcc   120
atggccttga actaacctct gcccttaagc cttgtcccac ctcctactcg tcactgatgc   180
cctccgggct gggtgggtgg gctgggaggg agaactacag caggttacca gggcctctag   240
ggctgggagg gacctggact ggttggagag attgcccaaa gccaagtcat ctgggagaas   300
aatgggggcg ggagctctgt gggattttgc ctctagaagc tgacagagaa agacctgggg   360
ctagagaagc agtggagcac agtggggctc tcagaaggca ctgcccttg ctgaccacac    420
agcctgggat tcccccttct gcacacccct ttctcacagc tgtcacttgc tggtgccagg   480
tcctgggcaa tcagcacctt acatgagtct gttgactcag gagggagagg tatgaattct   540
ccagcatctt tgcccctgga gggtcagccc tagggtatga cttacagtgt ccctctgga    599
```

<210> SEQ ID NO 369
<211> LENGTH: 599
<212> TYPE: DNA
<213> ORGANISM: Homo sapiens

<400> SEQUENCE: 369

```
cagcctccag gacacgagct caccctactc tactccactg gctcctggga aggggcttct    60
ccttccagat gctgcctagt ccttctgtgg actcaaaatt cttccttcca agacatggag   120
cctgacaacg gaaggctggg ttgagggagt ctggcaatac tgggtttgaa tcccagactg   180
gccacgactg agtgaccttg gggaagacat ttaccttctc tgtgccccag cttcctgctc   240
tgtaaaatgg ggacagtatc ggcatgctgc ccagaccact aaaacctccc atgcacggcr   300
tctggtgagg ctgaccttcc aggcagggga gttactgccc tccccgacg cccccccccc     360
gggaggtgga gctgaaatct gcctcctcca ctgctcccct gcagctggtt ctctgatacc   420
acacagaaca aggccagcca aagggtaaga aatattgggg tcaaatgacc acagagtgga   480
gaatacacaa aagagctgga ttttcaccca ggcccttttc ccaccggctg tgtggctgta   540
```

ggccaatcgc tcaggacctc tgacctcagc ttcctcctct gttcacagaa tgacatcac 599

<210> SEQ ID NO 370
<211> LENGTH: 599
<212> TYPE: DNA
<213> ORGANISM: Homo sapiens

<400> SEQUENCE: 370
ctgctgcccc tccagccttg gccccagacc cctgcctcag attggtgacc cagaccctag 60
ccttgcaggg cacattctgt tctggttctc agtcagctca aaaccagcct cagcccactt 120
cctccactct gggccctgtg ctggctgcag ccaagatcat cacttcctga ctccatgcct 180
atgactggct ggccttgggc ccaccaagga gatgagactt ctgggagata cgccttcccc 240
agcatctgcc ctgatggcca aggggcttcc tgcctgggag ctcagccatc cttcttctcr 300
ccttagcctc agctgtctcc ccaccccatt cacaccagtg gctgctggac ctccattgcc 360
caggtccaga tccagaacaa agtgtggagc acggtagagt ggtcacggga ttctgaagcc 420
aagatcacaa cctatctccc atttcagaga tggagaggct gaggcttggg catctggaag 480
gacctgtctc aatggctagt catagctggc actgtgccag tcacgttaca gccctcatca 540
catgtcatgg cccagcggca acttgagagg ggtgtgtctc ccctccagtt caccgttga 599

<210> SEQ ID NO 371
<211> LENGTH: 599
<212> TYPE: DNA
<213> ORGANISM: Homo sapiens

<400> SEQUENCE: 371
tgtgtgagca gcaccaaata aatgctgctt ccctttaagg aagaactcac actctctgcc 60
cagcatctgc tagctggacg ccagacggct tctcccacct gggtcatttc ttctgcgtag 120
gcctgagaag aaaacccaag tccccagata tcccagtcct gctccctccc ctgaacctag 180
ctcgggaccc ttccaggcca acagcacctg cttacacacc actgttcaca gggaaggtgg 240
tgggaactgt gaatctgcaa accccagcta agtcccccta agggaaggcc tccctgccay 300
ctggcacgcc ctccctccag ccatcactca ctggactctt ccatcagctt cttactgagt 360
tgctcgttca cgaagccatc gaggggatgg gcaagaagac tcatgctgat ggagtaccca 420
cctgtgtgcc aggcctggac aggcacccca cttccttcat ctcatttaat aacagttatt 480
atcagcccca atgtacaggg aaaaaacaga ggtgcaaaag ttgagcaagt tgtccatggg 540
gcagcttgca ctgcctcccc tggcccggag ggtgtggctc tgtgccaggc acactgcta 599

<210> SEQ ID NO 372
<211> LENGTH: 599
<212> TYPE: DNA
<213> ORGANISM: Homo sapiens

<400> SEQUENCE: 372
gaacagaaag aaagatggtg ctgtccttcc tatctgctgg gcccagggac cagataccgc 60
cccttccctg gctgcaaccc aggggtctcg gcctctgagg aaggctggga gcacatgtca 120
agaacacccc ccacacccaa cttgtctgtc ctgtttacag tctgggtcta acatgacctg 180
cccacataca ggagcctctc tgtgtcctgc atccctgggt ggctggtggg catagggctt 240
gaggggcaga aaaagacagt cactccacat cccttccact tccctgttca tgccaggags 300
tgtcagtcgg gatgaccaag atcttcaatg tggacactgc tttatttcag cagggcctca 360
ggtaccccct ctgggaggcc tgcagcctgt cacagcatgc tgagccaaag ccacctgccc 420
agggtaggtg ctggagggac aaggctaggt tgtgcccagc acccccttcgc ctggaattct 480 gggggtccct ctcagtgccc ttgttcctga gcagctccag atggtcctgg ccctatgtgg 540
ggggagtagg ggcagacagc tggtgaggct ggcacccaga ggcatcacag atcctccct 599

<210> SEQ ID NO 373
<211> LENGTH: 599
<212> TYPE: DNA
<213> ORGANISM: Homo sapiens

<400> SEQUENCE: 373
ccagtgttcc tggggggagt gtcttctggg aagagcccaa acaaacaaag cgtccctgag 60
aggaacaaac agatcgatga aaacgtcttt gtctggaaag gagagaacgg atgatggcaa 120
ccttttattg agtgcctact gtgtgccaag cccttggctc agcattttgt gctcttgcca 180
tatctgaccc tcccaagggg ctctgggaag ggtccttatc cccatgatgc agatgaggac 240
acagaggccc agctggtact tggcggagct gatattggaa ccaaggactg ccccgccccr 300
ttccttctga gggagaaact aggggttcct gagagccagg ggaaagaggc aagagtcaga 360
attcttggag agaaacctag gcatggagga ttttgtctct ctgactgcag tgattcatgc 420
tttaccttat gttagagtct tttccacttt tggcagcatg gaataggaga aacggttctg 480
gactgaggga ggaattatgg ccctatcaca aatatagtag gtgcaggcac atgttggtta 540
agtttgaatt aaaccaaatc cacttgggtc tcagatttcc cttctgtgaa gtgagtaaa 599

<210> SEQ ID NO 374
<211> LENGTH: 599
<212> TYPE: DNA
<213> ORGANISM: Homo sapiens

<400> SEQUENCE: 374
accccactca cacccccagg cctgtgcctt ctcatctgtt ccacaccaaa cagtcttgtc 60
tggggtgccc tgattactta ttcaatcaac aaacctgtcc tgctacctgc tctggggtca 120
taagtatatc agacctggtt ttcccctccc ttgaagggcc ggcccccagg cttgtggggg 180
aacagacaag atcagacaca cctggaccac ccaggtcgat cattttggag gcctggggaa 240
accctggggg cagggaaggc ttgcccgagc tggcctctgg gagtatcggc cccatctccr 300
cagaccaggg aagtgttcag ggtaggggga actgtgtgca caagagagtg tcttgtgttc 360
aggaactgaa aggaattcag tccaccggct caggtgcagg gacggggaag ggtgctgctc 420
agtgggcctg agcctgaagc tgtattaagg agtctaggct tcatcctggg cagcgggggc 480
ctgagccagg ctcgggctgt gtgaggaaca ctgtggtcaa attgtggagg atgctgaggg 540
ccctcaggtg gaggtgggag ggccagtgag gcctcaggtg tctatgtggg gagtgagga 599

<210> SEQ ID NO 375
<211> LENGTH: 599
<212> TYPE: DNA
<213> ORGANISM: Homo sapiens

<400> SEQUENCE: 375
actggctgga ctcttcctct gtaggcctcg ggttcctcac atttgtggtc aggcgaggtc 60
acctggcacc tcccttccta ctctgaagag ctctcaggag ttctggatgc ttgtgcaggg 120
gaaggcctca ccactctccc tgtctcctgc ctcagggttc tctgggttgc cccagcaggg 180
ctggggccat ggtgccctga gtgggggaca gccctcccgc tgccagggaa ctttgcccct 240
cgtgctttct cccttcagca gttggccccc tgagcccaga aggacattcc ttggtgtccy 300
gtgactggga gtggcagtgg cattgagcgc atgctgcagc ttagcacggg gagggagctc 360
tgcttccatc tatgtgaaaa tgggcagcca ggtgtggtag ctcatgccta taatcccaac 420
actttgggag gccgaggcgg gcagatcact tgaggtcagg agttcgagac cagcctggcc 480
aacatggtga aaccctgtct ctactaaaaa tacaaaaatt agccgggctt ggtggtgcgt 540
gcctgtaatc ccagctcctc gggaggctga ggcaggagaa tcgctggaac ccaggaggc 599

<210> SEQ ID NO 376
<211> LENGTH: 599
<212> TYPE: DNA
<213> ORGANISM: Homo sapiens

<400> SEQUENCE: 376
gggtctgatc tgaccctggg tccccaacac cgaggccaag tgcagcatga ggggtcccaa 60
agaggtttct caaatctggg aacttgtatt tctgctgagt ttgccacatt ggtgaggtct 120
ggatcttccc tcagaccaca ggcccccagg ggcaagggct ataccctggc tcggcccctc 180
ctcgcactta gccccttca gagcacccta acctgactgc catttatgac aagataacca 240
tgggggccct gagagagcct aagaggccca cctcatactt gtgcaaacac atgcgaacay 300
acagagacat ccaaaaagac atagggcaca tattcacgga cagacacagg tgacatgagt 360
gggcacactg gcgcaagcat acaggctccc agaagtacat ggagccatac aaagacaggt 420
ccacagggac acaaacatcc tggaaacagg gactcgggcc atggcctcgc tcagagtcac 480
ctgctccagg ggtgaagcct ttggctgggc cagggctcca ggctggtgct cggggctcca 540
gagcaggggc tcagggagac gtggcaacag ccacctgaac agtctggcct gttccattt 599

<210> SEQ ID NO 377
<211> LENGTH: 599
<212> TYPE: DNA
<213> ORGANISM: Homo sapiens

<400> SEQUENCE: 377
attggtgagg tctggatctt ccctcagacc acaggccccc aggggcaagg gctataccct 60
ggctcggccc ctcctcgcac ttagcccctt tcagagcacc ctaacctgac tgccatttat 120
gacaagataa ccatgggggc cctgagagag cctaagaggc ccacctcata cttgtgcaaa 180
cacatgcgaa cacacagaga catccaaaaa gacatagggc acatattcac ggacagacac 240
aggtgacatg agtgggcaca ctggcgcaag catacaggct cccagaagta catggagccr 300
tacaaagaca ggtccacagg gacacaaaca tcctggaaac agggactcgg gccatggcct 360
cgctcagagt cacctgctcc aggggtgaag cctttggctg ggccagggct ccaggctggt 420
gctcggggct ccagagcagg ggctcaggga gacgtggcaa cagccacctg aacagtctgg 480
cctgttccat ttggactctg aggctgtgat cagagtgggg aggggtgctg ggagaggaga 540
gggtgagaga gcaggagccg ctctccacag acagggctgg gggcagagga ggaggccac 599

<210> SEQ ID NO 378
<211> LENGTH: 599
<212> TYPE: DNA
<213> ORGANISM: Homo sapiens

<400> SEQUENCE: 378
ctctccagct ccaatattct gagattcacc acatgctcag ctgccctcat ggatgggtgc 60
aggtgagctg tgggtcctat agccatgggc aaaagggacc tgtccctaga gggaaagcgg 120
aaaacgagaa tgaatcccac ctactactca ctgcaagtct gctgtacgcc aagcatttca 180
acatgaacaa tttctactcc ttgcagcaat cccactgggc acggtggcag gtgaggaggg 240
ccttagattc agctaaagga ggctaaaagc cagggtccaa cccaggccca tccaacttcm 300
aaactcccta ctcttgtgac aagagccaag aagtggaaca acccaagggt ccatcgacag 360
gtgaacggac agacagaatg tggtctagcc acacaatgga gcagcactcc gcctgaacaa 420
agaaggggat ccagccacat gctgcagcat ggatgaacca tgaggacact atgctaagtg 480
aaataagcca aatattgtac acttccactt atatatggta tctaaaatag tcaaactcag 540
aaacagaaag tggaatggtg ggtgccaggg gccagagaaa gagggagaaa tggggagta 599

<210> SEQ ID NO 379
<211> LENGTH: 599
<212> TYPE: DNA
<213> ORGANISM: Homo sapiens

<400> SEQUENCE: 379
gaatccccac ccccagccgg ctcctgacag cctaagaggc tggatttatt tttctggact 60
acagagagct gggcaatcag gcctctgtcc ttgcttctgc tggggtgcat tgcactcaga 120
gtggttcatt aggcaggaga atgcaattaa gtcctgcctg gggcaccctg tctctcccag 180
cctatccctt ggctggcatc agccccttgg ggagacatga gcagaagggc tgagggggccc 240 ttaggaagaa ccatcccaga tccctacata ggaccctgac cacgtcacag ggtgggtggy 300
gatagtcccc tggtaatgcc ccatctcctg ccccaccctt gctcaaggtg ttcatagagt 360
gtcatcaaca agacttagcc acttcccctg gagcgtgacg tggtcatgcc aggtgccctt 420
ggtgctattc caagaggagc taggcagggt gtgggggttt cctaaggcaa gagacagcat 480
ggctttattg cagcgataaa tccccacctc ctcatgctgc aacaaaccag cccctcctct 540
ctctctcttg tggatgtaat aatatcatct cctagtttct tatccttata ggaatcctg 599

<210> SEQ ID NO 380
<211> LENGTH: 599
<212> TYPE: DNA
<213> ORGANISM: Homo sapiens

<400> SEQUENCE: 380
gggcagtgag gcaggggaag ggtgaggagt caggcaccac acagcaagtc attgtagcct 60
aggtcaggga gggtcacccc tgctcaaagc actgcagtgg ggctccgtct cacttggagt 120
cacaggccca cccctgcagg tccccaagga cctgtcctct gcctcccacc caggccctca 180
tcctccctac tccttcccct ccagccactc ctgacctctt ccatgttctt cactggccta 240
gcatgctgct gttccctctg cctggaatgc tcttccctta gaaacctgca tggcttccty 300
ctctttcccc tcctctcttc aggtcttagc tcaaatgtcc ttttctttttc tttttgagac 360 agagtcttgc tctgtcaccc aggctggagt gctgtggcac aatctcggct cactgcaacc 420
tctgcctcct gggttcaagc aattctcttg cctcagcctc ccaagtagct gggattacag 480
gtgcccacca catctggcta attttcgtat ttttgtagag ctggggtttt gccatgtagg 540
ccaggctggt ctcgaactcc tgacatcagg ttatccacct gcctcagcct cccaaagtg 599

<210> SEQ ID NO 381
<211> LENGTH: 599
<212> TYPE: DNA
<213> ORGANISM: Homo sapiens

<400> SEQUENCE: 381
tttgtgaagt tggcatgacg tcttcaagat tcatgttgtt gcctcaattc ctttttatta 60
cagacctgag cacttccatg tattacctca tttagtcctc attccctgat gggtaaagta 120
aggctcaggg aagaggtagt gacctgtcca aggtcacata gcaattcagt tgagggtgac 180
caggctagaa tccaggcact tcatgatcag aaaaggagct gagagcagtg cagtgcagtc 240
tggggggcac agcgtgggcc tggcagttat gggagggaga aagggtaggg gagcaggccr 300
gtgcgtcccg ggatgtgagg atgagacagg acgccggagg tgcacgccca tcccagcatc 360
ctgcctctgc tccatagtgc gtgtttattc catctcagtc atggactctt gcttttccct 420
gtgcaagcag gaggctgtgc aagtacaggg taggggccag gaattctgac agaaaatagg 480
actttgggct ggggaggggc cttggacatc aggctcagag gtgagagcgt tctcttgtcc 540
cagagccagc agtagctctt ggcaggggat ttcttgggaa cttggctggt atcagcagc 599

<210> SEQ ID NO 382
<211> LENGTH: 599
<212> TYPE: DNA
<213> ORGANISM: Homo sapiens

<400> SEQUENCE: 382
gcagtgagct atgattgtgc cactacactc cagcctgggc gacagagtga gactgtgtct 60
ctaaaaaaaa aaaaaaaatg aaaacccagg caggctgacc tcttcacaaa ccctgtgatt 120
tactgcctct caagagccca gcattaaact aagtttcctt aacctccaat ctgagggttg 180
aatgggcttc cacctccaga gaagatttat attttaaaag agaatcctag agaaagtgat 240
gcttcctcca aaggaatgaa tgacaaatag tggatttgga ggccttatat catggaattr 300
gcatgaacct tcaaggtggg ccagccagct cctgggactt tcttcctcag cattcgagca 360
agctcggttt tcattggtca ccaaggtgaa acctcgacat ttgaaggaag ggaggaaaag 420
tttaggcccc aggttctcgg acctgcctgg aagcagagac tgctgttctt tgcagaagac 480
tgtgaagagt agtgatgttc atgacagtga tgaaattagt atcctgtgcc agatttgagg 540
tcatcttaca ctagatatgg tacagaaatg tgcaaatgga tatcagaggt ttaagaaaa 599

<210> SEQ ID NO 383
<211> LENGTH: 599
<212> TYPE: DNA
<213> ORGANISM: Homo sapiens

<400> SEQUENCE: 383
gtacagtgag ttggtggcag ccggggatct ctccattcaa gccatcaaat gaggctatgc 60
aatggaaaat agactgagtc ttgagcaccc cggaaaagct acctgcagga ggctggggcc 120
ggagagcaca gggcagggcc ggggataggt gggttccaca tttcactggc tgggcttttt 180
ccagaatctt tcctgtctcc cccacctgca gccctcaccc tggggccaga gatttgtttt 240
gtgggtttgg gtttagttgt tttgttttgg gaaacggtcc acttggtgag ctgtttgggr 300
tgccctctgc cctgggagaa gccccaatca ctgccctccc tgccacctag gcttccgctg 360
tgctgtctcc ttacctaaaa tgcccttcct tctccccttt gtgctgcaaa tcttttctca 420
tttctgaatt ctgcatagat ctcaccatct cctggaagcc cctacacagt ggtcaggaaa 480
cacagatttg tgggatccag aagagatagt gacccagtca ggaagggctt cctggaggag 540
gggctacctg agctgagatg agcaggagtt tgccaggcat tgaggatagg tggaggggc 599

<210> SEQ ID NO 384
<211> LENGTH: 599
<212> TYPE: DNA
<213> ORGANISM: Homo sapiens

<400> SEQUENCE: 384
actattattt cagattttga aatggaggtt ctgagaagtg aacacactca gcaaggcggc 60
agagccagaa ttcaagctca aacctacaag tggcacaaaa tgtcacagcc atcaagcccc 120
tccccccatt agacagacat ggatattgag gtccagagag gggcagaaaa ctgaaatgac 180
caccagaaag ttggtgtgag aaatacaagt ccatgactcc atcccagtgc tccttccacc 240
acaccttact gcctgtcagg aaggaaagta ccgcagagtc tccccagggc tgtcagctcy 300
gctgtcagcc ttacctgggc ccatggctgc cctggaaact acctgtgggg ttgtctggac 360
gcggaggccg cccccatccc cactctgccc tctctccatc ctgcccaata ggctgggtga 420
ggcagaatgg tctcacatcc tcctgccatt cccctcctcc tacctccagc ctgtgcccac 480
tgccctgtgt caggtcaccc agctggggtc tcaggtagag ggtgacacgc ccgggtctgg 540
ctccaccccc accttgcctt cccagcacgg ggccaatggg agcctgtgag tcacctgaa 599

<210> SEQ ID NO 385
<211> LENGTH: 599
<212> TYPE: DNA
<213> ORGANISM: Homo sapiens

<400> SEQUENCE: 385
cattctgcct cacccagcct attgggcagg atggagagag ggcagagtgg ggatgggggc 60
ggcctccgcg tccagacaac ccccacaggta gtttccaggg cagccatggg cccaggtaag 120
gctgacagca gagctgacag ccctggggag actctgcggt actttccttc ctgacaggca 180
gtaaggtgtg gtggaaggag cactgggatg gagtcatgga cttgtatttc tcacaccaac 240
tttctggtgg tcatttcagt tttctgcccc tctctggacc tcaatatcca tgtctgtctr 300
atggggggag gggcttgatg gctgtgacat tttgtgccac ttgtaggttt gagcttgaat 360
tctggctctg ccgccttgct gagtgtgttc acttctcaga acctccattt caaaatctga 420
aataatagtc actttaagtg ttttacatat ggtaactaat ttaatcccca cattgaccct 480
atggggtagg ttttattagt agtagtattt tatacctaag gagattgagg cacagaaagg 540
ttaagtaatt tgcccaaggt cacacagtaa gagccaagat tctaacttgt gtagttcga 599

<210> SEQ ID NO 386
<211> LENGTH: 599
<212> TYPE: DNA
<213> ORGANISM: Homo sapiens

<400> SEQUENCE: 386
acctgtttcc tgaaccactc ctgcccctcc aggacccacg gatccaggat ccaaagccca 60
gccaccctgg gggcagaggc cctttcacgc tgcccagggt cctgcttctc tgaggtagct 120
gccaaaccag cttgttcttc taaagcagcc gctaagggaa ggacggtagc ccggaggtgg 180
gatctggggc accacaatta catgcctgag ctctgactca cgcaccacct cccccattgc 240
cagctcctgc agccagcagg gcaacccccc acccaggaat tgggaaaaga gatggtaccr 300
acaggccacg ggaagcagag gggccaggag aggtgaggag gagactgcag accagcattg 360
caggcttcag aggatgctga caccttgtct actagggaca ctgaggctgc aaggacggag 420
gcctacctac atcacataga ggcagagcca gggctgggac ctgagcctcc tggtgccaat 480
ataacaactc tccccaaccc aactggattc tagagccaca caccagcaag aaacacataa 540
ccaaacacac acctctgtgt gtgaaccaga ggtggacaga gctggactca gagacagct 599

<210> SEQ ID NO 387
<211> LENGTH: 599
<212> TYPE: DNA
<213> ORGANISM: Homo sapiens

<400> SEQUENCE: 387
cactcccctc tccctgggac ttaggaagag ccatcagaaa aagccaggct ggcccctgca 60
gctgaaccac tgggctcctg gaaggggctt gcacaagtca aactgagggt gggggatgct 120
gaaagtctct actacccca aatagtagtc ccggggcctt cactggctct gcctgctccc 180
cagagaacct gtcagtgtca ctgggggaga agggggtggg ggcaggatct cttcttagga 240
tggccttaat acagtcctgg tggcttggag aaaactactc agccctccag ggaggggagr 300
ggcctgtcac taggagtatg tgagtctagg gaagccactg accggtctgg agaggctgga 360
gaaccaccag taagagcagc acaggggatt tctgaatgga aggggaggct ggatggagtg 420
cctccaggac tttggtgctg atgttttgtg acttagcagt ctgaaatcca gggataattt 480
gaagatacca gttgaattat tcaatgagga ttccatgaca ctgtgagtct tgggtgaagt 540
gattctagag gtccaatttg gggcatttgg agcctgagat tttgagttct gagatgcta 599

<210> SEQ ID NO 388
<211> LENGTH: 599
<212> TYPE: DNA
<213> ORGANISM: Homo sapiens

<400> SEQUENCE: 388
ccaggagttg gaggttgcag tgagctgtga ttgcaccact gtactcctgc ctgggtgaca 60
gagggagact gtctcaaaaa aaaaaattaaa aaaataaata aaagtgggaa ggagacatcc 120
agagaaaagt ttgggggcag gagggtggca tatgggcaga cattttcgga acttcaccgt 180
cctgtgtgga aggtggcata gaaggggtga gaacagaggc agcaagatag tgaggagaca 240
ggagccacaa tcggagaagg atgaaggttt gacccacctg ggaagggaac ccccagcacr 300
tggcagaggg aggagctgag aatccttaga ggcacatctc taaggtgcca gaggtcccac 360
tccgcctgcc tttgagctcc ggatcctgaa tgcccccagg gaggctttgt aaagatcctt 420
cctaggactg gctacatttt gcaggaccca ttgccaaatg aaaatgcagg gctcctagta 480
aaaaagatta ctaagaattt caagatggcg acagcagagt actgaaataa gaacagggtt 540
ctttgcacag ggctgctgat acagaaagag aacataggac atccagttaa agttgaatt 599

<210> SEQ ID NO 389
<211> LENGTH: 599
<212> TYPE: DNA
<213> ORGANISM: Homo sapiens

<400> SEQUENCE: 389
aaggaattta agagatgctc taggccagcc gctgtcacat tttacagatg agaaaactga 60
ggttggccag aggaagtgac ttgcccaaag ccacccagca tgtaaaccaa tatgcaaacc 120
caggttctga cacccaagtc tgcgctcttc tgaatcattg ctgactcaga gtcacagtgg 180
ggctagaggg cagtgggagg agagtggcaa ggtatgactt caggacgcgg ctcaggtgtc 240
acttcctcac agaagccctg cctggaccca agctcttctc tgggctcccc gaggcctctr 300
tccactcatt taccagtcag ttctgtgaat gtcagcttgt gtgtctgctt ccatgaggcc 360
atgtccccag cacccagcat gggacccgga acatcgtgct acatgtgaag gtacacgcct 420
ctggtttcta ctgccctctc tggcagctca accctccagg acagaagagc aatcggttcc 480
gctattcgtt gcttccttcc tttcttcctg ctttaaataa atgtatactg agtgattact 540
tcatacagtc ctggggacac agcggtgaaa aattttgcct tcatgaaatt tactttcta 599

<210> SEQ ID NO 390
<211> LENGTH: 599
<212> TYPE: DNA
<213> ORGANISM: Homo sapiens

<400> SEQUENCE: 390
aatcctgtat tgtacctggc aactccacca ggtgggtcct gtttcctccc ttaactggag 60
ctcctgggag tggttcaggc ttagggttct tccaggataa tggttttcaa acttcagcct 120
gcatcagaaa catctggagg gcttggtaaa atccagattg cttcccccca gccagagttt 180
ctgattcatg cctagagtac agcccaagaa ttttcatttc tgacaggtac caaggtgatg 240
ctgatacaat tggtcctggg accacactct gagaaccact gctggggtac atcaccctar 300 gaagccccctc aaagagatag aaaatcatag tgacccaaaa cggacaccag agggcagaag 360
cgcccactgg tcaggctata ggacctgccc actggcctgg ggctgggctt acacctttgc 420
tgaacatttg ttctgtgcct gaccacgtcc agggccctgg agcagacaaa gaaagacgtg 480
ggtcagcatt agtctctgcc ctgaggggct cagggtgtgg aaagggagac agatgtacga 540
agtgagaatt acaattggtg ctgagatggg ggaagcacag gctgtgggag cccaggga 599

<210> SEQ ID NO 391
<211> LENGTH: 599
<212> TYPE: DNA
<213> ORGANISM: Homo sapiens

<400> SEQUENCE: 391
ccaggtttaa cgtacaatcc actgcagagg cctggggcac ctgcaggcgc cgagagaggg 60
tgcccttagg gtggtggtcc cagaggagaa agtggtctaa aaattccaga gccccctcac 120
tgtccaggag gcaggcaggg agtggctagg ttggggaggt gaatgtcagg aaaacaagtt 180
tgttcactcc tgggtattac tgctgcctgt ggtgggtcca gcactgtgcc aggctggggg 240
tgaggccggg agacaacttt gatccaccat caaggcctcc accccttacg cgtcctgccr 300
cctttgttca catgatgcgc ttggtgtgtt tgtctacacc tttagctcat gggctcctcc 360
agcaggggct gcgtctgtct gctgggcaca caggagagct caggaaatgt gcgttggtga 420
ctagattttt ggtgtctaga ctggcttggt agtaagagta tgaattcaag agaccctaaa 480
ccctctcgag ctctgtttac catctataaa aaatatctac tgcagccgga catggtggct 540
catgcctgta atcctagcac tttgggaggc caaggtgggg agatcactta agctcagga 599

<210> SEQ ID NO 392
<211> LENGTH: 599
<212> TYPE: DNA
<213> ORGANISM: Homo sapiens

<400> SEQUENCE: 392
gcctcccaaa gtgctgggat tacaggtgtg agccaccatg cctggccagg gacattttca 60
ccagcccaaa aagaaactcc acacctatta gcagtcactc cgcctttcct ccccaatcct 120
cccagcccct ggcattcact gagctacttt ctgtctcagt atttgcccat tctggtcatt 180
tcttatacat ggaatcatac aatatgtggc cttttgtgaa gttggcatga cgtcttcaag 240
attcatgttg ttgcctcaat tcctttttat tacagacctg agcacttcca tgtattaccy 300
catttagtcc tcattccctg atgggtaaag taaggctcag ggaagaggta gtgacctgtc 360
caaggtcaca tagcaattca gttgagggtg accaggctag aatccaggca cttcatgatc 420
agaaaaggag ctgagagcag tgcagtgcag tctggggggc acagcgtggg cctggcagtt 480
atgggaggga gaaagggtag gggagcaggc cagtgcgtcc cgggatgtga ggatgagaca 540
ggacgccgga ggtgcacgcc catcccagca tcctgcctct gctccatagt gcgtgttta 599

<210> SEQ ID NO 393
<211> LENGTH: 599
<212> TYPE: DNA
<213> ORGANISM: Homo sapiens

<400> SEQUENCE: 393
ggaattgaca gtgagacctg aggcctgtgg gaggggaccc aaagagggag gggatgcaat 60
agggaggggg ccaggggtga caaggattga ggaagggaga gaggggggaa aaaaagcaag 120
ggatgcctta gaaccacatt tcacagccaa gggaacagag gcccagaaag ggaaagtaac 180
ctgcttaggg tcacacagca ccttgctcag tggagagcca ggttttcctt cctgtgcact 240
cctccaagcc cagccagacc acctgaagtt ccccaggcat ctctgcctct attactccas 300
gacttgaact ttccgggtgc cggcaggta ccgggtctgg tctgctccct ctccctctgg 360
ccatcgctga ggttgaggtt ttttgaatgt acaagtatgg agaagggcac tgccttcaga 420
agcctgaacg tctcccctga gagggagggg gtgcacagga ctcaattgtt tcagcttgaa 480
aatgggggag agcggggaga aggggagatg gctctgcttg gggcagagcc cctgcgggga 540
aaggggcgcc tgaaaggacg tgcgattcgg agtgggctag cttatgcaga gagcctggg 599

<210> SEQ ID NO 394
<211> LENGTH: 599
<212> TYPE: DNA
<213> ORGANISM: Homo sapiens

<400> SEQUENCE: 394
tatgcctgta actcccacat ttccggacct ctcccagacc ccagacttgt gtatccaact 60
gtgtgcctga catctttact tggatgccta agacatctga aaatgaacgt gtccaatcct 120
gaattctgat ctgctcccca aaacctaccc ctctcgtctt cctcatgtca gacaagggtg 180
atgtcatcct tctaggtgat caagccaaaa catgggggtc atccttgact catctctttg 240
tctcacaacc tacatttaat tcatcagaaa atcctgtggc tctacctcca aaagacaccm 300
cagaatctga ctacctgtta cacggctcct gcggtcactg tatctgagcc gccatcacct 360
ctcctcagac tgcggcattc cccccctgtc tttaccgtat cccccaggtc taacttagaa 420
gtcaaacaat gacacctctt tacttagaac tctacaatgc cttcccattt caactggagt 480
aaaagtcaaa ttcctactgc aggctctagg ccctctgtga tttaatctct gtgacctcgt 540
aggctcgtct tttacctctc ccaaccccat caatcactgc ctccattcca gccacattg 599

<210> SEQ ID NO 395
<211> LENGTH: 599
<212> TYPE: DNA
<213> ORGANISM: Homo sapiens

<400> SEQUENCE: 395
aagacatctg aaaatgaacg tgtccaatcc tgaattctga tctgctcccc aaaacctacc 60
cctctcgtct tcctcatgtc agacaagggt gatgtcatcc ttctaggtga tcaagccaaa 120
acatgggggt catccttgac tcatctcttt gtctcacaac ctacatttaa ttcatcagaa 180
aatcctgtgg ctctacctcc aaaagacacc acagaatctg actacctgtt acacggctcc 240
tgcggtcact gtatctgagc cgccatcacc tctcctcaga ctgcggcatt cccccccctgy 300 ctttaccgta tcccccaggt ctaacttaga agtcaaacaa tgacacctct ttacttagaa 360
ctctacaatg ccttcccatt tcaactggag taaaagtcaa attcctactg caggctctag 420
gccctctgtg atttaatctc tgtgacctcg taggctcgtc ttttacctct cccaacccca 480
tcaatcactg cctccattcc agccacattg gcctcctagt gtgaacacac caggggcctt 540
cacacctgtc atctgcttca ggcttttact caaacgtcag cttccttgac tcctctaag 599

<210> SEQ ID NO 396
<211> LENGTH: 599
<212> TYPE: DNA
<213> ORGANISM: Homo sapiens

<400> SEQUENCE: 396
agaagagtca ctgtatagag gacctatgtc ccctgcactg ggcctggcac caaggaggta 60
cctatttagt tgtcagtcaa aaagctggtt aaatgtgaga cggaaggaaa aaaagaacca 120
atcaaagcat cttacaccac acaactgcag agccacttct gaaagcctga attctgcctc 180
tgaataataa ttagcctctt cccaatttac agaaaaaaaa attacaaaaa aaagactcaa 240
ttaggtactt ttctctcaca aatttttctt aaacctctga tatccatttg cacatttctr 300
taccatatct agtgtaagat gacctcaaat ctggcacagg atactaattt catcactgtc 360
atgaacatca ctactcttca cagtcttctg caaagaacag cagtctctgc ttccaggcag 420
gtccgagaac ctggggccta aacttttcct cccttccttc aaatgtcgag gtttcacctt 480
ggtgaccaat gaaaaccgag cttgctcgaa tgctgaggaa gaaagtccca ggagctggct 540
ggcccacctt gaaggttcat gctaattcca tgatataagg cctccaaatc cactatttg 599

<210> SEQ ID NO 397
<211> LENGTH: 599
<212> TYPE: DNA
<213> ORGANISM: Homo sapiens

<400> SEQUENCE: 397
cccagcaact tgggaaacca aagcaggggg atggcttaag gccagcagtt tgggaccagc 60
ctgagcaaca taacaagaat tgtctttaca aaaaaaaaaa aagctaccca ggcatggtgg 120
caggcaccag tagccccggc tactgaggag gctgaggcag gaagacagga agatcacttg 180
accctgggag tttgaggctg cagcgagcta tgatcgtgcc actgcactcc agcctcggtt 240
gcagagtgag acctcgtctc ttaaaaaaaa aattaggctc atcaatgcca gcaagaagtw 300
acagcccaaa tcaagtaaga ccttgatttg tctttacaat ggcctcgaaa gacagcagcc 360
cccacgttca ttttgactct ccattgtccc ctgactctct gtatatcctg tgacctcatg 420
ataacagagt ccctgcctgc tggtgaaatg ggaaagcttc ccttgagccc cttgcagggc 480
gtgcgatgcg ggtatgactt gcttcttcag tgcctcgctt ctttaacctc tagagcaggt 540
tgtggggctc cgggcccaca gcagcgtcta ggggtggatg attacagctc ctgaagccc 599

<210> SEQ ID NO 398
<211> LENGTH: 599

<212> TYPE: DNA
<213> ORGANISM: Homo sapiens

<400> SEQUENCE: 398
aaaaaaaagc tacccaggca tggtggcagg caccagtagc cccggctact gaggaggctg 60
aggcaggaag acaggaagat cacttgaccc tgggagtttg aggctgcagc gagctatgat 120
cgtgccactg cactccagcc tcggttgcag agtgagacct cgtctcttaa aaaaaaaatt 180
aggctcatca atgccagcaa gaagtaacag cccaaatcaa gtaagacctt gatttgtctt 240
tacaatggcc tcgaaagaca gcagccccca cgttcatttt gactctccat tgtcccctgw 300
ctctctgtat atcctgtgac ctcatgataa cagagtccct gcctgctggt gaaatgggaa 360
agcttccctt gagccccttg cagggcgtgc gatgcgggta tgacttgctt cttcagtgcc 420
tcgcttcttt aacctctaga gcaggttgtg ggctccgggg cccacagcag cgtctagggg 480
tggatgatta cagctcctga agccccagca ggcatgtgct actgtgtgct tttagttttg 540
ccgtctatag gcagcttgtg ttaaccagct caattagacc ctctaccttg ttgcgagga 599

<210> SEQ ID NO 399
<211> LENGTH: 599
<212> TYPE: DNA
<213> ORGANISM: Homo sapiens

<400> SEQUENCE: 399
aggctgcagc gagctatgat cgtgccactg cactccagcc tcggttgcag agtgagacct 60
cgtctcttaa aaaaaaaatt aggctcatca atgccagcaa gaagtaacag cccaaatcaa 120
gtaagacctt gatttgtctt tacaatggcc tcgaaagaca gcagccccca cgttcatttt 180
gactctccat tgtcccctga ctctctgtat atcctgtgac ctcatgataa cagagtccct 240
gcctgctggt gaaatgggaa agcttccctt gagccccttg cagggcgtgc gatgcgggtr 300
tgacttgctt cttcagtgcc tcgcttcttt aacctctaga gcaggttgtg ggctccgggg 360
cccacagcag cgtctagggg tggatgatta cagctcctga agccccagca ggcatgtgct 420
actgtgtgct tttagttttg ccgtctatag gcagcttgtg ttaaccagct caattagacc 480
ctctaccttg ttgcgaggac agaggacttt ctgtatcccg ggttcttgcc ttggtgttct 540
gaagaatcgg atcacacctg agctcagaga atgagtgcaa ggttttatgg agtggaggt 599

<210> SEQ ID NO 400
<211> LENGTH: 599
<212> TYPE: DNA
<213> ORGANISM: Homo sapiens

<400> SEQUENCE: 400
ccactggact ctctcccctg tgtgtgagcc cgtagtaaaa ccccatggct cattcgctgg 60
ctctgggtct cctctttggc ctcttgagcc tggtgccatc ctcactggca ctgatagggg 120
tttagctcaa cacctagtaa ctaccttgaa ataattttag tgaactggct cacaatcaca 180
gcagagttgg atgacttaag tggggtcaat tatcggtgag gatttgcaca gaggcctcca 240
atgttccctg gacaccctcc cctagattaa aaaaaaaaat cctctgacat tcttcagtty 300
tcccaggtgg gacaggggcc ccaagcaggt ggtgcagttg ggtgtccggg ttggaaaaac 360
aagcagattc agacaaggct tcattgttaa ggagagtctg acactttgac cattaaagca 420
aaactgagca aaacaaaatg cttactgcct tgtcttatct cttagagaga aaggggacag 480
tgggaagggc ccccgggctg ggtgttgatc ccaccctaac cagcgccagt ctcagagacc 540
tggcctcagg tggctggggc agggagttca gggtctcagt ccagcccggc gtcaggtat 599

<210> SEQ ID NO 401
<211> LENGTH: 599
<212> TYPE: DNA
<213> ORGANISM: Homo sapiens

<400> SEQUENCE: 401
ccattgactt tttgctctgt cacacctagg atgttgccgt taccatggtc cagaatggtt 60
cagcatcatg ccctccatcc cagtagcagg atgtgcatga gatagagaat ggtggtggga 120
gagaaagcat cccccatccc ttaaggacat taaccagaag ttatacacat tatttctgtt 180
tatatgatgt tggccagtct gtaaatatat gatcagaaag gctaaaaata tagtcattaa 240
tctgggtggc catataccca gctaaatttc gggatttctg ttatcatgag aaaagaaaay 300
gaatattcgg tgacacagcc ctttctgaag agcccagttg cagagattag gtgcaatagt 360
acagacgtaa gggctgggct tgttgcataa tagagttata ctcttaaaat gcagcataaa 420
tattgtatgt attgaaaagt gccatcagga ccctctttgg ttccagactc taaagtagaa 480
gagaaagggt atcacttcac caaggatcag cacccaaaaa tcttgttctg cccacccaaa 540
acagaatctc cttcaggaag gaactttagt atgtgttttg cttttatgca gtatccagg 599

<210> SEQ ID NO 402
<211> LENGTH: 599
<212> TYPE: DNA
<213> ORGANISM: Homo sapiens

<400> SEQUENCE: 402
gtctggactt catgtgaaat gccatctcaa gaaagggcat ctgaaagcgt gcttttacca 60
tttcatttca ggcacttctg gatccagctg tgtgatagcc gcactaggaa atacctggag 120
tcacagtgtg aatacccggc tgatcctcca gtaccttgat tcagagagaa gacaggtggg 180
tgctttgaca gtattctctg actatgaagg tcggggaatg agatatacca agcaatctga 240
gcgtcttctg aaaatgctgg ccgcattgtc tgtcctgagc cagcagcagc tattagggcm 300
taaagaaacc agcatttctg cttgtcccaa caacagttat aataaagtgg ggagacaagt 360
cacacacagg aaaaaacata agaattgatc ccacagagtc agcatttctc tgatatttgt 420
aagtgaccaa ggaccacacc tctaagggta tccaattctc tatctctaaa tgatcatttc 480
acttagattg tatttgttga ggactaattt gtatatgaat taaataatga tgatgctttt 540
tcttgaagta tgtgtacttt gaaaatctta ggccagcaga tgctgccaag tgaataaat 599

<210> SEQ ID NO 403
<211> LENGTH: 599
<212> TYPE: DNA
<213> ORGANISM: Homo sapiens

<400> SEQUENCE: 403
ttccttctgt gacccttgaa ggccagagct gccttgcctc tgctgcattt tctaatgggc 60
ctggacagga ggacccagct ctgtttctta tgggtcttgt ggatggcgct gggaaatcag 120
gcttgcctaa ctggatatac agagcttagc attaacagct ggacagagct cttgtgcatc 180
ttgttttttt tggttattta aatactcctg atttagggtg gagaaaggga atggatttct 240
gttgcttgaa attccttgcg acagtatttg tttgctttaa ttggcgctag attgaagttw 300
ccaaattcag atgatgatga aaccagttca cacttatttg aaaattgaaa ttggtgatac 360
ttatgttaac ttttgatttt ttaaaaaaac aataaaaaat aaaatttaaa tgtagtattt 420

```
gatggcgatg agcttactga caataaagtc aattctcact tccttcagca tacccaatgg    480

taatattaaa caaatggtaa cattaacaat tttagaaatg gttagaaata tgtacagttc    540

tgtagcatgt gtgtgaagtt gtacattagc cttgcacaca taggcactct cacatggac     599


<210> SEQ ID NO 404
<211> LENGTH: 599
<212> TYPE: DNA
<213> ORGANISM: Homo sapiens

<400> SEQUENCE: 404

acattgggaa ataatagcaa attttccaga gaaggagttg cttccaaaaa tttaaaaaat     60

agttaaagag aggcatttat aaccatgaag agtagtcaac agagaaaaca aacatgccag    120

tgaatgaaca tcctagcaga gggtggagag agcaagccag aatagtgtgg agggggtaca    180

aaagtttcaa attatcttcc ctatataaaa ttcccatgat cccccaggca gtcagtttta    240

actgcttacc ccagcactcc caaattccat tcttccggag gcctggcaaa gcacctccts    300

agcactcact acccagtccc aggcctcagg cgtgctctcc ccacacggct gctgtcccca    360

tcttcacttc cacatcatcc ttggatccta gatcactgtc cctacagctc acttccttgt    420

ttccactccc tgtccacaca ttaaatatcc atgctctggc ctggcagtca gcagtcccat    480

gacctggctc cagggcccct tcagccccaa gtcgcgtccc tcgcaggttt gatgcccaag    540

cagcagattt ctccccaaca gaggcctcag agagtgcctg gctgtgataa gcatgtgtt     599


<210> SEQ ID NO 405
<211> LENGTH: 599
<212> TYPE: DNA
<213> ORGANISM: Homo sapiens

<400> SEQUENCE: 405

tgcttctcat tatttccctc gtcaacagtc tccgtctcct ttgcagcctg tgggtattgg     60

cctgcagctt ggctggtctc cttttgggag aggtcatgcc gcacaggcct agccggcccc    120

tgttagcatt gctgtggtgc tttctgttaa cgagaggcca ctgaagctgg gcgatgcctc    180

ccagcagggg acgggcttgt gagaaggagc tgcttgttgt tgcccttccc cagagaggaa    240

gccgagtgca ggcctgagcg ggcagctggg gttggagaag cttcacgatc ccttacttaw    300

ggccacagag ttcatcagct tcccacgacc agcacccata gccttaaccc cggggtgggt    360

ggaaactctg ctatctcctc acagggctcc ccaccaccac aagggcacct tcccaagagc    420

ccaggagagg gctggctttc aggcctggtg tggtgttgat aatcaggtcg ggttgagctg    480

aaatggaaaa ccttgagagt gaggtggatg gtgggctcca ggctggcatc tcccactgaa    540

agagccgggt cgcagagaca cactcaacaa gtgccagtgg cctggctggc tgaggggac     599


<210> SEQ ID NO 406
<211> LENGTH: 599
<212> TYPE: DNA
<213> ORGANISM: Homo sapiens

<400> SEQUENCE: 406

caaaaaattt aaaaaaaaaa tgccagtcat aatggcatgc acctatagtc ccagcttctt     60

cgagggctga tatgggagga ttgctggagc ccagaaggtc aaggctacag tgagccatga    120

ttgtgctact acactccagc ctgggcaaca gagaaagacc ctgtctcaaa aaaaaaaaaa    180

aaaaaaaaaa gagataaaga aagaaaaaaa caaagttacc agggagaaaa gagagttatt    240
```

tataaaggaa tgatagctgc attgataata gacatcttac taacaataga ttccagcagr 300
cagtggagta gtatcttcaa atatctgaaa ggggaaaaaa atcacttgta aagccagagt 360 tttatacta gctaaactag ctttcaagag ccgatttaaa agaaagacag ttttaggatt 420
tttttaaaat gaagtttata tcagtcttga gtcttcactg aaagaaccat taaaatatgt 480
attatatcaa gaaaaactca gtttcaaggc aggacataga aatcaagaaa ctatagtgga 540
cacagaaata aataagttaa aatagactta cttcaactga ctataaaata actaaatct 599

<210> SEQ ID NO 407
<211> LENGTH: 599
<212> TYPE: DNA
<213> ORGANISM: Homo sapiens

<400> SEQUENCE: 407
atcagaactg attgcacaaa ccttttccca acttcacaat catgatgtca tatttgtagc 60
ttgagttgac caaggtggga atatttatac cacagaaatc agcaagctac aaaccaggct 120
tttccacctc cagagccagt tgttaaacat ttaccggcac accagtgcct ccactgtggc 180
tattgtcact caaagtatga ttctcagacc aattacatag gaatttccta gagatcagaa 240
atgaggtggg gcaggagggt tgttatttaa catgcagatt tcctggccaa cctgaattaw 300
ctgaatcaga ttctctggag gtagagcctg gggaaatgct ttttagcaag tccctgaggt 360
tattaataaa ttcaataaag tttgagactt cagccttagg gaataggaga aaagagtggg 420
cgtgcatctg actcttggca tctggaagga acagctggct tcagtcccag ttggcctaag 480
aatggacagc tgttttctct cgagatagaa acttcatgac aggaaaagag gtgggaattt 540
tggggtctca gctacccact gacaacacga ctggttctgc cttggatctc aggatgaat 599

<210> SEQ ID NO 408
<211> LENGTH: 599
<212> TYPE: DNA
<213> ORGANISM: Homo sapiens

<400> SEQUENCE: 408
ttccacctcc agagccagtt gttaaacatt taccggcaca ccagtgcctc cactgtggct 60
attgtcactc aaagtatgat tctcagacca attacatagg aatttcctag agatcagaaa 120
tgaggtgggg caggagggtt gttatttaac atgcagattt cctggccaac ctgaattaac 180
tgaatcagat tctctggagg tagagcctgg ggaaatgctt tttagcaagt ccctgaggtt 240
attaataaat tcaataaagt ttgagacttc agccttaggg aataggagaa aagagtgggy 300
gtgcatctga ctcttggcat ctggaaggaa cagctggctt cagtcccagt tggcctaaga 360
atggacagct gttttctctc gagatagaaa cttcatgaca ggaaaagagg tgggaatttt 420
ggggtctcag ctacccactg acaacacgac tggttctgcc ttggatctca ggatgaatcc 480
attttccaac ttgagacttt gacccaagac agcatgagca aatgcccaga tgtatgtaga 540
acgtggagaa agtcaccgtc atttgcacca ttggtgggac cagtggagcc cagggaaag 599

<210> SEQ ID NO 409
<211> LENGTH: 599
<212> TYPE: DNA
<213> ORGANISM: Homo sapiens

<400> SEQUENCE: 409
gatggcagtg aggggtgcac tattttacac acagtggggt caggaagacc tctctgaaga 60
ggtgacattt gagcagagat tggatgaaga gagagtaagc aatgttcaat ccagaaagaa 120 cattttcaagc agaaggaata gcaagtgcaa aggcctggaa taggaacaag tgtgatgtgt 180
ttggggaaca gtaaggaagc cagagactgg agtagagtga aaaaagggga caactgtgat 240
acattaggtc agagcagtgg gcaggggcca gccatggaag tggtgacttt gggttttgty 300
ctgagcttca caggatgtcc ttggaggttt tggaggagag tgatgcagca aagatgaaca 360
ttcagaggct atagagaggc tcatggaaca acaatgggcc agcttgggtt aaacactggc 420
attcagacac atggcaatgg tagctgcacc tcatgggtgg tgcttccagt gggaactgtt 480
gagagctaca tgtttcgaca gggtgaggct gggcctggga gctcactacc tctaccaatt 540
agtgttaagc ccagaaaaag gaaatgctgc agtttaaatt gtagggttgg aacctgtga 599

<210> SEQ ID NO 410
<211> LENGTH: 599
<212> TYPE: DNA
<213> ORGANISM: Homo sapiens

<400> SEQUENCE: 410
ggagagggcc cagaattatg actctctccc cggggtcatt tgactgcaag gttagaaggc 60
ctgagatcaa acaaggctat gagaaaccag ccttgtcact ttgcatagga tagaccagtg 120
ggagccaaga ttggaggcat ctgaaggtca ctgtaggacc ttaaaaatac caggggaggg 180
tactgtgaga aacagattcc catcaactgt ttactaaaca ctctatgcta tttaaaggga 240
caaaggcatg gccaggtcct atcatcaggg agtctaaatc tggggtctgc agctgagccr 300
ggaggggggt ccagtgccct tggcagcctg ctgtaacctt ctgaccctct gtgtccagcc 360
cccatcccca tttttacctc cagccaagct tccccctatg gggttaaca gggtaaatac 420 tgtccaggcc cttccctcaa agaagctgca aatctagtaa gagaataata tgtgcgtata 480
tgaaactata atttaagaca ctgtgatcaa taacctaaag ggaaaggctc tgaggacatc 540
caggggtctt gggctcaaag gctggagcgc cacacacaca cacacacaca cacatgcac 599

<210> SEQ ID NO 411
<211> LENGTH: 599
<212> TYPE: DNA
<213> ORGANISM: Homo sapiens

<400> SEQUENCE: 411
gtcatcaatt tgtgcattta ttcactcatt cattcttgta tttcataatg aagcttctct 60
tacgtatata gcaccacact agaggtttgt gggaccagaa ggagcagcaa caacaagaat 120
gggtcaaata gattatgtta aattgaggta acattaacca taaaacagta aagaaaacta 180
ataattagag agtacagata aagtatgaag agattagaga gagatgactt taggctggag 240
aaatcggctg aagcttctgg aagaggtgac atttgtattt agactttcag ggatgaaggr 300
cagaatgaag actgccagtg tggaagcttg cgaacagctg aggcagcccg cacggatacc 360
ctgtccagct cccttctttg tcttgaatca tgcaatatcc atgcagggaa aaaaaaaaaa 420
aaaaaaagcc cttatttgct gttatgtatc ctgcctcatt taatgtatta tcccagaaaa 480
gtagattgag ttgtatgtgg cagattggga gctgccatca tggtggttaa aagtacagac 540
caggtagtac agaaccaggt agcctgggtt ggaacccagc ttcagtactt ataagctac 599

<210> SEQ ID NO 412
<211> LENGTH: 599
<212> TYPE: DNA
<213> ORGANISM: Homo sapiens

<400> SEQUENCE: 412
gaagcttctc ttacgtatat agcaccacac tagaggtttg tgggaccaga aggagcagca 60
acaacaagaa tgggtcaaat agattatgtt aaattgaggt aacattaacc ataaaacagt 120
aaagaaaact aataattaga gagtacagat aaagtatgaa gagattagag agagatgact 180
ttaggctgga gaaatcggct gaagcttctg gaagaggtga catttgtatt tagactttca 240
gggatgaagg gcagaatgaa gactgccagt gtggaagctt gcgaacagct gaggcagccy 300
gcacggatac cctgtccagc tcccttcttt gtcttgaatc atgcaatatc catgcaggga 360
aaaaaaaaaa aaaaaaaagc ccttatttgc tgttatgtat cctgcctcat ttaatgtatt 420
atcccagaaa agtagattga gttgtatgtg gcagattggg agctgccatc atggtggtta 480
aaagtacaga ccaggtagta cagaaccagg tagcctgggt tggaacccag cttcagtact 540
tataagctac ctacctttga ggattattgt gaagattaac gtccattggt tgttgttgt 599

<210> SEQ ID NO 413
<211> LENGTH: 599
<212> TYPE: DNA
<213> ORGANISM: Homo sapiens

<400> SEQUENCE: 413
tcatttggtt tacctgtaaa acttagtgag ttatgtatta ggatagcccc tcccaccctg 60
gggcaggaac atgaaagcag tgagatgagg agcttcttct tgcttttttt ctcttgctct 120
aggcattatt tgactttgaa atactcctgg cattttcctg tgattctgaa gtgccccttc 180
ctctgcttgt gtgtgtgaga tttgaaagct tatcacacat gtggctaaag caggtccagc 240
ttggagcatt cgtcttctgg ctgctgttgc tgggggagta tccctgctgt gagatgctay 300
gccgcctgag cctgtggcct ctgcttatct cctggggtgg ctgtggctgt gaggtgcaca 360
gcatggtaca atgctagttt tcatttcaag tcctttcttg atgtcactga tgggtgcaat 420
gagtggagtg gggggacctc aggcccttcc aaattctttc ttttttgttg ttgttattta 480
gtttttattt cataatcata aacttaactc tgcaatccat ctaggcatgg gagggaacaa 540
ggaaaacatg gaacccaaag ggaactgcag cgagagcaca aagattctag gatactgcg 599

<210> SEQ ID NO 414
<211> LENGTH: 599
<212> TYPE: DNA
<213> ORGANISM: Homo sapiens

<400> SEQUENCE: 414
actagctttg tgaccttggt tggcagcgtc attttcatgt cggctatagt ttccatgcct 60
ataaacagaa tgatgatacc tgccaccaac ttttccctaa agggggctgg gagagtgcat 120
taattaatgt ttttgagcac ttggagttct ttggagaaag gcctttataa atataaggca 180
tgattaaagg atatcagttt gctaactctc agaggaagta cttaatggga tcaggcctgc 240
atatgttgat gactgagttt cattcttcat tcagatctgc acagggctcc catcactcar 300
ctctgccgcc attcatgtag tattcttctg ttctttcatt tctatatact catagtaggg 360
ggcccacaaa tgctgccctc cacatgcagg cccactacct cccctccctc ttgtcaaacc 420
caatggcttt tcctcactct gcattttcct tgtcctttct ggaacatgac actggtcact 480
acccctcctc acccttgaaa gtcttattct gtcattccca caagcccaac aggtctaaac 540
tgaagtcatc attgacccca aaccaattcc catcattact gccctatttc tcttcacca 599

<210> SEQ ID NO 415
<211> LENGTH: 599
<212> TYPE: DNA
<213> ORGANISM: Homo sapiens

<400> SEQUENCE: 415
tccaagacag agcagacaaa agacctgatc cccaagcccc acacctggcc ccaagatccc 60
tctgggatta tcttgcggcc actctctgaa gccttggacc ctgtagttga tctcatagcc 120
acgtctcacc agtaactttt tttttggtgg gggggtgggt cctggcaaga gatgggtgat 180
gtaggaatgg cctagctgca gaaggaggac agccaggtag gacatctgcc tggctcacct 240
ccttcctggc cacagactag ctttgtgacc ttggttggca gcgtcatttt catgtcggcy 300
atagtttcca tgcctataaa cagaatgatg atacctgcca ccaacttttc cctaaagggg 360
gctgggagag tgcattaatt aatgtttttg agcacttgga gttctttgga gaaaggcctt 420
tataaatata aggcatgatt aaaggatatc agtttgctaa ctctcagagg aagtacttaa 480
tgggatcagg cctgcatatg ttgatgactg agtttcattc ttcattcaga tctgcacagg 540
gctcccatca ctcagctctg ccgccattca tgtagtattc ttctgttctt tcatttcta 599

<210> SEQ ID NO 416
<211> LENGTH: 599
<212> TYPE: DNA
<213> ORGANISM: Homo sapiens

<400> SEQUENCE: 416
agaaaaaggt aaatgtatat gtttttctct tgttaatctg tgttttcttg tagtgctctc 60
agccacgaac cttgagatag gtgaggaaaa tatattattt ttcctccctt acattgagca 120
agatgctgtc tgttctctgc aactcctaat tgttctctct tcacctccat tgtctgccac 180
gaaaaaaaaa atgctacatt gttcacacat taaaatggat cactcaaaag tgtctgaaaa 240
aagcaagagg aaaacatatc ctaattccaa atgtcaaaaa ttaagtggct cctccttgar 300
actacctttt tgaccccaag aaacaataag agagtgccct atacccagtg tttgacaaac 360
caatacagta ctctcctgcc caaggccctc caggccttca ccacaaacca tgctgcaggg 420
acaggacgta agcactgcct ctgatatgga gcacttgctg cgtgtctgac acacacttta 480
catacacaat cttctctaat gcttccagta atcttacagg tagaattttg tattattcct 540
tctctacaga tgaggaactg aagcaggaga ggttcagttt gtcaccagaa aggatgaaa 599

<210> SEQ ID NO 417
<211> LENGTH: 599
<212> TYPE: DNA
<213> ORGANISM: Homo sapiens

<400> SEQUENCE: 417
tgaccaaaac aaaacaaaaa acgaaacaaa atgaaaaagc ctacatgctc tttggtattg 60
ttgggactga aaacaatgga actgagtttc ttgacttttt cttaacctta tccccatgaa 120
agaggtttga attacagtat ttttcaaagt aaaagccatc tgaacagctg cctgaactaa 180
cctgggagcc tagacagttt agcttcttga cctctgggat gtgggggaag gggacaaaag 240
gaaagagaga gtaggggagg agcgagctcc ttctgttttc tgggctggcc atttgaggcs 300
catgaaccaa ctgagctgat gtcagactct ggcactccca cttccaggag tcacaacaaa 360
gtggcaggga tcaggggcac ccctgggtct cagagaagta gcacattgta ggagaaagag 420
aatatgctgt gcagacacac ccagatttgt gttttgctgc tcctttcact ccatgtgatt 480
tagacaaatt acataacctc tctgcaaata ggaaaacttc cttgtgcctg ttggtcttgg 540
aaggactggg actacataat gcaccaatag aatgtctgga gcacatcaga tgtacaata 599

<210> SEQ ID NO 418
<211> LENGTH: 599
<212> TYPE: DNA
<213> ORGANISM: Homo sapiens

<400> SEQUENCE: 418
ttgcacagcc tgaagcataa gaattgaggt atttccttac tttacagctc tagagaattc 60
ttgtgtgtgg gtacccgtga aacacaaact gagtgcatgc tttcttgagt ttggaaattt 120
tgttattgtt tggtctcagc atttgctggt agtaaataag taagcagaag taagctgctt 180
aagttcccat gtagtccaag acagagcaga caaaagacct gatccccaag ccccacacct 240
ggccccaaga tccctctggg attatcttgc ggccactctc tgaagccttg gaccctgtar 300
ttgatctcat agccacgtct caccagtaac tttttttttg gtgggggggt gggtcctggc 360
aagagatggg tgatgtagga atggcctagc tgcagaagga ggacagccag gtaggacatc 420
tgcctggctc acctccttcc tggccacaga ctagctttgt gaccttggtt ggcagcgtca 480
ttttcatgtc ggctatagtt tccatgccta taaacagaat gatgatacct gccaccaact 540
tttccctaaa gggggctggg agagtgcatt aattaatgtt tttgagcact tggagttct 599

<210> SEQ ID NO 419
<211> LENGTH: 599
<212> TYPE: DNA
<213> ORGANISM: Homo sapiens

<400> SEQUENCE: 419
aatgtaataa caaccagaac aaaaaataag atgggttgat agataaatag atatgtgcta 60
aaaaacaagt gtaataaaat tattttggtc tttttgtttc cgtttttttga gacagggcct 120 tggtctgtca cccaggctgg agagctaatc atagctcatt acaacctcaa attcctgggt 180
tcaagtaata aaatgttaat ggcagaacca gttgatatgt ttatgggtat tcactataaa 240
attctttcac ttttgtttta tgtttgaaaa ggttcataat aaaatgttga ggaaaaaacm 300
gtaaactcaa aatgtcattc tgaccctgaa ctatttacta ttccataatt tactaagtta 360
acatcctact gatcagaaaa aattaatatt ttctttaagg agccctagct cttttctagg 420
caatactttc ttatactttg ggaacttgat gtgttatatt ataggtaaac attttgaaaa 480
caatcaccag agaggtgtta tacaagagca taatgatatt ctatgaggaa ataggatctt 540
ataacctcag ggtcaaaatt cctaagagac tcttcccaga gactacaatt atattattt 599

<210> SEQ ID NO 420
<211> LENGTH: 599
<212> TYPE: DNA
<213> ORGANISM: Homo sapiens

<400> SEQUENCE: 420
gtggcctggc tggctgaggg gacctcagag caccagtgtt tgggaccggg gctgggaagg 60
ccctgccatc caccctagtg acatccgtca tgtggccacc aggttcccac tgggtgaaca 120
cagcctctcc cctcactgag ccagattcca gcctccggcc ataggtgaaa gacaatttcc 180
gattattgtt ttcaaacatt ctacatccag cgcataaaaa cacaatagtg acaggaaaaa 240
tacacacaca cacatacaca cacacacacc ccacatgcac acaacacaaa ggtttaagcr 300
ctcactataa gaaggtcagg ggaccctttt ctcattccag tccttgatgt ggatccaagg 360
gaagcagtgc ctttgaagtc agcagcaacc gcagcaggct cagctgtgag ggtgtggaca 420
gggaggcaga caggatgtgc tgccttatca gggcccaatc taaggccctc ctgtaaggac 480
caagcttcct ccagcaaaag gtgacttaga ggtgtttgtt caataatgcg aggagactca 540
ttacaaccct ggggcacttg ggatctggct ctctcagagc caagcctttc tgtttggag 599

<210> SEQ ID NO 421
<211> LENGTH: 599
<212> TYPE: DNA
<213> ORGANISM: Homo sapiens

<400> SEQUENCE: 421
ggaacgaatt ttctaaggac aagctggccg agaaaagccg ccatctcacc gtgaaccaga 60
attaggtaac gtggcaccct tggagcagca gaggtgaccg gctggaacag tcggccagga 120
ggacagctgc actccccacc accttctggg tgtgttgcca atgtctgccc ctgacgggat 180
tagtgacttc aggacagctg gaacattcgc agtgctgttt ccttacgatg ggaagagaca 240
tgatcttgac tctgcttctg taggagatgg tgatgaggag tagctgaaag ctagataggk 300
tctttaaaac ctgtgacaga aatggcgtgt gccaggccta tctgttttgc aggagctttt 360
acagcagccc agctgtttcc ttctatgaac tcatttatta ctcccttcgt ccactcattg 420
ggcattactc tatggggaac acggtcctat gagccagaca aaaaaaagct gaattgtctt 480
agtcccttag ttttgctctt cccaattccc ttcatcatcc ttccataaaa ggagaagggc 540
cattgttctc cccagcccct ttcttttttg tcacattttc aaaactctga gcgtagggt 599

<210> SEQ ID NO 422
<211> LENGTH: 599
<212> TYPE: DNA
<213> ORGANISM: Homo sapiens

<400> SEQUENCE: 422
gcctgggttg gaacccagct tcagtactta taagctacct acctttgagg attattgtga 60
agattaacgt ccattggttg ttgttgttct catcagcatt attactgtag gaaccctgga 120
agtctcccct acccacccaa gtcctattgc actttctatc atgacagacc atttctcttt 180
tttgagagtc ttatattaca atgcagacac acctgagagg gctaatgcgt gaaggtttac 240
cagccctcac tttaggggta gagataatta gctgacagct tatttactaa gagcaaaatr 300
gaaacctggg gagagggaca taaaagaagg aggagagagt ttacaaggag aagcccatgg 360
gccccaatgg ccaatttcc ttccacgctt tatttagagt acataggcct ctgtgtttct 420
acttgtcatt ggagagaaac ctccacacac cagcataggg atgaagtgaa gaacagtgag 480
gaagatgcct gcccatcatt ctaggagccc tcagctgaaa agcaccgtat tgggccctag 540
agaagggaac agagtgagat tacagaaaat gccccagatc tgctgagtcc cactgaaaa 599

<210> SEQ ID NO 423
<211> LENGTH: 599
<212> TYPE: DNA
<213> ORGANISM: Homo sapiens

<400> SEQUENCE: 423
tttgatatag aaaaaacatg tctctgtcta gtgaccttat cttgccttag cagagggtgt 60
gcttagtgat tccctgagtc tttcctgtgg tcttatttta tgaaaaacca tagaagccat 120
acgaagcgaa ggcttttctg ggatatgtgc ataaaacagt actttaaagc taacctttaa 180
ggtaattgca ccaagtagta ctttcttata acaccattta gtagcagaac gtgcctagat 240
aattctaggg tagtaagacc tctgggacac cagccactta gagaagataa caggtatagk 300
tttttgtttt ttagggtttt ttttccaatg cccaagcaga ggccactaca cccagggatc 360
aaggttatgg gatgaggatt atattttatc ccgtttctat gacattgagc tctacaccag 420
ggctcttgaa tgtgaggctt agtttcagat cacaggcctg gaagggggtc aggtcaagct 480
gagcagacct tcaagccgat taacccaaga gctgaattgt gttgtctgag ggaaggagtc 540
ctccctggct gattattttc tttacaccct ggaaactttg caaaatttta taaccaaga 599

<210> SEQ ID NO 424
<211> LENGTH: 599
<212> TYPE: DNA
<213> ORGANISM: Homo sapiens

<400> SEQUENCE: 424
caggttgttg ctccccctga aacttcacaa ggcctgggcc tcatgcagtg cactgctcat 60
tcaccctgtg ttccactctc ccagcaaagg agtcctggtt ttggtttctt tcgatgttta 120
cttggcctct tgcttaagca tttgcctttc ctcctcaata acagtgaaag gactgaaaaa 180
taataaaata aagaaaagaa aatcccaggg ctggaaacat tttgtttcct acaaaaagaa 240
tattttgcgg ccagctctgt ggttgaaagt atttttcctg tggtctaggg atgagttggr 300
tcccatctct tcttggccag ggtctgagaa cttagcctgt ggcttcccat cgagtcagca 360
catagcatgc tatttttga acgagtgtct gatgatgttg aatgtgttca cgagtggacg 420
aataggtctg tttgggtgta taagaaatgt gcgcatgtgc ctctgactct tccagggcag 480
aaggaacctg ggagtggttt tccacatgct atacatatca acgtagcttt taagttttca 540
tcactcacat gatgaccaaa aaaattcaga tgctgacaaa tgagaggagg gtgatatgt 599

<210> SEQ ID NO 425
<211> LENGTH: 599
<212> TYPE: DNA
<213> ORGANISM: Homo sapiens

<400> SEQUENCE: 425
agaaaatccc agggctggaa acattttgtt tcctacaaaa agaatatttt gcggccagct 60
ctgtggttga aagtattttt cctgtggtct agggatgagt tggatcccat ctcttcttgg 120
ccagggtctg agaacttagc ctgtggcttc ccatcgagtc agcacatagc atgctatttt 180
ttgaacgagt gtctgatgat gttgaatgtg ttcacgagtg gacgaatagg tctgtttggg 240
tgtataagaa atgtgcgcat gtgcctctga ctcttccagg gcagaaggaa cctgggagtr 300
gttttccaca tgctatacat atcaacgtag cttttaagtt ttcatcactc acatgatgac 360
caaaaaaatt cagatgctga caaatgagag gagggtgata tgtgagcctt atgtggattt 420
gcaagtaatc agaaagccag ggaatctaag attccctatc acatttcttt ccattttcaa 480
atggaaaatg tcacatttct ttccattttt caaatgctca aaaccaagac atggggttgg 540
ttttattatg gcagggtggt ctgatggtaa tgcagaagat gggaattctg agagctgcc 599

<210> SEQ ID NO 426
<211> LENGTH: 599
<212> TYPE: DNA
<213> ORGANISM: Homo sapiens

<400> SEQUENCE: 426
attattgtgg gcttagggaa tagtaattaa ggagttccag ggatgggatg tgggagcagc 60

```
aaaggagtta ggtttcactt aaggtccttg ggaataaata aatattctgt cactaggatg    120

aatggggttg gttcttcaca gatcatgtaa agggacaggc ttagccctag aaccaactca    180

tgatctagat gagtttctgt tcagatggat aagggcatat ctttgagcac caggttccat    240

gggcacatat ctggttcatt attctttgct ttgcttgtgc aaaattattt tcaaaggcar    300

agacacgggg acaaagttgg gctctttgag gctgttcctt gagcaaagag gtgtatgcct    360

ctggctgccc acttggcagt ggatatcttc atgcttcttt tttccaccca aatattatgg    420

ccactggagt atttgtagga aacagtctaa aaaaagacaa cactcacttc cccttgcttc    480

aggctcttca cagtcaactc cactggcatg tttcaggcac ctgctgtgtg ccaggcattt    540

tttttcagaa tggaacaata ttgcccttgt ctttaatgcc ttaactgtct agcaggaaa     599
```

<210> SEQ ID NO 427
<211> LENGTH: 599
<212> TYPE: DNA
<213> ORGANISM: Homo sapiens

<400> SEQUENCE: 427

```
gcctccatta aatagattta aaagacctaa aatgcaacat ccattaccaa atagttccca     60

tgttaaaagt tcccatgaaa ggagaagcag aaaaatgcaa taatcatagt atttttttaa    120

aaataaatta tctggagcaa atttagtgca ttcccttaaa cacctgtccc atgatggaaa    180

aaaaaagtta gtaataacac gtttctgtgg aggcatttcc attctccacg cctcagttcc    240

cactgtaatg ttaattggtt atggttttct ttgcttctag tccttacatg tgcagctgty    300

aaccaggcac caccccagga aatgctgcac ttaaagggat aagtaagagg aactgaatca    360

catgcagctt ttctaaggag aaatgatatt gttaatattt ttgcttgttg ttctaattat    420

aaaaatacta tgtgcttata gtagaaattt cagagtaaag tactaagaat aagtaaaaat    480

ccctcatact ctcatcatca gaagataatc actgtttcta tttttgtata tttccttcca    540

gtctttcttc ctctatcgca catatttgtg tttgttgttg ctgatttcat tttgcttct     599
```

<210> SEQ ID NO 428
<211> LENGTH: 599
<212> TYPE: DNA
<213> ORGANISM: Homo sapiens

<400> SEQUENCE: 428

```
actttcctta tagacaacat cctgccacag ggctggctat gctaccgctc tcctacagac     60

agccatttgt gctcatggac atctccctta aatcctggct ccctagtccc catcttcata    120

ggctaaaggt gtgtaatggg agaaccaact ttgtctgatc ttgcgagcat gggagctttt    180

tggttatcac atttttgagt cagtcaatct ttattttgaa aaagcagggc aggacagagg    240

gaggaagaga ggctgagggc aggcagcagc ctgtgtggga acccatttcc tgccatcctr    300

gggtcccata gttgataatg gacaacatcc ttgcttggtt cttgtgcacc aggtgatact    360

aatttaaatt cctctttatt ttctagtgat ggaaaggagt tagcctttac tgagtaccta    420

tgagtttgca gggatcattt ttgacccttt gtgttttatt tccatcaatt cctccaataa    480

cccttcagca tagatctgat catctctatt tttacaaata gaagaactta gctgataaca    540

taaataactc atattcagtg atagcatcaa tatttgaaac caagtttgta tagttccag     599
```

<210> SEQ ID NO 429
<211> LENGTH: 599
<212> TYPE: DNA

<213> ORGANISM: Homo sapiens

<400> SEQUENCE: 429
gcaaaggagt cctggttttg gtttctttcg atgtttactt ggcctcttgc ttaagcattt 60
gcctttcctc ctcaataaca gtgaaaggac tgaaaaataa taaaataaag aaaagaaaat 120
cccagggctg gaaacatttt gtttcctaca aaaagaatat tttgcggcca gctctgtggt 180
tgaaagtatt tttcctgtgg tctagggatg agttggatcc catctcttct tggccagggt 240
ctgagaactt agcctgtggc ttcccatcga gtcagcacat agcatgctat tttttgaacs 300
agtgtctgat gatgttgaat gtgttcacga gtggacgaat aggtctgttt gggtgtataa 360
gaaatgtgcg catgtgcctc tgactcttcc agggcagaag gaacctggga gtggttttcc 420
acatgctata catatcaacg tagcttttaa gttttcatca ctcacatgat gaccaaaaaa 480
attcagatgc tgacaaatga gaggagggtg atatgtgagc cttatgtgga tttgcaagta 540
atcagaaagc cagggaatct aagattccct atcacatttc tttccatttt caaatggaa 599

<210> SEQ ID NO 430
<211> LENGTH: 599
<212> TYPE: DNA
<213> ORGANISM: Homo sapiens

<400> SEQUENCE: 430
gcccatactg aggaggacct tccaaaggct ttggaaagta gatactatag ggagctgagg 60
atggtcttca agaagtgaaa aatgtgctaa tccactgggg agagcttacg ggttatatac 120
aagggtgtta tttgtctgac agagaaaact cactttaaga ttacatgaat atatgatcca 180
tatagtctac caggacatct cttttatata ttgaccagaa taatctgaga aagctggaag 240
tacaggcatt taagccacta aagctgtgga ctacagttca ccctaagcaa ggaagcgagk 300
gttttttaac atgtcatctc ctggattccc gaggctttct gggttagctc aaacctgggc 360
catttagctt cttatgggca gggacctcat catgttcatc tttgctttcc ctaatgtcta 420
agccagtact tggaacatag gaggtactca gtaaatattt gttgaattaa tataacatta 480
aataaatcat tcagttctga gtagtcattg tttatacttg ctgtaaatat ggttttatgt 540
aatttccaag tgtgtctgcc ctttttaggt cctgtatttt cattttggca tagtctgct 599

<210> SEQ ID NO 431
<211> LENGTH: 599
<212> TYPE: DNA
<213> ORGANISM: Homo sapiens

<400> SEQUENCE: 431
tactcttgta aactgtttca tgaaccccag tgttgaagac ctcactgttt tgtttgactc 60
tgaaggccgc ctacgcatac ttgctgctgg aggaaggtta atactgactc agaagcaaga 120
ggaccactga ctgaatcacc accacttact acagtcctct gctctgtatt ccttggaaat 180
ctcttgcctc agcttgggct taacccaacc cacttagaag gagagaacaa ttttacagcc 240
ccgcatggag tgactccaag ccaatcgtat ctgtttccaa gtgatctgac gcagcaagcw 300
gattgtattt cctttggagg cttggctgag aattgttggg ttggcaacac tgaaccagag 360
tgaataaaat aagactgtca agaaaaatct gaaatggccc ctaaagagat aggactaatg 420
aaatgctcag gtcaggggtg gggtgctttc tgggcagact gaaaaaagaa aggaggacca 480
ggtgaccatg tgtgaaattc aagagtcaac aatgatctag gtaagccagg cagattggca 540
catgcccagt acttttctga gagcaggcat caagcctaaa aaaatgcaca aaatctacc 599

<210> SEQ ID NO 432
<211> LENGTH: 599
<212> TYPE: DNA
<213> ORGANISM: Homo sapiens

<400> SEQUENCE: 432
tggtctcgat ctcctgacct cgtgatccgc ccgtctcggc ctcccaaagt gctgggatta 60
caggcgtgag ccaccgcgcc cggccgccct ggacacattt ttatagaaag atccagatga 120
agggaaaaag aagtctgata ggtatttctt tttactaagt catgtgggaa gctacagcgg 180
aatcctgcca ctctctgctg actgatggtg agcttatgtt tggtgacagg aaacttgcca 240
tctacaaggc agcctcttaa aacttcggtc agctctgacc gttgtctaat aattcttcay 300
tgctgcaagt tttccagctg tcccccacat ctgttttagt ggtggtggag gattggggga 360
ctcagaagga gggcgtagat tgtcctgcta cagaaaaaga actagcagga ctcctctgag 420
ggagcaacat ggagagactt tctcacccct ctgcaggcag gctctgcccc ctttcactca 480
ctggagtgct cacttcctgt gcacacgctg cgccgtgctc cctcctggcc catgaggtgc 540
cagtcaccac acacttggat ttgtttactt ttcctcctgg aaatgtggac atgagggca 599

<210> SEQ ID NO 433
<211> LENGTH: 599
<212> TYPE: DNA
<213> ORGANISM: Homo sapiens

<400> SEQUENCE: 433
agttgtgagc ctataaaatt aaacaagtta tgtgcctcca aaatacaatg ataggaaagg 60
cataggatag acattcccat tccaaaaggg agaaataaaa aagaaaggag taactgatcc 120
caagttagtc caaaactcaa cagggaaaac aacctcaaat aaggctccag aataacctcc 180
ttttactcca tttccacctt ctgttcacac taaggcaggg gttgtaccca gaagaccttg 240
ggaagctcca accccatggc tttgctagtc tcaccctcac agcagctctt acgggttagy 300
cttgctgctt cagctgtccg aggctggggc tgcacattgg ttgctctgca gttctggagt 360
ctcaagtgac cctgccatga cacctatact aggtgtagag gggactccct gtggcagctg 420
caaccccaca gttccagtaa gcattgccct agatggggct ctctgccatg gctctgcccc 480
tgtgataaat ttctgcctgg atgtccaggc tatccaatat atcctttcaa atctaggtgg 540
aggctaccat ggcctaagag ctcatacatt ctgcatgcct gcagaattag cactatgtg 599

<210> SEQ ID NO 434
<211> LENGTH: 599
<212> TYPE: DNA
<213> ORGANISM: Homo sapiens

<400> SEQUENCE: 434
aaagtgggaa ggggagtgaa tagaggccca tccctgatcc tttgactaac cctagaaaaa 60
tgtgctttat gtgcagattc ttattgccaa gtcccctctg gctcccttca cctcatttgt 120
ctacaccatc aaggaggaag gcctggttct tcaaggtaag atccttggat taagccattt 180
ctttaagctt atgctcagtg ctgcccattg ctagtggtaa ttagtgctat ggttctgata 240
gaagctagct ccagacagaa tcaaaaacca agatgcattg gccagtgata tttaccctar 300
tgagagcaag agagcggcag ttgtggcaag aatttgacag agaagattga ggtagggccg 360
aaggagacct acagaatttc ctaacagaat gagacaatca aaacatgagg atcaaaccaa 420
gaaagctcgg aattgctacc accccattcc tctttgcaga tcctatggca tgaagtgggc 480
aatgattctg acaccagtgt ggaggtgagg agccagtgct gccccagagc cttcttgctt 540
aacaagctaa agaaccatct gggttggcag cctctggggc acaatgtcat ggctccatg 599

<210> SEQ ID NO 435
<211> LENGTH: 599
<212> TYPE: DNA
<213> ORGANISM: Homo sapiens

<400> SEQUENCE: 435
tgtaaggagt gttttggtca gccgcgtccc tatgcgaggc caagtctccc ccacagggct 60
gctttcaatg gctaccatca tagtggaagt attgggcatt tgttaaggac tgtggtgtgc 120
tagatatagc acaaaacatc taaatcatgg tcccctgcct ttgtgagggc ttcctggcta 180
cagatggcag ctggctttct caggggaaac ttgggggtca tagagaaagc tgaagagggg 240
tgcttgcttc tgtggatgac ctcttcccac ccagtgcagc gacactcccc ttttgtctak 300
agctatcctt agtcaagcca gggctgcggg accctaaccc acacttccgc tgtgtttctg 360
gatctctggt ttgcaaggcc agtggctctg tgggcaatac gtatgaaaga ggactgctgt 420
tggaggaaag ttccatttag gttgctggtg ggaagttagt gcatttcata acaatttttt 480
tttttcaaac tttctctttt tttttttttt cctttaggcc aagagaagcc atagggatac 540
tgtgaccttt gtctagagtt gatgggggtg tgatttgtga aataaaacag gaccgtact 599

<210> SEQ ID NO 436
<211> LENGTH: 599
<212> TYPE: DNA
<213> ORGANISM: Homo sapiens

<400> SEQUENCE: 436
cccagtacac agggtggcat tcagctcttc atttttagag gccttcttaa aagattagaa 60
gtatagtaag tagcaaattt cgttgaagat ttcaagaaat tctatggaag attacaagac 120
aatttcagga ggaaaaaagt ttgttctgct cagatgacgt gtgtgaagag gcttgatgtg 180
atacacgcac cctgatcact aggcattttg ttaaatagca tttctaagcc cggtcaaatc 240
tggataactt ttgggataac atttgtgaga agaagagtca ctgagttgcc tctctgatgy 300
tcattgctaa gatcatgatt ttaagaggga agagaaagtt atttagagaa agtagagcct 360
ggaaatacaa tgaattggta gagtttaaaa aactgcaagg aatgactttt cgaaaaagtt 420
ggaaaacagg ggagaaagtg gatcactaaa ggaggctgac ctggagctgt gtccaggaaa 480
gagaaaaatt caggaaaatg tcttataatt caagaacaac aaccagtaaa taaaatgctt 540
ggttaggaga cctcagaacc tcacctggtt gctttctaag ttgttttctc tatcccact 599

<210> SEQ ID NO 437
<211> LENGTH: 599
<212> TYPE: DNA
<213> ORGANISM: Homo sapiens

<400> SEQUENCE: 437
tatactagta tataatatta tagaatcttc aggttagaaa acccatagaa aagcaatatg 60
aattttcact ccagtcctct taccatgatg tttgcattga agtgtttgtg gtcattgatt 120
gctttgggcc tctaaccacc ttcttgtttg tcattttttc ttttggaatt tgggccccag 180
tccaaacaca ttgcatcagg catggtttcc tgggtgagga ggagagcagg actatcacct 240
cccttgttcc acatactata tctccattga tataacctga gaacttgcta gatttttgar 300

```
aattacatct cacagctgac taatattgaa ctatagttaa ccaacattcc attttctgaa    360
tgctgaatct cattctggct gttccataat gaatcattgg tgctctgttc tcaaggacaa    420
ggcatttcat ttagttcaat aaaattgcat cccaaacaat gtgtaggatt tgttccaaca    480
ttctaaccaa attgagattt gttttgatat catgtttatc tgatctaata tatgacctct    540
ttctctaaat tttttgtctt ctgttacctt cccatcaatt cagcatctca tcattgggt     599
```

<210> SEQ ID NO 438
<211> LENGTH: 599
<212> TYPE: DNA
<213> ORGANISM: Homo sapiens

<400> SEQUENCE: 438

```
gagacgtggc tatgagatca actacagggt ccaaggcttc agagagtggc cgcaagataa     60
tcccagaggg atcttggggc caggtgtggg gcttggggat caggtctttt gtctgctctg    120
tcttggacta catgggaact taagcagctt acttctgctt acttatttac taccagcaaa    180
tgctgagacc aaacaataac aaaatttcca aactcaagaa agcatgcact cagtttgtgt    240
ttcacgggta cccacacaca agaattctct agagctgtaa agtaaggaaa tacctcaaty    300
cttatgcttc aggctgtgca aaacccaacc atgtgctcag aagcaaaatg ctctttaaac    360
acaaagaata tccaggacag cccactaaga agatgatttg gccacctctg gtgatgatga    420
tgacacctgc caccagcttt tccctaaagg aggctgggag agtgaattaa ttgacatttt    480
tgagcacttg gagttctctg gacaaaggcc tttataaata taaggcatga ttaaagggta    540
tcagtttgct aactctcaga gcttgggttt tatcaggcca tgaaaggaag gaaatgcca     599
```

<210> SEQ ID NO 439
<211> LENGTH: 599
<212> TYPE: DNA
<213> ORGANISM: Homo sapiens

<400> SEQUENCE: 439

```
tctccaagtg accctgcctc accagacatt tgcagccctt ccagtgatac tgaaagaacc     60
actcaacagg tgggggccag atctttgcaa cggaaaatgc cacttttgaa cgccaaacct    120
ctgcctgacg aaggctgtgt gatctacagg gtgagacagg gagtttaagg tgggaaccaa    180
aggctcttga gcaaatgcag aaaggaaatg gacttatgca gaggcccata cagcccccag    240
tcaaccctgc ctttgccatg tcagctgtgg gggattttgt gctggtctca gcctctgagy    300
gctctctgcc tcagtttccc tctgcagggt ggagccagca cccacagcca tgttttggca    360
cgtggcaaac taactccttt tgtgtactgt gcagtcttag gagtaatgag gcagcaatat    420
tattgttagt tctctgttct aatgatcagc tgtgaggacc taagcaaatg agagttgcta    480
tagtgttatg aagaaaagac cctgacttgt tagagtggcc atttgtttcc ccacagctat    540
tcatccccct ggtgccctca tcaccagggc atatctaaaa gatgccatgc tagataccc     599
```

<210> SEQ ID NO 440
<211> LENGTH: 599
<212> TYPE: DNA
<213> ORGANISM: Homo sapiens

<400> SEQUENCE: 440

```
aaagaaggat atagaggtcc cacaggattg agggaaggct gaagaagcag tcttagaaat     60
gggtaagaag caggcaaatt ccagaaacta ggaagcagga aacacaaggc tcacaagagt    120
```

cccacaggtc tggtcaggac actccacttg gatgggatga aactcctgac atctccattc 180
tttttgtccc tctgttcaaa attcaccttc cattgaaggg agcatctgat tggcccaact 240
tgggtcaaaa acctcctaat tgccagcaat atccacagac tgtatcctac tgggaaaagr 300
taatccgcca aaaggaaatt agattgttat taggaaaggg agatgagtgc taggtgctct 360
ggcagccacc attcccaacc cctccctgga tgtttaagaa tatataaaac atttcaactt 420
gagaaagcag attgaatttt tttagaaaag aatatgtaaa actgtatttc ttctccagct 480
gtactttccg agccctacat tggtctaaat ggaaggatac ctttcagtac cagcccagtc 540
atgcttttgc atgattacct ctatcaaact ctatttcttt ggaaggaact cttaaattt 599

<210> SEQ ID NO 441
<211> LENGTH: 599
<212> TYPE: DNA
<213> ORGANISM: Homo sapiens

<400> SEQUENCE: 441
gatgagatct gcagcagatg agccgttgcc ttggcgacgc taatgaaaag caggctttag 60
agaggtccaa gaaccccgt gggctgagtt gtctcccccc tctgcagctc tccttgcctc 120
cccaccaaca gcctcagatc aaactccccg aatatttata aaatctctac cagaaacaga 180
gaaagtcagc cgcccagcca ggcgtctgcc cacgtctttc cggagctgct ggagtgacac 240
tctccaacgt ggctcattat tctgtttttc ttccttgcag tgagcaggac acccggggts 300
ggggtgggga ggaaaaaaat gtttgctctg ccctgttcca gctgattttg acttggggaa 360
tttacttagc atttaggggc cttacctggg acaggtcatc ctgtccccag cccctcccta 420
cccttctgcc ttctagtttg ttgctccctt tatcccacct ttgttaaaga taggctctga 480
cttggagcct gtttggctat tccttggttg cttgtttagc ccatcagcct cccgcctggg 540
gctcctcgtc aggagcccct gggaaagtcc gaggggagac tcgctaagaa cctctctgc 599

<210> SEQ ID NO 442
<211> LENGTH: 599
<212> TYPE: DNA
<213> ORGANISM: Homo sapiens

<400> SEQUENCE: 442
cagttatgat tcctgttttc tagacgaggc tactgaaacc cagagaggtt cattaacttg 60
cccacggtct cacagctaaa gaatggaaga tctgaactta gcagcctagc tctggagccc 120
tgccctcgag gccatgctgc aggcgggaat aaatcagttc cagttccgcc agcccttgct 180
gctggcccag ttctgacctg gtgcctcagt ctgacaacag gactctgtct tgcttctgtg 240
cctaggttcc ttctctagag acctggtatg ttccactttc tagcataccc taggatgcar 300
ggtccctcat ttcaagttct ggaatcccac cctgagccca ttctgatggc catggccatg 360
gaccttcctg atctcagacc ataagaatga cgtatcactc agtcccatat cccacgcaga 420
gccaagagca cggtgccctg cacacacata ggagctgttc aaatcacatt tgccgaaggg 480
aatcaatgcc aaaatgctct gtgcctcagt ttcctcatct atacaatgag gcaataagaa 540
tacatccaga gttttgtaag aatgaattaa gtgaatctat gtgtctggca tgtggccag 599

<210> SEQ ID NO 443
<211> LENGTH: 599
<212> TYPE: DNA
<213> ORGANISM: Homo sapiens

<400> SEQUENCE: 443

```
tgagagccca ccagagagcc catcatgggc ctggccctgt tccaagagcc tctcacatat     60
taactcattt agtccttaga acaattccat gaggtgggca gttatgattc ctgttttcta    120
gacgaggcta ctgaaaccca gagaggttca ttaacttgcc cacggtctca cagctaaaga    180
atggaagatc tgaacttagc agcctagctc tggagccctg ccctcgaggc catgctgcag    240
gcgggaataa atcagttcca gttccgccag cccttgctgc tggcccagtt ctgacctggk    300
gcctcagtct gacaacagga ctctgtcttg cttctgtgcc taggttcctt ctctagagac    360
ctggtatgtt ccactttcta gcatacccta ggatgcaagg tccctcattt caagttctgg    420
aatcccaccc tgagcccatt ctgatggcca tggccatgga ccttcctgat ctcagaccat    480
aagaatgacg tatcactcag tcccatatcc cacgcagagc caagagcacg gtgccctgca    540
cacacatagg agctgttcaa atcacatttg ccgaagggaa tcaatgccaa aatgctctg     599
```

<210> SEQ ID NO 444
<211> LENGTH: 599
<212> TYPE: DNA
<213> ORGANISM: Homo sapiens

<400> SEQUENCE: 444

```
agccagccca ggtgccaggc acctgcatct tggcctctgg agactaagaa ggaagggtcc     60
catgcccatt tgccaacctt ttatactaat gatgtgaatt ccctcttgtc ccattggatt    120
tcatctctcc ctccccatca aaccacctac agagacaggc cctaatcagt tcctactaca    180
attttcttct gtttgccact gggacaactt gtcccctacc tgcagcttct gcccactcag    240
catcaaaggg cccaatgatc atcggctggc gagagcttga gagcccacca gagagcccay    300
catgggcctg gccctgttcc aagagcctct cacatattaa ctcatttagt ccttagaaca    360
attccatgag gtgggcagtt atgattcctg ttttctagac gaggctactg aaacccagag    420
aggttcatta acttgcccac ggtctcacag ctaaagaatg gaagatctga acttagcagc    480
ctagctctgg agccctgccc tcgaggccat gctgcaggcg ggaataaatc agttccagtt    540
ccgccagccc ttgctgctgg cccagttctg acctggtgcc tcagtctgac aacaggact     599
```

<210> SEQ ID NO 445
<211> LENGTH: 599
<212> TYPE: DNA
<213> ORGANISM: Homo sapiens

<400> SEQUENCE: 445

```
ggaaggttct ctagcgatga atgaggcaga gcatgaggca gagaggagtg gccgaggcct     60
tcacttggga aactcttgct attacaaagt gccttctagc gagggctgga aaagctagag    120
taaggctggt tatacttgaa agaaggaaga aaaactcgat aaaaatattc acatttatac    180
aatttctcct caaatcctca tgaagtctgg tcttacaaac tacaaatggg attatataaa    240
ttttcaagtg ccctagaaag agtaatgaag taaatgaatc ctgactaagc ctcacacccs    300
cttgatgaaa taaatattat gactctctta tttcaacaaa ttggaaagag gtcttttttt    360
catataggag gtttatttaa atgaactttc taataatatt ttcatttcta tttaggaggc    420
accctgaaat tatgggatgc ttgaggggcg agcctgaagt acctagtaaa ttgttgacag    480
aaccaatatc actcaagctg ctgatccaca cttgaatctg taggcttttc tcaaagtcct    540
agttttgcat cttagaagta ttgcatcttg gaagtatttc tttgcatctt ggaaatatt     599
```

<210> SEQ ID NO 446

<211> LENGTH: 599
<212> TYPE: DNA
<213> ORGANISM: Homo sapiens

<400> SEQUENCE: 446
atggagtatt gaatgcatgc cccaacatac acacacacag gctgaaagat ttactgattc 60
acagcattta aggaaatctg tcatgtcatt agtggaccac gaagtggctt catgtataag 120
ggaccttcaa taaaattaac tgactgactt ctcatcagaa accacagaag ccagaaggta 180
attgaataac atattcaaac tgttgaaaca aaaagattgt caatccagaa ttctatatcc 240
agcaatatta tccttcaaaa ctgaaggaga aattaagaca tttccagaga aaacaaaatr 300
taagagaaac acctgccata cagaaaatac tacaaagaat tcttcaggct gaaatgaaag 360
gacactagag agtaactcaa atcagtatga aaaagtaaag tgtgtagcca ggtgtggtgg 420
ctcacacctg taatcccagc actttgggag gtcaagacag gtagatcacg aggtaaggag 480
atcaagacca tcctggctaa catggtgaga ccccatctct actaaaaata caaaaaaaaa 540
ttagccagac gtggtggcgg gcgcctgtag tcccagctac tcgggaggct gaggcagga 599

<210> SEQ ID NO 447
<211> LENGTH: 599
<212> TYPE: DNA
<213> ORGANISM: Homo sapiens

<400> SEQUENCE: 447
tacccgtgtc cttcatcaat cagctcagtg gaaatgttat tctcaccctt ggccacccag 60
atcaggaaat cggtctggac catgagtgac atgctggtgt tggccttctt caccataact 120
ataagaagct ggaatgttcc cctccaaggc tatgaaagaa ggatggagac aagaaggaaa 180
agacagaaat tctgtgaaag tctcaggtcc ttcctccttt cggaaccact tcacataatc 240
ctcttcctcc ccaggggctc ccgaaagatt aggcttcact tgcaggtccc aggccctggy 300
cctgcagagt ggttgggcct ttggggtctc tcagagagcc taatcattct gttttctgaa 360
caagtcatag ttttgctgac ttctgaccaa acccccatcg aaacccaaga gtggaagtgt 420
gattgtggtc atctataccc tgtcccccta caggactccc tgtcccacgg gatgcagcag 480
gcaggtgtgg gaaagcctac ctgatggccg agatcattaa gcagcggccc tctgattttc 540
tgtacagcta ctcagtgact tggaagggat tctttgcact aacaagcagt gcctccaca 599

<210> SEQ ID NO 448
<211> LENGTH: 599
<212> TYPE: DNA
<213> ORGANISM: Homo sapiens

<400> SEQUENCE: 448
acataaagag aaggccagtc cacaaaacag ctcaaaatgg agatgctctg gctgaaggaa 60
ggagtgttgg ggtccaggag ccccgctcac tcctcagcac ccgggagcat cacggaatct 120
aaggtgaacc tccggggcag gagacacagc actggcctta gagtccacaa gcccgggttc 180
cttggccctg tctctttccc tctctctgtt gtctgtagct ccctcctagc tctgaaactc 240
caagtacaag tgagcaggtc atgagtcacc aagcctcttt tcctgggcgt ttttccttcy 300
ggggagagaa cagccaggct tggacaaaaa gtgttgggac accctgaagc agaacacact 360
ccctgtcatt cctggcctca ctctcctcca gaacgaaagc acccagacct gcaggccttt 420
tttaggaatg aagtcactgg tctgtgtagg ttgacagagt gtccttggaa aaggctgctt 480
gggaaggaaa ctcacaaggc atgggtatcc ccactggaag aatccagagc aaaacccttc 540
tggaaatccc ccaccccaca tatacacaag gaaactccat ggaaggcatc ctgtcttgg 599

<210> SEQ ID NO 449
<211> LENGTH: 599
<212> TYPE: DNA
<213> ORGANISM: Homo sapiens

<400> SEQUENCE: 449
agaaaaagga caaaccaaaa gctttctagg acagttatgg actctccaaa ttattcatgt 60
ggtctaattc tgcaaagaca gcttcagaga cgtgctgtga ggcagacagg agcagctctg 120
aggacaaaga caatagctcg tgtacattgc tgccacaagg accatgctga gaactttgca 180
cacatgacct catttcatcc tcccactcgc cctctgcatg gaagactgtt gtcctccttt 240
tccagcagag gaaactacag agaccagaca agtcgggcca ccagtgtgac tctaaagccs 300
gtatgttcat tcaccaagct gcagtgcctt tgaggacaaa gctgaaggag ctcccgtctc 360
agaatgatgc catttagctc gagggcctgc tccctctggc ttgatggcct gtccagaagg 420
ctctgccagt gcccagatgt aaacatctct ccagcagcgt tgccacgtgg aaccctcacg 480
ctgctggtcc ctgagaagcc acacggggaa cttgccttcc tctgccctcc tcccaggccc 540
aggccttgac ctacctggtt tatatttata cctcagcctg aatcctcaca ctgctattc 599

<210> SEQ ID NO 450
<211> LENGTH: 599
<212> TYPE: DNA
<213> ORGANISM: Homo sapiens

<400> SEQUENCE: 450
cagatactta aatagaaata ctgtaagaat actgaagata ggaatacttt ttgcagaacc 60
agcctgctgt agtctatggg aggatgggag tcaggcttcc cctggaatct tatgggatag 120
cctttgtgta agcaagccag aaccctaaac acagacccag gctgagggag agaagggttc 180
tgcagctgct ttcagggacc agatagcatg aggagggtag gaaatctttg ttgctatctt 240
ctacaagtct taacttctcc tctctgtggt tggacaggct taatgaaaga ctgaataacy 300
aaagaaaagt tgataaattt tttttcccag ataagctaaa gggtagatgt ggggcagcat 360
gtcaggctta tattcatatt cacccaaaga aagatatcga ggatgatgtt ttacctgatg 420
taagtcatag ttgtatatct ccctactcct agattcctcc aaagaaggat tcaggcttag 480
ttgccctaac tcaaaaggaa cctctctccc ttggtggcat ggttccaggt cgctgtactt 540
gttctcttgt tttctactcc agctcacctg ctgtttttag gcaaggagga ttatgtgag 599

<210> SEQ ID NO 451
<211> LENGTH: 599
<212> TYPE: DNA
<213> ORGANISM: Homo sapiens

<400> SEQUENCE: 451
accataacta taagaagctg gaatgttccc ctccaaggct atgaaagaag gatggagaca 60
agaaggaaaa gacagaaatt ctgtgaaagt ctcaggtcct tcctcctttc ggaaccactt 120
cacataatcc tcttcctccc caggggctcc cgaaagatta ggcttcactt gcaggtccca 180
ggccctggtc ctgcagagtg gttgggcctt tggggtctct cagagagcct aatcattctg 240
ttttctgaac aagtcatagt tttgctgact tctgaccaaa cccccatcga aacccaagar 300
tggaagtgtg attgtggtca tctataccct gtccccctac aggactccct gtcccacggg 360

-continued

```
atgcagcagg caggtgtggg aaagcctacc tgatggccga gatcattaag cagcggccct    420

ctgattttct gtacagctac tcagtgactt ggaagggatt ctttgcacta acaagcagtg    480

cctccacaaa caatgagttg aggggaaaga ctcaaaagag gccgatacaa tgctgtttgg    540

gatgtttctc cctttggctg gcctcagggg actgggcccg tcatgtaatc actggagat     599
```

<210> SEQ ID NO 452
<211> LENGTH: 599
<212> TYPE: DNA
<213> ORGANISM: Homo sapiens

<400> SEQUENCE: 452

```
aggcagcccc ttgctttctt gcttgctcct acttttccca ctgagcttgg ccctggagaa     60

gcaaacccct aattcctctg ctggtctgag caggaaattc ccgtcagctt gtgggagagg    120

ccatctgaga gagatttcag cacatccatc ccccccgaga tccagaaccg tatcaagtcc    180

taccccagtc ccgcagagca gcttcttcct ccacagcttc tgagctgcac cgaagcaggc    240

ctccgccagc ctttgctacc caaggctgat gttgggtttt taacactcag ccaagtcatm    300

gggaagagta agatttacaa taattgggta catagcatag ctgactgggc tgcacagtgt    360

ggcttttggt cagttctggc attctggtgg gaaagctgca ctgaagaggc agagaaatgc    420

cagcccagat ggcagacatg gtgcatttaa aaaggcagtg tggtatagat cctcgctcct    480

ataaacgcgg gcctggaacc tgcagcagga gcatcacctg ggagcttgtt acagaagcag    540

aatctcaggc cctactgaat cagagaatgg gttttaacaa gctggccagc ggacacagg     599
```

<210> SEQ ID NO 453
<211> LENGTH: 599
<212> TYPE: DNA
<213> ORGANISM: Homo sapiens

<400> SEQUENCE: 453

```
ctgtcattcc ccctccagga actctcagcc aggaggagat gtactcaggg aaaaggagaa     60

atcacagtat aaccattgta aaatcctttc tgataaaatc gcagagtgtc taatactcct    120

gttccacata cataaaaaga aactaaagtg tagagaaggg aggaaagtcc cgaatttagt    180

gtgtagcaga tccaggagta aaacaagcat tcctcggtct ggggtaaatc ccaccgggac    240

tgtgttgaga cccaaattcc tctgagtcca cgggcccctt caagtcagat gaaattccar    300

acaagccaga gcctagctga acagttccac ggtgccgggc tccagtgtgt tctggaaggt    360

tctcgtgggc tgtgcctcca gaagacggag gcggggagga gccccacagg cccagggcag    420

tgtcaggttc cccctttttct gtcagcaggc atggaagagc ctttaagaaa atggagtatt    480

attattattt gtttgttttt acagtgactc agtctgtagt aactgggtta aagtccgctt    540

tgagaaaagg agaacaaaag acctcctgtt agtgctggaa gtttgcctct taagatatc     599
```

<210> SEQ ID NO 454
<211> LENGTH: 599
<212> TYPE: DNA
<213> ORGANISM: Homo sapiens

<400> SEQUENCE: 454

```
ctggaacatg acactggtca ctacccctcc tcacccttga aagtcttatt ctgtcattcc     60

cacaagccca acaggtctaa actgaagtca tcattgaccc caaaccaatt cccatcatta    120

ctgccctatt tctcttcacc attctcatgg gcctggattc caggtcttcc tctccactgc    180

cacccccctct gtgcaagcct tattgtccca acctgcttgg tcctttgaaa agcccatccc    240
```

```
tgggcagaaa tgggatgtgt atgtccctaa actgccccca aagacctctc tgcactgtay    300

ttgacctctg gccctcctgt tccctaactg gccttggtct cctgctccct tccgtgggcc    360

gctccagctc ttcccaccat gtgacctgcc ttcctgcttg tccaccttcc tgtctggtcc    420

ccagactcag tttctactct ccctcccagc aagctgggac acacaaacat agacatatgt    480

tatgttcaca caaacataga catatgttca catacccctc ccagcatcct gactggccca    540

gctgacctcc ctcacccact ctgaataacc agctctccct cctcctgcct ttgtccagt     599


<210> SEQ ID NO 455
<211> LENGTH: 599
<212> TYPE: DNA
<213> ORGANISM: Homo sapiens

<400> SEQUENCE: 455

tttgttaagg actgtggtgt gctagatata gcacaaaaca tctaaatcat ggtcccctgc     60

ctttgtgagg gcttcctggc tacagatggc agctggcttt ctcaggggaa acttgggggt    120

catagagaaa gctgaagagg ggtgcttgct tctgtggatg acctcttccc acccagtgca    180

gcgacactcc ccttttgtct atagctatcc ttagtcaagc cagggctgcg ggaccctaac    240

ccacacttcc gctgtgtttc tggatctctg gtttgcaagg ccagtggctc tgtgggcaay    300

acgtatgaaa gaggactgct gttggaggaa agttccattt aggttgctgg tgggaagtta    360

gtgcatttca taacaatttt tttttttcaa actttctctt tttttttttt ttcctttagg    420

ccaagagaag ccatagggat actgtgacct ttgtctagag ttgatggggg tgtgatttgt    480

gaaataaaac aggaccgtac tgcttggaag aaggaaacgg aagctgacat aatggggatt    540

aattagttga ttgctgttga gatggtaaca gatttgctcc taaaccattg agctagcga     599


<210> SEQ ID NO 456
<211> LENGTH: 599
<212> TYPE: DNA
<213> ORGANISM: Homo sapiens

<400> SEQUENCE: 456

gacaatgatt agaactcccc agatttatgg gatggatgaa catctgaacc agcacagcct     60

aaattacctg ctggggggtt gtctgctttg gaagaggata gtttatagtt tgaatggcag    120

aagggtcatg gggcattaat tcagatcaaa aaaagggagg aatctatatg tatccacaaa    180

gatacatggc aagcatcact ttttttcctg aaatatattg ggctagaaag ctaatttaca    240

cttcccctca ctagtatata atactataga atcttcaggt tagaaaactc aaaagcaatr    300

tgcatcttca tatagtatat actactagca tataatatta cagaatcttc aggttagaaa    360

actcatagtg aaagcaatat acatcttaat atagtatatg ctagtatata atattacaga    420

atcttcaggt tagaaaactc atagtgaaag caatatgcat cttcacataa tatgtactag    480

tgtataatac tagcatatga cagaatcttc aggttagaaa actcatagta aaagcaatat    540

gcatcttcac atagtatata ctagtatata atattataga atcttcaggt tagaaaacc     599


<210> SEQ ID NO 457
<211> LENGTH: 599
<212> TYPE: DNA
<213> ORGANISM: Homo sapiens

<400> SEQUENCE: 457

cttttcattt ctttatttat tagtttaaaa tatttccatg tgtaatctca ttttagtttt     60
```

-continued caaacgaatt ggttagaaga ggtattttgt ccccatttta attatgtaga aactggttca 120
cgaaaagatg atgatttacc caaggtcatg tagctaagtg gtcaaaaaac taggctgagc 180
atcaagatgt cttcatttct gggtgtttat ttaagtcagc gatctcaaac tggggccagt 240
aacacactta ggtcttgcta ggaggggacc ctgacttgga acccacgctt caaagagccy 300
aactctggct ctttccagtc ccatgggcca aagagccaag acacctcaca ttctgggtcc 360
caggttccca gagtcctgtc aaatgtcacc aagtccattt gagtctgtcc tcctaagggc 420
attctgcacc tttgatgtga gcaacattaa gccagaggga cagccaaggg gaggctgttt 480
gaggaatcag gggatagaca gagcttgact cccacaggtg tgcaggctgg agctggggtg 540
agaaggggag ggccgggggc caggagccag ctcttctctg ctgccctgta tctgtgtgc 599

<210> SEQ ID NO 458
<211> LENGTH: 599
<212> TYPE: DNA
<213> ORGANISM: Homo sapiens

<400> SEQUENCE: 458
tatttcgttg tccatcatta tcaatctata aagcacaatc cccaaaacta cagcacatgc 60
cattctgggg aaatttgtta gctcacggac ccccacagac cccagtgtgt ggctgtttca 120
tacgtcatgc aaacaggccc ttggactctg tctcatgtcc tctggcttag aagcagggat 180
gtttgtaatc tacaaacaaa aggtcgtctg gccaaccttt tgagatgtaa tctcgaatcc 240
agatatacta gtgggttccg ctaagtgtct attggtcccc tagtgtctct caaacccacr 300
gtgggcttca gtctctccca ggcatcagcc ctaaccctgt ggcatgggcc ctgcccagct 360
gcctcccaga cgtcacacct tgcaggctgg actgtgtcag cagctgcctt gctttccttg 420
ctggaaacct aaacctgctt tttaaggagc ccctcaaaac tcttgaaata agatgtgggc 480
attgctcact tgccctgagc tgccccttgc agctgggggg ctgcttggtt tgctctcttg 540
gcaaagcccc ttgtttttac tctgctgggg cccaactcct tccttctctg tttccttgc 599

<210> SEQ ID NO 459
<211> LENGTH: 599
<212> TYPE: DNA
<213> ORGANISM: Homo sapiens

<400> SEQUENCE: 459
tgctctgtcc tcagagtcta caagtatttg ctgaatgact gctgactggt ttcccaggtg 60
tagctgacaa aaccctatct tcagctctta cactctgtga ggaaactctg gagaattaat 120
aagaaggtga acctggtcta tttcccatag aattgtctga ttcatcccct ttgttagtaa 180
ttagaagaac aacgtcaagg ccaaatttca aacagcaagt cagcagcaaa tccaggcaaa 240
cccctcaaac ttgagcactg cttgtcttgt atgccctgtt atgccagctt cattcaaatk 300
gtgaccttga tccaactgag gaagctcata ctcaggaagc actataggat ctcattacca 360
ctgccagatt gaccactgtc ttctacagct ctgttcatgg acagtccagg gctcacagca 420
tacacctacc aagctgggag aaaccccccc ggtgcctcag tgactggggg catgcttgga 480
ttgcttttct ctctgaagtc tcatcaaatc ccactttcat gatgtcactt ctcagcccta 540
gaagctacaa gacttccttg tgttctccaa caccaaatcc caatttctct gcttggctt 599

<210> SEQ ID NO 460
<211> LENGTH: 599
<212> TYPE: DNA
<213> ORGANISM: Homo sapiens

<400> SEQUENCE: 460
tggcaccctc tgcttccgac ggtacaaagg ttgtgggtgt aaacctcaaa gctctgtttt 60
gtctagactt ggtttccggg tgggttcagg ctctctgctc catggaaccc aacagccagg 120
agatttgtgc cactgcttcc ttgagtctag actggcggag gagcaggggc tcatgactat 180
aacatgaacg tgaaccgtgg atcaaagtgg gtgttcaaga cagctgattg gacaaggtcc 240
tgagctatgc tgaggagtga tgctggcact ttggtaatgc agtggaatgg aatattccay 300
ggttaattag cagtcactga gtgtctattg tgagctggtc accatctgga tgaacaaact 360
ggcaagtaga ctctgaggag gtcacgtgcc caggagtttg tttagagagt gcagtttctt 420
ctcatattga ggtgtgcaga atgttcgctt acaggtgtgt gatcatgggg ttgggtcaaa 480
ctcctcaact ttcctatgga atgccagtcc taggaccctc tgcaatctga agccctcaca 540
caaagaacag agtatttatg tcaaactcta cccttctgtg ctaccaaaca aagctgagc 599

<210> SEQ ID NO 461
<211> LENGTH: 599
<212> TYPE: DNA
<213> ORGANISM: Homo sapiens

<400> SEQUENCE: 461
ttaaaacatc atggtggtat actctggttt ctcttcaaat cgcgtaaatc tttcgccttt 60
taaaacatca tggtggttct ctcacccgtg ttttgttttt attttatttg gctcaaaatc 120
tcctaggaaa gactgactct ccaccttagc aaaggtacac ggtctatcgt ggtcaaagca 180
tgggaaaggg gacccttcat ctccagcgtg ggagtcattg tacctgtgta ttttcagctg 240
gcaatttcca gcggaaccct cttaagagaa agttctctct acttgagctc attcagaaay 300
agtgatttct tggatatatt gactttttttc aaagggagtc ccatggtttg cttgtttgtt 360
tgtgggtggt aggaaagata caggtattct tatctcaaat gtggagatgg aaatgggaga 420
tgaccacttg ggtgtctgtg ttgccctttc tcagtccctg cactgtgagt agcagctcat 480
tgtattcatt cactgggacc acacactttc cgtaggattt cctcagattt taatacattt 540
gcctagtgcc tagtgccaat acattgcctg aaaaaaggga ttcttttaat gccaccatt 599

<210> SEQ ID NO 462
<211> LENGTH: 599
<212> TYPE: DNA
<213> ORGANISM: Homo sapiens

<400> SEQUENCE: 462
ccagaagccc agtggttaaa ttgcctgtgg tccccaagca aacctgtacc agaccattgg 60
catgatagga ttgtgtgtat cacctgcact tactgcttct ggaatcaaaa agaaagaata 120
gagccctatc tttcctggcc atcccttgct cttccaaggg ctgggtggag ttaagacaca 180
gaacttcctt gtattttttt catatacact accctgtgtt gctctgtgca caatagggtg 240
taccattcaa gcagtggaat tggatccctc tagaaccctc actgggcaac ctcaggaacr 300
ggcagccatt ttcaacaagc tttccttcaa agcttgcact gtttttggcc tacctcataa 360
gttcttcttc ttcctcgtcc tccctttctt cttcctctgc cctctctttg ccttctttct 420
catctttttt gatattttgg atgcaagaag tctggttaat tgataaaacc cagtgtgggc 480
aaaaatagag ttgtttcttc cccctgcatg gcttcctctc cccaacccag ttgctaagtg 540
gtcattggcc accatattgg aatttagatg tggctgggct tccacaatgc atggtccaa 599

<210> SEQ ID NO 463
<211> LENGTH: 599
<212> TYPE: DNA
<213> ORGANISM: Homo sapiens

<400> SEQUENCE: 463
ggcactaggc aaatgtatta aaatctgagg aaatcctacg gaaagtgtgt ggtcccagtg 60
aatgaataca atgagctgct actcacagtg cagggactga gaaagggcaa cacagacacc 120
caagtggtca tctcccattt ccatctccac atttgagata agaatacctg tatctttcct 180
accacccaca aacaaacaag caaaccatgg gactcccttt gaaaaaagtc aatatatcca 240
agaaatcact atttctgaat gagctcaagt agagagaact ttctcttaag agggttccgy 300
tggaaattgc cagctgaaaa tacacaggta caatgactcc cacgctggag atgaagggtc 360
ccctttccca tgctttgacc acgatagacc gtgtaccttt gctaaggtgg agagtcagtc 420
tttcctagga gattttgagc caaataaaat aaaaacaaaa cacgggtgag agaaccacca 480
tgatgtttta aaaggcgaaa gatttacgcg atttgaagag aaaccagagt ataccaccat 540
gatgttttaa acatcatttt ttatcaaata tagttacaaa attaaccgtt accaccatt 599

<210> SEQ ID NO 464
<211> LENGTH: 599
<212> TYPE: DNA
<213> ORGANISM: Homo sapiens

<400> SEQUENCE: 464
gagcattttt tcatgtattt gttggctacc tgtgtatctt cttttgggaa ctgtctgttc 60
atgtattttg cccatttttt aatggggtta tttatttttt gcttgttgaa ttgtttaagt 120
tccttataga ttctggatat tagacctttg tcagatgcat agtttgtaaa tattttctcc 180
aattctgtag gttgtctgtt tactctgttg ttagtttctt ttgctgttca gaagctcttt 240
aattaggttt tgtttgtcaa tttttgtttt tgttccattt gcttttgagg gcttagtcaw 300
aaattctttc tcaaggccaa catcagaatg gtatttccta gattttcttc taggattctt 360
atagtttgag ggcctacatt taagcattta atccaccttg agttaatttt tatatatggt 420
aaaatgtagg ggtctagttt tattcttctg cctatggcta cccagctatc ccagcaccat 480
gtattgacta gggagtcttt tccccattgc ttatttttct caactttgct gaagatcaga 540
tgactgtagg tgtgcagctt tatttctgaa ttctctattc tgttccattg gtctgtatg 599

<210> SEQ ID NO 465
<211> LENGTH: 599
<212> TYPE: DNA
<213> ORGANISM: Homo sapiens

<400> SEQUENCE: 465
ctagcctaaa aactggtctt ggaaccattt ggaagggtca ttttttccat gttttatttt 60
caatatcatc accatcactt ttatcctgtg gctgtgaaag gactttcttc attccactcc 120
agaattcaaa gaggcttctt ttgcacaaat ggagggaagg cactcatcac acttctcagc 180
caaacatcct aagtgtgaga gaaaacacac tgcctacttc tgaatttcgg tgagggcagg 240
gttcagatgg aacacatatt ttccaaaact ccaaatagat ctgggaggag aggaaaccaw 300
taaatcacta gacataagtc aggacacatt tggttttgtt ccctatcaaa cagtcccccc 360
aaatctcagt gacttgcaaa atccatgcat gtctgagact ctccagacaa gctctccatg 420
tgtgactcaa tattgcactt cagtattaac atgcactgcc acagttgcca cagtagggga 480
agggaaaggt ggatgggga gagagagaag aaagtaagaa agagagagag attgagcact 540
gataattaag tccttccctc aaaaaatgat atacattcct tctactctcc tggccatgc 599

<210> SEQ ID NO 466
<211> LENGTH: 599
<212> TYPE: DNA
<213> ORGANISM: Homo sapiens

<400> SEQUENCE: 466
aacagctgct gatgatatat ctgagactat ttcttatagg aaactgtagg tctatggagg 60
caggagaaat aatcacagcc cagcaaccag aagctaggat gctttcacta ctaagggaga 120
gatcactaac accatagctg ggaaagatct taaatcatca cttgattctg aaccagagac 180
ctctacaaaa tctctaggat agaagaaaat gaggagaaag aagaaagaag accttactct 240
ctaaattagt atccaagcaa aaatattcaa cactaagaaa accagtcaac aaaatcaacr 300
tttgttatct aatcttgtcc aaaagaaatt aaaataatgg aacaatctga ctaaaacttt 360
aaactaaatt tgcctaaata ctcaaagaga aataacatct actttaaaaa ggatattgtg 420
aaataaagca ggcagaaata agaattggca aatatgaaaa agaatgaatt aaaaagataa 480
aatacacaga taggataaat tctagacatg aaatagatga agataaaatt agtgaatagg 540
aagatagtat ttaagaagcc accaaaacgt agtgcaagtc agagttaagg gcatgaaga 599

<210> SEQ ID NO 467
<211> LENGTH: 599
<212> TYPE: DNA
<213> ORGANISM: Homo sapiens

<400> SEQUENCE: 467
cacagcccag caaccagaag ctaggatgct ttcactacta agggagagat cactaacacc 60
atagctggga aagatcttaa atcatcactt gattctgaac cagagacctc tacaaaatct 120
ctaggataga agaaaatgag gagaaagaag aaagaagacc ttactctcta aattagtatc 180
caagcaaaaa tattcaacac taagaaaacc agtcaacaaa atcaacattt gttatctaat 240
cttgtccaaa agaaattaaa ataatggaac aatctgacta aaactttaaa ctaaatttgy 300
ctaaatactc aaagagaaat aacatctact ttaaaaagga tattgtgaaa taaagcaggc 360
agaaataaga attggcaaat atgaaaaaga atgaattaaa aagataaaat acacagatag 420
gataaattct agacatgaaa tagatgaaga taaaattagt gaataggaag atagtattta 480
agaagccacc aaaacgtagt gcaagtcaga gttaagggca tgaagatata ctgagaagct 540
ccaattttta tacatacata tgagatagta aacctatcta cctcaaggat aaaaatgat 599

<210> SEQ ID NO 468
<211> LENGTH: 599
<212> TYPE: DNA
<213> ORGANISM: Homo sapiens

<400> SEQUENCE: 468
atacaaaaag attgacttgc atgagaagag aaggggcttt ggaagaagtc tgcacagtaa 60
cagccctgag ctgaaacctt gttacctttg taataaatct gcctctgcct gatttctcac 120
tgcctccttt tcttgtccat ctaagtgccg cccaacctct ccagggttac ttttacagtg 180
ctttttgcag tttacagagt gaagcacttt ttgttaactt cctaaacggt cccatgaaga 240
cctgtcctgg tctttcctct tcaacttatg ggtggaaaca aattgttttg acatcactcr 300
gagacactac ttgctgcagt caggacagag tcctccattc attgtgacct ggggatttcc 360
tttccacctg ggtgctgaag ctctctgttg caggaagcat gtctggttat caaaaattat 420
tatcctcggt cgggcacagt ggcttacacc tgtaatccca gcactttggg aggccaaggc 480
gggtggttca cctgaggtcg agagttcaag accagcctga gcaacatggt gaaatcctgt 540
ctctactaaa aatacaaaaa ttagctgagc atggtggtgg gtgcctgtaa tcccagcta 599

<210> SEQ ID NO 469
<211> LENGTH: 599
<212> TYPE: DNA
<213> ORGANISM: Homo sapiens

<400> SEQUENCE: 469
gactttagca gtggtagttt cctctctatt aatgtatcag tgctttcctc ctctacttag 60
ttagtaacgt tttcaggaat aaggaatggg gcatttccat ctcattctct cctggttggt 120
tcaggacgga tacagtcgtg gaaacctctc tggccacaaa agcacatttg attgggagac 180
agagggtcgt catcatccag agtgatgtat tctggattca gctgatcaga atcacttttg 240
taaattattt ggttcttctc aattagttga ttcagtgaaa agttttcaaa gagcttctty 300
tacatcatga ttattcaggc cactacggtc tctgattaca gtgatctttt gttgaaacca 360
ccaaaggctc ataattgtgg ccctgtgacc ttgaagtggt ttccttggat ttcaaacctt 420
atatacatgg gttgaccttt caagctggga gctgcagtat gttttcatgt ttccatggaa 480
cagccccaca gtcttgatcc tggtctggta ggagaaaatc ctgatgctcc tccactgccc 540
ccctcctcac ccccaactag aagccccagc agagcagttg cactggcttg cagaacttt 599

<210> SEQ ID NO 470
<211> LENGTH: 599
<212> TYPE: DNA
<213> ORGANISM: Homo sapiens

<400> SEQUENCE: 470
cgccatgatt tgtggatgtt ataactcctc ccccacactg taggtgagtg tggtagaacc 60
aactcttcaa tgtatcaaaa acttgtttct ggcctcccta ctgagtccct gctagatcct 120
ccagcaggaa agtacagctt gcaaggaagc cccatgttgg caagagaagg catgctgtcc 180
tggatggtgt gggcatgcct gggggctctc gtgggtgggg tgggtattgg ggtcttctct 240
tatggaggga gaccaggcca gacttaaggc ctgcagttca cgatggggaa gtaccagcty 300
gtgagccagg tgctctcact tgtactgttc ctaagccttg ttttccgttc ctgcccatgc 360
tgagccgagg ggaagagcgt tgtgagcttg tgtgaggggg agggtccctg aggcaagtgt 420
ggccacagtg gctgcagcag ctctgattaa tgggaaattc caagaggaag gtagacctgg 480
ggagaaagga gtggtggctg cagagtccaa ctgcccttct tgccaaacac ggagattctg 540
ccttttgcca accgtggagg ctctgcgtag gagattttat ttcaggtgat ggtgctcac 599

<210> SEQ ID NO 471
<211> LENGTH: 599
<212> TYPE: DNA
<213> ORGANISM: Homo sapiens

<400> SEQUENCE: 471
ggctgaggca ggcggatcac gaggtcagga gatcaagacc atcctggcta acacggtgaa 60
accctgtctc tactaaaaat acaaaaaaaa aaaaaaaatt agccaggcat ggtgacgggc 120
acctgtagtc ccagctactc gggaggctga ggcaggagaa tggtgtgaac ccagcaggct 180
gagcttgcag tgagctcaga tcgcaccact gcactccagc ctgggcgaca gagcgagact 240
ccgtttcaaa aaaaaaaaaa aaaaaaaaaa aagactgctc ctttttacat acttattagy 300
gtaattttat ttgccttcat ggtttgtgca tttaagagat tctttcttac cccgtgtcat 360
gaagataatt tcttgcattt cttcaactcc cttattagtt atatctttca catttaagta 420
cttagcctac ctgaaatttt cctttacatg tggtgtgaag tagggatgga tccacctcta 480
tttttctcta tgtagtaagc cagctttccc agttgcatct gctaaagggc atttttttc 540 tccactgagt tgtgattcta ccctatcata catgaagttt tgtggatgtg tgtgggtat 599

<210> SEQ ID NO 472
<211> LENGTH: 599
<212> TYPE: DNA
<213> ORGANISM: Homo sapiens

<400> SEQUENCE: 472
agatacttta ctctggcagc ggttttctta gccgtgcatt gcgacattca gcatatgggt 60
gtagacaccc ggtatggctg ggtgaacggt tcatcttgtg ggttcttcct taattgggct 120
gcccttcccc tctattagtt caagttttga cctttctgga agtgtcgtgt tccctgagct 180
ttaatcagca ccgttggcag ggcctgctgg gcacggcatt gagcagagga acgacatccc 240
caccttgatg tctgtgccgc gggaggcgcg ggctgcctgg ctcctcggga gctcagcggs 300
ccccccatgg gctgtctcct tctttctcgc cccctctcct gaagtggtgg cccctttgtt 360
ctgggctcca tcactgagga gagaagaggg cacctgcatt tacccatcgc tcacagcagg 420
acaagtaccg cgctgttgca gcatctcatt taaagctcag aacagccctg taaaggcatc 480
acctccccac tctaaaatga ggtaactgag acccagtaga tgactcactc caagccaaac 540
aaccagtgtg actttctgct tccagaccat atattatcct gcacgcagca gccttcact 599

<210> SEQ ID NO 473
<211> LENGTH: 599
<212> TYPE: DNA
<213> ORGANISM: Homo sapiens

<400> SEQUENCE: 473
gggtctcctt tgtacataca ccctccttca ttcaaccttg tcgagagtga tggcctcact 60
ggatcagctc gacagggagt gagccccagg ggttgcagca gggagacctg acctgcaggg 120
tcggaatcag agccccacac tgaggtagag ggctctggga gaggaagcgg cctggctggg 180
tggaattggg ctctgctgct gccagtgtag ggagggagcc cagtgtttta tgatgtctaa 240
ttagtgagtc caagacaatg gaacgcggcc acagatagct gggaagcccc agcggacgam 300
gcacagatgc tctgctgctg gggtgggggc agcctcgcct ccaagtgggg aacaagaccc 360
tgttgtagcc gggcgcggtg gctcacgcct gtaatgccag cactgtggga ggccgaggcg 420
ggcagatcat ttgaggtcag gagtttgaaa ccagcctggc caacatggcg aagccccgtc 480
tctactgaaa atataaaaat tactcaggtg tggtggcata ctcctgtaat cccagctact 540
cgggaggctg gggcaggaaa attgcttgag cccgggaggc agaggttgta gtaagcaga 599

<210> SEQ ID NO 474
<211> LENGTH: 599
<212> TYPE: DNA
<213> ORGANISM: Homo sapiens

<400> SEQUENCE: 474
gcctgctgga ttcagtgact gatgggattt ggtcggtggg gaggaggagg aggcctgggc 60
ttctggccag agtgactagg aggatgttga tctggggagt gcctgtgtgg ctgagggaca 120
cgtccaagct gcagtcggct ctgtggttgt ggacacctgg cagagccatg ccttctctag 180
tctgggtcat ccaaacacac gtggggtgca ggggccaggt ggagccctct tgtcgttttt 240
gttatctaac ggtaattacg gagtccagaa agagaattgg aaatgccggc agtttaattr 300
aagctgaatg gcaggagagg ggcatttgga ggctccctcc ctgccttcac tccccgtcct 360
gccgcccagg caggatgtca gatgaggaga cgttgagctc atcaaacacc caatgagaag 420
tcttacaaca tcagaagctg tctgccaatg cgcctgcgac agcttataga aactgctgcc 480
gcctcgaatc aacctctctc cccaggcatt gcacgtcagt aggtaaccag gtaaaggacg 540
ccgggggtgg gcagccagct ggagggggcg tgatttcctc ccccaacaaa atcggcttc 599

<210> SEQ ID NO 475
<211> LENGTH: 599
<212> TYPE: DNA
<213> ORGANISM: Homo sapiens

<400> SEQUENCE: 475
aacctccacc tcccgggttc aagccattct cctgcctcag cctccctggg attacaggtg 60
tgcgccacca tgcccggcta atttttgtat ttttggtaga gacgggtttc accatgttgg 120
ccagtctggt ctcaaaccct gacctcaggt gatccgcccg cctcggcctc ccaaagggct 180
gggatagttt atctatcagt gctcctgata gtttatctcc cacatgctgt ctaggccaga 240
gttcactttc ctctcatttc tgaacactcc aaggtgtcca gcttagagtg gacacatgty 300
gctgaggcct gtagtgtgtt tttatttaca tgagtggtat taggctatag atctcactct 360
ttaacatttt catttgaact atccatttta aatggaatta tccaagttac ggcacatgga 420
actagttcgt tacttctgtc tgctgtaaaa cattctatca cattcctcac attttcctta 480
cccagtcttc tagaaataga catctaagtc attgccagct ccttgctatc ccaaagaaag 540
atgcaggcaa catctttgtt ctggccccca tatagacctg tgcaaagatc caagagatt 599

<210> SEQ ID NO 476
<211> LENGTH: 599
<212> TYPE: DNA
<213> ORGANISM: Homo sapiens

<400> SEQUENCE: 476
ccttggcctc ccaaagtgct aggattacag gtgtgagcca ccttgcctgg ccctgataca 60
gtttcttaag agctgctgga agacccccag gatggggagg tggggatttg tccaggatga 120
agtacaagca cacggcctgc acccccaggc ccatctccag ggctcagata tgctcaaaga 180
tcgggggacg tggaactcca ggaatggtac aggtggagtt tttgactctt ggccaccagt 240
gaccccaggg cgaggtggta ccatctgagc agggcatgcc tctgtgggcg tgtagacacy 300
gtgtgcctca ccagtgcctt tccccaccca ggtcattgct gtggtcatgg acctcttcac 360
tgatggtgat atctttcaag acattgtgga tgctgcctgt aagcgccggg tcccagtgta 420
catcatcctg gacgaggcag gagtgaagta tttcctggag atgtgtcagg acctgcagct 480
cactgacttc cggattcggg taagttgcac cactggggtg gaaagtggac aggagatgag 540
acagagacta cctctgcccc gtcctgcagc tcccccctgc ctcttccctg aatgggggc 599

<210> SEQ ID NO 477
<211> LENGTH: 599

<212> TYPE: DNA
<213> ORGANISM: Homo sapiens

<400> SEQUENCE: 477
taaaaacatg atatcatggg ctcagaaccc agggaagccg attttgttgg gggaggaaat 60 cacgcccccct ccagctggct gcccaccccc ggcgtccttt acctggttac ctactgacgt 120
gcaatgcctg gggagagagg ttgattcgag gcggcagcag tttctataag ctgtcgcagg 180
cgcattggca gacagcttct gatgttgtaa gacttctcat tgggtgtttg atgagctcaa 240
cgtctcctca tctgacatcc tgcctgggcg gcaggacggg gagtgaaggc agggagggar 300
cctccaaatg cccctctcct gccattcagc tttaattaaa ctgccggcat ttccaattct 360
ctttctggac tccgtaatta ccgttagata acaaaaacga caagagggct ccacctggcc 420
cctgcacccc acgtgtgttt ggatgaccca gactagagaa ggcatggctc tgccaggtgt 480
ccacaaccac agagccgact gcagcttgga cgtgtccctc agccacacag gcactcccca 540
gatcaacatc ctcctagtca ctctggccag aagcccaggc ctcctcctcc tccccaccg 599

<210> SEQ ID NO 478
<211> LENGTH: 599
<212> TYPE: DNA
<213> ORGANISM: Homo sapiens

<400> SEQUENCE: 478
agctgtcgca ggcgcattgg cagacagctt ctgatgttgt aagacttctc attgggtgtt 60
tgatgagctc aacgtctcct catctgacat cctgcctggg cggcaggacg gggagtgaag 120
gcagggaggg agcctccaaa tgcccctctc ctgccattca gctttaatta aactgccggc 180
atttccaatt ctctttctgg actccgtaat taccgttaga taacaaaaac gacaagaggg 240
ctccacctgg cccctgcacc ccacgtgtgt ttggatgacc cagactagag aaggcatggy 300
tctgccaggt gtccacaacc acagagccga ctgcagcttg gacgtgtccc tcagccacac 360
aggcactccc cagatcaaca tcctcctagt cactctggcc agaagcccag gcctcctcct 420
cctccccacc gaccaaatcc catcagtcac tgaatccagc aggccccacc ccgggcacct 480
tctcagggtt aatcctttct gtccccactg gtaccgcccc agctcggact ctcctccttt 540
cctaccatgc tttgatgagc ttcctaactg ctctctccta ctcacctctg ccctccaat 599

<210> SEQ ID NO 479
<211> LENGTH: 599
<212> TYPE: DNA
<213> ORGANISM: Homo sapiens

<400> SEQUENCE: 479
ctgtcgaggt atttcttgat tgatctatca gggtaagaca aatggagttg gcagtttgcc 60
tgggaggtgc tgagacgcag caaggataac tctgtggcta ttgccagatg atgttacctg 120
ggagggcttc cctacggagg caagttgaga gtgcagggag ggatatgatt gaaagtgatc 180
aggagggcat tcaagtgatg gaaacagtgt gagtccacgt gtcctgggcc tccagttttg 240
tacacagcct gccctgcctt tccacaactg gctgattcag ccatcaattc ccaggaagcy 300
gctgttcacc tggagctcag tacaggtgca caagcctgag aatcgacaca tctcagttcc 360
catctagcat cctatttact ggtggtgtga ccttatcctc tctgaacctc agtttcctca 420
tccgtaaaat gaaaagctgc tagattgttg taaaaaaatt aaatggaata ggctaggcgc 480
ggtggctcac gcctgtaatc ccagcacttt agaaggtcga agagggtgga tcacttgagg 540
tcaggagttt tgagaccagc ctggccaaca cggtgaaacc ccatctctac taaaaataa 599

<210> SEQ ID NO 480
<211> LENGTH: 599
<212> TYPE: DNA
<213> ORGANISM: Homo sapiens

<400> SEQUENCE: 480
actggaatgc agtagtgcta tcatggctca ctgcagcctc aacctcatag gctcaagcaa 60
tcctcctgcc tcagcctccc aagtagctgg gactacaggc atgtgccacc atgcctagct 120
aatttttgta ttgtagagat agggttttgc catgttgccc aggtgggtct gaaactcctg 180
agctcaagca gtcctcctgt ctcagcctcc caaagtgctg ggattacagg tgtaagccac 240
tgtgcccagc ctaccttgtt gaactatgga gtgtgtagca ttttatagct acttagagts 300
agtctagagg cctcatacag caagtggctt caagccactt attaaataat agtaattatt 360
tagcttgagg gagagtgaga catgactgct attttatttt aattttatta ttttatttta 420
ttttatttta ttttaagatg gagtctctca ttgtccccca ggctggagtg cagtggcaca 480
atcttggctc actgcaactt ccgccttcct ggctcaagca attctcctgc ttcagcctcc 540
tgagtagctg ggattacagg cacccgccac cacgcctggc taatttttgt atttttagt 599

<210> SEQ ID NO 481
<211> LENGTH: 599
<212> TYPE: DNA
<213> ORGANISM: Homo sapiens

<400> SEQUENCE: 481
ctatatccat taacttgttt cccttctcaa ataacctagt aaggttggac ttcattttta 60
agagacaggg tctcactatg ttgcccaggc tgaactcaaa ctcctgggct taagggatcc 120
tcttgcctca gcctcccatg tagccaggac tactggccca tcactgcgcc cagctgaggt 180
gggacttatt gcccatattt cactgatgac aagacaaagg cccagaaaat aaaaataact 240
ttcctgggga cacacagcta atattaggaa agctggattc attcccagga ctctgtgatr 300
tgaaagttca tgctgttatt taccatctct gatatccttg ccatgcaaag tttggtcagt 360
ggaccagcac tcctagcatt acctgggggc ttgctagaaa tgcagagtct cgggcctcac 420
cccagaccta ctgaatcaga atctacattt taacaagccc cctggctgca caggaaaatt 480
ttggaagcac tattgtaaac cactttctac cagggataca cgagtactaa ttaagtcaaa 540
gaagtgttct cgtttaatcc ctacaccaac gtgggaggtc aggagagtta agcattatt 599

<210> SEQ ID NO 482
<211> LENGTH: 599
<212> TYPE: DNA
<213> ORGANISM: Homo sapiens

<400> SEQUENCE: 482
gctcactgac ttccggattc gggtaagttg caccactggg gtggaaagtg gacaggagat 60
gagacagaga ctacctctgc cccgtcctgc agctcccccc tgcctcttcc ctgaatgggg 120
gctcaggcga acttcaagat ctcaacacct ttccttttgt tgaaagtcaa gcctttaacc 180
ttggctttac tgttaactac tgaatcatat gcccagtttc aattttatcc ctaggctgct 240
gagactgaag gagggagctc tgggctggtc ctggggtgct tagcctgcag aatcactgay 300
gtcaaagtga gggctgttgt tctcttctgg ggccttttga gaagaggcag gaaccaccct 360
gggcttgtcc atgcctgaag caagatttgg ggacttcttc ctgctcgcca aagagggttc 420
cctatggaag gctgtaggaa gcagagcgtc tagtgaagac aggagcctgc aggcagggtc 480
catacacaag gggctcttc ctctgcagaa gcaaggacct ggcacggagg ctggcccaac 540
ccaggtgaca gggccttctg ctcttcccaa cagaacatcc gtgtccgctc tgtgacagg 599

<210> SEQ ID NO 483
<211> LENGTH: 599
<212> TYPE: DNA
<213> ORGANISM: Homo sapiens

<400> SEQUENCE: 483
ccaaaagtcc aggccactgg cgggtggagg gatcccatgc ggctgggagc caggagcctg 60
ggaatcgtca tttttgccct ggccatctct ttcctagctc actgggtgac gtggggtaca 120
tcatttagct ttgctgggcc tctgtttctg catctctaac atggggataa ttcttgcctt 180
cttatttcca caaattgttc tgagaaccta gttcaaggct atgagaaagc actttgagaa 240
gggtgagtga tgcgtgcagt aaaagggatt tctctgaaga agggctaatg ttgagtgacr 300
ggatcggtgc cctgtgtgcc atttcgtttc gttaatccaa ccctcagcac cttgcaaagg 360
aagagatatt ttccctgagg ctccgggaaa gcataaggtt gcagaactca gaagaggctg 420
ggggagattc cacccaggtc tcagctcaaa gtggtgtcca tccacggcag ttgcccttgg 480
gaattgtcct ctggggccat ctcttcctct aaaacttgca gaaacattca aagtctgtat 540
gtcgccagcc aggccctggg aggctcttgg accagttcta gagacagaca agtacacaa 599

<210> SEQ ID NO 484
<211> LENGTH: 599
<212> TYPE: DNA
<213> ORGANISM: Homo sapiens

<400> SEQUENCE: 484 ctccccctg cctcttccct gaatgggggc tcaggcgaac ttcaagatct caacaccttt 60
ccttttgttg aaagtcaagc ctttaacctt ggctttactg ttaactactg aatcatatgc 120
ccagtttcaa ttttatccct aggctgctga gactgaagga gggagctctg ggctggtcct 180
ggggtgctta gcctgcagaa tcactgatgt caaagtgagg gctgttgttc tcttctgggg 240
ccttttgaga agaggcagga accaccctgg gcttgtccat gcctgaagca agatttgggr 300
acttcttcct gctcgccaaa gagggttccc tatggaaggc tgtaggaagc agagcgtcta 360
gtgaagacag gagcctgcag gcagggtcca tacacaaggg ggctcttcct ctgcagaagc 420
aaggacctgg cacggaggct ggcccaaccc aggtgacagg gccttctgct cttcccaaca 480
gaacatccgt gtccgctctg tgacaggcgt cggcttctac atgcccatgg ggaggatcaa 540
ggggaccctg tcatcaaggt tcctgatggt ggacggtgac aaagtggcca ctggatctt 599

<210> SEQ ID NO 485
<211> LENGTH: 599
<212> TYPE: DNA
<213> ORGANISM: Homo sapiens

<400> SEQUENCE: 485
ttcttatgct tgctgttgga caaaaacaag gagggagata ttgtgccaga tactcatgtt 60
tgcaattata aatgcagatg aggccaaagt gtgtgtttgt acaggtggga tgaaataaac 120
aaatgacagt gaaagcctgc ttatcaggat cattatttgt tgttgtccct tattaggatt 180
cattatttgg aaaataagta tagagaggac agtttgggtt tttaagatat ttagtatgtg 240

-continued acatttaatt atttcttaat ttttaaaagc tgacttctgt cttagtctta catgatttgs 300
cctcacatgt gtggatgaga ttttaaatat gtgagaatca tagctagtta taaaagagtg 360
ccgggtattt gcattataac aaaacacctt tatttgtgta taatttatat acatcatata 420
tataaacttc acccagttta gatatacaat taaaacatag taaattgccc agttgtggta 480
gctcacacct agaatctcag cactttgaga ggctgagatg ggagactgc ttgaggccag 540 gagttaagag accagcctgg gcaacacagc tagaccccat ctctaaaaaa ataaaaata 599

<210> SEQ ID NO 486
<211> LENGTH: 599
<212> TYPE: DNA
<213> ORGANISM: Homo sapiens

<400> SEQUENCE: 486
atgaaacttc tcttgaatac gagctgatat tgctgtgtct tattcatctg gaagtatgag 60
atgcaaaagt agcagctttt caaagcttta agcttttaga attaagtaaa gcaaattctg 120
ctataaccaa tccaatatat tcatgtttca tatctcaact aagataattt ttagtacatg 180
tgtaaatatg gaagtagtta ttgtaatgtg gaagtcattt gtgaatagat gtgcatggta 240
agcaaattga acgttatggt taccatgtgt taggaaataa aatcattttg ctcaaaaaaw 300
atctagaatc cacaaaggtt tgactcccag ctttgccact tattggctgg acaagtgagt 360
taacttctct tagctgcatc tataaaatga ggataatacc acctaattca taagagttga 420
tgtgaggata aaaaagaaac agatacaacc tcttacataa aggtgctcaa taaaacagtc 480
tcttctaatc agctctgctg gtccctgcct atttgagaag cagtcaagta aatggtgccc 540
agtcttctga ccgaataggc gcacaggcaa cgccatcctt tcccccaaca ctgtactct 599

<210> SEQ ID NO 487
<211> LENGTH: 599
<212> TYPE: DNA
<213> ORGANISM: Homo sapiens

<400> SEQUENCE: 487
actctcactt gcttggatgc tctagagttc atgtactagt tggtcagcac atatacttac 60
ctcacatcca tgccttattc agttcttcct tagctccttg tcccaacctc tctttccttg 120
cattcattca agaaatatga gggcctactg tatgccagat actctctgtt tgttgctggg 180
gatacagtag tgactgaagg ccccaccttc agtgagttta cagtttcatg agggaaacat 240
acataaagta agttctaatt tgtgtgaaga gtatttccaa agaaaacaga cactatatcy 300
taactgattt gattgttccc ataattcaat tcatgtattc aaatggcttt tttttctttc 360
tttcctgaga tggaatcttg ctctgtcacc caggctggag tgcagtggca tgattttggc 420
tcaatgcagc ctccgcctcc caggttcaag ctattctcct gcctcagcca tccgagtagc 480
tgggactaca ggtgtgtgcc accacgcctg actaattttt gtatttttag tagagacgaa 540
gtttcaccat gttggccagg ctggtctaga actcctgatt tcaggtgatc cgcctgcct 599

<210> SEQ ID NO 488
<211> LENGTH: 599
<212> TYPE: DNA
<213> ORGANISM: Homo sapiens

<400> SEQUENCE: 488
taggaactga gaaggaaaac accactatac atttatataa tactttacaa agctactttc 60
atacgtatct catttgaccc tatgagccag aactggagtc attagtcatt atacccacta 120

```
ctacacaatg agaagaacta gtgtgccaag cttagagcaa cttagccaag ttcaccattg    180

gcaagatcaa accaagaact ttgggttctt gactaccaga ccactactgg gatattagct    240

gcctaccaca aaaaggcttc tgccctcaag gaattaatct ctgacaccta atgccttgay    300

tggtgtttct cagatgtacc aagtttcttc tcagaaagaa tctcactatc tcctggtcca    360

acatacactg aatctaatca agatatttat agaaaaaggt tatttattaa tatcactgac    420

aatgaacaga tgtgagttcc ttctggaggc cagaatcgtt aatgagactg aataaaactg    480

aattaggaca gagtgctcaa aatgtatctg tcactttggg ataaatacct cattttgctt    540

atggatatga tactgccctc tagtgccagg aagcacagta acaatcagca atctcagta     599
```

<210> SEQ ID NO 489
<211> LENGTH: 599
<212> TYPE: DNA
<213> ORGANISM: Homo sapiens

<400> SEQUENCE: 489

```
ccacaaaata aaacagagct ctatgcaatg gatactcaat aaacattatc agatactcac     60

agcatctagt ccactgtctt tcaacagatg ctcacaaatt actgaattct tagtaattta    120

tcatcattgc caactttcag gcaaagggaa atggaaagac ctcaaactca aaattagccc    180

ctgctaacga taacatctag actgtaggga tcgacattta tgtcaaaatg aagttaaaaa    240

attatctatg agtcttatcc atcctctctc atactgtatc taatcaagag actacatggy    300

ttaatagtca ggtgttttga ggtcaagggt ttaaactcta acttcagcat ttatcagcta    360

ggttccagtt tcttgcaaag taaaatttta cttatcttaa agaattgcta ttggagttaa    420

atgacataac tacttaaagt gcccgataca agagaagtag tcaatacatg gtagctaatc    480

ttactgttca ataagtaatg ccatggtttg aatatgtccc ctccaaaatt caggagttgt    540

caacgtgata gtattaggag gtgaggcctt taaaagatga ttaggctatg agggaacct     599
```

<210> SEQ ID NO 490
<211> LENGTH: 599
<212> TYPE: DNA
<213> ORGANISM: Homo sapiens

<400> SEQUENCE: 490

```
gtcaagagcc tcagcccaat tctgcttcag cctggcactc cctcccctcc tgcatctcag     60

ctgcctctca cacagggtgg ctgggtcctc ctcaccaatg atggcttcct tcaggctgga    120

ctcaacagga aggatgttct tctccaccag ctccatgggg ccaggcctct gtgcaatctt    180

ctcattgagg tcatcggcta gtctggctct cttcagcttc agctgcttgg cctggaggga    240

tggctcagcc gaggtctctg cccatgggag agaaaggggt gcaggaagat atatgagtgr    300

acgtggttct gccccgggaa ctccagagca gctctccttc ctcctgggca agaggagtga    360

ctgtcagaac ggtaagcata ttccaagcag agaagagtgg cctgtcttga agtttcacaa    420

agacaagaga aggggttccc actgtgacca ggcagtgcac agtcacacac aattataacc    480

aggcagaggc aaacccagaa gactttctga ggtggagcta cagaatggaa gcagcaacag    540

atgacagaat ggtctccact ctccctcaaa cttgctgtgt tactgaggca attcacatc     599
```

<210> SEQ ID NO 491
<211> LENGTH: 599
<212> TYPE: DNA
<213> ORGANISM: Homo sapiens

<400> SEQUENCE: 491
gcacctatat gtgacctctc catgttacct tacctacctc acagcatggc aggtgtgttc 60
taagagctaa cctcccaagg gaacaaggtg aaaatgcatg acatttttat gacataacct 120
cagaagctac acaatatcac catattctct tggttaaggg agtcacagag gtttgcctgg 180
gttcacgggg agtggatggg acgtagaccc caccattcaa tgggagaagt ttcgtcacat 240
ttgaagaaga gcatgtgtga gatacgttat attgtgttag cccatttttg gaaaataggr 300
tctccatgcc aagcatgtga taggggtttt aagaactttt tcacttattc tgcaggtacc 360
tattatccta attttactga tagggaagct gaggttaggg aagatgaatt ggccacacag 420
ccaagtggca gaacaagttg tcaggcccag gccttcttgc ttccacagta acactgtata 480
aaggtgaagg tagatttctt cagaaagtcc tgaaatacta tggaaggttt atttgtgtag 540
gtcataaaac aggtaattaa atatctcatg aaacaggcga ttactacttc aaacattta 599

<210> SEQ ID NO 492
<211> LENGTH: 599
<212> TYPE: DNA
<213> ORGANISM: Homo sapiens

<400> SEQUENCE: 492
ccccaaactt agccttgaca aacggatctc tgcccttcta ggggagagga gaggagaaga 60
aatggtggta gagaaagaaa ggcaagggga gctgtgcaga accacccgga agcttgagag 120
ttcaacgcgg agaacctgct ctgtgccagg cccccacctg ggaggtgtgg gcaaccttcc 180
tgccttccgg gtgctcagag tctagtctgg agacaataag aaaaatggtt aatcaccatg 240
gaatgtgcta gcgccttagc ccgaagcagg ggtctggtta ttgaggtttg ttgaaggaar 300
atgcctgtaa gggctgggtg cggtggctca cgcctgtaat cccagcactt tgggagacca 360
aggtgggcgg atcacctgag gtcaggtgtt cgagatcagc ttggtcaaca tggtgaaacc 420
ctgcctcttc taaaaatgca aaaattagcc aggcgtggca gtaggtgcct gtaatcccag 480
ctactcggga ggctgaggga ggagaagcac ttgaacccgg gaggcagagg ttgcaatgag 540
ctgagattgg ccactgcact ccagcctggg tgacaagagc aaaactcccc ctcaaaaaa 599

<210> SEQ ID NO 493
<211> LENGTH: 599
<212> TYPE: DNA
<213> ORGANISM: Homo sapiens

<400> SEQUENCE: 493
ggactccaag aacgcctgct aggcctcaca ttattctcag gacacctgca cacaggaagg 60
ggcacagatg catgccaaat taaccttact tcctcaacct cacgaggaat cataaagtgg 120
ccaaactgtt tcaatgggac agttaaaacc aaaaagatat atgtccactc ggcactattt 180
ccttcttcac tgcacctgtt atttatagtg ctgctaaaat taacttgaat ttcatctcta 240
aggactaaaa gaaccccatg gcaattgtat gtgaaggaac acacacaacc gacagctgas 300
acgaagggct cagctctatt ctggggatac cacacaaaga ccacaagtct cgacttctgc 360
aaacaacact caggtggcaa gaccaaacca agagcctcca gaaaggctgc accatgaatg 420
gaaggtctga ctccttttgt caaaaacttg gctgtaagga caaatagcaa cttaagacac 480
tctgaggatg agagggaaag gcctgactca cttcaagtag ggaacagagg caataagaga 540
gaaatttata agactgtggt cagtttcact tctcctgccc tagaatttcc aaagagctg 599

<210> SEQ ID NO 494
<211> LENGTH: 599
<212> TYPE: DNA
<213> ORGANISM: Homo sapiens

<400> SEQUENCE: 494
gtgtgaggag agagcctggg gaataagaaa ggacagagca caaagggtgc aggtggagca 60
agtcagggag gcgtgggcca ggcagaggtg tggggctggg gtccccgaga tcctggtgag 120
atcctggtgg ccaggcagct ctgtggagca gggaggactc tgcatgagct cttggtgcag 180
ctgaatttaa cagcagacac ctcagtccat gaggccagca atgcccagca caggtccccc 240
acaccgacag tggtaacccc cgcctcctgc aggcatttca ggccaggcct tgaaggaggr 300
gaacaccact cagtggcacc tcctgcatga ctctggccgc gtcacttcac ttctcagctc 360
ctctcttgta gcacagggct ctatttctgc cttgcggagt tgttgagtga acaagacata 420
atgtgtggga atgacttcat ggatgagagc aggagtgagg acctggaatg cccaaggcca 480
gcccatagcc acgaataatt ggtggctatg attgcaacag ccagtgtcat gatggacagc 540
agacagaacg ggaagaaact cccagaccaa tgggagaaga cacgcaccac accctctac 599

<210> SEQ ID NO 495
<211> LENGTH: 599
<212> TYPE: DNA
<213> ORGANISM: Homo sapiens

<400> SEQUENCE: 495
ctcaataccc cactgcacct gagttttgga aaactagagt gtggaaaaag cagcagcagc 60
tgcagcaaaa acactgatga gagtcaaact gaatgattat attacactaa tggtaccagc 120
tcccgacagg tgaataaaat gtgcctcatg atagcagtca tacaacaaat accttacaag 180
aaactcacag agaagagggg cagagcaact cagtggaaaa gcaggtgtgg tttcaaagcc 240
tggctctgcc ccgagccatg tgaccttagg aaatagactg tgtccctgag tttcaatcty 300
gtcacctgta aattaggagt aaccatacag atcgcaagtc aacacctgcc cttgcaccgc 360
tgcggggctc agcggtcact gacatgcagt gaaaaagtgg aagttctagc tgggcgcggt 420
ggcttatgtc tgtaatccca gtactctggg tggctgaggt gggcagatca tgaggtgagg 480
agttcgagac cagcctggcc aacatggtga aacttcgtct ctactaaaaa tacaaaaatt 540
agccaggcat ggtggcgtgt gcctgtaatc ctagctactc tggaggctga ggcaggaga 599

<210> SEQ ID NO 496
<211> LENGTH: 599
<212> TYPE: DNA
<213> ORGANISM: Homo sapiens

<400> SEQUENCE: 496
taaaaataaa aataataata attaaaaata tatatatata tatcaataat ccaggcaaga 60
aataataatg atggtgtgat ggtcagtttt atgtgtcagc ttgactaagc tacagtcccc 120
aattattcaa ccaaacatta atctgaagtg ttgctgtgaa agtattttgt agatgtaact 180
aacattcata atcacttggc tttaaataaa ggaggctgtc ctagataatc tggatgggcc 240
tgattcaatc cactgaaagg ctttaagggc tgagtgtggt ggctcacagg aagtgaaaas 300
taaagtagag aaaatctgtg ttgttgtata gagtacatat acttttataa acagaatgtt 360
ggtaaaaata tgaatgttaa aggtactctt gacaagcact cagaaggaaa tgaggaacac 420
gttattggaa actaacagaa agacgatcct cgttttacag tagcagaaag gttagctaaa 480
ttgtgtccaa cagttgtatg gaaagcagaa tttttaagca aggaatttgg aaatttagat 540
tcccaagcaa catactgaag gtacagcctg gtttcttctt gttatttgca gtaaaacat 599

<210> SEQ ID NO 497
<211> LENGTH: 599
<212> TYPE: DNA
<213> ORGANISM: Homo sapiens

<400> SEQUENCE: 497
tactctgaaa agtagagaca ttaactacaa ggtaatattt tcttgcaaac atttaacaga 60
aatttgacaa tttgccttaa actcctcccc cacctccaaa aaggctgctt gaaaattaaa 120
gcactatttt gacaagatga cttcattaca ttccttgaac tttattcatg cccacaaaca 180
ctacaggtat gctttcctta tgattctcaa tcctttttct atggtgttca aatgtgttcc 240
aatttttaaa ggtggaattc tatttgtctt ctagagttct tctctaagag actgagtgay 300
ggatatttag aagtccacac gctacgtata agagacctga ataaatttaa atatgatcat 360
ctgcacatat tttgtgtatt cacctacaaa attatgtaat ctgttatgag acaattttca 420
agttaggaat tcttcagtcg attctactct tacatcaaaa ctccatgcag caatcagcct 480
agacaacctg aaatgttgcc aggccacgga aaacctgcca cagtaagaaa atctaccaca 540
cagaaaatct acaataataa ttctgttcag gtatgaataa tataaaaaaa actatttttt 599

<210> SEQ ID NO 498
<211> LENGTH: 599
<212> TYPE: DNA
<213> ORGANISM: Homo sapiens

<400> SEQUENCE: 498
aatcctccaa acaaccctga agagtaggta tgaaatacta tgactgtacc tgttttacag 60
atggaagaat gaagcatcaa cttaataaac tcttggcgta gatagcgata gtagtagacc 120
ttaatcatgt gttgtggttt gtgatgtact agtgtgtact ctttctattt catctgatat 180
tctattctgt agatgagggt agtggtactc aagactttgc cagggtcgcc aaagctagta 240
aatggcttca agctggaatt ggaatgtaga gtctgagtat gtgttctttg tgttggcctr 300
aaatgcatac aattttggct ttggattatc tgttagggtg tcaaaattac cataaattgc 360
ataataactt agtagctaag aaaaaacttg gagaataaga gattaggagg aatgcagaaa 420
atttgtagta aggaaagtat gaattttgaa aagataaatt gcttgagggg aggaagcagt 480
atggccgtgc tgccctctgc tgctttgctt tggaaggagc ccagaggtgt catgtcttct 540
gtgactgtaa aggttccagg cagttctgcc acatgtggct gccgagtact tgaaatgca 599

<210> SEQ ID NO 499
<211> LENGTH: 599
<212> TYPE: DNA
<213> ORGANISM: Homo sapiens

<400> SEQUENCE: 499
ccagcctggc agacaaagtc agacgctgtc tcaaataata attcttattt tatattacag 60
atttgtcttt ctatcagatc agaataaaag ctccacagag acaggatttt gttttgttca 120
ctgtcctgtc taggatctag cctagggtgt gacacagagt aagcactcat gatgtgaaat 180
gagagaataa gagtggtgcc tgccatgtga ggtcaggata agtttaggac tcatcaatct 240
gaaaaagtaa gagttgagag gagactgaaa tttaaaatgg cattatgtta acagctacam 300
catagcacca gttcttccat ttatctattg ctgtttactg atcactccag aatttagcag 360
cttaaagcaa caataatcat tttattacta tctcttgctg ggggattggt tgttggtagg 420
tagtttttcc tggggtatct caagcagttg cagctaggtg ggactggagt catgtctaaa 480
gtttccttag atgtcttggg gttgatggtg gctgtcagct gggtcccacc tgggactgtt 540
ggccggagca cctatatgtg acctctccat gttaccttac ctacctcaca gcatggcag 599

<210> SEQ ID NO 500
<211> LENGTH: 599
<212> TYPE: DNA
<213> ORGANISM: Homo sapiens

<400> SEQUENCE: 500
atttaatcct ttaaaaaagc cctgtgagga tgctacagtt attatctcca ttttacagat 60
gaggaaacta agaatcagac ctttaaaagt ttgccttctg tcacacagct caaaggtact 120
ggaactagga ttcgtaccca catttctgtg actctaaagt ggaggcacct gatcatatgc 180
aatgtgcctc tttgtcagaa agaaaaagga gagccaagca ggataaaatc taagagggat 240
aaaagggcaa ataattgtca tcttttagag tgtttctaaa gcccagtgta agatgaactr 300
ttagaaaatt attaaatgtg acaaattaat tttatttcag agaataaggg aacaatgcaa 360
ttcagtaagt ctgaacactt caaagaaaca ataacataag caatggctat taatccaaga 420
ataattttga aatattaacc actagccttc ttaagtaaac catatatgaa tagggccata 480
gggatattac ataaacttct tgattgaaaa acttcttgct tcatgaacgc aaaaatttaa 540
atttatgaaa gctaacacat ttaataaatt tgattcaagt tttctgtgga gattacagt 599

<210> SEQ ID NO 501
<211> LENGTH: 599
<212> TYPE: DNA
<213> ORGANISM: Homo sapiens

<400> SEQUENCE: 501
ctgggcaaca gggtgagacc ctgtctcaaa aaataacaac aaatactaaa taaaggtcaa 60
aggggctctt cccagacaga gagacaggaa gaagtctaaa aggatgtaag aggacgtcac 120
aggactactg cctatctggc tctcagtgtg ggaacatcca ctccacaaaa gcagagagca 180
tttgcttcct ggtacaactt ccttcctgca ttcggccaca ggttcttttc gggcactagg 240
aagattgtca gttggctcgt tcattcattt attgaactaa tatgtatagg tgatacttay 300
aggtgataaa acaacatgaa cagataaggt caatatttat aggcaataaa acaacaacat 360
ggacagatga ggtccctgcc ctcatagaac atatgctcta gcagggaaaa cataataaat 420
aaggtgtacg tattataatt tcagggagta cattatgtga agaaaaatat agtggaacaa 480
gagaacagag agtgacaggg gtggtgataa ttttagatag ggtacacaga gaaggccctt 540
ttgaagagac cgatgactct tggacagaaa cctaaataat atgacaaacc ataaaaatg 599

<210> SEQ ID NO 502
<211> LENGTH: 599
<212> TYPE: DNA
<213> ORGANISM: Homo sapiens

<400> SEQUENCE: 502
ttgctcaggc tggtctcaaa ctcctggact caagtgatcc gctcacctca acctcccaaa 60
atgttgggat tacaggcttt gctgggattg ggcatgaggc actacacctg gcccttttct 120
atgggaagca gtagggaata gaaaggtgat taaaaattag accatatggg ttgggttata 180
gatagataga taattagata gacaaacaat ctgaagctta ttcaaatgtt tatgtatcaa 240
gttttctatg gataaagaaa aaaaaaacag taaattctca ctcttcagtc ctaaatgatr 300
taaaatttta gctatttgac tcaaaaagat aaaaatttaa aaataaaatt tgataaagtc 360
tgcagcaaaa tttgtcttct ctgtggaaga aagaaatcca taaaattaaa cttcatgtag 420
tgtctgagcg taaaagctac aaatcagcta aacttgttgg aatgggttaa aattctcaag 480
atcaaacaca taaaggagaa gccagatcat tataatacat taggagccca tttaactact 540
gtaggatttt cccactccac atcccccagg tttagtaaag acttttcaaa agcaaaggt 599

<210> SEQ ID NO 503
<211> LENGTH: 599
<212> TYPE: DNA
<213> ORGANISM: Homo sapiens

<400> SEQUENCE: 503
tagccaggca tggtggcgca tgcctgtaat cccagctact caggaggctg aggcaggaga 60
atcccttgaa cccaggaggc agaggttgca gtgagctgag atcgtgccac tgcacttcag 120
cctgggcaac agagcaagac tgtctcaagt ttaaaaaaaa aaaaattccc aggatactta 180
aaaaataata aactgcctga aacttcatag attaattcaa aagattcagt taaatttata 240
taaaattaat ttcacagctt taaatgtaaa tggtaaataa agttcaaaac tgaactgagr 300
atgatgagcc ttctctgcat aagttcatta ttttaagaaa acaaatattt tataattgaa 360
aattagatat aaaaattcat aactgactac ctaattgctt tgtggctgaa aaaaaattaa 420
cctagacttc tcaaatttct taagactcaa gttcttgtag ctgggcatag tagctcacat 480
ctgtaatccc aggtacttgg aaatttaagg cagaaggatc accagaaccc aacagttcaa 540
ggctgtacta agctatgatc acatcactat actccagcct gaggaagacc tggtctcta 599

<210> SEQ ID NO 504
<211> LENGTH: 599
<212> TYPE: DNA
<213> ORGANISM: Homo sapiens

<400> SEQUENCE: 504
aaaccagatg agtggtgaaa aacaatttaa cattacttct aattctaata tttttatgaa 60
aacaaggaac tgaaaattat tttctgaaac tagatcttaa aacttcaccc acacaaatgt 120
aagcaatcta aatgacaagg aaagaaagag gaaagcagtt acttatgtaa gtgagaaacc 180
tgaagaggat ttgatcagaa tcctcaactt agaatgaacc tcaagatgtg tgacaaaggc 240
catgccactc ttttttaaat tatgaaacat tccaaattgg aatgaattct ctggatatak 300
tatctttgag gaaactcagt cccgccaccc cttcatgtcc atcatcttac aaacatggct 360
taaaacttac ctattctaag aaaccttctc aaaaagctga tcctctactt gctgtacctt 420
caggataaag tttcctctta ttttgtagca taatgactat atctatcccc aaccgaatgc 480
taagctcttt gaggaaaagg attagccatg ttgtttactt tttttggcca caaaataaaa 540
cagagctcta tgcaatggat actcaataaa cattatcaga tactcacagc atctagtcc 599

<210> SEQ ID NO 505
<211> LENGTH: 599
<212> TYPE: DNA
<213> ORGANISM: Homo sapiens

<400> SEQUENCE: 505
acaattttgg aggccaaaac aggagaatca cttgagctca ggaccagcct gggcaacata 60
gcgagactct gcctctacca aaaaaaaaaa aaaaagaact tggtttctaa gattatcata 120
tgctttgtgt tcacggtagc ttttaacaag gtgctggtat caacagctca accctcaaac 180
atccatgcta acagcagaaa atacattgca cagaaagaaa agatggtaga cagtatcttt 240
tagagtgggc aggaatgctt gtatttgtat ttagtactga gtaattattt ccaattttcr 300
aggaagtcac aaagctgcca caaattgttt aactatacaa ttcttccttt gccagggtcc 360
agtgcctgct cagcttatca tttcatactg gcaaacaact atacaacttt tcctcatctg 420
tgatacaaag attaaaataa gcagaggtgg tcacattcta aatatttcct ggttcacacc 480
ttcccctatt agggaaatca cttttgggca caaaagatca tccattctaa ctcttactgg 540
gcaaatatct tgtttgtgtc aactaagtat tttgtacaca gaatataatg ccaatatca 599

<210> SEQ ID NO 506
<211> LENGTH: 599
<212> TYPE: DNA
<213> ORGANISM: Homo sapiens

<400> SEQUENCE: 506
atgaaaaaaa taatacaata ggaagagaat tatgagcctt tttatatacc agactatcaa 60
taagaagcag aaaataaggt gggtgcaatg gtacacacca gtagtcccac cagggacact 120
gaggcagaag gatcatgtga gctcaggagt ttgaggctgc agtgagctat gatcatgcca 180
ctactctcca gcctgagacc ctgtctctga aaaaagaaga cagcagagag tagccattga 240
gctgagaact gcaccatggc aaaagacatc aagaccaaaa tcaagaacta caggactgcy 300
ccttttgaca ggcgcttccc caaccagaac cagaccagga atggctggca gaaatacctg 360
gacctccacc acttcaagaa ggcaatgact gctaaaggag gtaatgtatg gccgggtgca 420
gtggctcacg cctgtaatcc cagtactttg ggaggccaaa gctggtggat tacttaaggt 480
caggagttcg agaccaacct ggccaacatg atgaaaccct gtctctacta aaaatacaaa 540
aattagttgg gcacgatggc agctgcctgt aatctcagct actcaggagg ctgaagcac 599

<210> SEQ ID NO 507
<211> LENGTH: 599
<212> TYPE: DNA
<213> ORGANISM: Homo sapiens

<400> SEQUENCE: 507
caccagggac actgaggcag aaggatcatg tgagctcagg agtttgaggc tgcagtgagc 60
tatgatcatg ccactactct ccagcctgag accctgtctc tgaaaaaaga agacagcaga 120
gagtagccat tgagctgaga actgcaccat ggcaaaagac atcaagacca aaatcaagaa 180
ctacaggact gccccttttg acaggcgctt ccccaaccag aaccagacca ggaatggctg 240
gcagaaatac ctggacctcc accacttcaa gaaggcaatg actgctaaag gaggtaatgy 300
atggccgggt gcagtggctc acgcctgtaa tcccagtact ttgggaggcc aaagctggtg 360
gattacttaa ggtcaggagt tcgagaccaa cctggccaac atgatgaaac cctgtctcta 420
ctaaaaatac aaaaattagt tgggcacgat ggcagctgcc tgtaatctca gctactcagg 480
aggctgaagc acttgaaact gagagatgga gtttgccgta agccgagatt gcaccactgc 540
agtccagcct gggtgacagg gcaagactcc ataattaata catacataca tacatacat 599

<210> SEQ ID NO 508
<211> LENGTH: 599
<212> TYPE: DNA

<213> ORGANISM: Homo sapiens

<400> SEQUENCE: 508
aaagaaggaa agaaagaaca gtacaaacaa taaccaggca tcactggaat gcgaagcaca 60
aattgtatta tttccatcaa ccatgaagat acaaagatta ctaaaggaat aatgccaatc 120
ttctttaacc actaaaccac tctagccatt caactactct taattttaga agttaaaccc 180
taccaaaaca cattcataat ggcaaacgcc ctcagaatct tcaggaaaat accttactct 240
cccaactgag aaaatatggc ctaattcccc tggaataatt cagagattac atactaaagy 300
tctgaaggat ttgttcaaaa agcttcctgc catgagcaat cactgttttt ttcactgatc 360
aggtctttat taaaaataag ctgtccaaaa ttatttgacc tttatggaat aaaccaacaa 420
gctcatgcag caggcttcgt ttcctctgtg gtaggttttt ttttcagcta ctgatgtctt 480
ggttggtagc tgctgccctt tttcccacca gaggtttctc ctgcttaaaa acaacaacct 540
tctttccttt cttccctacc acaggcttct tgactgcaac cccctttctc atctgattt 599

<210> SEQ ID NO 509
<211> LENGTH: 599
<212> TYPE: DNA
<213> ORGANISM: Homo sapiens

<400> SEQUENCE: 509
ccacctgcct cggccttcca aagtgctggg attacaggtg tgagccaccg cgcccagcct 60
caactttttt ttgtaactaa gataaaacat tatctactga tttaccaaag tatttagctt 120
aatttcacaa cagtgacgct attggcattt tgggtgaaca attctgagtt ttctccacca 180
aatgccagtg atgcatctcc cacccacagt cacttaacaa ccaaaaatgc ctccatactt 240
ttccaaatac cctttggata tatggtacct tccccattga gaaccactga aaaatttagy 300
tggtaactgt acttagatca atagattgcc agttaatgaa ctgtggcctc caattcaggt 360
cagagatgta acatagtaac agtgccttga atttaaccat ttccaacgta cacattaaga 420
tcatatagtc tgggccagat gtattggctc acacctataa tcccaatgct ttgggaagcc 480
aaaggcagag gactgctcga gcccaggagt tcgagaccac cctgggaaac atggcgagac 540
tccatctcta caaaaaattt aaaaattagc caggcatagt ggcacatgcc tgcaatcct 599

<210> SEQ ID NO 510
<211> LENGTH: 599
<212> TYPE: DNA
<213> ORGANISM: Homo sapiens

<400> SEQUENCE: 510
tctcttctaa agatacaaaa attagccggc cgtggtggca cacgcctgta gtcccagcta 60
ctcagatggc tgaggcagaa tagcttgaac ccggaaggtg gaggttgcag tgagccaaga 120
ttgtgccact gtactccagc ctgggtgaca aagcaagact ccgtctcaaa aaaagcaaaa 180
caaaacaaaa caaaaaaact acaatctcaa actgtccact tataagaaga gtttcaaact 240
ctataataaa gttcccagtt ttcccttcat ctgccagcat cccataataa gcatctcctr 300
tttgaccatt attaagactc agacatagta gctccagaga agtagatata gctctttcct 360
tttgaaactg caaagcaaaa cccactttac aatttttaag tttttgaact ttttttttgtt 420
tttttgagac atggtcttgc tctattgtgc agactggatc acagtggcac atctatagct 480
caatgcaacc tcaaactcct tggctcaagt gctcctccct gcctccgcct tcagaggagc 540
cagactacag gcatgtgcca ccatgcctgg ctaatttttt atttttgtag tgacagagt 599

<210> SEQ ID NO 511
<211> LENGTH: 599
<212> TYPE: DNA
<213> ORGANISM: Homo sapiens

<400> SEQUENCE: 511
cgcttgaact cgggaggtgg aggttgcagt gagccaagat cgcgccattg cactccagcc 60
aggttacaga gcaagactcc atctcaaaaa aaggaaaaaa aagagatacc taaattctaa 120
cgcttattcc tcactgaaca tactattcag cacgatcacc atgtgctgac ttaggcacca 180
acctaagtgc tgatgataca gtgataaaca gataaatgca atctgtctgt tgttgtcgtt 240
gaatgaatga ggcaagtatg tggtgccata aaccaaacaa gaagagacta atctatgacy 300
tatcaggaaa agcttcccag aggagttacc atctaagtta aattctgaaa aattaaaccc 360
caaaacacga atcatttatt tttgacccat gttaaccttt atcacttaca gattgtaaga 420
ccagcaagca aatgcctatt tctttatgaa gtaaccactt gtctgtaaag gaaaaattag 480
caaaccatca ctcattcaac aaatattaga tacccaccat atgctaacat actagacaaa 540
aaagataaaa catggtctct gctctgatgg ggtttataat ctaacagcac aggaaaaca 599

<210> SEQ ID NO 512
<211> LENGTH: 599
<212> TYPE: DNA
<213> ORGANISM: Homo sapiens

<400> SEQUENCE: 512
agctgagata aggcacgtgt gtaaaaggct gtacaaatgt tagttactat aaggttgtct 60
caaaaaaata aaacccacgg caaagagtat cccaaggcag gctcatttta ctccaattac 120
catttggcac cgagcagatc aggggactta ctgcatgaca cagcaagtca gtggaagagc 180
caaggagtgc actcatccaa gttactgatt ccgatgtcag caaaacctgc tgaaacccat 240
cttcacactg cagttcagag ggtgtcccca ggaagcacct ctctgcaaag catgttcaas 300
gtagttccca gtggcctgcc aaatggtcag cagcaaggtg taactggatg tcgcttccag 360
gaagcagagt gaaaagagac aaggagtagg aaactaatgt ccagagtcgg ccatttgccc 420
cagggaccgg agtggagact gcatttctaa gtgcttcctc tgtccacagc cctcctcccc 480
catacctttt aaaaacagat ttgctggctg ggtacggtgg ctcatgcctg taatcccagc 540
actttgggag gctgaggcag gtgaattgcc tgagctcagg agttcgagac caacctgga 599

<210> SEQ ID NO 513
<211> LENGTH: 599
<212> TYPE: DNA
<213> ORGANISM: Homo sapiens

<400> SEQUENCE: 513
gatacggatg tatagttaaa cctagctttc tgggatctgt gcataatcca cgatttatct 60
ctggaaataa gtcatgtgaa ctcattcaga agtcagccat tgaatacttt ttagcaaggt 120
gtgaccctgt aggtctgctg atttgcctgc taaaagaccc tagcaacagt ttggagagtt 180
ggctgtaagg agacagggat catgtcagaa caagttaggg gctactttaa aagtctgagg 240
ccacattggt gcagtggcca tgtaaatgga gaggaaggat atagatccag agtcgaaggy 300
agactggcca gcccagccct ggtggttgac cggagtgagt ataaagagct tggtgagtgg 360
ggcgctactg ccatttactg aggcaggagc tacaagggag gaatggcagg tatgtaatgg 420
tgagtaggag gaatgagaaa gtggctgagt tcagtttggg gattgaggta cccatagatc 480
aaccaggtgg acgtctcact cagtaggtat gaggtctggc acttgagcaa gtggtctggc 540
ctagaggtga cagatttgag ggtcgtgagg ttattggggt aatcataaga ttgaaggag 599

<210> SEQ ID NO 514
<211> LENGTH: 599
<212> TYPE: DNA
<213> ORGANISM: Homo sapiens

<400> SEQUENCE: 514
ctagtatcac aatctaggtc aaggtcattg gagaaatcac aaaatcacac catctcagca 60
ttggaaagtg atcatcatgt gtcaacaaat attttccaag tgaccatgtg ctagatgcta 120
aggaaacaca aatgattatg acaaaatccc tattcaagtc atgtgtgcta agtacttcaa 180
tacaggagtt aactaaggga tatgggagta tagcaggaag aataaaacag cagatttttc 240
aaaataagtt gccaagaatg aacttgggat caccacatcc accatctgcc aatattacam 300
acagaagaat cgtggtgatt caggataaag agaaagtaag gctgcagtca cagcagggct 360
aggacttgta gcctcctaga atcaaggtct tgctctccta tgtggttggt ttaaaaaata 420
gttaaaggca cccctgtaat cccagaactt tgggaggcca aggtagttgg atcacctgag 480
gtcaagagtt caagaccagc ctggccaaca tggtgaaacc ccatctccac ttaaaaaaaa 540
aaaaaaaaaa aattagcgag gcgtggtggc atgtgcctgt aatcccagtt actcaggag 599

<210> SEQ ID NO 515
<211> LENGTH: 599
<212> TYPE: DNA
<213> ORGANISM: Homo sapiens

<400> SEQUENCE: 515
tggcagaagg tgatgagcct ggctccagtc tgctggcgaa ctcccctctg atggaggatg 60
ctccacagag gctgcggtgg caggcccacc tggagttcac ccataaccac gatgtggggg 120
atctcacctg ggacaagatt gccgtctccc taccccgctc tgagaagctc cgctccctgg 180
tgctggccgg catcccacat ggcatgaggc cacaggtaag gtggccacag ggacccacag 240
ggtgttgaga gggtcctggc cccatgatca ggtgtcacga gaaagactga gtgcccttgy 300
ggctcccttc cctcagctgt ggatgcggct ctctggggcc ctgcagaaga agaggaactc 360
tgagctgtcc taccgcgaga ttgtgaagaa cagctccaac gatgagacca tcgctgccaa 420
gcaggtgagg ccggtggcac tgtgcaggaa gagctggagg ctgtgtgggc tcgcaggaga 480
gagggagcct gcctggggtt cttagagtgt gcccttgttg tggggtaggg gaggatattt 540
gctccttcct tggtcctctg caggccaaag aaagaattgt ccaaaaggcc atcagtgct 599

<210> SEQ ID NO 516
<211> LENGTH: 599
<212> TYPE: DNA
<213> ORGANISM: Homo sapiens

<400> SEQUENCE: 516
gtgggctgcc agctattttt tgcagcctaa tttttccagt gatggatgaa tgtaagacat 60
caatgtgttt attttctcat caatatctcc tggaattgct ttcagttgca ctcatttgct 120
gtatataatt tcctggcaaa actacttaca gaatttctaa atttggtttc tgtaaatcca 180
tctaagtaaa atggccacca tcatgccaag cactaaggat taagcaataa ataaaacaaa 240
gctcctcaag aagtattcat tctagaggga aatgacaggt taataaatat gtaaaaatgy 300

```
catgtggtga taagtgctgt aaataaaacc aagtgacaca gagtgtgttt tacattgaag    360

tcagggaaga cctctttgag aagatgacat ttgattccag agagcagaat gtgtgaggga    420

gtgaaccaag cagaggtctc aggcagaagg aacagtcaag agcaggatta tgttgttgtt    480

ttatttattg gagctttctt tttttttttt ttttggagac agaggcttac tctgttgccc    540

aggctggagt gcagtgccgc aatcttggct cactgcaagc tctgcctcct gggttcaag     599
```

<210> SEQ ID NO 517
<211> LENGTH: 599
<212> TYPE: DNA
<213> ORGANISM: Homo sapiens

<400> SEQUENCE: 517

```
tcctcttagg tgccctaatc tcctatgtta atataaaact ttcaatataa atgtctcagt     60

ggccttcttt gccagtcagc ccttaaggag ctttattttc ctcaaaaact cttgtctgct    120

atttttcaga gctacctgaa agctgagttg cagttagcta actagtattt atttcacttc    180

tacttctggg ggaggtggtt atccccccacc cctggtagtg ggaatgacag aaggtccatg    240

aagttgcttt ccttatcctt tccggaaact gccaggccat aaatattaga ggaatgatcs    300

agggagggac tcaggtaagt aaccagatta ctgtggatga ttgattattt gatatgagga    360

actagaggag cctggcacag ttatgagtgt gagcaagtcc gcgtagggca gctgagttta    420

actggtactc ctgtgcagga aggggacacg catacctgt gtgctgaatt ctagggtgag    480

gttcctgttt ccctgatata tgtttccagt ctgtgttctc ccttacacag tcacacctca    540

gtctcgccta aaggaacact ctatctctgt cacaaagaaa atattgactc agggaaggg     599
```

<210> SEQ ID NO 518
<211> LENGTH: 599
<212> TYPE: DNA
<213> ORGANISM: Homo sapiens

<400> SEQUENCE: 518

```
tatgtttcca gtctgtgttc tcccttacac agtcacacct cagtctcgcc taaaggaaca     60

ctctatctct gtcacaaaga aaatattgac tcagggaagg gtaagcagac ccagctgcaa    120

accttgtagc aggagtggag ttcaaggtag agtgtgattc ttagacttac tttgctcttc    180

tgctgatgcc agttttggag gaggcagctg agaaatttgt atgatactat ggatgttcac    240

ctcagatgtc cttgtcataa agggtgatat aaatgatcaa caaaaattac tagggtaacy    300

ggagggggag tcagttctag aagttctgtg ccactagctc cttcatcgtg gagtttggta    360

gggtccaggt ttcaaggctg tctttacata ttgctgagta attgctgtat ttagcagcat    420

tctgagagaa cacaggtggg ttccaagata acgttgccaa agcataaagt gcattggagg    480

caagtgcgag gcaggtgttc agagatgagg ctgcagggag tagcaggggc tgctaggtca    540

tgcagggtct tataaatcaa gttaacaaat ttggacttta aagcaaaggg aaggtttta     599
```

<210> SEQ ID NO 519
<211> LENGTH: 599
<212> TYPE: DNA
<213> ORGANISM: Homo sapiens

<400> SEQUENCE: 519

```
gaatataaaa aactaagtaa gtgtatttta aaaacagatt ttagatcagg catggtggct     60

tgtgcctaca atcacaatga cagagtcaga ctgtgtctta aacaaaacaa aacagatttt    120
```

```
ggcagagaga agcgatctca caccaaggga tggtgagacc ctggagaaga ggccaagcca    180

aactaacagc atgtgactgt gctttttgag agtccctcag accagtggca gctaccatgg    240

cacagctgtc gtacggtgtt aaggctctgg cttacccact gccaacagaa atgggagaar    300

aaagaggcag gaaggaaatg ggtagtgcag tagtgagtac acacagtgag aactggatct    360

agatggaaaa gcaattccaa tctccacacc ttccaaaatg tgcatcctga ccagctccga    420

tctctccggc cgggaacgaa tcttccgttt gagatagtcc tctgtctaca gaaaaaacac    480

accaagaaac tctcaaatcc aggtcacagg cttatggcat ggacaggatc acaacagcag    540

ccttggccat ggtagctgct gaccacctct gcagttccca caaccttaac ttggtgact     599
```

<210> SEQ ID NO 520
<211> LENGTH: 599
<212> TYPE: DNA
<213> ORGANISM: Homo sapiens

<400> SEQUENCE: 520

```
cttgctattc gtctctgggg gaggggagag acatatataa agagactttc agaaaacaga     60

tcaactgctt ttttcctctc aagaagagaa gatgaggttt tgttcaaaat cccactataa    120

gagactgctg ttaatgcagt ttagtggaac agattaaaca caatccaaac aactcaagct    180

catgaaagaa gcagtccaat tactgaccca ttgatgagag gtggggaaga agattaaaca    240

catataaaca catatataca aaatgtaagc tccataaatt ttctgaaaaa gaattccaay    300

ggctttttta tatgtggtat ttatagataa caggctaagg aagttgaaca tttaactaca    360

gaagctcaac tatttctcca cccccactcc aattaaaata tctgtttcaa aaagtcatct    420

gaatacattc cagagctgta atctgtcttt cagatctgtc agtcccctaa aagagcctct    480

tacttgtgcc tatattagac atacggtctg tgaatagaca gtatactgat gttatttgat    540

ttcatttact ttttttgtat gtttgagaca gggtctcact ccgttgccca gactggaat     599
```

<210> SEQ ID NO 521
<211> LENGTH: 599
<212> TYPE: DNA
<213> ORGANISM: Homo sapiens

<400> SEQUENCE: 521

```
cagtccaccc tggcggggtc gcagggttgg gatggcggct ggaggcgatc atggttcgcc     60

cgacagctac cgctcacctc ttgcctcccg ctatgccagc ccggagatgt gcttcgtgtt    120

tagcgacagg tataaattcc ggacatggcg gcagctgtgg ctgtggctgg cggaggccga    180

gcaggtaacg gatcccgggc tgaggggctg ggccgggagg gacgggcccg ccccagcacg    240

tgccgggctc tgttccgggc tgggcttagc caccccggag ctgcggcccg gctattttcr    300

gctgggtgtt ccctgtcctg aggagctgcg gccccaggaa agcaagggca ggagatccgg    360

gagccgccac ctgttgcctc acgtgttctc agtccgagag ggttcgagac gcggaggagg    420

ctgggagaaa ttcagcctgt agtttcaggg aattcatttt ggccatcccc gcaggagtac    480

gctgctaacc acagacaccg agcgcttgtt tcgtactgtt gtgctcatta tttcactaat    540

cttttcttgt gtaatccatg aagatcttgc aggcttgatg gtgtttttcc cacattgca     599
```

<210> SEQ ID NO 522
<211> LENGTH: 599
<212> TYPE: DNA
<213> ORGANISM: Homo sapiens

<400> SEQUENCE: 522
ctatgccagc ccggagatgt gcttcgtgtt tagcgacagg tataaattcc ggacatggcg 60
gcagctgtgg ctgtggctgg cggaggccga gcaggtaacg gatcccgggc tgaggggctg 120
ggccgggagg gacgggcccg ccccagcacg tgccgggctc tgttccgggc tgggcttagc 180
caccccggag ctgcggcccg gctattttca gctgggtgtt ccctgtcctg aggagctgcg 240
gccccaggaa agcaagggca ggagatccgg gagccgccac ctgttgcctc acgtgttcty 300
agtccgagag ggttcgagac gcggaggagg ctgggagaaa ttcagcctgt agtttcaggg 360
aattcatttt ggccatcccc gcaggagtac gctgctaacc acagacaccg agcgcttgtt 420
tcgtactgtt gtgctcatta tttcactaat cttttcttgt gtaatccatg aagatcttgc 480
aggcttgatg gtgtttttcc cacattgcag gggagaacaa agcccggaca gcttgttgtt 540
tgccctagcc catccagcta ttaagaacgg aactgggatt tgaacctggg tgcactcca 599

<210> SEQ ID NO 523
<211> LENGTH: 599
<212> TYPE: DNA
<213> ORGANISM: Homo sapiens

<400> SEQUENCE: 523
ggctgtggct ggcggaggcc gagcaggtaa cggatcccgg gctgaggggc tgggccggga 60
gggacgggcc cgccccagca cgtgccgggc tctgttccgg gctgggctta gccaccccgg 120
agctgcggcc cggctatttt cagctgggtg ttccctgtcc tgaggagctg cggccccagg 180
aaagcaaggg caggagatcc gggagccgcc acctgttgcc tcacgtgttc tcagtccgag 240
agggttcgag acgcggagga ggctgggaga aattcagcct gtagtttcag ggaattcath 300
ttggccatcc ccgcaggagt acgctgctaa ccacagacac cgagcgcttg tttcgtactg 360
ttgtgctcat tatttcacta atcttttctt gtgtaatcca tgaagatctt gcaggcttga 420
tggtgttttt cccacattgc aggggagaac aaagcccgga cagcttgttg tttgccctag 480
cccatccagc tattaagaac ggaactggga tttgaacctg ggtgcactcc agagcctgag 540
ctgagcacgt agccccttgg ttttccacag tgcctgtgta gttagtgaca ggactggaa 599

<210> SEQ ID NO 524
<211> LENGTH: 599
<212> TYPE: DNA
<213> ORGANISM: Homo sapiens

<400> SEQUENCE: 524
caaagtgatc aaataattcc tccataccac atacctcaat tttctagcat aattctgagt 60
gatgcagagt gccacaccta tcagcagaat gcttatttta aaaatgtccc tgatactacc 120
atgtactttt cctcctcctg attttcaaat catcccagta ttaacatcca tccctaagga 180
atctcactag tagtttcaga aaaatgaatt tgatttgttt tacacactgt gggacagaca 240
acaaacaaga ccccttttcc tctgcctctt cgatgcttct cctgggcatg aaaacagccy 300
gaactgtggc aacagctggg gatcattaaa ctgacagaaa tagcttagga gactccaatg 360
gtgtgtgaag gcgggaggag agcctgagta tcagattaaa aaaaatcaaa agggcaaaag 420
gaaagggggg cagggcaggg aagcctaagg agtgtatcac acctaaattt cctttaccac 480
agccaagaag atgcagtgaa gcaaatgaca ggatacatga atgcggccta aattgcttag 540
cctcctacct attcctagat ggaaggttta gtcaaaccta aaaatgtggg tctcaatga 599

<210> SEQ ID NO 525

<211> LENGTH: 599
<212> TYPE: DNA
<213> ORGANISM: Homo sapiens

<400> SEQUENCE: 525
tccagcccgg gcgcacggag ctgagaagtc gccgccagcg gagggcgtgt ggccagcggc 60
aaccaagagg gtgggaaaga tgggaccgtc gctctcgccg ccgcggccac cacagacact 120
gccgccgccg gctcctctca gccacggaag ctgcgggccc gcccaccacg cccgcctccc 180
gtcctgaaga ctgtccgctg gagaagtgac ggcggcgcta gccaatcaga ggcctgatcg 240
gggtcgtgat cggcggacta aagggcgggc ggagaaggaa gcggcatgaa gaaggcgaar 300
acggcggcct gacttcctgt gactgacggc acggcgcagc caatgggcaa cggggagatg 360
acctcatctc tgaggaaagt ctggaactgg ctgagctgcg gcgagggggt tggcgacgag 420
ccgggggcgg agctctgggc cttaaagagg ccgcagccct gtggtcaccc tgtgaaggga 480
agggcggtgg accctgccgg atcttgcgaa gttgccaagg ggtcaatgcc caggcgcgag 540
taattactgc attaatccca gaccccatcc cgattcttgt cggggactga agggtctcc 599

<210> SEQ ID NO 526
<211> LENGTH: 599
<212> TYPE: DNA
<213> ORGANISM: Homo sapiens

<400> SEQUENCE: 526
gttttttttt ttttttttt tttgagacaa agtctcactc tgccactcag gctaaaatgc 60
agtggcacaa tctcggctca ctgcaacctc cgcctcccag gttcaagtga ttctcatacc 120
tcagcctccc aagtagctgg gattacagtc gcccaccacc acacctggct aatttttata 180
tatattttta gttgagatgg ggtttcacca tgttggccca ggctggtctt gaactcctgg 240
cctcaagtga tccaccagcc ttggcctccc aacgtgttgg gaatccaggc ataagccacy 300
gcacccagcc tagttttaag ttgtttaaca gttttggcag ttattaacaa ttttttttt 360 tttttttga gacagaatct tgctctgtcg cccaggctgg agtgcagtgg cacaatctca 420
gctcactgca acctccacct cctgggttca agcgattctc ctgccttagc ctcccaagta 480
gctggactac gggcgcccac caccatgccc ggctaatttt tgtgtttttt gtttgagaca 540
gtctttctct gtagccaggc tggagtgcag tggcacgatc tcggctcact gcaacctcc 599

<210> SEQ ID NO 527
<211> LENGTH: 599
<212> TYPE: DNA
<213> ORGANISM: Homo sapiens

<400> SEQUENCE: 527
agtgatctgc ctgccttagc ctcccaaagt gatgggatta caggcatgaa ccaccgtgcc 60
tggctgaatt atgtacttct gaaaggtgaa ttttataata tgtgatttat atctcaactt 120
ttaagaacga gagccaggca cagaatccca tacctgtaat tccagaactt tgggaggcca 180
aggcaggaga atcatttgag cccaggaatt caagaccaga ctgggtaaca tagagaggcc 240
ctgtgtcttt aaaaaaaaaa aagatattca gtagaagatt cagatttaat aaatattttts 300 gctgggtgtg atggctcatg cctgtaatcc cagaactttg ggaggctgag gcaggtggat 360
cacttgaagc caggagtttg agacctattt aaaaataata atatttttac tactgcatca 420
aggatatttt tattttttt atagagatgt gaatctcact atgttgccca ggctggtctc 480
gaattcatgg gctcaaacaa tcctcctgcc ttggcctccc aaaatcctgg gattacaggg 540
ataagccact atgacaggtc tctgcatcag ggacatttgt aagttaaact attctttttt 599

<210> SEQ ID NO 528
<211> LENGTH: 599
<212> TYPE: DNA
<213> ORGANISM: Homo sapiens

<400> SEQUENCE: 528
agagatcagg gttgagagat gaaggcgatg ttgttttagc gttacctacc agtgctgccc 60
tctcttctca tgcttgctta cttccttcag gagtcatttt aactccaacc tccttgtgtc 120
caaactggct caaagcactc caaagtggag gtgaaaggca atcacgctga tttgttatac 180
ccaatttgag acatttttct gttgtacata aaagcaaaaa agaaataaaa gcaatagaat 240
gttccataaa cttaaaaaaa atgttataac aatcacaccc actcatgggt tctgaaaagy 300
acaataatgg agtcaggcta gtacaaacgc ctaagagcaa agtctgagtg aaagtgatca 360
atctagtttc actttggaaa ctggatagaa actagcaacg gaagtcagac tctatgaggt 420
aatttttgca atagttgttg gccttataat taataagaga taagataatt ttaacctaaa 480
ggtcatttta agcttacaac aactagagat aattttatta taagttttaa aaactaactt 540
tattgaactt caattcagac acaataaact tcacctagtg tacaattcaa agcgttctg 599

<210> SEQ ID NO 529
<211> LENGTH: 599
<212> TYPE: DNA
<213> ORGANISM: Homo sapiens

<400> SEQUENCE: 529
gtaaaaggca acatttacaa tctcattaaa acacacaaag tgtctaaaaa caaatctaac 60
taaagatgtg taagatcatc acagagaaaa attttaaaaa cccattggga ggccttacaa 120
aagatctaaa taaatgtgga aaatatgtat ttacagtata atattataaa aatatcagtt 180
cttcctaagt tggttcatag atgcaatgca attccaatca aaatcctgag taattttata 240
tggaaatgca aatgaccaag aacagacaag aatgaaactc ttgaacaaga acaaggtggr 300
aggacttact tctcccatac aacagggctt attacagtta tcgtaattaa aactgtgagg 360
gcaggaatac acaaatagcc caatggaacc aaatagcaag ctcagaaaca tacccacata 420
gctaagtcct tgatatatga aagacgtagc tctgttgatt agtggggaaa gaagagtatt 480
ttcaataaac ggaatccact tgaaaaaaaa ttaacttgtg tcttacctta ttcccatatg 540
aaaaattatt tccagaaaca caagacacaa aactcataaa ctataaaaga ctcatataa 599

<210> SEQ ID NO 530
<211> LENGTH: 599
<212> TYPE: DNA
<213> ORGANISM: Homo sapiens

<400> SEQUENCE: 530
acaacagtaa caaaaaatta gcagggcgtg gtggtgtgtg cctgtagtcc taactccttg 60
ggaggctgag gtgggaggat tgcttgagcc tgggaggtcg aggctgcagt gagctgtgat 120
cacaccactt ccctccagcc tggacaacag agcaagaccc tgctcaaaaa taaattaata 180
aattaaaaat acaagttgct gcagcttcta tttttgtaaa ttgtattttc ccccattgat 240
tcacataata taagcaatgt tttagcatga taatggttta gcatgatatt gggaagaacs 300
aagtaattag gaaaggttat agaaacattt tactagtcta tataagccat cagaaaagag 360

```
gtacacgctt ttctttttt ttcttttct tttttttgag acagggcctc attctgttgc    420

ccaggttgga gtgaagtggt atgattttgg ctcattgcaa cctccacctc cagggctcag    480

gcagtcctcc cacctgagcc tcccaagtag ctgggactac aggtgtgcac caccacactc    540

agctaatttt ttaaattttt tgtagtgatg aagcctcact atgttgccga ggctggtct     599
```

<210> SEQ ID NO 531
<211> LENGTH: 599
<212> TYPE: DNA
<213> ORGANISM: Homo sapiens

<400> SEQUENCE: 531

```
ttgccccact gcactcctgc ctgggcaaca gagcaacact ccgtctcaaa aaaaaaaaaa     60

aaaaaaaatg atgacgacta ctttttatgg cctattcaac acagctcatg gttggattct    120

tcttcggacc gaaccatgaa tacactcaga acatgaacac accactcact gcagagtatt    180

atttaaggat ttgttggcaa ctggccaaga aggaggttct atgctagtca ctgatcactg    240

aggtagaaac acactctaca acagcagaag cgagacaagg atgttgacac aaatgcaacr    300

taaaatgcct gggactgatg tgccttctcc tgtgataaaa gagaagattc ctgaagccac    360

atacctaaca caattttctc tcagcttcaa ctctagggat caggtcagcc tcacttctgg    420

aaaacatgtt tcactgtgat gtttatcaaa tgcaacttaa actagggatt caactacaat    480

tacacagtca cattcctgta gtgaggacac atcatctcac taggtagggt tctctgcctc    540

ttaaagaatg aaaagataag gaaacgatca ccaaatgggt tacaccacca tatcctgca     599
```

<210> SEQ ID NO 532
<211> LENGTH: 599
<212> TYPE: DNA
<213> ORGANISM: Homo sapiens

<400> SEQUENCE: 532

```
ataaaaatat aaaaaaccaa aactacaatg tacacttatg aaagaacaac agtaagaaag     60

ggaaattaca ttttagtata aatacataaa attttgattc atacccactg aaaatgtttc    120

aaggacacct aggggtcctc agaccacact ttgaaaacaa tgctctatac tgtagtgcct    180

cttcagttag ggcacgctat acaaatattt acaaggcatg gtctcaggaa catacttaac    240

ctaaaaaata tcctaatgat tttgctaaat cacccattca acaattatta agtgcttacr    300

atacacgaag tattcttata cacaaggcag agaatcaaag aggaaaaaaa aaatcctcct    360

tgtggcactt acattctacg aagagacagc cacaaccaat aaacaaatga actatctatt    420

ctgcaaataa gtggtatgaa ggaaaataaa agcaaggttt tacaaaatag gatggtcagg    480

gagtgcgcct aactaaaaaa gtaacttttt tttttttta agagacatgg tcttgctctg    540

tcacccaggc tggagtgcag tggcacagtc atagctcact gccacctcaa attcttggg     599
```

<210> SEQ ID NO 533
<211> LENGTH: 599
<212> TYPE: DNA
<213> ORGANISM: Homo sapiens

<400> SEQUENCE: 533

```
tttaagagac atggtcttgc tctgtcaccc aggctggagt gcagtggcac agtcatagct     60

cactgccacc tcaaattctt gggctcaact gatcctcccc actcagcctc ctgtgtagct    120

ggtactacaa gcacatgcca tcatgcctgg ctaatttgtt gttgttgttg ttgttgttgc    180

tgtttcacag agacagcatc tcaccatgat gcccgactag ccttgaactc ctggcttcaa    240
```

gtgatcctcc ccattcggcc tcccaaagcg ctgggattat aggtgtgagc caccataacr 300
ggcccaaaag taacatctga tcaaaaatct caaggtgatg cgggaacaag ccatgaggct 360
actcagggaa acgtgctcta aatagaagga ataacaagta caaaagccct gatatgcgag 420
ctaaggtgct cagggacaac aaacaaagcc aatatggttg gggtaaaaca agcaagggag 480
agaagagaag cagataaaat aagagttaca aagcagttca tgtgggactt tgtagacgag 540
tataaggact gtggcttttt cagtgaatga gaataactgg caggttctga gcaaggagg 599

<210> SEQ ID NO 534
<211> LENGTH: 599
<212> TYPE: DNA
<213> ORGANISM: Homo sapiens

<400> SEQUENCE: 534
tggaattcta aaatcctata cccttgcccg cacccattcg tgtagtgaag ggcgcgcgt 60 taggcgcaga ggccacacgc tccgcaagtg aacccgggca cctctctgaa cctattccgg 120
gctgagggcg gggagcgggt ggctgcccga tttaaaaaca tgtatatgta tgtgtatgtg 180
tatgtgtatg tgtatgtgta tgtgtatgtg tatatgtata tgtatatgta tatgtatatg 240
tatatgtata tgtattatga gtgaagtcca tgactgcaac agggagaaag gagaaaggcr 300
aaaggggaga gagcaacaag gtaagccagg cccactgtga tgacagctgc ggtcatgcag 360
gcccttcgta tccgccttcc tccccagcaa tgggagagag cccagaaaag gagaaataac 420
cccaactcga tggggtggaa aagggggaag cgctttccgg aaggcttccg ggatggggtc 480
accagagtca gaggaaggag taacagtaga tagaagaaga agtggtcagg ggcgttcttc 540
taggtttggg gcggacccgc gtgaagatgc aaagactgaa aaggggcggc tcactttac 599

<210> SEQ ID NO 535
<211> LENGTH: 599
<212> TYPE: DNA
<213> ORGANISM: Homo sapiens

<400> SEQUENCE: 535
ctgtcagcta gttcctgcct ccttttccaa cgttatctgc tactttcccc ctcatcacta 60
ctcttctaga tcttcacaga cctgatcgtt attctcatgt gagctgaaaa gtcatttcct 120
gagagaggcc ttccccaacc accaattaaa aataacccct ccactcctac ctgccacttt 180
gtaacctatt gttctgtttt cttcatggca tgtattatta ttctgaaatt atttacatat 240
ttattgtctg ttttctgtaa ctaataataa ctggcattta ttaagcacat gccacgtgcy 300
gaatattgtt acaagtacta cattttctca cttaacctca taagtagtat aggtattatt 360
tccattttac agaagaaatt gcaggttcat gaaagcaaga actttgtcca tcttgtttta 420
ctgctatatc tctaacacat ggaacagtgt ttgggatata gtagttgcaa aaaatttttt 480
ttgttggttg gatagatgaa tgaaaaactc ccaaattgac gtttctacct ctgacatctc 540
cccataaaca tagatttata gatgtaatca cctacttaac agctccactt ggatttcta 599

<210> SEQ ID NO 536
<211> LENGTH: 599
<212> TYPE: DNA
<213> ORGANISM: Homo sapiens

<400> SEQUENCE: 536
tcagttatgt ataacaagcc cctttccaca acacctgagc ttatgctaat gtgataatct 60

```
gggagagact aaggattggg ccagtcacca gagacaccaa gtgattagag gattagagga    120
ctggaaatat cagcgccatc caccaacctc caggaaagtg ggggtgggta tgtaggacat    180
agagtggggg ctctgagatc aagctctata aaaactcttg gataacagga tttgatgagt    240
ttctctagct actgggaggg tgaaggccag gagagggcag ggaagttcca ataccaccay    300
tccccctggc accccacgac actgtgccat ccgtccctcc ctctgactgt tcctctgcat    360
cctttacaat aagccaggaa atgttaagtg aagtgtttcc ccaggttctg tgagccatcc    420
tagcaaatta tcaagcccaa ggagagggta tgggaacccc aatctatagc tagttggtta    480
aaagcaaatg taaaataacc tggggcttgg gaccagcatg ggaagtgggg ctaagtcttg    540
tgggactgag tcctcaacct gtgggatcag acgctatctg caggtaaatg gcatctgaa     599
```

<210> SEQ ID NO 537
<211> LENGTH: 599
<212> TYPE: DNA
<213> ORGANISM: Homo sapiens

<400> SEQUENCE: 537

```
tccctcgtcc caccctctcc cacacgcttt catgaattcc tactcatcct tcagccccag     60
gcttggctgt cacctcctct gacagctgca cccttcctga tgcaaccagg ttgggtgacc    120
ctcctctgtg tttccaaagt accctgtgct ccctccagca cagcttctct atcctgccta    180
ttcacctgcc tgttacctgc tcctaggcgt gagctccata aggacaaagg aacttggtct    240
gccctgtggg gctgtggcct tagcacctag cacactgttt gggtccatca gtatttgttr    300
agtgaaatat ccgtggaaag ggccagtctc caagaagaga cttcactaat aaagagtatg    360
acacagattt ctaattcctg gcatctccac atgttcacac acactgatcc tgacatctat    420
ctactctgtg aaagaggaag caacccgagt ttacaaagat ggaaagtgaa cagagcaagg    480
cctctgttat tatttattgt tgtatgtccc tgtttcttaa agcaacaggc actatcccaa    540
gttcatacaa cctgtgcatg aggctctcaa actctgtgcc ttggttctcc caaggctaa     599
```

<210> SEQ ID NO 538
<211> LENGTH: 599
<212> TYPE: DNA
<213> ORGANISM: Homo sapiens

<400> SEQUENCE: 538

```
caatgtggtg aaaccctgtc tctactaaaa atacaaaaat tagccagatg tggtggctgg     60
cgcctgtaat cccagctact tgggaggctg aagcaggaga atcacttgaa ctcgtgaggt    120
ggaggctgca gtgagccaag actgcgccac tgcactccag cctgggcaac aagagcgaaa    180
ctccgtctca aaaaacaaac aaaaaaaacc aaaaaccaaa aaaaaacccc aaaaacctgt    240
aacactgcat gatctcatgg gcattttcca ttcattttga atggctgcca aatggaatay    300
gaattttgac acatggtagc aaagctctag ttcctcaaag tccaatgtcc taatttctgc    360
atttatgaga ctctgggcaa actaaaccag tccctcaaca gtcacagagc catcccacca    420
aacggggcta attataatat atatatattc ccctggacct gactctatag agtctgtgct    480
cttaacctct gcaccaacat tttcaaacca cagaacatta gtggatcaag accagcatag    540
gataagacaa gccaaaggac actaggcaat gaagcctcag aggacattat atatagtaa     599
```

<210> SEQ ID NO 539
<211> LENGTH: 599
<212> TYPE: DNA
<213> ORGANISM: Homo sapiens

<400> SEQUENCE: 539
agtctgtgct cctctttcct catttttaat tcttctctct gatagcagat tcagcaattt 60
caacagctac ttctgccagg tgaaaggagg agggagcact ggcccctctt ccttcaggtt 120
tgtgtcagga cttcctgctg ggtgtctctc agttcatctg gggagaggct ggagtagcca 180
cagcaagtgc tcttggtgca ctggggtttg aggtggagag ggcaactcct gtgtgtgtcc 240
cgccagcttt gttaaaagcc accatgtgga gggtagccta gtgaagggat gtaagagtgm 300
tacaggttaa gccctgggct ttcttgactg taggagcaaa tgacaatggg gagtcagatc 360
acctcaagtt ccatgccaag gaggtaagac acgaggaagc agaaaatagg tttccaagtt 420
taggcctctg ccaattgaag aaaaaaagga cttaaagtta ccccataaat gtgtgtccaa 480
ctacgagggc tgcattcatc ttagactcca tctcccctct ccctgctacc ttaatagctt 540
tgctaggagg agccagcata ttactcaaaa ctgcattttc ccagacactc caagaaagc 599

<210> SEQ ID NO 540
<211> LENGTH: 599
<212> TYPE: DNA
<213> ORGANISM: Homo sapiens

<400> SEQUENCE: 540
cttacacatc taaccaggta actttcaaag aataagctta tgaaaatcta acttaagtta 60
ttaaaatatg caagtgaaag gtctctatat tgtgtaataa cttataaaat ggtgtaaaca 120
tgcatgcatc atcttatttc tcacaacaaa gctatgcaga cgatacaact gtcataccat 180
tttgtagatg aggaaattga ggtttagacc gattaagcaa cttgctcaag gtcataaagt 240
aaaaggtaga gcagaaattg gaacccagct ctgtctgaat gtatagcctg aatcttcaay 300
cacctctctt ttctcataaa acacaccagt tctctgtatg tttatttttt ttttttttatg 360
ttttgtcaag atggggtcct gcattgttgc ccaggctggc cttgaattcc tggcctccag 420
ttatcctcct accttggcct cccaaattcc tgggattaca gtcatgatga aacactgcac 480
ccccactcct ctgttttaaa atgacactat attgatagtg ttatcagcat gacatgctga 540
tatggatgga aaaaagtgat ctacatactt actaactagg ggaaaatcca ggtgatttc 599

<210> SEQ ID NO 541
<211> LENGTH: 599
<212> TYPE: DNA
<213> ORGANISM: Homo sapiens

<400> SEQUENCE: 541
cctatctggc tctcagtgtg ggaacatcca ctccacaaaa gcagagagca tttgcttcct 60
ggtacaactt ccttcctgca ttcggccaca ggttcttttc gggcactagg aagattgtca 120
gttggctcgt tcattcattt attgaactaa tatgtatagg tgatacttac aggtgataaa 180
acaacatgaa cagataaggt caatatttat aggcaataaa acaacaacat ggacagatga 240
ggtccctgcc ctcatagaac atatgctcta gcagggaaaa cataataaat aaggtgtacr 300
tattataatt tcagggagta cattatgtga agaaaaatat agtggaacaa gagaacagag 360
agtgacaggg gtggtgataa ttttagatag ggtacacaga gaaggccctt ttgaagagac 420
cgatgactct tggacagaaa cctaaataat atgacaaacc ataaaaatga tctggagagt 480
attccagaca taagaaattg caagtgcaaa ggcactgaga aaaggcttgc cttgaaaaga 540
aaactaaaat agaagaaatg aggactctga ccaggcgcgg tggctcacgc ctgtaatcc 599

<210> SEQ ID NO 542
<211> LENGTH: 599
<212> TYPE: DNA
<213> ORGANISM: Homo sapiens

<400> SEQUENCE: 542
cattcattgc tgactccaca ggctcaaatc atcctgttaa aattattaaa atcccaaaga 60
aatctggaaa actcaaaaga aatgtctaag tgtttagaaa agtagcattt acataattat 120
tatacattgt atataaattc tgatagtaga taattagggt ttccaagata ggagaagaaa 180
atattgacaa ttctctttta ttcatatttg acaggatttg gataaagctc ctattgtcgt 240
ttttttcata acctagaact cttctaaaag aattttcctc aaatttaaaa gtgaacttty 300
ctaaataact caaatgtgtc cattctactc ccaaaggatt ttcttttcct gcagtataag 360
actatgaaag aagccgagca cggtggctca cacctgtaat cccagcactt tgggaggatg 420
aggcgggagg atcgcttaag gctggggttc aagaccagca tggccaaaat ggcaaaaccc 480
catctctaca aaaaatataa aaattagccg ggtgcagtgg tgcacgcctg tagtcctagc 540
tactcaggag gctgaggctg gagaatcact tgggcccagg aggtggaggt tgcagtgag 599

<210> SEQ ID NO 543
<211> LENGTH: 599
<212> TYPE: DNA
<213> ORGANISM: Homo sapiens

<400> SEQUENCE: 543
acttctcggt gaaggaatat ataaggctga tcacaaagaa ggcaagctca tgtgaggggc 60
tggtagggtt cttgaacctc tggccacctg cagataaata attgattgaa ataaaacccg 120
aaatgttctc cagaaacaga ttaatacaaa acagaatttt agagttcaaa aggtcctaaa 180
tgcttacaag aaaatgccag tgatgaaaat atcatgtgta cagtgcttta cttctcaaag 240
tgctttcact gaatcattaa ataaaaatta ttatgtacct gctatgtgtt aggaactggs 300
aatacagaaa ttggatacca cccctgcttt aaaggggcca tacttctaac aatgagacct 360
gctaggaatg aaaatgcagc aaacaatcag tctttggtgg tatgcagtaa acataaggag 420
agcacagcag aaggggcacc gaagtttctg gggaatcaa agacagcaca catctcagaa 480
gagacagccc ttgaagtgag gccagaaggc tggcaagcag aaagactaac ggttatatgc 540
aaaggaatat atgtgctttt tttaaaaaaa gcacgaagtg ttctgggaac caaaagctg 599

<210> SEQ ID NO 544
<211> LENGTH: 599
<212> TYPE: DNA
<213> ORGANISM: Homo sapiens

<400> SEQUENCE: 544
gcacattatg gttctttctg tatgaaaaaa aggctgatgg caatctggcc aggagtacac 60
aggggtgagc tgaacagtgc cctcaggtac tgcaatgcta agagtctcac tggagtgaag 120
cagctaatag atttagagca catccatgtc ttttgccaaa tgaggcaaaa taaagtaaaa 180
agtctttaac aaatggagct atgaaagagc ctgaaaagcc tgagagctac acaagagctc 240
tattactaat attcttccct gattaaaaaa aacagagctt tgttttgcct gtaacagacr 300
ctatcaatcc tcccagtaac ttgaaggcaa atatagccac atgacagctc attagcattt 360
cagagaaaaa aactatgata tttagtgaaa aacaaaatgt gtaataatga aaccatagct 420
ccctatgatg acactagggg cccagctcac aaactaggca gtcagaactt tggtaacctt 480
atcttttcta aagctaaatt ttcctgcaga agtgcctcaa gaccaaagaa gaggacaatt 540
ccccagcttt acctctggct ggattaggca cactcaagcc acaaaacata atacaaaga 599

<210> SEQ ID NO 545
<211> LENGTH: 599
<212> TYPE: DNA
<213> ORGANISM: Homo sapiens

<400> SEQUENCE: 545
gtggcacaat ctctgctcac tgcaacctcc gcctcctggg ttcaagcgac tctcctgcct 60
cagactcccg agtagttggg actacacacc cggctacttt tttatttta gtagggacgg 120 gacggtgttt caccatgttg gccaggctgg tctcaaactc ccgacctcag gtgatccacc 180
tgcctagccc tcccaacagt tctgggatta caggcatgag ccaccatgcc cggcctgtca 240
tctaacttaa ggtcctaatt ttacagagga aacaactcag acccagagag gttagacaay 300
ttgttcagta ttacgtagct gattagtgac agatgaaaaa ttttaaactt caagtctact 360
gatgcccctt tggccaggtg accttttaa ataatagctg ccacttatgg gataattaca 420
gtgcaccagg tgctgtagat gtgacctcat ttaatcccac cacaatccta tgagggaggc 480
actatcaaat ccattttaca aatgaggaaa ccaggactca acctcaggtc tgtttgatgc 540
caaagtcttt ggtcttaacc actacaccat gcctccctac tttccattca ttcattcat 599

<210> SEQ ID NO 546
<211> LENGTH: 599
<212> TYPE: DNA
<213> ORGANISM: Homo sapiens

<400> SEQUENCE: 546
cagcaatggg agagagccca gaaaaggaga aataacccca actcgatggg gtggaaaagg 60
gggaagcgct ttccggaagg cttccgggat ggggtcacca gagtcagagg aaggagtaac 120
agtagataga agaagaagtg gtcaggggcg ttcttctagg tttggggcgg acccgcgtga 180
agatgcaaag actgaaaagg ggcggctcac tttacattcc aaggtaaatt ctcactatga 240 ccccctttc cccatcaaag gcttctggga ctgcccatgg gtgaactcag agggagggtr 300
ggagagggtg ctgctctatc caatggcggc aaaagtcaaa gtggccttgg gtattcccaa 360
ttactcacta taaatcagct tccaatgccg gtcgcagaat cttggagtta gacgggatcc 420
tcgtgggctc ttagtcacac acaccttccc caaggcaaaa attcttgcac aaaatacctg 480
ataaaattat ttattcgata aatattttt gagtaagaac actgaggggg taagctagat 540
gagatacagt cactaccctg gggtgctta caccaaactg gaggatgcta aggcacgta 599

<210> SEQ ID NO 547
<211> LENGTH: 599
<212> TYPE: DNA
<213> ORGANISM: Homo sapiens

<400> SEQUENCE: 547
ttggcaccga gcagatcagg ggacttactg catgacacag caagtcagtg gaagagccaa 60
ggagtgcact catccaagtt actgattccg atgtcagcaa aacctgctga aacccatctt 120
cacactgcag ttcagagggt gtccccagga agcacctctc tgcaaagcat gttcaacgta 180
gttcccagtg gcctgccaaa tggtcagcag caaggtgtaa ctggatgtcg cttccaggaa 240
gcagagtgaa aagagacaag gagtaggaaa ctaatgtcca gagtcggcca tttgccccar 300
ggaccggagt ggagactgca tttctaagtg cttcctctgt ccacagccct cctcccccat 360
accttttaaa aacagatttg ctggctgggt acggtggctc atgcctgtaa tcccagcact 420
ttgggaggct gaggcaggtg aattgcctga gctcaggagt tcgagaccaa cctggacaaa 480
accctatctc tagcaaaaaa tacaaaaagt tagccgggcc ttgtggtgca tacctgtggt 540
tccagccact gggaaggctg aagtgggagg atcacttgag cctgggaggt ggaggttgg 599

<210> SEQ ID NO 548
<211> LENGTH: 599
<212> TYPE: DNA
<213> ORGANISM: Homo sapiens

<400> SEQUENCE: 548
ctgaacttca taatatgaca gagtaaaata tccagtgagg taacatgtcc atgtcaagtt 60
ttagggcaca gcagatctgg gtactgacag ttaccaggta tgtgactgta ggcttactcc 120
ttaaccttcc tgtgattcag cttcttcatc tgtaaactag agttaataat ccttacaaca 180
tgaggtcgtt ataaggatta tgaagaaatg taaagaggga agtaataggg gcatctactt 240
tatagtagac attgtgctac cttattaatc ctcatatgaa ctctgaaata agtggtagtr 300
gcagcatttt gcagatgagc aaagagaagc ttctagagga acttctagat aacaggattt 360
ttgttgttgt tttgcttttt tgtttttttt agacagagtc ttgctttgtc ttccagacat 420
gagtgtagtg gcagggtcat agctcactgt gtcctcaaac tcctgtaacc tcaaactgct 480
gaagcagttc tcctgcataa ctaggactat aggcgtgtgc catcatgccc ggctaaattt 540
ttttgtgcag gcggggtgtc acagtgttcc ccaggctgat cttgaactct tgccctcac 599

<210> SEQ ID NO 549
<211> LENGTH: 599
<212> TYPE: DNA
<213> ORGANISM: Homo sapiens

<400> SEQUENCE: 549
ctgagtcact atataatttt ttgaagacat tttaaatagc cctcaattca gtacacgcag 60
caccaacact gcacctaact cagctgaagt taagacaata tgaacagcta tgtttaattt 120
atcaaatttg caagcaatga tgattccatt aaaatgaaaa aaaatcatgt tttaggatta 180
gttaaatgtg gtagcaaatg ctggtactga ttagaattct tacaactgca agtgacagga 240
aacagactaa cttaagcaaa aggactgcat taagccagga aattccaaaa gtccctgtak 300
tataacagtt tcaggtatgg ctggattcag gactccagaa tataaccagg actcagtttc 360
ctgccatttc tctttctttt ccgcagggtt ggtgtcagtg gcaggtttca catgctggca 420
agctggagcc agcagctcca gctccagctc tagcacccct ggagttttga gtccagtgaa 480
aaaaacgatg agaggctttg tcccagatat tttagcctga gtctcaatgc ctctcattgg 540
ctccaacaga tcacatgccc agccctgagc caatcaacat ggccacatcc gggtcagtt 599

<210> SEQ ID NO 550
<211> LENGTH: 599
<212> TYPE: DNA
<213> ORGANISM: Homo sapiens

<400> SEQUENCE: 550
aaatgctggt actgattaga attcttacaa ctgcaagtga caggaaacag actaacttaa 60
gcaaaaggac tgcattaagc caggaaattc caaaagtccc tgtagtataa cagtttcagg 120
tatggctgga ttcaggactc cagaatataa ccaggactca gtttcctgcc atttctcttt 180
cttttccgca gggttggtgt cagtggcagg tttcacatgc tggcaagctg gagccagcag 240
ctccagctcc agctctagca cccctggagt tttgagtcca gtgaaaaaaa cgatgagagk 300
ctttgtccca gatattttag cctgagtctc aatgcctctc attggctcca acagatcaca 360
tgcccagccc tgagccaatc aacatggcca catccgggtc agttactact gcctccgccc 420
catgctgtgg agcccggctg gaagcccggg ggttgttggg tcttcacccg ggaaatgggg 480
agagagactg cggggcagct ggcaccacat acgtgcctta caggtggggt gtggggactt 540
aggagggctt agcacccaga gcattagccc agggcctggc ccctggtggc ttctcccgg 599

<210> SEQ ID NO 551
<211> LENGTH: 599
<212> TYPE: DNA
<213> ORGANISM: Homo sapiens

<400> SEQUENCE: 551
gagacccggt cttcaagaaa aaaaaaagtt gttcctctgc tctttctgct catgttcctc 60
ctggacaaag ttagggaaca agccacatgc tatttatctt cacggttgct cagcaacctt 120
cattcatctc tagttgactt ttcatcatat ttccttcagc gatactttca aatcattctc 180
ataattcttc tgaaacccaa ctactctctg ctgccactca cccccagctg agggactgta 240
ctccagcttt aacgaagctc agcttattag acttaagctt cctcaacttc cttattctcy 300
gtgtcaaaac ggcttttcac ctgtttgctc tttctgcccg ccctctcaga agagaaagtg 360
gttttcttcc ttcctacgtt aaattctcca cccacgagaa cctttcaacc catttccttt 420
atactctttt cctttgtgca tcttcagtct tttcttctcc aatggcttcg tgtccactgc 480
aaatacttag atctcctgaa ccctgaatta aacaaaacaa aacaaagcaa ctatccctgt 540
acccactcaa gctgttacct ttctagctct tatccctctg cctcactgcc atactttt 599

<210> SEQ ID NO 552
<211> LENGTH: 599
<212> TYPE: DNA
<213> ORGANISM: Homo sapiens

<400> SEQUENCE: 552
gggaacagcc tttgggaggt gagggtagca acagggaggt cagcaggagg gccactgcag 60
tgatctggat gaaggaccat ggcttggaca agggccatgg tcaggggtgg tgagacgtaa 120
aggaatcctg tgggtttgct gatggactga gtgtggggtc tgggcgaggg aggagccaga 180
ggtgactccg aggtttaggc tgagcatcgg gagaatggag gtgtcatttc tggatccggg 240
tagtactatg gtaggagtgg ctttgaggag aaggtgaaga gctttgctcc tcatggggtr 300
catgttagag gctcacctgg agctgtcaga aagccattag ctatgggaat ctggatatgg 360
tgggagagag ctggcctaga gccatgaagc tcagaccctc ctgaagacgg aggcttggct 420
gcttggagaa cacgtagtag agaatgcttt ttctttcctc cttggctctc tcttggcaga 480
aggtgatgag cctggctcca gtctgctggc gaactcccct ctgatggagg atgctccaca 540
gaggctgcgg tggcaggccc acctggagtt cacccataac cacgatgtgg gggatctca 599

<210> SEQ ID NO 553
<211> LENGTH: 599
<212> TYPE: DNA
<213> ORGANISM: Homo sapiens

<400> SEQUENCE: 553

```
tttttctttc ctccttggct ctctcttggc agaaggtgat gagcctggct ccagtctgct     60

ggcgaactcc cctctgatgg aggatgctcc acagaggctg cggtggcagg cccacctgga    120

gttcacccat aaccacgatg tgggggatct cacctgggac aagattgccg tctccctacc    180

ccgctctgag aagctccgct ccctggtgct ggccggcatc ccacatggca tgaggccaca    240

ggtaaggtgg ccacagggac ccacagggtg ttgagagggt cctggcccca tgatcaggtr    300

tcacgagaaa gactgagtgc ccttgcggct cccttccctc agctgtggat gcggctctct    360

ggggccctgc agaagaagag gaactctgag ctgtcctacc gcgagattgt gaagaacagc    420

tccaacgatg agaccatcgc tgccaagcag gtgaggccgg tggcactgtg caggaagagc    480

tggaggctgt gtgggctcgc aggagagagg gagcctgcct ggggttctta gagtgtgccc    540

ttgttgtggg gtaggggagg atatttgctc cttccttggt cctctgcagg ccaaagaaa      599
```

<210> SEQ ID NO 554
<211> LENGTH: 599
<212> TYPE: DNA
<213> ORGANISM: Homo sapiens

<400> SEQUENCE: 554

```
tgaggacttt aatctaactt gctttagttg aagaaaccaa caaaatattg aacagccatg     60

aagtgaagaa aggcactaga aactaaaaag acaattatga tctaacttca agtaaagcaa    120

tagtgtgccc aaacctgact gtagttctgg ctgatacatt tcacagaaaa taaactggac    180

tggaaaagat ccagataaca gtaattaaca tgagggagat aatattatga agaaaaaaga    240

tactaaggac tctctactcc aaagagactg gaagaagata taagggagac aagttcaaaw    300

aaaaatttga actcagtatt aggaactcaa tattctcaag ggtaattgag catgggcaaa    360

caatgggaaa aggatttctt ttagggtttg aataatttta taaattacaa aacaacaaat    420

gtctaccaac aaaattcaga atctaaactt caaagaattc ttttccatct tgtctatgat    480

ttattatggt ttgaaccatg tctctgtgtg tactgggaaa aaaacaactg ttacacagga    540

ttaatccatc cggctgagta ttctttgtca ttgactctga aagagcatgt ctgcttctt      599
```

<210> SEQ ID NO 555
<211> LENGTH: 599
<212> TYPE: DNA
<213> ORGANISM: Homo sapiens

<400> SEQUENCE: 555

```
ctggatttct gagaaaaaga tcttaaggcc tgttgtacaa agtggtagag ccatcccgtc     60

tgtcaccaca aaagaagtaa accttgaaaa acgggtaaga agagacgcac cagatgttca    120

aaaacacgga gggcctgcct gtcacaggta ggtgctctta ttgaggaata cagatcactg    180

cagagactgt aaagaccttt gttaccaaag gctttgtttt aaatttgaat tattttaaaa    240

atgtgtaaat ggctaaggag taatatattg tagaattaaa ggtgattgtt tagaccttar    300

cgtctgaccc agttttcctc accagagatg tgtccttcca tcaccttggg tgagtttagt    360

gtccacatgg aaaatccacc tataacctgg gcttctcaac ccttcctcca gcccacccca    420

gtcacacata cccatgctca cccaaaactg ctccccacca gagtcactaa ttttagcatc    480

ctggaccatg acctcctctc cttccaactg gatcccactc ctctggctat gttgacttca    540

tcaaccatac ccgcctaatc cggtttagat tctgtagcct gtaatttcag taacacgct      599
```

<210> SEQ ID NO 556
<211> LENGTH: 599

<212> TYPE: DNA
<213> ORGANISM: Homo sapiens

<400> SEQUENCE: 556
tcactgcaga gactgtaaag acctttgtta ccaaaggctt tgttttaaat ttgaattatt 60
ttaaaaatgt gtaaatggct aaggagtaat atattgtaga attaaaggtg attgtttaga 120
ccttaacgtc tgacccagtt ttcctcacca gagatgtgtc cttccatcac cttgggtgag 180
tttagtgtcc acatggaaaa tccacctata acctgggctt ctcaaccctt cctccagccc 240
accccagtca cacataccca tgctcaccca aaactgctcc ccaccagagt cactaattty 300
agcatcctgg accatgacct cctctccttc caactggatc ccactcctct ggctatgttg 360
acttcatcaa ccatacccgc ctaatccggt ttagattctg tagcctgtaa tttcagtaac 420
acgcttgcta atacccatac tttacctgcc gctctgtttt cttgacacct gtctgaccac 480
attcccactt tggaaaaact ctgtccccca gcacccaaaa gcagcccagc attgctggaa 540
aaaaaagtca ctacagggca tatgaggact cctgtaaatc cactgtaacg taccccccta 599

<210> SEQ ID NO 557
<211> LENGTH: 599
<212> TYPE: DNA
<213> ORGANISM: Homo sapiens

<400> SEQUENCE: 557
tagagatgag gtctcactgt gttgcccagg ctggccttat cctcctgcct aagcctccca 60
aagtgctggg attacaaaag tgagccacca tgtgcagcta cccttcccaa tttaagacct 120
tttctgattt caaatcttaa ccccctttct ctctcaactg aagactttgc ctactagtac 180
acagataaaa ttagagatat cagaaaaatg ccctcaaatt cctgcttcca cactatgaga 240
aagatctgtc tcccttcttt ttctggttcc ttcgttgctc aggatccttc ctttcttgcy 300
ttctggtaac ttttacctcc gttacccatt ctctctccat gtgttcactg gggccctcgc 360
tccctccaca tgctcaagtc catcccatga taaagatcat attccagctg ctgccttacc 420
aactgctgcc acatttttac tctccagaaa tgttctccct tccccttaca gtcttccaat 480
ctggtttcta cccctatcat ttcactaaaa gagctttctt gaaggtcact aacaatctcc 540
ctaagtccag tggacatgac catttgcctg ttgagaccac aaatcctaga tttccttct 599

<210> SEQ ID NO 558
<211> LENGTH: 599
<212> TYPE: DNA
<213> ORGANISM: Homo sapiens

<400> SEQUENCE: 558
agtagccagg tgtagtggtg tgcacctgta ggcccagcta ctcgggaggc tgaggtggga 60
ggatcactta aacccaggca aaggctgcag tgagccatgg ttgtgccact gcactccagc 120
ctgggggaca gagcaagacg ctgtctcaga gaaaaaatga tgaatttaaa aaatttttat 180
agagatgggg gtctcacttt cttgcccagg atggtcttaa actcctgggc tcacgggatc 240
ctcccacctc agcctcccaa agtgctggga ttacaggcgt gagccactgc acctgggcgr 300
gaaattcggt ttttaaaagc ttgaaataaa aacaaaacac tcagaagacg tgttcattga 360
attagggctc aagaaacaaa aaaaaatttc tatttagaga tgttgcttta ggtaacagtg 420
aaagccagct ggaagtgtct acgcagcggc ctttaaagat caagaatcaa aactggagaa 480
cctgtggact cagaaggtaa gtcttgcaga tgtgcaaggc gtgtccaagg gaggaaaggt 540
gaatcaattt tttttttttt tttttgagac agagtctcac tctgtcaccc aggctgggg 599

<210> SEQ ID NO 559
<211> LENGTH: 599
<212> TYPE: DNA
<213> ORGANISM: Homo sapiens

<400> SEQUENCE: 559
tacgtgctct ggtttctctt cagattatat aaatctttcc accttttaca agaggcatgg 60
gtagaaaatg agaaaagtaa atttatcaca gtgtatcaaa gcaatgagtg ccaggaagca 120
ctctgcaaag agtggggagt ttgatggagc aaattcttca tctttccaga actgtgactg 180
ccctcacccc caaaaccagt cctctgcagt tcaagagggg aggtggaaga agacttcagt 240
gacgagccca ggtgactgac aggcttctct gatggcctga atattctgaa attggcacts 300
tagtcaattc tgacagctaa ctctggagtt caggtggagg catgaacaag ccagggaatg 360
aggacaccga ggaagtgtgg aggaagagga agtatagtgg cagaatctaa cttgtatcat 420
ggctattgtg ggcgttattt ctcttactgg gctaggctcc tttggggcag catttatgca 480
tccagcaaac atttactgag cacctatgct atgccaggtt tggggctcag tgccaggaac 540
acagacatga tctcttgccc cactgagttt gccatcaatg agcaaggcaa gcaacactg 599

<210> SEQ ID NO 560
<211> LENGTH: 599
<212> TYPE: DNA
<213> ORGANISM: Homo sapiens

<400> SEQUENCE: 560
ggaacttaaa tggggctaga tgaggcaaaa agttgtcatt aattcatggt tagttcagat 60
ggttgtctaa cttttacaac atgggagtga agtgtatgga cctgattgtt gaaatcagca 120
ttattaagtg tgaaataata taaagatatg gactgcttaa ccctaaggtt cacaacagta 180
agaggacaac ctcgtgacgt atcttctggg atttctgttg gtaatgatgc tgatctgaat 240
gtaatccaat gggcctgtct ctagctgttt ccaagttttt gattcagttt cagattaaar 300
tagtagaaat cagagacttc tggtctggct atgctgcttt aaatcagtct tttgacctct 360
agtccaattt tcttactttt tttttttttt tttttttttt tttaataaaa agacaactag 420
agatcaggtc tcgctatgtt gcccaggctg gtcttgaact cctggcctca agcagtcctc 480
ttgtctcaat ctcccaaagt gttcgggtta catatgtgag ccagtgtgcc tggcccctag 540
tttctttttt caaaaagtat gagagatgaa cccaaaggat ccttctaact ctataattc 599

<210> SEQ ID NO 561
<211> LENGTH: 599
<212> TYPE: DNA
<213> ORGANISM: Homo sapiens

<400> SEQUENCE: 561
gttttgttcc catttctctc atattaggaa atggcatcat cataagccca ggagtacaga 60
ctggaaacct aggccttgcc tgtggccact cccattctca ttccccacat ccaactctgc 120
ggcaaggcct gttgattcta cctctgattg tgtcttgaat ctgttgcttc tctttttctc 180
cactgtcact tcagcctcat tctccgtaat ctttcctctg cacgccacac ttgcctgcaa 240
gcatccactc ttgtctctct acaagctatt tgcccacgta gcagccagat tggagccacr 300
tacattttag aggtgtgctg aagaataggc gccaaggaga aaaaccagga agaaaaccag 360
tatttggtac ccttaccttg aaaaaggtat tcatatattt tttcctttc taaaaaatgt 420

-continued

```
tcatgtttct ttgagcattt attgtctgat tttacccctt tttagcatct atagaagcca    480

cattaatctt tttttactcc agcctttctt ggactttccc ggctttgtgc ttctctatct    540

aggtgagttt ttatcgatag cttcaagtgt cctcttcccc tcctcacaga ggaaatgca     599


<210> SEQ ID NO 562
<211> LENGTH: 599
<212> TYPE: DNA
<213> ORGANISM: Homo sapiens

<400> SEQUENCE: 562

acctaggcct tgcctgtggc cactcccatt ctcattcccc acatccaact ctgcggcaag     60

gcctgttgat tctacctctg attgtgtctt gaatctgttg cttctctttt tctccactgt    120

cacttcagcc tcattctccg taatctttcc tctgcacgcc acacttgcct gcaagcatcc    180

actcttgtct ctctacaagc tatttgccca cgtagcagcc agattggagc cacgtacatt    240

ttagaggtgt gctgaagaat aggcgccaag gagaaaaacc aggaagaaaa ccagtatttk    300

gtacccttac cttgaaaaag gtattcatat attttttcct tttctaaaaa atgttcatgt    360

ttctttgagc atttattgtc tgattttacc cctttttagc atctatagaa gccacattaa    420

tcttttttta ctccagcctt tcttggactt tcccggcttt gtgcttctct atctaggtga    480

gtttttatcg atagcttcaa gtgtcctctt cccctcctca cagaggaaat gcagtcttca    540

gcatctgaga ggcctcttag aagtattttt gctcaggccg ggtgcggtgg ctcacacct     599
```

GENETIC VARIANTS FOR BREAST CANCER RISK ASSESSMENT

CROSS-REFERENCE TO RELATED APPLICATIONS

This application is a U.S. National Phase of International Application No. PCT/IS2009/000008 filed Jul. 3, 2009, incorporated herein by reference, which claims priority benefit of Iceland Patent Application No. 8746 filed Jul. 7, 2008.

INTRODUCTION

Breast cancer is by far the most common cancer in women worldwide. Current global incidence is in excess of 1,151,000 new cases diagnosed each year [Parkin, et al., (2005), CA Cancer J Clin, 55, 74-108]. Breast cancer incidence is highest in developed countries, particularly amongst populations of Northern European ethnic origin, and is increasing. In the United States the annual age-standardized incidence rate is approximately 125 cases per 100,000 populations, more than three times the world average. Rates in Northern European countries are similarly high. In the year 2008 it is estimated that 184,450 new cases of invasive breast cancer will be diagnosed in the U.S.A. and 40,930 people will die from the disease [Jemal, et al., (2008), CA Cancer J Clin, 58, 71-96]. To this FIGURE must be added a further 67,770 ductal and lobular carcinoma in-situ diagnoses expected in 2008. From an individual perspective, the lifetime probability of developing breast cancer is 12.3% in U.S. women (i.e., 1 in 8 women will develop breast cancer during their lives). As with most cancers, early detection and appropriate treatment are important factors. Overall, the 5-year survival rate for breast cancer is 89%. However, in individuals presenting with regionally invasive or metastatic disease, the rate declines to 84% and 27%, respectively [Jemal, et al., (2008), CA Cancer 3 Clin, 58, 71-96].

Increasingly, emphasis is falling on the identification individuals who are at high risk for primary or recurrent breast cancer. Such individuals can be managed by more intensive screening, preventative chemotherapies, hormonal therapies and, in cases of individuals at extremely high risk, prophylactic surgery. Mass screening programs constitute a huge economic burden on health services, while preventative therapies have associated risks and quality of life consequences.

Genetic Predisposition to Breast Cancer

The two primary classes of known risk factors for breast cancer are endocrine factors and genetics. Regarding the latter, approximately 12% of breast cancer patients have one or more first degree relatives with breast cancer [(2001), Lancet, 358, 1389-99]. The well known, dominant breast cancer predisposition genes BRCA1 and BRCA2 confer greatly increased breast cancer risk to carriers, with lifetime penetrance estimates ranging from 40-80%. The presence of BRCA1 and BRCA2 mutations can account for the majority of families with 6 or more cases of breast cancer and for a large proportion of families comprising breast and ovarian or male breast cancer. However such families are very rare indeed. BRCA1 and BRCA2 mutations are found much less frequently in families with fewer cases or in families characterized by breast cancer cases only. Together, mutations in BRCA1 and BRCA2 can account for 15-20% of the risk for familial breast cancer. In non-founder populations, if all common BRCA mutations could be detected, between 2-3% of incident breast cancer patients would be expected to harbor a mutation [Gorski, et al., (2005), Breast Cancer Res Treat, 92, 19-24; (2000), Br J Cancer, 83, 1301-8]. This low "chance to find" statistic precludes the responsible use of BRCA mutation testing outside families with an obvious hereditary predisposition (Anon [(2003), J Clin Oncol, 21, 2397-406]). Rare, high penetrance mutations are known to occur in the TP53 and PTEN genes, however, these together account for no more than 5% of the total genetic risk for breast cancer [Easton, (1999), Breast Cancer Res, 1, 14-7]. Linkage studies have been largely unsuccessful in identifying any more, widespread mutations conferring high risk for breast cancer [Smith, et al., (2006), Genes Chromosomes Cancer, 45, 646-55].

Recent epidemiological studies have indicated that the majority of breast cancer cases arise in a predisposed, susceptible minority of the population [Antoniou, et al., (2002), Br J Cancer, 86, 76-83; Pharoah, et al., (2002), Nat Genet, 31, 33-6]. Data from twin studies and observations of the constant, high incidence of cancer in the contralateral breast of patients surviving primary breast cancer indicate that a substantial portion of the uncharacterized risk for breast cancer is related to endogenous factors, most probably genetic [Lichtenstein, et al., (2000), N Engl J Med, 343, 78-85; Peto and Mack, (2000), Nat Genet, 26, 411-4]. Knowledge of the genetic factors that underpin this widespread risk is very limited. Segregation analyses predict that the uncharacterized genetic risk for breast cancer is most likely to be polygenic in nature, with risk alleles that confer low to moderate risk and which may interact with each other and with hormonal risk factors. Nevertheless, these studies predict as much as 40-fold differences in relative risk between the highest and lowest quintiles of a distribution that could be defined by genetic profiling that captures these low to moderate risk alleles [Antoniou, et al., (2002), Br J Cancer, 86, 76-83; Pharoah, et al., (2002), Nat Genet, 31, 33-6]. 88% of all breast cancer cases are expected to arise amongst a predisposed 50% of the population and the 12% of the population at highest risk accounts for 50% of all breast cancer cases [Pharoah, et al., (2002), Nat Genet, 31, 33-6; Pharoah, (2003), Recent Results Cancer Res, 163, 7-18; discussion 264-6]. Much focus is therefore directed towards the identification of such genetically predisposed individuals and developing personalized medical management strategies for them.

We and others have shown that there is a significant familial risk of breast cancer in Iceland which extends to at least $5^{th}$ degree relatives [Amundadottir, et al., (2004), PLoS Med, 1, e65; Tulinius, et al., (2002), J Med Genet, 39, 457-62]. The contribution of BRCA1 mutations to familial risk in Iceland is thought to be minimal [Arason, et al., (1998), J Med Genet, 35, 446-9; Bergthorsson, et al., (1998), Hum Mutat, Suppl 1, S195-7]. A single founder mutation in the BRCA2 gene (999del5) is present at a carrier frequency of 0.6-0.8% in the general Icelandic population and 7.7-8.6% in female breast cancer patients [Thorlacius, et al., (1997), Am J Hum Genet, 60, 1079-84; Gudmundsson, et al., (1996), Am J Hum Genet, 58, 749-56]. This single mutation is estimated to account for approximately 40% of the inherited breast cancer risk to first through third degree relatives [Tulinius, et al., (2002), J Med Genet, 39, 457-62]. Although this estimate is higher than the 15-25% of familial risk attributed to all BRCA 1 and 2 mutations combined in non-founder populations, there is still some 60% of Icelandic familial breast cancer risk to be explained. First degree relatives of patients who test negative for BRCA2 999del5 remain at a 1.72 fold the population risk for breast cancer (95% CI 1.49-1.96) [Tulinius, et al., (2002), J Med Genet, 39, 457-62].

Genetic risk is conferred by subtle differences in the genome among individuals in a population. Variations in the human genome are most frequently due to single nucleotide polymorphisms (SNPs), although other variations are also important. SNPs are located on average every 1000 base pairs in the human genome. Accordingly, a typical human gene containing 250,000 base pairs may contain 250 different SNPs. Only a minor number of SNPs are located in exons and alter the amino acid sequence of the protein encoded by the gene. Most SNPs may have little or no effect on gene function, while others may alter transcription, splicing, translation, or stability of the mRNA encoded by the gene. Additional genetic polymorphisms in the human genome are caused by insertions, deletions, translocations or inversion of either short or long stretches of DNA. Genetic polymorphisms conferring disease risk may directly alter the amino acid sequence of proteins, may increase the amount of protein produced from the gene, or may decrease the amount of protein produced by the gene.

As genetic polymorphisms conferring risk of common diseases are uncovered, genetic testing for such risk factors is becoming increasingly important for clinical medicine. Examples are apolipoprotein E testing to identify genetic carriers of the apoE4 polymorphism in dementia patients for the differential diagnosis of Alzheimer's disease, and of Factor V Leiden testing for predisposition to deep venous thrombosis. More importantly, in the treatment of cancer, diagnosis of genetic variants in tumor cells is used for the selection of the most appropriate treatment regime for the individual patient. In breast cancer, genetic variation in estrogen receptor expression or heregulin type 2 (Her2) receptor tyrosine kinase expression determine if anti-estrogenic drugs (tamoxifen) or anti-Her2 antibody (Herceptin) will be incorporated into the treatment plan. In chronic myeloid leukemia (CML) diagnosis of the Philadelphia chromosome genetic translocation fusing the genes encoding the Bcr and Abl receptor tyrosine kinases indicates that Gleevec (STI571), a specific inhibitor of the Bcr-Abl kinase should be used for treatment of the cancer. For CML patients with such a genetic alteration, inhibition of the Bcr-Abl kinase leads to rapid elimination of the tumor cells and remission from leukemia. Furthermore, genetic testing services are now available, providing individuals with information about their disease risk based on the discovery that certain SNPs have been associated with risk of many of the common diseases.

Understanding of the genetic factors contributing to the residual genetic risk for breast cancer is limited. Variants in two genes have been rigorously confirmed as low penetrance breast cancer risk genes; CHEK2 and ATM [Renwick, et al., (2006), Nat Genet, 38, 873-5; (2004), Am J Hum Genet, 74, 1175-82]. Furthermore, a recent report establishes a link between variants on chromosomes 2q35 and 16q12 and increased risk of estrogen receptor positive breast cancer (Simon, S N. et al. *Nat Genet* 39:865-9 (2007)). Further, variants in or near the FGFR2, TNRC9, MAP3K1 and LSP1 genes (Easton, D. F., et al. *Nature* 447:1087-93 (2007)), as well as the FGFR2 gene (Hunter, D. J., et al *Nat Genet* 39:870-4 (2007)) have been reported. Many other genes have been implicated however their contribution to breast cancer risk has not been confirmed in analyses employing very large sample sets [Breast Cancer Association, (2006), J Natl Cancer Inst, 98, 1382-96].

No universally successful method for the prevention or treatment of breast cancer is currently available. Management of breast cancer currently relies on a combination of primary prevention, early diagnosis, appropriate treatments and secondary prevention. There are clear clinical imperatives for integrating genetic testing into all aspects of these management areas. Identification of cancer susceptibility genes may also reveal key molecular pathways that may be manipulated (e.g., using small or large molecular weight drugs) and may lead to more effective treatments. The present invention provides additional genetic variants for breast cancer than can be integrated in prevention programmes for breast cancer.

SUMMARY OF THE INVENTION

The present invention relates to methods of assessing a susceptibility to breast cancer. The invention includes methods of diagnosing an increased susceptibility to breast cancer, as well as methods of diagnosing a decreased susceptibility to breast cancer or diagnosing a protection against cancer, by evaluating certain markers or haplotypes that have been found to be associated with increased or decreased susceptibility of breast cancer. The invention also relates to methods of assessing prognosis of individuals diagnosed with breast cancer, methods of assessing the probability of response to a breast cancer therapeutic agent or breast cancer therapy, as well as methods of monitoring progress of treatment of an individual diagnosed with breast cancer.

In one aspect, the present invention relates to a method of diagnosing a susceptibility to breast cancer in a human individual, the method comprising determining the presence or absence of at least one allele of at least one polymorphic marker selected from the group consisting of rs999737 (SEQ ID NO:6), rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs9956546 (SEQ ID NO:7), rs11912922 (SEQ ID NO:8), rs6001954 (SEQ ID NO:9) and markers in linkage disequilibrium therewith, in a nucleic acid sample obtained from the individual, wherein the presence of the at least one allele is indicative of a susceptibility to breast cancer. The invention also relates to a method of determining a susceptibility to breast cancer, by determining the presence or absence of at least one allele of at least one polymorphic selected from the group consisting of rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8), rs6001954 (SEQ ID NO:9) and markers in linkage disequilibrium therewith, wherein the determination of the presence of the at least one allele is indicative of a susceptibility to breast cancer.

In another aspect, the invention relates to a method of determining a susceptibility to breast cancer in a human individual, comprising determining whether at least one at-risk allele in at least one polymorphic marker is present in a genotype dataset derived from the individual, wherein the at least one polymorphic marker is selected from markers selected from the group consisting of rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8), rs6001954 (SEQ ID NO:9) and markers in linkage disequilibrium therewith, and wherein determination of the presence of the at least one at-risk allele is indicative of increased susceptibility to breast cancer in the individual.

The invention furthermore relates to a method for determining a susceptibility to breast cancer in a human individual, comprising determining whether at least one allele of at least one polymorphic marker is present in a nucleic acid sample obtained from the individual or in a genotype dataset derived from the individual, wherein the at least one polymorphic marker is selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8), rs6001954 (SEQ ID NO:9) and markers in linkage disequilibrium therewith, and wherein the presence of the at least one allele is indicative of a susceptibility to breast cancer for the individual.

The genotype dataset comprises in one embodiment information about marker identity, and the allelic status of the individual, i.e. information about the identity of the two alleles carried by the individual for the marker. The genotype dataset may comprise allelic information about one or more marker, including two or more markers, three or more markers, five or more markers, one hundred or more markers, etc. In some embodiments, the genotype dataset comprises genotype information from a whole-genome assessment of the individual that may include hundreds of thousands of markers, or even one million or more markers.

In certain embodiments, the at least one polymorphic marker is associated with the PAX5 (PAIRED BOX GENE 5, also known as BSAP) gene, the TUB (Tubby homolog (mouse, rd5)) gene, the SERPINH1 (serpin peptidase inhibitor, clade H (heat shock protein 47), member 1, (collagen binding protein 1)) gene, the RAD51L1 (REC2; R51H2; hREC2; RAD51B; MGC34245) gene, the FHOD3 (formin homology 2 domain containing 3, also known as FHOS2; Formactin2) gene or the TNRC6B (trinucleotide repeat containing 6B or KIAA1093) gene.

In certain such embodiments, the at least one polymorphic marker is in linkage disequilibrium with any one of the above-mentioned genes, i.e. any one of the PAX5 (PAIRED BOX GENE 5, also known as BSAP) gene, the TUB (Tubby homolog (mouse, rd5)) gene, the SERPINH1 (serpin peptidase inhibitor, clade H (heat shock protein 47), member 1, (collagen binding protein 1)) gene, the RAD51L1 (REC2; R51H2; hREC2; RAD51B; MGC34245) gene, the FHOD3 (formin homology 2 domain containing 3, also known as FHOS2; Formactin2) gene and the TNRC6B (trinucleotide repeat containing 6B or KIAA1093) gene.

Another aspect of the invention relates to a method of determining a susceptibility to breast cancer in a human individual, the method comprising:

obtaining nucleic acid sequence data about a human individual identifying at least one allele of at least one polymorphic marker selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8), rs6001954 (SEQ ID NO:9), and markers in linkage disequilibrium therewith, wherein different alleles of the at least one polymorphic marker are associated with different susceptibilities to breast cancer in humans, and determining a susceptibility to breast cancer from the nucleic acid sequence data.

In a general sense, genetic markers lead to alternate sequences at the nucleic acid level. If the nucleic acid marker changes the codon of a polypeptide encoded by the nucleic acid, then the marker will also result in alternate sequence at the amino acid level of the encoded polypeptide (polypeptide markers). Determination of the identity of particular alleles at polymorphic markers in a nucleic acid or particular alleles at polypeptide markers comprises whether particular alleles are present at a certain position in the sequence. Sequence data identifying a particular allele at a marker comprises sufficient sequence to detect the particular allele. For single nucleotide polymorphisms (SNPs) or amino acid polymorphisms described herein, sequence data can comprise sequence at a single position, i.e. the identity of a nucleotide or amino acid at a single position within a sequence. Nucleic acid sequence data identifying particular alleles of polymorphic markers is sometimes also referred to as genotype data. Nucleic acid sequence data can be obtained for example by analyzing sequence of the at least one polymorphic marker in a biological sample from the individual. Alternatively, nucleic acid sequence data can be obtained in a genotype dataset from the human individual and analyzing sequence of the at least one polymorphic marker in the dataset. Such analysis in certain embodiments comprises determining the presence or absence of a particular allele of specific polymorphic markers. Identification of particular alleles in general terms should be taken to mean that determination of the presence or absence of the allele(s) is made. Usually, determination of both allelic copies in the genome of an individual is performed, by determining the occurrence of all possible alleles of the particular polymorphism in a particular individual (for SNPs, each of the two possible nucleotides possible for the allelic site). It is also possible to determine whether only particular alleles are present or not. For example, in certain embodiments, determination of the presence or absence of certain alleles that have been shown to associate with risk of glaucoma is made, but not necessarily other alleles of the particular marker, and a determination of susceptibility is made based on such determination.

In certain embodiments, it may be useful to determine the nucleic acid sequence for at least two polymorphic markers. In other embodiments, the nucleic acid sequence for at least three, at least four or at least five or more polymorphic markers is determined. Haplotype information can be derived from an analysis of two or more polymorphic markers. Thus, in certain embodiments, a further step is performed, whereby haplotype information is derived based on sequence data for at least two polymorphic markers.

The invention also provides a method of determining a susceptibility to breast cancer in a human individual, the method comprising obtaining nucleic acid sequence data about a human individual identifying both alleles of at least two polymorphic markers selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8), rs6001954 (SEQ ID NO:9) and markers in linkage disequilibrium therewith, determine the identity of at least one haplotype based on the sequence data, and determine a susceptibility to breast cancer from the haplotype data.

In certain embodiments, determination of a susceptibility comprises comparing the nucleic acid sequence data to a database containing correlation data between the at least one polymorphic marker and susceptibility to breast cancer. In some embodiments, the database comprises at least one risk measure of susceptibility to breast cancer for the at least one marker. The sequence database can for example be provided as a look-up table that contains data that indicates the susceptibility of breast cancer for any one, or a plurality of, particular polymorphisms. The database may also contain data that indicates the susceptibility for a particular haplotype that comprises at least two polymorphic markers.

Obtaining nucleic acid sequence data can in certain embodiments comprise obtaining a biological sample from the human individual and analyzing sequence of the at least one polymorphic marker in nucleic acid in the sample. Analyzing sequence can comprise determining the presence or absence of at least one allele of the at least one polymorphic marker. Determination of the presence of a particular susceptibility allele (e.g., an at-risk allele) is indicative of susceptibility to breast cancer in the human individual. Determination of the absence of a particular susceptibility allele is indicative that the particular susceptibility is not present in the individual.

In some embodiments, obtaining nucleic acid sequence data comprises obtaining nucleic acid sequence information from a preexisting record. The preexisting record can for example be a computer file or database containing sequence data, such as genotype data, for the human individual, for at least one polymorphic marker.

Susceptibility determined by the diagnostic methods of the invention can be reported to a particular entity. In some embodiments, the at least one entity is selected from the group consisting of the individual, a guardian of the individual, a genetic service provider, a physician, a medical organization, and a medical insurer.

In certain embodiments of the invention, determination of a susceptibility comprises comparing the nucleic acid sequence data to a database containing correlation data between the at least one polymorphic marker and susceptibility to breast cancer. In one such embodiment, the database comprises at least one risk measure of susceptibility to breast cancer for the at least one polymorphic marker. In another embodiment, the database comprises a look-up table containing at least one risk measure of the at least one condition for the at least one polymorphic marker.

In certain embodiments, obtaining nucleic acid sequence data comprises obtaining a biological sample from the human individual and analyzing sequence of the at least one polymorphic marker in nucleic acid in the sample. Analyzing sequence of the at least one polymorphic marker can comprise determining the presence or absence of at least one allele of the at least one polymorphic marker. Obtaining nucleic acid sequence data can also comprise obtaining nucleic acid sequence information from a preexisting record.

Certain embodiments of the invention relate to obtaining nucleic acid sequence data about at least two polymorphic markers selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8), rs6001954 (SEQ ID NO:9) and markers in linkage disequilibrium therewith.

In certain embodiments of the invention, the at least one polymorphic marker is selected from the markers set forth in Table 4. In one embodiment, the at least one polymorphic marker is selected from the markers as set forth in SEQ ID NO:1-562. In one embodiment, the at least one marker is in linkage disequilibrium with at least one of rs2005154, rs2184380, rs2224696, rs2242503, rs12291026, rs999737, rs9956546, rs11912922 and rs6001954. In one embodiment, markers in linkage disequilibrium with rs999737 are selected from the group consisting of rs999737, rs10134446, rs10138140, rs10146772, rs10467820, rs10483812, rs10483813, rs11158749, rs11158751, rs11621276, rs11624097, rs11624164, rs11624333, rs11628293, rs11846360, rs11847185, rs11849916, rs12878761, rs12879200, rs12886864, rs12889251, rs12894230, rs1468279, rs1468280, rs1547012, rs17105675, rs17755657, rs17755734, rs17755752, rs17755925, rs17756000, rs17828691, rs17828721, rs17828763, rs17828907, rs17828955, rs1956534, rs2074563, rs2074565, rs2097800, rs2107340, rs2145157, rs2158357, rs2189517, rs2253317, rs2257111, rs2257116; rs2257127, rs2331701, rs2331705, rs2331775, rs2525503, rs2525530, rs2842327, rs3784121, rs4531674, rs4899246, rs4902604, rs4902606, rs4902608, rs5004090, rs6573837, rs7140266, rs7146456, rs7153476, rs739874, rs746663, rs8007194, rs8010439, rs8012610, rs9323512, rs9323513, and rs9323514.

In one embodiment, markers in linkage disequilibrium with rs2005154 are selected from the group consisting of rs2005154, rs4878662, and rs4880019.

In one embodiment, markers in linkage disequilibrium with rs2184380 are selected from the group consisting of rs2184380, rs10466295, rs10508363, rs10508364, rs10508365, rs10795670, rs10905411, rs10905414, rs10905415, rs10905430, rs10905437, rs10905439, rs10905440, rs10905443, rs10905444, rs10905445, rs10905446, rs10905447, rs10905454, rs11255764, rs11255776, rs11255777, rs11255778, rs11255779, rs11255790, rs11255795, rs11255797, rs11255800, rs11255804, rs11255805, rs11255820, rs11255821, rs11255822, rs11255832, rs11255836, rs11255840, rs11255858, rs11255862, rs11255869, rs11255870, rs11255871, rs11255882, rs11255884, rs12049705, rs12218610, rs12250379, rs12259226, rs1325874, rs1334549, rs1334550, rs1334559, rs1360749, rs1413678, rs1413683, rs1537601, rs1537602, rs1537603, rs17407711, rs17407781, rs17407830, rs17408204, rs17408337, rs17408580, rs17484150, rs17485426, rs17485998, rs17486082, rs17486795, rs17486816, rs1970170, rs1999638, rs2031561, rs2182292, rs2388821, rs2388825, rs2388826, rs2892613, rs4112287, rs4112288, rs4345867, rs4454616, rs4747806, rs4749805, rs4749807, rs4749812, rs6602328, rs6602329, rs7069110, rs7080765, rs7083359, rs7477023, rs7904921, rs7912413, rs7912704, rs7912831, rs827389, and rs966562.

In one embodiment, markers in linkage disequilibrium with rs2224696 are selected from the group consisting of rs2224696, rs10905509, rs11256045, rs12761213, rs12761461, rs12766048, rs12772042, rs12776383, rs12778120, rs12780218, rs12781427, rs1475189, rs1573109, rs1573110, rs17145088, rs17145095, rs17145118, rs17145120, rs17145151, rs17145164, rs17145169, rs17145188, rs17145193, rs17145221, rs17363338, rs1775559, rs1857230, rs1891532, rs1935813, rs2013364, rs2025289, rs2057442, rs2093625, rs2093626, rs2146598, rs2185817, rs2397336, rs2760204, rs2797266, rs391733, rs4550140, rs7081544, rs852273, rs860418, rs861172, rs962993, and rs965307.

In one embodiment, markers in linkage disequilibrium with rs2242503 are selected from the group consisting of rs2242503, rs10431029, rs1055233, rs10734629, rs10743052, rs10743053, rs10743054, rs10743055, rs10769872, rs10769873, rs10769878, rs10769882, rs10839976, rs10839984, rs11041740, rs11041742, rs11041788, rs11041791, rs11041794, rs1108277, rs12146654, rs12808387, rs1528125, rs1569128, rs1970880, rs1997262, rs2049684, rs2141321, rs2242501, rs2272383, rs3750955, rs3752898, rs3849986, rs3849990, rs3911309, rs3911310, rs4340037, rs4343012, rs4385931, rs4575312, rs4578424, rs4636658, rs4758040, rs4758042, rs4758287, rs4758309, rs4758310, rs7103334, rs7112519, rs7115706, and rs7122690, rs7127738, rs7358396, rs7479156, rs7479738, rs7480804, rs7481667, rs7481683, rs7482611, rs7927368, and rs7940668.

In one embodiment, markers in linkage disequilibrium with rs12291026 are selected from the group consisting of rs12291026, rs1004856, rs10899091, rs11236449, rs11236452, rs11236454, rs12362081, rs1540210, rs1540211, rs1557471, rs1631470, rs1783551, rs1783556, rs1783559, rs1790144, rs1790152, rs1790307, rs1793396, rs1793397, rs1793398; rs1793399, rs1793414, rs1938800, rs2853066, rs499613, rs504793, rs514477, rs549034, rs550881, rs581007, rs589724, rs600387, rs606460, rs617617, rs618202, rs628972, rs640649, rs662279, rs667410, rs667531, rs670100, rs670491, rs682292, rs7128888, rs7129014, rs7129150, and rs947844.

In one embodiment, markers in linkage disequilibrium with rs11912922 are selected from the group consisting of rs11912922, rs11089967, rs11704971, rs11705454, rs17406386, rs17406434, rs2071771, rs2958650, rs2958651, rs2958659, rs7284488, rs7285507, rs7291782, rs739145, rs9611246, and rs9611265.

In one embodiment, markers in linkage disequilibrium with rs6001954 are selected from the group consisting of rs6001954, rs10483203, rs10483204, rs10483205, rs10483206, rs1106673, rs11913132, rs12158399, rs12158872, rs12159200, rs12159970, rs12484697, rs12627881, rs133036, rs133038, rs16985899, rs17001846, rs17001868, rs17001943, rs17001974, rs17001977, rs17001993, rs17001994, rs17001997, rs17002019, rs17002020, rs17002026, rs17002027, rs17002034, rs17002036, rs17002038, rs17002069, rs2075764, rs2187832, rs2235318, rs2280790, rs2294348, rs2294350, rs2294352, rs2413624, rs3788577, rs3788578, rs3788579, rs3827381, rs3827382, rs4140512, rs470113, rs5750957, rs5750960, rs5750966, rs5757976, rs5757998, rs5758001, rs5995849, rs5995856, rs5995870, rs5995871, rs5995886, rs6001900, rs6001910, rs6001911, rs6001912, rs6001913, rs6001930, rs6001931, rs6001932, rs6001935, rs6001950, rs6001974, rs6001980, rs6001990, rs6002000, rs718193, rs7292804, rs7293100, rs742140, rs760700, rs760701, rs9306345, rs932379, rs9607721, rs9611310, rs9611311, rs9611312, rs9611316, rs9611318, rs9611324, rs9611325, rs9611328, and rs9611329.

In certain embodiments of the invention, a further step of assessing the frequency of at least one haplotype in the individual is performed. In such embodiments, two or more markers, including three, four, five, six, seven, eight, nine or ten or more markers can be included in the haplotype. In certain embodiments, the at least one haplotype comprises markers that are all in LD with at least one of rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8) and rs6001954 (SEQ ID NO:9). In such embodiments, the at least one haplotype is representative of the genomic structure of a particular genomic region (LD block) to which any one of the above-mentioned markers reside. In one embodiment, the haplotype comprises markers in linkage disequilibrium with rs999737.

The markers conferring risk of breast cancer, as described herein, can be combined with other genetic markers for breast cancer. Such markers are typically not in linkage disequilibrium with any one of the markers described herein, in particular markers rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8), rs6001954 (SEQ ID NO:9) and markers in linkage disequilibrium therewith. Any of the methods described herein can be practiced by combining the genetic risk factors described herein with additional genetic risk factors for breast cancer.

Thus, in certain embodiments, a further step is included, comprising determining whether at least one at-risk allele of at least one at-risk variant for breast cancer not in linkage disequilibrium with any one of the markers set forth in Table 1 and/or Table 4 is present in an individual. In other words, genetic markers in other locations in the genome can be useful in combination with the markers of the present invention, so as to determine overall risk of breast cancer based on multiple genetic factors. Selection of markers that are not in linkage disequilibrium (not in LD) can be based on a suitable measure for linkage disequilibrium, as described further herein. In certain embodiments, markers that are not in linkage disequilibrium have values for the LD measure $r^2$ between the markers of less than 0.2. In certain other embodiments, markers that are not in LD have values for $r^2$ between the markers of less than 0.15, including less than 0.10, less than 0.05, less than 0.02 and less than 0.01. Other suitable cutoff values for establishing that markers are not in LD are contemplated, including values bridging any of these values. Examples of such genetic risk factors include markers on chromosome 5p12 and chromosome 10q26, e.g., marker rs10941679 and marker rs1219648. Alternatively, markers in LD with any one of these markers could be assessed. Other markers known to confer risk of breast cancer can also be assessed together with the markers described herein, include markers on chromosome 2q14 (e.g., marker rs4848543 or markers in linkage disequilibrium therewith), 2q35 (e.g., marker rs13387042, or markers in linkage disequilibrium therewith), and chromosome 16 (e.g., marker rs3803662, or markers in linkage disequilibrium therewith).

In certain embodiments, multiple markers as described herein are determined to determine overall risk of breast cancer. Thus, in certain embodiments, an additional step is included, the step comprising determining whether at least one allele in each of at least two polymorphic markers is present in a sample comprising genomic DNA from a human individual or a genotype, dataset derived from a human individual, wherein the presence of the at least one allele in the at least two polymorphic markers is indicative of an increased susceptibility to breast cancer. In one embodiment, the markers are selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8) and rs6001954 (SEQ ID NO:9) and markers in linkage disequilibrium therewith.

Risk assessment based on the markers of the present invention can also be combined with assessment for the presence of absence of at least one high penetrant genetic factor for breast cancer in a nucleic acid sample obtained from the individual or in a genotype dataset derived from the individual. The high penetrant genetic factor for breast cancer can for example be a BRCA1 mutation, a BRCA2 mutation, a TP53 mutation or a PTEN mutation. Together, mutations in BRCA1 and BRCA2 can account for 15-20% of the risk for familial breast cancer, and these can account for between 2-3% of incident breast cancer patients [Gorski, et al., (2005), Breast Cancer Res Treat, 92, 19-24; (2000), Br J Cancer, 83, 1301-8]. Known mutations in the TP53 and PTEN genes account for about 5% of the total genetic risk for breast cancer [Easton, (1999), Breast Cancer Res, 1, 14-7]. In one embodiment, the high penetrant genetic factor is BRCA2 999del5.

The genetic markers of the invention can also be combined with non-genetic information to establish overall risk for an individual. Thus, in certain embodiments, a further step is included, comprising analyzing non-genetic information to make risk assessment, diagnosis, or prognosis of the individual. The non-genetic information can be any information pertaining to the disease status of the individual or other information that can influence the estimate of overall risk of breast cancer for the individual. In one embodiment, the non-genetic information is selected from age, gender, ethnicity, socioeconomic status, previous disease diagnosis, medical history of subject, family history of breast cancer, biochemical measurements, and clinical measurements.

In another aspect, the invention relates to a method of assessing risk of developing at least a second primary tumor in an individual previously diagnosed with breast cancer, the method comprising determining the presence or absence of at least one allele of at least one polymorphic marker in a nucleic acid sample obtained from the individual, wherein the at least one polymorphic marker is selected from the group consisting of the polymorphic markers listed in Tables 1 and 4, and markers in linkage disequilibrium therewith, wherein the presence of the at least one allele is indicative of risk of developing at least a second primary tumor. Alternatively, the invention relates to a method of determining risk of developing at least a second primary tumor in an individual previously diagnosed with breast cancer, the method comprising determining whether at least one allele of at least one polymorphic marker is present in a nucleic acid sample obtained from the individual, or in a genotype dataset derived from the individual, wherein the at least one polymorphic marker is selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8) and rs6001954 (SEQ ID NO:9) and markers in linkage disequilibrium therewith, and wherein the presence of the at least one allele is indicative of risk of developing at least a second primary tumor. In one such embodiment, the at least one polymorphic marker is selected from the markers set forth in Table 4.

The invention also provides computer-implemented aspects. In one such aspect, the invention provides a computer-readable medium having computer executable instructions for determining susceptibility to breast cancer in an individual, the computer readable medium comprising:

data representing at least one polymorphic marker; and a routine stored on the computer readable medium and adapted to be executed by a processor to determine susceptibility to breast cancer in an individual based on the allelic status of at least one allele of said at least one polymorphic marker in the individual.

In one embodiment, said data representing at least one polymorphic marker comprises at least one parameter indicative of the susceptibility to breast cancer linked to said at least one polymorphic marker. In another embodiment, said data represents at least one polymorphic marker comprises data indicative of the allelic status of at least one allele of said at least one allelic marker in said individual. In another embodiment, said routine is adapted to receive input data indicative of the allelic status for at least one allele of said at least one allelic marker in said individual. In a preferred embodiment, the at least one marker is selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8), rs6001954 (SEQ ID NO:9) and markers in linkage disequilibrium therewith. In another preferred embodiment, the at least one polymorphic marker is selected from the markers set forth in Table 4.

The invention further provides an apparatus for determining a genetic indicator for breast cancer in a human individual, comprising:

a processor, a computer readable memory having computer executable instructions adapted to be executed on the processor to analyze marker and/or haplotype information for at least one human individual with respect to breast cancer, and generate an output based on the marker or haplotype information, wherein the output comprises a risk measure of the at least one marker or haplotype as a genetic indicator of breast cancer for the human individual. In one embodiment, the computer readable memory comprises data indicative of the frequency of at least one allele of at least one polymorphic marker or at least one haplotype in a plurality of individuals diagnosed with breast cancer, and data indicative of the frequency of at the least one allele of at least one polymorphic marker or at least one haplotype in a plurality of reference individuals, and wherein a risk measure is based on a comparison of the at least one marker and/or haplotype status for the human individual to the data indicative of the frequency of the at least one marker and/or haplotype information for the plurality of individuals diagnosed with breast cancer. In an alternative embodiment, the computer readable memory further comprises data indicative of the risk of developing breast cancer associated with at least one allele of at least one polymorphic marker or at least one haplotype, and wherein a risk measure for the human individual is based on a comparison of the genotype status for the human individual to the risk associated with the at least one allele of the at least one polymorphic marker or the at least one haplotype. In another embodiment, the computer readable memory further comprises data indicative of the frequency of at least one allele of at least one polymorphic marker or at least one haplotype in a plurality of individuals diagnosed with breast cancer, and data indicative of the frequency of at the least one allele of at least one polymorphic marker or at least one haplotype in a plurality of reference individuals, and wherein risk of developing breast cancer is based on a comparison of the frequency of the at least one allele or haplotype in individuals diagnosed with breast cancer, and reference individuals. In a preferred embodiment, the at least one marker is selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8), rs6001954 (SEQ ID NO:9) and markers in linkage disequilibrium therewith. In another preferred embodiment, the at least one polymorphic marker is selected from the markers set forth in Tables 4.

In another aspect, the invention relates to a method of identification of a marker for use in assessing susceptibility to breast cancer, the method comprising: identifying at least one polymorphic marker in linkage disequilibrium with at least one of rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8) and rs6001954 (SEQ ID NO:9); determining the genotype status of a sample of individuals diagnosed with, or having a susceptibility to, breast cancer; and determining the genotype status of a sample of control individuals; wherein a significant difference in frequency of at least one allele in at least one polymorphism in individuals diagnosed with, or having a susceptibility to, breast cancer, as compared with the frequency of the at least one allele in the control sample is indicative of the at least one polymorphism being useful for assessing susceptibility to breast cancer. Significant difference can be estimated on statistical analysis of allelic counts at certain polymorphic markers in breast cancer patients and controls. In one embodiment, a significant difference is based on a calculated P-value between breast cancer patients and controls of less than 0.05. In other embodiments, a significant difference is based on a lower value of the calculated P-value, such as less than 0.005, 0.0005, or 0.00005. In one embodiment, an increase in frequency of the at least one allele in the at least one polymorphism in individuals diagnosed with, or having a susceptibility to, breast cancer, as compared with the frequency of the at least one allele in the control sample is indicative of the at least one polymorphism being useful for assessing increased susceptibility to breast cancer. In another embodiment, a decrease in frequency of the at least one allele in the at least one polymorphism in individuals diagnosed with, or having a susceptibility to, breast cancer, as compared with the frequency of the at least one allele in the control sample is indicative of the at least one polymorphism being useful for assessing decreased susceptibility to, or protection against, breast cancer.

The invention also relates to a method of genotyping a nucleic acid sample obtained from a human individual comprising determining whether at least one allele of at least one polymorphic marker is present in a nucleic acid sample from the individual sample, wherein the at least one marker is selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8) and rs6001954 (SEQ ID NO:9) and markers in linkage disequilibrium therewith, and wherein determination of the presence of the at least one allele in the sample is indicative of a susceptibility to breast cancer in the individual. In one embodiment, determination of the presence of rs2005154 allele T, rs2184380 allele G, rs2224696 allele T, rs2242503 allele C, rs12291026 allele G, rs999737 allele C, rs9956546 allele A, rs11912922 allele T and rs6001954 allele G is indicative of increased susceptibility of breast cancer in the individual. In one embodiment, genotyping comprises amplifying a segment of a nucleic acid that comprises the at least one polymorphic marker by Polymerase Chain Reaction (PCR), using a nucleotide primer pair flanking the at least one polymorphic marker. In another embodiment, genotyping is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, single-stranded conformation analysis and microarray technology. In one embodiment, the microarray technology is Molecular Inversion Probe array technology or BeadArray Technologies. In one embodiment, the process comprises allele-specific probe hybridization. In another embodiment, the process comprises microrray technology. One preferred embodiment comprises the steps of (1) contacting copies of the nucleic acid with a detection oligonucleotide probe and an enhancer oligonucleotide probe under conditions for specific hybridization of the oligonucleotide probe with the nucleic acid; wherein (a) the detection oligonucleotide probe is from 5-100 nucleotides in length and specifically hybridizes to a first segment of a nucleic acid whose nucleotide sequence is given by any one of SEQ ID NO:1-562; (b) the detection oligonucleotide probe comprises a detectable label at its 3' terminus and a quenching moiety at its 5' terminus; (c) the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; and (d) a single base gap exists between the first segment and the second segment, such that when the oligonucleotide probe and the enhancer oligonucleotide probe are both hybridized to the nucleic acid, a single base gap exists between the oligonucleotides; (2) treating the nucleic acid with an endonuclease that will cleave the detectable label from the 3' terminus of the detection probe to release free detectable label when the detection probe is hybridized to the nucleic acid; and (3) measuring free detectable label, wherein the presence of the free detectable label indicates that the detection probe specifically hybridizes to the first segment of the nucleic acid, and indicates the sequence of the polymorphic site as the complement of the detection probe.

A further aspect of the invention pertains to a method of assessing an individual for probability of response to a breast cancer therapeutic agent, comprising: determining whether at least one allele of at least one polymorphic marker is present in a nucleic acid sample obtained from the individual, or in a genotype dataset derived from the individual, wherein the at least one polymorphic marker is selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8) and rs6001954 (SEQ ID NO:9) and markers in linkage disequilibrium therewith, wherein the presence of the at least one allele of the at least one marker is indicative of a probability of a positive response to the therapeutic agent The invention in another aspect relates to a method of predicting prognosis of an individual diagnosed with breast cancer, the method comprising determining whether at least one allele of at least one polymorphic marker is present in a nucleic acid sample obtained from the individual, or in a genotype dataset derived from the individual, wherein the at least one polymorphic marker is selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8) and rs6001954 (SEQ ID NO:9), and markers in linkage disequilibrium therewith, wherein the presence of the at least one allele is indicative of a worse prognosis of the breast cancer in the individual.

Yet another aspect of the invention relates to a method of monitoring progress of treatment of an individual undergoing treatment for breast cancer, the method comprising determining whether at least one allele of at least one polymorphic marker is present in a nucleic acid sample obtained from the individual, or in a genotype dataset derived from the individual, wherein the at least one polymorphic marker is selected rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8) and rs6001954 (SEQ ID NO:9) and markers in linkage disequilibrium therewith, wherein the presence of the at least one allele is indicative of the treatment outcome of the individual. In one embodiment, the treatment is treatment by surgery, treatment by radiation therapy, or treatment by drug administration.

The invention also relates to the use of an oligonucleotide probe in the manufacture of a reagent for diagnosing and/or assessing susceptibility to breast cancer in a human individual, wherein the probe hybridizes to a segment of a nucleic acid with nucleotide sequence as set forth in any one of SEQ ID NO:1-562, wherein the probe is 15-500 nucleotides in length. In certain embodiments, the probe is about 16 to about 100 nucleotides in length. In certain other embodiments, the probe is about 20 to about 50 nucleotides in length. In certain other embodiments, the probe is about 20 to about 30 nucleotides in length.

Various diagnoses and categories of the breast cancer phenotype are within scope of the present invention. In its broadest sense, the invention relates to any breast cancer phenotype. Breast cancer, in certain embodiments, includes any clinical diagnosis of breast cancer, including, but not limited to: invasive ductal, invasive lobular, tubular, or as otherwise invasive or mixed invasive, medullary, DCIS (Ductal Carcinoma In-Situ), LCIS (Lobular Carcinoma In-Situ), or otherwise non-invasive; Invasive breast cancer, including stage 0, stage 1, stage 2 (including stage 2a and stage 2b), stage 3 (including stage 3a, stage 3b and stage 3c) and stage 4 breast cancer. In certain embodiments, the breast cancer phenotype is selected from All Breast Cancer, Multiple Primary Breast Cancer, and early onset Breast Cancer. In some embodiments, the markers of the invention are associated with risk of breast cancer in individuals with a family history of breast cancer. In one such embodiment, the summed family history (FHS) is the phenotype associated with breast cancer. In another embodiment, the breast cancer associated with the variants of the invention is estrogen receptor (ER) positive and/or progesterone receptor (PR) positive breast cancer. In one embodiment, the breast cancer associated with the variants of the invention is estrogen receptor (ER) positive. In another embodiment, the breast cancer associated with the variants of the invention is progesterone receptor (ER) positive. In one such embodiment, the markers described herein to be associated with increased risk or susceptibility of breast cancer confers increased risk or susceptibility of ER-positive and/or PR-positive breast cancer. Thus, in certain embodiments, presence of at least one of the at-risk variants of the invention is predictive of ER positive or PR positive breast cancer in the individual.

In some embodiments of the methods of the invention, the susceptibility determined in the method is increased susceptibility. In one such embodiment, the increased susceptibility is characterized by a relative risk (RR) of at least 1.10. In another embodiment, the increased susceptibility is characterized by a relative risk of at least 1.20. In another embodiment, the increased susceptibility is characterized by a relative risk of at least 1.30. In another embodiment, the increased susceptibility is characterized by a relative risk of at least 1.40. In yet another embodiment, the increased susceptibility is characterized by a relative risk of at least 1.50. In a further embodiment, the increased susceptibility is characterized by a relative risk of at least 1.70. In yet another embodiment, the increased susceptibility is characterized by a relative risk of at least 2.0. Other embodiments are characterized by relative risk of at least 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35. Other numeric values for risk bridging any of these above-mentioned values are also possible, and these are also within scope of the invention.

In some embodiments of the methods of the invention, the susceptibility determined in the method is decreased susceptibility. In one such embodiment, the decreased susceptibility is characterized by a relative risk (RR) of less than 0.9. In another embodiment, the decreased susceptibility is characterized by a relative risk (RR) of less than 0.8. In another embodiment, the decreased susceptibility is characterized by a relative risk (RR) of less than 0.7. In yet another embodiment, the decreased susceptibility is characterized by a relative risk (RR) of less than 0.5. Other cutoffs, such as relative risk of less than 0.89, 0.88, 0.87, 0.86, 0.85, 0.84, 0.83, 0.82, 0.81, 0.80, 0.79, 0.78, 0.77, 0.76, 0.75, 0.74, 0.73, 0.72, 0.71, 0.70, and so on, are within scope of the invention.

The invention also relates to kits. In one such aspect, the invention relates to a kit for assessing susceptibility to breast cancer in a human individual, the kit comprising reagents necessary for selectively detecting at least one allele of at least one polymorphic marker selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8), rs6001954 (SEQ ID NO:9) and markers in linkage disequilibrium therewith, in the genome of the individual, wherein the presence of the at least one allele is indicative of increased susceptibility to breast cancer. In one embodiment, the kit further comprises a collection of data comprising correlation data between the at least one polymorphism and susceptibility to breast cancer. The correlation data may be in any suitable formation, for example as a Relative Risk measure (RR), odds ratio (OR), or other convenient measure known to the skilled person. In one embodiment, the collection of data is on a computer-readable medium. In another aspect, the invention relates to a kit for assessing susceptibility to breast cancer in a human individual, the kit comprising reagents for selectively detecting at least one allele of at least one polymorphic marker in the genome of the individual, wherein the polymorphic marker is selected from rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8) and rs6001954 (SEQ ID NO:9), and wherein the presence of the at least one allele is indicative of a susceptibility to breast cancer. In one embodiment, the at least one polymorphic marker is selected from the markers set forth in Table 4.

Kit reagents may in one embodiment comprise at least one contiguous oligonucleotide that hybridizes to a fragment of the genome of the individual comprising the at least one polymorphic marker. In another embodiment, the kit comprises at least one pair of oligonucleotides that hybridize to opposite strands of a genomic segment obtained from the subject, wherein each oligonucleotide primer pair is designed to selectively amplify a fragment of the genome of the individual that includes one polymorphism, wherein the polymorphism is selected from the group consisting of the polymorphisms as defined in Table 4, and wherein the fragment is at least 20 base pairs in size. In one embodiment, the oligonucleotide is completely complementary to the genome of the individual. In another embodiment, the kit further contains buffer and enzyme for amplifying said segment. In another embodiment, the reagents further comprise a label for detecting said fragment.

In one preferred embodiment, the kit comprises: a detection oligonucleotide probe that is from 5-100 nucleotides in length; an enhancer oligonucleotide probe that is from 5-100 nucleotides in length; and an endonuclease enzyme; wherein the detection oligonucleotide probe specifically hybridizes to a first segment of the nucleic acid whose nucleotide sequence is set forth in any one of SEQ ID NO:1-562, and wherein the detection oligonucleotide probe comprises a detectable label at its 3' terminus and a quenching moiety at its 5' terminus; wherein the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; wherein a single base gap exists between the first segment and the second segment, such that when the oligonucleotide probe and the enhancer oligonucleotide probe are both hybridized to the nucleic acid, a single base gap exists between the oligonucleotides; and wherein treating the nucleic acid with the endonuclease will cleave the detectable label from the 3' terminus of the detection probe to release free detectable label when the detection probe is hybridized to the nucleic acid.

Kits according to the present invention may also be used in the other methods of the invention, including methods of assessing risk of developing at least a second primary tumor in an individual previously diagnosed with breast cancer, methods of assessing an individual for probability of response to a breast cancer therapeutic agent, and methods of monitoring progress of a treatment of an individual diagnosed with breast cancer and given a treatment for the disease.

The markers that are described herein to be associated with breast cancer can all be used in the various aspects of the invention, including the methods, kits, uses, apparatus, procedures described herein. In a general sense, the invention relates to markers associated with any one of LD block C09, LD block C10A, LD block 10B, LD block C11A, LD block C11B, LD block C14, LD block C18, LD block C22A, and LD block C22B as defined herein. In certain embodiments, the invention relates to the markers set forth in Table 1 or Table 4, and markers in linkage disequilibrium therewith. In certain other embodiments, the invention relates to the markers set forth in Table 4. In certain other embodiments, the invention relates to markers rs2005154, rs2184380, rs2224696, rs2242503, rs12291026, rs999737, rs9956546, rs11912922 and rs6001954, and markers in linkage disequilibrium therewith. In some other preferred embodiments, the invention relates to any one of rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs999737 (SEQ ID NO:6), rs9956546 (SEQ ID NO:7), rs11912922 (SEQ ID NO:8) and rs6001954 (SEQ ID NO:9).

In certain embodiments, the at least one marker allele conferring increased risk of breast cancer is selected from rs2005154 allele T, rs2184380 allele G, rs2224696 allele T, rs2242503 allele C, rs12291026 allele G, rs999737 allele C, rs9956546 allele A, rs11912922 allele T and rs6001954 allele G. In these embodiments, the presence of the allele (the at-risk allele) is indicative of increased risk of breast cancer.

In certain embodiments of the invention, linkage disequilibrium is determined using the linkage disequilibrium measures $r^2$ and |D'|, which give a quantitative measure of the extent of linkage disequilibrium (LD) between two genetic element (e.g., polymorphic markers). Certain numerical values of these measures for particular markers are indicative of the markers being in linkage disequilibrium, as described further herein. In one embodiment of the invention, linkage disequilibrium between markers (i.e., LD values indicative of the markers being in linkage disequilibrium) is defined as $r^2>0.1$. In another embodiment, linkage disequilibrium is defined as $r^2>0.2$. Other embodiments can include other definitions of linkage disequilibrium, such as $r^2>0.25$, $r^2>0.3$, $r^2>0.35$, $r^2>0.4$, $r^2>0.45$, $r^2>0.5$, $r^2>0.55$, $r^2>0.6$, $r^2>0.65$, $r^2>0.7$, $r^2>0.75$, $r^2>0.8$, $r^2>0.85$, $r^2>0.9$, $r^2>0.95$, $r^2>0.96$, $r^2>0.97$, $r^2>0.98$, or $r^2>0.99$. Linkage disequilibrium can in certain embodiments also be defined as |D'|>0.2, or as |D'|>0.3, |D'|>0.4, |D'|>0.5, |D'|>0.6, |D'|>0.7, |D'|>0.8, |D'|>0.9, |D'|>0.95, |D'|>0.98 or |D'|>0.99. In certain embodiments, linkage disequilibrium is defined as fulfilling two criteria of $r^2$ and |D'|, such as $r^2>0.2$ and |D'|>0.8. Other combinations of values for $r^2$ and |D'| are also possible and within scope of the present invention, including but not limited to the values for these parameters set forth in the above.

It should be understood that all combinations of features described herein are contemplated, even if the combination of feature is not specifically found in the same sentence or paragraph herein. This includes in particular the use of all markers disclosed herein, alone or in combination, for analysis individually or in haplotypes, in all aspects of the invention as described herein.

BRIEF DESCRIPTION OF THE DRAWING

The foregoing and other objects, features and advantages of the invention will be apparent from the following more particular description of preferred embodiments of the invention.

FIG. 1 provides a diagram illustrating a computer-implemented system utilizing risk variants as described herein.

DETAILED DESCRIPTION

The present invention discloses polymorphic variants and haplotypes that have been found to be associated with breast cancer. Particular alleles at polymorphic markers on chromosomes 9, 10, 11, 14, 18 and 22 have been found to be associated with risk of developing breast cancer. Such markers and haplotypes are useful for diagnostic purposes, for methods of predicting drug response, and methods for predicting treatment progress, as described in further detail herein. Further applications of the present invention includes methods for assessing response to breast cancer therapy by surgery or radiation utilizing the polymorphic markers of the invention, as well as kits for use in the methods of the invention.

Definitions

Unless otherwise indicated, nucleic acid sequences are written left to right in a 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by the ordinary person skilled in the art to which the invention pertains.

The following terms shall, in the present context, have the meaning as indicated:

A "polymorphic marker", sometimes referred to as a "marker", as described herein, refers to a genomic polymorphic site. Each polymorphic marker has at least two sequence variations characteristic of particular alleles at the polymorphic site. Thus, genetic association to a polymorphic marker implies that there is association to at least one specific allele of that particular polymorphic marker. The marker can comprise any allele of any variant type found in the genome, including single nucleotide polymorphisms (SNPs), mini- or microsatellites, translocations and copy number variations (insertions, deletions, duplications). Polymorphic markers can be of any measurable frequency in the population. For mapping of disease genes, polymorphic markers with population frequency higher than 5-10% are in general most useful. However, polymorphic markers may also have lower population frequencies, such as 1-5% frequency, or even lower frequency, in particular copy number variations (CNVs). The term shall, in the present context, be taken to include polymorphic markers with any population frequency.

An "allele" refers to the nucleotide sequence of a given locus (position) on a chromosome. A polymorphic marker allele thus refers to the composition (i.e., sequence) of the marker on a chromosome. Genomic DNA from an individual contains two alleles for any given polymorphic marker, representative of each copy of the marker on each chromosome. Sequence codes for nucleotides used herein are: A=1, C=2, G=3, T=4. For microsatellite alleles, the CEPH sample (Centre d'Etudes du Polymorphisme Humain, genomics repository, CEPH sample 1347-02) is used as a reference, the shorter allele of each microsatellite in this sample is set as 0 and all other alleles in other samples are numbered in relation to this reference. Thus, e.g., allele 1 is 1 bp longer than the shorter allele in the CEPH sample, allele 2 is 2 bp longer than the shorter allele in the CEPH sample, allele 3 is 3 bp longer than the lower allele in the CEPH sample, etc., and allele −1 is 1 bp shorter than the shorter allele in the CEPH sample, allele −2 is 2 bp shorter than the shorter allele in the CEPH sample, etc.

A "Single Nucleotide Polymorphism" or "SNP" is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI).

Sequence conucleotide ambiguity as described herein is as proposed by IUPAC-IUB. These codes are compatible with the codes used by the EMBL, GenBank, and PIR databases.

| IUB code | Meaning |
|---|---|
| A | Adenosine |
| C | Cytidine |
| G | Guanine |
| T | Thymidine |
| R | G or A |
| Y | T or C |
| K | G or T |
| M | A or C |
| S | G or C |
| W | A or T |
| B | C G or T |
| D | A G or T |
| H | A C or T |
| V | A C or G |
| N | A C G or T (Any base) |

The sequence listing presented herein provides flanking sequence for the polymorphic markers shown herein in Tables 1-4, with the polymorphic site indicated in the sequence using the sequence conucleotide ambiguity code as shown above.

A nucleotide position at which more than one sequence is possible in a population (either a natural population or a synthetic population, e.g., a library of synthetic molecules) is referred to herein as a "polymorphic site".

A "variant", as described herein, refers to a segment of DNA that differs from the reference DNA. A "marker" or a "polymorphic marker", as defined herein, is a variant. Alleles that differ from the reference are referred to as "variant" alleles.

A "microsatellite" is a polymorphic marker that has multiple small repeats of bases that are 2-8 nucleotides in length (such as CA repeats) at a particular site, in which the number of repeat lengths varies in the general population.

An "indel" is a common form of polymorphism comprising a small insertion or deletion that is typically only a few nucleotides long.

A "haplotype," as described herein, refers to a segment of genomic DNA within one strand of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles.

The term "susceptibility", as described herein, encompasses both increased susceptibility and decreased susceptibility. Thus, particular polymorphic markers and/or haplotypes of the invention may be characteristic of increased susceptibility (i.e., increased risk) of breast cancer, as characterized by a relative risk (RR) of greater than one, or as an odds ratio (OR) of greater than one. Alternatively, the markers and/or haplotypes of the invention are characteristic of decreased susceptibility (i.e., decreased risk) of breast cancer, as characterized by a relative risk of less than one, or an odds ratio of less than one. Haplotypes are described herein in the context of the marker name and the allele of the marker in that haplotype, e.g., "A rs9956546" refers to the A allele of marker rs9956546 being in the haplotype, and this nomenclature is equivalent to "rs9956546 allele A" and "A-rs9956546". Furthermore, allelic codes in haplotypes are as for individual markers, i.e. 1=A, 2=C, 3=G and 4=T.

The term "susceptibility", as described herein, refers to the proneness of an individual towards the development of a certain state (e.g., a certain trait, phenotype or disease, e.g., breast cancer), or towards being less able to resist a particular state than the average individual. The term encompasses both increased susceptibility and decreased susceptibility. Thus, particular alleles at polymorphic markers and/or haplotypes of the invention as described herein may be characteristic of increased susceptibility (i.e., increased risk) of breast cancer, as characterized by a relative risk (RR) or odds ratio (OR) of greater than one for the particular allele or haplotype. Alternatively, the markers and/or haplotypes of the invention are characteristic of decreased susceptibility (i.e., decreased risk) of breast cancer, as characterized by a relative risk of less than one.

The term "and/or" shall in the present context be understood to indicate that either or both of the items connected by it are involved. In other words, the term herein shall be taken 1.0 mean "one or the other or both".

The term "look-up table", as described herein, is a table that correlates one form of data to another form, or one or more forms of data to a predicted outcome to which the data is relevant, such as phenotype or trait. For example, a look-up table can comprise a correlation between allelic data for at least one polymorphic marker and a particular trait or phenotype, such as a particular disease diagnosis, that an individual who comprises the particular allelic data is likely to display, or is more likely to display than individuals who do not comprise the particular allelic data. Look-up tables can be multidimensional, i.e. they can contain information about multiple alleles for single markers simultaneously, or they can contain information about multiple markers, and they may also comprise other factors, such as particulars about diseases diagnoses, racial information, biomarkers, biochemical measurements, therapeutic methods or drugs, etc.

A "computer-readable medium", is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

A "nucleic acid sample" is a sample obtained from an individual that contains nucleic acid (DNA or RNA). In certain embodiments, i.e. the detection of specific polymorphic markers and/or haplotypes, the nucleic acid sample comprises genomic DNA. Such a nucleic acid sample can be obtained from any source that contains genomic DNA, including as a blood sample, sample of amniotic fluid, sample of cerebrospinal fluid, or tissue sample from skin, muscle, buccal or conjunctival mucosa, placenta, gastrointestinal tract or other organs.

The term "breast cancer therapeutic agent" refers to an agent that can be used to ameliorate or prevent symptoms associated with breast cancer.

The term "breast cancer-associated nucleic acid", as described herein, refers to a nucleic acid that has been found to be associated to breast cancer. This includes, but is not limited to, the markers and haplotypes described herein and markers and haplotypes in strong linkage disequilibrium (LD) therewith.

The term "Breast Cancer", as described herein, refers to any clinical diagnosis of breast cancer, and includes any and all particular subphenotypes of breast cancer. For example, breast cancer is sometimes categorized as estrogen receptor (ER) positive breast or estrogen receptor negative breast cancer; breast cancer is sometimes also categorized as progesterone receptor (PR) positive or negative. Breast cancer is furthermore sometimes diagnosed as invasive ductal, as invasive lobular, as tubular, or as otherwise invasive or mixed invasive. Breast cancer can also be categorized as medullary DCIS (Ductal Carcinoma In-Situ) or LCIS (Lobular Carcinoma In-Situ, or otherwise non-invasive. Invasive breast cancer can also be defined as stage 0, stage 1, stage 2 (including stage 2a and stage 2b), stage 3 (including stage 3a, stage 3b and stage 3c) or stage 4 breast cancer. In the present context, "breast cancer" can include any of these subphenotypes of breast cancer, and also includes any other clinically applicable subphenotypes of breast cancer.

The term "All Breast Cancer", or "All BC", refers to all individuals diagnosed with breast cancer.

The term "Medium Predisposition" breast cancer or "MedPre" breast cancer, refers to a sub-phenotype of breast cancer. The definition of this phenotype requires that the proband fulfills at least one of the following criteria:

- The proband is a member of a cluster of breast cancer cases containing 3 or more affected relatives within a genetic distance of 3 meiotic events (3M).
- The proband is a member of an affected pair related within 3M, one of whom was diagnosed when aged 50 or younger.
- The proband is a member of an affected pair related within 3M, one of whom was diagnosed with a second primary tumor of any type.
- The proband has been diagnosed with a second primary tumor of any type.

The term "Multiple Primary Breast Tumor", or "MPBC", as described herein, refers to cases where at least one Primary tumor is diagnosed in addition to the first breast cancer diagnosis, and the two tumors confirmed both clinically and by histology to be independent primary tumors, arising simultaneously or subsequently to the first breast cancer and occurring in the contralateral or ipsilateral breast.

The term "family history score" or "FHS", as described herein, is defined based on the number of relatives affected with breast cancer for a proband with the disease. For each proband, a score of 1 is assigned for each affected first-degree relative, 0.5 for each affected second degree relative, and 0.25 for each third-degree relative. The total sum thus obtained over all affected relatives represents the summed family history score or FHS.

The term "estrogen receptor positive breast cancer", or "ER-positive breast cancer", as described herein, refers to tumors determined to be positive for estrogen receptor. In the present context, ER levels of greater than or equal to 10 fmol/mg and/or an immunohistochemical observation of greater than or equal to 10% positive nuclei is considered to be ER positive. Breast cancer that does not fulfill the criteria of being ER positive is defined herein as "ER negative" or "estrogen receptor negative".

The term "progesterone receptor positive breast cancer", or "PR-positive breast cancer", as described herein, refers to tumors determined to be positive for progesterone receptor. In the present context, PR levels of greater than or equal to 10 fmol/mg and/or an immunohistochemical observation of greater than or equal to 10% positive nuclei is considered to be PR positive. Breast cancer that does not fulfill the criteria of being PR positive is defined herein as "PR negative" or "progesterone receptor negative".

The term "PAX5" or "PAX5 gene", as described herein, refers to the PAIRED BOX GENE 5 gene, also known as BSAP on human chromosome 9p13.

The term "TUB" or "rd5 gene", as described herein, refers to the Tubby homolog (mouse) gene on human chromosome 11p15.5.

The term "SERPINH1" as described herein, refers to serpin peptidase inhibitor, clade H (heat shock protein 47), member 1, (collagen binding protein 1) gene on human chromosome 11.

Also, the term "RAD51L1 X-gene" also termed; "REC2; R51H2; hREC2; RAD51B or MGC34245" as described herein, refers to a protein coding gene located on human chromosome 14q23-24.

Furthermore, the term "FHOD3gene" also known as "FHOS2gene" or "Formactin2" as described herein, stands for formin homology 2 domain containing 3 gene, a protein coding gene located on human chromosome 18q12.

Finally, the term "TNRC6B" or"TNRC6B gene", also known as "KIAA1093" as described herein, refers to trinucleotide repeat containing 6B, a protein coding gene located on human chromosome 22q13.

Through association analysis of a population of individuals diagnosed with breast cancer according to the present invention, it has been discovered that certain alleles at certain polymorphic markers on chromosomes 9, 10, 11, 14, 18 and 22 are associated with breast cancer. A genome-wide analysis for variants associated with cancer revealed association of breast cancer to nine chromosomal regions i.e.

chromosome 9, between positions 36,806,001 and 36,859,001 (LD block C09);

chromosome 10, between positions 8,643,001 and 8,817,001 (LD block C10A);

chromosome 10, between positions 9,077,001 and 9,264,001 (LD block C10B);

chromosome 11, between positions 8,053,268 and 8,191,268 (LD block C11A);

chromosome 11, between positions 74,886,341 and 74,971,341 (LD block C11B);

chromosome 14, between positions 68,035,712 and 68,130,712 (LD block C14);

chromosome 18, between positions 32,110,012 and 32,145,012 (LD block C18);

chromosome 22, between positions 38,704,907 and 38,859,907 (LD block C22A);

chromosome 22, between positions 38,859,907 and 39,411,907 (LD block C22B);

wherein all positions correspond to NCBI Build 36 coordinates).

Particular markers within these regions were found to be associated with an increased risk of breast cancer in these locations.

Through genotyping of approximately 1840 Icelandic breast cancer patients and an average of 30,350 controls using the Illumina HumanHap300 microarray technology, a large number of markers at several chromosomal locations were found to show association to breast cancer (Table 1). In particular, nine SNPs; rs2005154, rs2184380, rs2224696, rs2242503, rs12291026, rs999737, rs9956546, rs11912922 and rs6001954 were found to be associated with an increased risk of breast cancer.

Follow-up analysis in additional cohorts from Iceland, Holland, Spain and Sweden showed that the association signals of the nine markers are indeed significant (Table 3). These markers, and surrogate markers in linkage disequilibrium with any one of these markers, are therefore useful for predicting risk of breast cancer in individuals. Exemplary surrogate markers are presented in Table 4 herein.

These markers thus identify nine chromosomal regions that in particular are expected to contain markers predictive of breast cancer, by virtue of their LD with any one of the above-mentioned markers. These regions are also called herein LD block C09, LD block C10A, LD block 10B, LD block C11A, LD block C11B, LD block C14, LD block C18, LD block C22A, and LD block C22B.

The skilled person will appreciate that markers in LD with any of the nine anchor markers rs2005154, rs2184380, rs2224696, rs2242503, rs12291026, rs999737, rs9956546, rs11912922 and rs6001954 can be located outside the LD blocks as defined herein. This is a consequence of the fact that LD can extend beyond the apparent physical boundaries of LD blocks as usually defined (boundaries usually defined by regions of high recombination rates). Such surrogate markers in LD with these nine markers are specifically also contemplated to be useful for the present invention, and are therefore also within scope of the present invention.

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome. For example, the human genome exhibits sequence variations which occur on average every 500 base pairs. The most common sequence variant consists of base variations at a single base position in the genome, and such sequence variants, or polymorphisms, are commonly called Single Nucleotide Polymorphisms ("SNPs"). These SNPs are believed to have arisen by a single mutational event, and therefore there are usually two possible alleles possible at each SNPsite; the original allele and the mutated (alternate) allele. Due to natural genetic drift and possibly also selective pressure, the original mutation has resulted in a polymorphism characterized by a particular frequency of its alleles in any given population. Many other types of sequence variants are found in the human genome, including mini- and microsatellites, and insertions, deletions, inversions (also called copy number variations (CNVs)). A polymorphic microsatellite has multiple small repeats of bases (such as CA repeats, TG on the complimentary strand) at a particular site in which the number of repeat lengths varies in the general population. In general terms, each version of the sequence with respect to the polymorphic site represents a specific allele of the polymorphic site. All sequence variants can be referred to as polymorphisms, occurring at specific polymorphic sites characteristic of the sequence variant in question. In general, polymorphisms can comprise any number of specific alleles within the population, although each human individual has two alleles at each polymorphic site—one maternal and one paternal allele. Thus in one embodiment of the invention, the polymorphism is characterized by the presence of two or more alleles in a population. In another embodiment, the polymorphism is characterized by the presence of three or more alleles. In other embodiments, the polymorphism is characterized by four or more alleles, five or more alleles, six or more alleles, seven or more alleles, nine or more alleles, or ten or more alleles. All such polymorphisms can be utilized in the methods and kits of the present invention, and are thus within the scope of the invention.

Due to their abundance, SNPs account for a majority of sequence variation in the human genome. Over 6 million human SNPs have been validated to date (http://www.ncbi.nlm.nih.gov/projects/SNP/snp_summary.cgi). However, CNVs are receiving increased attention. These large-scale polymorphisms (typically 1 kb or larger) account for polymorphic variation affecting a substantial proportion of the assembled human genome; known CNVs covery over 15% of the human genome sequence (Estivill, X Armengol; L., PloS Genetics 3:1787-99 (2007). http://projects.tcag.ca/variation/). Most of these polymorphisms are however very rare, and on average affect only a fraction of the genomic sequence of each individual. CNVs are known to affect gene expression, phenotypic variation and adaptation by disrupting gene dosage, and are also known to cause disease (microdeletion and microduplication disorders) and confer risk of common complex diseases, including HIV-1 infection and glomerulonephritis (Redon, R., et al. Nature 23:444-454 (2006)). It is thus possible that either previously described or unknown CNVs represent causative variants in linkage disequilibrium with the disease-associated markers described herein. Methods for detecting CNVs include comparative genomic hybridization (CGH) and genotyping, including use of genotyping arrays, as described by Carter (Nature Genetics 39:S16-S21 (2007)). The Database of Genomic Variants (http://projects.tcag.ca/variation/) contains updated information about the location, type and size of described CNVs. The database currently contains data for over 21,000 CNVs.

In some instances, reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a trait or disease phenotype).

Alleles for SNP markers as referred to herein refer to the bases A, C, G or T as they occur at the polymorphic site. The allele codes for SNPs used herein are as follows: 1=A, 2=C, 3=G, 4=T. Since human DNA is double-stranded, the person skilled in the art will realize that by assaying or reading the opposite DNA strand, the complementary allele can in each case be measured. Thus, for a polymorphic site (polymorphic marker) characterized by an A/G polymorphism, the methodology employed to detect the marker may be designed to specifically detect the presence of one or both of the two bases possible, i.e. A and G. Alternatively, by designing an assay that is designed to detect the opposite strand on the DNA template, the presence of the complementary bases T and C can be measured. Quantitatively (for example, in terms of relative risk), identical results would be obtained from measurement of either DNA strand (+ strand or − strand).

Typically, a reference sequence is referred to for a particular sequence. Alleles that differ from the reference are sometimes referred to as "variant" alleles. A variant sequence, as used herein, refers to a sequence that differs from the reference sequence but is otherwise substantially similar. Alleles at the polymorphic genetic markers described herein are variants. Variants can include changes that affect a polypeptide. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level. The polypeptide encoded by the reference nucleotide sequence is the "reference" polypeptide with a particular reference amino acid sequence, and polypeptides encoded by variant alleles are referred to as "variant" polypeptides with variant amino acid sequences.

A haplotype refers to a single-stranded segment of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles, each allele corresponding to a specific polymorphic marker along the segment. Haplotypes can comprise a combination of various polymorphic markers, e.g., SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (Chen, X. et al., *Genome Res.* 9(5): 492-98 (1999)), utilizing PCR, LCR, Nested PCR and other techniques for nucleic acid amplification. Specific commercial methodologies available for SNP genotyping include, but are not limited to, TaqMan genotyping assays and SNPlex platforms (Applied Biosystems), gel electrophoresis (Applied Biosystems), mass spectrometry (e.g., MassARRAY system from Sequenom), minisequencing methods, real-time PCR, Bio-Plex system (BioRad), CEQ and SNPstream systems (Beckman), array hybridization technology (e.g., Affymetrix GeneChip; Perlegen), BeadArray Technologies (e.g., Illumina GoldenGate and Infinium assays), array tag technology (e.g., Parallele), and endonuclease-based fluorescence hybridization technology (Invader; Third Wave). Some of the available array platforms, including Affymetrix SNP Array 6.0 and Illumina CNV370-Duo and 1M BeadChips, include SNPs that tag certain CNVs. This allows detection of CNVs via surrogate SNPs included in these platforms. Thus, by use of these or other methods available to the person skilled in the art, one or more alleles at polymorphic markers, including microsatellites, SNPs or other types of polymorphic markers, can be identified.

In certain embodiments, polymorphic markers are detected by sequencing technologies. Obtaining sequence information about an individual identifies particular nucleotides in the context of a sequence. For SNPs, sequence information about a single unique sequence site is sufficient to identify alleles at that particular SNP. For markers comprising more than one nucleotide, sequence information about the nucleotides of the individual that contain the polymorphic site identifies the alleles of the individual for the particular site. The sequence information can be obtained from a sample from the individual. In certain embodiments, the sample is a nucleic acid sample. In certain other embodiments, the sample is a protein sample.

Various methods for obtaining nucleic acid sequence are known to the skilled person, and all such methods are useful for practicing the invention. Sanger sequencing is a well-known method for generating nucleic acid sequence information. Recent methods for obtaining large amounts of sequence data have been developed, and such methods are also contemplated to be useful for obtaining sequence information. These include pyrosequencing technology (Ronaghi, M. et al. *Anal Biochem* 267:65-71 (1999); Ronaghi, et al., *Biotechniques* 25:876-878 (1998)), e.g. 454 pyrosequencing (Nyren, P., et al. *Anal Biochem* 208:171-175 (1993)), Illumina/Solexa sequencing technology (http://www.illumina.com; see also Strausberg, R L, et al *Drug Disc Today* 13:569-577 (2008)), and Supported Oligonucleotide Ligation and Detection Platform (SOLiD) technology (Applied Biosystems, http://www.appliedbiosystems.com); Strausberg, R L, et al *Drug Disc Today* 13:569-577 (2008).

It is possible to impute or predict genotypes for un-genotyped relatives of genotyped individuals. For every un-genotyped case, it is possible to calculate the probability of the genotypes of its relatives given its four possible phased genotypes. In practice it may be preferable to include only the genotypes of the case's parents, children, siblings, half-siblings (and the half-sibling's parents), grand-parents, grand-children (and the grand-children's parents) and spouses. It will be assumed that the individuals in the small sub-pedigrees created around each case are not related through any path not included in the pedigree. It is also assumed that alleles that are not transmitted to the case have the same frequency—the population allele frequency. Let us consider a SNP marker with the alleles A and G. The probability of the genotypes of the case's relatives can then be computed by:

$$Pr(\text{genotypes of relatives}; \theta) = \sum_{h \in \{AA, AG, GA, GG\}} Pr(h; \theta) Pr(\text{genotypes of relatives} \mid h),$$

where θ denotes the A allele's frequency in the cases. Assuming the genotypes of each set of relatives are independent, this allows us to write down a likelihood function for θ:

$$L(\theta) = \prod_i Pr(\text{genotypes of relatives of case } i; \theta). \quad (*)$$

This assumption of independence is usually not correct. Accounting for the dependence between individuals is a difficult and potentially prohibitively expensive computational task. The likelihood function in (*) may be thought of as a pseudolikelihood approximation of the full likelihood function for θ which properly accounts for all dependencies. In general, the genotyped cases and controls in a case-control association study are not independent and applying the case-control method to related cases and controls is an analogous approximation. The method of genomic control (Devlin, B. et al., *Nat Genet* 36, 1129-30; author reply 1131 (2004)) has proven to be successful at adjusting case-control test statistics for relatedness. We therefore apply the method of genomic control to account for the dependence between the terms in our pseudolikelihood and produce a valid test statistic.

Fisher's information can be used to estimate the effective sample size of the part of the pseudolikelihood due to ungenotyped cases. Breaking the total Fisher information, I, into the part due to genotyped cases, $I_g$, and the part due to ungenotyped cases, $I_u$, $I=I_g+I_u$, and denoting the number of genotyped cases with N, the effective sample size due to the ungenotyped cases is estimated by $$\frac{I_u}{I_g}N.$$

In the present context, an individual who is at an increased susceptibility (i.e., increased risk) for a disease, is an individual in whom at least one specific allele at one or more polymorphic marker or haplotype conferring increased susceptibility (increased risk) for the disease is identified (i.e., at-risk marker alleles or haplotypes). The at-risk marker or haplotype is one that confers an increased risk (increased susceptibility) of the disease. In one embodiment, significance associated with a marker or haplotype is measured by a relative risk (RR). In another embodiment, significance associated with a marker or haplotye is measured by an odds ratio (OR). In a further embodiment, the significance is measured by a percentage. In one embodiment, a significant increased risk is measured as a risk (relative risk and/or odds ratio) of at least 1.2, including but not limited to: at least 1.2, at least 1.3, at least 1.4, at least 1.5, at least 1.6, at least 1.7, 1.8, at least 1.9, at least 2.0, at least 2.5, at least 3.0, at least 4.0, and at least 5.0. In a particular embodiment, a risk (relative risk and/or odds ratio) of at least 1.2 is significant. In another particular embodiment, a risk of at least 1.3 is significant. In yet another embodiment, a risk of at least 1.4 is significant. In a further embodiment, a relative risk of at least 1.5 is significant. In another further embodiment, a significant increase in risk is at least 1.7 is significant. However, other cutoffs are also contemplated, e.g., at least 1.15, 1.25, 1.35, and so on, and such cutoffs are also within scope of the present invention. In other embodiments, a significant increase in risk is at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, and 500%. In one particular embodiment, a significant increase in risk is at least 20%. In other embodiments, a significant increase in risk is at least 30%, at least 40%, at least 50%, at least 60%, at least 70%, at least 80%, at least 90% and at least 100%. Other cutoffs or ranges as deemed suitable by the person skilled in the art to characterize the invention are however also contemplated, and those are also within scope of the present invention. In certain embodiments, a significant increase in risk is characterized by a p-value, such as a p-value of less than 0.05, less than 0.01, less than 0.001, less than 0.0001, less than 0.00001, less than 0.000001, less than 0.0000001, less than 0.00000001, or less than 0.000000001.

An at-risk polymorphic marker or haplotype of the present invention is one where at least one allele of at least one marker or haplotype is more frequently present in an individual at risk for the disease or trait (affected), or diagnosed with the disease or trait, compared to the frequency of its presence in a comparison group (control), such that the presence of the marker or haplotype is indicative of susceptibility to the disease or trait (e.g., breast cancer). The control group may in one embodiment be a population sample, i.e. a random sample from the general population. In another embodiment, the control group is represented by a group of individuals who are disease-free, i.e. individuals who have not been diagnosed with breast cancer. Such disease-free control may in one embodiment be characterized by the absence of one or more specific disease-associated symptoms. In another embodiment, the disease-free control group is characterized by the absence of one or more disease-specific risk factors. Such risk factors are in one embodiment at least one environmental risk factor. Representative environmental factors are natural products, minerals or other chemicals which are known to affect, or contemplated to affect, the risk of developing the specific disease or trait. Other environmental risk factors are risk factors related to lifestyle, including but not limited to food and drink habits, geographical location of main habitat, and occupational risk factors. In another embodiment, the risk factors are at least one genetic risk factor.

As an example of a simple test for correlation would be a Fisher-exact test on a two by two table. Given a cohort of chromosomes, the two by two table is constructed out of the number of chromosomes that include both of the markers or haplotypes, one of the markers or haplotypes but not the other and neither of the markers or haplotypes. Other statistical tests of association known to the skilled person are also contemplated and are also within scope of the invention.

The person skilled in the art will appreciate that for markers with two alleles present in the population being studied (such as SNPs), and wherein one allele is found in increased frequency in a group of individuals with a trait or disease in the population, compared with controls, the other allele of the marker will be found in decreased frequency in the group of individuals with the trait or disease, compared with controls. In such a case, one allele of the marker (the one found in increased frequency in individuals with the trait or disease) will be the at-risk allele, while the other allele will be a protective allele.

Thus is other embodiments of the invention, an individual who is at a decreased susceptibility (i.e., at a decreased risk) for a disease or trait is an individual in whom at least one specific allele at one or more polymorphic marker or haplotype conferring decreased susceptibility for the disease or trait is identified. The marker alleles and/or haplotypes conferring decreased risk are also said to be protective. In one aspect, the protective marker or haplotype is one that confers a significant decreased risk (or susceptibility) of the disease or trait. In one embodiment, significant decreased risk is measured as a relative risk of less than 0.90, including but not limited to less than 0.85, less than 0.80, less than 0.75, less than 0.7, less than 0.6, less than 0.5, less than 0.4, less than 0.3, less than 0.2 and less than 0.1. In one particular embodiment, significant decreased risk is less than 0.90. In another embodiment, significant decreased risk is less than 0.85. In yet another embodiment, significant decreased risk is less than 0.80. In another embodiment, the decrease in risk (or susceptibility) is at least 10%, including but not limited to at least 15%, at least 20%, at least 25%, at least 30%, at least 35%, at least 40%, at least 45%, at least 50%, at least 55%, at least 60%, at least 65%, at least 70%, at least 80%, at least 85%, at least 90%, at least 95% and at least 98%. In one particular embodiment, a significant decrease in risk is at least about 15%. In another embodiment, a significant decrease in risk at least about 20%. In another embodiment, the decrease in risk is at least about 25%. Other cutoffs or ranges as deemed suitable by the person skilled in the art to characterize the invention are however also contemplated, and those are also within scope of the present invention.

A genetic variant associated with a disease or a trait (e.g. breast cancer) can be used alone to predict the risk of the disease for a given genotype. For a biallelic marker, such as a SNP, there are 3 possible genotypes: homozygote for the at risk variant, heterozygote, and non carrier of the at risk variant. Risk associated with variants at multiple loci can be used to estimate overall risk. For multiple SNP variants, there are k possible genotypes $k=3^n\times2^p$; where n is the number autosomal loci and p the number of gonosomal (sex chromosomal) loci. Overall risk assessment calculations usually assume that the relative risks of different genetic variants multiply, i.e. the overall risk (e.g., RR or OR) associated with a particular genotype combination is the product of the risk values for the genotype at each locus. If the risk presented is the relative risk for a person, or a specific genotype for a person, compared to a reference population with matched gender and ethnicity, then the combined risk is the product of the locus specific risk values and also corresponds to an overall risk estimate compared with the population. If the risk for a person is based on a comparison to non-carriers of the at risk allele, then the combined risk corresponds to an estimate that compares the person with a given combination of genotypes at all loci to a group of individuals who do not carry risk variants at any of those loci. The group of non-carriers of any at risk variant has the lowest estimated risk and has a combined risk, compared with itself (i.e., non-carriers) of 1.0, but has an overall risk, compare with the population, of less than 1.0. It should be noted that the group of non-carriers can potentially be very small, especially for large number of loci, and in that case, its relevance is correspondingly small.

The multiplicative model is a parsimonious model that usually fits the data of complex traits reasonably well. Deviations from multiplicity have been rarely described in the context of common variants for common diseases, and if reported are usually only suggestive since very large sample sizes are usually required to be able to demonstrate statistical interactions between loci.

By way of an example, let us consider the case were a total of seven variants that have been associated with breast cancer. One such example is provided by the markers rs13387042, rs4415084, rs1219648, rs3803662, rs13281615, rs3817198 and rs889312, all of which are used in the marketed deCODE BreastCancer test for breast cancer susceptibility (http://www.decodediagnostics.com). The total number of theoretical genotypic combinations is then $3^7=2187$. Some of those genotypic classes are very rare, but are still possible, and should be considered for overall risk assessment. It is likely that the multiplicative model applied in the case of multiple genetic variant will also be valid in conjugation with non-genetic risk variants assuming that the genetic variant does not clearly correlate with the "environmental" factor. In other words, genetic and non-genetic at-risk variants can be assessed under the multiplicative model to estimate combined risk, assuming that the non-genetic and genetic risk factors do not interact.

Using the same quantitative approach, the combined or overall risk associated with any plurality of these and other variants associated with breast cancer may be assessed. This includes the variants that are shown and claimed herein to be predictive of breast cancer risk.

Linkage Disequilibrium

The natural phenomenon of recombination, which occurs on average once for each chromosomal pair during each meiotic event, represents one way in which nature provides variations in sequence (and biological function by consequence). It has been discovered that recombination does not occur randombly in the genome; rather, there are large variations in the frequency of recombination rates, resulting in small regions of high recombination frequency (also called recombination hotspots) and larger regions of low recombination frequency, which are commonly referred to as Linkage Disequilibrium (LD) blocks (Myers, S. et al., *Biochem Soc Trans* 34:526-530 (2006); Jeffreys, A. J., et al., *Nature Genet* 29:217-222 (2001); May, C. A., et al., *Nature Genet* 31:272-275 (2002)).

Linkage Disequilibrium (LD) refers to a non-random assortment of two genetic elements. For example, if a particular genetic element (e.g., an allele of a polymorphic marker, or a haplotype) occurs in a population at a frequency of 0.50 (50%) and another element occurs at a frequency of 0.50 (50%), then the predicted occurrance of a person's having both elements is 0.25 (25%), assuming a random distribution of the elements. However, if it is discovered that the two elements occur together at a frequency higher than 0.125, then the elements are said to be in linkage disequilibrium, since they tend to be inherited together at a higher rate than what their independent frequencies of occurrence (e.g., allele or haplotype frequencies) would predict. Roughly speaking, LD is generally correlated with the frequency of recombination events between the two elements. Allele or haplotype frequencies can be determined in a population by genotyping individuals in a population and determining the frequency of the occurrence of each allele or haplotype in the population. For populations of diploids, e.g., human populations, individuals will typically have two alleles for each genetic element (e.g., a marker, haplotype or gene).

Many different measures have been proposed for assessing the strength of linkage disequilibrium (LD; reviewed in Devlin, B. & Risch, N., *Genomics* 29:311-22 (1995)). Most capture the strength of association between pairs of biallelic sites. Two Important pairwise measures of LD are $r^2$ (sometimes denoted $\Delta^2$) and $|D'|$ (Lewontin, R., *Genetics* 49:49-67 (1964); Hill, W. G. & Robertson, A. *Theor. Appl. Genet.* 22:226-231 (1968)). Both measures range from 0 (no disequilibrium) to 1 ('complete' disequilibrium), but their interpretation is slightly different. $|D'|$ is defined in such a way that it is equal to 1 if just two or three of the possible haplotypes for two markers are present, and it is <1 if all four possible haplotypes are present. Therefore, a value of $|D'|$ that is <1 indicates that historical recombination may have occurred between two sites (recurrent mutation can also cause $|D'|$ to be <1, but for single nucleotide polymorphisms (SNPs) this is usually regarded as being less likely than recombination).

The measure $r^2$ represents the statistical correlation between two sites, and takes the value of 1 if only two haplotypes are present.

The $r^2$ measure is arguably the most relevant measure for association mapping, because there is a simple inverse relationship between $r^2$ and the sample size required to detect association between susceptibility loci and particular SNPs. These measures are defined for pairs of sites, but for some applications a determination of how strong LD is across an entire region that contains many polymorphic sites might be desirable (e.g., testing whether the strength of LD differs significantly among loci or across populations, or whether there is more or less LD in a region than predicted under a particular model). Roughly speaking, r measures how much recombination would be required under a particular population model to generate the LD that is seen in the data. This type of method can potentially also provide a statistically rigorous approach to the problem of determining whether LD data provide evidence for the presence of recombination hotspots. For the methods described herein, a significant $r^2$ value between markers indicative of the markers being in linkage disequilibrium can be at least 0.1, such as at least 0.15, 0.20, 0.25, 0.30, 0.35, 0.40, 0.45, 0.50, 0.55, 0.60, 0.65, 0.70, 0.75, 0.80, 0.85, 0.90, 0.91, 0.92, 0.93, 0.94, 0.95, 0.96, 0.97, 0.98, or at least 0.99. In one preferred embodiment, the significant $r^2$ value can be at least 0.2. Alternatively, markers in linkage disequilibrium are characterized by values of $|D'|$ of at least 0.2, such as 0.3, 0.4, 0.5, 0.6, 0.7, 0.8, 0.85, 0.9, 0.95, 0.96, 0.97, 0.98, or at least 0.99. Thus, linkage disequilibrium represents a correlation between alleles of distinct markers. In certain embodiments, linkage disequilibrium is defined in terms of values for both the $r^2$ and $|D'|$ measures. In one such embodiment, a significant linkage disequilibrium is defined as $r^2>0.1$ and $|D'|>0.8$, and markers fulfilling these criteria are said to be in linkage disequilibrium. In another embodiment, a significant linkage disequilibrium is defined as $r^2>0.2$ and $>0.9$. Other combinations and permutations of values of $r^2$ and $|D'|$ for determining linkage disequilibrium are also contemplated, and are also within the scope of the invention. Linkage disequilibrium can be determined in a single human population, as defined herein, or it can be determined in a collection of samples comprising individuals from more than one human population. In one embodiment of the invention, LD is determined in a sample from one or more of the HapMap populations (Caucasian, African (Yuroban), Japanese, Chinese), as defined (http://www.hapmap.org). In one such embodiment, LD is determined in the CEU population of the HapMap samples (Utah residents with ancestry from northern and western Europe). In another embodiment, LD is determined in the YRI population of the HapMap samples (Yuroba in Ibadan, Nigeria). In another embodiment, LD is determined in the CHB population of the HapMap samples (Han Chinese from Beijing, China). In another embodiment, LD is determined in the JPT population of the HapMap samples (Japanese from Tokyo, Japan). In yet another embodiment, LD is determined in samples from the Icelandic population.

If all polymorphisms in the genome were identical at the population level, then every single one of them would need to be investigated in association studies. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms may give an association signal due to the fact that these polymorphisms are strongly correlated.

Genomic LD maps have been generated across the genome, and such LD maps have been proposed to serve as framework for mapping disease-genes (Risch, N. & Merkiangas, K, *Science* 273:1516-1517 (1996); Maniatis, N., et al., *Proc Natl Acad Sci USA* 99:2228-2233 (2002); Reich, D E et al., *Nature* 411:199-204 (2001)).

It is now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., *Nature Reviews Genetics* 4:587-597 (2003); Daly, M. et al., *Nature Genet.* 29:229-232 (2001); Gabriel, S. B. et al., *Science* 296:2225-2229 (2002); Patil, N. et al., *Science* 294:1719-1723 (2001); Dawson, E. et al., *Nature* 418:544-548 (2002); Phillips, M. S. et al., *Nature Genet.* 33:382-387 (2003)).

There are two main methods for defining these haplotype blocks: blocks can be defined as regions of DNA that have limited haplotype diversity (see, e.g., Daly, M. et al., *Nature Genet.* 29:229-232 (2001); Patil, N. et al., *Science* 294:1719-1723 (2001); Dawson, E. et al., *Nature* 418:544-548 (2002); Zhang, K. et al., *Proc. Natl. Acad. Sci. USA* 99:7335-7339 (2002)), or as regions between transition zones having extensive historical recombination, identified using linkage disequilibrium (see, e.g., Gabriel, S. B. et al., *Science* 296:2225-2229 (2002); Phillips, M. S. et al., *Nature Genet.* 33:382-387 (2003); Wang, N. et al., *Am. J. Hum. Genet.* 71:1227-1234 (2002); Stumpf, M. P., and Goldstein, D. B., *Curr. Biol.* 13:1-8 (2003)). More recently, a fine-scale map of recombination rates and corresponding hotspots across the human genome has been generated (Myers, S., et al., *Science* 310:321-32324 (2005); Myers, S. et al., *Biochem Soc Trans* 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions.

For example The term "LD block C09", as described herein, refers to the Linkage Disequilibrium (LD) block on Chromosome 9 between positions 36,806,001 and 36,859,001 of NCBI (National Center for Biotechnology Information) Build 36. The following table defines choromosomal positions of the nine LD blocks in NCBI Build 36, referred to in this application:

Table of LD-blocks (positions from NCBI Build 36)

| Chromosome | LD Block | Block Start B36 | Block End B36 |
|---|---|---|---|
| C09 | LD block C09 | 36,806,001 | 36,859,001 |
| C10 | LD block C10A | 8,643,001 | 8,817,001 |
| C10 | LD block C10B | 9,077,001 | 9,264,001 |
| C11 | LD block C11A | 8,053,268 | 8,191,268 |
| C11 | LD block C11B | 74,886,341 | 74,971,341 |
| C14 | LD block C14 | 68,035,712 | 68,130,712 |
| C18 | LD block C18 | 32,110,012 | 32,145,012 |
| C22 | LD block C22A | 38,704,907 | 38,859,907 |
| C22 | LD block C22B | 38,859,907 | 39,411,907 |

Haplotype blocks (LD blocks) can be used to map associations between phenotype and haplotype status, using single markers or haplotypes comprising a plurality of markers. The main haplotypes can be identified in each haplotype block, and then a set of "tagging" SNPs or markers (the smallest set of SNPs or markers needed to distinguish among the haplotypes) can then be identified. These tagging SNPs or markers can then be used in assessment of samples from groups of individuals, in order to identify association between phenotype and haplotype. Markers shown herein to be associated with breast cancer are such tagging markers. If desired, neighboring haplotype blocks can be assessed concurrently, as there may also exist linkage disequilibrium among the haplotype blocks.

It has thus become apparent that for any given observed association to a polymorphic marker in the genome, that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block) that is associating with a given disease or trait. One or more causative (functional) variants or mutations may reside within the region found to be associating to the disease or trait. The functional variant may be another SNP, a tandem repeat polymorphism (such as a minisatellite or a microsatellite), a transposable element, or a copy number variation, such as an inversion, deletion or insertion. Such variants in LD with the variants described herein may confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in certain embodiments of the invention, markers that are in LD with the markers originally used to detect an association may be used as surrogate markers. The surrogate markers have in one embodiment relative risk (RR) and/or odds ratio (OR) values smaller than originally detected. In other embodiments, the surrogate markers have RR or OR values greater than those initially determined for the markers initially found to be associating with the disease. An example of such an embodiment would be a rare, or relatively rare (<10% allelic population frequency) variant in LD with a more common variant (>10% population frequency) initially found to be associating with the disease. Identifying and using such surrogate markers for detecting the association can be performed by routine methods well known to the person skilled in the art, and are therefore within the scope of the present invention.

Determination of Haplotype Frequency

The frequencies of haplotypes in patient and control groups can be estimated using an expectation-maximization algorithm (Dempster A. et al., *J. R. Stat. Soc.* 8, 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistical significance.

To look for at-risk and protective markers and haplotypes within a susceptibility region, for example, within an LD block region, association of all possible combinations of genotyped markers within the region is studied. The combined patient and control groups can be randomly divided into two sets, equal in size to the original group of patients and controls. The marker and haplotype analysis is then repeated and the most significant p-value registered is determined. This randomization scheme can be repeated, for example, over 100 times to construct an empirical distribution of p-values. In a preferred embodiment, a p-value of <0.05 is indicative of an significant marker and/or haplotype association.

Haplotype Analysis

One general approach to haplotype analysis involves using likelihood-based inference applied to NEsted MOdels (Gretarsdottir S., et al., Nat. Genet. 35:131-38 (2003)). The method is implemented in the program NEMO, which allows for many polymorphic markers, SNPs and microsatellites. The method and software are specifically designed for case-control studies where the purpose is to identify haplotype groups that confer different risks. It is also a tool for studying LD structures. In NEMO, maximum likelihood estimates, likelihood ratios and p-values are calculated directly, with the aid of the EM algorithm, for the observed data treating it as a missing-data problem.

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. The information measure for haplotype analysis is described in Nicolae and Kong (Technical Report 537, Department of Statistics, University of Statistics, University of Chicago; *Biometrics,* 60(2):368-75 (2004)) as a natural extension of information measures defined for linkage analysis, and is implemented in NEMO.

Association Analysis

For single marker association to a disease, the Fisher exact test can be used to calculate two-sided p-values for each individual allele. Correcting for relatedness among patients can be done by extending a variance adjustment procedure previously described (Risch, N. & Teng, J. *Genome Res.,* 8:1273-1288 (1998)) for sibships so that it can be applied to general familial relationships. The method of genomic controls (Devlin, B. & Roeder, K. *Biometrics* 55:997 (1999)) can also be used to adjust for the relatedness of the individuals and possible stratification.

For both single-marker and haplotype analyses, relative risk (RR) and the population attributable risk (PAR) can be calculated assuming a multiplicative model (haplotype relative risk model) (Terwilliger, J. D. & Ott, J., Hum. Hered. 42:337-46 (1992) and Falk, C. T. & Rubinstein, P, Ann. Hum. Genet. 51 (Pt 3):227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes, $h_i$ and $h_j$, $risk(h_i)/risk(h_j)=(f_i/p_i)/(f_j/p_j)$, where f and p denote, respectively, frequencies in the affected population and in the control population. While there is some power loss if the true model is not multiplicative, the loss tends to be mild except for extreme cases. Most importantly, p-values are always valid since they are computed with respect to null hypothesis.

An association signal detected in one association study may be replicated in a second cohort, ideally from a different population (e.g., different region of same country, or a different country) of the same or different ethnicity. The advantage of replication studies is that the number of tests performed in the replication study is usually quite small, and hence the less stringent the statistical measure that needs to be applied. For example, for a genome-wide search for susceptibility variants for a particular disease or trait using 300,000 SNPs, a correction for the 300,000 tests performed (one for each SNP) can be performed. Since many SNPs on the arrays typically used are correlated (i.e., in LD), they are not independent. Thus, the correction is conservative. Nevertheless, applying this correction factor requires an observed P-value of less than $0.05/300{,}000=1.7\times10^{-7}$ for the signal to be considered significant applying this conservative test on results from a single study cohort. Obviously, signals found in a genome-wide association study with P-values less than this conservative threshold (i.e., more significant) are a measure of a true genetic effect, and replication in additional cohorts is not necessarily from a statistical point of view. Importantly, however, signals with P-values that are greater than this threshold may also be due to a true genetic effect. The sample size in the first study may not have been sufficiently large to provide an observed P-value that meets the conservative threshold for genome-wide significance, or the first study may not have reached genome-wide significance due to inherent fluctuations due to sampling. Since the correction factor depends on the number of statistical tests performed, if one signal (one SNP) from an initial study is replicated in a second case-control cohort, the appropriate statistical test for significance is that for a single statistical test, i.e., P-value less than 0.05. Replication studies in one or even several additional case-control cohorts have the added advantage of providing assessment of the association signal in additional populations, thus simultaneously confirming the initial finding and providing an assessment of the overall significance of the genetic variant(s) being tested in human populations in general.

The results from several case-control cohorts can also be combined to provide an overall assessment of the underlying effect. The methodology commonly used to combine results from multiple genetic association studies is the Mantel-Haenszel model (Mantel and Haenszel, J Natl Cancer Inst 22:719-48 (1959)). The model is designed to deal with the situation where association results from different populations, with each possibly having a different population frequency of the genetic variant, are combined. The model combines the results assuming that the effect of the variant on the risk of the disease, a measured by the OR or RR, is the same in all populations, while the frequency of the variant may differ between the populations. Combining the results from several populations has the added advantage that the overall power to detect a real underlying association signal is increased, due to the increased statistical power provided by the combined cohorts. Furthermore, any deficiencies, in individual studies, for example due to unequal matching of cases and controls or population stratification will tend to balance out when results from multiple cohorts are combined, again providing a better estimate of the true underlying genetic effect.

Risk Assessment and Diagnostics

Within any given population, there is an absolute risk of developing a disease or trait, defined as the chance of a person developing the specific disease or trait over a specified time-period. For example, a woman's lifetime absolute risk of breast cancer is one in nine. That is to say, one woman in every nine will develop breast cancer at some point in their lives. Risk is typically measured by looking at very large numbers of people, rather than at a particular individual. Risk is often presented in terms of Absolute Risk (AR) and Relative Risk (RR). Relative Risk is used to compare risks associating with two variants or the risks of two different groups of people. For example, it can be used to compare a group of people with a certain genotype with another group having a different genotype. For a disease, a relative risk of 2 means that one group has twice the chance of developing a disease as the other group. The Risk presented is usually the relative risk for a person, or a specific genotype of a person, compared to the population with matched gender and ethnicity. Risks of two individuals of the same gender and ethnicity could be compared in a simple manner. For example, if, compared to the population, the first Individual has relative risk 1.5 and the second has relative risk 0.5, then the risk of the first Individual compared to the second individual is 1.5/0.5=3.

Risk Calculations

The creation of a model to calculate the overall genetic risk involves two steps: i) conversion of odds-ratios for a single genetic variant into relative risk and ii) combination of risk from multiple variants in different genetic loci into a single relative risk value.

Deriving Risk from Odds-Ratios

Most gene discovery studies for complex diseases that have been published to date in authoritative journals have employed a case-control design because of their retrospective setup. These studies sample and genotype a selected set of cases (people who have the specified disease condition) and control individuals. The interest is in genetic variants (alleles) which frequency in cases and controls differ significantly.

The results are typically reported in odds ratios, that is the ratio between the fraction (probability) with the risk variant (carriers) versus the non-risk variant (non-carriers) in the groups of affected versus the controls, i.e. expressed in terms of probabilities conditional on the affection status:

$$OR=(Pr(c|A)/Pr(nc|A))/(Pr(c|C)/Pr(nc|C))$$

Sometimes it is however the absolute risk for the disease that we are interested in, i.e. the fraction of those individuals carrying the risk variant who get the disease or in other words the probability of getting the disease. This number cannot be directly measured in case-control studies, in part, because the ratio of cases versus controls is typically not the same as that in the general population. However, under certain assumption, we can estimate the risk from the odds ratio.

It is well known that under the rare disease assumption, the relative risk of a disease can be approximated by the odds ratio. This assumption may however not hold for many common diseases. Still, it turns out that the risk of one genotype variant relative to another can be estimated from the odds ratio expressed above. The calculation is particularly simple under the assumption of random population controls where the controls are random samples from the same population as the cases, including affected people rather than being strictly unaffected individuals. To increase sample size and power, many of the large genome-wide association and replication studies use controls that were neither age-matched with the cases, nor were they carefully scrutinized to ensure that they did not have the disease at the time of the study.

Hence, while not exactly, they often approximate a random sample from the general population. It is noted that this assumption is rarely expected to be satisfied exactly, but the risk estimates are usually robust to moderate deviations from this assumption.

Calculations show that for the dominant and the recessive models, where we have a risk variant carrier, "c", and a non-carrier, "nc", the odds ratio of individuals is the same as the risk ratio between these variants:

$$OR=Pr(A|c)/Pr(A|nc)=r$$

And likewise for the multiplicative model, where the risk is the product of the risk associated with the two allele copies, the allelic odds ratio equals the risk factor:

$$OR=Pr(A|aa)/Pr(A|ab)=Pr(A|ab)/Pr(A|bb)=r$$

Here "a" denotes the risk allele and "b" the non-risk allele. The factor "r" is therefore the relative risk between the allele types.

For many of the studies published in the last few years, reporting common variants associated with complex diseases, the multiplicative model has been found to summarize the effect adequately and most often provide a fit to the data superior to alternative models such as the dominant and recessive models.

The Risk Relative to the Average Population Risk

It is most convenient to represent the risk of a genetic variant relative to the average population since it makes it easier to communicate the lifetime risk for developing the disease compared with the baseline population risk. For example, in the multiplicative model we can calculate the relative population risk for variant "aa" as:

$$RR(aa)=Pr(A|aa)/Pr(A)=(Pr(A|aa)/Pr(A|bb))/(Pr(A)/Pr(A|bb))=r^2/(Pr(aa)r^2+Pr(ab)r+Pr(bb))=r^2/(p^2r^2+2pqr+q^2)=r^2/R$$

Here "p" and "q" are the allele frequencies of "a" and "b" respectively. Likewise, we get that RR(ab)=r/R and RR(bb)=1/R. The allele frequency estimates may be obtained from the publications that report the odds-ratios and from the HapMap database. Note that in the case where we do not know the genotypes of an individual, the relative genetic risk for that test or marker is simply equal to one.

As an example, for marker rs999737 on chromosome 14, allele C has an allelic OR for breast cancer of 1.15 and a frequency (p) around 0.76 in Caucasian populations. The genotype relative risk compared to genotype TT are estimated based on the multiplicative model.

For CC it is 1.15×1.15=1.32; for CT it is simply the OR 1.15, and for TT it is 1.0 by definition.

The frequency of allele T is q=1−p=1−0.76=0.24. Population frequency of each of the three possible genotypes at this marker is:

$$Pr(CC)=p^2=0.58, Pr(CT)=2pq=0.36, \text{and } Pr(TT)=q^2=0.06$$

The average population risk relative to genotype TT (which is defined to have a risk of one) is:

$$R=0.50\times1.32+0.36\times1.15+0.06\times1=1.13$$

Therefore, the risk relative to the general population (RR) for individuals who have one of the following genotypes at this marker is:

$$RR(CC)=1.32/1.13=1.17, RR(CT)=1.15/1.13=1.02, RR(TT)=1/1.13=0.88.$$

Combining the risk from multiple markers:

When genotypes of many SNP variants are used to estimate the risk for an individual a multiplicative model for risk can generally be assumed. This means that the combined genetic risk relative to the population is calculated as the product of the corresponding estimates for individual markers, e.g. for two markers g1 and g2:

$$RR(g1,g2)=RR(g1)RR(g2)$$

The underlying assumption is that the risk factors occur and behave independently, i.e. that the joint conditional probabilities can be represented as products:

$$Pr(A|g1,g2)=Pr(A|g1)Pr(A|g2)/Pr(A) \text{ and } Pr(g1,g2)=Pr(g1)Pr(g2)$$

Obvious violations to this assumption are markers that are closely spaced on the genome, i.e. in linkage disequilibrium, such that the concurrence of two or more risk alleles is correlated. In such cases, we can use so called haplotype modeling where the odds-ratios are defined for all allele combinations of the correlated SNPs.

As is in most situations where a statistical model is utilized, the model applied is not expected to be exactly true since it is not based on an underlying bio-physical model. However, the multiplicative model has so far been found to fit the data adequately, i.e. no significant deviations are detected for many common diseases for which many risk variants have been discovered.

As an example, an individual who has the following genotypes at 4 hypothetical markers associated with a particular disease along with the risk relative to the population at each marker:

| Marker | Genotype | Calculated risk |
|---|---|---|
| M1 | CC | 1.03 |
| M2 | GG | 1.30 |
| M3 | AG | 0.88 |
| M4 | TT | 1.54 |

Combined, the overall risk relative to the population for this individual is: 1.03×1.30×0.88×1.54=1.81. In an analogous fashion, overall risk for any plurality of markers (or haplotypes) may be assessed.

Adjusted Life-Time Risk

The lifetime risk of an individual is derived by multiplying the overall genetic risk relative to the population with the average life-time risk of the disease in the general population of the same ethnicity and gender and in the region of the individual's geographical origin. As there are usually several epidemiologic studies to choose from when defining the general population risk, we will pick studies that are well-powered for the disease definition that has been used for the genetic variants.

For example, for a particular disease, if the overall genetic risk relative to the population is 1.8 for an individual, and if the average life-time risk of the disease for individuals of his demographic is 20%, then the adjusted lifetime risk for him is 20%×1.8=36%.

Note that since the average RR for a population is one, this multiplication model provides the same average adjusted life-time risk of the disease. Furthermore, since the actual life-time risk cannot exceed 100%, there must be an upper limit to the genetic RR.

Risk Assessment for Breast Cancer

As described herein, certain polymorphic markers and haplotypes comprising such markers are found to be useful for risk assessment of breast cancer. Risk assessment can involve the use of the markers for diagnosing a susceptibility to breast cancer. Particular alleles of certain polymorphic markers are found more frequently in individuals with breast cancer, than in individuals without diagnosis of breast cancer. Therefore, these marker alleles have predictive value for detecting breast cancer, or a susceptibility to breast cancer, in an individual. Tagging markers in linkage disequilibrium with at-risk variants (or protective variants) described herein can be used as surrogates for these markers (and/or haplotypes). Such surrogate markers can be located within a particular haplotype block or LD block. Such surrogate markers can also sometimes be located outside the physical boundaries of such a haplotype block or LD block, either in close vicinity of the LD block/haplotype block, but possibly also located in a more distant genomic location.

Long-distance LD can for example arise if particular genomic regions (e.g., genes) are in a functional relationship. For example, if two genes encode proteins that play a role in a shared metabolic pathway, then particular variants in one gene may have a direct impact on observed variants for the other gene. Let us consider the case where a variant in one gene leads to increased expression of the gene product. To counteract this effect and preserve overall flux of the particular pathway, this variant may have led to selection of one (or more) variants at a second gene that confers decreased expression levels of that gene. These two genes may be located in different genomic locations, possibly on different chromosomes, but variants within the genes are in apparent LD, not because of their shared physical location within a region of high LD, but rather due to evolutionary forces. Such LD is also contemplated and within scope of the present invention. The skilled person will appreciate that many other scenarios of functional gene-gene interaction are possible, and the particular example discussed here represents only one such possible scenario.

Markers with values of $r^2$ equal to 1 are perfect surrogates for the at-risk variants (anchor variants), i.e. genotypes for one marker perfectly predicts genotypes for the other. Markers with smaller values of $r^2$ than 1 can also be surrogates for the at-risk variant, or alternatively represent variants with relative risk values as high as or possibly even higher than the at-risk variant. In certain preferred embodiments, markers with values of $r^2$ to the at-risk anchor variant are useful surrogate markers. The at-risk variant identified may not be the functional variant itself, but is in this instance in linkage disequilibrium with the true functional variant. The functional variant may be a SNP, but may also for example be a tandem repeat, such as a minisatellite or a microsatellite, a transposable element (e.g., an Alu element), or a structural alteration, such as a deletion, insertion or inversion (sometimes also called copy number variations, or CNVs). The present invention encompasses the assessment of such surrogate markers for the markers as disclosed herein. Such markers are annotated, mapped and listed in public databases, as well known to the skilled person, or can alternatively be readily identified by sequencing the region or a part of the region identified by the markers of the present invention in a group of individuals, and identify polymorphisms in the resulting group of sequences. As a consequence, the person skilled in the art can readily and without undue experimentation identify and genotype surrogate markers in linkage disequilibrium with the markers and/or haplotypes as described herein. The tagging or surrogate markers in LD with the at-risk variants detected also have predictive value.

The present invention can in certain embodiments be practiced by assessing a sample comprising genomic DNA from an individual for the presence of certain variants described herein to be associated with breast cancer. Such assessment includes steps of detecting the presence or absence of at least one allele of at least one polymorphic marker, using methods well known to the skilled person and further described herein, and based on the outcome of such assessment, determine whether the individual from whom the sample is derived is at increased or decreased risk (increased or decreased susceptibility) of breast cancer. Alternatively, the invention can be practiced utilizing a dataset comprising information about the genotype status of at least one polymorphic marker described herein to be associated with breast cancer (or markers in linkage disequilibrium with at least one marker shown herein to be associated with breast cancer). In other words, a dataset containing information about such genetic status, for example in the form of genotype counts at a certain polymorphic marker, or a plurality of markers (e.g., an indication of the presence or absence of certain at-risk alleles), or actual genotypes for one or more markers, can be queried for the presence or absence of certain at-risk alleles at certain polymorphic markers shown by the present inventors to be associated with breast cancer. A positive result for a variant (e.g., marker allele) associated with increased risk of breast cancer, as shown herein, is indicative of the individual from which the dataset is derived is at increased susceptibility (increased risk) of breast cancer.

In certain embodiments of the invention, a polymorphic marker is correlated to breast cancer by referencing genotype data for the polymorphic marker to a database, such as a look-up table that comprises correlations datas between at least one allele of the polymorphism and breast cancer. In some embodiments, the table comprises a correlation for one polymorphism. In other embodiments, the table comprises a correlation for a plurality of polymorphisms. In both scenarios, by referencing to a look-up table that gives an indication of a correlation between a marker and breast cancer, a risk for breast cancer, or a susceptibility to breast cancer, can be identified in the individual from whom the sample is derived. In some embodiments, the correlation is reported as a statistical measure. The statistical measure may be reported as a risk measure, such as a relative risk (RR), an absolute risk (AR) or an odds ratio (OR).

Risk markers may be useful for risk assessment and diagnostic purposes, either alone or in combination. Results of disease risk assessment based on the markers described herein can also be combined with data for other genetic markers or risk factors for the disease, to establish overall risk. Thus, even in cases where the increase in risk by individual markers is relatively modest, e.g. on the order of 10-30%, the association may have significant implications when combined with other risk markers. Thus, relatively common variants may have significant contribution to the overall risk (Population Attributable Risk is high), or combination of markers can be used to define groups of individual who, based on the combined risk of the markers, is at significant combined risk of developing the disease. For example, combined risk can be assessed based on genotype results for any one of, or combinations of rs2005154, rs2184380, rs2224696, rs2242503, rs12291026, rs999737, rs9956546, rs11912922, and rs6001954. Such combinations can also include other susceptibility markers for breast cancer, such as markers on chromosome 5p12 and chromosome 10q26, e.g., marker rs10941679 and marker rs1219648 (Stacey, S. N. et al *Nat Genet* 40:703-6 (2008)). Alternatively, markers in LD with any one of these markers could be assessed. Other markers known to confer risk of breast cancer can also be assessed together with the markers described herein, such as markers on chromosome 2q14 (e.g., marker rs4848543 or markers in linkage disequilibrium therewith), 2q35 (e.g., marker rs13387042, or markers in linkage disequilibrium therewith), and chromosome 16 (e.g., marker rs3803662, or markers in linkage disequilibrium therewith) (Stacey, S. N. et al. *Nat Genet* 39:865-9 (2007)).

Thus, in certain embodiment of the invention, a plurality of variants (markers and/or haplotypes) is used for overall risk assessment. These variants are in one embodiment selected from the variants as disclosed herein. Other embodiments include the use of the variants of the present invention in combination with other variants known to be useful for diagnosing a susceptibility to breast cancer In such embodiments, the genotype status of a plurality of markers and/or haplotypes is determined in an individual, and the status of the individual compared with the population frequency of the associated variants, or the frequency of the variants in clinically healthy subjects, such as age-matched and sex-matched subjects. Methods known in the art, such as multivariate analyses or joint risk analyses, such as those described herein, or other methods known to the skilled person, may subsequently be used to determine the overall risk conferred based on the genotype status at the multiple loci. Assessment of risk based on such analysis may subsequently be used in the methods, uses and kits of the invention, as described herein.

In a general sense, the methods and kits described herein can be utilized from samples containing nucleic acid material (DNA or RNA) from any source and from any individual, or from genotype or sequence data derived from such samples. In preferred embodiments, the individual is a human individual. The individual can be an adult, child, or fetus. The nucleic acid source may be any sample comprising nucleic acid material, including biological samples, or a sample comprising nucleic acid material derived there from. The present invention also provides for assessing markers and/or haplotypes in individuals who are members of a target population. Such a target population is in one embodiment a population or group of individuals at risk of developing the disease, based on other genetic factors, biomarkers, biophysical parameters (e.g., weight, BMD, blood pressure), or general health and/or lifestyle parameters (e.g., history of cancer, history of breast cancer, previous diagnosis of disease, family history of cancer, family history of breast cancer).

The invention provides for embodiments that include individuals from specific age subgroups, such as those over the age of 40, over age of 45, or over age of 50, 55, 60, 65, 70, 75, 80, or 85. Other embodiments of the invention pertain to other age groups, such as individuals aged less than 85, such as less than age 80, less than age 75, or less than age 70, 65, 60, 55, 50, 45, 40, 35, or age 30. Other embodiments relate to individuals with age at onset of breast cancer in any of the age ranges described in the above. It is also contemplated that a range of ages may be relevant in certain embodiments, such as age at onset at more than age 45 but less than age 60. Other age ranges are however also contemplated, including all age ranges bracketed by the age values listed in the above. The invention furthermore relates to individuals of either gender, males or females.

The Icelandic population is a Caucasian population of Northern European ancestry. A large number of studies reporting results of genetic linkage and association in the Icelandic population have been published in the last few years. Many of those studies show replication of variants, originally identified in the Icelandic population as being associating with a particular disease, in other populations (Sulem, P., et al. *Nat Genet* May 17, 2009 (Epub ahead of print); Rafnar, T., et al. *Nat Genet* 41:221-7 (2009); Gretarsdottir, S., et al. *Ann Neurol* 64:402-9 (2008); Stacey, S. N., et al. *Nat Genet* 40:1313-18 (2008); Gudbjartsson, D. F., et al. *Nat Genet* 40:886-91 (2008); Styrkarsdottir, U., et al. *N Engl J Med* 358:2355-65 (2008); Thorgeirsson, T., et al. *Nature* 452: 638-42 (2008); Gudmundsson, J., et al. *Nat Genet.* 40:281-3 (2008); Stacey, S. N., et al., *Nat Genet.* 39:865-69 (2007); Helgadottir, A., et al., *Science* 316:1491-93 (2007); Steinthorsdottir, V., et al., *Nat Genet.* 39:770-75 (2007); Gudmundsson, J., et al., *Nat Genet.* 39:631-37 (2007); Frayling, T M, *Nature Reviews Genet* 8:657-662 (2007); Amundadottir, L. T., et al., *Nat Genet.* 38:652-58 (2006); Grant, S. F., et al., *Nat Genet.* 38:320-23 (2006)). Thus, genetic findings in the Icelandic population have in general been replicated in other populations, including populations from Africa and Asia.

It is thus believed that the markers described herein to be associated with risk of breast cancer will show similar association in other human populations. Particular embodiments comprising individual human populations are thus also contemplated and within the scope of the invention. Such embodiments relate to human subjects that are from one or more human population including, but not limited to, Caucasian populations, European populations, American populations, Eurasian populations, Asian populations, Central/South Asian populations, East Asian populations, Middle Eastern populations, African populations, Hispanic populations, and Oceanian populations. European populations include, but are not limited to, Swedish, Norwegian, Finnish, Russian, Danish, Icelandic, Irish, Kelt, English, Scottish, Dutch, Belgian, French, German, Spanish, Portuguese, Italian, Polish, Bulgarian, Slavic, Serbian, Bosnian, Czech, Greek and Turkish populations. In one embodiment, the invention relates to individuals of Caucasian origin.

The racial contribution in individual subjects may also be determined by genetic analysis. Genetic analysis of ancestry may be carried out using unlinked microsatellite markers such as those set out in Smith et al. (*Am J Hum Genet* 74, 1001-13 (2004)).

In certain embodiments, the invention relates to markers and/or haplotypes identified in specific populations, as described in the above. The person skilled in the art will appreciate that measures of linkage disequilibrium (LD) may give different results when applied to different populations. This is due to different population history of different human populations as well as differential selective pressures that may have led to differences in LD in specific genomic regions. It is also well known to the person skilled in the art that certain markers, e.g. SNP markers, are polymorphic in one population but not in another. The person skilled in the art will however apply the methods available and as thought herein to practice the present invention in any given human population. This may include assessment of polymorphic markers in the LD region of the present invention, so as to identify those markers that give strongest association within the specific population. Thus, the at-risk variants of the present invention may reside on different haplotype background and in different frequencies in various human populations. However, utilizing methods known in the art and the markers of the present invention, the invention can be practiced in any given human population.

Models to Predict Inherited Risk for Breast Cancer

The goal of breast cancer risk assessment is to provide a rational framework for the development of personalized medical management strategies for all women with the aim of increasing survival and quality of life in high-risk women while minimizing costs, unnecessary interventions and anxiety in women at lower risk. Risk prediction models attempt to estimate the risk for breast cancer in an individual who has a given set of congenital risk characteristics (e.g., family history, prior benign breast lesion, previous breast tumor). The breast cancer risk assessment models most commonly employed in clinical practice estimate inherited risk factors by considering family history. The risk estimates are based on the observations of increased risk to individuals with one or more close relatives previously diagnosed with breast cancer. They do not take into account complex pedigree structures. These models have the further disadvantage of not being able to differentiate between carriers and non-carriers of genes with breast cancer predisposing mutations.

More sophisticated risk models have better mechanisms to deal with specific family histories and have an ability to take into account carrier status for BRCA1 and BRCA2 mutations. For example, the Breast and Ovarian Analysis of Disease Incidence and Carrier Estimation Algorithm (BOADICEA) (Antoniou et al., 2004) takes into account family history based on individual pedigree structures through the pedigree analysis program MENDEL. Information on known BRCA1 and BRCA2 status is also taken into account. The main limitations of the BOADICEA and all other breast cancer risk models currently in use are that they do not incorporate genotypic information from other predisposition genes. Current models depend strongly on family history to act as a surrogate to compensate for the lack of knowledge of non-BRCA genetic determinants of risk. Therefore the available models are limited to situations where there is a known family history of disease. Lower penetrance breast cancer predisposition genes may be relatively common in the population and may not show such strong tendencies to drive familial clustering as do the BRCA1 and BRCA2 genes. Patients with a relatively high genetic load of predisposition alleles may show little or no family history of disease. There is a need therefore to construct models which incorporate inherited susceptibility data obtained directly through gene-based testing. In addition to making the models more precise, this will reduce the dependency on family history parameters and assist in the extension of the risk profiling into the wider at-risk population where family history is not such a key factor.

Integration of Improved Genetic Risk Models into Clinical Management of Breast Cancer Primary Prevention Clinical primary prevention options currently can be classified as chemopreventative (or hormonal) treatments and prophylactic surgery. Patients identified as high risk can be prescribed long-term courses of chemopreventative therapies. This concept is well accepted in the field of cardiovascular medicine, but is only now beginning to make an impact in clinical oncology. The most widely used oncology chemopreventative is Tamoxifen, a Selective Estrogen Receptor Modulator (SERM). Initially used as an adjuvant therapy directed against breast cancer recurrence, Tamoxifen now has proven efficacy as a breast cancer preventative agent [Cuzick, et al., (2003), Lancet, 361, 296-300] [Martino, et al., (2004), Oncologist, 9, 116-25]. The FDA has approved the use of Tamoxifen as a chemopreventative agent in certain high risk women.

Unfortunately, long term Tamoxifen use increases risks for endometrial cancer approximately 2.5-fold, the risk of venous thrombosis approximately 2.0-fold. Risks for pulmonary embolism, stroke, and cataracts are also increased [Cuzick, et al., (2003), Lancet, 361, 296-300]. Accordingly, the benefits in Tamoxifen use for reducing breast cancer incidence may not be easily translated into corresponding decreases in overall mortality. Another SERM called Raloxifene may be more efficacious in a preventative mode, and does not carry the same risks for endometrial cancer. However risk for thrombosis is still elevated in patients treated long-term with Raloxifene [Cuzick, et al., (2003), Lancet, 361, 296-300; Martino, et al., (2004), Oncologist, 9, 116-25]. Moreover, both Tamoxifen and Raloxifene have quality of life issues associated with them. To make a rational risk: benefit analysis of SERM therapy in a chemopreventative mode, there is a clinical need to identify individuals who are most at risk for breast cancer. Given that a substantial proportion of risk for breast cancer is genetic, there is a clear clinical need for genetic tests to quantify individuals' risks in this context. One can anticipate similar issues arising from any future cancer chemo-preventative therapies that may become available, such as the aromatase inhibitors. Moreover, as chemopreventative therapies become safer, there is an increased need to identify patients who are genetically predisposed, but do not have massively elevated risks associated with BRCA1 & 2 mutation carriers.

Patients who are identified as being at high risk for breast cancer are considered for prophylactic surgery; either bilateral mastectomy or oophorectomy or both. Clearly such drastic treatments are recommended only for patients who are perceived to be at extremely high risk. In practice, such risks can currently be identified only in individuals who carry mutations in BRCA1, BRCA2 or genes known to be involved in rare breast cancer predisposition syndromes like p53 in Li-Fraumeni Syndrome, PTEN in Cowden's Syndrome.

Estimates of the penetrance of BRCA1 and BRCA2 mutations tend to be higher when they are derived from multiple-case families than when they are derived from population-based estimates. This is because different mutation-carrying families exhibit different penetrances for breast cancer (see [Thorlacius, et al., (1997), Am J Hum Genet, 60, 1079-84] for example). One of the major factors contributing to this variation is the action of as yet unknown predisposition genes whose effects modify the penetrance of BRCA1 and BRCA2 mutations. Therefore the absolute risk to an individual who carries a mutation in the BRCA1 or BRCA2 genes cannot be accurately quantified in the absence of knowledge of the existence and action of modifying genes. Since the treatment options for BRCA1 and BRCA2 carriers can be severe, it is important in this context to quantify the risks to individual BRCA carriers with the greatest accuracy possible. There is a need, therefore, to identify predisposition genes whose effects modify the penetrance of breast cancer in BRCA1 and BRCA2 carriers and to develop improved risk assessment models based on these genes.

Furthermore, there are individuals who are perceived to be at very high risk for breast cancer, perhaps because of a strong family history of breast cancer, but in whom no mutations in known predisposition genes can be identified. Consideration of prophylactic surgery is difficult in such cases because one cannot test the individual to discover whether or not she has inherited a high penetrance predisposition gene. Accordingly, the individual's risk cannot be assessed accurately. There is a clear clinical need, therefore, to identify any high penetrance predisposition genes that remain undiscovered and to develop associated genetic tests for use in primary prevention strategies. Such genes may for example be the genes disclosed herein to be associated with risk of breast cancer. Although the variants shown herein to be associated with risk of breast cancer are fairly common, and conferring a relatively low risk of breast cancer, it is quite possible that higher risk variants exist within one or more of these genes. It is thus contemplated that high-risk genetic variants within, or associated with, one or more of the PAX5, TUB, SERPINH1, RAD51L1, FHOD3 and/or TNRC6B genes could be useful for determining whether an individual is a carrier of a high risk (and high penetrance) genetic factor for breast cancer.

Early Diagnosis

Clinical screening for breast cancer in most western countries consists of periodic clinical breast examination (CBE)

and X-ray mammography. There is good evidence to indicate that CBE has little added benefit when used in the context of a good mammographic screening program. In the United Kingdom, women between the ages of 50 and 70 are invited to undergo screening mammography every three years. The situation in the United States varies depending on healthcare provider, however the American Cancer Society recommends annual mammographic screening from age 40. Mammographic screening has proven effectiveness in reducing mortality amongst screened women over the age of 50.

It is unlikely that genetic testing would ever be employed as a means of reducing access to existing mammographic screening programs. However, mammographic screening is not without shortcomings and it is conceivable that genetic testing should be used to select people for augmented screening programs. One of the drawbacks of mammographic screening is that is has thus far not been possible to demonstrate a significant effect on improved survival for women screened under 50 years of age.

One reason that mammography is less effective in women under 50 may be that the density of breast tissue is higher in younger women, making mammographic detection of tumors more difficult. However, breast cancers in predisposed individuals tend to occur at early ages groups and there is a clear association between high breast density and breast cancer risk. Therefore there is a problem with simple increases in mammographic screening for individuals with high predisposition because they would be managed by a technique that performs sub-optimally in the group at highest risk. Recent studies have shown that contrast-enhanced magnetic resonance imaging (CE-MRI) is more sensitive and detects tumors at an earlier stage in this high-risk group than mammographic screening does [Warner, et al., (2004), Jama, 292, 1317-25; Leach, et al., (2005), Lancet, 365, 1769-78]. CE-MRI strategies work particularly well when used in combination with routine X-ray mammography [Leach, et al., (2005), Lancet, 365, 1769-78]. Because CE-MRI requires specialist centers that incur high costs, screening of under-50's must be restricted to those individuals at the highest risk. Present CE-MRI trials restrict entry to those individuals with BRCA1, BRCA2 or p53 mutations or very strong family histories of disease. The extension of this screening modality to a wider range of high-risk patients would be greatly assisted by the provision of gene-based risk profiling tools.

There is good evidence to support the notion that early-onset breast cancers and cancers occurring in genetically predisposed women grow faster than cancers in older, less strongly predisposed women. This comes from observations of higher rates of interval cancers in younger women, that is, cancers that arise in the intervals between screening visits in a well-screened population are higher amongst younger women. Therefore there are suggestions that screening intervals, by whatever method, should be reduced for younger women. There is a paradox here in that more frequent screening using more expensive methodologies seems to be required for an age group in which the overall rates of breast cancer are comparatively low. There is a clear clinical need here to identify those young individuals who are most strongly predisposed to develop the disease early, and channel them into more expensive and extensive screening regimes. The variants disclosed herein to confer risk of breast cancer can be useful for identification of individuals who are at particularly high risk of developing breast cancer. Such individuals are likely to most benefit from early and aggressive screening programs, so as to maximizing the likelihood of early identification of the cancer.

Treatment

Currently, primary breast cancer is treated by surgery, adjuvant chemotherapy, radiotherapy, followed by long term hormonal therapy. Often combinations of three or four therapies are used.

Breast cancer patients with the same stage of disease can have very different responses to adjuvant chemotherapy resulting in a broad variation in overall treatment outcomes. Consensus guidelines (the St Galen and NIH criteria) have been developed for determining the eligibility of breast cancer patients for adjuvant chemotherapy treatment. However, even the strongest clinical and histological predictors of metastasis fail to predict accurately the clinical responses of breast tumors [Goldhirsch, et al., (1998), J Natl Cancer Inst, 90, 1601-8; Eifel, et al., (2001), J Natl Cancer Inst, 93, 979-89]. Chemotherapy or hormonal therapy reduces the risk of metastasis only by approximately ⅓, however 70-80% of patients receiving this treatment would have survived without it. Therefore the majority of breast cancer patients are currently offered treatment that is either ineffective or unnecessary. There is a clear clinical need for improvements in the development of prognostic measures which will allow clinicians to tailor treatments more appropriately to those who will best benefit. It is reasonable to expect that profiling individuals for genetic predisposition may reveal information relevant to their treatment outcome and thereby aid in rational treatment planning. The markers of the present invention, conferring risk of breast cancer, are contemplated to be useful in this context.

Several previous studies exemplify this concept: Breast cancer patients who are BRCA mutation carriers appear to show better clinical response rates and survival when treated with adjuvant chemotherapies [Chappuis, et al., (2002), J Med Genet, 39, 608-10; Goffin, et al., (2003), Cancer, 97, 527-36]. BRCA mutation carriers demonstrate improved responses to platinum chemotherapy for ovarian cancer than non-carriers [Cass, et al., (2003), Cancer, 97, 2187-95]. Similar considerations may apply to predisposed patients in whom the genes involved are not known. For example, infiltrating lobular breast carcinoma (ILBC) is known to have a strong familial component but the genetic variants involved have not yet been identified. Patients with ILBC demonstrate poorer responses to common chemotherapy regimes [Mathieu, et al., (2004), Eur J Cancer, 40, 342-51].

Genetic predisposition models may not only aid in the individualization of treatment strategies, but may play an integral role in the design of these strategies. For example, BRCA1 and BRCA2 mutant tumor cells have been found to be profoundly sensitive to poly (ADP-ribose) polymerase (PARP) inhibitors as a result of their defective DNA repair pathway [Farmer, et al., (2005), Nature, 434, 917-21]. This has stimulated development of small molecule drugs targeted on PARP with a view to their use specifically in BRCA carrier patients. From this example it is clear that knowledge of genetic predisposition may identify drug targets that lead to the development of personalized chemotherapy regimes to be used in combination with genetic risk profiling. Similarly, the markers of the present invention may aid in the identification of novel drugs that target, for example, one or more of the PAX5, TUB, SERPINH1, RAD51L1, FHOD3 and/or TNRC6B genes.

Cancer chemotherapy has well known, dose-limiting side effects on normal tissues particularly the highly proliferative hemopoetic and gut epithelial cell compartments. It can be anticipated that genetically-based individual differences exist in sensitivities of normal tissues to cytotoxic drugs. An understanding of these factors might aid in rational treatment planning and in the development of drugs designed to protect normal tissues from the adverse effects of chemotherapy.

Genetic profiling may also contribute to improved radiotherapy approaches: Within groups of breast cancer patients undergoing standard radiotherapy regimes, a proportion of patients will experience adverse reactions to doses of radiation that are normally tolerated. Acute reactions include erythema, moist desquamation, edema and radiation pneumatitis. Long term reactions, including telanglectasia, edema, pulmonary fibrosis and breast fibrosis may arise many years after radiotherapy. Both acute and long-term reactions are considerable sources of morbidity and can be fatal. In one study, 87% of patients were found to have some adverse side effects to radiotherapy while 11% had serious adverse reactions (LENT/SOMA Grade 3-4); [Hoeller, et al., (2003), Int J Radiat Oncol Biol Phys, 55, 1013-8]. The probability of experiencing an adverse reaction to radiotherapy is due primarily to constitutive individual differences in normal tissue reactions and there is a suspicion that these have a strong genetic component. Several of the known breast cancer predisposition genes (e.g. BRCA1, BRCA2, ATM) affect pathways of DNA double strand break repair. DNA double strand breaks are the primary cytotoxic lesion induced by radiotherapy. This has led to concern that individuals who are genetically predisposed to breast cancer through carriage of variants in genes belonging to these pathways might also be at higher risk of suffering excessive normal tissue damage from radiotherapy. It is contemplated that the genetic variants described herein to confer risk of breast cancer, for example through one or more of the PAX5, TUB, SERPINH1, RAD51L1, FHOD3 and/or TNRC6B genes, may be useful for identifying individuals at particular risk of adverse reaction to radiotherapy.

The existence of constitutively radiosensitive individuals in the population means that radiotherapy dose rates for the majority of the patient population must be restricted, in order to keep the frequency of adverse reactions to an acceptable level. There is a clinical need, therefore, for reliable tests that can identify individuals who are at elevated risk for adverse reactions to radiotherapy. Such tests would indicate conservative or alternative treatments for individuals who are radiosensitive, while permitting escalation of radiotherapeutic doses for the majority of patients who are relatively radioresistant. It has been estimated that the dose escalations made possible by a test to triage breast cancer patients simply into radiosensitive, intermediate and radioresistant categories would result in an approximately 35% increase in local tumor control and consequent improvements in survival rates [Burnet, et al., (1996), Clin Oncol (R Coll Radiol), 8, 25-34].

Exposure to ionizing radiation is a proven factor contributing to oncogenesis in the breast [Dumitrescu and Cotarla, (2005), J Cell Mol Med, 9, 208-21]. Known breast cancer predisposition genes encode pathway components of the cellular response to radiation-induced DNA damage [Narod and Foulkes, (2004), Nat Rev Cancer, 4, 665-76]. Accordingly, there is concern that the risk for second primary breast tumors may be increased by irradiation of normal tissues within the radiotherapy field. There does not appear to be any measurable increased risk for BRCA carriers from radiotherapy, however their risk for second primary tumors is already exceptionally high. There is evidence to suggest that risk for second primary tumors is increased in carriers in breast cancer predisposing alleles of the ATM and CHEK2 genes who are treated with radiotherapy [Bernstein, et al., (2004), Breast Cancer Res, 6, R199-214; Broeks, et al., (2004), Breast Cancer Res Treat, 83, 91-3]. It is expected that the risk of second primary tumors from radiotherapy (and, possibly, from intensive mammographic screening) will be better defined by obtaining accurate genetic risk profiles from patients during the treatment planning stage.

Secondary Prevention

Approximately 30% of patients who are diagnosed with a stage 1 or 2 breast cancer will experience either a locoregional or distant metastatic recurrence of their original tumor. Patients who have had a primary breast cancer are also at greatly increased risk for being diagnosed with a second primary tumor, either in the contralateral breast or in the ipsilateral breast when breast-conserving surgery has been carried out. Secondary prevention refers to methods used to prevent recurrences or second primary tumors from developing. Methods currently in use comprise; long-term treatment with Tamoxifen or another SERM either alone or alternated with an aromatase inhibitor, risk-reducing mastectomy of the contralateral breast, and risk-reducing oophorectomy (in patients who are at risk for familial breast-ovarian cancer). Considerations regarding the use of Tamoxifen have been discussed above. With risk-reducing surgical options, it is clear that the risk needs to be quantified as well as possible in order to make an informed cost versus benefit analysis.

There are some indications that patients with known genetic predispositions to breast cancer fare worse than the majority of patients. Patients carrying the CHEK2 gene 1100delC variant have an estimated 2.8-fold increased risk of distant metastasis and a 3.9-fold increased risk of disease recurrence compared to non-carriers [de Bock, et al., (2004), J Med Genet, 41, 731-5]. Patients with BRCA1 node-negative tumors have a greater risk of metastasis than similar patients who do not carry a BRCA1 mutation [Goffin, et al., (2003), Cancer, 97, 527-36; Moller, et al., (2002), Int J Cancer, 101, 555-9; Eerola, et al., (2001), Int J Cancer, 93, 368-72]. Genetic profiling can therefore be used to help assess the risk of local recurrence and metastasis, thereby guiding the choice of secondary preventative treatment. Genetic profiling based on the variants described herein may be useful in this context. In certain embodiments, such profiling may be based on one or more of the variants described herein. In other embodiments, such profiling may include one or several other known genetic risk factors for breast cancer. Such risk factors may be well established high-penetrant risk factors, or they may be one or more of the common, lower penetrance risk factors that have been previously described (e.g., markers rs2005154, rs2184380, rs2224696, rs2242503, rs12291026, rs999737, rs9956546, rs11912922 and rs6001954 or markers in linkage disequilibrium therewith, e.g. markers in Table 4).

In general, patients with a primary tumor diagnosis are at risk for second primary tumors at a constant annual incidence of 0.7% [Peto and Mack, (2000), Nat Genet, 26, 411-4]. Patients with BRCA mutations are at significantly greater risks for second primary tumors than most breast cancer patients, with absolute risks in the range 40-60% [Easton, (1999), Breast Cancer Res, 1, 14-7]. Carriers of BRCA mutations have a greatly increased risk for second primary tumors [Stacey, et al., (2006), PLoS Med, 3, e217; Metcalfe, et al., (2004), J Clin Oncol, 22, 2328-35], Patients with mutations in the CHEK2 gene have an estimated 5.7-fold increased risk of contralateral breast cancer [de Bock, et al., (2004), J Med Genet, 41, 731-5]. Carriers of the BARD1 Cys557Ser variant are 2.7 fold more likely to be diagnosed with a second primary tumor [Stacey, et al., (2006), PLoS Med, 3, e217]. Genetic risk profiling can be used to assess the risk of second primary tumors in patients and will inform decisions on how aggressive the preventative measures should be.

Methods

Methods for disease risk assessment and risk management are described herein and are encompassed by the invention. The invention also encompasses methods of assessing an individual for probability of response to a therapeutic agents, methods for predicting the effectiveness of a therapeutic agents, nucleic acids, polypeptides and antibodies and computer-implemented functions. Kits for use in the various methods presented herein are also encompassed by the invention.

Diagnostic and Screening Methods

In certain embodiments, the present invention pertains to methods of diagnosing, or aiding in the diagnosis of, breast cancer or a susceptibility to breast cancer, by detecting particular alleles at genetic markers that appear more frequently in breast cancer subjects or subjects who are susceptible to breast cancer. In particular embodiments, the invention is a method of determining a susceptibility to breast cancer by detecting at least one allele of at least one polymorphic marker (e.g., the markers described herein). In other embodiments, the invention relates to a method of diagnosing a susceptibility to breast cancer by detecting at least one allele of at least one polymorphic marker. The present invention describes methods whereby detection of particular alleles of particular markers or haplotypes is indicative of a susceptibility to breast cancer. Such prognostic or predictive assays can also be used to determine prophylactic treatment of a subject prior to the onset of symptoms associated with breast cancer.

The present invention pertains in some embodiments to methods of clinical applications of diagnosis, e.g., diagnosis performed by a medical professional. In other embodiments, the invention pertains to methods of diagnosis or determination of a susceptibility performed by a layman. The layman can be the customer of a genotyping service. The layman may also be a genotype service provider, who performs genotype analysis on a DNA sample from an individual, in order to provide service related to genetic risk factors for particular traits or diseases, based on the genotype status of the individual (i.e., the customer). Recent technological advances in genotyping technologies, including high-throughput genotyping of SNP markers, such as Molecular Inversion Probe array technology (e.g., Affymetrix GeneChip), and BeadArray Technologies (e.g., Illumina GoldenGate and Infinium assays) have made it possible for individuals to have their own genome assessed for up to one million SNPs simultaneously, at relatively little cost. The resulting genotype information, which can be made available to the individual, can be compared to information about disease or trait risk associated with various SNPs, including information from public literature and scientific publications. The diagnostic application of disease-associated alleles as described herein, can thus for example be performed by the individual, through analysis of his/her genotype data, by a health professional based on results of a clinical test, or by a third party, including the genotype service provider. The third party may also be service provider who interprets genotype information from the customer to provide service related to specific genetic risk factors, including the genetic markers described herein. In other words, the diagnosis or determination of a susceptibility of genetic risk can be made by health professionals, genetic counselors, third parties providing genotyping service, third parties providing risk assessment service or by the layman (e.g., the individual), based on information about the genotype status of an individual and knowledge about the risk conferred by particular genetic risk factors (e.g., particular SNPs). In the present context, the term "diagnosing", "diagnose a susceptibility" and "determine a susceptibility" is meant to refer to any available diagnostic method, including those mentioned above.

In certain embodiments, a sample containing genomic DNA from an individual is collected. Such sample can for example be a buccal swab, a saliva sample, a blood sample, or other suitable samples containing genomic DNA, as described further herein. The genomic DNA is then analyzed using any common technique available to the skilled person, such as high-throughput array technologies. Results from such genotyping are stored in a convenient data storage unit, such as a data carrier, including computer databases, data storage disks, or by other convenient data storage means. In certain embodiments, the computer database is an object database, a relational database or a post-relational database. The genotype data is subsequently analyzed for the presence of certain variants known to be susceptibility variants for a particular human conditions, such as the genetic variants described herein. Genotype data can be retrieved from the data storage unit using any convenient data query method. Calculating risk conferred by a particular genotype for the individual can be based on comparing the genotype of the individual to previously determined risk (expressed as a relative risk (RR) or and odds ratio (OR), for example) for the genotype, for example for an heterozygous carrier of an at-risk variant for a particular disease or trait. The calculated risk for the individual can be the relative risk for a person, or for a specific genotype of a person, compared to the average population with matched gender and ethnicity. The average population risk can be expressed as a weighted average of the risks of different genotypes, using results from a reference population, and the appropriate calculations to calculate the risk of a genotype group relative to the population can then be performed. Alternatively, the risk for an individual is based on a comparison of particular genotypes, for example heterozygous carriers of an at-risk allele of a marker compared with non-carriers of the at-risk allele. Using the population average may in certain embodiments be more convenient, since it provides a measure which is easy to interpret for the user, i.e. a measure that gives the risk for the individual, based on his/her genotype, compared with the average in the population. The calculated risk estimated can be made available to the customer via a website, preferably a secure website.

In certain embodiments, a service provider will include in the provided service all of the steps of isolating genomic DNA from a sample provided by the customer, performing genotyping of the isolated DNA, calculating genetic risk based on the genotype data, and report the risk to the customer. In some other embodiments, the service provider will include in the service the interpretation of genotype data for the individual, i.e., risk estimates for particular genetic variants based on the genotype data for the individual. In some other embodiments, the service provider may include service that includes genotyping service and interpretation of the genotype data, starting from a sample of isolated DNA from the individual (the customer).

Overall risk for multiple risk variants can be performed using standard methodology. For example, assuming a multiplicative model, i.e. assuming that the risk of individual risk variants multiply to establish the overall effect, allows for a straight-forward calculation of the overall risk for multiple markers.

In addition, in certain other embodiments, the present invention pertains to methods of diagnosing, or aiding in the diagnosis of, a decreased susceptibility to breast cancer, by detecting particular genetic marker alleles or haplotypes that appear less frequently in breast cancer patients than in individual not diagnosed with breast cancer or in the general population.

As described and exemplified herein, particular marker alleles or haplotypes are associated with risk of breast cancer. In one embodiment, the marker allele or haplotype is one that confers a significant risk or susceptibility to breast cancer. In another embodiment, the invention relates to a method of determining a susceptibility to breast cancer in a human individual, the method comprising determining the presence or absence of at least one allele of at least one polymorphic marker in a nucleic acid sample obtained from the individual. In another embodiment, the invention pertains to methods of determining a susceptibility to breast cancer in a human individual, by screening for at least one marker allele or haplotype as described herein. In another embodiment, the marker allele or haplotype is more frequently present in a subject having, or who is susceptible to, breast cancer (affected), as compared to the frequency of its presence in a healthy subject (control, such as population controls). In certain embodiments, the significance of association of the at least one marker allele or haplotype is characterized by a p value <0.05. In other embodiments, the significance of association is characterized by smaller p-values, such as <0.01, <0.001, <0.0001, <0.00001, <0.000001, <0.0000001, <0.00000001 or <0.000000001.

In these embodiments, determination of the presence of the at least one marker allele or haplotype is indicative of a susceptibility to breast cancer. These diagnostic methods involve detecting the presence or absence of at least one marker allele or haplotype that is associated with breast cancer. The detection of the particular genetic marker alleles that make up the particular haplotypes can be performed by a variety of methods described herein and/or known in the art. For example, genetic markers can be detected at the nucleic acid level (e.g., by direct nucleotide sequencing or by other means known to the skilled in the art) or at the amino acid level if the genetic marker affects the coding sequence of a protein encoded by a breast cancer—associated nucleic acid (e.g., by protein sequencing or by immunoassays using antibodies that recognize such a protein). The marker alleles or haplotypes correspond to fragments of a genomic DNA sequence associated with breast cancer. Such fragments encompass the DNA sequence of the polymorphic marker or haplotype in question, but may also include DNA segments in strong LD (linkage disequilibrium) with the marker or haplotype. In one embodiment, such segments comprises segments in LD with the marker or haplotype (as determined by a value of $r^2$ greater than 0.1 and/or |D'|>0.8).

In one embodiment, diagnosis of a susceptibility to breast cancer can be accomplished using hybridization methods (see Current Protocols in Molecular Biology, Ausubel, F. et al., eds., John. Wiley & Sons, including all supplements). A biological sample from a test subject or individual (a "test sample") of genomic DNA, RNA, or cDNA is obtained from a subject suspected of having, being susceptible to, or predisposed for breast cancer (the "test subject"). The subject can be an adult, child, or fetus. The test sample can be from any source that contains genomic DNA, such as a blood sample, sample of amniotic fluid, sample of cerebrospinal fluid, or tissue sample from skin, muscle, buccal or conjunctival mucosa, placenta, gastrointestinal tract or other organs. A test sample of DNA from fetal cells or tissue can be obtained by appropriate methods, such as by amniocentesis or chorionic villus sampling. The DNA, RNA, or cDNA sample is then examined. The presence of a specific marker allele can be indicated by sequence-specific hybridization of a nucleic acid probe specific for the particular allele. The presence of more than specific marker allele or a specific haplotype can be indicated by using several sequence-specific nucleic acid probes, each being specific for a particular allele. In one embodiment, a haplotype can be indicated by a single nucleic acid probe that is specific for the specific haplotype (i.e., hybridizes specifically to a DNA strand comprising the specific marker alleles characteristic of the haplotype). A sequence-specific probe can be directed to hybridize to genomic DNA, RNA, or cDNA. A "nucleic acid probe", as used herein, can be a DNA probe or an RNA probe that hybridizes to a complementary sequence. One of skill in the art would know how to design such a probe so that sequence specific hybridization will occur only if a particular allele is present in a genomic sequence from a test sample. The invention can also be reduced to practice using any convenient genotyping method, including commercially available technologies and methods for genotyping particular polymorphic markers.

To determine a susceptibility to breast cancer, a hybridization sample can be formed by contacting the test sample, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length that is sufficient to specifically hybridize under stringent conditions to appropriate mRNA or genomic DNA. In certain embodiments, the oligonucleotide is from about 15 to about 100 nucleotides in length. In certain other embodiments, the oligonucleotide is from about 20 to about 50 nucleotides in length. The nucleic acid probe can comprise all or a portion of a nucleotide sequence of any one of LD block C09, LD block C10A, LD block 10B, LD block C11A, LD block C11B, LD block C14, LD block C18, LD block C22A, and LD block C22B as defined herein; alternatively, the nucleic acid probe can comprise all or a portion of a nucleotide sequence comprising the markers set forth in Tables 1 and 4 herein (SEQ ID NO:1-562), or a nucleotide sequence comprising any one of the PAX5, TUB, SERPINH1, RAD51L1, FHOD3 and TNRC6B genes, as described herein, optionally comprising at least one allele of a marker described herein, or at least one haplotype described herein, or the probe can be the complementary sequence of such a sequence. In a particular embodiment, the nucleic acid probe is a portion of the nucleotide sequence of comprising the markers listed in any one of Tables 1, 2, 3 and 4 (SEQ ID NO:1-562), or a nucleotide sequence comprising any one of the PAX5, TUB, SERPINH1, RAD51L1, FHOD3 and TNRC6B genes or fragments thereof, as described herein, optionally comprising at least one allele of a marker described herein, or at least one allele of one polymorphic marker or haplotype comprising at least one polymorphic marker described herein, or the probe can be the complementary sequence of such a sequence. Other suitable probes for use in the diagnostic assays of the invention are described herein. Hybridization can be performed by methods well known to the person skilled in the art (see, e.g., Current Protocols in Molecular Biology, Ausubel, F. et al., eds., John Wiley & Sons, including all supplements). In one embodiment, hybridization refers to specific hybridization, i.e., hybridization with no mismatches (exact hybridization). In one embodiment, the hybridization conditions for specific hybridization are high stringency.

Specific hybridization, if present, is detected using standard methods. If specific hybridization occurs between the nucleic acid probe and the nucleic acid in the test sample, then the sample contains the allele that is complementary to the nucleotide that is present in the nucleic acid probe. The process can be repeated for any markers of the present invention, or markers that make up a haplotype of the present invention, or multiple probes can be used concurrently to detect more than one marker alleles at a time. It is also possible to design a single probe containing more than one marker alleles of a particular haplotype (e.g., a probe containing alleles complementary to 2, 3, 4, 5 or all of the markers that make up a particular haplotype). Detection of the particular markers of the haplotype in the sample is indicative that the source of the sample has the particular haplotype (e.g., a haplotype) and therefore is susceptible to breast cancer.

In one preferred embodiment, a method utilizing a detection oligonucleotide probe comprising a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

Additionally, or alternatively, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, Nielsen, P., et al., *Bioconjug. Chem.* 5:3-7 (1994)). The PNA probe can be designed to specifically hybridize to a molecule in a sample suspected of containing one or more of the marker alleles or haplotypes that are associated with breast cancer. In one embodiment of the invention, a test sample containing genomic DNA obtained from the subject is collected and the polymerase chain reaction (PCR) is used to amplify a fragment comprising one or more markers or haplotypes of the present invention. As described herein, identification of a particular marker allele or haplotype associated with breast cancer can be accomplished using a variety of methods (e.g., sequence analysis, analysis by restriction digestion, specific hybridization, single stranded conformation polymorphism assays (SSCP), electrophoretic analysis, etc.). In another embodiment, diagnosis is accomplished by expression analysis, for example by using quantitative PCR (kinetic thermal cycling). This technique can, for example, utilize commercially available technologies, such as TaqMan® (Applied Biosystems, Foster City, Calif.). The technique can assess the presence of an alteration in the expression or composition of a polypeptide or splicing variant(s) that is encoded by a nucleic acid associated with breast cancer. Further, the expression of the variant(s) can be quantified as physically or functionally different.

In another method of the invention, analysis by restriction digestion can be used to detect a particular allele if the allele results in the creation or elimination of a restriction site relative to a reference sequence. Restriction fragment length polymorphism (RFLP) analysis can be conducted, e.g., as described in Current Protocols in Molecular Biology, supra. The digestion pattern of the relevant DNA fragment indicates the presence or absence of the particular allele in the sample.

Sequence analysis can also be used to detect specific alleles or haplotypes. Therefore, in one embodiment, determination of the presence or absence of a particular marker alleles or haplotypes comprises sequence analysis of a test sample of DNA or RNA obtained from a subject or individual. PCR or other appropriate methods can be used to amplify a portion of a nucleic acid associated with breast cancer, and the presence of a specific allele can then be detected directly by sequencing the polymorphic site (or multiple polymorphic sites in a haplotype) of the genomic DNA in the sample.

In another embodiment, arrays of oligonucleotide probes that are complementary to target nucleic acid sequence segments from a subject, can be used to identify particular alleles at polymorphic sites. For example, an oligonucleotide array can be used. Oligonucleotide arrays typically comprise a plurality of different oligonucleotide probes that are coupled to a surface of a substrate in different known locations. These arrays can generally be produced using mechanical synthesis methods or light directed synthesis methods that incorporate a combination of photolithographic methods and solid phase oligonucleotide synthesis methods, or by other methods known to the person skilled in the art (see, e.g., Bier, F. F., et al. *Adv Biochem Eng Biotechnol* 109:433-53 (2008);

Hoheisel, J. D., *Nat Rev Genet.* 7:200-10 (2006); Fan, J. B., et al. *Methods Enzymol* 410:57-73 (2006); Raqoussis, J. & Elvidge, G., *Expert Rev Mol Diagn* 6:145-52 (2006); Mockler, T. C., et al *Genomics* 85:1-15 (2005), and references cited therein, the entire teachings of each of which are incorporated by reference herein). Many additional descriptions of the preparation and use of oligonucleotide arrays for detection of polymorphisms can be found, for example, in U.S. Pat. No. 6,858,394, U.S. Pat. No. 6,429,027, U.S. Pat. No. 5,445,934, U.S. Pat. No. 5,700,637, U.S. Pat. No. 5,744,305, U.S. Pat. No. 5,945,334, U.S. Pat. No. 6,054,270, U.S. Pat. No. 6,300,063, U.S. Pat. No. 6,733,977, U.S. Pat. No. 7,364,858, EP 619 321, and EP 373 203, the entire teachings of which are incorporated by reference herein.

Other methods of nucleic acid analysis that are available to those skilled in the art can be used to detect a particular allele at a polymorphic site associated with breast cancer. Representative methods include, for example, direct manual sequencing (Church and Gilbert, *Proc. Natl. Acad. Sci. USA,* 81: 1991-1995 (1988); Sanger, F., et al., *Proc. Natl. Acad. Sci. USA,* 74:5463-5467 (1977); Beavis, et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V., et al., *Proc. Natl. Acad. Sci. USA,* 86:232-236 (1989)), mobility shift analysis (Orita, M., et al., *Proc. Natl. Acad. Sci. USA,* 86:2766-2770 (1989)), restriction enzyme analysis (Flavell, R., et al., *Cell,* 15:25-41 (1978); Geever, R., et al., *Proc. Natl. Acad. Sci. USA,* 78:5081-5085 (1981)); heteroduplex analysis; chemical mismatch cleavage (CMC) (Cotton, R., et al., *Proc. Natl. Acad. Sci. USA,* 85:4397-4401 (1985)); RNase protection assays (Myers, R., et al., *Science,* 230:1242-1246 (1985); use of polypeptides that recognize nucleotide mismatches, such as *E. coli* mutS protein; and allele-specific PCR.

In another embodiment of the invention, determination of a susceptibility to breast cancer can be made by examining expression and/or composition of a polypeptide encoded by a nucleic acid associated with breast cancer in those instances where the genetic marker(s) or haplotype(s) of the present invention result in a change in the composition or expression of the polypeptide. Thus, diagnosis of a susceptibility to breast cancer can be made by examining expression and/or composition of one of these polypeptides, or another polypeptide encoded by a nucleic acid associated with breast cancer, in those instances where the genetic marker or haplotype of the present invention results in a change in the composition or expression of the polypeptide (e.g., one or more of the PAX5, TUB, SERPINH1, RAD51L1, FHOD3 and TNRC6B genes). The markers described herein that show association to breast cancer may also affect expression of nearby genes. It is well known that regulatory element affecting gene expression may be located far away, even as far as tenths or hundreds of kilobases away, from the promoter region of a gene. By assaying for the presence or absence of at least one allele of at least one polymorphic marker of the present invention, it is thus possible to assess the expression level of such nearby genes. Possible mechanisms affecting these genes include, e.g., effects on transcription, effects on RNA splicing, alterations in relative amounts of alternative splice forms of mRNA, effects on RNA stability, effects on transport from the nucleus to cytoplasm, and effects on the efficiency and accuracy of translation.

A variety of methods can be used for detecting protein expression levels, including enzyme linked immunosorbent assays (ELISA), Western blots, immunoprecipitations and immunofluorescence. A test sample from a subject is assessed for the presence of an alteration in the expression and/or an alteration in composition of the polypeptide encoded by a nucleic acid associated with breast cancer. An alteration in expression of a polypeptide encoded by a nucleic acid associated with breast cancer can be, for example, an alteration in the quantitative polypeptide expression (i.e., the amount of polypeptide produced). An alteration in the composition of a polypeptide encoded by a nucleic acid associated with breast cancer is an alteration in the qualitative polypeptide expression (e.g., expression of a mutant polypeptide or of a different splicing variant). In one embodiment, diagnosis of a susceptibility to breast cancer is made by detecting a particular splicing variant encoded by a nucleic acid associated with breast cancer, or a particular pattern of splicing variants (e.g., the nucleic acids encoding the PAX5, TUB, SERPINH1, RAD51L1, FHOD3 and TNRC6B genes).

Both such alterations (quantitative and qualitative) can also be present. An "alteration" in the polypeptide expression or composition, as used herein, refers to an alteration in expression or composition in a test sample, as compared to the expression or composition of the polypeptide in a control sample. A control sample is a sample that corresponds to the test sample (e.g., is from the same type of cells), and is from a subject who is not affected by, and/or who does not have a susceptibility to, breast cancer. In one embodiment, the control sample is from a subject that does not possess a marker allele or haplotype as described herein. Similarly, the presence of one or more different splicing variants in the test sample, or the presence of significantly different amounts of different splicing variants in the test sample, as compared with the control sample, can be indicative of a susceptibility to breast cancer. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a nucleic acid are known to the person skilled in the art and can be used, including spectroscopy, colorimetry, electrophoresis, isoelectric focusing, and immunoassays (e.g., David et al., U.S. Pat. No. 4,376,110) such as immunoblotting (see, e.g., Current Protocols in Molecular Biology, particularly chapter 10, supra).

For example, in one embodiment, an antibody (e.g., an antibody with a detectable label) that is capable of binding to a polypeptide encoded by a nucleic acid associated with breast cancer can be used. Antibodies can be polyclonal or monoclonal. An intact antibody, or a fragment thereof (e.g., Fv, Fab, Fab', $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g., a fluorescently-labeled secondary antibody) and end-labeling of a DNA probe with biotin such that it can be detected with fluorescently-labeled streptavidin.

In one embodiment of this method, the level or amount of polypeptide encoded by a nucleic acid associated with breast cancer (e.g., PAX5, TUB, SERPINH1, RAD51L1, FHOD3 and/or TNRC6B genes) in a test sample is compared with the level or amount of the polypeptide in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid, and is diagnostic for a particular allele or haplotype responsible for causing the difference in expression. Alternatively, the composition of the polypeptide in a test sample is compared with the composition of the polypeptide in a control sample. In another embodiment, both the level or amount and the composition of the polypeptide can be assessed in the test sample and in the control sample.

In another embodiment, determination of a susceptibility to breast cancer is made by detecting at least one marker or haplotype of the present invention, in combination with an additional protein-based, RNA-based or DNA-based assay.

Kits

Kits useful in the methods of the invention comprise components useful in any of the methods described herein, including for example, primers for nucleic acid amplification, hybridization probes, restriction enzymes (e.g., for RFLP analysis), allele-specific oligonucleotides, antibodies that bind to an altered polypeptide encoded by a nucleic acid of the invention as described herein (e.g., a genomic segment comprising at least one polymorphic marker and/or haplotype of the present invention) or to a non-altered (native) polypeptide encoded by a nucleic acid of the invention as described herein, means for amplification of a nucleic acid associated with breast cancer, means for analyzing the nucleic acid sequence of a nucleic acid associated with breast cancer, means for analyzing the amino acid sequence of a polypeptide encoded by a nucleic acid associated with breast cancer, etc. The kits can for example include necessary buffers, nucleic acid primers for amplifying nucleic acids of the invention (e.g., one or more of the polymorphic markers as described herein), and reagents for allele-specific detection of the fragments amplified using such primers and necessary enzymes (e.g., DNA polymerase). Additionally, kits can provide reagents for assays to be used in combination with the methods of the present invention, e.g., reagents for use with breast cancer diagnostic assays.

In one embodiment, the invention is a kit for assaying a sample from a subject to detect the presence of a breast cancer or a susceptibility breast cancer in a subject, wherein the kit comprises reagents necessary for selectively detecting at least one allele of at least one polymorphism of the present invention in the genome of the individual. In a particular embodiment, the reagents comprise at least one contiguous oligonucleotide that hybridizes to a fragment of the genome of the individual comprising at least one polymorphism of the present invention. In another embodiment, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism, wherein the polymorphism is selected from the group consisting of the polymorphisms as listed in Tables 1 and 4 (SEQ ID NO:1-562), and polymorphic markers in linkage disequilibrium therewith. In yet another embodiment the fragment is at least 20 base pairs in size. Such oligonucleotides or nucleic acids (e.g., oligonucleotide primers) can be designed using portions of the nucleic acid sequence flanking polymorphisms (e.g., SNPs or microsatellites) that are indicative of breast cancer. In another embodiment, the kit comprises one or more labeled nucleic acids capable of allele-specific detection of one or more specific polymorphic markers or haplotypes associated with breast cancer, and reagents for detection of the label. Suitable labels include, e.g., a radioisotope, a fluorescent label, an enzyme label, an enzyme co-factor label, a magnetic label, a spin label, an epitope label.

In particular embodiments, the polymorphic marker or haplotype to be detected by the reagents of the kit comprises one or more markers, two or more markers, three or more markers, four or more markers or five or more markers selected from the group consisting of the markers in Tables 1 and 4. In another embodiment, the marker or haplotype to be detected comprises at least one marker from the group of markers in strong linkage disequilibrium, as defined by values of $r^2$ greater than 0.2, to at least one of the group of markers consisting of the markers listed in Tables 1, 2, 3 and 4. In another embodiment, the marker or haplotype to be detected comprises at least one marker selected from the group of markers consisting of markers rs2005154, rs2184380, rs2224696, rs2242503, rs12291026, rs999737, rs9956546, rs11912922 and rs6001954.

In a preferred embodiment, the DNA template containing the SNP polymorphism is amplified by Polymerase Chain Reaction (PCR) prior to detection, and primers for such amplification are included in the reagent kit. In such an embodiment, the amplified DNA serves as the template for the detection probe and the enhancer probe.

In one embodiment, the DNA template is amplified by means of Whole Genome Amplification (WGA) methods, prior to assessment for the presence of specific polymorphic markers as described herein. Standard methods well known to the skilled person for performing WGA may be utilized, and are within scope of the invention. In one such embodiment, reagents for performing WGA are included in the reagent kit.

In certain embodiments, determination of the presence of a particular marker allele or haplotype is indicative of a susceptibility (increased susceptibility or decreased susceptibility) to breast cancer. In another embodiment, determination of the presence of the marker allele or haplotype is indicative of response to a therapeutic agent for breast cancer. In another embodiment, the presence of the marker allele or haplotype is indicative of breast cancer prognosis. In yet another embodiment, the presence of the marker allele or haplotype is indicative of progress of breast cancer treatment. Such treatment may include intervention by surgery, medication or by other means (e.g., lifestyle changes).

In a further aspect of the present invention, a pharmaceutical pack (kit) is provided, the pack comprising a therapeutic agent and a set of instructions for administration of the therapeutic agent to humans diagnostically tested for one or more variants of the present invention, as disclosed herein. The therapeutic agent can be a small molecule drug, an antibody, a peptide, an antisense or rnai molecule, or other therapeutic molecules. In one embodiment, an individual identified as a carrier of at least one variant of the present invention is instructed to take a prescribed dose of the therapeutic agent. In one such embodiment, an individual identified as a homozygous carrier of at least one variant of the present invention is instructed to take a prescribed dose of the therapeutic agent. In another embodiment, an individual identified as a non-carrier of at least one variant of the present invention is instructed to take a prescribed dose of the therapeutic agent.

In certain embodiments, the kit further comprises a set of instructions for using the reagents comprising the kit. In certain embodiments, the kit further comprises a collection of data comprising correlation data between the polymorphic markers assessed by the kit and susceptibility to breast cancer.

Therapeutic Agents

The risk variants for breast cancer presented herein can be useful in the identification of novel therapeutic targets for breast cancer. For example, genes containing, or in linkage disequilibrium with, variants (markers and/or haplotypes) associated with breast cancer (e.g., one or more of the PAX2, TUB, SERPINH1, RAD51L1, FHOD3 and TNRC6B genes, or their products, as well as genes or their products that are directly or indirectly regulated by or interact with these variant genes or their products, can be targeted for the development of therapeutic agents to treat breast cancer, or prevent or delay onset of symptoms associated with breast cancer. Therapeutic agents may comprise one or more of, for example, small non-protein and non-nucleic acid molecules, proteins, peptides, protein fragments, nucleic acids (DNA, RNA), PNA (peptide nucleic acids), or their derivatives or mimetics which can modulate the function and/or levels of the target genes or their gene products.

The nucleic acids and/or variants described herein, or nucleic acids comprising their complementary sequence, may be used as antisense constructs to control gene expression in cells, tissues or organs. The methodology associated with antisense techniques is well known to the skilled artisan, and is for example described and reviewed in *Antisense Drug Technology: Principles, Strategies, and Applications*, Crooke, ed., Marcel Dekker Inc., New York (2001). In general, antisense agents (antisense oligonucleotides) are comprised of single stranded oligonucleotides (RNA or DNA) that are capable of binding to a complimentary nucleotide segment. By binding the appropriate target sequence, an RNA-RNA, DNA-DNA or RNA-DNA duplex is formed. The antisense oligonucleotides are complementary to the sense or coding strand of a gene. It is also possible to form a triple helix, where the antisense oligonucleotide binds to duplex DNA.

Several classes of antisense oligonucleotide are known to those skilled in the art, including cleavers and blockers. The former bind to target RNA sites, activate intracellular nucleases (e.g., RnaseH or Rnase L), that cleave the target RNA. Blockers bind to target RNA, inhibit protein translation by steric hindrance of the ribosomes. Examples of blockers include nucleic acids, morpholino compounds, locked nucleic acids and methylphosphonates (Thompson, *Drug Discovery Today,* 7:912-917 (2002)). Antisense oligonucleotides are useful directly as therapeutic agents, and are also useful for determining and validating gene function, for example by gene knock-out or gene knock-down experiments. Antisense technology is further described in Layery et al., *Curr. Opin. Drug Discov. Devel.* 6:561-569 (2003), Stephens et al., *Curr. Opin. Mol. Ther.* 5:118-122 (2003), Kurreck, *Eur. J. Biochem.* 270:1628-44 (2003), Dias et al., *Mol. Cancer Ter.* 1:347-55 (2002), Chen, *Methods Mol. Med.* 75:621-636 (2003), Wang et al., *Curr. Cancer Drug Targets* 1:177-96 (2001), and Bennett, *Antisense Nucleic Acid Drug. Dev.* 12:215-24 (2002).

In certain embodiments, the antisense agent is an oligonucleotide that is capable of binding to a particular nucleotide segment. In certain embodiments, the nucleotide segment comprises any of the PAX5, TUB, SERPINH1, RAD51L1, FHOD3 and TNRC6B genes. In certain other embodiments, the antisense nucleotide is capable of binding to a nucleotide segment of as set forth in SEQ ID NO:1-562. Antisense nucleotides can be from 5-500 nucleotides in length, including 5-200 nucleotides, 5-100 nucleotides, 10-50 nucleotides, and 10-30 nucleotides. In certain preferred embodiments, the antisense nucleotides are from 14-50 nucleotides in length, including 14-40 nucleotides and 14-30 nucleotides. The variants described herein can also be used for the selection and design of antisense reagents that are specific for particular variants. Using information about the variants described herein, antisense oligonucleotides or other antisense molecules that specifically target mRNA molecules that contain one or more variants of the invention can be designed. In this manner, expression of mRNA molecules that contain one or more variant of the present invention (i.e. certain marker alleles and/or haplotypes) can be inhibited or blocked. In one embodiment, the antisense molecules are designed to specifically bind a particular allelic form (i.e., one or several variants (alleles and/or haplotypes)) of the target nucleic acid, thereby inhibiting translation of a product originating from this specific allele or haplotype, but which do not bind other or alternate variants at the specific polymorphic sites of the target nucleic acid molecule. As antisense molecules can be used to inactivate mRNA so as to inhibit gene expression, and thus protein expression, the molecules can be used for disease treatment. The methodology can involve cleavage by means of ribozymes containing nucleotide sequences complementary to one or more regions in the mRNA that attenuate the ability of the mRNA to be translated. Such mRNA regions include, for example, protein-coding regions, in particular protein-coding regions corresponding to catalytic activity, substrate and/or ligand binding sites, or other functional domains of a protein.

The phenomenon of RNA interference (RNAi) has been actively studied for the last decade, since its original discovery in *C. elegans* (Fire et al., *Nature* 391:806-11 (1998)), and in recent years its potential use in treatment of human disease has been actively pursued (reviewed in Kim & Rossi, *Nature Rev. Genet.* 8:173-204 (2007)). RNA interference (RNAi), also called gene silencing, is based on using double-stranded RNA molecules (dsRNA) to turn off specific genes. In the cytoplasmic double-stranded RNA molecules (dsRNA) are processed by cellular complexes into small interfering RNA (siRNA). The siRNA guide the targeting of a protein-RNA complex to specific sites on a target mRNA, leading to cleavage of the mRNA (Thompson, *Drug Discovery Today,* 7:912-917 (2002)). The siRNA molecules are typically about 20, 21, 22 or 23 nucleotides in length. Thus, one aspect of the invention relates to isolated nucleic acid molecules, and the use of those molecules for RNA interference, i.e. as small interfering RNA molecules (siRNA). In one embodiment, the Isolated nucleic acid molecules are 18-26 nucleotides in length, preferably 19-25 nucleotides in length, more preferably 20-24 nucleotides in length, and more preferably 21, 22 or 23 nucleotides in length.

Another pathway for RNAi-mediated gene silencing originates in endogenously encoded primary microRNA (pri-miRNA) transcripts, which are processed in the cell to generate precursor miRNA (pre-miRNA). These miRNA molecules are exported from the nucleus to the cytoplasm, where they undergo processing to generate mature miRNA molecules (miRNA), which direct translational inhibition by recognizing target sites in the 3' untranslated regions of mRNAs, and subsequent mRNA degradation by processing P-bodies (reviewed in Kim & Rossi, *Nature Rev. Genet.* 8:173-204 (2007)).

Clinical applications of RNAi include the incorporation of synthetic siRNA duplexes, which preferably are approximately 20-23 nucleotides in size, and preferably have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules (typically 25-30 nucleotides in length, preferably about 27 nucleotides), as well as small hairpin RNAs (shRNAs; typically about 29 nucleotides in length). The latter are naturally expressed, as described in Amarzguioui et al. (*FEBS Lett.*

579:5974-81 (2005)). Chemically synthetic siRNAs and shRNAs are substrates for in vivo processing, and in some cases provide more potent gene-silencing than shorter designs (Kim et al., *Nature Biotechnol.* 23:222-226 (2005); Siolas et al., *Nature Biotechnol.* 23:227-231 (2005)). In general siRNAs provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., *Nature Biotechnol.* 23:559-565 (2006); Brummelkamp et al., *Science* 296: 550-553 (2002)).

Since RNAi molecules, including siRNA, miRNA and shRNA, act in a sequence-dependent manner, the variants presented herein can be used to design RNAi reagents that recognize specific nucleic acid molecules comprising specific alleles and/or haplotypes (e.g., the alleles and/or haplotypes of the present invention), while not recognizing nucleic acid molecules comprising other alleles or haplotypes. These RNAi reagents can thus recognize and destroy the target nucleic acid molecules. As with antisense reagents, RNAi reagents can be useful as therapeutic agents (i.e., for turning off disease-associated genes or disease-associated gene variants), but may also be useful for characterizing and validating gene function (e.g., by gene knock-out or gene knock-down experiments).

Delivery of RNAi may be performed by a range of methodologies known to those skilled in the art. Methods utilizing non-viral delivery include cholesterol, stable nucleic acid-lipid particle (SNALP), heavy-chain antibody fragment (Fab), aptamers and nanoparticles. Viral delivery methods include use of lentivirus, adenovirus and adeno-associated virus. The siRNA molecules are in some embodiments chemically modified to increase their stability. This can include modifications at the 2' position of the ribose, including 2'-O-methylpurines and 2'-fluoropyrimidines, which provide resistance to Rnase activity. Other chemical modifications are possible and known to those skilled in the art.

The following references provide a further summary of RNAi, and possibilities for targeting specific genes using RNAi: Kim & Rossi, *Nat. Rev. Genet.* 8:173-184 (2007), Chen & Rajewsky, *Nat. Rev. Genet.* 8: 93-103 (2007), Reynolds, et al., *Nat. Biotechnol.* 22:326-330 (2004), Chi et al., *Proc. Natl. Acad. Sci. USA* 100:6343-6346 (2003), Vickers et al., *J. Biol. Chem.* 278:7108-7118 (2003), Agami, *Curr. Opin. Chem. Biol.* 6:829-834 (2002), Layery, et al., *Curr. Opin. Drug Discov. Devel.* 6:561-569 (2003), Shi, *Trends Genet.* 19:9-12 (2003), Shuey et al., *Drug Discov. Today* 7:1040-46 (2002), McManus et al., *Nat. Rev. Genet.* 3:737-747 (2002), Xia et al., *Nat. Biotechnol.* 20:1006-10 (2002), Plasterk et al., *curr. Opin. Genet. Dev.* 10:562-7 (2000), Bosher et al., *Nat. Cell Biol.* 2:E31-6 (2000), and Hunter, *Curr. Biol.* 9:R440-442 (1999).

A genetic defect leading to increased predisposition or risk for development of breast cancer, or a defect causing breast cancer, may be corrected permanently by administering to a subject carrying the defect a nucleic acid fragment that incorporates a repair sequence that supplies the normal/wild-type nucleotide(s) at the site of the genetic defect. Such site-specific repair sequence may concompass an RNA/DNA oligonucleotide that operates to promote endogenous repair of a subject's genomic DNA. The administration of the repair sequence may be performed by an appropriate vehicle, such as a complex with polyethelenimine, encapsulated in anionic liposomes, a viral vector such as an adenovirus vector, or other pharmaceutical compositions suitable for promoting intracellular uptake of the administered nucleic acid. The genetic defect may then be overcome, since the chimeric oligonucleotides induce the incorporation of the normal sequence into the genome of the subject, leading to expression of the normal/wild-type gene product. The replacement is propagated, thus rendering a permanent repair and alleviation of the symptoms associated with the disease or condition.

The present invention provides methods for identifying compounds or agents that can be used to treat breast cancer. Thus, the variants of the invention are useful as targets for the identification and/or development of therapeutic agents. In certain embodiments, such methods include assaying the ability of an agent or compound to modulate the activity and/or expression of a nucleic acid that includes at least one of the variants (markers and/or haplotypes) of the present invention, or the encoded product of the nucleic acid. This includes, for example, one or more of the FGF10, MRPS30, HCN1 and FGFR2 genes, and their gene products. This in turn can be used to identify agents or compounds that inhibit or alter the undesired activity or expression of the encoded nucleic acid product. Assays for performing such experiments can be performed in cell-based systems or in cell-free systems, as known to the skilled person. Cell-based systems include cells naturally expressing the nucleic acid molecules of interest, or recombinant cells that have been genetically modified so as to express a certain desired nucleic acid molecule.

Variant gene expression in a patient can be assessed by expression of a variant-containing nucleic acid sequence (for example, a gene containing at least one variant of the present invention, which can be transcribed into RNA containing the at least one variant, and in turn translated into protein), or by altered expression of a normal/wild-type nucleic acid sequence due to variants affecting the level or pattern of expression of the normal transcripts, for example variants in the regulatory or control region of the gene. Assays for gene expression include direct nucleic acid assays (mRNA), assays for expressed protein levels, or assays of collateral compounds involved in a pathway, for example a signal pathway. Furthermore, the expression of genes that are up- or down-regulated in response to the signal pathway can also be assayed. One embodiment includes operably linking a reporter gene, such as luciferase, to the regulatory region of the gene(s) of interest.

Modulators of gene expression can in one embodiment be identified when a cell is contacted with a candidate compound or agent, and the expression of mRNA is determined. The expression level of mRNA in the presence of the candidate compound or agent is compared to the expression level in the absence of the compound or agent. Based on this comparison, candidate compounds or agents for treating breast cancer can be identified as those modulating the gene expression of the variant gene. When expression of mRNA or the encoded protein is statistically significantly greater in the presence of the candidate compound or agent than in its absence, then the candidate compound or agent is identified as a stimulator or up-regulator of expression of the nucleic acid. When nucleic acid expression or protein level is statistically significantly less in the presence of the candidate compound or agent than in its absence, then the candidate compound is identified as an inhibitor or down-regulator of the nucleic acid expression.

The invention further provides methods of treatment using a compound identified through drug (compound and/or agent) screening as a gene modulator (i.e. stimulator and/or inhibitor of gene expression).

Methods of Assessing Probability of Response to Therapeutic Agents, Methods of Monitoring Progress of Treatment and Methods for Treating Breast Cancer As is known in the art, individuals can have differential responses to a particular therapy (e.g., a therapeutic agent or therapeutic method). The basis of the differential response may be genetically determined in part. Pharmacogenomics addresses the issue of how genetic variations (e.g., the variants (markers and/or haplotypes) of the present invention) affect drug response, due to altered drug disposition and/or abnormal or altered action of the drug. Thus, the basis of the differential response may be genetically determined in part. Clinical outcomes due to genetic variations affecting drug response may result in toxicity of the drug in certain individuals (e.g., carriers or non-carriers of the genetic variants of the present invention), or therapeutic failure of the drug. Therefore, the variants of the present invention may determine the manner in which a therapeutic agent and/or method acts on the body, or the way in which the body metabolizes the therapeutic agent.

Accordingly, in one embodiment, the presence of a particular allele at a polymorphic site or haplotype is indicative of a different response rate to a particular treatment modality. This means that a patient diagnosed with breast cancer, and carrying a certain allele at a polymorphic or haplotype of the present invention (e.g., the at-risk and protective alleles and/or haplotypes of the invention) would respond better to, or worse to, a specific therapeutic, drug and/or other therapy used to treat the disease. Therefore, the presence or absence of the marker allele or haplotype could aid in deciding what treatment should be used for the patient. For example, for a newly diagnosed patient, the presence of a marker or haplotype of the present invention may be assessed (e.g., through testing DNA derived from a blood sample, as described herein). If the patient is positive for a marker allele or haplotype (that is, at least one specific allele of the marker, or haplotype, is present), then the physician recommends one particular therapy, while if the patient is negative for the at least one allele of a marker, or a haplotype, then a different course of therapy may be recommended (which may include recommending that no immediate therapy, other than serial monitoring for progression of the disease, be performed). Thus, the patient's carrier status could be used to help determine whether a particular treatment modality should be administered. The value lies within the possibilities of being able to diagnose the disease at an early stage, to select the most appropriate treatment, and provide information to the clinician about prognosis/aggressiveness of the disease in order to be able to apply the most appropriate treatment.

As described further herein, current clinical preventive options for breast cancer are mainly chemopreventive (chemotherapy, or hormonal therapy) and prophylactic surgery. The most common chemopreventive is Tamoxifen and Raloxifene; other options include other Selective Estrogen Receptor Modulator (SERM) and aromatase inhibitors. Treatment options also include radiation therapy, for which a proportion of patients experience adverse symptoms. The markers of the invention, as described herein, may be used to assess response to these therapeutic options, or to predict the progress of therapy using any one of these treatment options. Thus, genetic profiling can be used to select the appropriate treatment strategy based on the genetic status of the individual, or it may be used to predict the outcome of the particular treatment option, and thus be useful in the strategic selection of treatment options or a combination of available treatment options.

The present invention also relates to methods of monitoring progress or effectiveness of a treatment for a breast cancer. This can be done based on the genotype and/or haplotype status of the markers and haplotypes of the present invention, i.e., by assessing the absence or presence of at least one allele of at least one polymorphic marker as disclosed herein, or by monitoring expression of genes that are associated with the variants (markers and haplotypes) of the present invention. The risk gene mRNA or the encoded polypeptide can be measured in a tissue sample (e.g., a peripheral blood sample, or a biopsy sample). Expression levels and/or mRNA levels can thus be determined before and during treatment to monitor its effectiveness. Alternatively, or concomitantly, the genotype and/or haplotype status of at least one risk variant for breast cancer as presented herein is determined before and during treatment to monitor its effectiveness.

Alternatively, biological networks or metabolic pathways related to the markers and haplotypes of the present invention can be monitored by determining mRNA and/or polypeptide levels. This can be done for example, by monitoring expression levels or polypeptides for several genes belonging to the network and/or pathway, in samples taken before and during treatment. Alternatively, metabolites belonging to the biological network or metabolic pathway can be determined before and during treatment. Effectiveness of the treatment is determined by comparing observed changes in expression levels/metabolite levels during treatment to corresponding data from healthy subjects.

In a further aspect, the markers of the present invention can be used to increase power and effectiveness of clinical trials. Thus, individuals who are carriers of the at-risk variants of the present invention, i.e. individuals who are carriers of at least one allele of at least one polymorphic marker conferring increased risk of developing breast cancer may be more likely to respond to a particular treatment modality. In one embodiment, individuals who carry at-risk variants for gene(s) in a pathway and/or metabolic network for which a particular treatment (e.g., small molecule drug) is targeting are more likely to be responders to the treatment. In another embodiment, individuals who carry at-risk variants for a gene, which expression and/or function is altered by the at-risk variant, are more likely to be responders to a treatment modality targeting that gene, its expression or its gene product.

In a further aspect, the markers and haplotypes of the present invention can be used for targeting the selection of pharmaceutical agents for specific individuals. Personalized selection of treatment modalities, lifestyle changes or combination of the two, can be realized by the utilization of the at-risk variants of the present invention. Thus, the knowledge of an individual's status for particular markers of the present invention, can be useful for selection of treatment options that target genes or gene products affected by the at-risk variants of the invention. Certain combinations of variants may be suitable for one selection of treatment options, while other gene variant combinations may target other treatment options. Such combination of variant may include one variant, two variants, three variants, or four or more variants, as needed to determine with clinically reliable accuracy the selection of treatment module.

Computer-Implemented Aspects

As understood by those of ordinary skill in the art, the methods and information described herein may be implemented, in all or in part, as computer executable instructions on known computer readable media. For example, the methods described herein may be implemented in hardware. Alternatively, the method may be implemented in software stored in, for example, one or more memories or other computer readable medium and implemented on one or more processors. As is known, the processors may be associated with one or more controllers, calculation units and/or other units of a computer system, or implanted in firmware as desired. If implemented in software, the routines may be stored in any computer readable memory such as in RAM, ROM, flash memory, a magnetic disk, a laser disk, or other storage medium, as is also known. Likewise, this software may be delivered to a computing device via any known delivery method including, for example, over a communication channel such as a telephone line, the Internet, a wireless connection, etc., or via a transportable medium, such as a computer readable disk, flash drive, etc.

More generally, and as understood by those of ordinary skill in the art, the various steps described above may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any known computer readable medium such as on a magnetic disk, an optical disk, or other storage medium, in a RAM or ROM or flash memory of a computer, processor, hard disk drive, optical disk drive, tape drive, etc. Likewise, the software may be delivered to a user or a computing system via any known delivery method including, for example, on a computer readable disk or other transportable computer storage mechanism.

FIG. 1 illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method or apparatus of the claims. Neither should the computing environment 100 be interpreted as having any dependency or requirement relating to any one or combination of components illustrated in the exemplary operating environment 100.

The steps of the claimed method and system are operational with numerous other general purpose or special purpose computing system environments or configurations. Examples of well known computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The steps of the claimed method and system may be described in the general context of computer-executable instructions, such as program modules, being executed by a computer. Generally, program modules include routines, programs, objects, components, data structures, etc. that performs particular tasks or implement particular abstract data types. The methods and apparatus may also be practiced in distributed computing environments where tasks are performed by remote processing devices that are linked through a communications network. In both integrated and distributed computing environments, program modules may be located in both local and remote computer storage media including memory storage devices.

With reference to FIG. 1, an exemplary system for implementing the steps of the claimed method and system includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (USA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 1 illustrates operating system 134, application programs 135, other program modules 136, and program data 137.

The computer 110 may also include other removable/non-removable, volatile/nonvolatile computer storage media. By way of example only, FIG. 1 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 1, provide storage of computer readable instructions, data structures, program modules and other data for the computer 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 1. The logical connections depicted in FIG. 1 include a local area network (LAN) 171 and a wide area network (WAN) 173, but may also include other networks. Such networking environments are commonplace in offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, FIG. 1 illustrates remote application programs 185 as residing on memory device 181. It will be appreciated that the network connections shown are exemplary and other means of establishing a communications link between the computers may be used.

Although the forgoing text sets forth a detailed description of numerous different embodiments of the invention, it should be understood that the scope of the invention is defined by the words of the claims set forth at the end of this patent. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of the claims defining the invention.

While the risk evaluation system and method, and other elements, have been described as preferably being implemented in software, they may be implemented in hardware, firmware, etc., and may be implemented by any other processor. Thus, the elements described herein may be implemented in a standard multi-purpose CPU or on specifically designed hardware or firmware such as an application-specific integrated circuit (ASIC) or other hard-wired device as desired, including, but not limited to, the computer 110 of FIG. 1. When implemented in software, the software routine may be stored in any computer readable memory such as on a magnetic disk, a laser disk, or other storage medium, in a RAM or ROM of a computer or processor, in any database, etc. Likewise, this software may be delivered to a user or a diagnostic system via any known or desired delivery method including, for example, on a computer readable disk or other transportable computer storage mechanism or over a communication channel such as a telephone line, the internet, wireless communication, etc. (which are viewed as being the same as or interchangeable with providing such software via a transportable storage medium).

Thus, many modifications and variations may be made in the techniques and structures described and illustrated herein without departing from the spirit and scope of the present invention. Thus, it should be understood that the methods and apparatus described herein are illustrative only and are not limiting upon the scope of the invention.

Accordingly, the invention relates to computer-implemented applications of the polymorphic markers and haplotypes described herein to be associated with breast cancer. Such applications can be useful for storing, manipulating or otherwise analyzing genotype data that is useful in the methods of the invention. One example pertains to storing genotype information derived from an individual on readable media, so as to be able to provide the genotype information to a third party (e.g., the individual, a guardian of the individual, a health care provider or genetic analysis service provider), or for deriving information from the genotype data, e.g., by comparing the genotype data to information about genetic risk factors contributing to increased susceptibility to the cancer, and reporting results based on such comparison.

In general terms, computer-readable media has capabilities of storing (i) identifier information for at least one polymorphic marker or a haplotype, as described herein; (ii) an indicator of the frequency of at least one allele of said at least one marker, or the frequency of a haplotype, in individuals with the disease; and an indicator of the frequency of at least one allele of said at least one marker, or the frequency of a haplotype, in a reference population. The reference population can be a disease-free population of individuals. Alternatively, the reference population is a random sample from the general population, and is thus representative of the population at large. The frequency indicator may be a calculated frequency, a count of alleles and/or haplotype copies, or normalized or otherwise manipulated values of the actual frequencies that are suitable for the particular medium.

The markers and haplotypes described herein to be associated with increased susceptibility (increased risk) of breast cancer, are in certain embodiments useful for interpretation and/or analysis of genotype data. Thus in certain embodiments, determination of the presence of an at-risk allele for breast cancer, as shown herein, or determination of the presence of an allele at a polymorphic marker in LD with any such risk allele, is indicative of the individual from whom the genotype data originates is at increased risk of breast cancer. In one such embodiment, genotype data is generated for at least one polymorphic marker shown herein to be associated with breast cancer, or a marker in linkage disequilibrium therewith. The genotype data is subsequently made available to a third party, such as the individual from whom the data originates, his/her guardian or representative, a physician or health care worker, genetic counselor, or insurance agent, for example via a user interface accessible over the internet, together with an interpretation of the genotype data, e.g., in the form of a risk measure (such as an absolute risk (AR), risk ratio (RR) or odds ratio (OR)) for the disease. In another embodiment, at-risk markers identified in a genotype dataset derived from an individual are assessed and results from the assessment of the risk conferred by the presence of such at-risk variants in the dataset are made available to the third party, for example via a secure web interface, or by other communication means. The results of such risk assessment can be reported in numeric form (e.g., by risk values, such as absolute risk, relative risk, and/or an odds ratio, or by a percentage increase in risk compared with a reference), by graphical means, or by other means suitable to illustrate the risk to the individual from whom the genotype data is derived.

Nucleic Acids and Polypeptides

The nucleic acids and polypeptides described herein can be used in methods and kits of the present invention, as described in the above. An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention can be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material can be purified to essential homogeneity, for example as determined by polyacrylamide gel electrophoresis (PAGE) or column chromatography (e.g., HPLC). An isolated nucleic acid molecule of the invention can comprise at least about 50%, at least about 80% or at least about 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells or heterologous organisms, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Such isolated nucleotide sequences are useful, for example, in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis or other hybridization techniques.

The invention also pertains to nucleic acid molecules that hybridize under high stringency hybridization conditions, such as for selective hybridization, to a nucleotide sequence described herein (e.g., nucleic acid molecules that specifically hybridize to a nucleotide sequence containing a polymorphic site associated with a marker or haplotype described herein). Such nucleic acid molecules can be detected and/or isolated by allele- or sequence-specific hybridization (e.g., under high stringency conditions). Stringency conditions and methods for nucleic acid hybridizations are well known to the skilled person (see, e.g., *Current Protocols in Molecular Biology*, Ausubel, F. et al, John Wiley & Sons, (1998), and Kraus, M. and Aaronson, S., *Methods Enzymol.,* 200:546-556 (1991), the entire teachings of which are incorporated by reference herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S. and Altschul, S., *Proc. Natl. Acad. Sci. USA,* 90:5873-5877 (1993). Such an algorithm is incorporated into the NBLAST and XBLAST programs (version 2.0), as described in Altschul, S. et al., *Nucleic Acids Res.,* 25:3389-3402 (1997). When utilizing BLAST and Gapped BLAST programs, the default parameters of the respective programs (e.g., NBLAST) can be used. See the website on the World Wide Web at ncbi.nlm.nih.gov. In one embodiment, parameters for sequence comparison can be set at score=100, wordlength=12, or can be varied (e.g., W=5 or W=20). Another example of an algorithm is BLAT (Kent, W. J. *Genome Res.* 12:656-64 (2002)).

Other examples include the algorithm of Myers and Miller, CABIOS (1989), ADVANCE and ADAM as described in Torellis, A. and Robotti, C., *Comput. Appl. Biosci.* 10:3-5 (1994); and FASTA described in Pearson, W. and Lipman, D., *Proc. Natl. Acad. Sci. USA,* 85:2444-48 (1988).

In another embodiment, the percent identity between two amino acid sequences can be accomplished using the GAP program in the GCG software package (Accelrys, Cambridge, UK).

The present invention also provides isolated nucleic acid molecules that contain a fragment or portion that hybridizes under highly stringent conditions to a nucleic acid that comprises, or consists of, a nucleotide sequence comprising all or a portion of LD block C09, LD block C10A, LD block 10B, LD block C11A, LD block C11B, LD block C14, LD block C18, LD block C22A, and LD block C22B, as defined herein; or a nucleic acid that comprises at least one of the polymorphic markers listed in and Table 4 herein (SEQ ID NO:1-562); or a nucleotide sequence of any one of the PAX5, TUB, SERPINH1, RAD51L1, FHOD3 and TNRC6B genes; or a nucleotide sequence comprising, or consisting of, the complement of a nucleotide sequence comprising all or a portion of LD block C09, LD block C10A, LD block 10B, LD block C11A, LD block C11B, LD block C14, LD block C18, LD block C22A, and LD block C22B, as defined herein; or a nucleic acid that comprises at least one of the polymorphic markers listed in and Table 4 herein (SEQ ID NO:1-562); or a nucleotide sequence of any one of the PAX5, TUB, SERPINH1, RAD51L1, FHOD3 and TNRC6B genes.

The nucleic acid fragments of the invention are at least about 15, at least about 18, 20, 23 or 25 nucleotides, and can be 30, 40, 50, 100, 200, 500, 1000, 10,000 or more nucleotides in length.

The nucleic acid fragments of the invention are used as probes or primers in assays such as those described herein. "Probes" or "primers" are oligonucleotides that hybridize in a base-specific manner to a complementary strand of a nucleic acid molecule. In addition to DNA and RNA, such probes and primers include polypeptide nucleic acids (PNA), as described in Nielsen, P. et al., *Science* 254:1497-1500 (1991). A probe or primer comprises a region of nucleotide sequence that hybridizes to at least about 15, typically about 20-25, and in certain embodiments about 40, 50 or 75, consecutive nucleotides of a nucleic acid molecule. In one embodiment, the probe or primer comprises at least one allele of at least one polymorphic marker or at least one haplotype described herein, or the complement thereof. In particular embodiments, a probe or primer can comprise 100 or fewer nucleotides; for example, in certain embodiments from 6 to 50 nucleotides, or, for example, from 12 to 30 nucleotides. In other embodiments, the probe or primer is at least 70% identical, at least 80% identical, at least 85% identical, at least 90% identical, or at least 95% identical, to the contiguous nucleotide sequence or to the complement of the contiguous nucleotide sequence. In another embodiment, the probe or primer is capable of selectively hybridizing to the contiguous nucleotide sequence or to the complement of the contiguous nucleotide sequence. Often, the probe or primer further comprises a label, e.g., a radioisotope, a fluorescent label, an enzyme label, an enzyme co-factor label, a magnetic label, a spin label, an epitope label.

The nucleic acid molecules of the invention, such as those described above, can be identified and isolated using standard molecular biology techniques well known to the skilled person. The amplified DNA can be labeled (e.g., radiolabeled) and used as a probe for screening a cDNA library derived from human cells. The cDNA can be derived from mRNA and contained in a suitable vector. Corresponding clones can be isolated, DNA can obtained following in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

Antibodies

The invention also provides antibodies which bind to an epitope comprising either a variant amino acid sequence (e.g., comprising an amino acid substitution) encoded by a variant allele or the reference amino acid sequence encoded by the corresponding non-variant or wild-type allele. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4: 72 (1983)), the EBV-hybridoma technique (Cole et al., *Monoclonal Antibodies and Cancer Therapy*, Alan R. Liss, 1985, Inc., pp. 77-96) or trioma techniques. The technology for producing hybridomas is well known (see generally *Current Protocols in Immunology* (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology*, supra; Galfre et al., *Nature* 266:55052 (1977); R. H. Kenneth, in *Monoclonal Antibodies: A New Dimension In Biological Analyses*, Plenum Publishing Corp., New York, N.Y. (1980); and Lerner, *Yale J. Biol. Med.* 54:387-402

(1981)). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for, generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology* 9: 1370-1372 (1991); Hay et al., *Hum. Antibod. Hybridomas* 3:81-85 (1992); Huse et al., *Science* 246: 1275-1281 (1989); and Griffiths et al., *EMBO J.* 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention (e.g. a polypetide encoded by any one of the PAX5, TUB, SERPINH1, RAD51L1, FHOD3 and TNRC6B genes) by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies may also be useful in pharmacogenomic analysis. In such embodiments, antibodies against variant proteins encoded by nucleic acids according to the invention such as variant proteins that are encoded by nucleic acids that contain at least one polymorphic marker of the invention, can be used to identify individuals that require modified treatment modalities.

Antibodies can furthermore be useful for assessing expression of variant proteins in disease states, such as in active stages of a disease, or in an individual with a predisposition to a disease related to the function of the protein, in particular breast cancer. Antibodies specific for a variant protein of the present invention that is encoded by a nucleic acid that comprises at least one polymorphic marker or haplotype as described herein can be used to screen for the presence of the variant protein, for example to screen for a predisposition to breast cancer as indicated by the presence of the variant protein.

Antibodies can be used in other methods. Thus, antibodies are useful as diagnostic tools for evaluating proteins, such as variant proteins of the invention in conjunction with analysis by electrophoretic mobility, isoelectric point, tryptic or other protease digest, or for use in other physical assays known to those skilled in the art. Antibodies may also be used in tissue typing. In one such embodiment, a specific variant protein has been correlated with expression in a specific tissue type, and antibodies specific for the variant protein can then be used to identify the specific tissue type.

Subcellular localization of proteins, including variant proteins, can also be determined using antibodies, and can be applied to assess aberrant subcellular localization of the protein in cells in various tissues. Such use can be applied in genetic testing, but also in monitoring a particular treatment modality. In the case where treatment is aimed at correcting the expression level or presence of the variant protein or aberrant tissue distribution or developmental expression of the variant protein, antibodies specific for the variant protein or fragments thereof can be used to monitor therapeutic efficacy.

Antibodies are further useful for inhibiting variant protein function, for example by blocking the binding of a variant protein to a binding molecule or partner. Such uses can also be applied in a therapeutic context in which treatment involves inhibiting a variant protein's function. An antibody can be for example be used to block or competitively inhibit binding, thereby modulating (i.e., agonizing or antagonizing) the activity of the protein. Antibodies can be prepared against specific protein fragments containing sites required for specific function or against an intact protein that is associated with a cell or cell membrane. For administration in vivo, an antibody may be linked with an additional therapeutic payload, such as radionuclide, an enzyme, an immunogenic epitope, or a cytotoxic agent, including bacterial toxins (diphtheria or plant toxins, such as ricin). The in vivo half-life of an antibody or a fragment thereof may be increased by pegylation through conjugation to polyethylene glycol.

The present invention further relates to kits for using antibodies in the methods described herein. This includes, but is not limited to, kits for detecting the presence of a variant protein in a test sample. One preferred embodiment comprises antibodies such as a labeled or labelable antibody and a compound or agent for detecting variant proteins in a biological sample, means for determining the amount or the presence and/or absence of variant protein in the sample, and means for comparing the amount of variant protein in the sample with a standard, as well as instructions for use of the kit.

The present invention will now be exemplified by the following non-limiting example.

EXAMPLIFICATION

Identification of Variants on Nine Chromosomal Locations that Associate with Risk of Breast Cancer In order to search widely for alleles of common SNPs associating to breast cancer susceptibility, we carried out a genome-wide SNP association study using Illumina HumanHap300 microarray technology. Genotyping was carried out on approximately 1835 Icelandic breast cancer patients and 30,320 controls. After removing SNPs that failed quality control checks, 311,524 SNPs remained and were tested for association with breast cancer. The results were adjusted for relatedness among individuals and potential population stratification using the method of genomic control [Devlin and Roeder, (1999), Biometrics, 55, 997-1004] (see Methods). Signals were ranked by P-value. A set of SNPs from various locations on the genome, most notably from Chromosomes 9,10 (2 regions A and B), 11 (2 regions A and B), 14, 18 and 22 (2 regions A and B) showed the highest ranks. The regions of interest containing these markers (called LD Blocks) are defined in the LD Block Table; all co-ordinates herein being from NCBI Build 36. Results from genotyping of the Illumina SNPs in these regions are presented in Table 1.

In order to further investigate the signals related to the highly ranked nine markers; e.g. rs2005154 (C09), rs2184380 (C10A), rs2224696 (C10B), rs2242503 (C11A), rs12291026 (C11B), rs999737 (C14), rs9956546 (C18), rs11912922 (C22A) and rs6001954 (C22B), we generated and validated Centaurus assays for these SNPs. The SNP assays were used to genotype an additional sample of approximately 450 Icelandic Breast Cancer patients and over 5000 controls. The combined data form the Illumina and Centaurus assays for the Icelandic Breast Cancer patients (2280) and controls (35650) is shown in Table 2. All SNPs show a significant association with breast cancer in the combined Icelandic cohorts, confirming the original observations with the results in Table 1.

Methods

Patient and Control Selection:

Collection of blood samples and medical information from study subjects was conducted with informed consent and ethical review board approval in accordance with the Declaration of Helsinki.

Iceland:

Records of breast cancer diagnoses were obtained from the Icelandic Cancer Registry (ICR). The ICR contains all cases of invasive breast tumours and ductal or lobular carcinoma in-situ diagnosed in Iceland from Jan. 1, 1955. All prevalent cases living in Iceland who had a diagnosis entered into the ICR up to the end of December 2006 were eligible to participate in the study. The ICR contained records of 4785 individuals diagnosed during this period. Consent, samples and successful genotypes were obtained from approximately 2280 patients. Of these, genotypes were derived from Illumina Hap300 chips for 1835 patients and from Centaurus assays for 445 patients. The roughly 35500 Icelandic controls consisted of individuals selected from ongoing Illumina-based genome-wide association studies at deCODE genetics. Individuals with a diagnosis of breast cancer in the ICR were excluded. Both male and female genders were included. In the Icelandic controls (and the foreign replication control groups described below) there were no significant differences between genders in the frequencies of SNPs listed in Table 6. Therefore we considered that these control groups provided reasonable representations of the population frequencies of the SNPs under investigation.

Spain:

The Spanish study patients were recruited from the Oncology Department of Zaragoza Hospital between March 2006 and August 2007. Genotyping was carried out satisfactorily on approximately 825 patients. The successfully genotyped controls (about 1730) had attended the University Hospital in Zaragoza for diseases other than cancer. Controls were questioned to rule out prior cancers before drawing the blood sample. All patients and controls were of European ethnicity.

Sweden:

The Swedish sample sets consisted of Familial and Consecutive patient series. The Familial breast cancer recruitment group consisted of 347 breast cancer patients who had been referred to the ontogenetic counseling clinic of the Karolinska University Hospital, Stockholm for investigation of a family history of breast cancer. Each patient came from a distinct family. All cases who met the current criteria for BRCA mutation screening had tested negative. The Consecutive breast cancer recruitment group was comprised of 482 consecutively recruited patients who were treated surgically for primary invasive breast cancer at the Departments of Oncology at Huddinge and Söder Hospitals (covering the population of southern Stockholm) from October 1998 to May 2000. Family history was not taken into account in the selection of patients for recruitment. Controls were 1302 blood donors and 448 cancer-free individuals of both genders. All controls were collected at the Karolinska University Hospital, Stockholm. There was no evidence of significant heterogeneity between the Familial and Consecutive series for any of the SNPs tested.

Holland:

Female patients diagnosed with breast cancer in the period 2005-2006 were selected from the regional cancer registry held by the Comprehensive Cancer Centre East in Nijmegen, the Netherlands. This cancer center keeps a population-based cancer registry and covers the eastern part of the Netherlands, a region with 1.3 million inhabitants. All patients diagnosed with breast cancer before the age of 70 were invited to participate in the study. The Comprehensive Cancer Centre East collected the clinical and pathology data for all patients in the cancer registry. These standard cancer registry data were supplemented with more detailed data by extraction from the medical files in the hospitals where the patients were treated.

Controls were collected in a survey in 2002-2003 by the Radboud University Nijmegen Medical Center. This survey, The Nijmegen Biomedical Study, was based on an age-stratified random sample of the population of Nijmegen. From this group 2034 control individuals, age-matched by frequency to the patient population, were selected and genotyped.

CGEMS (The Cancer Genetics Markers of Susceptibility):

Is a project of the U.S. National Cancer Institute that has released data to the public domain on a genome-wide SNP association study for breast cancer susceptibility based on 1145 patients and 1142 controls genotyped with approximately 530,000 SNPs using the Illumina platform. These data are available at: https://caintegrator.nci.nih.gov/cgems/.

Genotyping

Approximately 1840 Icelandic patients and 3020 controls were genotyped on Illumina Hap300 SNP arrays, as described previously [Stacey, et al., (2007), Nat Genet 39:865-9] Results are shown in Table 1. All other genotyping was carried out using Nanongen Centaurus assays [Kutyavin, et al., (2006), Nucleic Acids Res, 34, e128] that were generated for SNPs shown in Tables 2 and 3. Centaurus SNP assays were validated by genotyping the HapMap CEU samples and comparing the genotypes with published data. Assays were rejected if they showed ≥1.5% mismatches with the HapMap data. Approximately 10% of the Icelandic case samples were genotyped on both Illumina and Nanogen platforms and the observed mismatch rate was lower than 0.5%. All genotyping was carried out at the deCODE genetics facility. All physical coordinates are given according to NCBI Build 36.

Illumine Genotyping

DNA samples were genotyped according to the manufacturer's instructions on Illumina Infinium HumanHap300 SNP bead microarrays (Illumina, San Diego, Calif., USA), containing 317,503 SNPs derived from Phase I of the International HapMap project. This chip provides about 75% genomic coverage in the Utah CEPH (CEU) HapMap samples for common SNPs at $r^2 \geq 0.8$ [Barrett and Cardon, (2006), Nat Genet, 38, 659-62]. Of the total number of SNPs on the chip, 5979 were deemed unsuitable either because they were monomorphic (i.e. the minor allele frequency in the combined patients and control set was less than 0.001), or had low (<95%) yield or showed a very significant distortion from Hardy-Weinberg equilibrium in the controls ($P<1\times10^{-10}$). All of these problematic SNPs were removed from the analysis. Thus 311,524 SNPs were used in the association analysis. Any chips with an overall call rate below 98% of the SNPs were also excluded from the genome-wide association analysis.

Centaurus SNP Genotyping

Centaurus assays [Kutyavin, et al., (2006), Nucleic Acids Res, 34, e128] were designed for all nine variants: e.g. rs2005154, rs2184380, rs2224696, rs2242503, rs12291026, rs999737, rs9956546, rs11912922 and rs6001954 and validated by genotyping the HapMap CEU sample and comparing the genotypes with published data. The assays gave <1.5% mis-matches with HapMap data. Table 2 shows the Seq ID Number reference for the sequence context for these SNPs, e.g. Seq ID No 1, Seq ID No 2, Seq ID No 3, Seq ID No 4, Seq ID No 5, Seq ID No 6, Seq ID No 7, Seq ID No 8 and Seq ID No 9.

Statistical Methods

We calculated the odds ratio (OR) of a SNP allele assuming the multiplicative model, i.e. assuming that the relative risk of the two alleles that a person carries multiplies. Allelic frequencies rather than carrier frequencies are presented for the markers. The associated P-values were calculated with a standard likelihood ratio Chi-squared statistic as implemented in the NEMO software package [Gretarsdottir, et al., (2003), Nat Genet, 35, 131-8]. Confidence intervals were calculated assuming that the estimate of the OR has a log-normal distribution.

Some Icelandic patients and controls are related, both within and between groups, causing the Chi-squared test statistic to have a mean greater than one and a median larger than $0.675^2$. We estimated the inflation factor for Iceland 1 using a method of genomic control [Devlin and Roeder, (1999), Biometrics, 55, 997-1004] by calculating the average of the observed Chi-squared statistics for the genome-wide SNP set, which accounts for relatedness and for potential population stratification. For Iceland 2, which was not typed with a genome-wide set of markers, the inflation factor was estimated by simulating genotypes through the Icelandic genealogy [Grant, et al., (2006), Nat Genet, 38, 320-3]. The estimated inflation factors were 1.105 for Iceland 1 and 1.11 for Iceland 2. The estimated inflation factor for the joint analyses of the Iceland 1 and Iceland 2 sample sets was 1.08, obtained by simulation.

All P-values are reported as two-sided.

TABLE 1

SNPs from the Illumina Infinium HumanHap300 chip found in association to breast cancer in Icelandic case- and control-samples. The table shows the rs-name of the SNP, P-value for the association with Breast Cancer, the associated risk, number and frequency of associated allele in affecteds and controls, identity of the at-risk allele, chromosome and position on the chromosome (NCBI Build36) of the associated marker, and reference to the sequence ID showing flanking sequence of the SNP. Allelic codes are: 1 = A; 2 = C; 3 = G; 4 = T.

| SNP | P-value | OR | Aff | Aff. freq | Contrl. | Con. freq | Allele | Chr | Pos in Build 36 | Seq ID No |
|---|---|---|---|---|---|---|---|---|---|---|
| rs2800256 | 0.1454055 | 1.0545 | 1835 | 0.323706 | 30311 | 0.312197 | 4 | C09 | 36,806,714 | 12 |
| rs2851696 | 0.1540843 | 1.0513 | 1836 | 0.630174 | 30363 | 0.618434 | 1 | C09 | 36,809,706 | 15 |
| rs2851695 | 0.4950720 | 1.024 | 1833 | 0.603382 | 30308 | 0.597697 | 4 | C09 | 36,810,262 | 14 |
| rs2800266 | 0.0940407 | 1.0605 | 1833 | 0.625477 | 30301 | 0.61163 | 1 | C09 | 36,810,604 | 13 |
| rs7848675 | 0.0424981 | 1.0789 | 1837 | 0.715024 | 30383 | 0.699306 | 1 | C09 | 36,814,086 | 18 |
| rs2800252 | 0.5399746 | 1.0477 | 1837 | 0.948013 | 30370 | 0.94567 | 3 | C09 | 36,820,616 | 11 |
| rs4880018 | 0.8570986 | 1.0154 | 1837 | 0.958628 | 30345 | 0.958016 | 2 | C09 | 36,833,844 | 17 |
| rs3780136 | 0.0670526 | 1.0972 | 1831 | 0.873839 | 30243 | 0.863258 | 2 | C09 | 36,835,973 | 16 |
| rs7852051 | 0.0515094 | 1.077 | 1837 | 0.279532 | 30380 | 0.264845 | 4 | C09 | 36,841,358 | 19 |
| rs1051193 | 0.2874298 | 1.056 | 1837 | 0.128198 | 30380 | 0.122235 | 4 | C09 | 36,846,268 | 10 |
| rs2005154 | 0.0009612 | 1.2026 | 1837 | 0.902831 | 30353 | 0.885398 | 4 | C09 | 36,846,828 | 1 |
| rs2031557 | 0.0127968 | 1.0884 | 1831 | 0.513381 | 30326 | 0.492201 | 1 | C10 | 8,651,020 | 32 |
| rs1325881 | 0.5529599 | 1.0381 | 1837 | 0.080022 | 30376 | 0.077314 | 1 | C10 | 8,653,900 | 28 |
| rs1079565 | 0.6949928 | 1.0221 | 1837 | 0.104246 | 30380 | 0.102222 | 2 | C10 | 8,656,133 | 22 |
| rs1125575 | 0.0423179 | 1.0728 | 1834 | 0.41385 | 30330 | 0.396917 | 3 | C10 | 8,659,854 | 25 |
| rs1090540 | 0.7733530 | 1.016 | 1837 | 0.106696 | 30378 | 0.105191 | 2 | C10 | 8,663,595 | 23 |
| rs7921734 | 0.3601882 | 1.0528 | 1836 | 0.103486 | 30381 | 0.098812 | 2 | C10 | 8,668,422 | 40 |
| rs7069464 | 0.4623737 | 1.0515 | 1836 | 0.067266 | 30375 | 0.064181 | 3 | C10 | 8,677,428 | 38 |
| rs4747806 | 0.0000274 | 1.1555 | 1837 | 0.595808 | 30379 | 0.560568 | 4 | C10 | 8,678,241 | 35 |
| rs1090541 | 0.0328102 | 1.0772 | 1837 | 0.39657 | 30382 | 0.378925 | 2 | C10 | 8,685,729 | 24 |
| rs1241208 | 0.0297294 | 1.1385 | 1835 | 0.092916 | 30225 | 0.082548 | 1 | C10 | 8,691,311 | 27 |
| rs6602329 | 0.0004012 | 1.1281 | 1836 | 0.541939 | 30380 | 0.511899 | 4 | C10 | 8,700,101 | 36 |
| rs4454616 | 0.0008570 | 1.1202 | 1837 | 0.47877 | 30369 | 0.450542 | 1 | C10 | 8,705,153 | 33 |
| rs4584486 | 0.6199739 | 1.0318 | 1837 | 0.079477 | 30388 | 0.077218 | 4 | C10 | 8,708,704 | 34 |
| rs1050836 | 0.1309007 | 1.0717 | 1837 | 0.167665 | 30388 | 0.15822 | 1 | C10 | 8,714,527 | 20 |
| rs7083359 | 1.76E−06 | 1.1923 | 1837 | 0.704954 | 30380 | 0.6671 | 2 | C10 | 8,722,685 | 39 |

TABLE 1-continued

SNPs from the Illumina Infinium HumanHap300 chip found in association to breast cancer in Icelandic case- and control-samples. The table shows the rs-name of the SNP, P-value for the association with Breast Cancer, the associated risk, number and frequency of associated allele in affecteds and controls, identity of the at-risk allele, chromosome and position on the chromosome (NCBI Build36) of the associated marker, and reference to the sequence ID showing flanking sequence of the SNP. Allelic codes are: 1 = A; 2 = C; 3 = G; 4 = T.

| SNP | P-value | OR | Aff | Aff. freq | Contrl. | Con. freq | Allele | Chr | Pos in Build 36 | Seq ID No |
|---|---|---|---|---|---|---|---|---|---|---|
| rs827402 | 0.7315722 | 1.0268 | 1829 | 0.051668 | 30287 | 0.050385 | 4 | C10 | 8,726,332 | 41 |
| rs827405 | 0.0002462 | 1.1624 | 1837 | 0.228634 | 30375 | 0.203177 | 4 | C10 | 8,729,009 | 42 |
| rs1334553 | 0.6242464 | 1.0218 | 1837 | 0.183723 | 30377 | 0.180515 | 3 | C10 | 8,733,175 | 30 |
| rs706771 | 0.0249670 | 1.0848 | 1837 | 0.33043 | 30365 | 0.312679 | 1 | C10 | 8,736,452 | 37 |
| rs1334549 | 4.86E−08 | 1.2428 | 1834 | 0.773991 | 30247 | 0.733726 | 1 | C10 | 8,744,989 | 29 |
| rs2184380 | 2.13E−08 | 1.2496 | 1836 | 0.773693 | 30351 | 0.732332 | 3 | C10 | 8,754,080 | 2 |
| rs1537603 | 0.0063633 | 1.0978 | 1833 | 0.455265 | 30293 | 0.432229 | 3 | C10 | 8,774,301 | 31 |
| rs1225037 | 5.32E−06 | 1.1696 | 1837 | 0.593087 | 30380 | 0.554789 | 4 | C10 | 8,802,201 | 26 |
| rs1075214 | 0.4819822 | 1.0344 | 1837 | 0.147795 | 30375 | 0.143588 | 1 | C10 | 8,815,736 | 21 |
| rs4749829 | 0.9501223 | 1.0042 | 1828 | 0.068107 | 30108 | 0.067839 | 3 | C10 | 9,078,140 | 61 |
| rs1912584 | 0.2426291 | 1.0945 | 1835 | 0.052589 | 30237 | 0.048269 | 4 | C10 | 9,081,164 | 56 |
| rs1775551 | 0.2937532 | 1.0477 | 1837 | 0.82417 | 30336 | 0.817313 | 1 | C10 | 9,093,049 | 55 |
| rs962993 | 0.2774384 | 1.0386 | 1836 | 0.393519 | 30288 | 0.384525 | 4 | C10 | 9,093,138 | 67 |
| rs7916897 | 0.2492789 | 1.0426 | 1832 | 0.674945 | 30120 | 0.66572 | 3 | C10 | 9,101,110 | 64 |
| rs2197415 | 0.2826170 | 1.0382 | 1834 | 0.39313 | 30349 | 0.38423 | 4 | C10 | 9,102,862 | 57 |
| rs1444788 | 0.2798396 | 1.0491 | 1837 | 0.82417 | 30368 | 0.81711 | 4 | C10 | 9,104,126 | 54 |
| rs2476175 | 0.8776101 | 1.0064 | 1837 | 0.217746 | 30376 | 0.216668 | 4 | C10 | 9,114,133 | 58 |
| rs2797266 | 0.3487364 | 1.0331 | 1836 | 0.396786 | 30364 | 0.389013 | 2 | C10 | 9,129,166 | 59 |
| rs860419 | 0.2755681 | 1.0382 | 1835 | 0.432425 | 30218 | 0.423258 | 4 | C10 | 9,132,868 | 65 |
| rs1276604 | 0.0466943 | 1.119 | 1835 | 0.104087 | 30349 | 0.094056 | 2 | C10 | 9,133,679 | 52 |
| rs1079569 | 0.1235447 | 1.064 | 1810 | 0.767956 | 30063 | 0.756711 | 2 | C10 | 9,148,549 | 44 |
| rs7067548 | 0.1945938 | 1.0599 | 1834 | 0.829062 | 30143 | 0.820655 | 1 | C10 | 9,150,794 | 62 |
| rs961945 | 0.1230478 | 1.0542 | 1834 | 0.445747 | 30375 | 0.432741 | 3 | C10 | 9,166,649 | 66 |
| rs1278142 | 0.0040593 | 1.1397 | 1837 | 0.173925 | 30379 | 0.15593 | 3 | C10 | 9,167,711 | 53 |
| rs2224696 | 0.0010448 | 1.1626 | 1837 | 0.170659 | 30377 | 0.150377 | 4 | C10 | 9,168,781 | 3 |
| rs1049094 | 0.4748388 | 1.0506 | 1836 | 0.936275 | 30382 | 0.933266 | 2 | C10 | 9,183,517 | 43 |
| rs1125606 | 0.0894290 | 1.0937 | 1837 | 0.120849 | 30372 | 0.111649 | 2 | C10 | 9,187,738 | 45 |
| rs372712 | 0.0755905 | 1.0628 | 1837 | 0.43767 | 30369 | 0.422734 | 1 | C10 | 9,194,043 | 60 |
| rs7898051 | 0.6463330 | 1.0192 | 1837 | 0.788242 | 30318 | 0.785045 | 3 | C10 | 9,204,690 | 63 |
| rs1149923 | 0.0228098 | 1.0815 | 1796 | 0.496381 | 28769 | 0.476815 | 4 | C10 | 9,222,722 | 46 |
| rs1149928 | 0.4126463 | 1.0305 | 1836 | 0.314815 | 30374 | 0.308372 | 3 | C10 | 9,231,471 | 47 |
| rs1149938 | 0.9114461 | 1.0038 | 1834 | 0.493184 | 30279 | 0.492239 | 4 | C10 | 9,240,108 | 48 |
| rs1149945 | 0.8799003 | 1.0052 | 1837 | 0.43767 | 30368 | 0.436397 | 3 | C10 | 9,247,627 | 49 |
| rs1149952 | 0.4948711 | 1.0248 | 1802 | 0.358213 | 29500 | 0.35261 | 2 | C10 | 9,256,962 | 50 |
| rs1242987 | 0.9668504 | 1.0014 | 1835 | 0.415259 | 30374 | 0.414911 | 3 | C10 | 9,263,430 | 51 |
| rs1540210 | 0.4912002 | 1.0262 | 1836 | 0.288126 | 30368 | 0.282847 | 3 | C11 | 74,887,046 | 78 |
| rs1790144 | 0.1544257 | 1.0705 | 1837 | 0.151062 | 30376 | 0.14253 | 4 | C11 | 74,889,549 | 79 |
| rs1793399 | 0.0609546 | 1.0906 | 1837 | 0.164671 | 30385 | 0.153085 | 2 | C11 | 74,898,153 | 80 |
| rs618202 | 0.0017623 | 1.1675 | 1837 | 0.142896 | 30362 | 0.124959 | 4 | C11 | 74,916,133 | 86 |
| rs633473 | 0.0053293 | 1.113 | 1836 | 0.740741 | 30362 | 0.71965 | 2 | C11 | 74,930,524 | 87 |
| rs1229102 | 0.0007803 | 1.1935 | 1837 | 0.12466 | 30384 | 0.106602 | 3 | C11 | 74,932,878 | 5 |
| rs1938800 | 0.1182986 | 1.0798 | 1836 | 0.141885 | 30372 | 0.132787 | 1 | C11 | 74,933,770 | 81 |
| rs662279 | 0.6695122 | 1.0159 | 1837 | 0.303756 | 30370 | 0.300428 | 2 | C11 | 74,939,444 | 90 |
| rs4945015 | 0.0274668 | 1.2223 | 1800 | 0.965556 | 29750 | 0.958218 | 1 | C11 | 74,944,615 | 82 |
| rs608585 | 0.9731233 | 1.0015 | 1836 | 0.826797 | 30383 | 0.826581 | 3 | C11 | 74,946,352 | 84 |
| rs640649 | 0.0066177 | 1.1668 | 1837 | 0.104246 | 30371 | 0.090695 | 4 | C11 | 74,949,499 | 88 |
| rs652054 | 0.8326146 | 1.008 | 1836 | 0.714052 | 30368 | 0.712428 | 2 | C11 | 74,953,180 | 89 |
| rs609309 | 0.2081718 | 1.0523 | 1837 | 0.774633 | 30209 | 0.765616 | 3 | C11 | 74,964,989 | 85 |
| rs585433 | 0.3707179 | 1.0312 | 1834 | 0.43675 | 30358 | 0.429211 | 1 | C11 | 74,970,249 | 83 |
| rs3794018 | 0.1981440 | 1.0455 | 1835 | 0.414169 | 30364 | 0.403422 | 2 | C11 | 8,054,010 | 74 |
| rs4758040 | 0.0129157 | 1.0895 | 1834 | 0.588604 | 30343 | 0.567709 | 4 | C11 | 8,057,749 | 76 |
| rs4578424 | 0.1068004 | 1.0722 | 1837 | 0.81301 | 30373 | 0.802176 | 2 | C11 | 8,064,861 | 75 |
| rs1881237 | 0.0243448 | 1.1965 | 1835 | 0.955041 | 30380 | 0.946675 | 4 | C11 | 8,067,055 | 71 |
| rs2242503 | 0.0001113 | 1.1522 | 1837 | 0.697877 | 30352 | 0.667205 | 2 | C11 | 8,075,048 | 4 |
| rs2242504 | 0.0277748 | 1.1826 | 1836 | 0.950436 | 30375 | 0.941909 | 2 | C11 | 8,079,519 | 73 |
| rs2049684 | 0.0030921 | 1.1133 | 1837 | 0.683179 | 30387 | 0.659509 | 3 | C11 | 8,127,695 | 72 |
| rs1083998 | 0.0239367 | 1.0939 | 1837 | 0.765378 | 30383 | 0.748873 | 1 | C11 | 8,137,470 | 68 |
| rs1104179 | 0.0101003 | 1.0987 | 1837 | 0.692433 | 30363 | 0.672035 | 4 | C11 | 8,168,818 | 69 |
| rs1881229 | 0.3637320 | 1.0428 | 1837 | 0.840501 | 30372 | 0.834798 | 3 | C11 | 8,184,540 | 70 |
| rs7951027 | 0.7460144 | 1.0117 | 1837 | 0.336962 | 30383 | 0.334365 | 1 | C11 | 8,190,452 | 77 |
| rs737387 | 0.7483800 | 1.011 | 1835 | 0.452316 | 30359 | 0.449603 | 1 | C14 | 68,037,135 | 111 |
| rs757369 | 0.2989297 | 1.0362 | 1836 | 0.559913 | 30378 | 0.551139 | 3 | C14 | 68,043,299 | 112 |
| rs1541390 | 0.6290307 | 1.021 | 1837 | 0.195427 | 30382 | 0.192186 | 3 | C14 | 68,049,682 | 98 |
| rs1023529 | 0.3683977 | 1.0323 | 1834 | 0.366957 | 30379 | 0.359607 | 2 | C14 | 68,059,561 | 92 |
| rs8012659 | 0.6278097 | 1.0364 | 1837 | 0.056886 | 30383 | 0.054998 | 4 | C14 | 68,060,343 | 114 |
| rs916962 | 0.3596030 | 1.0387 | 1836 | 0.215959 | 30363 | 0.209597 | 1 | C14 | 68,063,331 | 115 |
| rs1162127 | 0.0099335 | 1.1003 | 1837 | 0.707403 | 30367 | 0.687226 | 1 | C14 | 68,066,219 | 96 |
| rs1013444 | 0.6226353 | 1.0171 | 1837 | 0.418345 | 30370 | 0.414225 | 3 | C14 | 68,067,388 | 91 |
| rs727392 | 0.6708335 | 1.0309 | 1837 | 0.060425 | 30382 | 0.058719 | 2 | C14 | 68,071,554 | 110 |

TABLE 1-continued

SNPs from the Illumina Infinium HumanHap300 chip found in association to breast cancer in Icelandic case- and control-samples. The table shows the rs-name of the SNP, P-value for the association with Breast Cancer, the associated risk, number and frequency of associated allele in affecteds and controls, identity of the at-risk allele, chromosome and position on the chromosome (NCBI Build36) of the associated marker, and reference to the sequence ID showing flanking sequence of the SNP. Allelic codes are: 1 = A; 2 = C; 3 = G; 4 = T.

| SNP | P-value | OR | Aff | Aff. freq | Contrl. | Con. freq | Allele | Chr | Pos in Build 36 | Seq ID No |
|---|---|---|---|---|---|---|---|---|---|---|
| rs1115875 | 0.0561406 | 1.0802 | 1835 | 0.234877 | 30355 | 0.221298 | 2 | C14 | 68,076,508 | 94 |
| rs1710581 | 0.8079818 | 1.0104 | 1837 | 0.803484 | 30382 | 0.80184 | 4 | C14 | 68,078,080 | 99 |
| rs2842331 | 0.2212033 | 1.0527 | 1808 | 0.213772 | 29730 | 0.205264 | 2 | C14 | 68,080,443 | 107 |
| rs2158358 | 0.3127803 | 1.0405 | 1835 | 0.251226 | 30275 | 0.243832 | 2 | C14 | 68,081,725 | 101 |
| rs2842329 | 0.3199784 | 1.04 | 1827 | 0.250137 | 30229 | 0.242846 | 2 | C14 | 68,087,348 | 106 |
| rs2244814 | 0.3779656 | 1.0343 | 1822 | 0.276345 | 29822 | 0.26965 | 3 | C14 | 68,095,623 | 102 |
| rs2525503 | 0.0007823 | 1.1213 | 1837 | 0.550898 | 30365 | 0.522427 | 3 | C14 | 68,098,356 | 105 |
| rs1710583 | 0.0138473 | 1.1027 | 1837 | 0.247142 | 30373 | 0.229398 | 1 | C14 | 68,098,494 | 100 |
| rs1115875 | 0.8363170 | 1.0071 | 1837 | 0.468699 | 30376 | 0.466948 | 1 | C14 | 68,101,178 | 95 |
| rs999737 | 0.0017229 | 1.1326 | 1836 | 0.766885 | 30385 | 0.743887 | 2 | C14 | 68,104,435 | 6 |
| rs6573841 | 0.3860408 | 1.0386 | 1837 | 0.816277 | 30382 | 0.810529 | 2 | C14 | 68,107,274 | 109 |
| rs8009944 | 0.0319682 | 1.0851 | 1833 | 0.28096 | 30307 | 0.264757 | 2 | C14 | 68,109,341 | 113 |
| rs2285883 | 0.2432548 | 1.0508 | 1836 | 0.203431 | 30344 | 0.195525 | 1 | C14 | 68,113,723 | 104 |
| rs1290999 | 0.0505573 | 1.0811 | 1835 | 0.243869 | 30359 | 0.229784 | 1 | C14 | 68,115,629 | 97 |
| rs2256224 | 0.3955036 | 1.0321 | 1836 | 0.704793 | 30374 | 0.698179 | 1 | C14 | 68,122,500 | 103 |
| rs1048381 | 0.0804077 | 1.1317 | 1837 | 0.063963 | 30381 | 0.056943 | 1 | C14 | 68,125,552 | 93 |
| rs4899246 | 0.4842718 | 1.0287 | 1836 | 0.773148 | 30366 | 0.768145 | 1 | C14 | 68,129,955 | 108 |
| rs559325 | 0.5198271 | 1.0224 | 1837 | 0.581383 | 30369 | 0.575982 | 4 | C18 | 32,116,417 | 121 |
| rs1296146 | 0.7436940 | 1.0159 | 1833 | 0.14539 | 30306 | 0.143437 | 3 | C18 | 32,119,988 | 117 |
| rs4799863 | 0.5350597 | 1.0215 | 1837 | 0.434404 | 30382 | 0.429185 | 3 | C18 | 32,127,413 | 119 |
| rs9956546 | 0.0000702 | 1.2177 | 1836 | 0.144608 | 30375 | 0.121909 | 1 | C18 | 32,136,446 | 7 |
| rs680423 | 0.1990102 | 1.0817 | 1835 | 0.917711 | 30339 | 0.911582 | 4 | C18 | 32,136,736 | 122 |
| rs7243619 | 0.2091339 | 1.0454 | 1837 | 0.642352 | 30371 | 0.632083 | 4 | C18 | 32,139,089 | 125 |
| rs686784 | 0.5894600 | 1.0287 | 1837 | 0.120033 | 30374 | 0.117074 | 4 | C18 | 32,142,076 | 123 |
| rs492392 | 0.0498932 | 1.0841 | 1836 | 0.222767 | 30363 | 0.209103 | 1 | C18 | 32,142,779 | 120 |
| rs7240720 | 0.0271451 | 1.1376 | 1837 | 0.097441 | 30354 | 0.086677 | 3 | C18 | 32,142,893 | 124 |
| rs1272559 | 0.9364776 | 1.0031 | 1837 | 0.268645 | 30383 | 0.268045 | 3 | C18 | 32,142,971 | 116 |
| rs4531816 | 0.1177158 | 1.0929 | 1837 | 0.903375 | 30374 | 0.895338 | 4 | C18 | 32,143,579 | 118 |
| rs114607 | 0.4201611 | 1.0281 | 1835 | 0.426158 | 30375 | 0.419391 | 1 | C22 | 38,706,329 | 126 |
| rs2958658 | 0.7075628 | 1.0145 | 1837 | 0.731355 | 30360 | 0.728524 | 4 | C22 | 38,718,953 | 127 |
| rs3021222 | 0.0121019 | 1.0919 | 1837 | 0.62847 | 30368 | 0.607729 | 3 | C22 | 38,722,550 | 128 |
| rs3021274 | 0.0110828 | 1.0932 | 1837 | 0.631464 | 30372 | 0.610497 | 2 | C22 | 38,725,030 | 129 |
| rs1191292 | 0.0005138 | 1.1298 | 1837 | 0.383234 | 30385 | 0.35483 | 4 | C22 | 38,733,117 | 8 |
| rs6001722 | 0.6476742 | 1.0178 | 1836 | 0.739379 | 30361 | 0.735961 | 3 | C22 | 38,758,379 | 130 |
| rs9623117 | 0.0169431 | 1.1073 | 1837 | 0.808383 | 30374 | 0.792092 | 4 | C22 | 38,782,065 | 134 |
| rs6001749 | 0.0153071 | 1.1091 | 1837 | 0.808383 | 30382 | 0.791834 | 1 | C22 | 38,805,272 | 131 |
| rs6001762 | 0.0654330 | 1.085 | 1836 | 0.824891 | 30380 | 0.812788 | 2 | C22 | 38,825,419 | 132 |
| rs6001794 | 0.1618358 | 1.0563 | 1837 | 0.255035 | 30382 | 0.244767 | 4 | C22 | 38,859,361 | 133 |
| rs1108997 | 0.0832280 | 1.0697 | 1837 | 0.260751 | 30365 | 0.247966 | 4 | C22 | 38,873,554 | 136 |
| rs9611280 | 0.6602329 | 1.0241 | 1837 | 0.890038 | 30384 | 0.887688 | 3 | C22 | 38,882,065 | 169 |
| rs1108997 | 0.8500487 | 1.0072 | 1837 | 0.272727 | 30378 | 0.271298 | 4 | C22 | 38,892,173 | 137 |
| rs9611286 | 0.9363221 | 1.0031 | 1834 | 0.272083 | 30286 | 0.271479 | 2 | C22 | 38,914,908 | 170 |
| rs8137636 | 0.0133127 | 1.0931 | 1836 | 0.669662 | 30296 | 0.64969 | 1 | C22 | 38,929,577 | 166 |
| rs138021 | 0.8870477 | 1.0054 | 1837 | 0.272455 | 30365 | 0.271382 | 3 | C22 | 38,942,920 | 147 |
| rs739182 | 0.0242520 | 1.0817 | 1835 | 0.397275 | 30343 | 0.378638 | 4 | C22 | 38,945,222 | 163 |
| rs138027 | 0.8504863 | 1.0072 | 1837 | 0.272727 | 30372 | 0.271303 | 3 | C22 | 38,946,058 | 148 |
| rs138039 | 0.0145794 | 1.0918 | 1836 | 0.66939 | 30368 | 0.649681 | 3 | C22 | 38,951,234 | 149 |
| rs1305673 | 0.6304407 | 1.0295 | 1837 | 0.087099 | 30385 | 0.084812 | 4 | C22 | 38,976,018 | 140 |
| rs9611302 | 0.6750492 | 1.023 | 1837 | 0.890038 | 30378 | 0.887797 | 3 | C22 | 38,980,230 | 171 |
| rs733381 | 0.1003993 | 1.0658 | 1837 | 0.262657 | 30348 | 0.250494 | 3 | C22 | 38,999,594 | 162 |
| rs139921 | 0.0014652 | 1.1167 | 1834 | 0.607688 | 30282 | 0.581088 | 3 | C22 | 39,056,708 | 150 |
| rs470113 | 0.0017857 | 1.128 | 1835 | 0.27248 | 30377 | 0.249268 | 3 | C22 | 39,059,560 | 155 |
| rs1248469 | 0.0009138 | 1.1368 | 1836 | 0.270153 | 30368 | 0.24562 | 1 | C22 | 39,066,418 | 139 |
| rs8135371 | 0.4303623 | 1.037 | 1837 | 0.164126 | 30370 | 0.159203 | 2 | C22 | 39,087,174 | 164 |
| rs9611324 | 0.0008177 | 1.1381 | 1836 | 0.270697 | 30357 | 0.245924 | 2 | C22 | 39,111,108 | 172 |
| rs2072856 | 0.9278854 | 1.0031 | 1837 | 0.537289 | 30365 | 0.536522 | 3 | C22 | 39,146,695 | 152 |
| rs5757949 | 0.0045246 | 1.1225 | 1836 | 0.781863 | 30315 | 0.761521 | 4 | C22 | 39,150,097 | 158 |
| rs9306345 | 0.0014298 | 1.1507 | 1837 | 0.189439 | 30377 | 0.168812 | 3 | C22 | 39,162,321 | 167 |
| rs4507196 | 0.0163338 | 1.0897 | 1834 | 0.662214 | 30343 | 0.642735 | 1 | C22 | 39,179,650 | 154 |
| rs8135759 | 0.6212354 | 1.017 | 1836 | 0.535948 | 30354 | 0.531759 | 2 | C22 | 39,188,950 | 165 |
| rs9607721 | 0.0013221 | 1.1517 | 1837 | 0.189984 | 30380 | 0.16919 | 3 | C22 | 39,192,066 | 168 |
| rs6001932 | 0.0170002 | 1.1289 | 1837 | 0.133097 | 30380 | 0.119717 | 1 | C22 | 39,207,581 | 161 |
| rs3827382 | 0.0210574 | 1.1247 | 1835 | 0.132425 | 30372 | 0.119502 | 1 | C22 | 39,211,349 | 153 |
| rs5750948 | 0.5730917 | 1.0346 | 1837 | 0.914262 | 30353 | 0.911557 | 1 | C22 | 39,216,690 | 156 |
| rs9611367 | 0.0038990 | 1.1159 | 1837 | 0.731083 | 30360 | 0.708992 | 4 | C22 | 39,244,895 | 173 |
| rs6001954 | 0.0053978 | 1.1537 | 1829 | 0.131219 | 30092 | 0.115762 | 3 | C22 | 39,251,626 | 9 |
| rs5758001 | 0.0228856 | 1.0817 | 1833 | 0.423622 | 30282 | 0.40458 | 1 | C22 | 39,276,253 | 159 |
| rs5758008 | 0.0060923 | 1.1104 | 1837 | 0.735166 | 30371 | 0.714283 | 1 | C22 | 39,289,206 | 160 |
| rs5750960 | 0.4684336 | 1.0255 | 1836 | 0.603214 | 30342 | 0.597176 | 2 | C22 | 39,289,866 | 157 |

TABLE 1-continued

SNPs from the Illumina Infinium HumanHap300 chip found in association to breast cancer in Icelandic case- and control-samples. The table shows the rs-name of the SNP, P-value for the association with Breast Cancer, the associated risk, number and frequency of associated allele in affecteds and controls, identity of the at-risk allele, chromosome and position on the chromosome (NCBI Build36) of the associated marker, and reference to the sequence ID showing flanking sequence of the SNP. Allelic codes are: 1 = A; 2 = C; 3 = G; 4 = T.

| SNP | P-value | OR | Aff | Aff. freq | Contrl. | Con. freq | Allele | Chr | Pos in Build 36 | Seq ID No |
|---|---|---|---|---|---|---|---|---|---|---|
| rs1022533 | 0.0084935 | 1.1059 | 1832 | 0.735535 | 30222 | 0.715489 | 2 | C22 | 39,302,493 | 135 |
| rs1700203 | 0.0175391 | 1.1304 | 1834 | 0.12868 | 30350 | 0.115552 | 4 | C22 | 39,326,313 | 151 |
| rs133036 | 0.4223034 | 1.0282 | 1837 | 0.604518 | 30371 | 0.59784 | 2 | C22 | 39,342,384 | 141 |
| rs133047 | 0.3858756 | 1.0467 | 1836 | 0.883715 | 30385 | 0.878937 | 2 | C22 | 39,357,765 | 142 |
| rs1215920 | 0.0507958 | 1.0818 | 1837 | 0.236799 | 30368 | 0.222883 | 2 | C22 | 39,372,037 | 138 |
| rs133067 | 0.5254346 | 1.0263 | 1837 | 0.780348 | 30374 | 0.775861 | 4 | C22 | 39,404,114 | 143 |
| rs133072 | 0.7468165 | 1.0113 | 1826 | 0.59885 | 30062 | 0.596151 | 3 | C22 | 39,405,489 | 144 |
| rs133074 | 0.6315619 | 1.0164 | 1834 | 0.505725 | 30331 | 0.501648 | 2 | C22 | 39,408,419 | 145 |
| rs133076 | 0.0627455 | 1.0659 | 1836 | 0.572712 | 30373 | 0.557024 | 2 | C22 | 39,411,507 | 146 |

TABLE 2

Anchor SNPs resulting from the Illumina Infinium HumanHap300 chip found in association to breast cancer in Icelandic case- and control-samples and found to replicate in several Caucasian cohorts. Icelandic data shown in the table are from analysis of data using Illumina and Centaurus assays combined.

| SNP | Allele | Chromosome | Pos in Build 36 | P-value | OR | # Aff | Aff. freq | # Con | Con. freq | Seq ID No |
|---|---|---|---|---|---|---|---|---|---|---|
| rs2005154 | 4 | C09 | 36,846,828 | 5.21E−04 | 1.19 | 2282 | 0.90 | 35552 | 0.89 | 1 |
| rs2184380 | 3 | C10 | 8,754,080 | 1.33E−06 | 1.19 | 2282 | 0.77 | 35928 | 0.73 | 2 |
| rs2224696 | 4 | C10 | 9,168,781 | 3.48E−04 | 1.16 | 2277 | 0.17 | 35631 | 0.15 | 3 |
| rs2242503 | 2 | C11 | 8,075,048 | 9.39E−04 | 1.11 | 2280 | 0.69 | 35582 | 0.67 | 4 |
| rs12291026 | 3 | C11 | 74,932,878 | 3.98E−04 | 1.18 | 2280 | 0.12 | 35635 | 0.11 | 5 |
| rs999737 | 2 | C14 | 68,104,435 | 8.79E−05 | 1.15 | 2279 | 0.77 | 35638 | 0.74 | 6 |
| rs9956546 | 1 | C18 | 32,136,446 | 2.11E−06 | 1.23 | 2282 | 0.15 | 36015 | 0.12 | 7 |
| rs11912922 | 4 | C22 | 38,733,117 | 3.33E−05 | 1.14 | 2285 | 0.38 | 35631 | 0.35 | 8 |
| rs6001954 | 3 | C22 | 39,251,626 | 1.28E−03 | 1.16 | 2267 | 0.13 | 35210 | 0.12 | 9 |

TABLE 3

Association with breast cancer for nine variants on Chromosomes; 9, 10, 11, 14, 18 and 22 shown for individual and combined Caucasian cohorts.

| POPULATION | P | OR | # Affected | Aff. freq | # Con | Con freq | Allele | SNP | Chromosome | Cand. Gene |
|---|---|---|---|---|---|---|---|---|---|---|
| AllCauc | 1.80E−04 | 1.14 | NA | NA | NA | NA | 4 | rs2005154 | C09 | PAX5 |
| AllCaucexcluCGEMS | 8.30E−04 | 1.13 | NA | NA | NA | NA | 4 | rs2005154 | C09 | PAX5 |
| CGEMS | 7.05E−02 | 1.22 | 1144 | 0.88 | 1140 | 0.85 | 4 | rs2005154 | C09 | PAX5 |
| Holland | 1.02E−01 | 1.16 | 735 | 0.88 | 2017 | 0.86 | 4 | rs2005154 | C09 | PAX5 |
| Iceland | 5.21E−04 | 1.19 | 2282 | 0.90 | 35552 | 0.89 | 4 | rs2005154 | C09 | PAX5 |
| Spain | 9.92E−01 | 1.00 | 633 | 0.89 | 1502 | 0.89 | 4 | rs2005154 | C09 | PAX5 |
| Sweden | 4.52E−01 | 1.07 | 827 | 0.86 | 1738 | 0.86 | 4 | rs2005154 | C09 | PAX5 |
| AllCauc | 3.00E−04 | 1.11 | NA | NA | NA | NA | 3 | rs2184380 | C10 | |
| AllCaucexcluCGEMS | 2.50E−04 | 1.11 | NA | NA | NA | NA | 3 | rs2184380 | C10 | |
| CGEMS | 8.81E−01 | 0.96 | 1144 | 0.79 | 1141 | 0.80 | 3 | rs2184380 | C10 | |
| Holland | 8.80E−01 | 1.01 | 741 | 0.80 | 2019 | 0.80 | 3 | rs2184380 | C10 | |
| Iceland | 1.33E−06 | 1.19 | 2282 | 0.77 | 35928 | 0.73 | 3 | rs2184380 | C10 | |
| Spain | 1.89E−01 | 0.88 | 459 | 0.75 | 986 | 0.77 | 3 | rs2184380 | C10 | |
| Sweden | 2.47E−01 | 1.09 | 820 | 0.82 | 1717 | 0.80 | 3 | rs2184380 | C10 | |
| AllCauc | 3.70E−04 | 1.12 | NA | NA | NA | NA | 4 | rs2224696 | C10 | |
| AllCaucexcluCGEMS | 1.10E−03 | 1.12 | NA | NA | NA | NA | 4 | rs2224696 | C10 | |
| CGEMS | 1.25E−01 | 1.19 | 1144 | 0.16 | 1141 | 0.14 | 4 | rs2224696 | C10 | |
| Holland | 2.56E−01 | 0.90 | 738 | 0.12 | 2025 | 0.13 | 4 | rs2224696 | C10 | |
| Iceland | 3.48E−04 | 1.16 | 2277 | 0.17 | 35631 | 0.15 | 4 | rs2224696 | C10 | |
| Spain | 3.32E−01 | 1.10 | 632 | 0.15 | 1507 | 0.14 | 4 | rs2224696 | C10 | |
| Sweden | 6.07E−02 | 1.18 | 831 | 0.15 | 1743 | 0.13 | 4 | rs2224696 | C10 | |
| AllCauc | 2.20E−05 | 1.08 | NA | NA | NA | NA | 2 | rs2242503 | C11 | TUB |
| AllCaucexcluCGEMS | 1.90E−03 | 1.08 | NA | NA | NA | NA | 2 | rs2242503 | C11 | TUB |
| CGEMS | 3.93E−03 | 1.08 | 1144 | 0.67 | 1140 | 0.65 | 2 | rs2242503 | C11 | TUB |
| Holland | 9.86E−01 | 1.00 | 739 | 0.67 | 2005 | 0.67 | 2 | rs2242503 | C11 | TUB |
| Iceland | 9.39E−04 | 1.11 | 2280 | 0.69 | 35582 | 0.67 | 2 | rs2242503 | C11 | TUB |
| Spain | 2.79E−01 | 1.09 | 636 | 0.74 | 1485 | 0.72 | 2 | rs2242503 | C11 | TUB |

TABLE 3-continued

Association with breast cancer for nine variants on Chromosomes; 9, 10, 11, 14, 18 and 22 shown for individual and combined Caucasian cohorts.

| POPULATION | P | OR | # Affected | Aff. freq | # Con | Con freq | Allele | SNP | Chromosome | Cand. Gene |
|---|---|---|---|---|---|---|---|---|---|---|
| Sweden | 3.04E−01 | 1.07 | 814 | 0.67 | 1729 | 0.66 | 2 | rs2242503 | C11 | TUB |
| AllCauc | 7.00E−04 | 1.13 | NA | NA | NA | NA | 3 | rs12291026 | C11 | SERPINH1 |
| AllCaucexcluCGEMS | 1.60E−03 | 1.12 | NA | NA | NA | NA | 3 | rs12291026 | C11 | SERPINH1 |
| CGEMS | 1.91E−01 | 1.18 | 1139 | 0.13 | 1138 | 0.11 | 3 | rs12291026 | C11 | SERPINH1 |
| Holland | 8.65E−01 | 0.98 | 737 | 0.12 | 2012 | 0.12 | 3 | rs12291026 | C11 | SERPINH1 |
| Iceland | 3.98E−04 | 1.18 | 2280 | 0.12 | 35635 | 0.11 | 3 | rs12291026 | C11 | SERPINH1 |
| Spain | 9.31E−02 | 1.18 | 641 | 0.14 | 1518 | 0.12 | 3 | rs12291026 | C11 | SERPINH1 |
| Sweden | 7.97E−01 | 1.03 | 829 | 0.10 | 1740 | 0.10 | 3 | rs12291026 | C11 | SERPINH1 |
| AllCauc | 1.70E−07 | 1.15 | NA | NA | NA | NA | 2 | rs999737 | C14 | RAD51L1 |
| AllCaucexcluCGEMS | 3.50E−06 | 1.14 | NA | NA | NA | NA | 2 | rs999737 | C14 | RAD51L1 |
| CGEMS | 1.31E−02 | 1.19 | 1143 | 0.79 | 1141 | 0.76 | 2 | rs999737 | C14 | RAD51L1 |
| Holland | 3.18E−01 | 1.08 | 740 | 0.78 | 2006 | 0.77 | 2 | rs999737 | C14 | RAD51L1 |
| Iceland | 8.79E−05 | 1.15 | 2279 | 0.77 | 35638 | 0.74 | 2 | rs999737 | C14 | RAD51L1 |
| Spain | 2.49E−02 | 1.21 | 638 | 0.81 | 1514 | 0.78 | 2 | rs999737 | C14 | RAD51L1 |
| Sweden | 8.90E−02 | 1.13 | 831 | 0.80 | 1733 | 0.78 | 2 | rs999737 | C14 | RAD51L1 |
| AllCauc | 3.90E−06 | 1.17 | NA | NA | NA | NA | 1 | rs9956546 | C18 | FHOD3 |
| AllCaucexcluCGEMS | 1.50E−05 | 1.17 | NA | NA | NA | NA | 1 | rs9956546 | C18 | FHOD3 |
| CGEMS | 1.04E−01 | 1.21 | 1144 | 0.13 | 1140 | 0.11 | 1 | rs9956546 | C18 | FHOD3 |
| Holland | 4.71E−01 | 1.07 | 740 | 0.12 | 2022 | 0.11 | 1 | rs9956546 | C18 | FHOD3 |
| Iceland | 2.11E−06 | 1.23 | 2282 | 0.15 | 36015 | 0.12 | 1 | rs9956546 | C18 | FHOD3 |
| Spain | 7.07E−01 | 1.04 | 458 | 0.14 | 993 | 0.13 | 1 | rs9956546 | C18 | FHOD3 |
| Sweden | 2.56E−01 | 1.11 | 819 | 0.12 | 1732 | 0.11 | 1 | rs9956546 | C18 | FHOD3 |
| AllCauc | 5.00E−06 | 1.11 | NA | NA | NA | NA | 4 | rs11912922 | C22 | TNRC6B |
| AllCaucexcluCGEMS | 3.40E−05 | 1.11 | NA | NA | NA | NA | 4 | rs11912922 | C22 | TNRC6B |
| CGEMS | 4.72E−02 | 1.16 | 1143 | 0.32 | 1141 | 0.29 | 4 | rs11912922 | C22 | TNRC6B |
| Holland | 4.80E−01 | 0.96 | 741 | 0.32 | 2011 | 0.33 | 4 | rs11912922 | C22 | TNRC6B |
| Iceland | 3.33E−05 | 1.14 | 2285 | 0.38 | 35631 | 0.35 | 4 | rs11912922 | C22 | TNRC6B |
| Spain | 3.77E−02 | 1.16 | 639 | 0.34 | 1529 | 0.30 | 4 | rs11912922 | C22 | TNRC6B |
| Sweden | 6.66E−02 | 1.12 | 826 | 0.36 | 1702 | 0.33 | 4 | rs11912922 | C22 | TNRC6B |
| AllCauc | 8.90E−06 | 1.17 | NA | NA | NA | NA | 3 | rs6001954 | C22 | TNRC6B |
| AllCaucexcluCGEMS | 3.70E−05 | 1.17 | NA | NA | NA | NA | 3 | rs6001954 | C22 | TNRC6B |
| CGEMS | 9.30E−02 | 1.22 | 1101 | 0.11 | 1105 | 0.09 | 3 | rs6001954 | C22 | TNRC6B |
| Holland | 1.35E−01 | 1.16 | 741 | 0.12 | 2017 | 0.10 | 3 | rs6001954 | C22 | TNRC6B |
| Iceland | 1.28E−03 | 1.16 | 2267 | 0.13 | 35210 | 0.12 | 3 | rs6001954 | C22 | TNRC6B |
| Spain | 6.68E−02 | 1.22 | 640 | 0.11 | 1533 | 0.10 | 3 | rs6001954 | C22 | TNRC6B |
| Sweden | 1.26E−01 | 1.16 | 825 | 0.12 | 1724 | 0.10 | 3 | rs6001954 | C22 | TNRC6B |

Allelic Odds Ratios calculated under the multiplicative model. All P values are two sided and have been adjusted for relatedness and other potential

TABLE 4

Surrogate markers for the nine Anchor SNPs. Markers with values of $R^2$ greater than 0.2 to an Anchor marker in the HapMap CEU dataset (http://www.hapmap.org) in a 1 Mb interval flanking the marker were selected. Shown is the name of the correlated SNP, values for $R^2$ and D' to that marker and the corresponding P-value, as well as the position of the surrogate marker in NCBI Build 36 and a reference to the sequence ID containing flanking sequences for that marker.

| Anchor | Surrogate | D' | $R^2$ | P-value | Chromosome | Pos Build 36 | Seq ID |
|---|---|---|---|---|---|---|---|
| rs2005154 | rs2005154 | 1 | 1 | — | C09 | 36,846,828 | 1 |
| rs2005154 | rs4878662 | 1 | 1 | 1.07E−16 | C09 | 36,851,331 | 174 |
| rs2005154 | rs4880019 | 1 | 0.900826 | 3.20E−15 | C09 | 36,853,450 | 175 |
| rs2184380 | rs2184380 | 1 | 1 | — | C10 | 8,754,080 | 2 |
| rs2184380 | rs10466295 | 1 | 1 | 1.53E−28 | C10 | 8,747,556 | 176 |
| rs2184380 | rs10508363 | 1 | 1 | 1.53E−28 | C10 | 8,736,508 | 177 |
| rs2184380 | rs10508364 | 0.948936 | 0.856732 | 1.01E−22 | C10 | 8,808,518 | 178 |
| rs2184380 | rs10508365 | 0.948936 | 0.856732 | 1.01E−22 | C10 | 8,808,985 | 179 |
| rs2184380 | rs10795670 | 1 | 0.209877 | 4.71E−09 | C10 | 8,765,045 | 180 |
| rs2184380 | rs10905411 | 0.874714 | 0.387964 | 3.45E−11 | C10 | 8,678,685 | 181 |
| rs2184380 | rs10905414 | 0.870352 | 0.356105 | 3.50E−10 | C10 | 8,680,134 | 182 |
| rs2184380 | rs10905415 | 0.91879 | 0.237472 | 4.68E−08 | C10 | 8,680,223 | 183 |
| rs2184380 | rs10905430 | 0.844581 | 0.2373 | 1.96E−07 | C10 | 8,704,489 | 184 |
| rs2184380 | rs10905437 | 1 | 0.304695 | 1.26E−11 | C10 | 8,735,801 | 185 |
| rs2184380 | rs10905439 | 0.947367 | 0.897401 | 6.59E−23 | C10 | 8,753,333 | 186 |
| rs2184380 | rs10905440 | 1 | 0.951417 | 1.10E−26 | C10 | 8,755,150 | 187 |
| rs2184380 | rs10905443 | 1 | 1 | 1.53E−28 | C10 | 8,757,369 | 188 |
| rs2184380 | rs10905444 | 1 | 1 | 1.53E−28 | C10 | 8,757,533 | 189 |
| rs2184380 | rs10905445 | 1 | 1 | 1.53E−28 | C10 | 8,758,377 | 190 |
| rs2184380 | rs10905446 | 1 | 1 | 1.53E−28 | C10 | 8,758,390 | 191 |
| rs2184380 | rs10905447 | 1 | 1 | 1.53E−28 | C10 | 8,758,955 | 192 |
| rs2184380 | rs10905454 | 0.895085 | 0.796777 | 4.82E−19 | C10 | 8,807,933 | 193 |
| rs2184380 | rs11255764 | 0.885251 | 0.566844 | 9.13E−15 | C10 | 8,676,745 | 194 |
| rs2184380 | rs11255776 | 0.844286 | 0.245302 | 2.21E−07 | C10 | 8,701,838 | 195 |

TABLE 4-continued

Surrogate markers for the nine Anchor SNPs. Markers with values of $R^2$ greater than 0.2 to an Anchor marker in the HapMap CEU dataset (http://www.hapmap.org) in a 1 Mb interval flanking the marker were selected. Shown is the name of the correlated SNP, values for $R^2$ and D' to that marker and the corresponding P-value, as well as the position of the surrogate marker in NCBI Build 36 and a reference to the sequence ID containing flanking sequences for that marker.

| Anchor | Surrogate | D' | $R^2$ | P-value | Chromosome | Pos Build 36 | Seq ID |
|---|---|---|---|---|---|---|---|
| rs2184380 | rs11255777 | 0.847467 | 0.247154 | 1.12E−07 | C10 | 8,702,017 | 196 |
| rs2184380 | rs11255778 | 0.848675 | 0.247226 | 9.24E−08 | C10 | 8,703,356 | 197 |
| rs2184380 | rs11255779 | 0.840039 | 0.241626 | 3.17E−07 | C10 | 8,703,789 | 198 |
| rs2184380 | rs11255790 | 0.937236 | 0.429299 | 1.11E−12 | C10 | 8,722,186 | 199 |
| rs2184380 | rs11255795 | 1 | 1 | 1.93E−28 | C10 | 8,731,572 | 200 |
| rs2184380 | rs11255797 | 1 | 1 | 1.53E−28 | C10 | 8,737,159 | 201 |
| rs2184380 | rs11255800 | 1 | 1 | 3.91E−27 | C10 | 8,742,581 | 202 |
| rs2184380 | rs11255804 | 0.94445 | 0.792459 | 3.17E−19 | C10 | 8,747,207 | 203 |
| rs2184380 | rs11255805 | 1 | 1 | 1.53E−28 | C10 | 8,747,459 | 204 |
| rs2184380 | rs11255820 | 1 | 1 | 1.53E−28 | C10 | 8,759,525 | 205 |
| rs2184380 | rs11255821 | 1 | 1 | 9.41E−28 | C10 | 8,759,540 | 206 |
| rs2184380 | rs11255822 | 1 | 1 | 2.45E−28 | C10 | 8,759,613 | 207 |
| rs2184380 | rs11255832 | 1 | 0.949367 | 2.82E−26 | C10 | 8,770,466 | 208 |
| rs2184380 | rs11255836 | 1 | 1 | 1.53E−28 | C10 | 8,773,212 | 209 |
| rs2184380 | rs11255840 | 1 | 0.95 | 4.16E−26 | C10 | 8,779,199 | 210 |
| rs2184380 | rs11255858 | 0.948936 | 0.856732 | 1.01E−22 | C10 | 8,790,639 | 211 |
| rs2184380 | rs11255862 | 0.948936 | 0.856732 | 1.01E−22 | C10 | 8,793,888 | 212 |
| rs2184380 | rs11255869 | 0.948925 | 0.855817 | 1.27E−22 | C10 | 8,801,802 | 213 |
| rs2184380 | rs11255870 | 0.948936 | 0.856732 | 1.01E−22 | C10 | 8,803,268 | 214 |
| rs2184380 | rs11255871 | 0.948936 | 0.856732 | 1.01E−22 | C10 | 8,803,763 | 215 |
| rs2184380 | rs11255882 | 0.884394 | 0.542127 | 3.04E−14 | C10 | 8,810,853 | 216 |
| rs2184380 | rs11255884 | 0.933202 | 0.665922 | 4.29E−14 | C10 | 8,811,968 | 217 |
| rs2184380 | rs12049705 | 0.885669 | 0.565013 | 5.63E−15 | C10 | 8,679,446 | 218 |
| rs2184380 | rs12218610 | 0.856757 | 0.38242 | 1.22E−09 | C10 | 8,706,615 | 219 |
| rs2184380 | rs12250379 | 0.926804 | 0.305824 | 1.61E−09 | C10 | 8,802,201 | 26 |
| rs2184380 | rs12259226 | 0.946719 | 0.85359 | 2.31E−21 | C10 | 8,806,948 | 220 |
| rs2184380 | rs1325874 | 1 | 1 | 1.53E−28 | C10 | 8,740,707 | 221 |
| rs2184380 | rs1334549 | 1 | 1 | 1.53E−28 | C10 | 8,744,989 | 29 |
| rs2184380 | rs1334550 | 1 | 1 | 1.53E−28 | C10 | 8,744,845 | 222 |
| rs2184380 | rs1334559 | 0.948936 | 0.856732 | 1.01E−22 | C10 | 8,796,810 | 223 |
| rs2184380 | rs1360749 | 1 | 1 | 1.53E−28 | C10 | 8,759,215 | 224 |
| rs2184380 | rs1413678 | 0.924198 | 0.284149 | 5.54E−09 | C10 | 8,794,683 | 225 |
| rs2184380 | rs1413683 | 0.944299 | 0.850224 | 5.27E−20 | C10 | 8,804,953 | 226 |
| rs2184380 | rs1537601 | 0.949468 | 0.901005 | 7.18E−24 | C10 | 8,785,004 | 227 |
| rs2184380 | rs1537602 | 0.949474 | 0.9015 | 5.73E−24 | C10 | 8,784,898 | 228 |
| rs2184380 | rs1537603 | 1 | 0.201238 | 7.61E−09 | C10 | 8,774,301 | 31 |
| rs2184380 | rs17407711 | 1 | 1 | 1.53E−28 | C10 | 8,769,001 | 229 |
| rs2184380 | rs17407781 | 1 | 1 | 1.93E−28 | C10 | 8,773,088 | 230 |
| rs2184380 | rs17407830 | 0.943872 | 0.805805 | 5.02E−20 | C10 | 8,775,487 | 231 |
| rs2184380 | rs17408204 | 0.948913 | 0.854883 | 1.59E−22 | C10 | 8,790,006 | 232 |
| rs2184380 | rs17408337 | 0.948936 | 0.856732 | 1.01E−22 | C10 | 8,791,931 | 233 |
| rs2184380 | rs17408580 | 0.946832 | 0.854684 | 4.55E−22 | C10 | 8,794,975 | 234 |
| rs2184380 | rs17484150 | 0.874978 | 0.400207 | 3.72E−11 | C10 | 8,707,041 | 235 |
| rs2184380 | rs17485426 | 1 | 1 | 1.53E−28 | C10 | 8,743,013 | 236 |
| rs2184380 | rs17485998 | 1 | 1 | 1.53E−28 | C10 | 8,759,878 | 237 |
| rs2184380 | rs17486082 | 1 | 1 | 1.53E−28 | C10 | 8,767,474 | 238 |
| rs2184380 | rs17486795 | 0.948936 | 0.856732 | 1.01E−22 | C10 | 8,792,167 | 239 |
| rs2184380 | rs17486816 | 0.948936 | 0.856732 | 1.01E−22 | C10 | 8,792,191 | 240 |
| rs2184380 | rs1970170 | 0.949389 | 0.899443 | 2.68E−23 | C10 | 8,785,426 | 241 |
| rs2184380 | rs1999638 | 1 | 0.95 | 4.16E−26 | C10 | 8,783,743 | 242 |
| rs2184380 | rs2031561 | 0.874358 | 0.384902 | 4.27E−11 | C10 | 8,683,505 | 243 |
| rs2184380 | rs2182292 | 0.872839 | 0.372331 | 7.65E−11 | C10 | 8,683,484 | 244 |
| rs2184380 | rs2388821 | 1 | 0.318315 | 4.75E−12 | C10 | 8,736,687 | 245 |
| rs2184380 | rs2388825 | 1 | 1 | 1.53E−28 | C10 | 8,756,643 | 246 |
| rs2184380 | rs2388826 | 0.946678 | 0.850726 | 4.53E−21 | C10 | 8,805,023 | 247 |
| rs2184380 | rs2892613 | 1 | 1 | 1.53E−28 | C10 | 8,756,702 | 248 |
| rs2184380 | rs4112287 | 0.948936 | 0.856732 | 1.01E−22 | C10 | 8,791,551 | 249 |
| rs2184380 | rs4112288 | 0.948936 | 0.856732 | 1.01E−22 | C10 | 8,791,525 | 250 |
| rs2184380 | rs4345867 | 1 | 0.283927 | 4.34E−11 | C10 | 8,736,698 | 251 |
| rs2184380 | rs4454616 | 0.911606 | 0.211521 | 4.36E−07 | C10 | 8,705,153 | 33 |
| rs2184380 | rs4747806 | 0.870907 | 0.357423 | 1.65E−10 | C10 | 8,678,241 | 35 |
| rs2184380 | rs4749805 | 1 | 1 | 7.43E−28 | C10 | 8,751,692 | 252 |
| rs2184380 | rs4749807 | 1 | 1 | 1.53E−28 | C10 | 8,751,763 | 253 |
| rs2184380 | rs4749812 | 1 | 0.201238 | 7.61E−09 | C10 | 8,777,570 | 254 |
| rs2184380 | rs6602328 | 0.8255 | 0.21783 | 3.95E−06 | C10 | 8,700,007 | 255 |
| rs2184380 | rs6602329 | 0.843632 | 0.234214 | 2.42E−07 | C10 | 8,700,101 | 36 |
| rs2184380 | rs7069110 | 1 | 0.318315 | 4.75E−12 | C10 | 8,735,184 | 256 |
| rs2184380 | rs7080765 | 0.922785 | 0.313611 | 2.97E−09 | C10 | 8,797,824 | 257 |
| rs2184380 | rs7083359 | 0.937236 | 0.429299 | 1.11E−12 | C10 | 8,722,685 | 39 |
| rs2184380 | rs7477023 | 1 | 1 | 1.53E−28 | C10 | 8,753,932 | 258 |
| rs2184380 | rs7904921 | 0.948936 | 0.856732 | 1.01E−22 | C10 | 8,792,331 | 259 |
| rs2184380 | rs7912413 | 1 | 1 | 2.03E−24 | C10 | 8,762,126 | 260 |

TABLE 4-continued

Surrogate markers for the nine Anchor SNPs. Markers with values of $R^2$ greater than 0.2 to an Anchor marker in the HapMap CEU dataset (http://www.hapmap.org) in a 1 Mb interval flanking the marker were selected. Shown is the name of the correlated SNP, values for $R^2$ and D' to that marker and the corresponding P-value, as well as the position of the surrogate marker in NCBI Build 36 and a reference to the sequence ID containing flanking sequences for that marker.

| Anchor | Surrogate | D' | $R^2$ | P-value | Chromosome | Pos Build 36 | Seq ID |
|---|---|---|---|---|---|---|---|
| rs2184380 | rs7912704 | 1 | 0.201238 | 7.61E−09 | C10 | 8,771,181 | 261 |
| rs2184380 | rs7912831 | 1 | 0.201238 | 7.61E−09 | C10 | 8,771,261 | 262 |
| rs2184380 | rs827389 | 1 | 0.417761 | 1.41E−13 | C10 | 8,740,261 | 263 |
| rs2184380 | rs9665623 | 0.948936 | 0.856732 | 1.01E−22 | C10 | 8,797,122 | 264 |
| rs2224696 | rs2224696 | 1 | 1 | — | C10 | 9,168,781 | 3 |
| rs2224696 | rs10905509 | 1 | 0.461682 | 4.95E−12 | C10 | 9,160,368 | 265 |
| rs2224696 | rs11256045 | 0.807004 | 0.329629 | 6.26E−08 | C10 | 9,157,239 | 266 |
| rs2224696 | rs12761213 | 0.88785 | 0.589831 | 1.21E−10 | C10 | 9,106,345 | 267 |
| rs2224696 | rs12761461 | 0.906382 | 0.751312 | 1.87E−13 | C10 | 9,158,901 | 268 |
| rs2224696 | rs12766048 | 1 | 0.66736 | 4.52E−12 | C10 | 9,133,679 | 52 |
| rs2224696 | rs12772042 | 1 | 0.919893 | 4.43E−18 | C10 | 9,164,748 | 269 |
| rs2224696 | rs12776383 | 1 | 0.727891 | 1.42E−12 | C10 | 9,227,620 | 270 |
| rs2224696 | rs12778120 | 0.621966 | 0.221569 | 0.000014 | C10 | 9,253,860 | 271 |
| rs2224696 | rs12780218 | 0.906382 | 0.751312 | 1.87E−13 | C10 | 9,159,062 | 272 |
| rs2224696 | rs12781427 | 1 | 0.919192 | 4.98E−18 | C10 | 9,167,711 | 53 |
| rs2224696 | rs1475189 | 1 | 0.830628 | 2.85E−15 | C10 | 9,147,691 | 273 |
| rs2224696 | rs1573109 | 0.772073 | 0.519575 | 1.43E−08 | C10 | 9,141,049 | 274 |
| rs2224696 | rs1573110 | 0.794588 | 0.591124 | 4.06E−10 | C10 | 9,135,501 | 275 |
| rs2224696 | rs17145088 | 1 | 0.830628 | 2.85E−15 | C10 | 9,116,440 | 276 |
| rs2224696 | rs17145095 | 1 | 0.830628 | 2.85E−15 | C10 | 9,116,991 | 277 |
| rs2224696 | rs17145118 | 1 | 0.66736 | 5.30E−12 | C10 | 9,121,203 | 278 |
| rs2224696 | rs17145120 | 1 | 0.830628 | 3.46E−15 | C10 | 9,122,007 | 279 |
| rs2224696 | rs17145151 | 1 | 0.830628 | 2.85E−15 | C10 | 9,130,711 | 280 |
| rs2224696 | rs17145164 | 1 | 0.830628 | 2.85E−15 | C10 | 9,146,874 | 281 |
| rs2224696 | rs17145169 | 1 | 0.66736 | 4.90E−12 | C10 | 9,147,141 | 282 |
| rs2224696 | rs17145188 | 0.621966 | 0.221569 | 0.000014 | C10 | 9,148,524 | 283 |
| rs2224696 | rs17145193 | 0.883003 | 0.562854 | 1.15E−09 | C10 | 9,155,959 | 284 |
| rs2224696 | rs17145221 | 1 | 0.89916 | 5.67E−15 | C10 | 9,168,824 | 285 |
| rs2224696 | rs17363338 | 0.906382 | 0.751312 | 1.87E−13 | C10 | 9,161,882 | 286 |
| rs2224696 | rs1775559 | 0.820762 | 0.495886 | 1.94E−10 | C10 | 9,115,547 | 287 |
| rs2224696 | rs1857230 | 1 | 0.270147 | 1.73E−08 | C10 | 9,127,246 | 288 |
| rs2224696 | rs1891532 | 1 | 0.209856 | 7.58E−08 | C10 | 9,120,032 | 289 |
| rs2224696 | rs1935813 | 1 | 0.830628 | 2.85E−15 | C10 | 9,118,559 | 290 |
| rs2224696 | rs2013364 | 1 | 1 | 1.16E−19 | C10 | 9,168,159 | 291 |
| rs2224696 | rs2025289 | 0.906382 | 0.751312 | 1.87E−13 | C10 | 9,161,060 | 292 |
| rs2224696 | rs2057442 | 1 | 0.242991 | 1.64E−08 | C10 | 9,129,940 | 293 |
| rs2224696 | rs2093625 | 1 | 0.310553 | 1.63E−08 | C10 | 9,126,798 | 294 |
| rs2224696 | rs2093626 | 1 | 0.252336 | 1.09E−08 | C10 | 9,126,888 | 295 |
| rs2224696 | rs2146598 | 1 | 0.66736 | 4.52E−12 | C10 | 9,118,227 | 296 |
| rs2224696 | rs2185817 | 0.796105 | 0.599318 | 1.59E−08 | C10 | 9,140,970 | 297 |
| rs2224696 | rs2397336 | 1 | 0.267074 | 2.33E−08 | C10 | 9,147,920 | 298 |
| rs2224696 | rs2760204 | 1 | 0.242991 | 1.64E−08 | C10 | 9,139,981 | 299 |
| rs2224696 | rs2797266 | 1 | 0.242991 | 1.64E−08 | C10 | 9,129,166 | 59 |
| rs2224696 | rs391733 | 0.780788 | 0.203685 | 0.00001 | C10 | 9,191,976 | 300 |
| rs2224696 | rs4550140 | 1 | 0.25 | 1.23E−08 | C10 | 9,145,853 | 301 |
| rs2224696 | rs7081544 | 1 | 0.830628 | 2.85E−15 | C10 | 9,144,695 | 302 |
| rs2224696 | rs852273 | 1 | 0.276161 | 4.18E−09 | C10 | 9,133,645 | 303 |
| rs2224696 | rs860418 | 1 | 0.245283 | 5.19E−08 | C10 | 9,131,906 | 304 |
| rs2224696 | rs861172 | 1 | 0.240684 | 1.85E−08 | C10 | 9,133,432 | 305 |
| rs2224696 | rs962993 | 0.885222 | 0.209643 | 1.52E−06 | C10 | 9,093,138 | 67 |
| rs2224696 | rs965307 | 1 | 0.830628 | 2.85E−15 | C10 | 9,119,005 | 306 |
| rs2242503 | rs2242503 | 1 | 1 | — | C11 | 8,075,048 | 4 |
| rs2242503 | rs10431029 | 0.723593 | 0.468793 | 4.39E−13 | C11 | 8,133,019 | 307 |
| rs2242503 | rs1055233 | 0.76309 | 0.517167 | 1.34E−14 | C11 | 8,084,071 | 308 |
| rs2242503 | rs10734629 | 0.720552 | 0.46649 | 6.01E−13 | C11 | 8,143,253 | 309 |
| rs2242503 | rs10743052 | 0.717443 | 0.464136 | 8.24E−13 | C11 | 8,131,542 | 310 |
| rs2242503 | rs10743053 | 0.553357 | 0.295358 | 9.02E−09 | C11 | 8,158,239 | 311 |
| rs2242503 | rs10743054 | 0.553357 | 0.295358 | 9.02E−09 | C11 | 8,158,291 | 312 |
| rs2242503 | rs10743055 | 0.553357 | 0.295358 | 9.02E−09 | C11 | 8,158,376 | 313 |
| rs2242503 | rs10769872 | 0.732431 | 0.432469 | 1.14E−11 | C11 | 8,110,090 | 314 |
| rs2242503 | rs10769873 | 0.734884 | 0.322358 | 2.52E−09 | C11 | 8,114,186 | 315 |
| rs2242503 | rs10769878 | 0.717939 | 0.348534 | 1.89E−08 | C11 | 8,143,862 | 316 |
| rs2242503 | rs10769882 | 0.5497 | 0.229219 | 5.61E−06 | C11 | 8,154,849 | 317 |
| rs2242503 | rs10839976 | 0.724865 | 0.308568 | 1.44E−08 | C11 | 8,116,468 | 318 |
| rs2242503 | rs10839984 | 0.734884 | 0.322358 | 2.52E−09 | C11 | 8,137,470 | 68 |
| rs2242503 | rs11041740 | 0.941774 | 0.461102 | 4.78E−14 | C11 | 8,074,094 | 319 |
| rs2242503 | rs11041742 | 0.734884 | 0.322358 | 2.52E−09 | C11 | 8,083,499 | 320 |
| rs2242503 | rs11041788 | 0.539249 | 0.212989 | 0.000025 | C11 | 8,164,924 | 321 |
| rs2242503 | rs11041791 | 0.553934 | 0.235484 | 7.51E−07 | C11 | 8,168,818 | 69 |
| rs2242503 | rs11041794 | 0.644371 | 0.240003 | 2.20E−06 | C11 | 8,172,242 | 322 |
| rs2242503 | rs1108277 | 1 | 0.705954 | 1.08E−24 | C11 | 8,077,794 | 323 |
| rs2242503 | rs12146654 | 0.64592 | 0.38833 | 1.53E−08 | C11 | 8,152,036 | 324 |

TABLE 4-continued

Surrogate markers for the nine Anchor SNPs. Markers with values of $R^2$ greater than 0.2 to an Anchor marker in the HapMap CEU dataset (http://www.hapmap.org) in a 1 Mb interval flanking the marker were selected. Shown is the name of the correlated SNP, values for $R^2$ and D' to that marker and the corresponding P-value, as well as the position of the surrogate marker in NCBI Build 36 and a reference to the sequence ID containing flanking sequences for that marker.

| Anchor | Surrogate | D' | $R^2$ | P-value | Chromosome | Pos Build 36 | Seq ID |
|---|---|---|---|---|---|---|---|
| rs2242503 | rs12808387 | 0.553357 | 0.295358 | 9.02E−09 | C11 | 8,159,414 | 325 |
| rs2242503 | rs1528125 | 0.553357 | 0.295358 | 9.02E−09 | C11 | 8,156,792 | 326 |
| rs2242503 | rs1569128 | 0.723593 | 0.468793 | 4.39E−13 | C11 | 8,089,461 | 327 |
| rs2242503 | rs1970880 | 0.544244 | 0.288701 | 1.80E−08 | C11 | 8,160,092 | 328 |
| rs2242503 | rs1997262 | 0.522176 | 0.272668 | 3.97E−08 | C11 | 8,158,988 | 329 |
| rs2242503 | rs2049684 | 0.723593 | 0.468793 | 4.39E−13 | C11 | 8,127,695 | 72 |
| rs2242503 | rs2141321 | 0.789386 | 0.513662 | 2.21E−14 | C11 | 8,086,752 | 330 |
| rs2242503 | rs2242501 | 0.737441 | 0.335833 | 2.13E−09 | C11 | 8,074,679 | 331 |
| rs2242503 | rs2272383 | 0.63086 | 0.397985 | 3.43E−11 | C11 | 8,080,075 | 332 |
| rs2242503 | rs3750955 | 0.784744 | 0.385656 | 1.72E−10 | C11 | 8,082,818 | 333 |
| rs2242503 | rs3752898 | 0.900696 | 0.245488 | 5.00E−07 | C11 | 8,073,496 | 334 |
| rs2242503 | rs3849986 | 0.522176 | 0.272668 | 3.97E−08 | C11 | 8,159,303 | 335 |
| rs2242503 | rs3849990 | 0.665217 | 0.252525 | 3.28E−07 | C11 | 8,175,019 | 336 |
| rs2242503 | rs3911309 | 0.554372 | 0.202829 | 2.81E−06 | C11 | 8,173,902 | 337 |
| rs2242503 | rs3911310 | 0.554372 | 0.202829 | 2.81E−06 | C11 | 8,174,324 | 338 |
| rs2242503 | rs4340037 | 0.782801 | 0.349689 | 2.40E−10 | C11 | 8,084,734 | 339 |
| rs2242503 | rs4343012 | 0.734884 | 0.322358 | 2.52E−09 | C11 | 8,089,751 | 340 |
| rs2242503 | rs4385931 | 0.770418 | 0.551609 | 6.82E−16 | C11 | 8,066,224 | 341 |
| rs2242503 | rs4575312 | 0.669287 | 0.255625 | 1.73E−07 | C11 | 8,065,299 | 342 |
| rs2242503 | rs4578424 | 0.642849 | 0.214843 | 2.18E−06 | C11 | 8,064,861 | 75 |
| rs2242503 | rs4636658 | 0.590173 | 0.221903 | 1.11E−06 | C11 | 8,178,862 | 343 |
| rs2242503 | rs4758040 | 0.834104 | 0.50807 | 1.52E−15 | C11 | 8,057,749 | 76 |
| rs2242503 | rs4758042 | 0.717439 | 0.45831 | 2.74E−12 | C11 | 8,085,872 | 344 |
| rs2242503 | rs4758287 | 0.63975 | 0.255278 | 1.71E−07 | C11 | 8,056,489 | 345 |
| rs2242503 | rs4758309 | 0.544875 | 0.227845 | 2.57E−06 | C11 | 8,165,306 | 346 |
| rs2242503 | rs4758310 | 0.553934 | 0.235484 | 7.51E−07 | C11 | 8,165,969 | 347 |
| rs2242503 | rs7103334 | 0.546807 | 0.278288 | 2.54E−08 | C11 | 8,157,501 | 348 |
| rs2242503 | rs7112519 | 0.535211 | 0.217411 | 3.18E−06 | C11 | 8,169,345 | 349 |
| rs2242503 | rs7115706 | 0.544644 | 0.223928 | 1.40E−06 | C11 | 8,169,421 | 350 |
| rs2242503 | rs7122690 | 0.522176 | 0.272668 | 3.97E−08 | C11 | 8,159,397 | 351 |
| rs2242503 | rs7127738 | 0.527011 | 0.276798 | 1.88E−07 | C11 | 8,154,963 | 352 |
| rs2242503 | rs7358396 | 0.71764 | 0.42377 | 2.13E−10 | C11 | 8,141,858 | 353 |
| rs2242503 | rs7479156 | 0.551079 | 0.289269 | 1.57E−08 | C11 | 8,157,993 | 354 |
| rs2242503 | rs7479738 | 0.553357 | 0.295358 | 9.02E−09 | C11 | 8,157,931 | 355 |
| rs2242503 | rs7480804 | 1 | 0.236507 | 1.40E−08 | C11 | 8,066,385 | 356 |
| rs2242503 | rs7481667 | 0.553357 | 0.295358 | 9.02E−09 | C11 | 8,157,701 | 357 |
| rs2242503 | rs7481683 | 0.553357 | 0.295358 | 9.02E−09 | C11 | 8,157,762 | 358 |
| rs2242503 | rs7482611 | 0.693202 | 0.457371 | 2.46E−10 | C11 | 8,106,602 | 359 |
| rs2242503 | rs7927368 | 0.643226 | 0.370442 | 1.47E−10 | C11 | 8,152,196 | 360 |
| rs2242503 | rs7940668 | 0.643226 | 0.370442 | 1.47E−10 | C11 | 8,152,710 | 361 |
| rs12291026 | rs12291026 | 1 | 1 | — | C11 | 74,932,878 | 5 |
| rs12291026 | rs1004856 | 0.795363 | 0.22224 | 3.36E−06 | C11 | 74,858,615 | 362 |
| rs12291026 | rs10899091 | 1 | 1 | 1.43E−20 | C11 | 74,933,440 | 363 |
| rs12291026 | rs11236449 | 1 | 0.919893 | 4.43E−18 | C11 | 74,918,745 | 364 |
| rs12291026 | rs11236452 | 1 | 0.919893 | 4.98E−18 | C11 | 74,927,534 | 365 |
| rs12291026 | rs11236454 | 1 | 0.906687 | 6.96E−16 | C11 | 74,932,272 | 366 |
| rs12291026 | rs12362081 | 1 | 0.84127 | 3.43E−16 | C11 | 74,899,292 | 367 |
| rs12291026 | rs1540210 | 0.800306 | 0.242864 | 1.38E−06 | C11 | 74,887,046 | 78 |
| rs12291026 | rs1540211 | 0.750347 | 0.450541 | 1.04E−09 | C11 | 74,887,332 | 368 |
| rs12291026 | rs1557471 | 0.79757 | 0.231043 | 2.21E−06 | C11 | 74,857,322 | 369 |
| rs12291026 | rs1631470 | 0.799311 | 0.23844 | 1.70E−06 | C11 | 74,864,790 | 370 |
| rs12291026 | rs1783551 | 0.837984 | 0.701135 | 2.54E−13 | C11 | 74,908,860 | 371 |
| rs12291026 | rs1783556 | 0.876315 | 0.242246 | 0.000013 | C11 | 74,897,710 | 372 |
| rs12291026 | rs1783559 | 0.820042 | 0.540279 | 1.73E−10 | C11 | 74,894,676 | 373 |
| rs12291026 | rs1790144 | 0.750347 | 0.450541 | 1.04E−09 | C11 | 74,889,549 | 79 |
| rs12291026 | rs1790152 | 0.79757 | 0.231043 | 2.21E−06 | C11 | 74,862,499 | 374 |
| rs12291026 | rs1790307 | 0.830991 | 0.514897 | 7.92E−11 | C11 | 74,898,758 | 375 |
| rs12291026 | rs1793396 | 0.895234 | 0.292441 | 6.02E−08 | C11 | 74,890,048 | 376 |
| rs12291026 | rs1793397 | 0.750347 | 0.450541 | 1.04E−09 | C11 | 74,890,155 | 377 |
| rs12291026 | rs1793398 | 0.906458 | 0.369032 | 1.79E−09 | C11 | 74,893,069 | 378 |
| rs12291026 | rs1793399 | 0.831094 | 0.516953 | 7.12E−11 | C11 | 74,898,153 | 80 |
| rs12291026 | rs1793414 | 0.792872 | 0.226475 | 4.83E−06 | C11 | 74,860,335 | 379 |
| rs12291026 | rs1938800 | 1 | 0.748428 | 2.23E−16 | C11 | 74,933,770 | 81 |
| rs12291026 | rs2853066 | 0.804722 | 0.264424 | 6.22E−07 | C11 | 74,866,805 | 380 |
| rs12291026 | rs499613 | 0.792872 | 0.226475 | 4.83E−06 | C11 | 74,872,133 | 381 |
| rs12291026 | rs504793 | 0.800306 | 0.242864 | 1.38E−06 | C11 | 74,878,212 | 382 |
| rs12291026 | rs514477 | 0.800306 | 0.242864 | 1.38E−06 | C11 | 74,875,650 | 383 |
| rs12291026 | rs549034 | 0.799814 | 0.24066 | 1.53E−06 | C11 | 74,880,782 | 384 |
| rs12291026 | rs550881 | 0.800306 | 0.242864 | 1.38E−06 | C11 | 74,880,612 | 385 |
| rs12291026 | rs581007 | 0.800306 | 0.242864 | 1.38E−06 | C11 | 74,879,594 | 386 |
| rs12291026 | rs589724 | 0.805181 | 0.254846 | 6.34E−07 | C11 | 74,876,829 | 387 |
| rs12291026 | rs600387 | 1 | 0.293756 | 1.11E−09 | C11 | 74,935,675 | 388 |

TABLE 4-continued

Surrogate markers for the nine Anchor SNPs. Markers with values of $R^2$ greater than 0.2 to an Anchor marker in the HapMap CEU dataset (http://www.hapmap.org) in a 1 Mb interval flanking the marker were selected. Shown is the name of the correlated SNP, values for $R^2$ and D' to that marker and the corresponding P-value, as well as the position of the surrogate marker in NCBI Build 36 and a reference to the sequence ID containing flanking sequences for that marker.

| Anchor | Surrogate | D' | $R^2$ | P-value | Chromosome | Pos Build 36 | Seq ID |
|---|---|---|---|---|---|---|---|
| rs12291026 | rs606460 | 0.902797 | 0.333104 | 1.27E−08 | C11 | 74,926,105 | 389 |
| rs12291026 | rs617617 | 1 | 0.425837 | 7.51E−12 | C11 | 74,936,378 | 390 |
| rs12291026 | rs618202 | 0.838016 | 0.70227 | 2.28E−13 | C11 | 74,916,133 | 86 |
| rs12291026 | rs628972 | 0.800306 | 0.242864 | 1.38E−06 | C11 | 74,885,999 | 391 |
| rs12291026 | rs640649 | 0.793071 | 0.480582 | 5.31E−09 | C11 | 74,949,499 | 88 |
| rs12291026 | rs662279 | 1 | 0.334073 | 2.08E−10 | C11 | 74,939,444 | 90 |
| rs12291026 | rs667410 | 0.891296 | 0.289518 | 1.94E−07 | C11 | 74,872,345 | 392 |
| rs12291026 | rs667531 | 0.721513 | 0.369086 | 1.84E−07 | C11 | 74,950,364 | 393 |
| rs12291026 | rs670100 | 0.89343 | 0.292234 | 1.02E−07 | C11 | 74,926,922 | 394 |
| rs12291026 | rs670491 | 0.902797 | 0.333104 | 1.27E−08 | C11 | 74,926,833 | 395 |
| rs12291026 | rs682292 | 0.800306 | 0.242864 | 1.38E−06 | C11 | 74,877,949 | 396 |
| rs12291026 | rs7128888 | 1 | 1 | 1.43E−20 | C11 | 74,931,631 | 397 |
| rs12291026 | rs7129014 | 1 | 1 | 1.43E−20 | C11 | 74,931,725 | 398 |
| rs12291026 | rs7129150 | 1 | 0.921773 | 7.97E−18 | C11 | 74,931,825 | 399 |
| rs12291026 | rs947844 | 1 | 0.84127 | 3.43E−16 | C11 | 74,906,532 | 400 |
| rs999737 | rs999737 | 1 | 1 | — | C14 | 68,104,435 | 6 |
| rs999737 | rs10134446 | 1 | 0.22 | 1.39E−09 | C14 | 68,067,388 | 91 |
| rs999737 | rs10138140 | 0.674626 | 0.269357 | 4.17E−08 | C14 | 68,011,742 | 401 |
| rs999737 | rs10146772 | 0.659865 | 0.223224 | 3.27E−07 | C14 | 67,948,122 | 402 |
| rs999737 | rs10467820 | 0.674626 | 0.269357 | 4.17E−08 | C14 | 67,988,769 | 403 |
| rs999737 | rs10483812 | 1 | 0.914924 | 1.84E−27 | C14 | 68,087,596 | 404 |
| rs999737 | rs10483813 | 1 | 1 | 1.04E−30 | C14 | 68,101,037 | 405 |
| rs999737 | rs11158749 | 1 | 0.224097 | 1.07E−09 | C14 | 68,067,049 | 406 |
| rs999737 | rs11158751 | 1 | 0.340659 | 4.73E−13 | C14 | 68,101,178 | 95 |
| rs999737 | rs11621276 | 1 | 0.87513 | 3.15E−26 | C14 | 68,066,219 | 96 |
| rs999737 | rs11624097 | 0.953506 | 0.831825 | 5.44E−24 | C14 | 68,055,789 | 407 |
| rs999737 | rs11624164 | 0.953471 | 0.82933 | 9.30E−24 | C14 | 68,055,910 | 408 |
| rs999737 | rs11624333 | 0.953506 | 0.831825 | 5.44E−24 | C14 | 68,049,588 | 409 |
| rs999737 | rs11628293 | 1 | 0.954597 | 2.00E−28 | C14 | 68,107,073 | 410 |
| rs999737 | rs11846360 | 0.528484 | 0.243633 | 1.31E−06 | C14 | 67,997,698 | 411 |
| rs999737 | rs11847185 | 0.499138 | 0.226969 | 2.79E−06 | C14 | 67,997,747 | 412 |
| rs999737 | rs11849916 | 0.499138 | 0.226969 | 2.79E−06 | C14 | 67,957,791 | 413 |
| rs999737 | rs12878761 | 0.527934 | 0.255003 | 2.88E−07 | C14 | 68,138,118 | 414 |
| rs999737 | rs12879200 | 0.739817 | 0.228092 | 4.95E−07 | C14 | 68,137,863 | 415 |
| rs999737 | rs12886864 | 0.662607 | 0.259908 | 1.17E−07 | C14 | 68,017,871 | 416 |
| rs999737 | rs12889251 | 1 | 0.876374 | 2.38E−26 | C14 | 68,063,893 | 417 |
| rs999737 | rs12894230 | 0.544425 | 0.273137 | 2.77E−07 | C14 | 68,137,669 | 418 |
| rs999737 | rs1468279 | 0.659722 | 0.26746 | 2.08E−07 | C14 | 67,994,846 | 419 |
| rs999737 | rs1468280 | 1 | 0.310873 | 3.99E−12 | C14 | 68,101,613 | 420 |
| rs999737 | rs1547012 | 0.575976 | 0.303524 | 1.93E−08 | C14 | 68,133,183 | 421 |
| rs999737 | rs17105675 | 0.499138 | 0.226969 | 2.79E−06 | C14 | 67,998,259 | 422 |
| rs999737 | rs17755657 | 0.511149 | 0.219511 | 2.63E−06 | C14 | 67,950,390 | 423 |
| rs999737 | rs17755734 | 0.499138 | 0.226969 | 2.79E−06 | C14 | 67,979,708 | 424 |
| rs999737 | rs17755752 | 0.499138 | 0.226969 | 2.79E−06 | C14 | 67,979,904 | 425 |
| rs999737 | rs17755925 | 1 | 0.876374 | 2.38E−26 | C14 | 68,081,699 | 426 |
| rs999737 | rs17756000 | 1 | 0.914924 | 1.84E−27 | C14 | 68,089,291 | 427 |
| rs999737 | rs17828691 | 0.499138 | 0.226969 | 2.79E−06 | C14 | 67,956,346 | 428 |
| rs999737 | rs17828721 | 0.499138 | 0.226969 | 2.79E−06 | C14 | 67,979,791 | 429 |
| rs999737 | rs17828763 | 0.499138 | 0.226969 | 2.79E−06 | C14 | 67,984,862 | 430 |
| rs999737 | rs17828907 | 1 | 0.914924 | 1.84E−27 | C14 | 68,080,958 | 431 |
| rs999737 | rs17828955 | 1 | 0.914924 | 1.84E−27 | C14 | 68,086,398 | 432 |
| rs999737 | rs1956534 | 0.587868 | 0.237655 | 4.20E−07 | C14 | 67,963,825 | 433 |
| rs999737 | rs2074563 | 0.674626 | 0.269357 | 4.17E−08 | C14 | 68,004,865 | 434 |
| rs999737 | rs2074565 | 0.674626 | 0.269357 | 4.17E−08 | C14 | 68,013,900 | 435 |
| rs999737 | rs2097800 | 0.66475 | 0.25742 | 2.25E−07 | C14 | 68,006,440 | 436 |
| rs999737 | rs2107340 | 0.674626 | 0.269357 | 4.17E−08 | C14 | 68,000,418 | 437 |
| rs999737 | rs2145157 | 0.739817 | 0.228092 | 4.95E−07 | C14 | 68,137,391 | 438 |
| rs999737 | rs2158357 | 1 | 0.956044 | 8.64E−29 | C14 | 68,098,956 | 439 |
| rs999737 | rs2189517 | 1 | 0.219935 | 1.39E−09 | C14 | 68,072,741 | 440 |
| rs999737 | rs2253317 | 0.923817 | 0.281194 | 1.03E−08 | C14 | 68,122,156 | 441 |
| rs999737 | rs2257111 | 0.532356 | 0.267955 | 1.67E−07 | C14 | 68,129,446 | 442 |
| rs999737 | rs2257116 | 0.533815 | 0.272433 | 1.21E−07 | C14 | 68,129,544 | 443 |
| rs999737 | rs2257127 | 0.533815 | 0.272433 | 1.21E−07 | C14 | 68,129,821 | 444 |
| rs999737 | rs2331701 | 0.669937 | 0.256122 | 8.50E−08 | C14 | 67,952,384 | 445 |
| rs999737 | rs2331705 | 0.510976 | 0.244712 | 1.44E−06 | C14 | 67,991,800 | 446 |
| rs999737 | rs2331775 | 0.739817 | 0.228092 | 4.95E−07 | C14 | 68,136,385 | 447 |
| rs999737 | rs2525503 | 1 | 0.318681 | 1.88E−12 | C14 | 68,098,356 | 105 |
| rs999737 | rs2525530 | 1 | 0.205178 | 4.00E−09 | C14 | 68,084,205 | 448 |
| rs999737 | rs2842327 | 1 | 0.382208 | 4.73E−13 | C14 | 68,098,285 | 449 |
| rs999737 | rs3784121 | 0.499138 | 0.226969 | 2.79E−06 | C14 | 67,953,441 | 450 |
| rs999737 | rs4531674 | 0.527934 | 0.255003 | 2.88E−07 | C14 | 68,136,496 | 451 |
| rs999737 | rs4899246 | 0.533815 | 0.272433 | 1.21E−07 | C14 | 68,129,955 | 108 |

TABLE 4-continued

Surrogate markers for the nine Anchor SNPs. Markers with values of $R^2$ greater than 0.2 to an Anchor marker in the HapMap CEU dataset (http://www.hapmap.org) in a 1 Mb interval flanking the marker were selected. Shown is the name of the correlated SNP, values for $R^2$ and D' to that marker and the corresponding P-value, as well as the position of the surrogate marker in NCBI Build 36 and a reference to the sequence ID containing flanking sequences for that marker.

| Anchor | Surrogate | D' | $R^2$ | P-value | Chromosome | Pos Build 36 | Seq ID |
|---|---|---|---|---|---|---|---|
| rs999737 | rs4902604 | 0.561463 | 0.264852 | 2.16E−07 | C14 | 68,124,238 | 452 |
| rs999737 | rs4902606 | 0.739817 | 0.228092 | 4.95E−07 | C14 | 68,135,119 | 453 |
| rs999737 | rs4902608 | 0.739817 | 0.228092 | 4.95E−07 | C14 | 68,138,576 | 454 |
| rs999737 | rs5004090 | 0.674626 | 0.269357 | 4.17E−08 | C14 | 68,013,998 | 455 |
| rs999737 | rs6573837 | 0.77856 | 0.353726 | 5.97E−10 | C14 | 67,999,862 | 456 |
| rs999737 | rs7140266 | 1 | 0.219935 | 1.39E−09 | C14 | 68,074,558 | 457 |
| rs999737 | rs7146456 | 1 | 0.260433 | 1.04E−10 | C14 | 68,108,734 | 458 |
| rs999737 | rs7153476 | 1 | 0.308233 | 3.65E−12 | C14 | 68,102,983 | 459 |
| rs999737 | rs739874 | 0.952339 | 0.761982 | 7.28E−22 | C14 | 68,044,163 | 460 |
| rs999737 | rs746663 | 0.61957 | 0.227187 | 5.55E−07 | C14 | 67,954,305 | 461 |
| rs999737 | rs8007194 | 1 | 0.281975 | 2.77E−11 | C14 | 68,105,178 | 462 |
| rs999737 | rs8010439 | 0.587868 | 0.237655 | 4.20E−07 | C14 | 67,954,354 | 463 |
| rs999737 | rs8012610 | 0.659865 | 0.223224 | 3.27E−07 | C14 | 67,972,552 | 464 |
| rs999737 | rs9323512 | 0.674626 | 0.269357 | 4.17E−08 | C14 | 68,019,310 | 465 |
| rs999737 | rs9323513 | 1 | 0.220532 | 1.43E−09 | C14 | 68,066,244 | 466 |
| rs999737 | rs9323514 | 1 | 0.315043 | 2.49E−12 | C14 | 68,066,317 | 467 |
| rs9956546 | rs9956546 | 1 | 1 | — | C18 | 32,136,446 | 7 |
| rs9956546 | rs16960059 | 1 | 0.66736 | 4.52E−12 | C18 | 32,120,094 | 468 |
| rs9956546 | rs492392 | 1 | 0.399199 | 3.93E−11 | C18 | 32,142,779 | 120 |
| rs9956546 | rs7239113 | 1 | 0.66736 | 4.52E−12 | C18 | 32,133,395 | 469 |
| rs9956546 | rs7240720 | 0.524852 | 0.251926 | 0.000036 | C18 | 32,142,893 | 124 |
| rs9956546 | rs9304157 | 1 | 0.211045 | 0.000182 | C18 | 32,143,156 | 470 |
| rs11912922 | rs11912922 | 1 | 1 | — | C22 | 38,733,117 | 8 |
| rs11912922 | rs11089967 | 1 | 1 | 9.56E−34 | C22 | 38,739,085 | 471 |
| rs11912922 | rs11704971 | 1 | 1 | 1.57E−30 | C22 | 38,734,239 | 472 |
| rs11912922 | rs11705454 | 1 | 1 | 6.56E−31 | C22 | 38,731,841 | 473 |
| rs11912922 | rs17406386 | 1 | 1 | 1.37E−33 | C22 | 38,735,844 | 474 |
| rs11912922 | rs17406434 | 1 | 1 | 3.28E−33 | C22 | 38,737,520 | 475 |
| rs11912922 | rs2071771 | 1 | 0.214286 | 1.52E−09 | C22 | 38,745,086 | 476 |
| rs11912922 | rs2958650 | 1 | 1 | 3.28E−33 | C22 | 38,735,877 | 477 |
| rs11912922 | rs2958651 | 1 | 0.958241 | 2.48E−29 | C22 | 38,735,709 | 478 |
| rs11912922 | rs2958659 | 1 | 1 | 9.56E−34 | C22 | 38,730,858 | 479 |
| rs11912922 | rs7284488 | 1 | 0.239332 | 2.31E−10 | C22 | 38,742,497 | 480 |
| rs11912922 | rs7285507 | 0.747862 | 0.497836 | 2.02E−12 | C22 | 38,718,254 | 481 |
| rs11912922 | rs7291782 | 1 | 0.924812 | 2.56E−30 | C22 | 38,745,563 | 482 |
| rs11912922 | rs739145 | 1 | 0.24812 | 1.20E−10 | C22 | 38,728,791 | 483 |
| rs11912922 | rs9611246 | 1 | 0.214286 | 1.52E−09 | C22 | 38,745,655 | 484 |
| rs11912922 | rs9611265 | 0.957937 | 0.846507 | 5.98E−24 | C22 | 38,828,439 | 485 |
| rs6001954 | rs6001954 | 1 | 1 | — | C22 | 39,251,626 | 9 |
| rs6001954 | rs10483203 | 0.922166 | 0.736052 | 7.16E−15 | C22 | 39,159,899 | 486 |
| rs6001954 | rs10483204 | 1 | 0.865546 | 9.75E−19 | C22 | 39,200,740 | 487 |
| rs6001954 | rs10483205 | 1 | 0.800222 | 4.35E−17 | C22 | 39,213,545 | 488 |
| rs6001954 | rs10483206 | 1 | 0.865546 | 9.75E−19 | C22 | 39,231,291 | 489 |
| rs6001954 | rs1106673 | 0.922166 | 0.736052 | 7.16E−15 | C22 | 39,155,760 | 490 |
| rs6001954 | rs11913132 | 0.696801 | 0.304518 | 1.56E−07 | C22 | 39,108,724 | 491 |
| rs6001954 | rs12158399 | 1 | 0.568501 | 2.92E−15 | C22 | 39,378,887 | 492 |
| rs6001954 | rs12158872 | 0.922166 | 0.736052 | 7.16E−15 | C22 | 39,162,447 | 493 |
| rs6001954 | rs12159200 | 1 | 0.542302 | 7.76E−15 | C22 | 39,372,037 | 138 |
| rs6001954 | rs12159970 | 1 | 0.800222 | 4.35E−17 | C22 | 39,149,100 | 494 |
| rs6001954 | rs12484697 | 0.624393 | 0.257388 | 1.79E−06 | C22 | 39,066,418 | 139 |
| rs6001954 | rs12627881 | 0.925127 | 0.534379 | 1.11E−12 | C22 | 39,374,539 | 495 |
| rs6001954 | rs133036 | 1 | 0.231068 | 6.07E−09 | C22 | 39,342,384 | 141 |
| rs6001954 | rs133038 | 1 | 0.223301 | 9.26E−09 | C22 | 39,345,215 | 496 |
| rs6001954 | rs16985899 | 1 | 0.932127 | 1.30E−20 | C22 | 39,293,348 | 497 |
| rs6001954 | rs17001846 | 0.624393 | 0.257388 | 1.79E−06 | C22 | 39,073,999 | 498 |
| rs6001954 | rs17001868 | 0.635691 | 0.328651 | 4.59E−07 | C22 | 39,108,177 | 499 |
| rs6001954 | rs17001943 | 0.922166 | 0.736052 | 7.16E−15 | C22 | 39,192,559 | 500 |
| rs6001954 | rs17001974 | 1 | 0.865546 | 9.75E−19 | C22 | 39,207,330 | 501 |
| rs6001954 | rs17001977 | 1 | 0.779103 | 6.11E−16 | C22 | 39,210,159 | 502 |
| rs6001954 | rs17001993 | 1 | 0.800222 | 4.35E−17 | C22 | 39,230,023 | 503 |
| rs6001954 | rs17001994 | 1 | 0.788111 | 8.57E−16 | C22 | 39,230,764 | 504 |
| rs6001954 | rs17001997 | 1 | 0.788111 | 4.07E−16 | C22 | 39,235,018 | 505 |
| rs6001954 | rs17002019 | 1 | 0.932127 | 1.30E−20 | C22 | 39,295,282 | 506 |
| rs6001954 | rs17002020 | 1 | 0.930025 | 1.15E−19 | C22 | 39,295,389 | 507 |
| rs6001954 | rs17002026 | 1 | 0.930456 | 2.22E−19 | C22 | 39,312,527 | 508 |
| rs6001954 | rs17002027 | 1 | 0.925154 | 2.26E−18 | C22 | 39,314,517 | 509 |
| rs6001954 | rs17002034 | 1 | 0.865546 | 9.75E−19 | C22 | 39,326,313 | 151 |
| rs6001954 | rs17002036 | 1 | 0.932127 | 1.30E−20 | C22 | 39,327,057 | 510 |
| rs6001954 | rs17002038 | 1 | 0.925548 | 4.67E−19 | C22 | 39,330,910 | 511 |
| rs6001954 | rs17002069 | 0.923881 | 0.509328 | 4.13E−12 | C22 | 39,380,932 | 512 |
| rs6001954 | rs2075764 | 0.624393 | 0.257388 | 1.79E−06 | C22 | 39,088,527 | 513 |
| rs6001954 | rs2187832 | 1 | 0.223301 | 9.26E−09 | C22 | 39,328,395 | 514 |

TABLE 4-continued

Surrogate markers for the nine Anchor SNPs. Markers with values of $R^2$ greater than 0.2 to an Anchor marker in the HapMap CEU dataset (http://www.hapmap.org) in a 1 Mb interval flanking the marker were selected. Shown is the name of the correlated SNP, values for $R^2$ and D' to that marker and the corresponding P-value, as well as the position of the surrogate marker in NCBI Build 36 and a reference to the sequence ID containing flanking sequences for that marker.

| Anchor | Surrogate | D' | $R^2$ | P-value | Chromosome | Pos Build 36 | Seq ID |
|---|---|---|---|---|---|---|---|
| rs6001954 | rs2235318 | 0.628984 | 0.275382 | 9.11E−07 | C22 | 39,130,490 | 515 |
| rs6001954 | rs2280790 | 0.624393 | 0.257388 | 1.79E−06 | C22 | 39,075,127 | 516 |
| rs6001954 | rs2294348 | 0.694473 | 0.293289 | 2.75E−07 | C22 | 39,113,726 | 517 |
| rs6001954 | rs2294350 | 0.624393 | 0.257388 | 1.79E−06 | C22 | 39,114,224 | 518 |
| rs6001954 | rs2294352 | 0.922166 | 0.736052 | 7.16E−15 | C22 | 39,157,265 | 519 |
| rs6001954 | rs2413624 | 1 | 0.260204 | 3.65E−09 | C22 | 39,260,158 | 520 |
| rs6001954 | rs3788577 | 0.624393 | 0.257388 | 1.79E−06 | C22 | 39,072,777 | 521 |
| rs6001954 | rs3788578 | 0.624393 | 0.257388 | 1.79E−06 | C22 | 39,072,867 | 522 |
| rs6001954 | rs3788579 | 0.624453 | 0.267064 | 1.98E−06 | C22 | 39,072,935 | 523 |
| rs6001954 | rs3827381 | 1 | 0.865546 | 9.75E−19 | C22 | 39,211,348 | 524 |
| rs6001954 | rs3827382 | 1 | 0.800222 | 4.35E−17 | C22 | 39,211,349 | 153 |
| rs6001954 | rs4140512 | 1 | 0.568501 | 2.92E−15 | C22 | 39,362,809 | 525 |
| rs6001954 | rs470113 | 0.624393 | 0.257388 | 1.79E−06 | C22 | 39,059,560 | 155 |
| rs6001954 | rs5750957 | 1 | 0.265513 | 1.01E−09 | C22 | 39,265,239 | 526 |
| rs6001954 | rs5750960 | 1 | 0.231068 | 6.07E−09 | C22 | 39,289,866 | 157 |
| rs6001954 | rs5750966 | 1 | 0.213336 | 1.64E−08 | C22 | 39,299,739 | 527 |
| rs6001954 | rs5757976 | 1 | 0.223301 | 9.26E−09 | C22 | 39,245,664 | 528 |
| rs6001954 | rs5757998 | 1 | 0.265513 | 1.01E−09 | C22 | 39,269,856 | 529 |
| rs6001954 | rs5758001 | 0.90345 | 0.224527 | 3.42E−07 | C22 | 39,276,253 | 159 |
| rs6001954 | rs5995849 | 0.696801 | 0.304518 | 1.56E−07 | C22 | 39,107,018 | 530 |
| rs6001954 | rs5995856 | 0.927089 | 0.801157 | 1.72E−16 | C22 | 39,179,008 | 531 |
| rs6001954 | rs5995870 | 1 | 1 | 4.37E−23 | C22 | 39,251,762 | 532 |
| rs6001954 | rs5995871 | 1 | 1 | 5.10E−23 | C22 | 39,252,278 | 533 |
| rs6001954 | rs5995886 | 1 | 0.563253 | 6.45E−15 | C22 | 39,363,747 | 534 |
| rs6001954 | rs6001900 | 0.693507 | 0.310492 | 4.91E−07 | C22 | 39,120,948 | 535 |
| rs6001954 | rs6001910 | 1 | 0.800222 | 4.35E−17 | C22 | 39,153,955 | 536 |
| rs6001954 | rs6001911 | 0.922166 | 0.736052 | 7.16E−15 | C22 | 39,155,139 | 537 |
| rs6001954 | rs6001912 | 0.922166 | 0.736052 | 7.16E−15 | C22 | 39,158,307 | 538 |
| rs6001954 | rs6001913 | 1 | 0.800222 | 4.35E−17 | C22 | 39,166,699 | 539 |
| rs6001954 | rs6001930 | 1 | 0.865546 | 9.75E−19 | C22 | 39,206,180 | 540 |
| rs6001954 | rs6001931 | 1 | 0.857313 | 9.26E−18 | C22 | 39,207,460 | 541 |
| rs6001954 | rs6001932 | 1 | 0.865546 | 9.75E−19 | C22 | 39,207,581 | 161 |
| rs6001954 | rs6001935 | 1 | 0.865546 | 9.75E−19 | C22 | 39,216,939 | 542 |
| rs6001954 | rs6001950 | 1 | 0.865546 | 9.75E−19 | C22 | 39,236,581 | 543 |
| rs6001954 | rs6001974 | 1 | 1 | 4.37E−23 | C22 | 39,309,110 | 544 |
| rs6001954 | rs6001980 | 1 | 1 | 4.37E−23 | C22 | 39,334,330 | 545 |
| rs6001954 | rs6001990 | 1 | 0.568501 | 2.92E−15 | C22 | 39,364,131 | 546 |
| rs6001954 | rs6002000 | 1 | 0.568501 | 2.92E−15 | C22 | 39,381,055 | 547 |
| rs6001954 | rs718193 | 1 | 0.932127 | 1.30E−20 | C22 | 39,354,010 | 548 |
| rs6001954 | rs7292804 | 0.923881 | 0.509328 | 4.13E−12 | C22 | 39,377,502 | 549 |
| rs6001954 | rs7293100 | 0.92505 | 0.531874 | 1.29E−12 | C22 | 39,377,697 | 550 |
| rs6001954 | rs742140 | 0.624393 | 0.257388 | 1.79E−06 | C22 | 39,111,532 | 551 |
| rs6001954 | rs760700 | 0.624393 | 0.257388 | 1.79E−06 | C22 | 39,130,017 | 552 |
| rs6001954 | rs760701 | 0.628984 | 0.275382 | 9.11E−07 | C22 | 39,130,464 | 553 |
| rs6001954 | rs9306345 | 0.780144 | 0.423648 | 8.54E−10 | C22 | 39,162,321 | 167 |
| rs6001954 | rs932379 | 1 | 0.932127 | 1.30E−20 | C22 | 39,282,480 | 554 |
| rs6001954 | rs9607721 | 0.851982 | 0.479217 | 3.33E−11 | C22 | 39,192,066 | 168 |
| rs6001954 | rs9611310 | 0.624393 | 0.257388 | 1.79E−06 | C22 | 39,063,723 | 555 |
| rs6001954 | rs9611311 | 0.694782 | 0.31869 | 2.91E−07 | C22 | 39,063,897 | 556 |
| rs6001954 | rs9611312 | 0.61091 | 0.260998 | 7.16E−06 | C22 | 39,064,736 | 557 |
| rs6001954 | rs9611316 | 0.673329 | 0.320213 | 8.89E−07 | C22 | 39,066,973 | 558 |
| rs6001954 | rs9611318 | 0.624393 | 0.257388 | 1.79E−06 | C22 | 39,069,360 | 559 |
| rs6001954 | rs9611324 | 0.696801 | 0.304518 | 1.56E−07 | C22 | 39,111,108 | 172 |
| rs6001954 | rs9611325 | 0.624393 | 0.257388 | 1.79E−06 | C22 | 39,112,436 | 560 |
| rs6001954 | rs9611328 | 0.624393 | 0.257388 | 1.79E−06 | C22 | 39,121,918 | 561 |
| rs6001954 | rs9611329 | 0.624393 | 0.257388 | 1.79E−06 | C22 | 39,121,984 | 562 |

TABLE 5

Association with breast cancer for rs 6001954 on Chromosome 22 is shown for individual cohorts including Taiwanese. Also presented are combined European results as well as results of all combined cohorts

| Sample Set | SNP | Allele | P-value | OR | N cases | F cases | N controls | F controls | 95% CI | Phet |
|---|---|---|---|---|---|---|---|---|---|---|
| ICELAND | rs6001954 | 3 | 7.20E−04 | 1.18 | 2321 | 0.134 | 35787 | 0.117 | | |
| DKFZ-Sweden | rs6001954 | 3 | 5.59E−01 | 1.06 | 937 | 0.137 | 930 | 0.130 | | |
| HOLLAND | rs6001954 | 3 | 2.90E−01 | 1.11 | 743 | 0.116 | 2031 | 0.106 | | |
| MAYO-U.S.A. | rs6001954 | 3 | 7.29E−02 | 1.17 | 1508 | 0.120 | 1264 | 0.104 | | |

TABLE 5-continued

Association with breast cancer for rs 6001954 on Chromosome 22 is shown for individual cohorts including Taiwanese. Also presented are combined European results as well as results of all combined cohorts

| Sample Set | SNP | Allele | P-value | OR | N cases | F cases | N controls | F controls | 95% CI | Phet |
|---|---|---|---|---|---|---|---|---|---|---|
| SPAIN | rs6001954 | 3 | 2.99E−01 | 1.10 | 912 | 0.108 | 1864 | 0.099 | | |
| SWEDEN-Karolinska | rs6001954 | 3 | 1.26E−01 | 1.16 | 825 | 0.119 | 1724 | 0.105 | | |
| CGEMS | rs6001954 | 3 | 9.30E−02 | 1.22 | 1101 | 0.109 | 1105 | 0.091 | | |
| TAIWAN | rs6001954 | 3 | 1.02E−01 | 1.13 | 1026 | 0.243 | 901 | 0.221 | | |
| ALL European | rs6001954 | 3 | 5.20E−06 | 1.15 | 8347 | N/A | 44705 | N/A | (1.08, 1.22) | 0.95 |
| ALL Combined | rs6001954 | 3 | 1.30E−06 | 1.15 | 9373 | N/A | 45606 | N/A | (1.08, 1.21) | 0.98 |

The invention claimed is:

1. A method for determining a susceptibility to breast cancer in a human individual, comprising:

analyzing nucleic acid from a biological sample from the individual with respect to at least one allele of at least one polymorphic marker, selected from the group consisting of rs999737 (SEQ ID NO:6) allele C, rs2005154 (SEQ ID NO:1) allele T, rs2184380 (SEQ ID NO:2) allele G, rs2224696 (SEQ ID NO:3) allele T, rs2242503 (SEQ ID NO:4) allele C, rs12291026 (SEQ ID NO:5) allele G, rs9956546 (SEQ ID NO:7) allele A, rs11912922 (SEQ ID NO:8) allele T, rs6001954 (SEQ ID NO:9) allele G, and correlated alleles of polymorphic markers in linkage disequilibrium therewith, wherein the step of analyzing the nucleic acid sample comprises at least one nucleic acid analysis technique selected from: polymerase chain reaction, allele-specific probe hybridization, allele-specific primer extension, allele-specific amplification, nucleic acid sequencing, 5'-exonuclease digestion, molecular beacon assay, oligonucleotide ligation assay, size analysis, single-stranded conformation analysis and microarray technology, detecting the presence of the at least one allele in the nucleic acid, determining an increased susceptibility to breast cancer for the individual from the presence of the at least one allele in the nucleic acid by calculating risk measure for the individual that includes a relative risk or odds ratio of at least 1.08 attributable to the presence of the at least one allele in the nucleic acid, wherein the calculating of the risk measure is performed with an apparatus that comprises:

a processor a computer readable memory having computer executable instructions adapted to be executed on the processor to analyze marker information for at least one human individual with respect to the at least one polymorphic marker and generate an output based on the marker information, wherein the output comprises the risk measure for the human individual with respect to breast cancer, and performing a clinical screening for breast cancer selected from clinical breast examination (CBE), X-ray mammography, and contrast-enhanced magnetic resonance imaging (CE-MRI) in the individual determined to have the increased susceptibility.

2. The method according to claim 1, wherein the at least one polymorphic marker is selected from the markers set forth in Table 4.

3. The method according to claim 1, wherein the at least one polymorphic marker is selected from rs999737 (SEQ ID NO:6), rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs9956546 (SEQ ID NO:7), rs11912922 (SEQ ID NO:8), rs6001954 (SEQ ID NO:9).

4. The method according to claim 2, wherein the at least one polymorphic marker is selected from the markers set forth in Table 4 having an $r^2$ value in Table 4 of at least 0.8.

5. The method according to claim 2, wherein the at least one polymorphic marker is selected from the markers set forth in Table 4 having an $r^2$ value in Table 4 of at least 0.5.

6. The method according to claim 3, wherein any one of allele T in rs2005154, allele G in rs2184380, allele Tin rs2224696, allele C in rs2242503, allele G in rs12291026, allele C in rs999737, allele A in rs9956546, allele T in rs11912922, allele G in rs6001954 is determined to be present in the nucleic acid, indicative of increased susceptibility to breast cancer in the individual.

7. The method according to claim 1, further comprising assessing the frequency of at least one haplotype in the individual.

8. The method according to claim 1 that comprises calculating a risk measure for the individual that includes a relative risk (RR) or odds ratio (OR) of at least 1.10 attributed to the presence of the at least one allele in the nucleic acid.

9. The method of claim 1, further comprising analyzing the nucleic acid to determine whether at least one at-risk allele of at least one at-risk variant for breast cancer not in linkage disequilibrium with any one of the markers set forth in Table 4 is present in the sample, and calculating a combined risk measure based on the presence of the at least one allele and whether the at least one at-risk variant is present.

10. The method of claim 9, comprising calculating combined risk using a multiplicative model.

11. The method of claim 1, comprising analyzing the nucleic acid to determine whether at least one at-risk allele in each of at least two of the polymorphic markers is present in the sample, identifying the presence of an at-risk allele of the at least two polymorphic markers in the nucleic acid; and determining an increased susceptibility to breast cancer for the individual from the presence of the at-risk alleles of the least two polymorphic markers in the nucleic acid by calculating a risk measure for the individual that includes a relative risk or odds ratio of at least 1.08 attributable to each of the at-risk alleles determined to be present, wherein the at least two alleles are independent, and wherein a multiplicative model is used for combined risk.

12. The method according to claim 1, further comprising a step of determining the presence or absence of at least one high penetrant genetic factor for breast cancer in a nucleic acid sample obtained from the individual or in a genotype dataset derived from the individual, and calculating combined risk using a multiplicative model.

13. The method according to claim 12, wherein the high penetrant genetic factor is a mutation in BRCA1, BRCA2, TP53 and/or PTEN.

14. The method of claim 1, further comprising analyzing non-genetic information to make risk assessment of the individual, and calculating combined risk using a multiplicative model.

15. The method of claim 14, wherein the non-genetic information is selected from age, gender, ethnicity, socioeconomic status, previous disease diagnosis, medical history of subject, family history of breast cancer, biochemical measurements, and clinical measurements.

16. The method of claim 1, wherein determination of the presence of at least one risk allele for breast cancer is predictive of estrogen receptor positive or progesterone receptor positive breast cancer.

17. The method of claim 1, wherein linkage disequilibrium between markers is characterized by values of $r^2$ of at least 0.2.

18. The method of claim 1, wherein the human individual is of an ancestry that includes European ancestry.

19. The method of claim 1, further comprising reporting the susceptibility to at least one entity selected from the group consisting of the individual, a guardian of the individual, a genetic service provider, a physician, a medical organization, and a medical insurer.

20. The method according to claim 19, wherein the reporting comprises making the determination of susceptibility available to the at least one person via a secure website.

21. The method according to claim 1, wherein the computer readable memory further comprises data indicative of the risk of developing breast cancer associated with the at least one allele of the at least one polymorphic marker, and wherein the risk measure for the human individual is based on a comparison of the genotype status for the human individual for the at least one polymorphic marker to the risk of developing breast cancer associated with the at least one allele.

22. The method according to claim 21, wherein the computer readable memory further comprises data indicative of the frequency of the at least one allele of at least one polymorphic marker in a plurality of individuals diagnosed with breast cancer, and data indicative of the frequency of the least one allele of at least one polymorphic marker in a plurality of reference individuals, and wherein risk of developing breast cancer associated with the at least one allele is based on a comparison of the frequency of the at least one allele in individuals diagnosed with breast cancer and reference individuals.

23. The method according to claim 22, wherein the at least one marker comprises at least one marker selected from the markers set forth in Table 4.

24. The method according to claim 22, wherein the at least one polymorphic marker is selected from the markers set forth in Table 4 having an $r^2$ value in Table 4 of at least 0.8.

25. The method according to claim 22, wherein the at least one marker is selected from the group consisting of rs999737 (SEQ ID NO:6), rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs9956546 (SEQ ID NO:7), rs11912922 (SEQ ID NO:8), and rs6001954 (SEQ ID NO:9).

26. An apparatus for determining a genetic indicator for breast cancer in a human individual, comprising:

a processor a computer readable memory having computer executable instructions adapted to be executed on the processor to analyze marker information for at least one human individual with respect to at least one polymorphic marker selected from rs999737 (SEQ ID NO:6), rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs9956546 (SEQ ID NO:7), rs11912922 (SEQ ID NO:8), rs6001954 (SEQ ID NO:9), and markers in linkage disequilibrium therewith, and generate an output based on the marker information, wherein the output comprises a risk measure of the at least one marker as a genetic indicator of breast cancer for the human individual.

27. The apparatus according to claim 26, wherein the computer readable memory further comprises data indicative of the risk of developing breast cancer associated with at least one allele of the at least one polymorphic marker, and wherein the risk measure for the human individual is based on a comparison of the genotype status for the human individual for the at least one polymorphic marker to the risk of developing breast cancer associated with the at least one allele.

28. The apparatus according to claim 27, wherein the computer readable memory further comprises data indicative of the frequency of the at least one allele of at least one polymorphic marker in a plurality of individuals diagnosed with breast cancer, and data indicative of the frequency of the least one allele of at least one polymorphic marker in a plurality of reference individuals, and wherein risk of developing breast cancer associated with the at least one allele is based on a comparison of the frequency of the at least one allele in individuals diagnosed with breast cancer and reference individuals.

29. The apparatus according to claim 26, wherein the at least one marker comprises at least one marker selected from the markers set forth in Table 4.

30. The apparatus according to claim 26, wherein the at least one marker is selected from the group consisting of rs999737 (SEQ ID NO:6), rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs9956546 (SEQ ID NO:7), rs11912922 (SEQ ID NO:8), rs6001954 (SEQ ID NO:9).

31. The apparatus according to claim 26, wherein the risk measure is characterized by an Odds Ratio (OR) or a Relative Risk (RR).

32. A method of determining a susceptibility to breast cancer in a human individual, the method comprising:

analyzing nucleic acid from a biological sample from the individual to obtain nucleic acid sequence data about a human individual identifying the presence or absence of at least one allele of at least one polymorphic marker selected from rs999737 (SEQ ID NO:6) allele C, rs2005154 (SEQ ID NO:1) allele T, rs2184380 (SEQ ID NO:2) allele G, rs2224696 (SEQ ID NO:3) allele T, rs2242503 (SEQ ID NO:4) allele C, rs12291026 (SEQ ID NO:5) allele G, rs9956546 (SEQ ID NO:7) allele A, rs11912922 (SEQ ID NO:8) allele T, rs6001954 (SEQ ID NO:9) allele G, and correlated alleles of polymorphic markers in linkage disequilibrium therewith, wherein the step of analyzing the nucleic acid sample comprises at least one nucleic acid analysis technique selected from: polymerase chain reaction, allele-specific probe hybridization, allele-specific primer extension, allele-specific amplification, nucleic acid sequencing, 5'-exonuclease digestion, molecular beacon assay, oligonucleotide ligation assay, size analysis, single-stranded conformation analysis and microarray technology, wherein different alleles of the at least one polymorphic marker are associated with different susceptibilities to breast cancer in humans, detecting the presence of the at least one allele in the nucleic acid, and determining an increased susceptibility to breast cancer for the human individual from the nucleic acid sequence data by calculating risk measure for the individual that includes a relative risk or odds ratio of at least 1.08 attributable to the presence of the at least one allele in the nucleic acid, using an apparatus that comprises:

a processor and a computer readable memory having computer executable instructions adapted to be executed on the processor to analyze marker information for at least one human individual with respect to the at least one polymorphic marker and generate an output based on the marker information, wherein the output comprises the risk measure for the human individual with respect to breast cancer, and performing a clinical screening for breast cancer selected from clinical breast examination (CBE), X-ray mammography, and contrast-enhanced magnetic resonance imaging (CE-MRI) in the individual determined to have the increased susceptibility.

33. The method of claim 32, comprising obtaining nucleic acid sequence data about the human individual with respect to at least two independent polymorphic markers selected from rs999737 (SEQ ID NO:6), rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs9956546 (SEQ ID NO:7), rs11912922 (SEQ ID NO:8), rs6001954 (SEQ ID NO:9) and markers in linkage disequilibrium therewith.

34. The method of claim 32, wherein determination of a susceptibility comprises comparing the nucleic acid sequence data to a database containing correlation data between the at least one polymorphic marker and susceptibility to breast cancer.

35. The method of claim 34, wherein the database comprises at least one risk measure of susceptibility to breast cancer for the at least one polymorphic marker.

36. The method of claim 34, wherein the database comprises a look-up table containing at least one risk measure of the at least one condition for the at least one polymorphic marker.

37. The method of claim 32, further comprising reporting the susceptibility to at least one entity selected from the group consisting of the individual, a guardian of the individual, a genetic service provider, a physician, a medical organization, and a medical insurer.

38. The method of claim 32, wherein the at least one polymorphic marker is selected from the group consisting of the markers listed in Table 4.

39. The method according to claim 38, wherein the at least one polymorphic marker is selected from the markers set forth in Table 4 having an $r^2$ value in Table 4 of at least 0.8.

40. The method of claim 32, wherein the at least one polymorphic marker is selected from the group consisting of rs999737 (SEQ ID NO:6), rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs9956546 (SEQ ID NO:7), rs11912922 (SEQ ID NO:8), rs6001954 (SEQ ID NO:9).

41. A method of using a nucleic acid sample isolated from a human individual to calculate a risk for developing breast cancer, the method comprising:

analyzing polymorphic marker rs999737 in the nucleic acid sample, wherein the step of analyzing the nucleic acid sample comprises at least one nucleic acid analysis technique selected from: polymerase chain reaction, allele-specific hybridization, allele-specific primer extension, allele-specific amplification, nucleic acid sequencing, 5'-exonuclease digestion, molecular beacon assay, oligonucleotide ligation assay, size analysis, single-stranded conformation analysis and microarray technology, calculating a risk measure score for breast cancer for the individual that includes a genetic risk factor based on whether or not allele C of polymorphic marker rs999737 is present in the sample, and performing a clinical screening for breast cancer selected from clinical breast examination (CBE), X-ray mammography, and contrast-enhanced magnetic resonance imaging (CE-MRI) in an individual determined to have an increased risk of breast cancer attributable to allele C of polymorphic marker rs999737 being present in the nucleic acid.

42. The method of claim 41, further comprising reporting the risk measure to at least one entity selected from the group consisting of the individual, a guardian of the individual, a genetic service provider, a physician, a medical organization, and a medical insurer.

43. The method according to claim 42, wherein the reporting comprises making the risk measure available to the at least one person via a secure web site.

44. A method for determining a susceptibility to breast cancer in a human individual, comprising:

analyzing nucleic acid from a biological sample from the individual with respect to at least one allele of at least one polymorphic marker, selected from the group consisting of rs999737 (SEQ ID NO:6) allele C, rs2005154 (SEQ ID NO:1) allele T, rs2184380 (SEQ ID NO:2) allele G, rs2224696 (SEQ ID NO:3) allele T, rs2242503 (SEQ ID NO:4) allele C, rs12291026 (SEQ ID NO:5) allele G, rs9956546 (SEQ ID NO:7) allele A, rs11912922 (SEQ ID NO:8) allele T, rs6001954 (SEQ ID NO:9) allele G, and correlated alleles of polymorphic markers in linkage disequilibrium therewith, detecting the presence of the at least one allele in the nucleic acid, and determining an increased susceptibility to breast cancer for the individual from the presence of the at least one allele in the nucleic acid, and performing a clinical screening for breast cancer selected from clinical breast examination (CBE), X-ray mammography, and contrast-enhanced magnetic resonance imaging (CE-MRI) in the subject determined to have the increased susceptibility.

45. The method of claim 44, wherein the at least one polymorphic marker is selected from the markers set forth in Table 4.

46. The method according to claim 45, wherein the at least one polymorphic marker is selected from the markers set forth in Table 4 having an $r^2$ value in Table 4 of at least 0.5.

47. The method according to claim 45, wherein the at least one polymorphic marker is selected from the markers set forth in Table 4 having an $r^2$ value in Table 4 of at least 0.8.

48. The method according to claim 45, wherein the at least one polymorphic marker is selected from the markers set forth in Table 4 having an $r^2$ value in Table 4 of at least 0.8.

49. The method according to claim 44, wherein the at least one polymorphic marker is selected from rs999737 (SEQ ID NO:6), rs2005154 (SEQ ID NO:1), rs2184380 (SEQ ID NO:2), rs2224696 (SEQ ID NO:3), rs2242503 (SEQ ID NO:4), rs12291026 (SEQ ID NO:5), rs9956546 (SEQ ID NO:7), rs11912922 (SEQ ID NO:8), rs6001954 (SEQ ID NO:9).

50. The method of claim 49, further comprising reporting the susceptibility to at least one entity selected from the group consisting of the individual, a guardian of the individual, a genetic service provider, a physician, a medical organization, and a medical insurer.

51. The method according to claim 50, wherein the reporting comprises making the determination of susceptibility available to the at least one person via a secure website.

52. The method of claim 44, further comprising reporting the susceptibility to at least one entity selected from the group consisting of the individual, a guardian of the individual, a genetic service provider, a physician, a medical organization, and a medical insurer.

53. The method according to claim 52, wherein the reporting comprises making the determination of susceptibility available to the at least one person via a secure website.

* * * * *